US010519118B2

(12) United States Patent
Rienhoff, Jr. et al.

(10) Patent No.: US 10,519,118 B2
(45) Date of Patent: *Dec. 31, 2019

(54) KDM1A INHIBITORS FOR THE TREATMENT OF DISEASE

(71) Applicant: Imago Biosciences, Inc., San Carlos, CA (US)

(72) Inventors: Hugh Y. Rienhoff, Jr., San Carlos, CA (US); John M. McCall, Boca Grande, FL (US); Michael Clare, Skokie, IL (US); Cassandra Celatka, Hull, MD (US); Amy E. Tapper, Boston, MA (US)

(73) Assignee: Imago Biosciences, Inc., San Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/952,073

(22) Filed: Apr. 12, 2018

(65) Prior Publication Data

US 2018/0312474 A1    Nov. 1, 2018

Related U.S. Application Data

(63) Continuation of application No. 15/043,121, filed on Feb. 12, 2016, now Pat. No. 9,981,922.

(Continued)

(51) Int. Cl.
| | |
|---|---|
| C07D 249/06 | (2006.01) |
| A61K 31/495 | (2006.01) |
| A61K 31/41 | (2006.01) |
| C07D 401/12 | (2006.01) |
| C07D 403/12 | (2006.01) |
| C07D 491/107 | (2006.01) |
| C07D 471/10 | (2006.01) |
| C07D 498/08 | (2006.01) |
| C07C 309/30 | (2006.01) |
| A61K 9/00 | (2006.01) |
| A61K 31/496 | (2006.01) |
| C07D 239/26 | (2006.01) |

(Continued)

(52) U.S. Cl.
CPC .......... *C07D 249/06* (2013.01); *A61K 9/0053* (2013.01); *A61K 9/1623* (2013.01); *A61K 9/4858* (2013.01); *A61K 31/397* (2013.01); *A61K 31/41* (2013.01); *A61K 31/4162* (2013.01); *A61K 31/4192* (2013.01); *A61K 31/4196* (2013.01); *A61K 31/435* (2013.01); *A61K 31/445* (2013.01); *A61K 31/454* (2013.01); *A61K 31/495* (2013.01); *A61K 31/496* (2013.01); *A61K 31/4995* (2013.01); *A61K 31/501* (2013.01); *A61K 31/506* (2013.01); *A61K 31/5377* (2013.01); *A61K 31/5383* (2013.01); *A61K 31/54* (2013.01); *A61K 31/541* (2013.01); *A61K 31/551* (2013.01); *A61K 45/06* (2013.01); *A61P 29/00* (2018.01); *A61P 35/00* (2018.01); *A61P 35/02* (2018.01); *A61P 43/00* (2018.01); *C07B 59/002* (2013.01); *C07C 53/18* (2013.01); *C07C 309/30* (2013.01); *C07D 205/04* (2013.01); *C07D 211/66* (2013.01); *C07D 215/54* (2013.01); *C07D 231/12* (2013.01); *C07D 237/08* (2013.01); *C07D 239/26* (2013.01); *C07D 239/42* (2013.01); *C07D 249/08* (2013.01); *C07D 263/32* (2013.01); *C07D 279/12* (2013.01); *C07D 295/192* (2013.01); *C07D 295/26* (2013.01); *C07D 401/04* (2013.01); *C07D 401/12* (2013.01); *C07D 403/12* (2013.01); *C07D 413/12* (2013.01); *C07D 471/10* (2013.01); *C07D 487/04* (2013.01); *C07D 487/08* (2013.01); *C07D 491/107* (2013.01); *C07D 498/08* (2013.01); *C07B 2200/05* (2013.01); *C07B 2200/07* (2013.01); *C07B 2200/13* (2013.01)

(58) Field of Classification Search
CPC .... A61K 31/454; A61K 31/495; A61K 31/54; A61K 31/496; A61K 2300/00; C07D 249/06; C07D 401/12; C07D 403/12; C07D 491/107; C07D 471/10; C07D 498/08

See application file for complete search history.

(56) References Cited

U.S. PATENT DOCUMENTS

| | | |
|---|---|---|
| 9,790,195 B2 | 10/2017 | Mccall et al. |
| 9,981,922 B2 | 5/2018 | Rienhoff, Jr. |

(Continued)

FOREIGN PATENT DOCUMENTS

| | | |
|---|---|---|
| CN | 102947265 A | 2/2003 |
| EP | 2177502 A1 | 4/2010 |

(Continued)

OTHER PUBLICATIONS

Kleppe, Maria. Blood Journal, 126(23), 601 (2015).*

(Continued)

*Primary Examiner* — Emily A Bernhardt
*Assistant Examiner* — Laura M Daniel
(74) *Attorney, Agent, or Firm* — Dennis A. Bennett; Cynthia Hathaway; John Desper

(57) ABSTRACT

Disclosed herein are new compounds and compositions and their application as pharmaceuticals for the treatment of diseases. Methods of inhibition of KDM1A, methods of increasing gamma globin gene expression, and methods to induce differentiation of cancer cells in a human or animal subject are also provided for the treatment of diseases such as acute myelogenous leukemia.

22 Claims, 27 Drawing Sheets

Related U.S. Application Data

(60) Provisional application No. 62/115,474, filed on Feb. 12, 2015.

(51) Int. Cl.

| | | |
|---|---|---|
| A61K 31/506 | (2006.01) |
| C07D 295/192 | (2006.01) |
| C07D 279/12 | (2006.01) |
| A61K 31/54 | (2006.01) |
| C07D 205/04 | (2006.01) |
| A61K 31/397 | (2006.01) |
| C07D 295/26 | (2006.01) |
| C07D 215/54 | (2006.01) |
| C07C 53/18 | (2006.01) |
| C07D 231/12 | (2006.01) |
| C07D 263/32 | (2006.01) |
| A61K 31/541 | (2006.01) |
| C07B 59/00 | (2006.01) |
| A61K 31/4192 | (2006.01) |
| A61K 31/454 | (2006.01) |
| C07D 249/08 | (2006.01) |
| A61K 31/4196 | (2006.01) |
| C07D 211/66 | (2006.01) |
| A61K 31/445 | (2006.01) |
| C07D 239/42 | (2006.01) |
| C07D 413/12 | (2006.01) |
| A61K 31/5377 | (2006.01) |
| A61K 31/5383 | (2006.01) |
| A61K 31/435 | (2006.01) |
| C07D 401/04 | (2006.01) |
| C07D 487/04 | (2006.01) |
| A61K 31/4162 | (2006.01) |
| C07D 487/08 | (2006.01) |
| A61K 31/4995 | (2006.01) |
| A61K 31/551 | (2006.01) |
| C07D 237/08 | (2006.01) |
| A61K 31/501 | (2006.01) |
| A61K 9/16 | (2006.01) |
| A61K 9/48 | (2006.01) |
| A61K 45/06 | (2006.01) |
| A61P 29/00 | (2006.01) |
| A61P 35/00 | (2006.01) |
| A61P 35/02 | (2006.01) |
| A61P 43/00 | (2006.01) |

(56) References Cited

U.S. PATENT DOCUMENTS

| | | |
|---|---|---|
| 2012/0108500 A1 | 5/2012 | Sakane |
| 2013/0090386 A1 | 4/2013 | Ortega |
| 2015/0225401 A1 | 8/2015 | Wu |
| 2015/0232436 A1 | 8/2015 | Baker |
| 2016/0130215 A1 | 5/2016 | Tomita |
| 2016/0237043 A1 | 8/2016 | Rienhoff |
| 2016/0257662 A1 | 9/2016 | McCall |
| 2017/0334873 A1 | 11/2017 | Mccall |

FOREIGN PATENT DOCUMENTS

| | | |
|---|---|---|
| EP | 2927212 | 10/2015 |
| EP | 2927212 A1 | 10/2015 |
| WO | 2010043721 A1 | 4/2010 |
| WO | 2010143582 A1 | 12/2010 |
| WO | 2011035941 A1 | 3/2011 |
| WO | 2011042217 A1 | 4/2011 |
| WO | 2011131576 A1 | 10/2011 |
| WO | 2011131697 A1 | 10/2011 |
| WO | 2012013727 A1 | 2/2012 |
| WO | 2012013728 A1 | 2/2012 |
| WO | 2012034116 A2 | 3/2012 |
| WO | 2012045883 A1 | 4/2012 |
| WO | 2012047852 | 4/2012 |
| WO | 2012071469 A2 | 5/2012 |
| WO | 2012107498 | 8/2012 |
| WO | 2012107498 A1 | 8/2012 |
| WO | 2012107499 A1 | 8/2012 |
| WO | 2012135113 A2 | 10/2012 |
| WO | 2013057320 A1 | 4/2013 |
| WO | 2013057322 A1 | 4/2013 |
| WO | 2014084298 | 6/2014 |
| WO | 2014084298 A1 | 6/2014 |
| WO | 2014164867 | 10/2014 |
| WO | 2014164867 A1 | 10/2014 |
| WO | 2014164867 A3 | 10/2014 |
| WO | 2015021128 A1 | 2/2015 |
| WO | 2016130952 | 8/2016 |
| WO | 2016130952 A1 | 8/2016 |
| WO | 2017079753 A1 | 5/2017 |
| WO | 2018035249 | 2/2018 |
| WO | 2018035259 | 2/2018 |

OTHER PUBLICATIONS

The Cleveland Clinic. Myelofibrosis: Prevention. Web <https://my.clevelandclinic.org/health/diseases/15672-myelofibrosis/prevention> (2015).*

Myeloproliferative disorders: University of Maryland Medical Center. (2016).Web: <http://umm.edu/health/medical/altmed/condition/myeloproliferative-disorders>.*

International Application No. PCT/US2014/023659; International Search Report and Written Opinion of the International Search Authority, dated Jul. 29, 2014; 9 pages.

Alvarez-Lanrán A et al. "Red cell mass measurement in patients with clinically suspected diagnosis of polycythemia vera or essential thrombocythemia", Haematologica. Nov. 2012;97(11):1704-7.

Banker, Gilbert S. et al., Modern Pharmaceutics, Marcel Dekker, New York, 1996.

Benelkebir H et al., Enantioselective synthesis of tranylcypromine analogues as lysine-specific demethylase (LSD1) Inhibitors, Bioorganic & Medicinal Chemistry 19 (Feb. 13, 2011) 3709-3716.

Binda C et al., Biochemical, Structural, and Biological Evaluation of Tranylcypromine Derivatives as Inhibitors of Histone Demethylases LSD1 and LSD2, J. Am. Chem. Soc. (Apr. 23, 2010) 132:19, 6827-6833.

Byrn, S. et al., Solid-State Chemistry of Drugs, 2nd Ed., Ch. 11 Hydrates and Solvates, 1999, 233-247.

Cardama, et al., "Therapy with the histone deacetylase inhibitor pracinostat for patients with myelofibrosis," Leuk Res. 2012, vol. 36(9), pp. 1124-1127. Title; abstract; p. 2, para 1; p. 3, para 1; p. 5, para 4 to p. 6, para 1.

Gooden, DM et al., Facile synthesis of substituted trans-2-arylcyclopropylamine inhibitors of the human histone demethylase LSD1 and monoamine oxidases A and B, Bioorg Med Chem Lett, (epub Jan. 8, 2008); 18(10):3047-51.

International Application No. PCT/US2014/023659; International Preliminary Report on Patentability, dated Sep. 15, 2015; 06 pages.

International Application No. PCT/US2014/023659; International Search Report and Written Opinion of the International Search Authority, dated Jul. 29, 2014; 09 pages.

International Application No. PCT/US2014/049906; International Preliminary Report on Patentability, dated Feb. 9, 2016; 07 pages.

International Application No. PCT/US2014/049906; International Search Report and Written Opinion of the International Search Authority, dated Oct. 27, 2016; 08 pages.

International Application No. PCT/US2016/017809; International Preliminary Report on Patentability dated Aug. 24, 2017; 06 pages.

International Application No. PCT/US2016/017809; International Search Report and Written Opinion of the International Search Authority, dated May 5, 2016; 08 pages.

International Application No. PCT/US2016/060847; International Preliminary Report on Patentability, dated May 17, 2018; 10 pages.

(56) References Cited

OTHER PUBLICATIONS

International Application No. PCT/US2016/060847; International Search Report and Written Opinion of the International Search Authority, dated Jan. 24, 2017; 14 pages.
International Application No. PCT/US2017/047208; International Search Report and Written Opinion of the International Search Authority, dated Oct. 30, 2017; 06 pages.
Kreipe H et al., "Clonal granulocytes and bone marrow cells in the cellular phase of agnogenic myeloid metaplasia", Blood. Oct. 1, 1991;78(7):1814-1847.
Leoni F. et al., "The histone deacetylase inhibitor ITF2357 reduces production of pro-inflammatory cytokines in vitro and systemic inflammation in vivo", Mol Med. Jan.-Dec. 2005;11(1-12):1-15.
Lerchner A et al., Macrocyclic BACE-1 inhibitors acutely reduce Abeta in brain after po application, Bioorg Med Chem Lett. Jan. 15, 2010; 20(2):603-607.
Lizcano F et al, Epigenetic control and cancer: the potential of histone demethylases as therapeutic targets, Pharmaceuticals (Basel). Sep. 12, 2012; 5(9):963-90.
Mesa RA et al., "The Myelofibrosis Symptom Assessment Form (MFSAF): an evidence-based brief inventory to measure quality of life and symptomatic response to treatment in myelofibrosis", Leuk Res. Sep. 2009; 33(9): pp. 1199-1203.
Morissette, S. et al., High-Throughput Crystallization: Polymorphs, Salts, Co-Crystals and Solvates of Pharmaceutical Solids, Adv Drug Delivery Rev, 56, 2004, 275-300.
Ogasawara, D et al., Synthesis and biological activity of optically active NCL-1, a lysine-specific demethylase 1 selective inhibitor, Bioorg Med Chem. Jun. 15, 2011; 19(12):3702-8. EpubDec. 22, 2010.
Ogasawara, et al., Lysine-specific demethylase 1-selective inactivators: Protein-targeted drug delivery mechanism, Angewandte Chemie, International Edition, 52(33), 8620-8624 (2013).
Rouhi, Chem & Eng News, Science and Technology—The Right Stuff, 81(8), 2003, 32-35.
Sareddy GR et al., KDM1 is a novel therapeutic target for the treatment of gliomas, Oncotarget. Jan. 2013; 4(1):18-28.
Schnittger S et al., "FLT3 length mutations as marker for follow-up studies in acute myeloid leukaemia", Acta Haematol., 2004; 112(1-2): pp. 68-78.
Tefferi A et al., "Splenectomy in myelofibrosis with myeloid metaplasia: a single-institution experience with 223 patients", Blood. Apr. 1, 2000;95(7): pp. 2226-2233.
U.S. Appl. No. 14/910,423; Applicant Intiated Interview Summary dated Jun. 12, 2017; 02 pages.
U.S. Appl. No. 14/910,423; Final Office Action dated Apr. 18, 2017; 07 pages.
U.S. Appl. No. 14/910,423; Non-Final Office Action dated Sep. 16, 2016; 13 pages.
U.S. Appl. No. 14/910,423; Notice of Allowance dated Jun. 12, 2017; 04 pages.
U.S. Appl. No. 14/910,423; Notice of Allowance dated May 2, 2017; 07 pages.
U.S. Appl. No. 15/043,121; Examiner Intiated Interview Summary dated Jan. 12, 2018; 01 page.
U.S. Appl. No. 15/043,121; Examiner Intiated Interview Summary dated Sep. 18, 2017; 01 page.
U.S. Appl. No. 15/043,121; Non-Final Office Action dated May 19, 2017; 12 pages.
U.S. Appl. No. 15/043,121; Notice of Allowance dated Jan. 12, 2018; 07 pages.
U.S. Appl. No. 15/043,121; Notice of Allowance dated Sep. 18, 2017; 09 pages.
U.S. Appl. No. 15/773,911; U.S. Patent Application as filed dated May 4, 2018; 125 pages.
U.S. Appl. No. 15/952,073; U.S. Patent Application as filed dated Apr. 12, 2018; 296 pages.
Wang J et al., Novel Histone Demethylase LSD1 Inhibitors Selectively Target Cancer Cells with Pluripotent Stem Cell Properties, (Epub Oct. 5, 2011), 71 (23):7238-49.
WO 2010143582 A1, Dec. 16, 2016 (Machine English translation).
Wolff, Manfred E., Burger's Medicinal Chemistry and Drug Discovery, Fifth Ed. vol. 1: Principles and Practice, John Wiley & Sons, 1995, 975-977.
Zeppa P et al., "Fine-needle aspiration biopsy and flow cytometry immunophenotyping of lymphoid and myeloproliferative disorders of the spleen", Cancer, Apr. 25, 203; 99(2): pp. 118-127.
International Application No. PCT/US17/47192; International Search Report and Written Opinion of the International Search Authority, dated Jan. 9, 2018; 9 pages.
U.S. Appl. No. 15/667,166; Non-Final Office Action dated Aug. 23, 2018; 9 pages.

* cited by examiner

KDM1A INHIBITORS FOR THE TREATMENT OF DISEASE

This application claims the benefit of priority of U.S. Provisional Application No. 62/115,474, filed Feb. 12, 2015, the disclosure of which is hereby incorporated by reference as if written herein in its entirety.

The present disclosure relates to new compounds and compositions and their application as pharmaceuticals for the treatment of diseases.

Inhibiting the enzyme KDM1A (also known as lysine-specific demethylase 1, LSD1, Flavin-containing Amine Oxidase Domain-Containing Protein, AOF2, BRAF35-HDAC Complex Protein BHC110, FAD-Binding Protein BRAF35-HDAC Complex), may alter gene expression in cells sufficient to restore their proper physiologic function or that of the tissue, organ or the patient as a whole. This may be achieved either by enhancing transcription of a gene or genes that are pathologically silenced, e.g., as is the case in some cancer cells and heritable diseases, or decreasing transcription of a gene or genes participating in the pathological state. As such, inhibiting KDM1A would be useful for the treatment of diseases such as cancer and heritable diseases such as Wilson disease, cardiomyopathies, and hemoglobinopathies.

Gene expression is regulated through the recruitment of the RNA polymerase II transcription apparatus to the DNA template. The probability of this large multi-protein complex arriving near or at the start of DNA transcription and progressing through the entire coding region of a gene is determined in part by specific DNA sequences called promoters and enhancers, modifications of DNA sequence in the vicinity of the start of transcription, proteins bound to DNA and the topology of the DNA template itself. Factors enhancing the probability of RNA synthesis of protein-coding genes are known as transcription factors some of which participate in the transcription of all protein-coding genes and some of which are specific for the transcription of individual genes.

One major mechanism of transcription control consists of limiting the physical accessibility of the transcriptional regulatory regions to proteins that can activate or complete transcription; proteins bound to promoter or enhancer DNA sequences can occlude activating factors from binding to these DNA sequences resulting in fewer transcription initiations or extension of the activated progressing RNA polymerase complex. Likewise, topological constraints that do not allow the template DNA to unwind sufficiently to permit the steady progression of RNA polymerase on the template also serve to limit transcription rates.

The most important general factors influencing RNA synthesis using a DNA template in vivo are modifications of histones proteins that control among other factors the topology of the DNA template for transcription and its accessibility by the RNA polymerase complex. A small family of histone proteins—H2A, H2B, H3 and H4—combines to create a scaffold called the histone octamer upon which DNA is spatially and topologically organized into a regular repetitive structure called the nucleosome along the length of DNA. The conglomerate of histones, other proteins, various RNAs and DNA is called chromatin. Both DNA and histones are chemically modified in such a way as to attract and bind or repel other proteins with the effect of enhancing or repressing transcription.

The modification of DNA and associated RNAs and proteins that influence the regulation of transcription and replication that does not involve substitution of the canonical DNA bases is termed epigenetic. These epigenetic influences involve reversible chemical modifications of the four DNA bases themselves or post-translational chemical changes to the chromatin proteins and RNDs that associate with DNA. These epigenetic processes can play a pivotal role in activating or silencing the expression of a gene; in addition, the epigenetic modifications can be maintained for the life of an organism or can be dynamically modified in response to specific biochemical signals that originate either internally within the cell or extracellularly. These chromatin alterations can happen quickly or be very stable, e.g., during the hormonal induction of gene expression, chromatin structure at a specific locus can change radically within seconds to permit maximal transcription or chromatin structure can be modified to fully suppress gene expression, a state of chromatin which can be stably maintained over multiple cell divisions and even transgenerationally.

The methylation of cytosine at the 5' position is a common DNA base modification that is in turn recognized by a class of proteins most often associated with transcriptional repression. Similarly, histone proteins are chemically modified but with a wider variety of chemical adducts each of which either alone or in combination enhances or represses transcription of nearby genes. These histone modifications include, among others methylation, acetylation, sumoylation, phosphorylation, ubiquitylation, and myristoylation are recognized by other chromatin-associated proteins that in turn influence transcription rates and DNA replication. The dynamic state of gene expression and the associated chromatin states imply that histone modifications are not permanent but instead are added and removed according to the needs of the cell for specific gene products at specific times during ontogeny, adult life and the changing influences of the environment. Indeed, the specific chemical modifications of histones are each made by classes of enzymes acting at specific sites. These histone-modifying enzymes are in turn subject to tight regulation. These enzymes can potentially be targeted by compounds that inhibit their activity with the consequence of altering gene expression in a therapeutic manner.

Changes in the state of histone methylation are now known to play critical roles in normal regulation of the cell cycle and growth, the response to DNA damage and stress, and pre-natal development including differentiation. Pathological states such as cancer are associated with altered patterns of histone modifications and dysregulated histone-modifying proteins including chromatin-modifying enzymes. The need to closely regulate histone modifications is evidenced by the association of histone methylation status with human morbidity including ageing.

Histone methylation can occur on any of the three basic amino acid residues—lysine (K), arginine (R), and histidine (H). Methylation of histone H3 on lysines at positions 4 (H3K4), 9 (H3K9), 27 (H3K27), 36 (H3K36) and 79 (H3K79) are among the best studied of histone modifications that influence gene expression. Lysine tri-methylation (Kme3) on histone 3 (H3) at position 4 (H3K4me3) is a histone mark generally associated with activation of gene expression while H3K9me1 or H3K27me3 are associated with the repression of gene transcription. H3K4me1 is associated with DNA enhancers of gene transcription while H3K4me3 is associated with gene promoter activity. Likewise, loss of the methyl group at H3K4 is associated with repression of gene expression. Thus, the addition and removal of methyl groups at H3K4 constitutes a gene transcription switch. It is also evident that lysine can be modified with a mono-, di- or tri-methyl groups, each modification having a different biological effect through the attraction of different proteins recognizing those specific methylation modifications at that site.

A critical aspect of the regulation of the state of histone methylation is the recruitment of methyltransferases and demethylases to specific genetic loci. DNA sequence-specific binding proteins including transcription factors are one class of proteins responsible for this recruitment through the assemblage of protein complexes that bind these methyl-transferring enzymes. A well-studied example is the *Drosophila melanogaster* trithrorax group (TrxG) response elements (TREs) which recruit the H3K4 methyltransferase, TRX, to specific genes via transcription factors that recognize the TRE DNA sequence.

The histone methylation marks are recognized by methyl-binding domains in a diverse group of proteins; these domains include PHD fingers, WD40 and ankyrin repeats, CW and PWWP domains, and the Royal superfamily of proteins. These proteins, in turn, determine which additional activities are recruited into chromatin sites and ultimately the state of transcription at a given locus. Indeed, depending on which methyl-recognition protein binds the marked histone, the same methyl-lysine modification can have opposing effects on transcription. H3K4me2 and H3K4me3 are associated with transcriptional activation, but when bound by the PHD-domain-containing co-repressor protein Inhibitor of Growth family member 2 (ING2), an associated histone deacetylase complex is stabilized repressing gene expression. Thus, these effector proteins recognizing the methyl-lysine histone modifications significantly influence the level of transcriptional activity.

The ability to alter gene expression selectively by modifying the state of chromatin allows a novel therapeutic strategy to induce or de-repress the expression of genes that can provide a benefit, especially for genes whose expression has been suppressed by pathological mechanism as in the case of some cancers or suppressed by physiologic mechanism but who de-repression can phenotypically suppress mutations in paralogous genes with complementary function.

Many genes within a genome are members of gene families as a consequence of gene duplication. These genes are termed paralogs of one another. Following gene duplication, patterns of expression of two genes will evolve in a distinct manner in part to control the effects of gene dosage. Following gene duplication, random genetic drift arising from naturally occurring mutations and the subsequent selection of nucleotide sequence is commonly observed first in non-coding regions of duplicated genes, often in transcriptional regulatory regions. DNA changes in regulatory sequences can influence any or all aspects of gene expression: the magnitude of expression, its developmental timing, induction by stimuli outside the cell including hormonal or metabolic signals, and the cell type in which expression is restricted. In instances in which the duplication is recent in evolutionary time or where natural selection has maintained a high degree of protein-coding sequence similarity, the gene product of one paralog, gene A, can complement the pathological loss or silencing of the other paralog, gene B, if expression of gene A is not limiting in the same cell.

Altering patterns of gene expression may offer profound therapeutic benefits for genetic conditions in which enhanced expression of a paralogous gene "rescues" a phenotype caused by a mutation in a paralog. This might be called autologous gene complementation. In the case of Wilson disease caused by mutations in ATP7B, enhanced expression by pharmacologic induction of ATP7A, a closely related copper transporter protein, might rescue mutations in ATP7B, another copper transporter. The basic function of each copper transporter protein has been preserved but following the duplication of the common ancestral gene, the expression of these two genes has been separated spatially, one confined to intestinal enterocytes, the other to hepatocytes. This is one of many examples of paralogous gene in which one gene can complement the loss of the second if appropriately expressed in the same cell or tissue.

A notable example of a paralogous gene family is the well-studied alpha and beta family of globin genes coding for the alpha and beta subunits of hemoglobin. Five beta-like genes each arising by gene duplication are arrayed next to each other on chromosome 16 with each gene being transcribed in a temporally-specific manner throughout the 9 months of human embryonic and fetal development. The five beta-like globin proteins share a high degree of protein sequence similarity, so much so that genetic mutations inactivating the adult beta globin gene can be clinically silent if expression of any one of the other 4 subunit members of the beta-like globin family is adequate. Activation of expression and subsequent transcriptional silencing of each specific embryonic and fetal beta-like globin gene is regulated in part by epigenetic mechanisms. The rescue of mutations in the beta globin gene, mutations which are responsible for diseases such as thalassemia major or sickle cell anemia, by transcriptional induction of one or more of the other beta-like genes through the pharmacologic manipulation of epigenetic silencing would be clinically beneficial. Autologous activation with a pharmacologic agent of a functionally complementary paralog of a mutated or pathologically silenced gene may be a more successful therapeutic strategy than replacing or repairing the mutated gene with a wild-type (normal) copy.

Interest in influencing the activity of histone modifications for therapeutic effect derive from observations that the expression of specific genes under epigenetic control could be altered by altering epigenetic marks such as methylation. In the case of cancer, loss of specific histone methylation marks concomitant with overexpression of histone demethylases is associated with the recurrence of those cancers with attendant poorer outcomes. These studies suggest that specific tumor suppressor genes are silenced by loss of methylation modifications that in turn enhance the survival and growth potential of neoplastic cells. This had led to the proposition that inhibition of histone demethylase activity might have therapeutic value.

KDM1A (also known as Lysine-Specific Demethylase 1 (LSD1) or AOF2 or BHC110) was the first enzyme with specific lysine demethylase activity to be described demonstrating unequivocally that histone modifications are reversible rather than permanent. Among its demethylase substrates, KDM1A is a histone H3 lysine demethylase that catalyzes the oxidative demethylation of H3K4me1 or me2 and H3K9me1 or me2 but not the substrate H3K4me3. The enzyme also demethylates non-histone proteins such as p53 and Gfi1. KDM1A contains an amine oxidase domain that demethylates H3Kme substrate in a flavin adenine dinucleotide (FAD)-dependent manner similar to other monoamine (MAO) and polyamine oxidase inhibitors. Indeed, nonspecific inhibitors of MAO enzymes can inhibit the demethylase activity of KDM1A KDM1A is over-expressed in many human cancers including Wilm's tumor, small-cell lung, bladder, prostate, breast, head & neck, colon, and ovarian cancer and associated with more frequent relapses. KDM1A is required for transcriptional regulation mediated by the androgen receptor in prostate cancer, the estrogen receptor in breast carcinomas, and the TLX receptor in neuroblastoma. Knockdown of KDM1A expression decreases proliferation of cancer cells. KDM1A is also overexpressed in cancer cells that are nuclear hormone receptor-independent including ER-negative breast. Potent, selective small molecule inhibitors of KDM1A should be useful for treatment of these and other cancers in which KDM1A activity is overabundant.

The structure and state of chromatin can also influence the ability of a pathogenic virus to insert into host DNA, undergo transcription and replicate. Infection by the alpha herpes viruses herpes simplex virus (HSV) and varicella-zoster virus (VSV) effect the remodeling of chromatin after infection of host cells to counter the rapid deposition of nucleosomes containing histones with transcriptional repressive marks by employing virus-encoded transcription factors to recruit the host HCF-1 co-activator complex that contains KDM1A and the histone H3K4 methyltransferases Set1 or MLL family members. It has been demonstrated that inhibition of KDM1A in cells infected with HSV1 inhibits HSV IE gene expression, suppresses lytic infection and reduces viral loads. Similarly, inhibiting KDM1A causes a decrease in the expression of the immediate early genes in cells infected with human cytomegalovirus and adenovirus suggesting a broader role for KDM1A in viral pathogenesis.

The influence KDM1A activity has on the transcription of specific genes is dependent on recruitment of KDM1A to a specific gene promoter region via DNA binding proteins. In the case of androgen-dependent gene expression, KDM1A associates with the androgen steroid receptor which specifically targets DNA binding sites in the promoters of androgen-responsive genes. Thus, proteins that bind KDM1A determine where along the chromosome the demethylase activity is targeted. Many proteins have been reported to interact with KDM1A including the CoREST, CtBP, NuRD, BRAF35 complexes, DNMT1, MTA1/2, Mi2beta, RbAp46/48, HDAC1, 2, and 3, TIF1beta, Blimp-1, ZNF217 and ZNF198, a subset of which form larger and in some cases complexes that mutually exclude one another. The KDM1A/CoREST complex which may also include DNMT1 and NuRD among other factors is particularly important for the repression of expression of specific genes.

KDM1A is recruited to the promoter region of genes through site-specific transcription factors. Such factors include among others the androgen receptor, the estrogen receptor alpha, Snail1, Slug, HIV Tat, ZEB1, RBP-J, PIT1, REST, NR2C1, NR2C2 and isoforms of Gfi1b. These transcription factors can recruit KDM1A to participate in activation of gene expression or silencing of gene expression depending on the cell type and the specific transcription factors.

Many of the enzyme activities that regulate the state of chromatin are influenced allosterically or require as co-factors metabolic intermediates, mediators or end-products of cell metabolism. These intermolecular relationships between gene expression and metabolism provide cells with signaling pathways connecting the external and internal cellular environment including nutrients with mechanisms modulating gene expression. This cellular sensing can alter both short and long term adjustments to gene expression patterns constituting an epigenetic memory of historical metabolic states and environmental conditions. For example, beta-hydroxybutyrate, a product of long chain fatty acid metabolism and a major source of energy for mammals during starvation or prolonged exertion, inhibits class I histone deacetylases (HDAC) but not class 2b HDAC. Thus the effects of starvation and nutrient loss can be epigenetically coded and preserved. Acetyl-coenzyme A, nicotinamide adenine dinucleotide (NAD) and alpha-ketoglutarate also influence histone methylation and acetylation states.

Flavin adenine dinucleotide (FAD) is a required co-factor for KDM1A. FAD, in conjunction with NAD and NADP act as cellular redox sensors. KDM1A temporarily converts FAD to FADH after which an electron acceptor, likely $O_2$ and others, completes the catalytic cycle by regenerating FAD and $H_2O_2$. Thus, the cellular redox state influences KDM1A activity both by its ability to oxidize FADH and other electron acceptors. In a general sense, chromatin states, hence gene expression, can be altered by the variable concentrations of metabolic intermediates and in the specific case of KDM1A that activity is entirely dependent on FAD whose concentration fluctuates as a function of the energetic economy of the cell. In addition, it has been shown that inhibition of KDM1A can lower serum glucose, reduced hepatic glycogen, and is a powerful insulin secretogogue. Pharmaceutical manipulation of KDM1A activity may thus prove useful for the treatment of diseases that represent pathological aberrations of the energy status of the cell including metabolic syndrome, dyslipidemias, diabetes, obesity, anorexia, failure to thrive, cachexia, lipodystrophies, and steatohepatitis.

The steroid hormones estradiol and testosterone and related compound play a key role in both normal development and in pathological states such as breast and prostate cancer in which tumor cell growth is dependent on hormonal signaling. The biological effects of steroid hormones are mediated by structurally and functionally distinct ligand-binding receptors that function as a transcription factor recruited to a specific DNA binding site. The ligand-bound steroid receptors act as the principal transcriptional regulator of hormone effects. Transcriptional activation of gene expression for all steroid-dependent hormones is dependent on chromatin structure and the presence of co-factors. The estrogen receptor employs, for example, the co-factors SRC1, SRC2, AIB1, PELP1, CBP, p300, PCAF, CARM1, PRMT1 and co-repressors such as NCoR, SMRT and MTA1. The transcriptional response to hormone stimulation is dependent on the interaction of these co-factors and repressors as well as the state of chromatin, especially modification of histones by histone-modifying enzymes associated with the co-regulators. Both estrogenic and androgenic hormone stimulation induces several histone modifications at the promoters of target genes that alter the acetylation, phosphorylation and methylation state of local histones. To affect the maximal rate of transcription for a hormone-responsive gene, KDM1A activity is required. Thus, KDMA1 should prove useful as a therapeutic target of pharmaceuticals in blunting or ablating the hormone-dependence of tumor cells. This same therapeutic logic applies to other ligand-dependent transcription factors whose transcriptional activation is partly or wholly dependent on KDM1A activity to alter chromatin states sufficiently to facilitate transcription—examples of these would include the vitamin D, retinoid and lipid-activated receptors.

Numerous therapeutic agents have been identified that have the effect of altering gene expression acting either directly on proteins, generally enzymes, that alter chromatin states or indirectly. Though the precise mechanisms of their action have not all been fully elucidated, those mechanism can be inferred from our understanding of the protein complexes that participate in the activation of specific gene expression. These agents include 5'-azacytadine and 5'-aza-2' deoxycytidine (decitabine) which inhibit DNMT1 or other DNA methyltransferases known to be present and active at promoter sites of silenced genes such as gamma globin promoter; vorinostat and panobinostat or other inhibitors of histone deacetylase (HDAC) enzymes; hydroxyurea (HU), valproate and sodium butyrate and its analogues each of which may interfere with the activity of orphan nuclear receptors. All of these agents enjoy some clinical use principally in the management of neoplastic disease. Though some clinical utility of these agents for other disease states has been demonstrated, these agents have not been widely adopted because of their modest therapeutic effects and their toxicity.

The use of agents that inhibit any enzymatic activity resident in the protein complex bound to gene promoter has the potential to disrupt the repression of gamma globin gene expression and result in increased levels of fetal hemoglobin also known as hemoglobin F (HbF). Such targets include any of the interfaces of the specific protein-protein contacts, for example, the NuRD complex and KDM1A; the DNA binding recognition domains of, for example, NR2C1 and NR2C2; the ligand binding domains of, for example, NR2C1 and NR2C2; the enzyme activities such as lysine demethylase, for example, KDM1A; histone deacetylases (HDAC), for example HDAC1, 2, or 3; DNA methyltransferases, for example, DNMT1.

There remains a need for compositions and methods for altering gene expression in cells and tissues sufficient to restore the cell or tissue to normal physiologic function including, e.g., appropriate apoptosis in the case of cancer, or to alter the pathological phenotype of the cell, tissue, organ or organism by inducing the expression of one or more genes sufficiently to suppress the pathological state.

Accordingly, the inventors herein disclose new compounds, compositions and methods for treating diseases associated with KDM1A activity.

DETAILED DESCRIPTION

Figure 1:
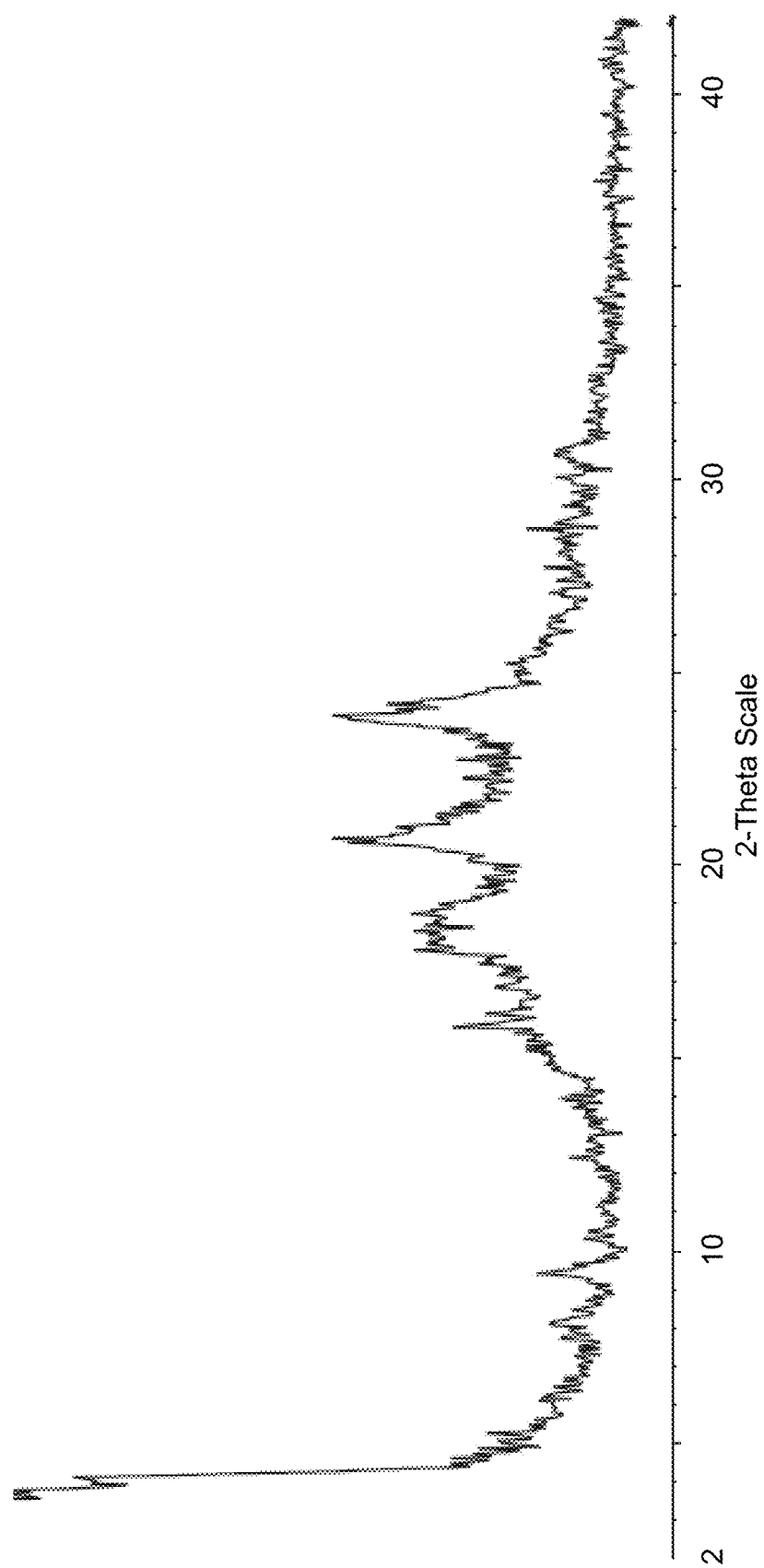
FIG. 1. shows an XRPD diffractogram of amorphous Example 1 bis-tosylate.
Figure 2:
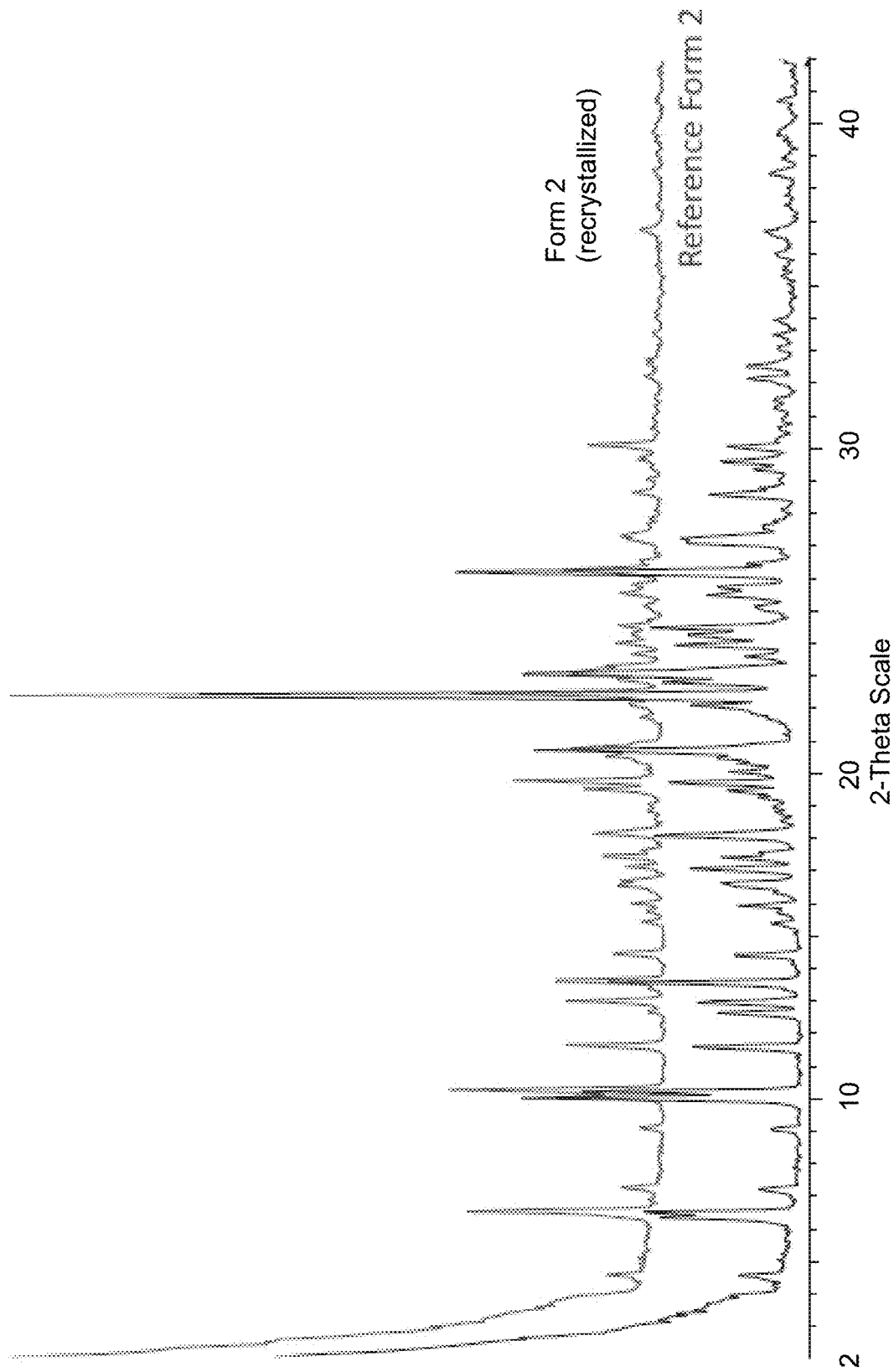
FIG. 2 shows XRPD diffractograms of Example 1 bis-tosylate Form 2; the upper was recrystallized from semicrystalline solid.
Figure 3:
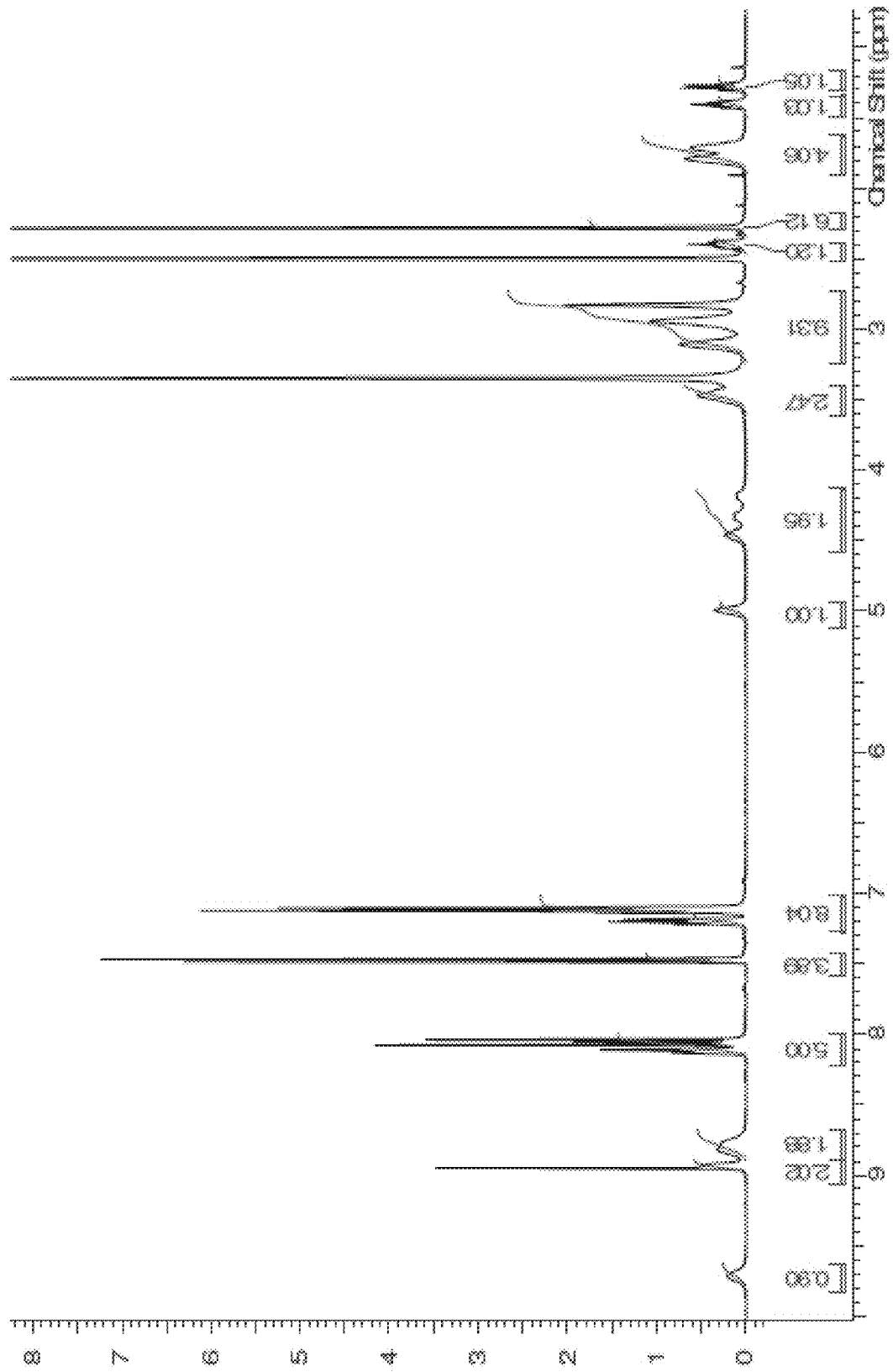
FIG. 3 shows the 1H NMR spectrum of Example 1 bis-tosylate Form 2 recrystallized from semicrystalline solid.
Figure 4:
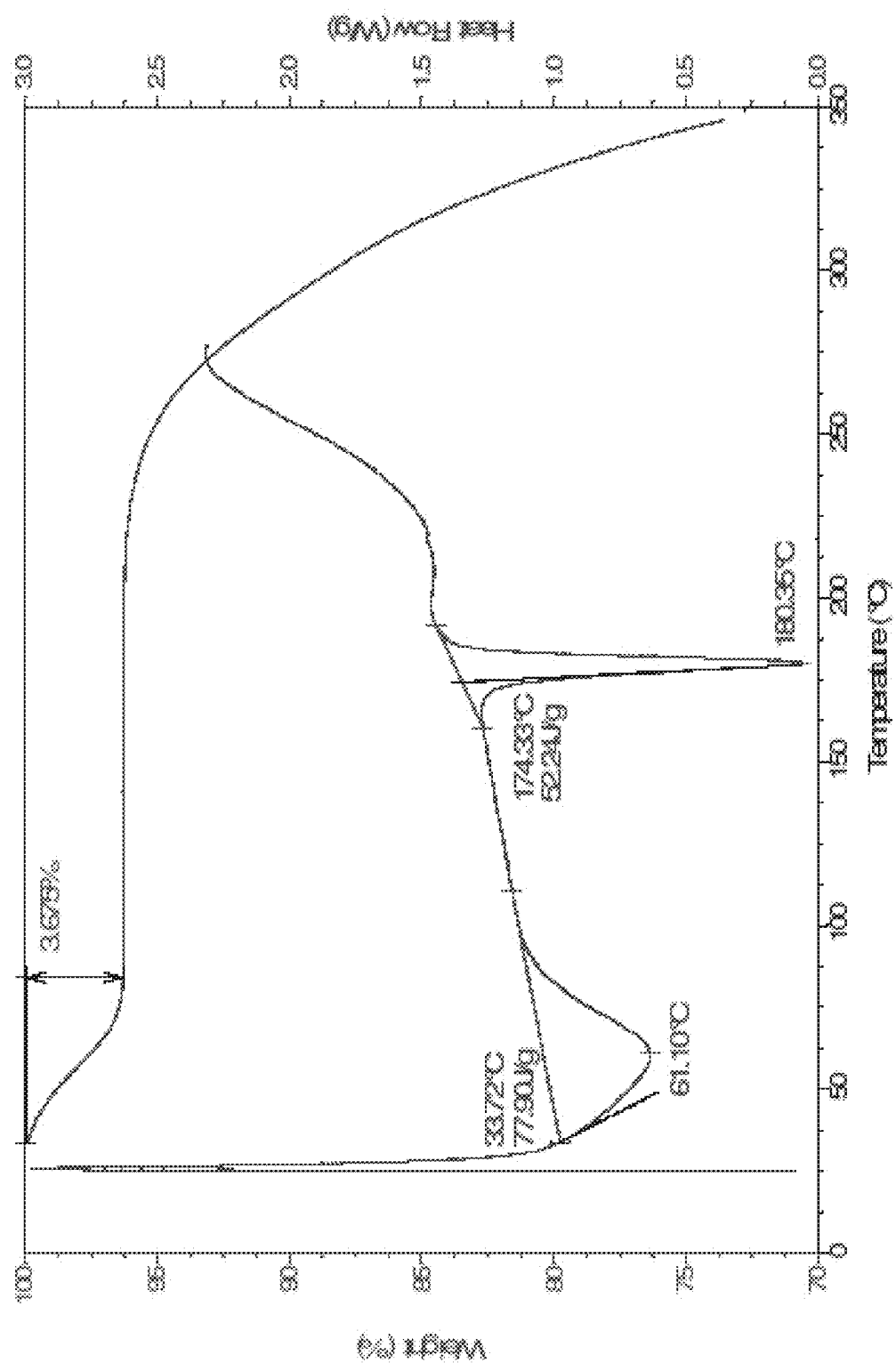
FIG. 4 shows the DCS and TGA of Example 1 bis-tosylate Form 2 recrystallized from semicrystalline solid.
Figure 5:
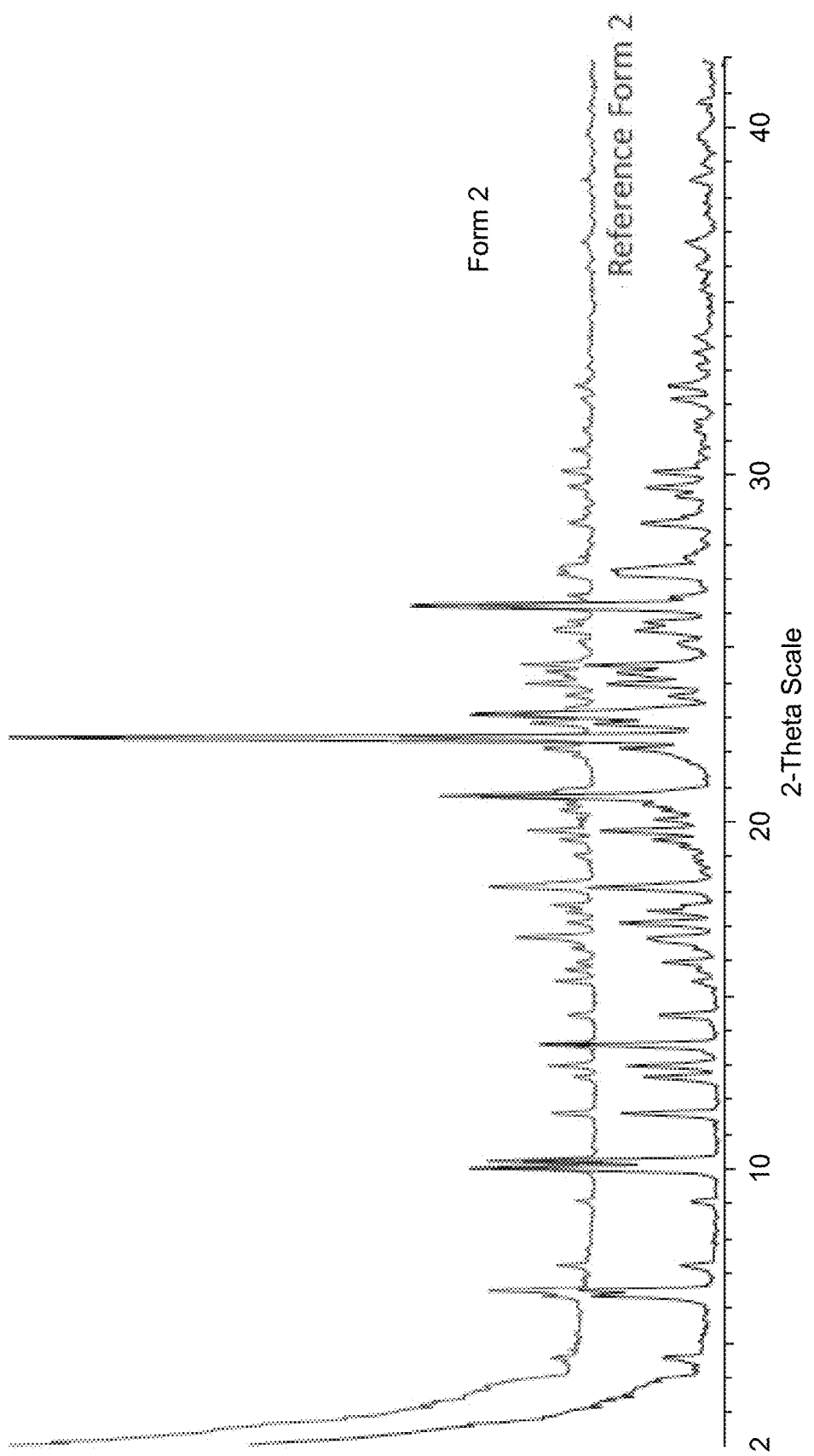
FIG. 5 shows XRPD diffractograms of Example 1 bis-tosylate Form 2; the upper was synthesized in ACN.
Figure 6:
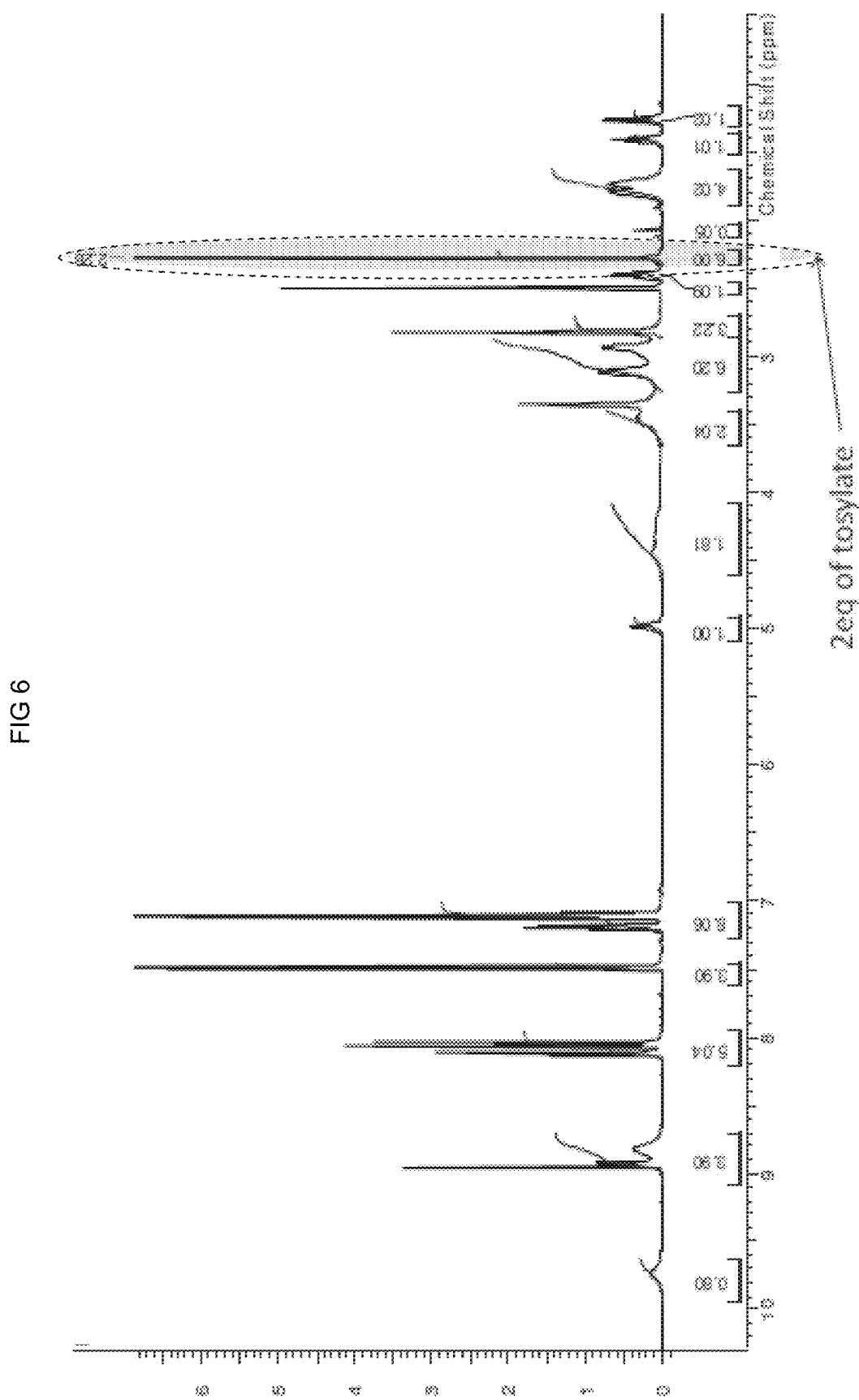
FIG. 6 shows the 1H NMR spectrum of Example 1 bis-tosylate Form 2 synthesized in ACN.
Figure 7:
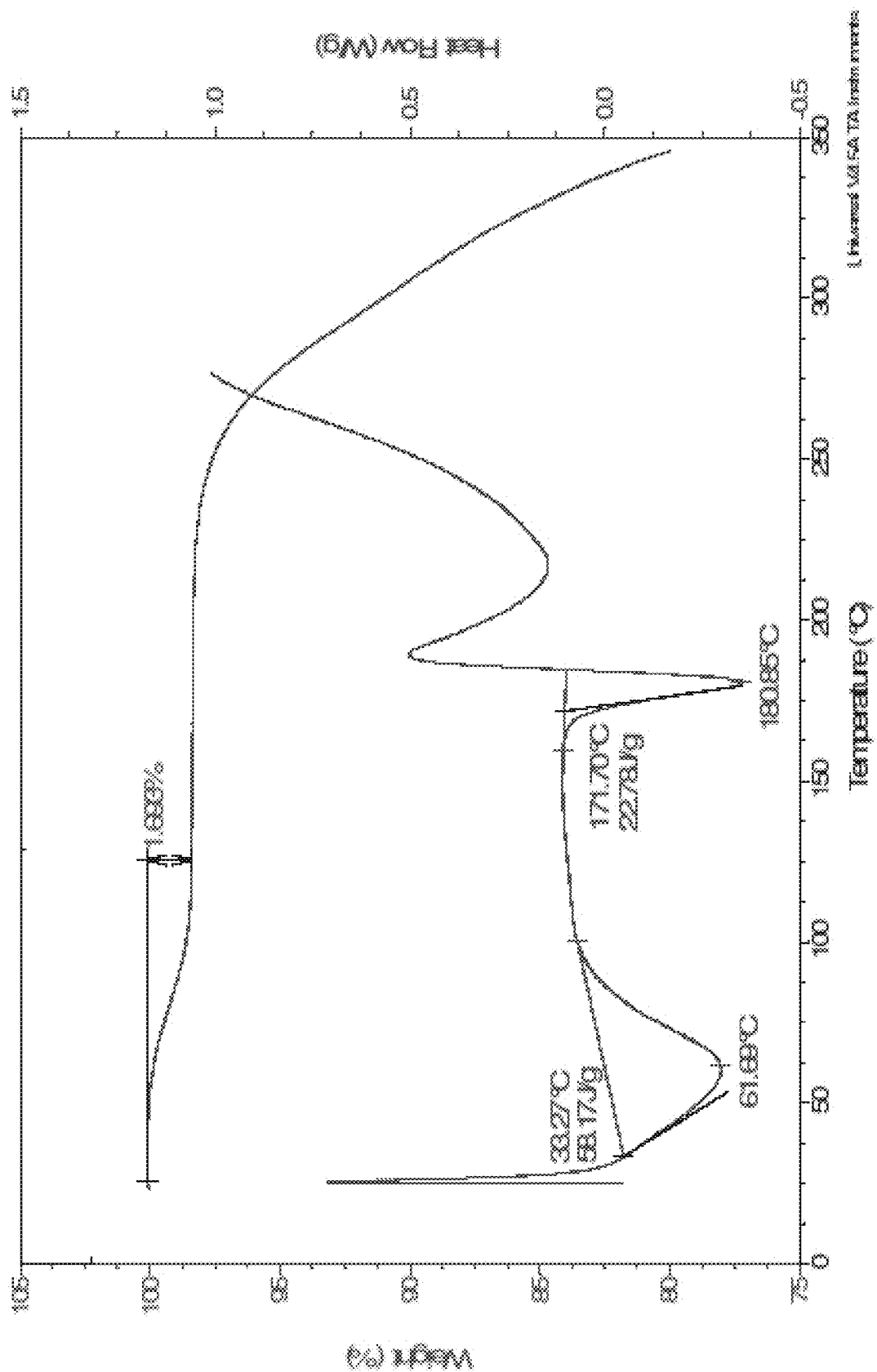
FIG. 7 shows the DCS and TGA of Example 1 bis-tosylate Form 2 synthesized in ACN.
Figure 8:
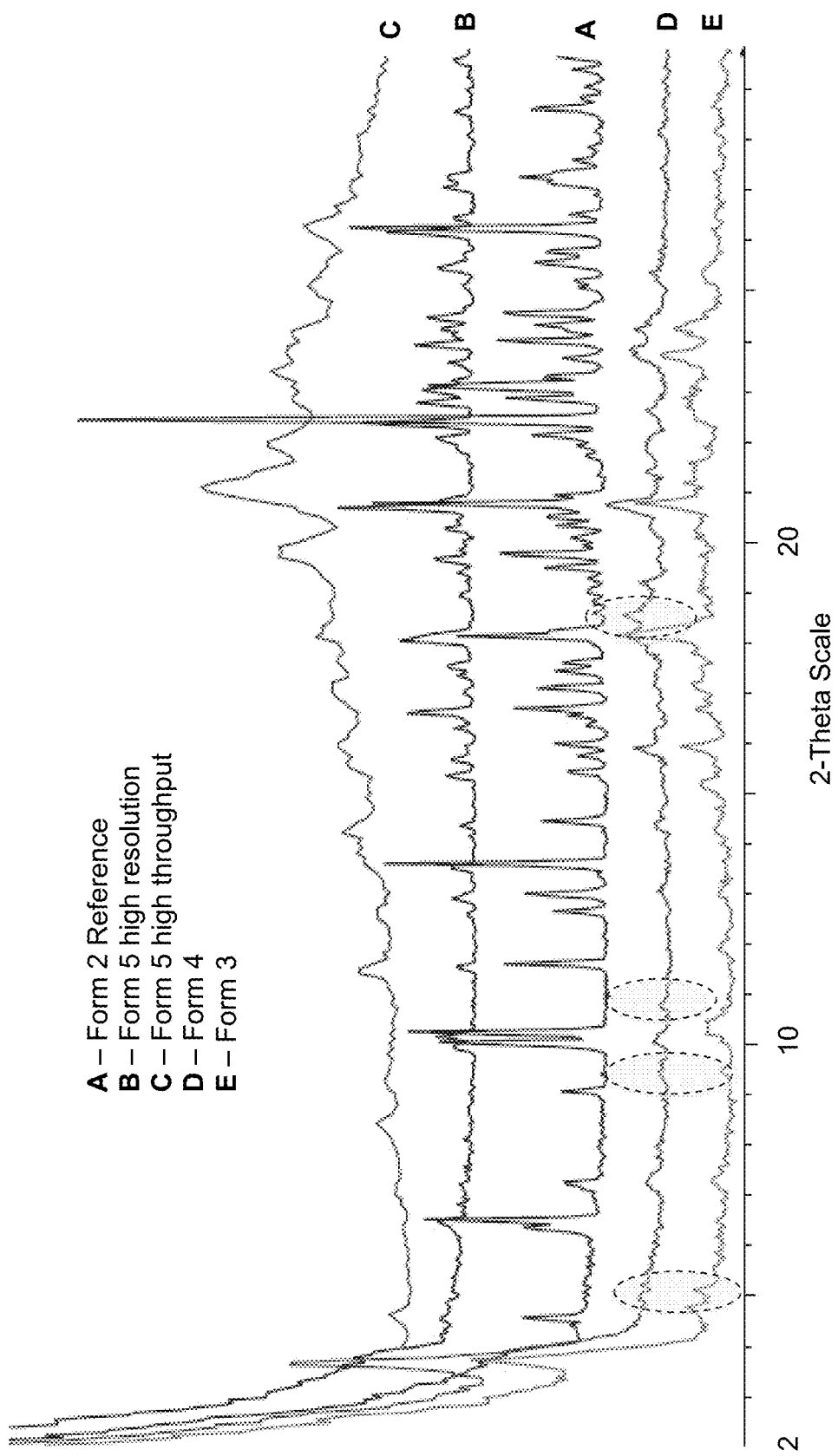
FIG. 8. shows XRPD diffractograms of Example 1 bis-tosylate forms 2 (A), 3 (E), 4 (D), and 5 (B and C, from high-resolution and high-throughput scans, respectively); extra peaks compared to Form 2, noted with dashed lines, prompted additional characterization of Forms 3, 4, and 5.
Figure 9:
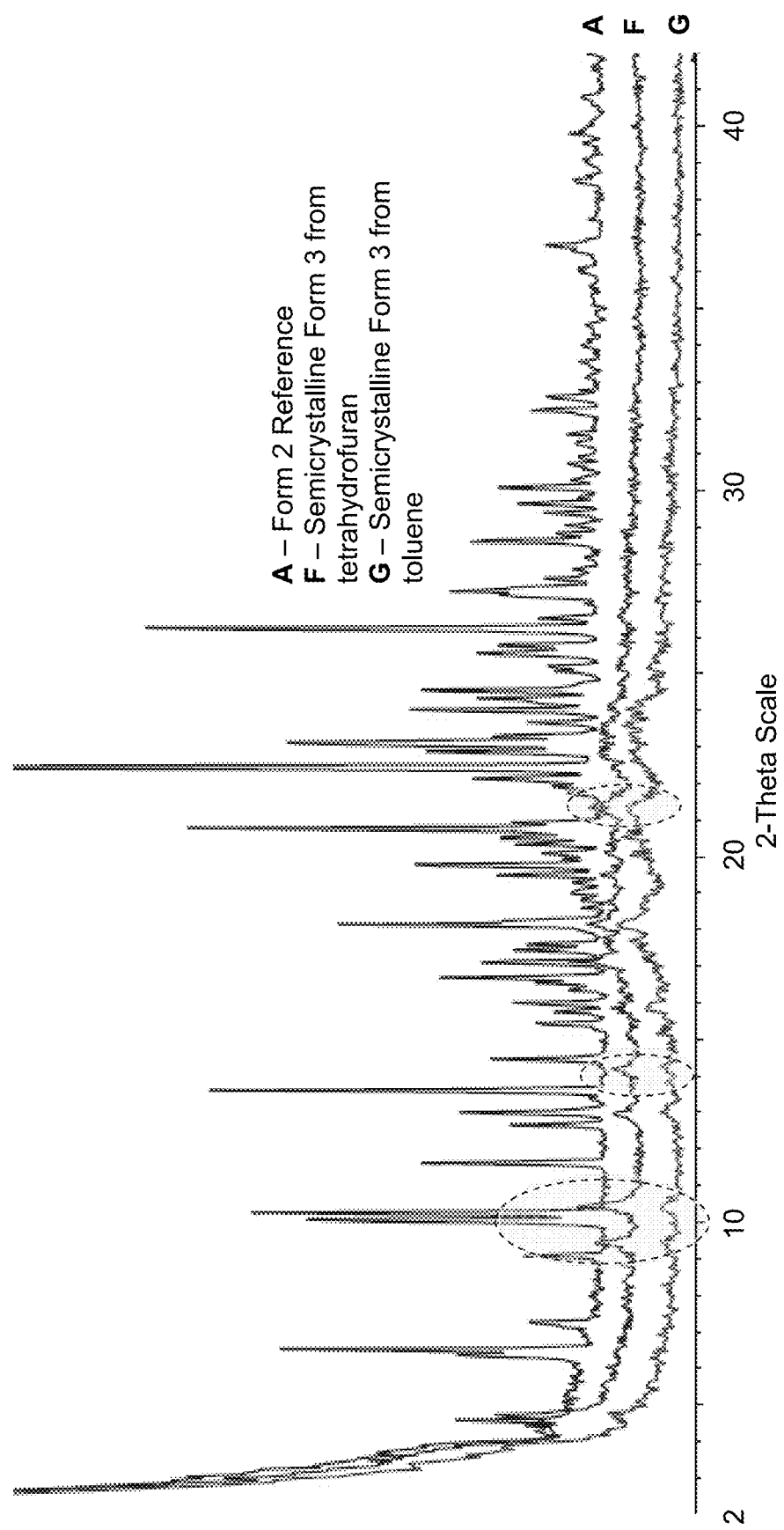
FIG. 9. shows XRPD diffractograms of Example 1 bis-tosylate form 2 and semicrystalline form 3 from tetrahydrofuran (F) and toluene (G); extra peaks compared to Form 2, noted with dashed lines, prompted additional characterization.
Figure 10:
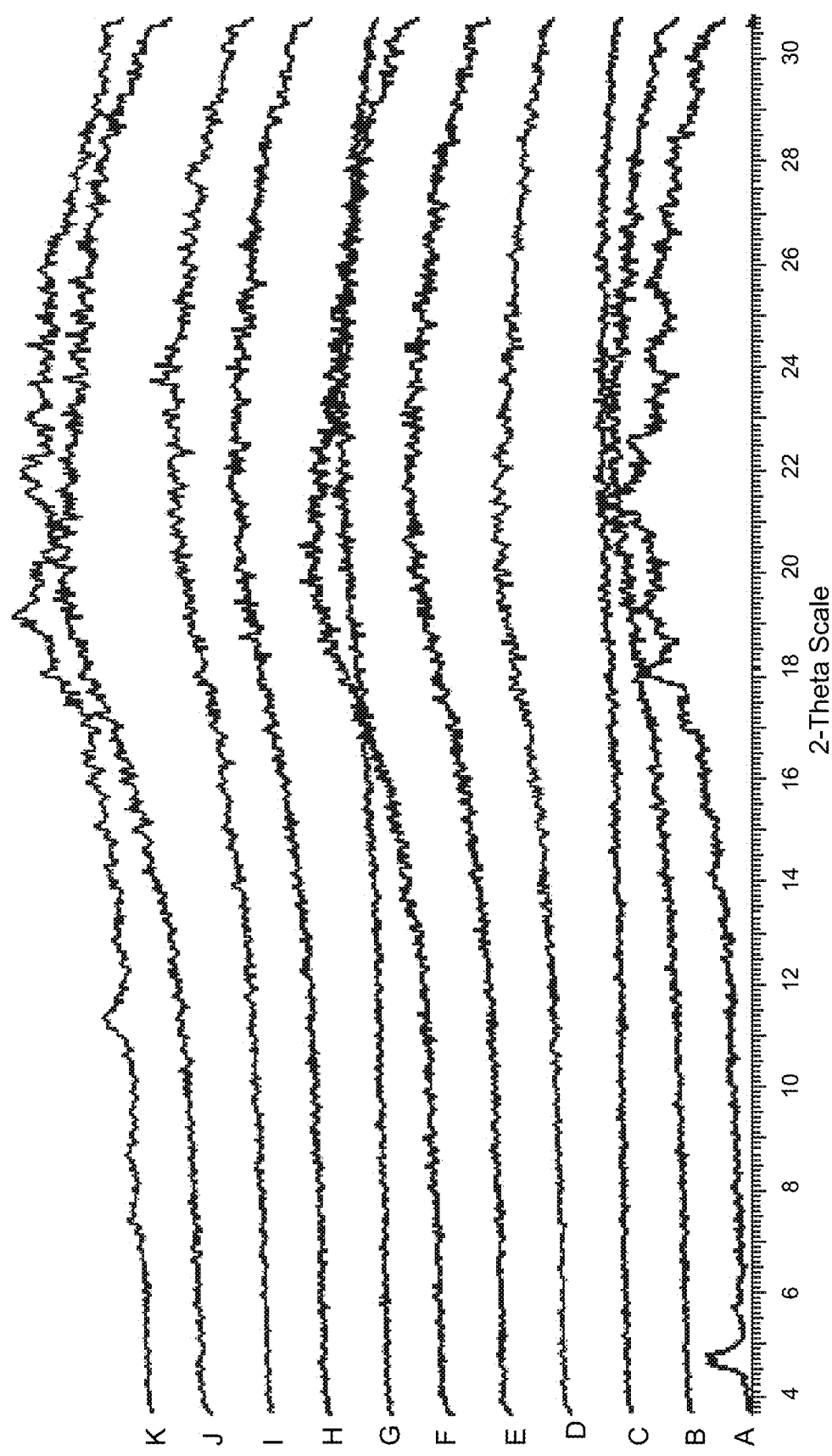
FIG. 10 shows XRPD diffractograms of solid material recovered in salt experiments in various solvents. A is a weakly crystalline sulfate; B is amorphous phosphate; C is amorphous tartrate; D is amorphous sulfate; E is amorphous phosphate; F is amorphous tartrate; G is amorphous fumarate; H is amorphous sulfate; I is amorphous phosphate; J is amorphous tartrate; and K is weakly crystalline fumarate.
Figure 11:
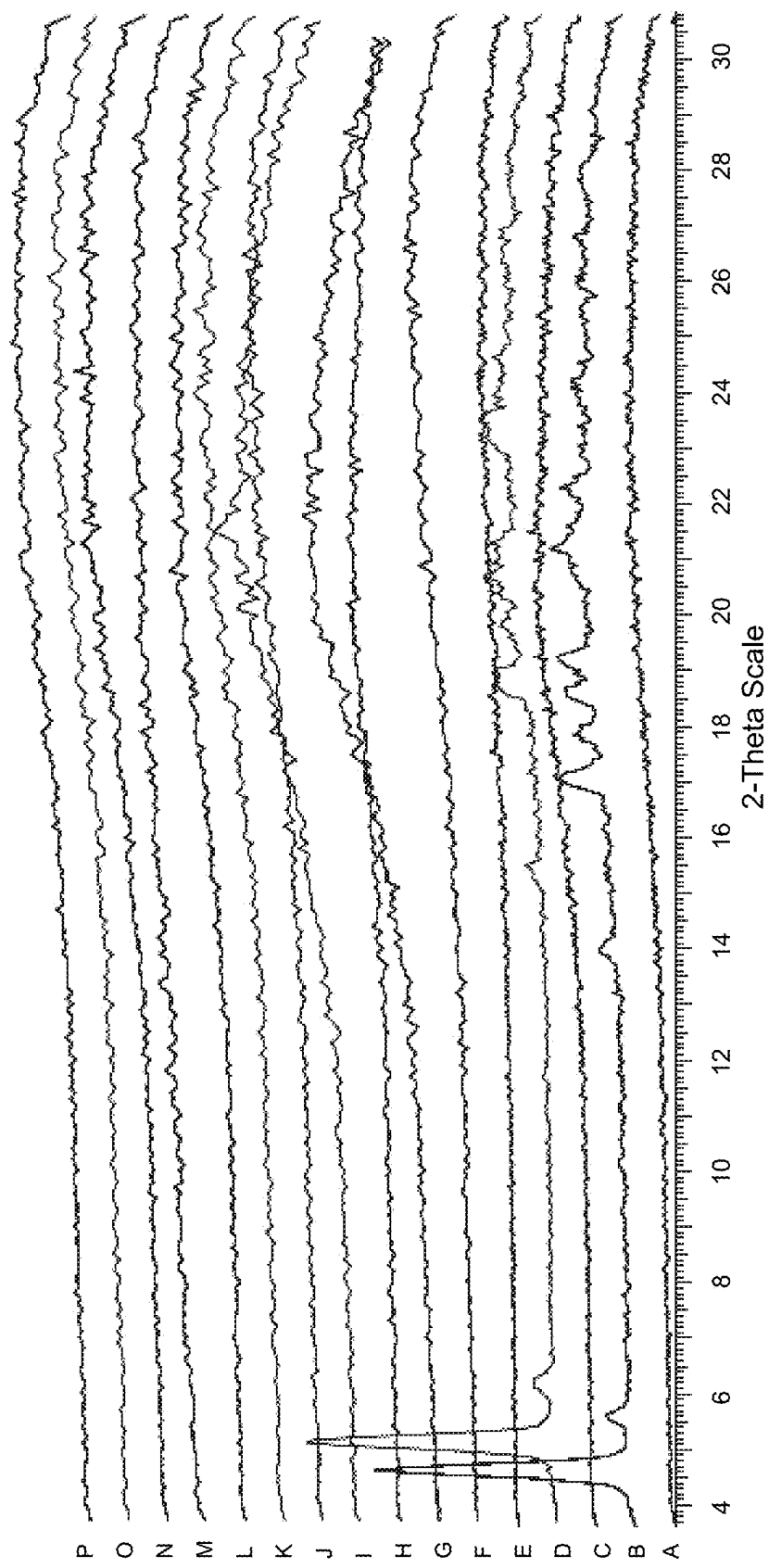
FIG. 11 shows XRPD diffractograms of solid material recovered in salt experiments in various solvents after maturation. A is amorphous hydrochloride from MTBE; B is partially crystalline sulfate pattern 1; C is amorphous mesylate from IPA; D is partially crystalline phosphate pattern 1; E is amorphous tartrate; F is amorphous fumarate; G is amorphous sulfate; H is amorphous mesylate from MTBE; I is amorphous phosphate; J is amorphous tartrate; K is amorphous fumarate; L is amorphous sulfate; M is amorphous mesylate from MTBE; N is amorphous phosphate; O is amorphous tartrate; and P is weakly crystalline fumarate pattern 1.
Figure 12:
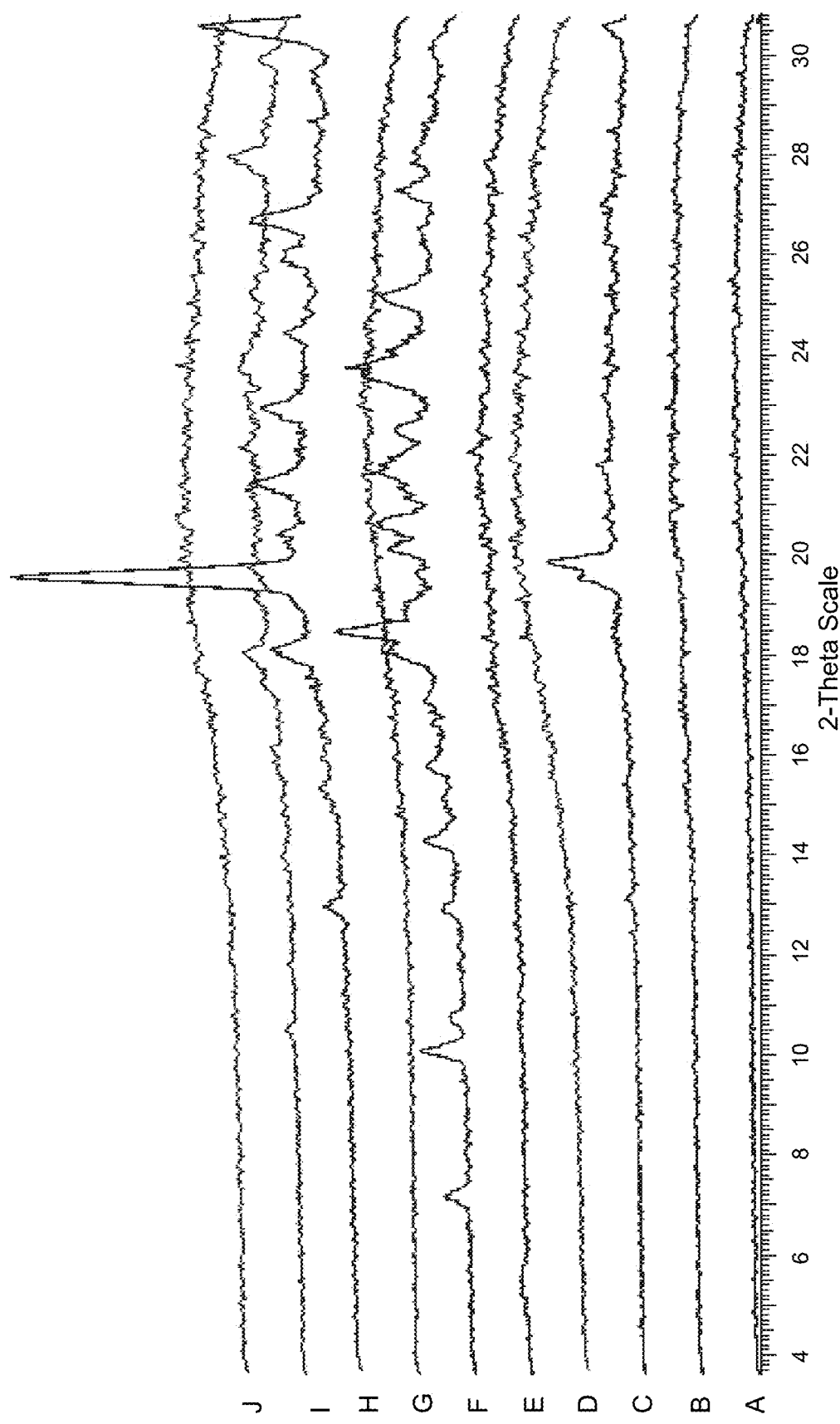
FIG. 12 shows XRPD diffractograms of solid material recovered in salt experiments in methylethyl ketone. A is amorphous sulfate; B is amorphous oxalate; C is galactaric acid; D is amorphous tartrate; E is amorphous sulfate; F is p-TSA (tosylate) Form 1; G is amorphous oxalate; H is galactaric acid; I is weakly crystalline ascorbate; J is amorphous tartrate.
Figure 13:
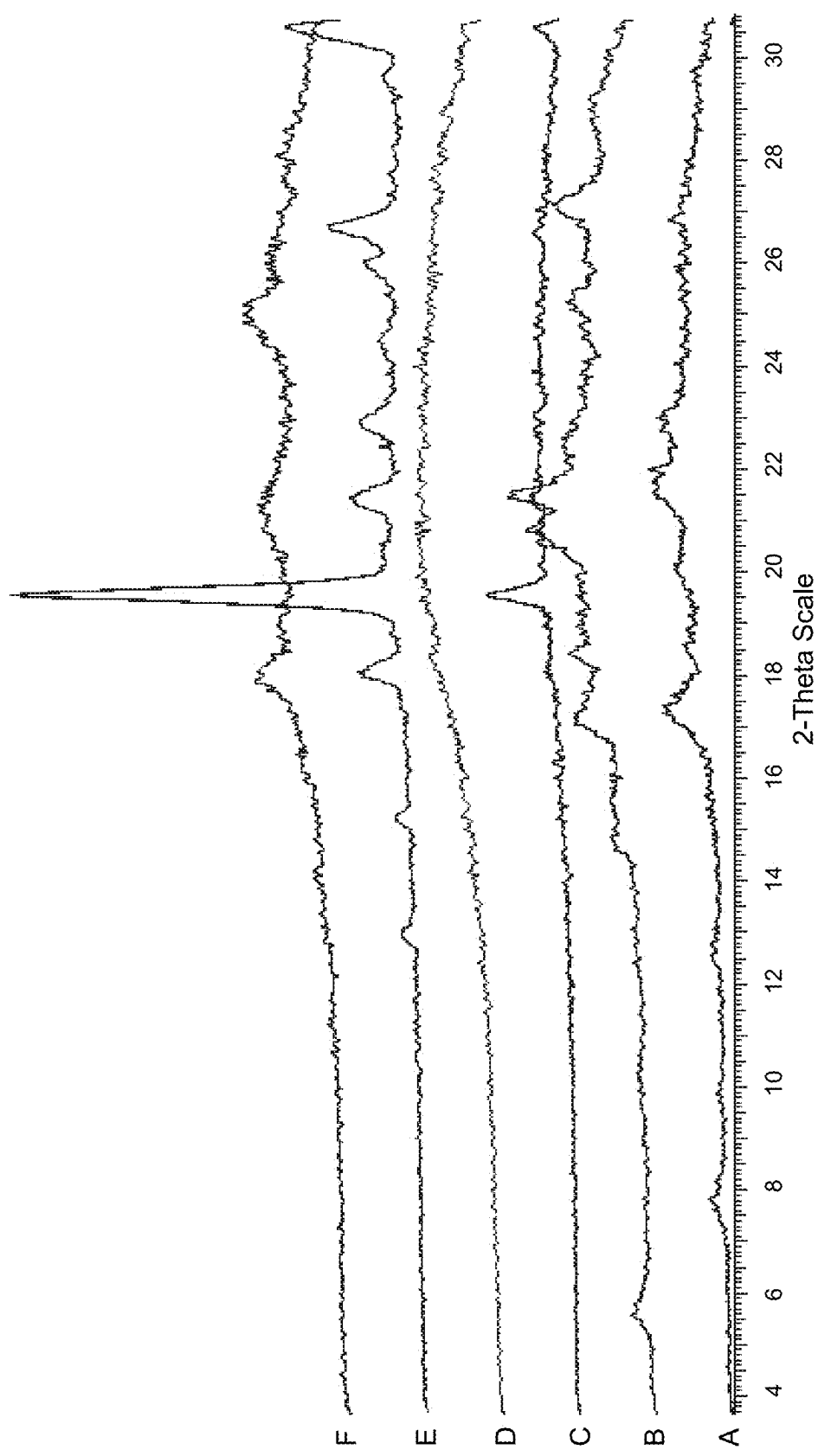
FIG. 13 shows XRPD diffractograms of solid material recovered in salt experiments in methylethyl ketone after maturation. A is the sulfate pattern 2; B is the oxalate Form 1; C is galactaric acid; D is amorphous tartrate; E is galactaric acid; and F is weakly crystalline tartrate.
Figure 14:
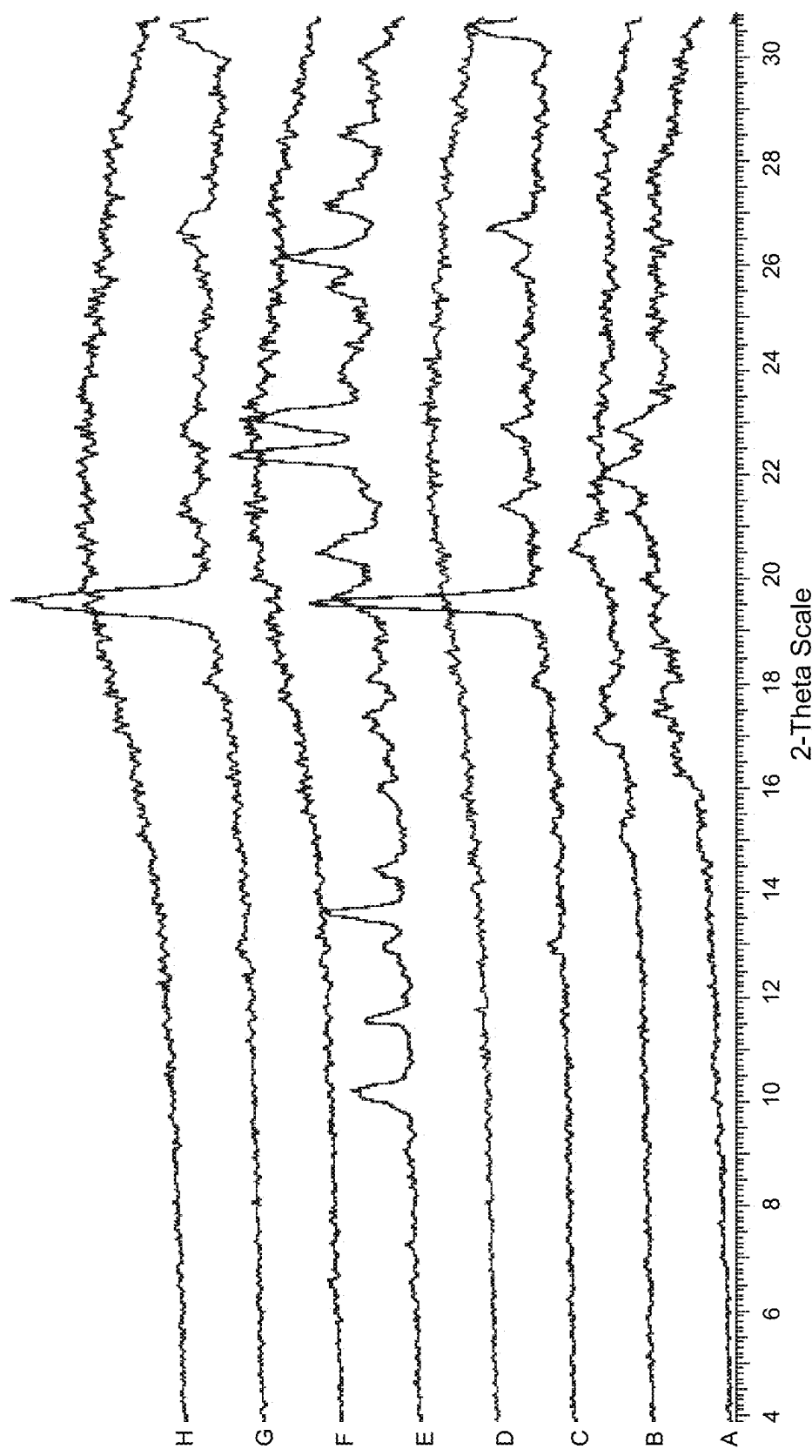
FIG. 14 shows XRPD diffractograms of solid material recovered in salt experiments in MeCN. A is weakly crystalline sulfate; B is weakly crystalline oxalate; C is galactaric acid; D is amorphous sulfate; E is tosylate Form 2; F is amorphous oxalate; G is galactaric acid; H is amorphous tartrate.
Figure 15:
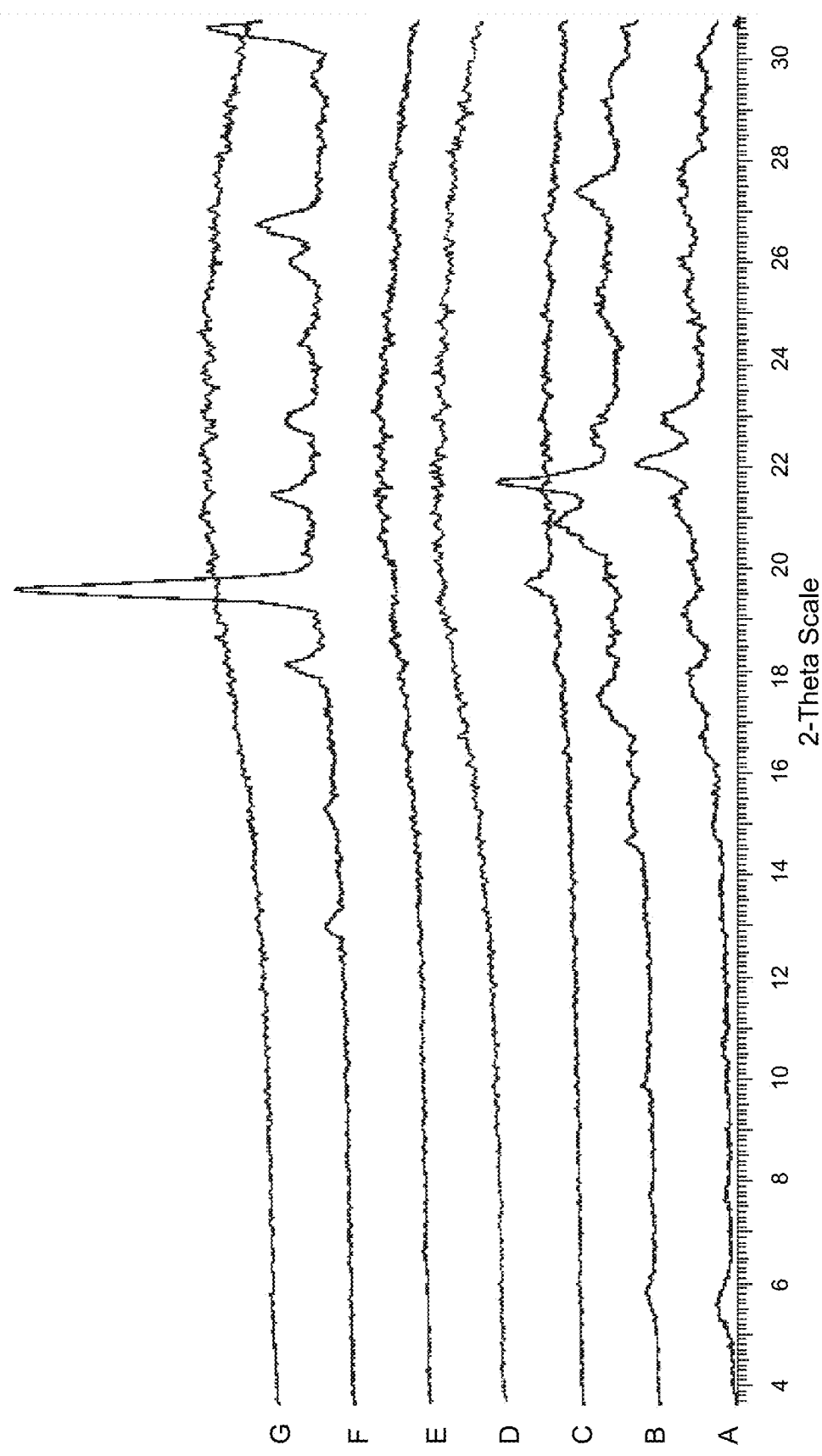
FIG. 15 shows XRPD diffractograms of solid material recovered in salt experiments in MeCN after maturation. A is sulfate pattern 3; B is oxalate form 1; C is galactaric acid; D is amorphous tartrate; E is amorphous oxalate; F is galactaric acid; G is amorphous tartrate.
Figure 16:
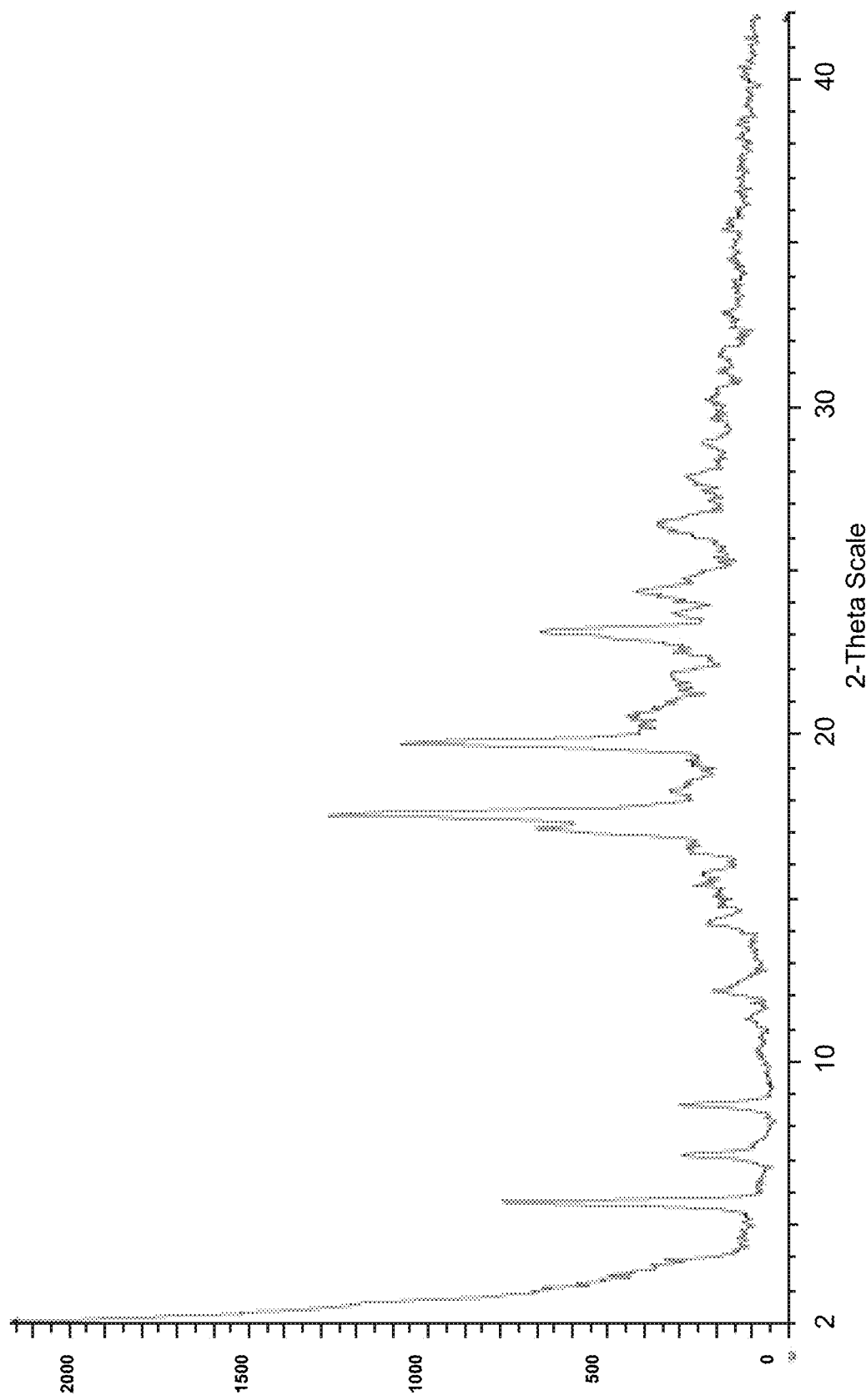
FIG. 16 is a high-resolution XRPD diffractogram of the tartrate form 2 salt.
Figure 17:
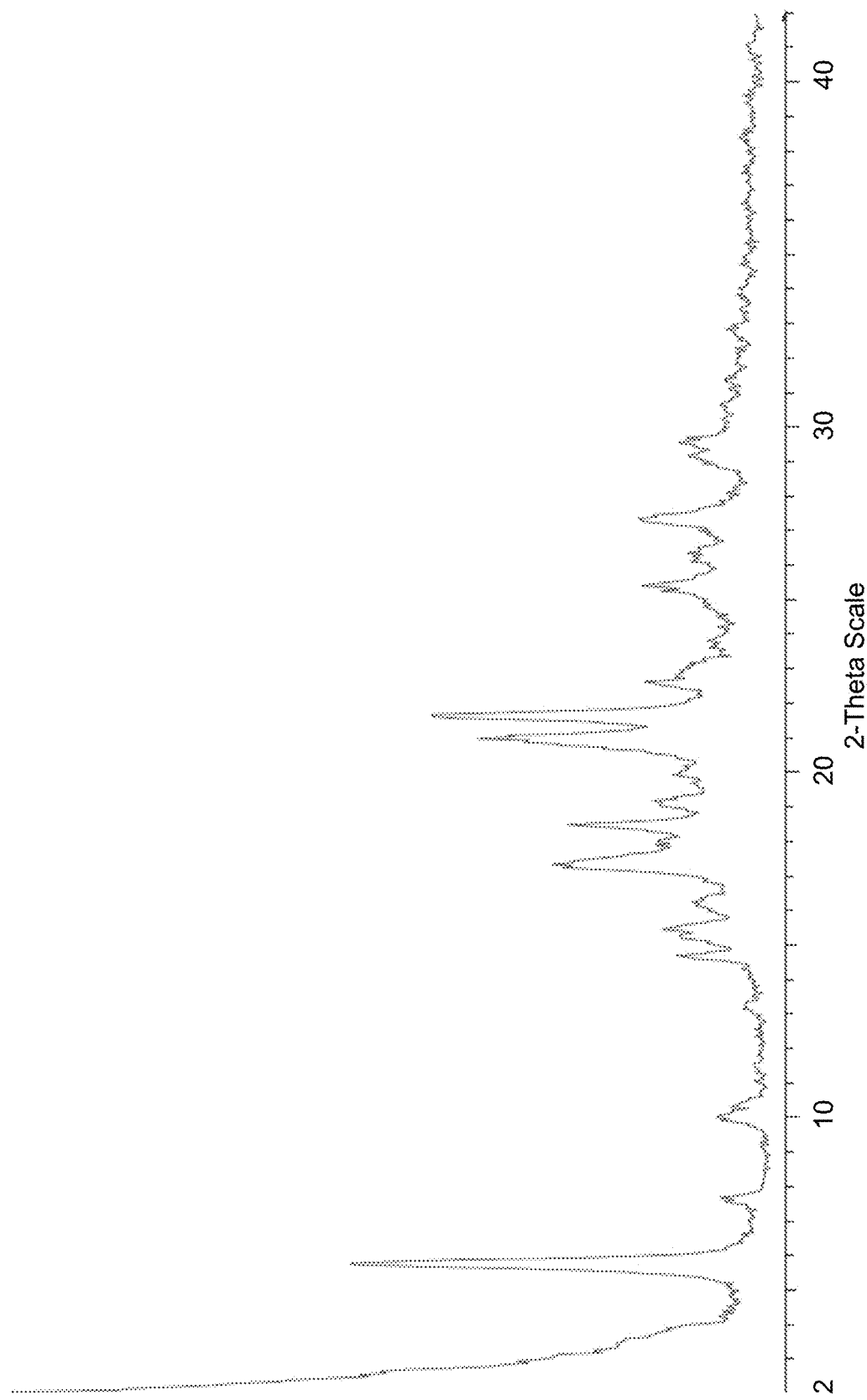
FIG. 17 is a high-resolution XRPD diffractogram of the oxalate form 1 salt.
Figure 18:
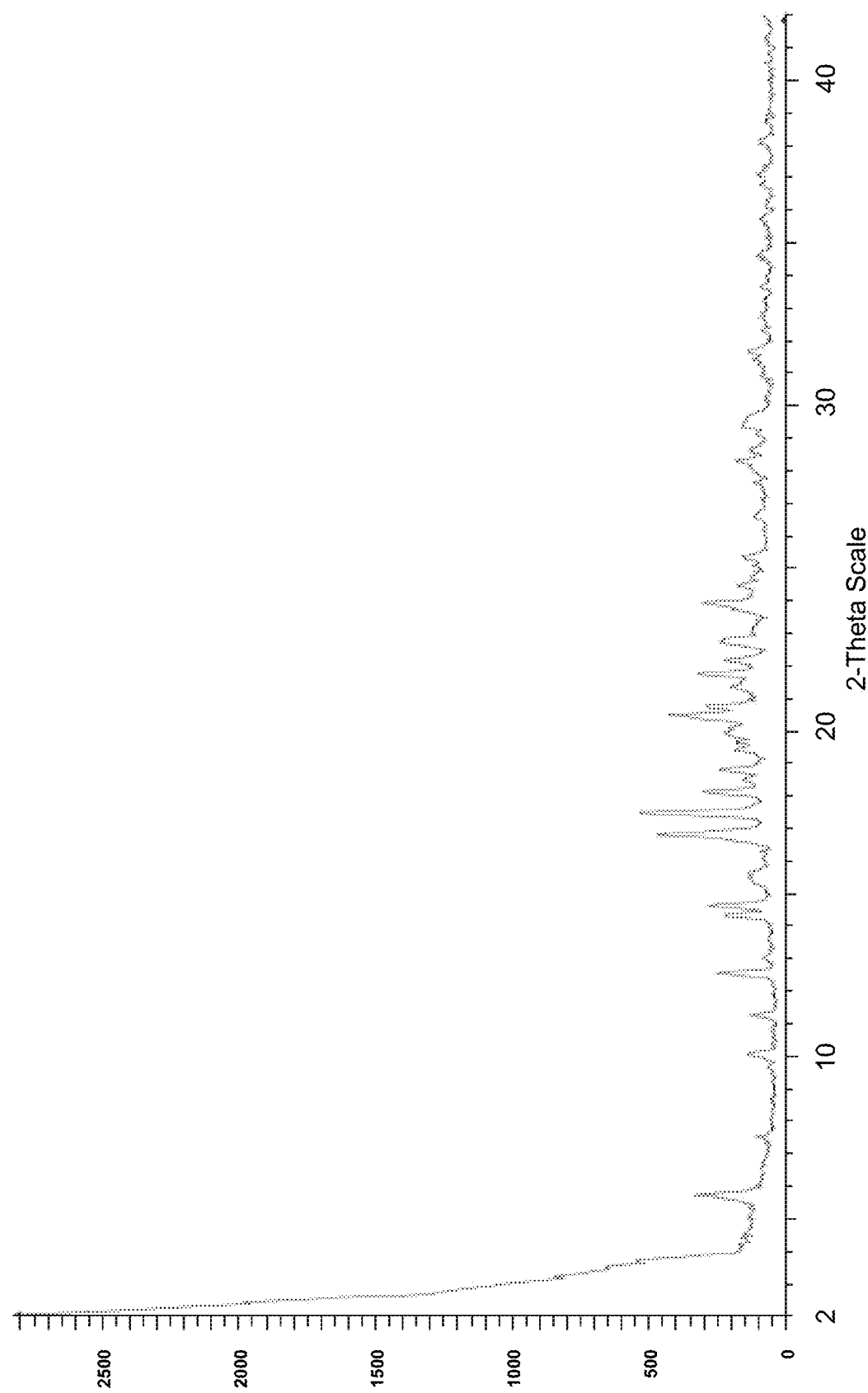
FIG. 18 is a high-resolution XRPD diffractogram of the tartrate form 1 salt.
Figure 19:
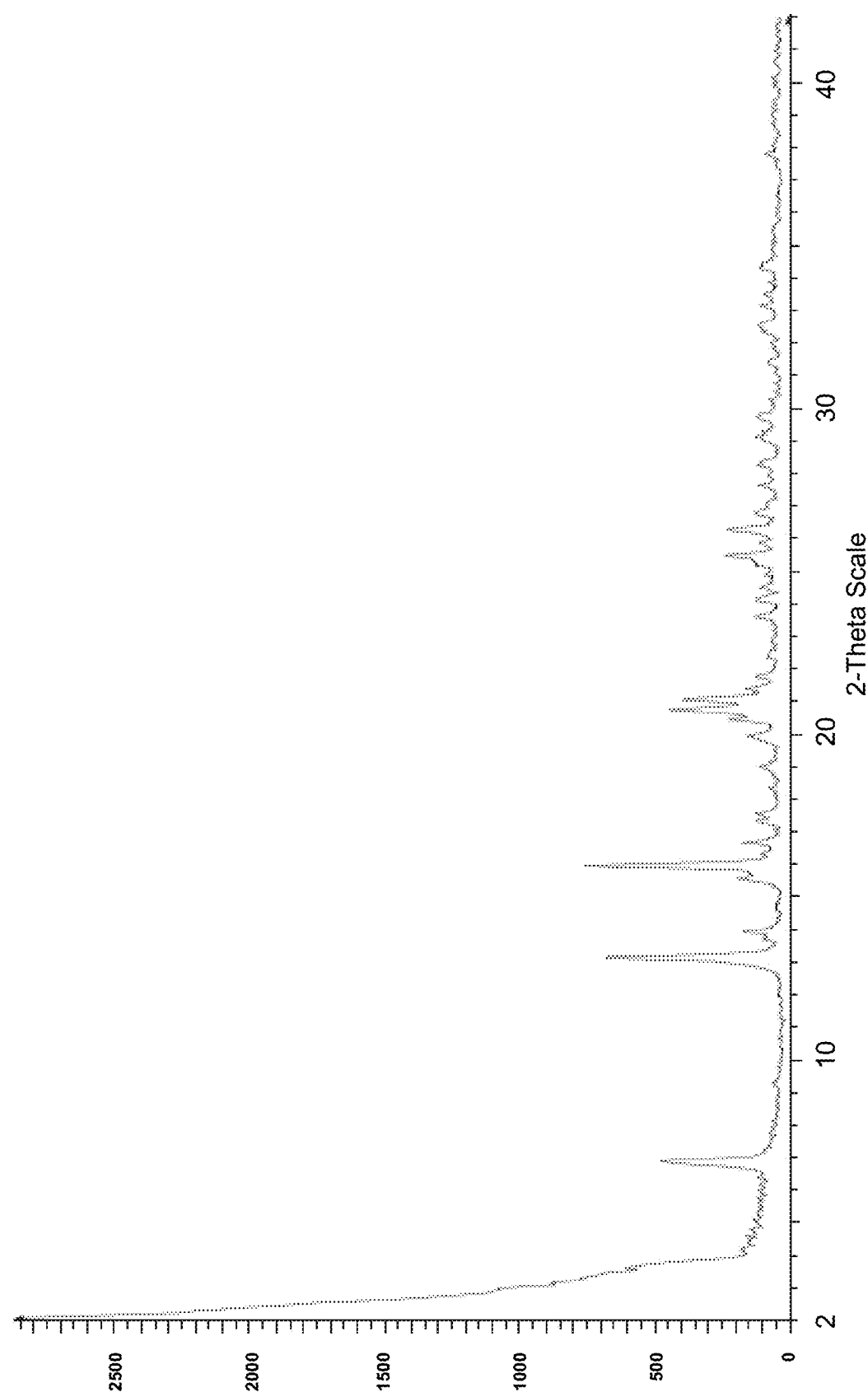
FIG. 19 is a high-resolution XRPD diffractogram of the tartrate form 3 salt.
Figure 20:
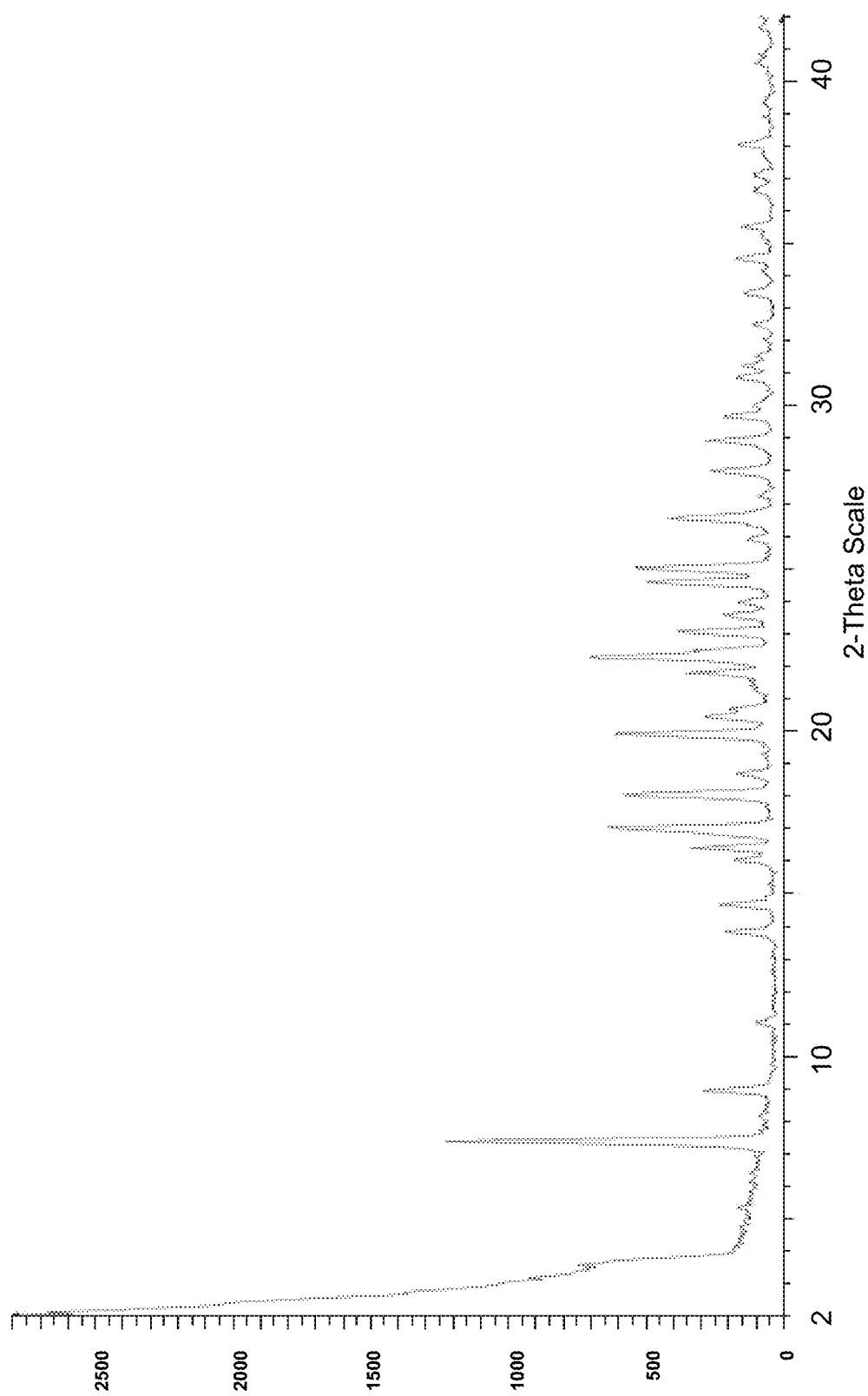
FIG. 20 is a high-resolution XRPD diffractogram of the oxalate form 2 salt.
Figure 21:
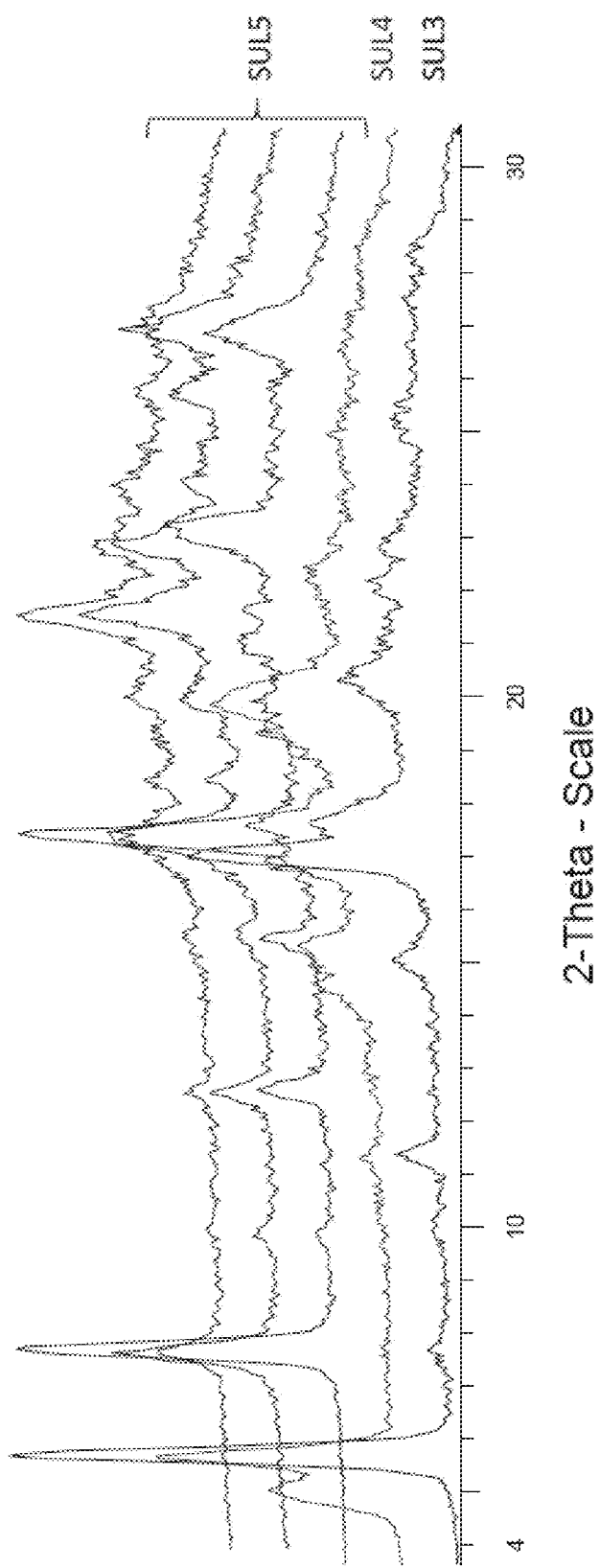
FIG. 21 shows XRPD diffractograms of sulfate salt forms from the second salt experiment.
Figure 22:
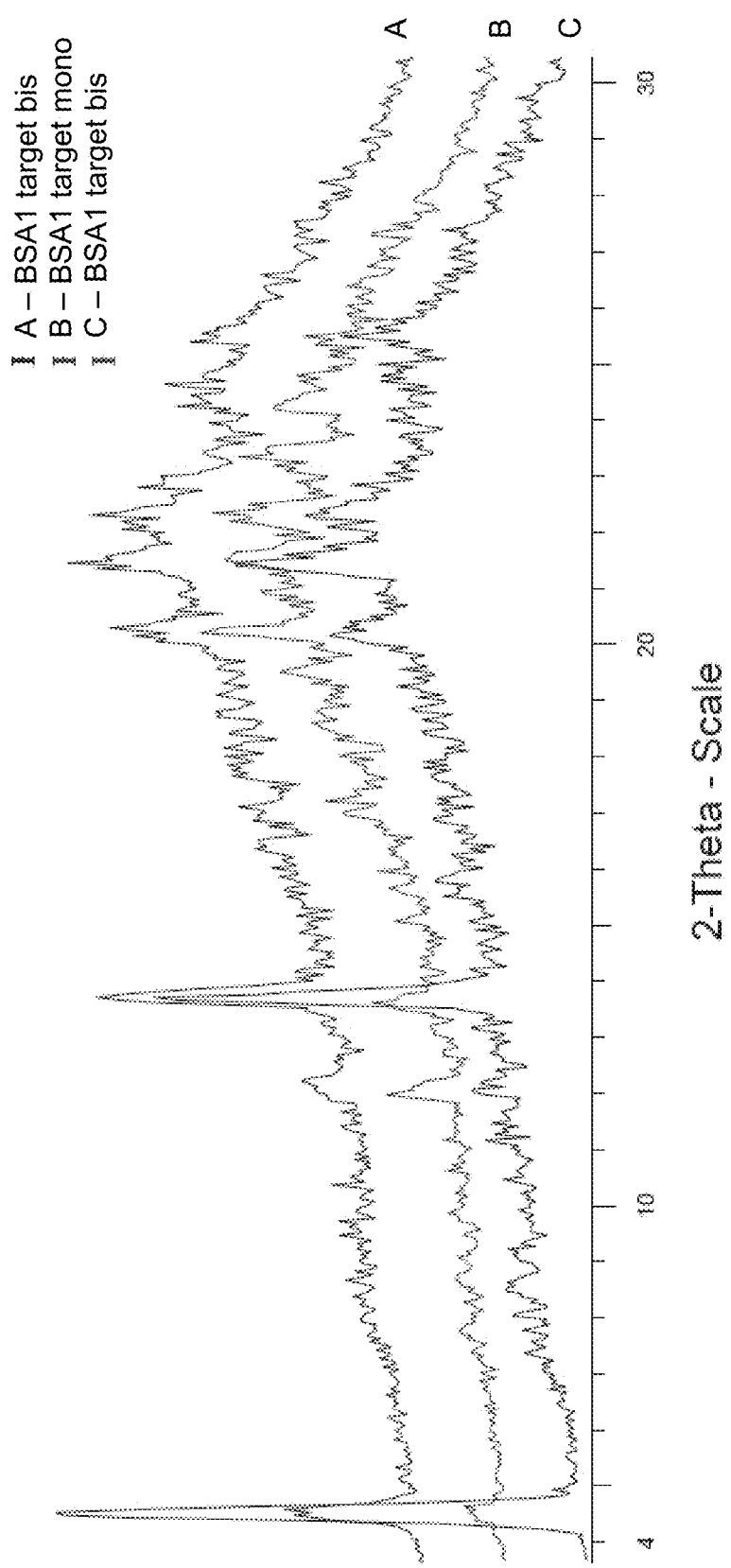
FIG. 22 shows XRPD diffractograms of benzenesulfonate salt forms from the second salt experiment.
Figure 23:
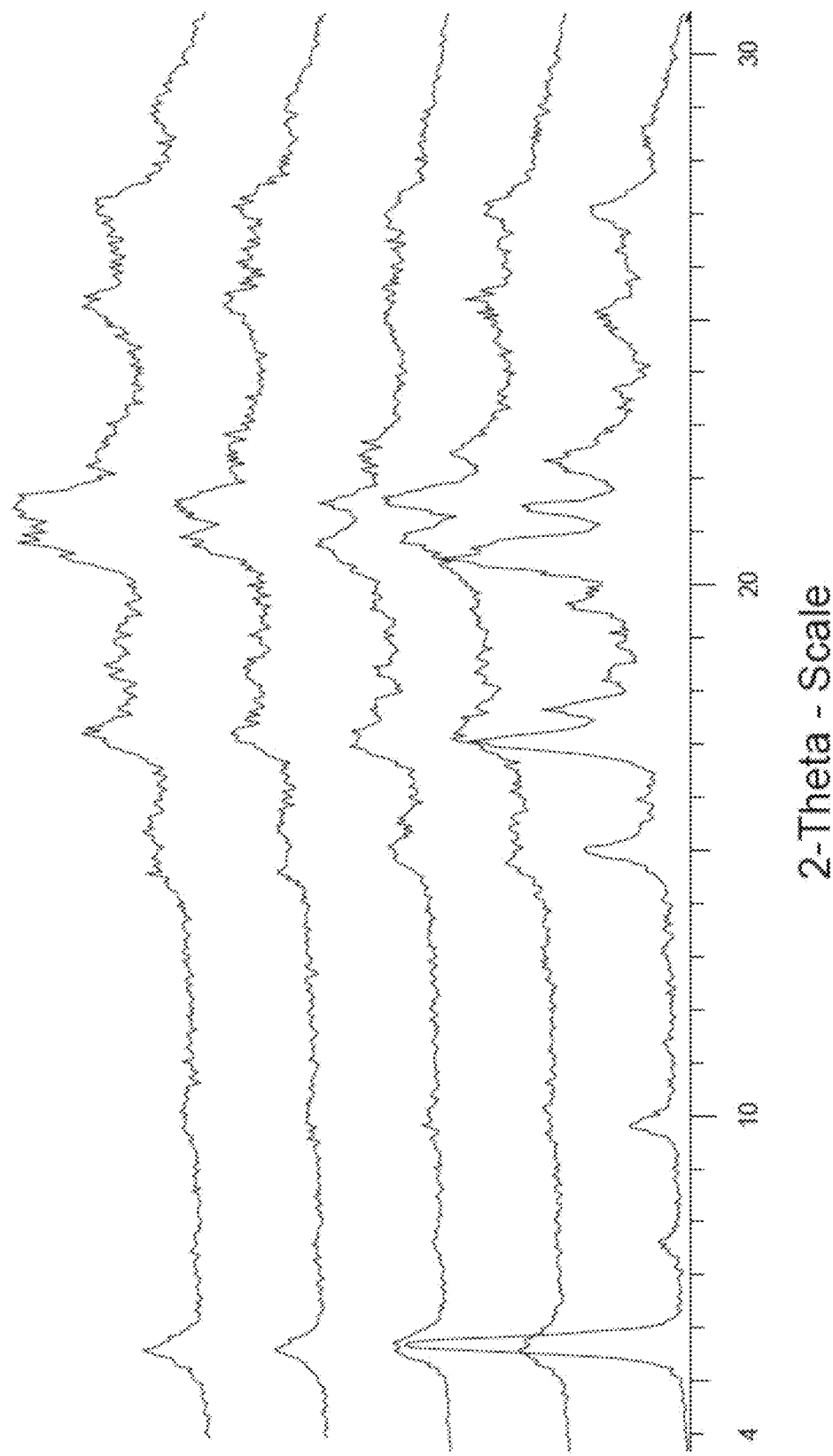
FIG. 23 shows XRPD diffractograms of oxalate salt forms from the second salt experiment.
Figure 24:
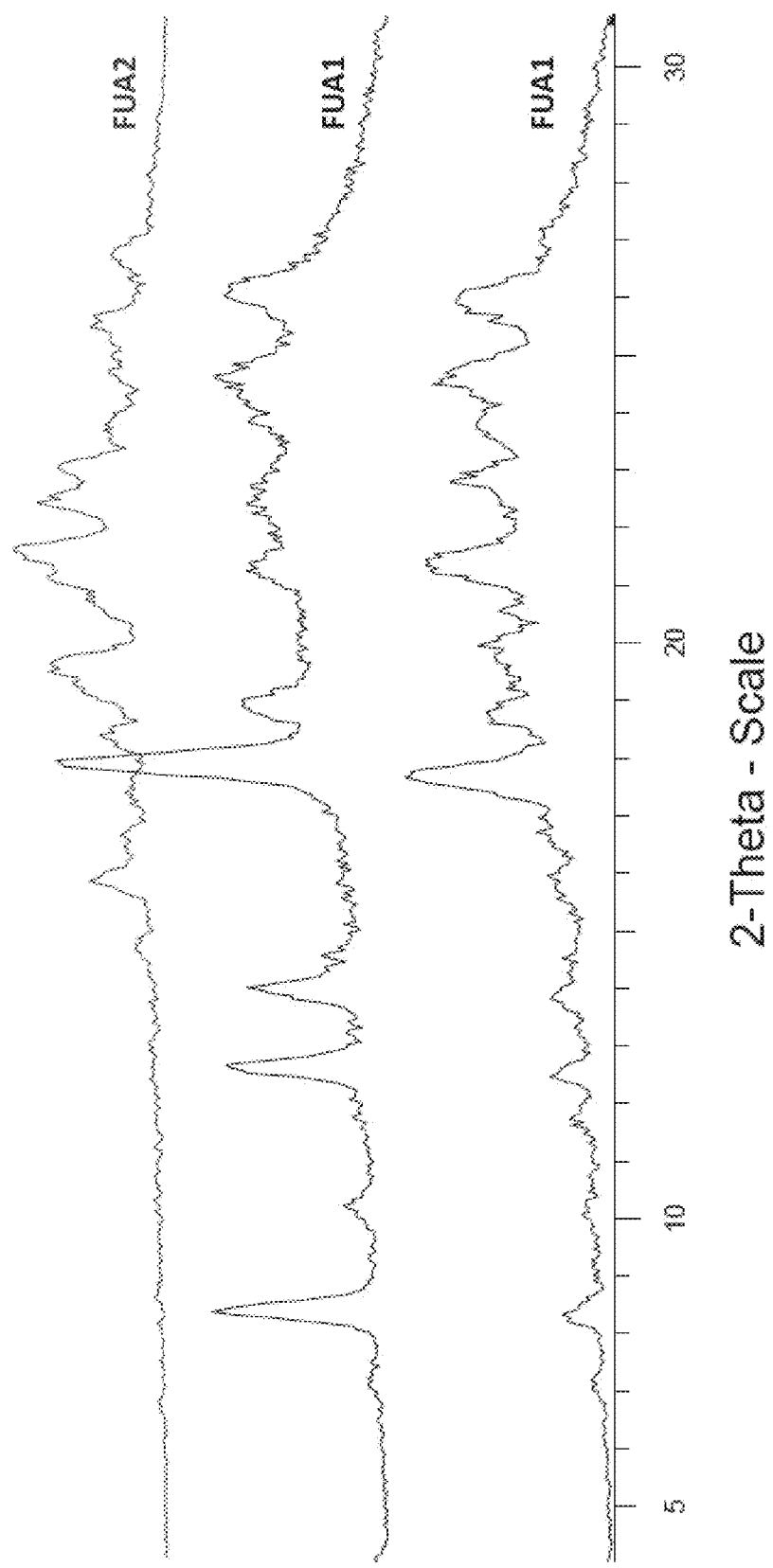
FIG. 24 is an XRPD diffractogram of fumarate salt forms from the second salt experiment.
Figure 25:
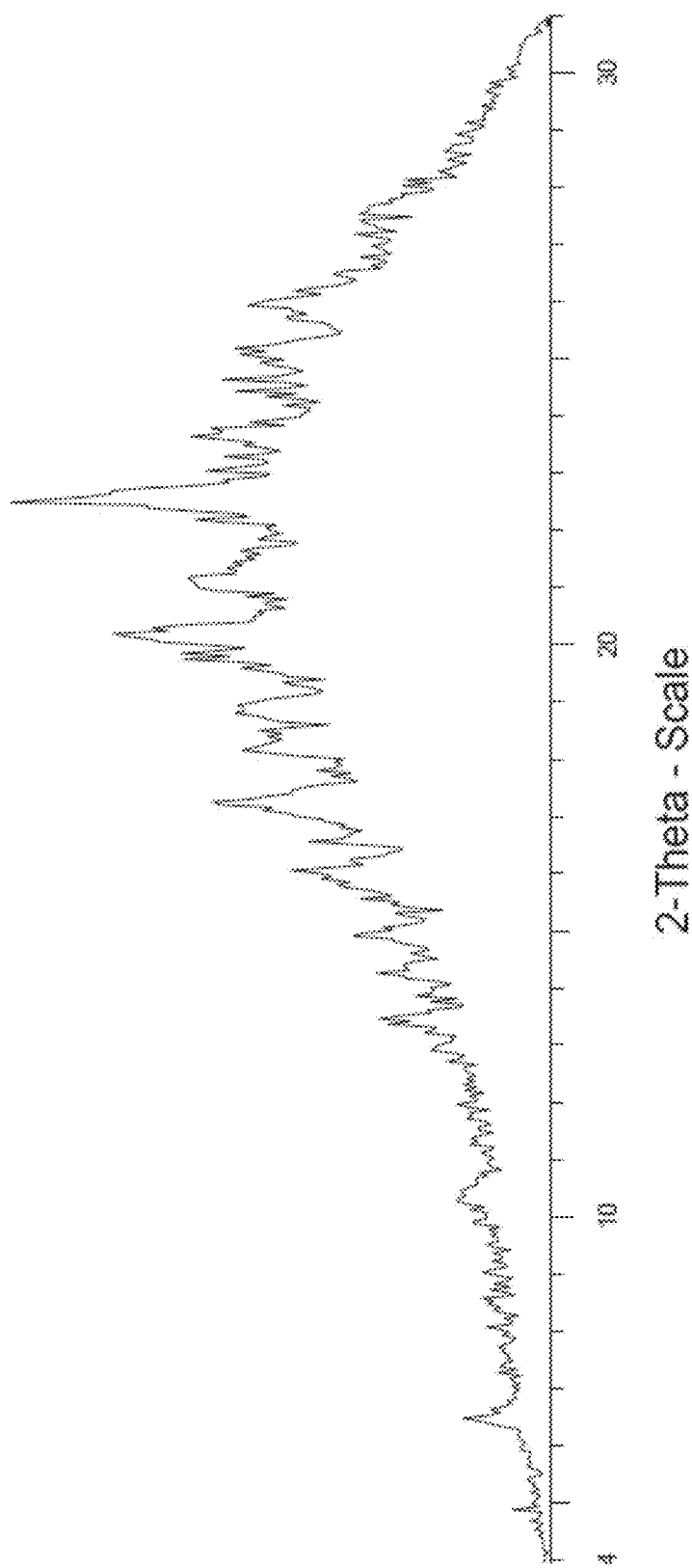
FIG. 25 is an XRPD diffractogram of the besylate salt from the second salt experiment.
Figure 26:
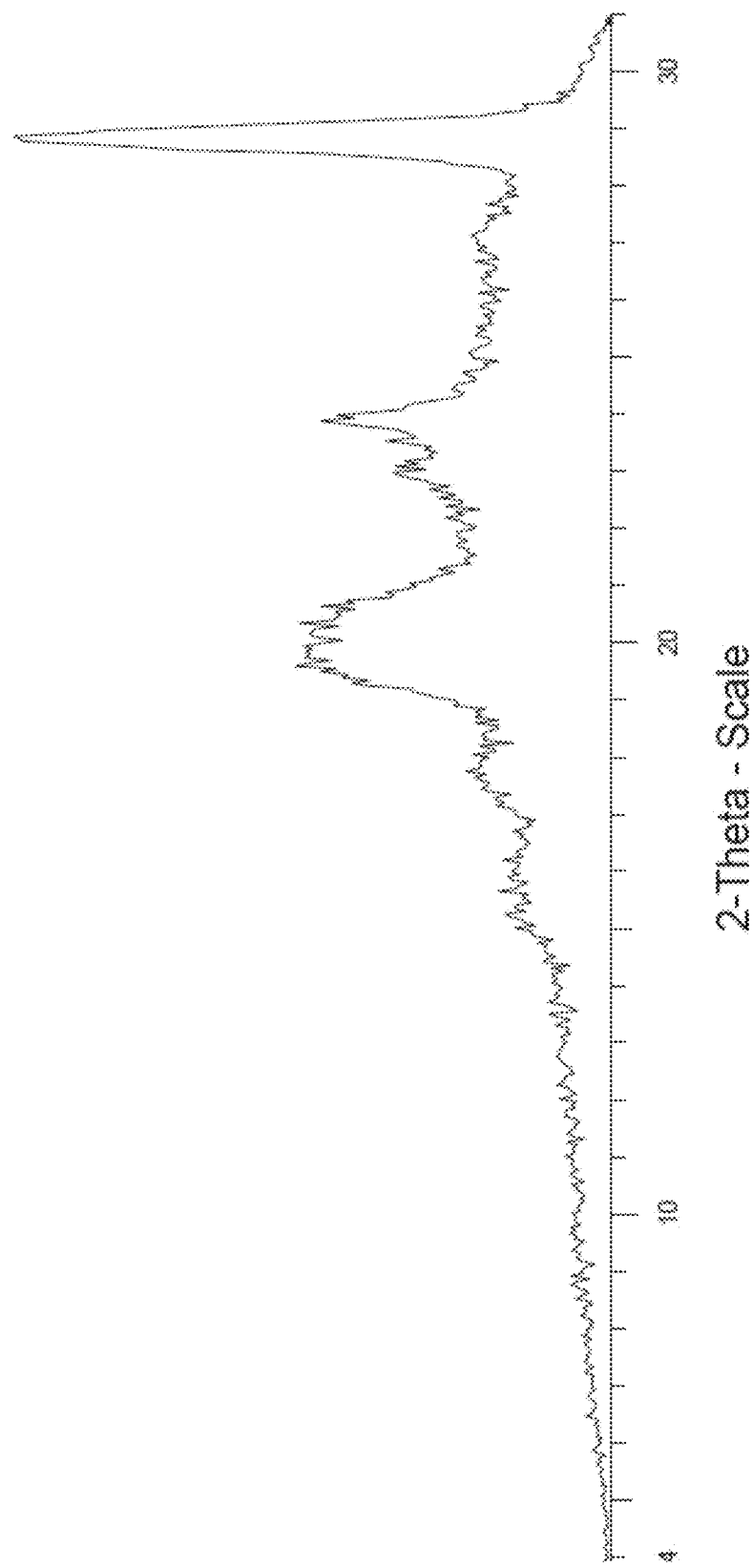
FIG. 26 is an XRPD diffractogram of L-malate salt from the second salt experiment.
Figure 27:
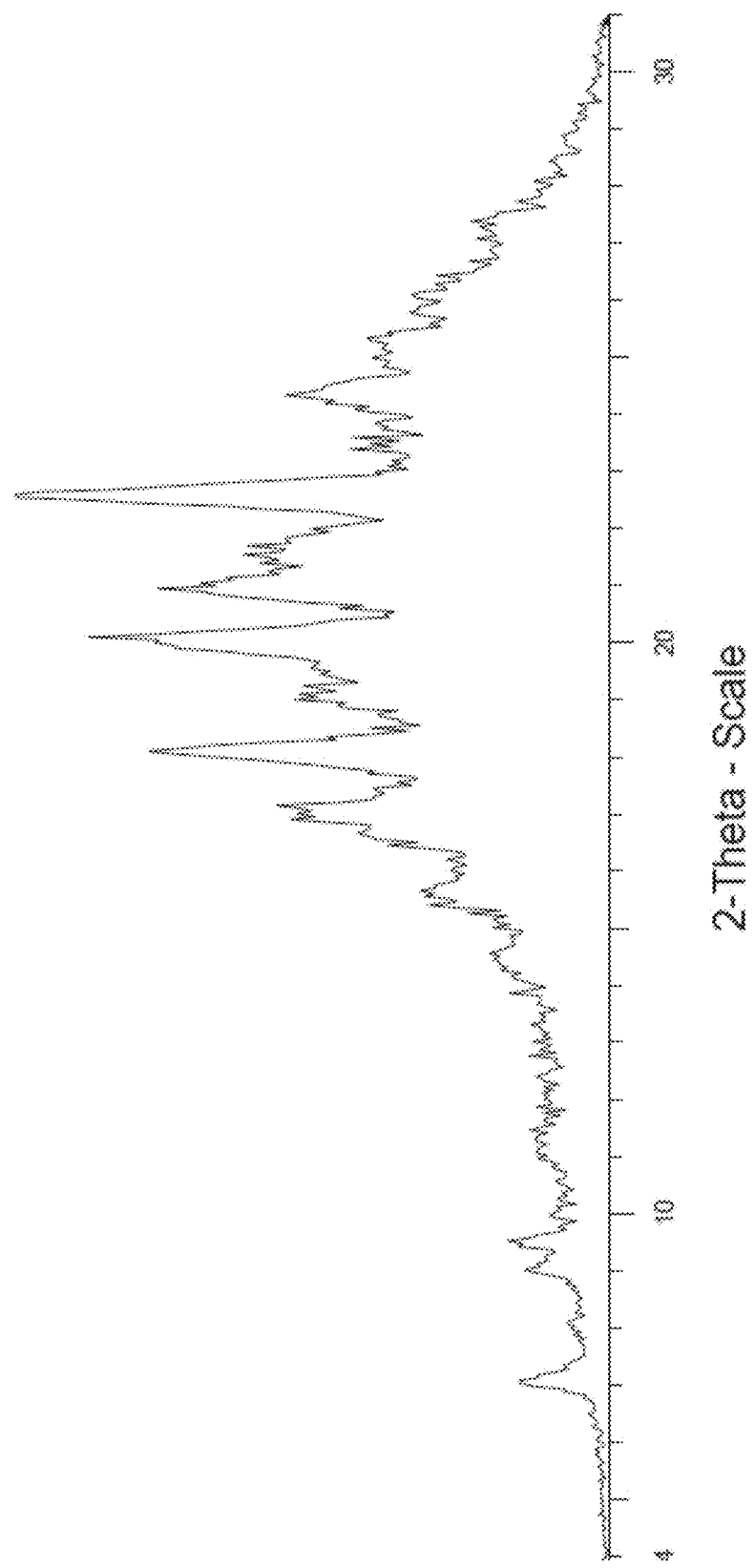
FIG. 27 is an XRPD diffractogram of L-malate salt from the second salt experiment.

Accordingly, provided herein are compounds of the formula (I):

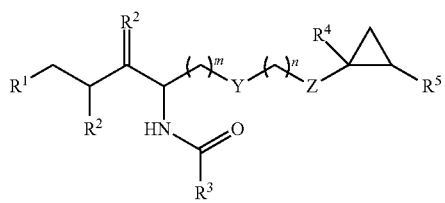

(I)

or a salt, polymorph, or solvate thereof, wherein:
Y is chosen from a bond, $NR^{4a}$, O, C(O)NH, NHC(O), S, $SO_2$, CHOH, and $CH_2$;
Z is chosen from a bond, $NR^{4b}$, O, C(O)NH, NHC(O), S, $SO_2$, and $CH_2$;
m is chosen from 0, 1, 2, 3, 4, and 5;
n is chosen from 0, 1, 2, and 3;
$R^1$ and $R^2$ are each independently chosen from alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;
$R^3$ is chosen from alkylamino, cycloalkylamino, arylamino, heteroarylamino, heterocycloalkylamino, cycloalkyl, cycloalkylalkyl, aryl, arylalkyl, heteroaryl, heteroarylalkyl, heterocycloalkyl, and heterocycloalkylalkyl any of which may be optionally substituted with between 0 and 3 $R^6$ groups;
$R^4$, $R^{4a}$, and $R^{4b}$ are independently chosen from hydrogen, alkyl, alkenyl, alkynyl, and cycloalkyl;
$R^5$ is chosen from aryl and heteroaryl, any of which may be optionally substituted with between 0 and 3 $R^6$ groups;
each $R^6$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^7$, $SO_2R^7$, $NHSO_2R^7$, $NHSO_2NHR^7$, $NHCOR^7$, $NHCONHR^7$, $CONHR^7$, and $CONR^7R^8$; and
$R^7$ and $R^8$ are independently chosen from hydrogen, aryl, and lower alkyl; or $R^7$ and $R^8$ may be taken together to form a nitrogen-containing heterocycloalkyl or heteroaryl ring, which may be optionally substituted with lower alkyl.

In certain embodiments, the compound has Formula Ia, Ib, Ic, or Id:

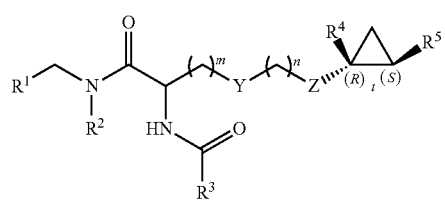

(Ia)

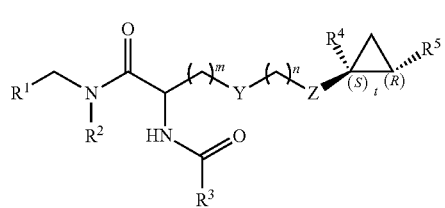

(Ib)

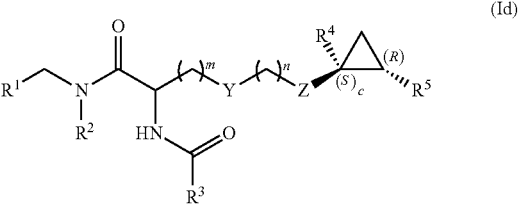

(Ic)

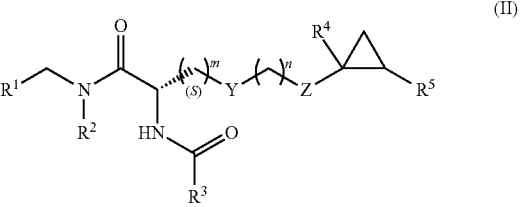

(Id)

or a salt, polymorph, or solvate thereof, wherein all groups are as defined for Formula I.

In certain embodiments, the compound has Formula II or III:

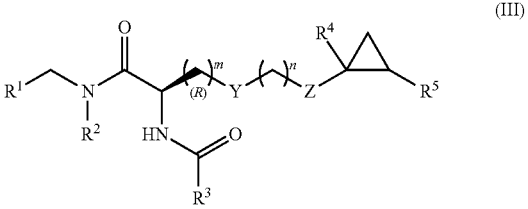

(II)

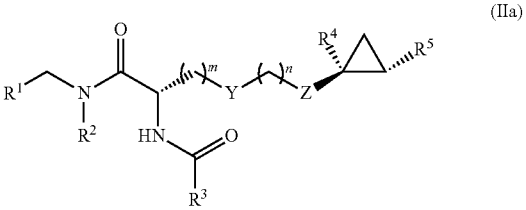

(III)

or a salt, polymorph, or solvate thereof, wherein all groups are as defined for Formula I.

In certain embodiments, the compound has Formula IIa, IIb, IIc, or IId:

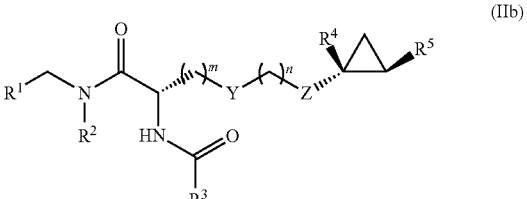

(IIa)

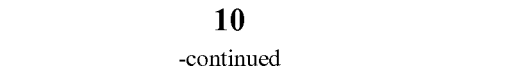

(IIb)

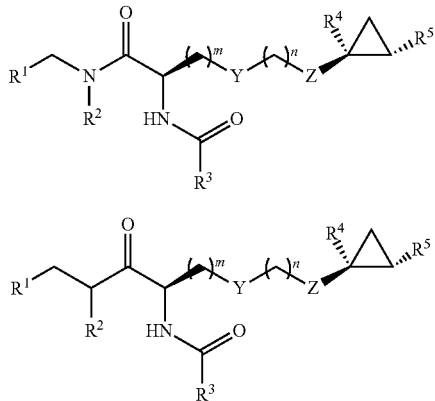

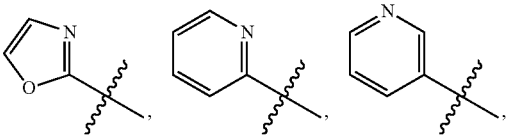

or a salt, polymorph, or solvate thereof, wherein all groups are as defined for Formula I. All cis and trans isomers are contemplated.

In certain embodiments, Z is $NR^{4b}$.

In certain embodiments, $R^{4b}$ is chosen from methyl and hydrogen.

In certain embodiments, $R^{4b}$ is hydrogen.

In certain embodiments, the alkyl, whether by itself or as a named part of another non-cyclic substituent, is $C_1$-$C_8$ alkyl.

In certain embodiments, $R^3$ is aryl, which may be optionally substituted with between 0 and 3 $R^6$ groups.

In certain embodiments, $R^3$ is chosen from aryl and heteroaryl, either of which is substituted with an $R^6$ group called $R^{6a}$, chosen from heteroaryl, cyano, and $S(O)_2N(CH_3)_2$. In certain embodiments, $R^3$ remains optionally substituted with 1-2 additional $R^6$ groups.

In certain embodiments, m is 0; Y is $CH_2$; and n is chosen from 0, 1, and 2.

In certain embodiments, m is 0; Y is $CH_2$; and n is 2.

In certain embodiments, $R^3$ is chosen from phenyl and heteroaryl, either of which is substituted with an $R^6$ group called $R^{6a}$, chosen from heteroaryl, cyano, and $S(O)_2N(CH_3)_2$.

In certain embodiments, $R^{6a}$ is chosen from cyano, $S(O)_2N(CH_3)_2$,

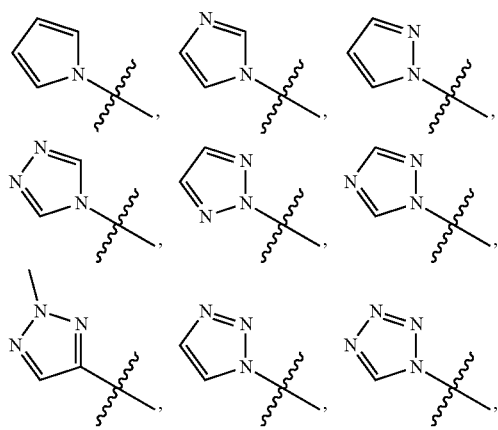

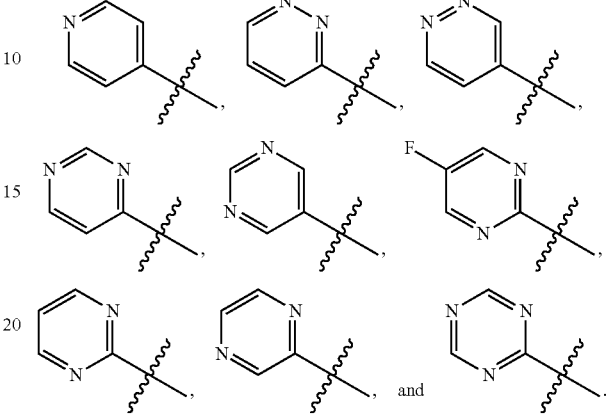

In certain embodiments, $R^{6a}$ is heteroaryl.

In certain embodiments, $R^{6a}$ is chosen from:

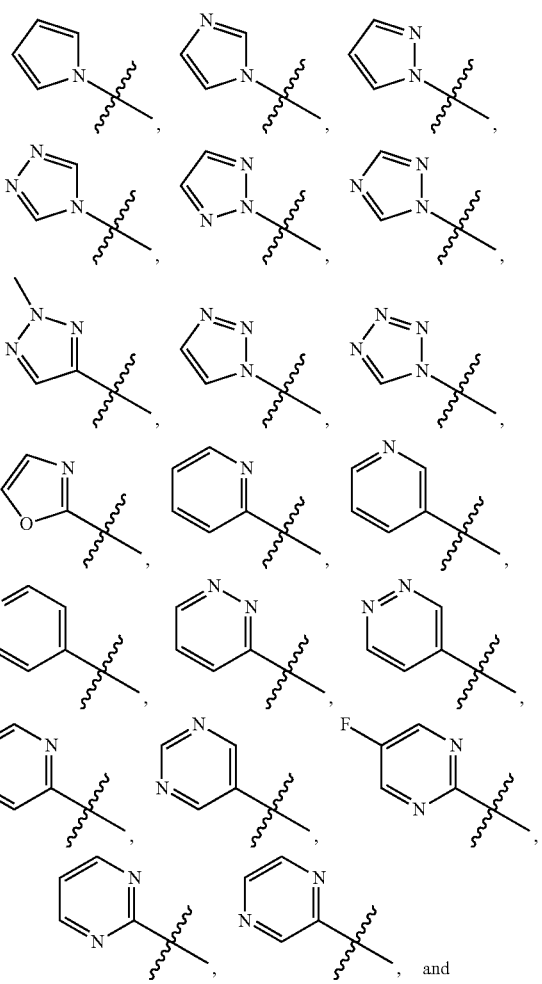

-continued

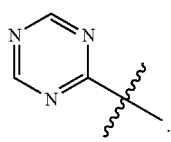

In certain embodiments, $R^{6a}$ is

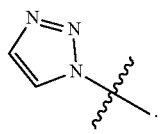 [SMILES: *n1ccnn1]

In certain embodiments, $R^4$ is hydrogen.

In certain embodiments, nitrogen-containing heterocycloalkyl or heteroaryl ring formed by $R^1$ and $R^2$ together with the nitrogen to which they are attached contains 3 to eight atoms.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is chosen from:

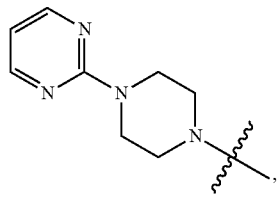

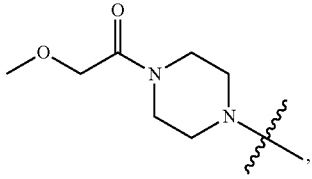

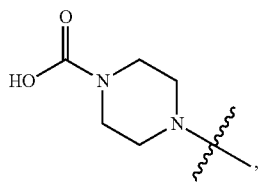

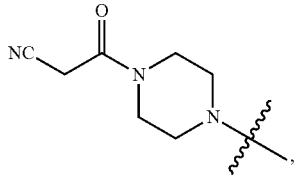

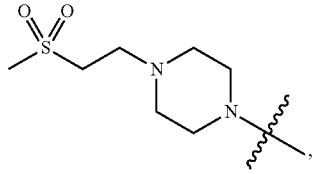

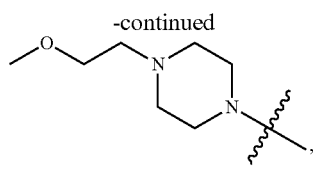

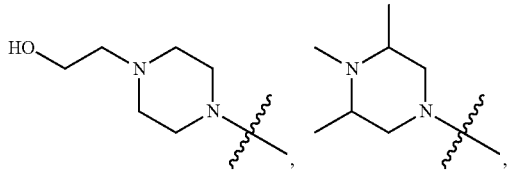

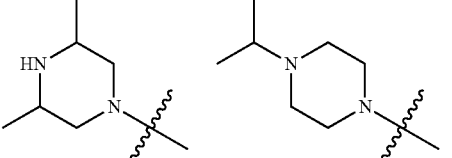

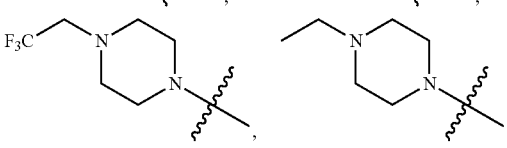

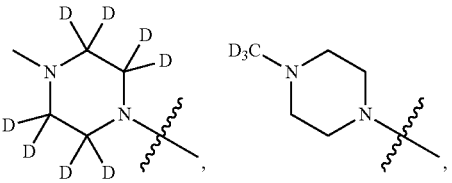

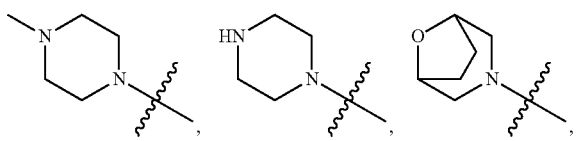

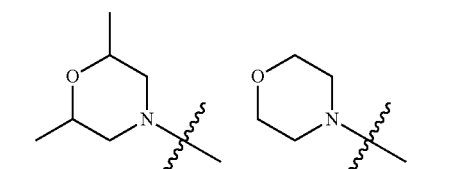

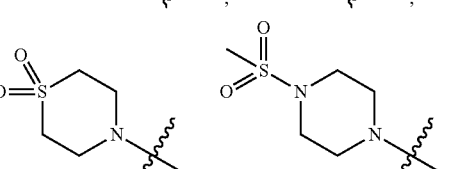

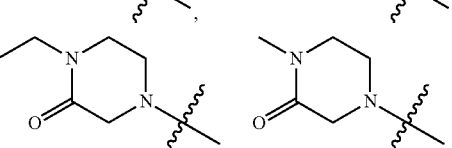

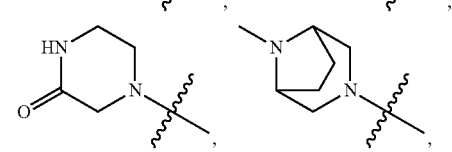

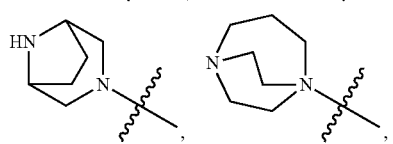

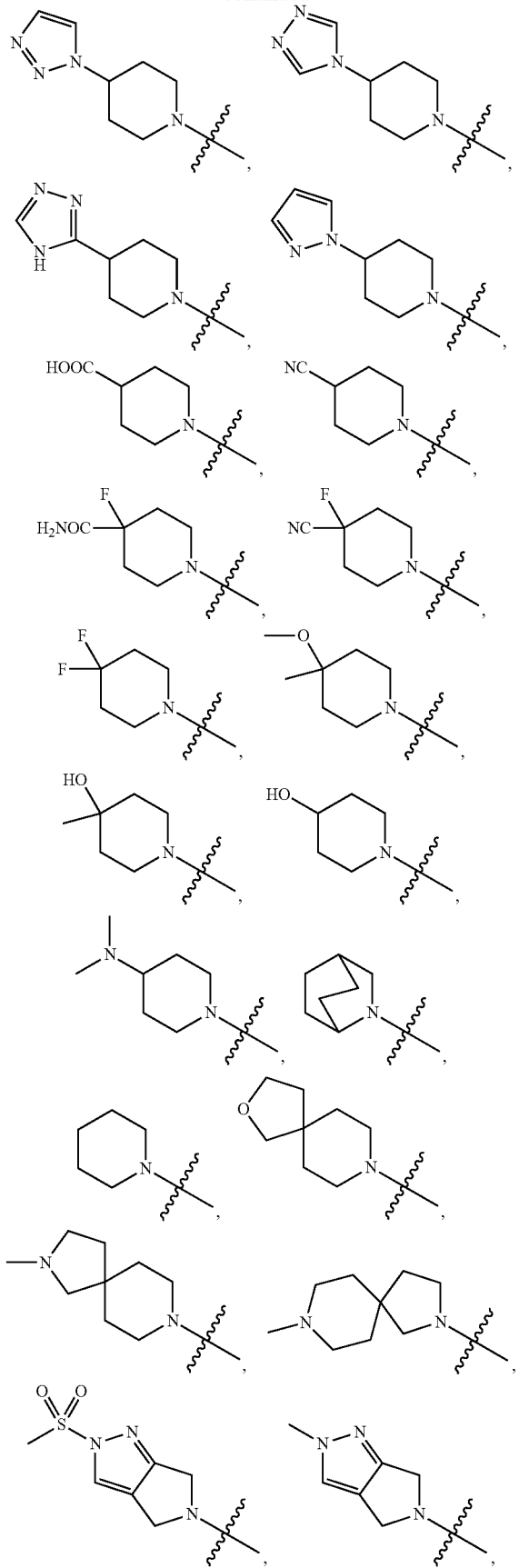
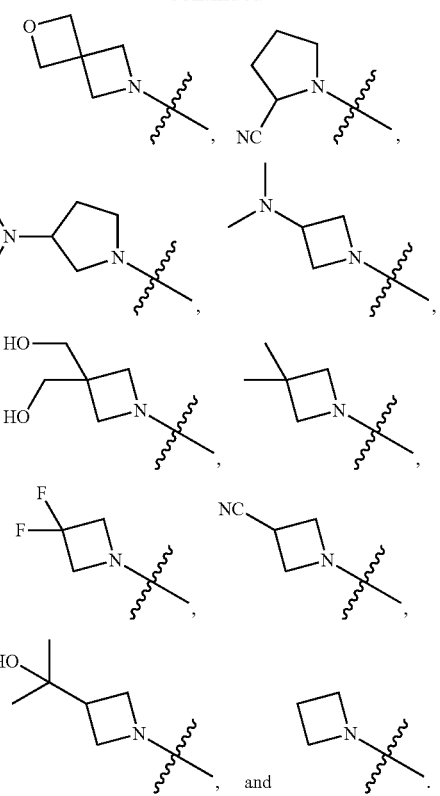
In certain embodiments, the nitrogen-containing heterocycloalkyl is chosen from:
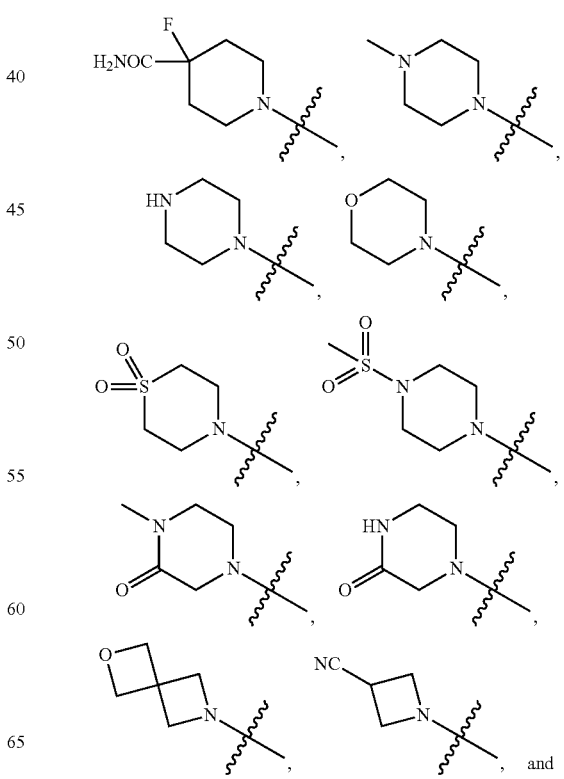

-continued

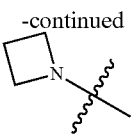

In certain embodiments, the nitrogen-containing heterocycloalkyl is:

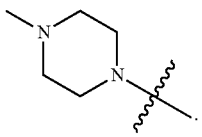 [SMILES: *N1CCN(C)CC1]

In certain embodiments, the nitrogen-containing heterocycloalkyl is optionally substituted with between 0 and 3 $R^6$ groups chosen from alkyl and oxo.

In certain embodiments, $R^5$ is phenyl, which may be optionally substituted with between 0 and 3 $R^6$ groups.

In certain embodiments, $R^5$ is:

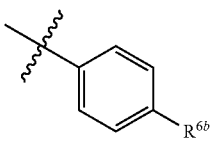

wherein $R^{6b}$ is chosen from halogen and hydroxy.

In certain embodiments, $R^{6b}$ is chosen from fluoro, methoxy, and hydroxy.

In certain embodiments, $R^{6b}$ is fluoro.

In certain embodiments, $R^{4b}$ is chosen from methyl and hydrogen.

In certain embodiments, $R^{4b}$ is hydrogen.

In certain embodiments, the compound has Formula IV:

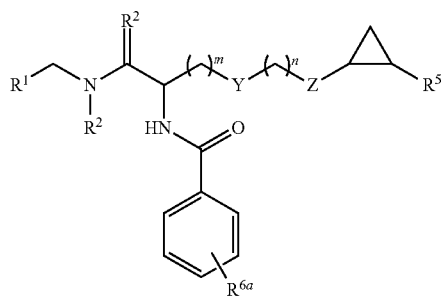

(IV)

or a salt, polymorph, or solvate thereof, wherein:

Y is chosen from a bond, $NR^{4a}$, O, C(O)NH, NHC(O), S, $SO_2$, CHOH, and $CH_2$;

Z is chosen from a bond, $NR^{4b}$, O, C(O)NH, NHC(O), S, $SO_2$, and $CH_2$;

m is chosen from 0, 1, 2, 3, 4, and 5;

n is chosen from 0, 1, 2, and 3;

$R^1$ and $R^2$ are each independently chosen from alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;

$R^3$ is chosen from alkylamino, cycloalkylamino, arylamino, heteroarylamino, heterocycloalkylamino, cycloalkyl, cycloalkylalkyl, aryl, arylalkyl, heteroaryl, heteroarylalkyl, heterocycloalkyl, and heterocycloalkylalkyl any of which may be optionally substituted with between 0 and 3 $R^6$ groups;

$R^{4a}$ and $R^{4b}$ are independently chosen from hydrogen, alkyl, alkenyl, alkynyl, and cycloalkyl;

$R^5$ is chosen from aryl and heteroaryl, any of which may be optionally substituted with between 0 and 3 $R^6$ groups;

$R^{6a}$ is chosen from heteroaryl, cyano, and $S(O)_2N(CH_3)_2$;

each $R^6$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^7$, $SO_2R^7$, $NHSO_2R^7$, $NHSO_2NHR^7$, $NHCOR^7$, $NHCONHR^7$, $CONHR^7$, and $CONR^7R^8$; and $R^7$ and $R^8$ are independently chosen from hydrogen, aryl, and lower alkyl; or $R^7$ and $R^8$ may be taken together to form a nitrogen-containing heterocycloalkyl or heteroaryl ring, which may be optionally substituted with lower alkyl.

In certain embodiments, Z is $NR^{4b}$.

In certain embodiments, $R^{4b}$ is chosen from methyl and hydrogen.

In certain embodiments, $R^{4b}$ is hydrogen.

In certain embodiments, the alkyl, whether by itself or as a named part of another non-cyclic substituent, is $C_1$-$C_8$ alkyl.

In certain embodiments, m is 0; Y is $CH_2$; and n is chosen from 0, 1, and 2.

In certain embodiments, n is 2.

In certain embodiments, $R^1$ and $R^2$ are each independently chosen from alkyl, aminoalkyl, alkylsulfonylalkyl, alkoxyalkyl, and heteroaryl, and $R^1$ and $R^2$, together with the nitrogen to which they attach, form a nitrogen-containing heterocycloalkyl or heteroaryl ring, which may be optionally substituted with between 0 and 3 $R^6$ groups.

In certain embodiments, the nitrogen-containing heterocycloalkyl or heteroaryl ring formed by $R^1$ and $R^2$ together with the nitrogen to which they are attached contains 3 to eight atoms.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is optionally substituted with between 0 and 3 $R^6$ groups chosen from alkyl, alkoxy, alkoxyalkyl, halogen, haloalkyl, haloalkoxy, hydroxy, hydroxyalkyl, alkylsulfonyl, alkylsulfonylalkyl, deuterium, trideuteromethyl, amino, —COOH, —$CONH_2$, —$SO_2CH^3$, cyano, spiro-heterocycloalkyl, heteroaryl, and oxo.

In certain embodiments, the nitrogen-containing heterocycloalkyl is optionally substituted with between 0 and 3 $R^6$ groups chosen from alkyl, halogen, $CONH_2$, $SO_2CH^3$, cyano, spiro-heterocycloalkyl, and oxo.

In certain embodiments, the nitrogen-containing heterocycloalkyl is chosen from:

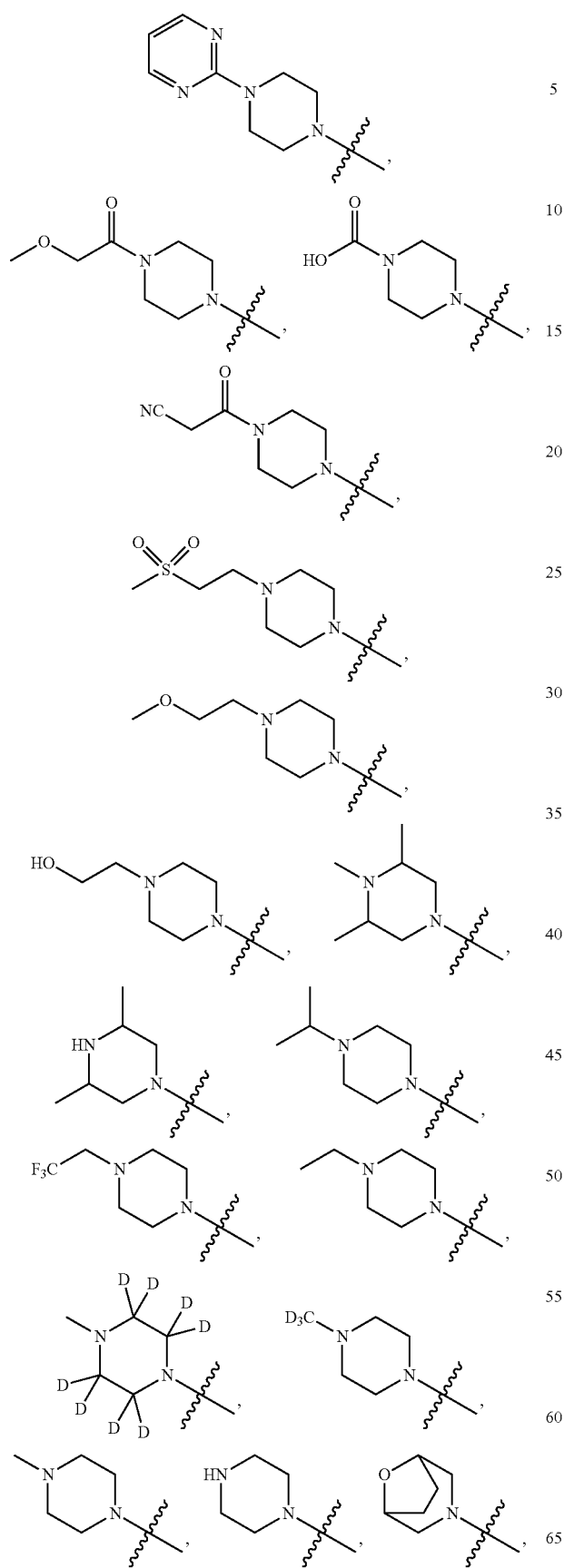
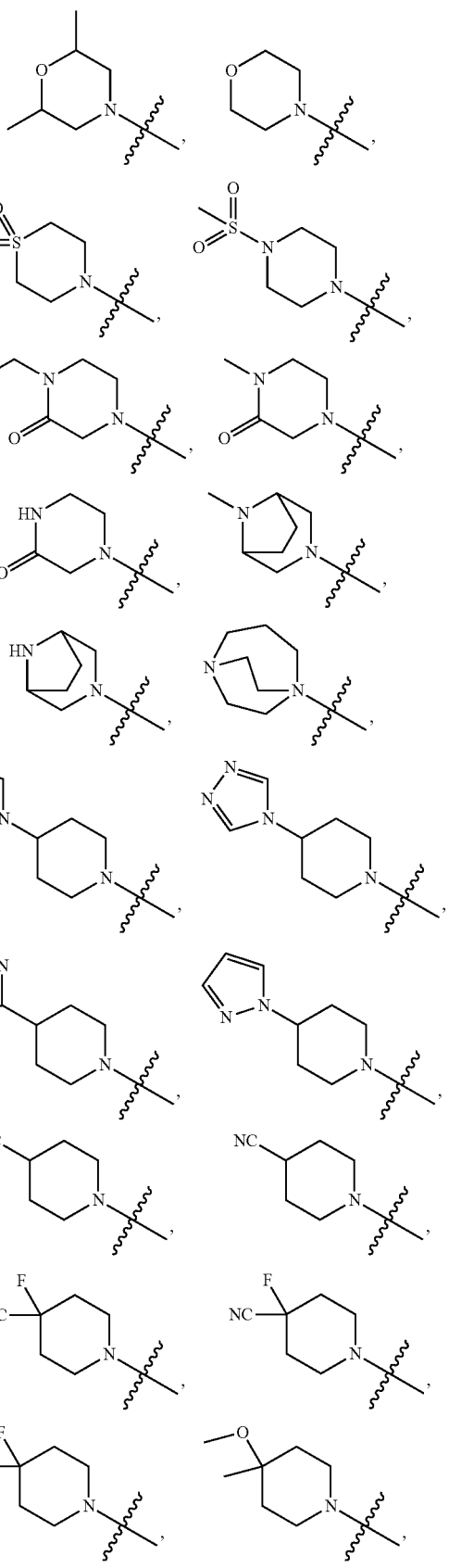

-continued
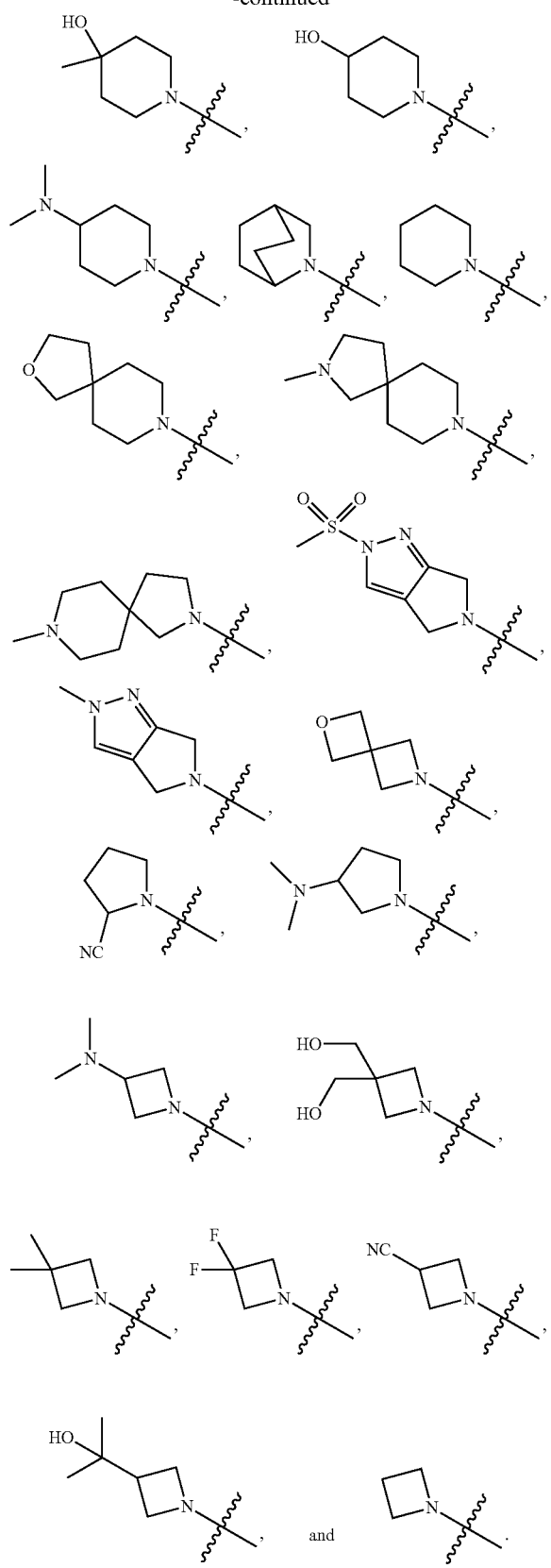
In certain embodiments, the nitrogen-containing heterocycloalkyl is chosen from:
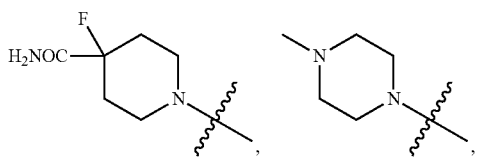
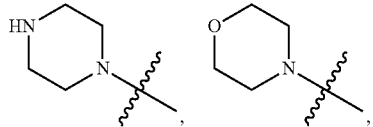
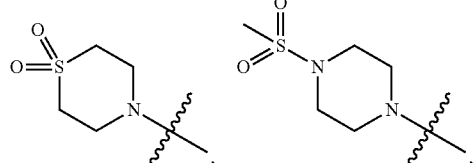
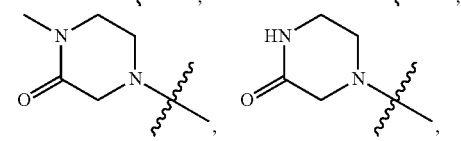
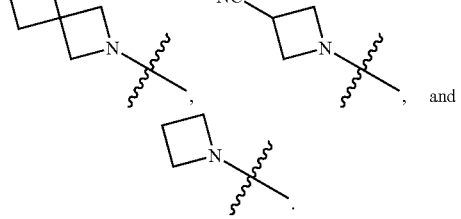
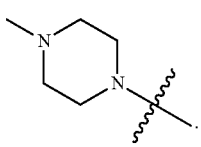 [SMILES: *N1CCN(C)CC1]
In certain embodiments, the nitrogen-containing heterocycloalkyl is:
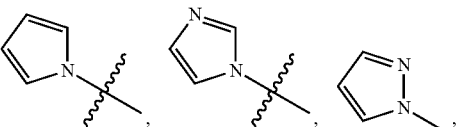
In certain embodiments, $R^{6a}$ is heteroaryl.
In certain embodiments, $R^{6a}$ is chosen from cyano, $S(O)_2N(CH_3)_2$,
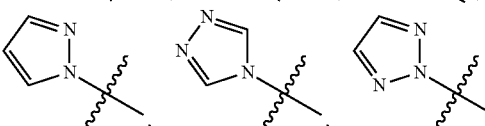
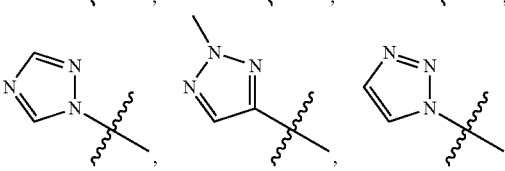

-continued

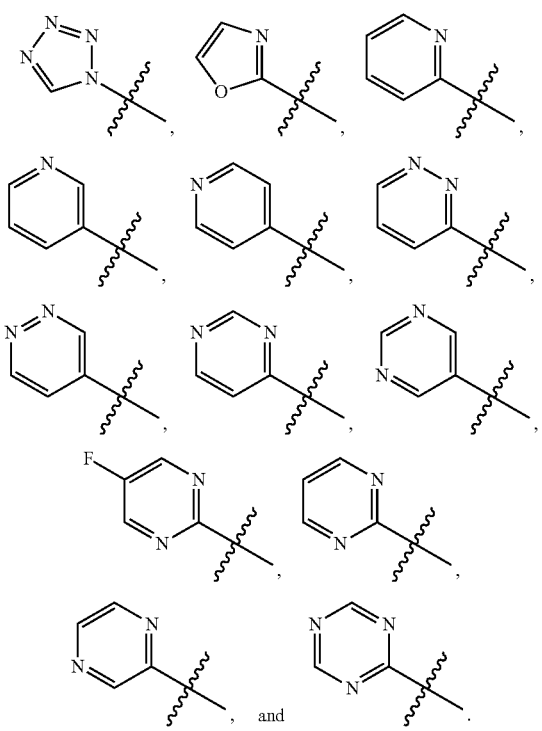

In certain embodiments, $R^{6a}$ is chosen from

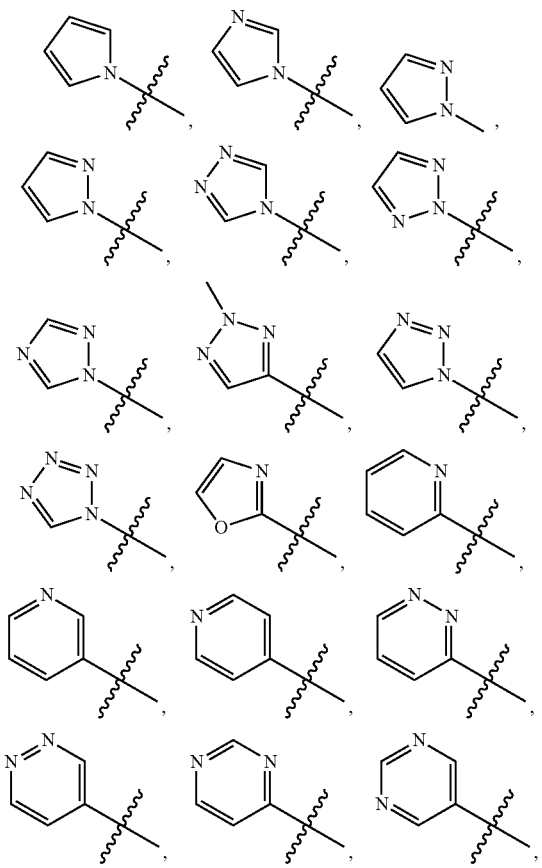

-continued

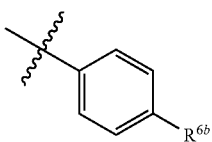
, and

In certain embodiments, $R^5$ is phenyl, which may be optionally substituted with between 0 and 3 $R^6$ groups.

In certain embodiments, $R^5$ is:

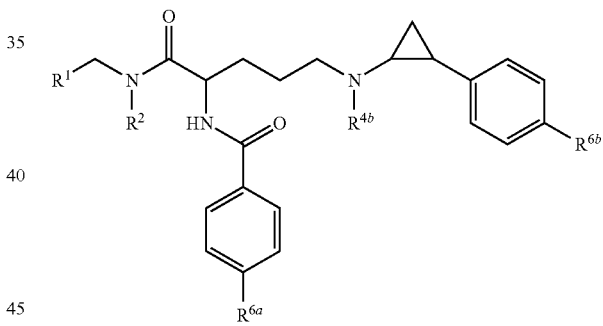

wherein $R^{6b}$ is chosen from halogen, hydroxy, and methoxy.

In certain embodiments, $R^{6b}$ is chosen from fluoro, methoxy, and hydroxy.

In certain embodiments, $R^{6b}$ is fluoro.

In certain embodiments, the compound has Formula V:

(V)

or a salt, polymorph, or solvate thereof, wherein:

$R^1$ and $R^2$ are each independently chosen from alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;

$R^{4b}$ is chosen from hydrogen, alkyl, alkenyl, alkynyl, and cycloalkyl;

$R^{6a}$ is chosen from heteroaryl, cyano, and $S(O)_2N(CH_3)_2$;

each $R^6$ and each $R^{6b}$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^7$, $SO_2R^7$, $NHSO_2R^7$, $NHSO_2NHR^7$, $NHCOR^7$, $NHCONHR^7$, $CONHR^7$, and $CONR^7R^8$; and $R^7$ and $R^8$ are independently chosen from hydrogen, aryl, and lower alkyl; or $R^7$ and $R^8$ may be taken together to form a nitrogen-containing heterocycloalkyl or heteroaryl ring, which may be optionally substituted with lower alkyl.

In certain embodiments, $R^{4b}$ is chosen from methyl and hydrogen.

In certain embodiments, $R^{4b}$ is hydrogen.

In certain embodiments, $R^{6a}$ is chosen from cyano, $S(O)_2N(CH_3)_2$,

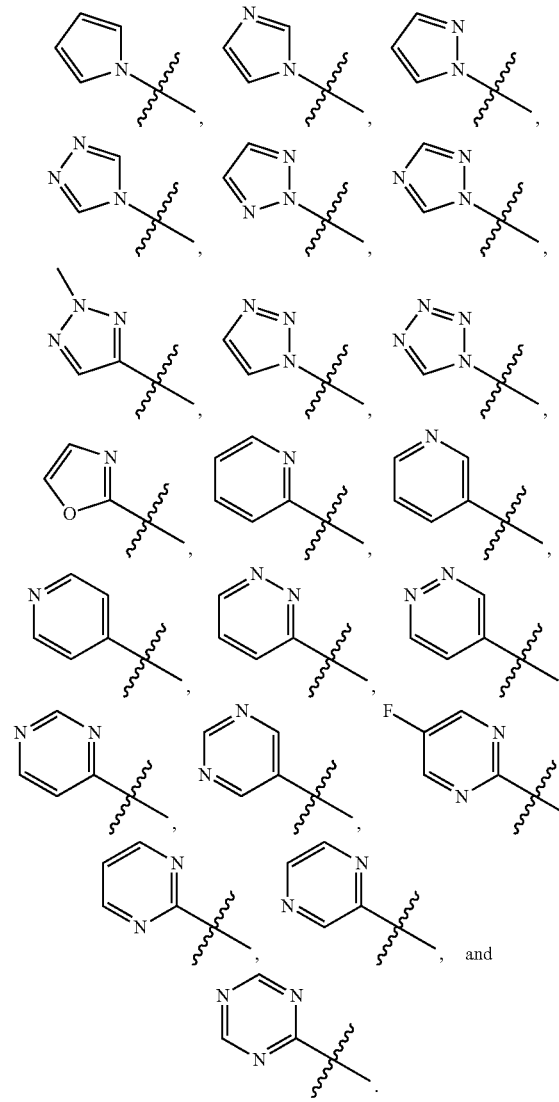

In certain embodiments, $R^1$ and $R^2$ are each independently chosen from alkyl, aminoalkyl, alkylsulfonylalkyl, alkoxyalkyl, and heteroaryl, and $R^1$ and $R^2$, together with the nitrogen to which they attach, form a nitrogen-containing heterocycloalkyl or heteroaryl ring, which may be optionally substituted with between 0 and 3 $R^6$ groups.

In certain embodiments, the nitrogen-containing heterocycloalkyl or heteroaryl ring formed by $R^1$ and $R^2$ together with the nitrogen to which they are attached contains 3 to eight atoms.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl is chosen from:

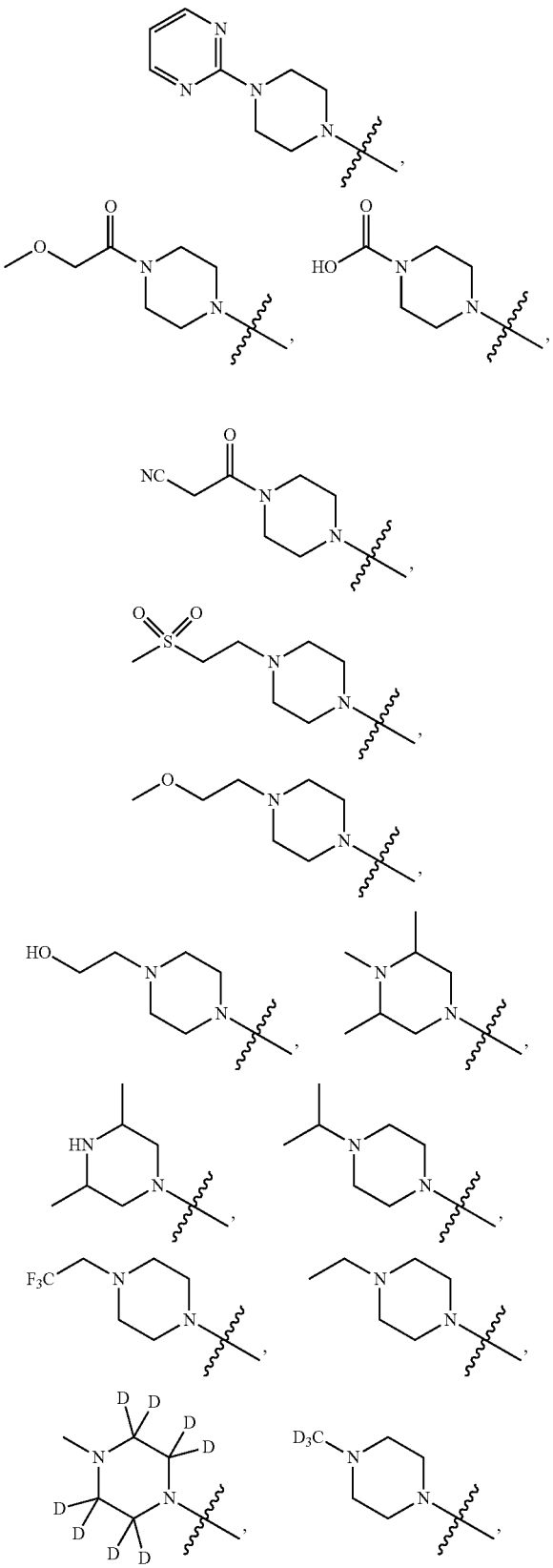

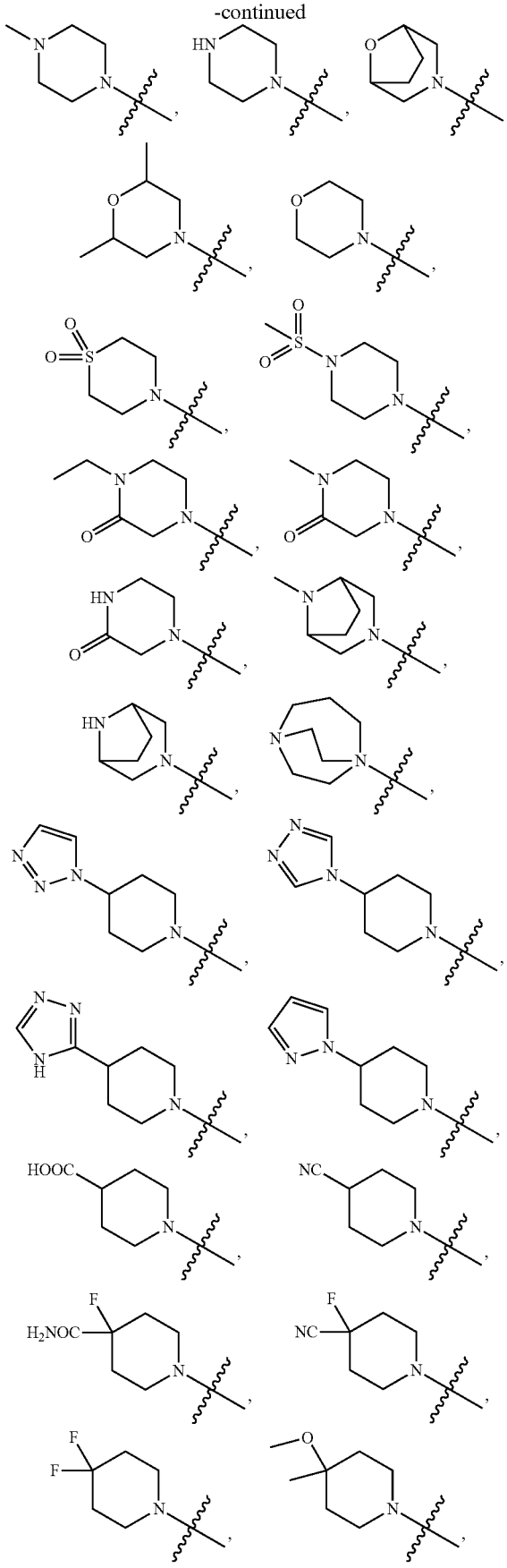
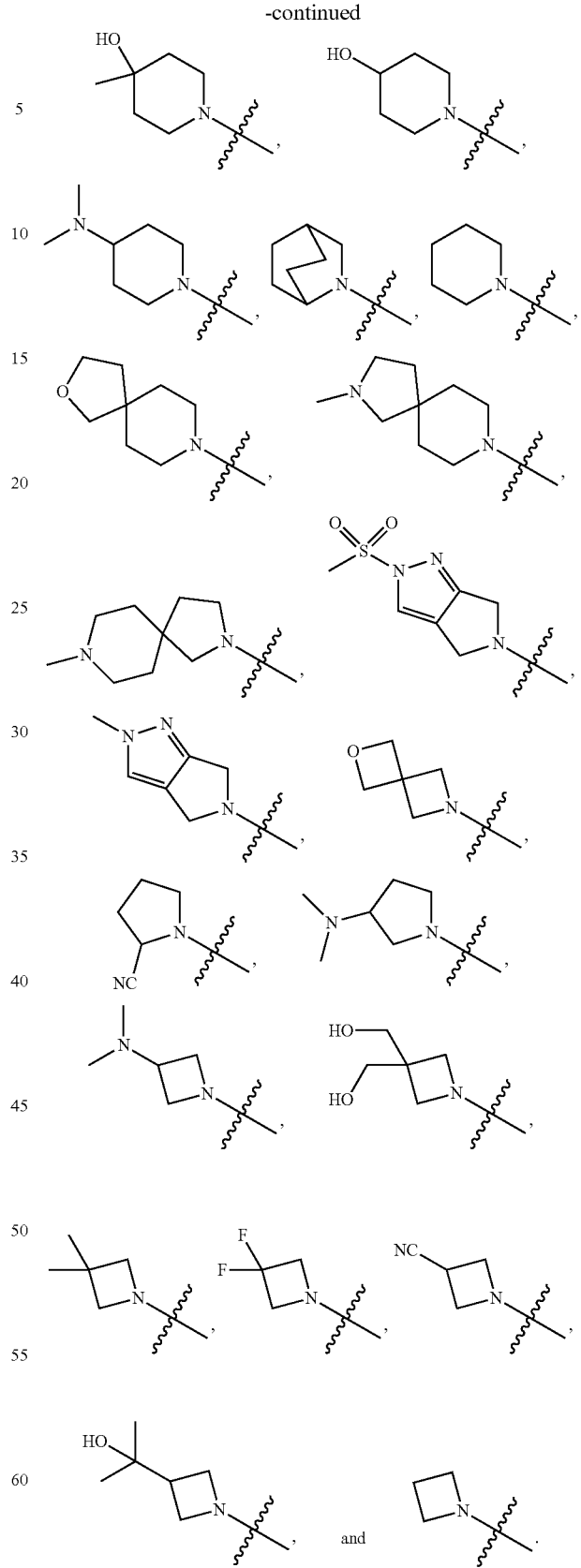
In certain embodiments, the nitrogen-containing heterocycloalkyl is chosen from:

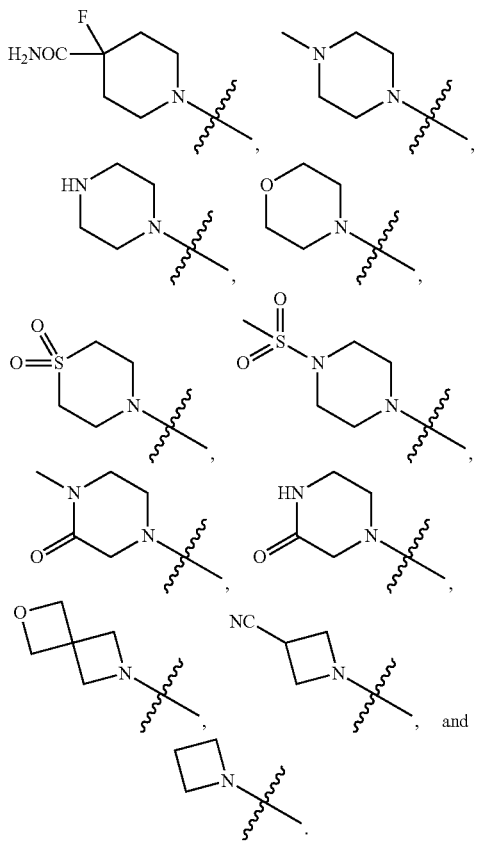

In certain embodiments, the nitrogen-containing heterocycloalkyl is:

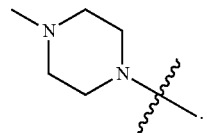 [SMILES: *N1CCN(C)CC1]

In certain embodiments, $R^{6b}$ is chosen from fluoro, methoxy, and hydroxy.

In certain embodiments, $R^{6b}$ is fluoro.

Also provided are embodiments wherein any embodiment above may be combined with any one or more of these embodiments, provided the combination is not mutually exclusive. As used herein, two embodiments are "mutually exclusive" when one is defined to be something which cannot overlap with the other. For example, an embodiment wherein Y is $CH_2$ is mutually exclusive with an embodiment wherein Y is $NR^{4b}$. However, an embodiment wherein $R^1$ and $R^2$ are taken together to form a nitrogen-containing heterocycloalkyl is not mutually exclusive with an embodiment wherein $R^5$ is phenyl optionally substituted with fluorine.

In certain embodiments, the compound is chosen from the Examples disclosed herein, or a salt, polymorph, or solvate thereof. In certain embodiments, the compound is chosen from the Examples disclosed herein, or a salt, polymorph, or solvate thereof, wherein $R^{6a}$ is chosen from heteroaryl, cyano, and $S(O)_2N(CH_3)_2$. In certain embodiments, the compound is chosen from the Examples disclosed herein, or a salt, polymorph, or solvate thereof, wherein $R^{6a}$ is chosen from heteroaryl and cyano. In certain embodiments, the compound is chosen from the Examples disclosed herein, or a salt, polymorph, or solvate thereof, wherein $R^{6a}$ is heteroaryl.

TABLE 1

Compound Examples

| Ex # | Structure | Name |
|---|---|---|
| 1 | 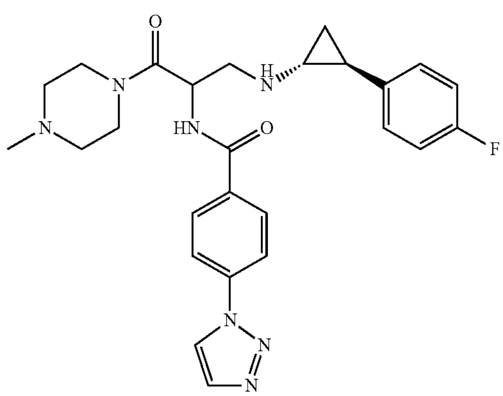 [SMILES: CN1CCN(C(=O)C(CN[C@@H]2C[C@H]2c2ccc(F)cc2)NC(=O)c2ccc(-n3ccnn3)cc2)CC1] | N-[3-[[(1R,2S)-2-(4-Fluorophenyl)cyclopropyl]amino]-1-(4-methylpiperazin-1-yl)-1-oxopropan-2-yl]-4-(1H-pyrazol-1-yl)benzamide |

TABLE 1-continued

Compound Examples

| Ex # | Structure | Name |
|---|---|---|
| 2 | 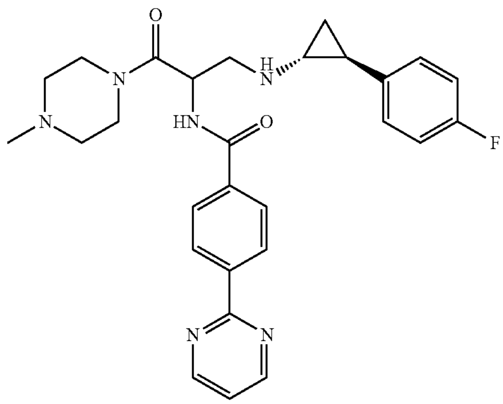 [SMILES: CN1CCN(C(=O)C(CN[C@@H]2C[C@H]2c2ccc(F)cc2)NC(=O)c2ccc(-c3ncccn3)cc2)CC1] | N-[3-[[(1R,2S)-2-(4-Fluorophenyl)cyclopropyl]amino]-1-(4-methylpiperazin-1-yl)-1-oxopropan-2-yl]-4-(pyrimidin-2-yl)benzamide |
| 3 | 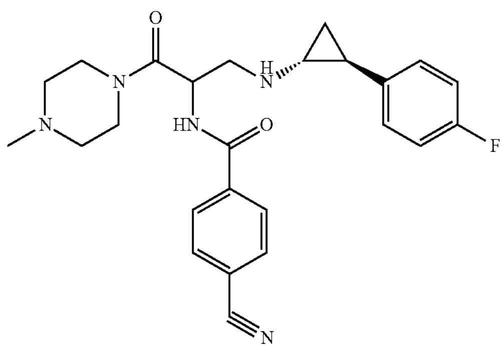 [SMILES: CN1CCN(C(=O)C(CN[C@@H]2C[C@H]2c2ccc(F)cc2)NC(=O)c2ccc(C#N)cc2)CC1] | N-[3-[[(1R,2S)-2-(4-Fluorophenyl)cyclopropyl]amino]-1-(4-methylpiperazin-1-yl)-1-oxopropan-2-yl]-4-cyanobenzamide |
| 4 | 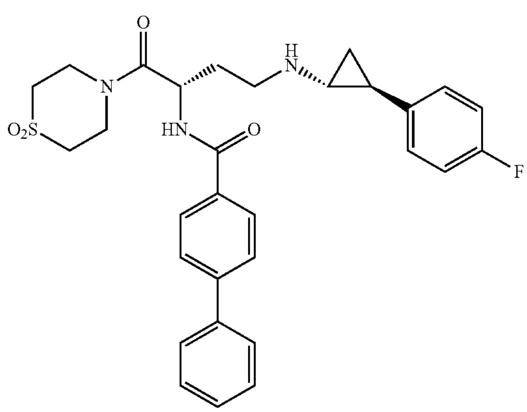 [SMILES: O=C(N[C@@H](CCN[C@@H]1C[C@H]1c1ccc(F)cc1)C(=O)N1CCS(=O)(=O)CC1)c1ccc(-c2ccccc2)cc1] | N-((S)-4-((1R,2S)-2-(4-fluorophenyl)cyclopropylamino)-1-oxo-1-(thiomorpholino-4,4-dioxide-1-yl)-butan-2-yl)biphenyl-4-carboxamide |
| 5 | 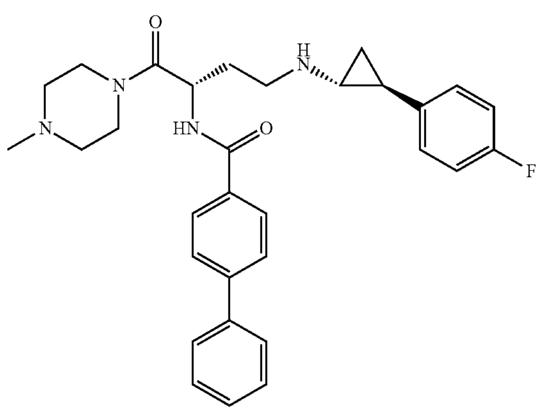 [SMILES: CN1CCN(C(=O)[C@H](CCN[C@@H]2C[C@H]2c2ccc(F)cc2)NC(=O)c2ccc(-c3ccccc3)cc2)CC1] | N-((S)-4-((1R,2S)-2-(4-fluorophenyl)cyclopropylamino)-1-(4-methylpiperazin-1-yl)-1-oxobutan-2-yl)biphenyl-4-carboxamide |

TABLE 1-continued

Compound Examples

| Ex # | Structure | Name |
|---|---|---|
| 6 | 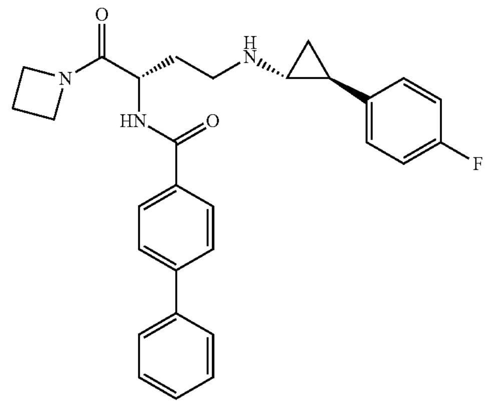 [SMILES: O=C(N[C@@H](CCN[C@@H]1C[C@H]1c1ccc(F)cc1)C(=O)N1CCC1)c1ccc(-c2ccccc2)cc1] | N-((S)-1-(azetidin-1-yl)-4-((1R,2S)-2-(4-fluorophenyl)cyclopropylamino)-1-oxobutan-2-yl)biphenyl-4-carboxamide |
| 7 | 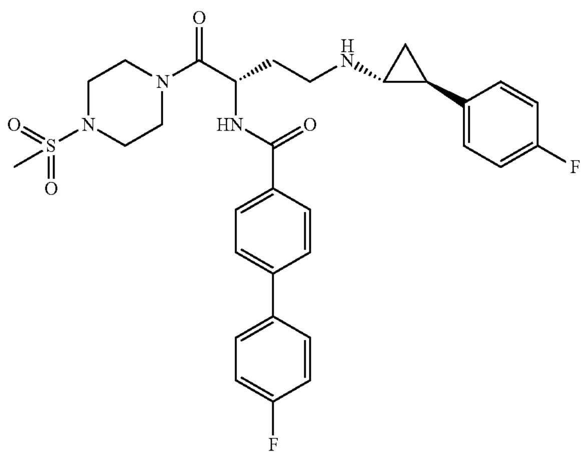 [SMILES: CS(=O)(=O)N1CCN(C(=O)[C@H](CCN[C@@H]2C[C@H]2c2ccc(F)cc2)NC(=O)c2ccc(-c3ccc(F)cc3)cc2)CC1] | 4'-fluoro-N-((S)-4-((1R,2S)-2-(4-fluorophenyl)cyclopropylamino)-1-(4-(methylsulfonyl)piperazin-1-yl)-1-oxobutan-2-yl)biphenyl-4-carboxamide |
| 8 | 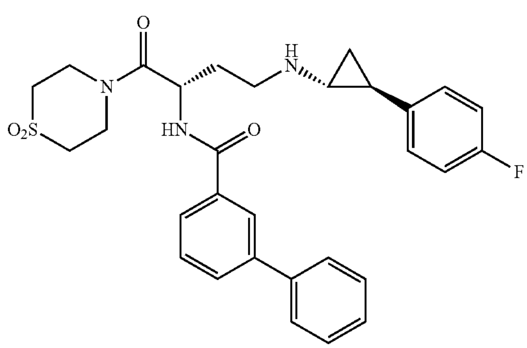 [SMILES: O=C(N[C@@H](CCN[C@@H]1C[C@H]1c1ccc(F)cc1)C(=O)N1CCS(=O)(=O)CC1)c1cccc(-c2ccccc2)c1] | N-((S)-4-((1R,2S)-2-(4-fluorophenyl)cyclopropylamino)-1-oxo-1-(thiomorpholino-4,4-dioxide-1-yl)-butan-2-yl)biphenyl-3-carboxamide |
| 9 | 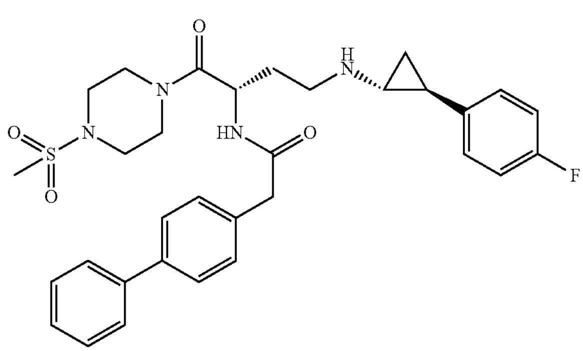 [SMILES: CS(=O)(=O)N1CCN(C(=O)[C@H](CCN[C@@H]2C[C@H]2c2ccc(F)cc2)NC(=O)Cc2ccc(-c3ccccc3)cc2)CC1] | 2-(biphenyl-4-yl)-N-((S)-4-((1R,2S)-2-(4-fluorophenyl)cyclopropylamino)-1-(4-(methylsulfonyl)piperazin-1-yl)-1-oxobutan-2-yl)acetamide |

TABLE 1-continued

Compound Examples

| Ex # | Structure | Name |
|---|---|---|
| 10 | 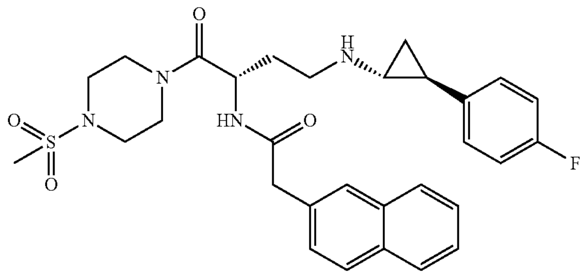 [SMILES: CS(=O)(=O)N1CCN(C(=O)[C@H](CCN[C@@H]2C[C@H]2c2ccc(F)cc2)NC(=O)Cc2ccc3ccccc3c2)CC1] | N-((S)-4-((1R,2S)-2-(4-fluorophenyl)cyclopropylamino)-1-(4-(methylsulfonyl)piperazin-1-yl)-1-oxobutan-2-yl)-2-(naphthalen-2-yl)acetamide |
| 11 | 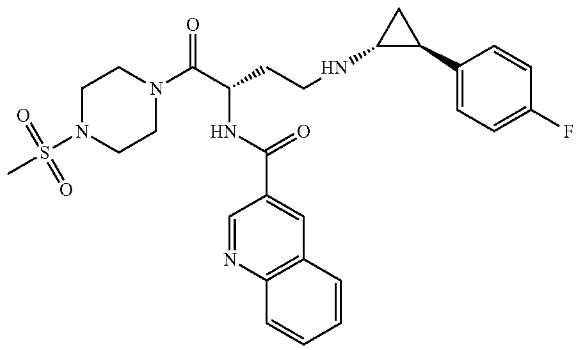 [SMILES: CS(=O)(=O)N1CCN(C(=O)[C@H](CCN[C@@H]2C[C@H]2c2ccc(F)cc2)NC(=O)c2cnc3ccccc3c2)CC1] | N-((S)-4-((1R,2S)-2-(4-fluorophenyl)cyclopropylamino)-1-(4-(methylsulfonyl)piperazin-1-yl)-1-oxobutan-2-yl)quinoline-3-carboxamide |
| 12 | 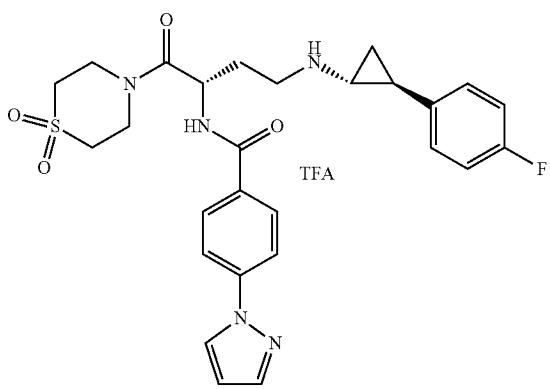 [SMILES: O=C(N[C@@H](CCN[C@@H]1C[C@H]1c1ccc(F)cc1)C(=O)N1CCS(=O)(=O)CC1)c1ccc(-n2cccn2)cc1] | N-((S)-4-((1R,2S)-2-(4-fluorophenyl)cyclopropylamino)-1-oxo-1-(thiomorpholino-4,4-dioxide-1-yl)-butan-2-yl)-4-(1H-pyrazol-1-yl)benzamide trifluoroacetic acid salt |
| 13 | 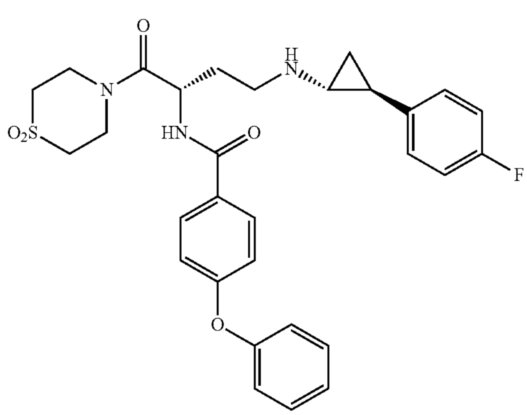 [SMILES: O=C(N[C@@H](CCN[C@@H]1C[C@H]1c1ccc(F)cc1)C(=O)N1CCS(=O)(=O)CC1)c1ccc(Oc2ccccc2)cc1] | N-((S)-4-((1R,2S)-2-(4-fluorophenyl)cyclopropylamino)-1-oxo-1-(thiomorpholino-4,4-dioxide-1-yl)-butan-2-yl)-4-phenoxybenzamide |

TABLE 1-continued

Compound Examples

| Ex # | Structure | Name |
|---|---|---|
| 14 | 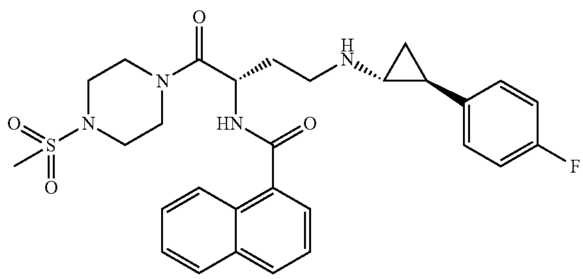 [SMILES: CS(=O)(=O)N1CCN(C(=O)[C@H](CCN[C@@H]2C[C@H]2c2ccc(F)cc2)NC(=O)c2cccc3ccccc23)CC1] | N-((S)-4-((1R,2S)-2-(4-fluorophenyl)cyclopropylamino)-1-(4-(methylsulfonyl)piperazin-1-yl)-1-oxobutan-2-yl)-1-naphthamide |
| 15 | 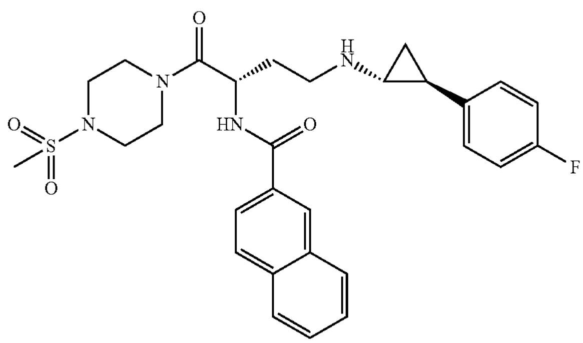 [SMILES: CS(=O)(=O)N1CCN(C(=O)[C@H](CCN[C@@H]2C[C@H]2c2ccc(F)cc2)NC(=O)c2ccc3ccccc3c2)CC1] | N-((S)-4-((1R,2S)-2-(4-fluorophenyl)cyclopropylamino)-1-(4-(methylsulfonyl)piperazin-1-yl)-1-oxobutan-2-yl)-2-naphthamide |
| 16 | 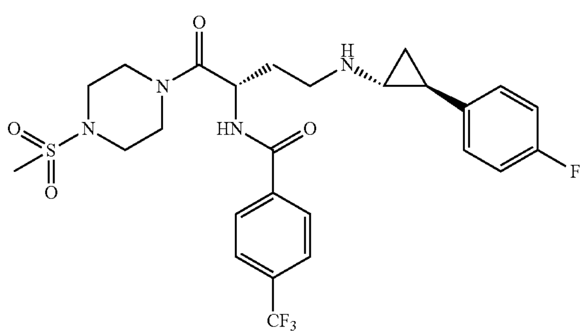 [SMILES: CS(=O)(=O)N1CCN(C(=O)[C@H](CCN[C@@H]2C[C@H]2c2ccc(F)cc2)NC(=O)c2ccc(C(F)(F)F)cc2)CC1] | N-((S)-4-((1R,2S)-2-(4-fluorophenyl)cyclopropylamino)-1-(4-(methylsulfonyl)piperazin-1-yl)-1-oxobutan-2-yl)-4-(trifluoromethyl)benzamide |
| 17 | 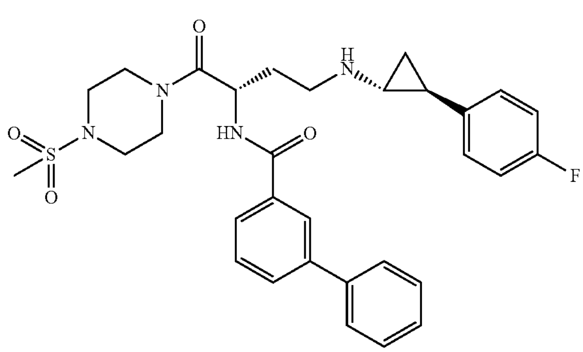 [SMILES: CS(=O)(=O)N1CCN(C(=O)[C@H](CCN[C@@H]2C[C@H]2c2ccc(F)cc2)NC(=O)c2cccc(-c3ccccc3)c2)CC1] | N-((S)-4-((1R,2S)-2-(4-fluorophenyl)cyclopropylamino)-1-(4-(methylsulfonyl)piperazin-1-yl)-1-oxobutan-2-yl)biphenyl-3-carboxamide |

TABLE 1-continued

Compound Examples

| Ex # | Structure | Name |
|---|---|---|
| 18 | 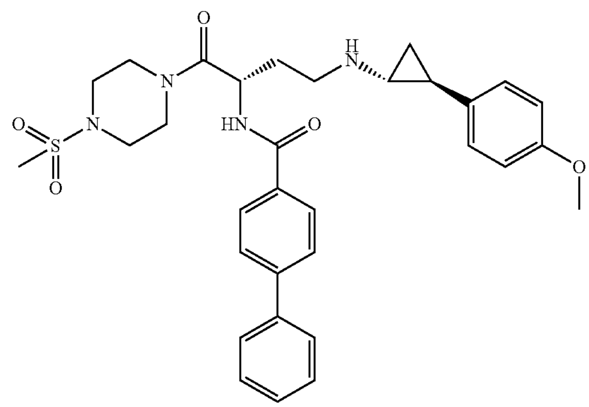 [SMILES: COc1ccc([C@@H]2C[C@H]2NCC[C@H](NC(=O)c2ccc(-c3ccccc3)cc2)C(=O)N2CCN(S(C)(=O)=O)CC2)cc1] | N-((S)-4-((1R,2S)-2-(4-methoxyphenyl)cyclopropylamino)-1-(4-(methylsulfonyl)piperazin-1-yl)-1-oxobutan-2-yl)biphenyl-4-carboxamide |
| 19 | 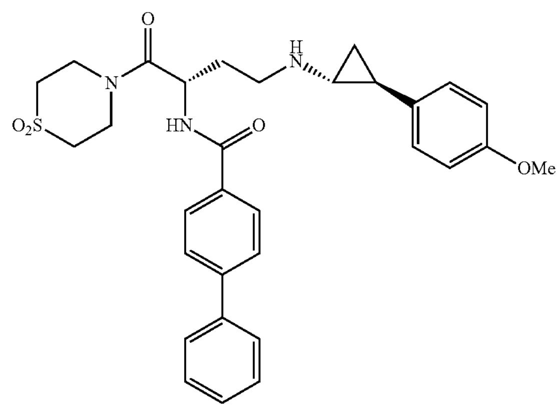 [SMILES: COc1ccc([C@@H]2C[C@H]2NCC[C@H](NC(=O)c2ccc(-c3ccccc3)cc2)C(=O)N2CCS(=O)(=O)CC2)cc1] | N-((S)-4-((1R,2S)-2-(4-methoxyphenyl)cyclopropylamino)-1-oxo-1-(thiomorpholino-4,4-dioxide-1-yl)-butan-2-yl)biphenyl-4-carboxamide |
| 20 | 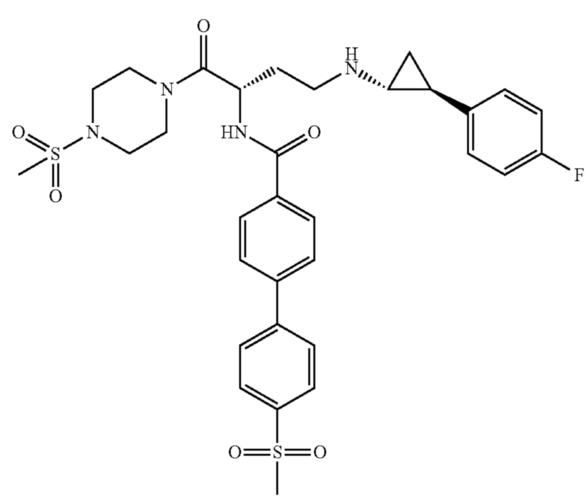 [SMILES: CS(=O)(=O)c1ccc(-c2ccc(C(=O)N[C@@H](CCN[C@@H]3C[C@H]3c3ccc(F)cc3)C(=O)N3CCN(S(C)(=O)=O)CC3)cc2)cc1] | N-((S)-4-((1R,2S)-2-(4-fluorophenyl)cyclopropylamino)-1-(4-(methylsulfonyl)piperazin-1-yl)-1-oxobutan-2-yl)-4'-(methylsulfonyl)biphenyl-4-carboxamide |

TABLE 1-continued
Compound Examples
| Ex # | Structure | Name |
|---|---|---|
| 21 | 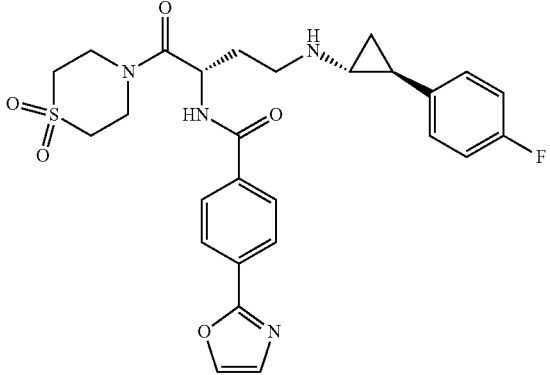 [SMILES: O=C(N[C@@H](CCN[C@@H]1C[C@H]1c1ccc(F)cc1)C(=O)N1CCS(=O)(=O)CC1)c1ccc(-c2ncco2)cc1] | N-((S)-4-((1R,2S)-2-(4-fluorophenyl)cyclopropylamino)-1-oxo-1-(thiomorpholino-4,4-dioxide-1-yl)-butan-2-yl)-4-(oxazol-2-yl)benzamide |
| 22 | 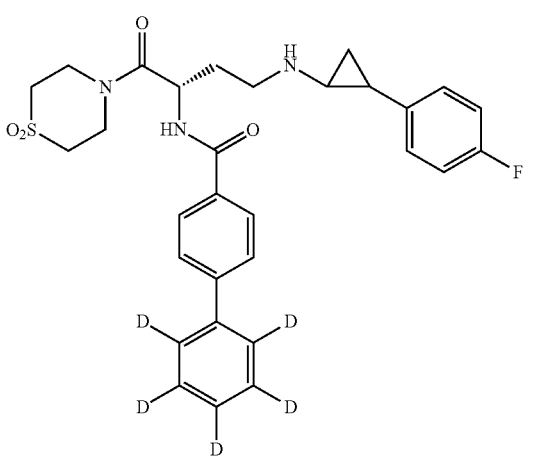 [SMILES: [2H]c1c([2H])c([2H])c(-c2ccc(C(=O)N[C@@H](CCNC3CC3c3ccc(F)cc3)C(=O)N3CCS(=O)(=O)CC3)cc2)c([2H])c1[2H]] | N-((2S)-4-(2-(4-fluorophenyl)cyclopropylamino)-1-oxo-1-(thiomorpholino-4,4-dioxide-1-yl)-butan-2-yl)-(2',3',4',5',6'-$d_5$)-biphenyl-4-carboxamide |
| 23 | 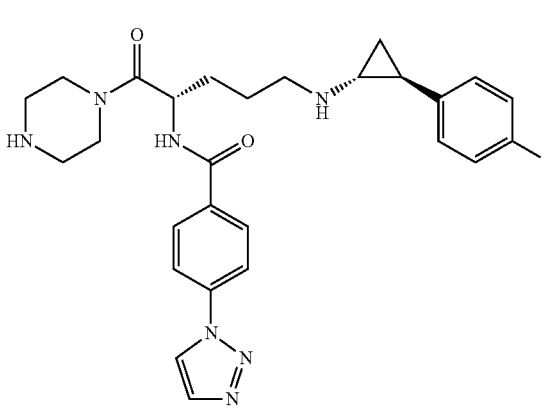 | N-[(2S)-5-[[(1R,2S)-2-(4-fluorophenyl)cyclopropyl]amino]-1-oxo-1-(1H-1,2,3-triazin-1-yl)pentan-2-yl]-4-(pyrimidin-2-yl)benzamide |

TABLE 1-continued

Compound Examples

| Ex # | Structure | Name |
|---|---|---|
| 24 | 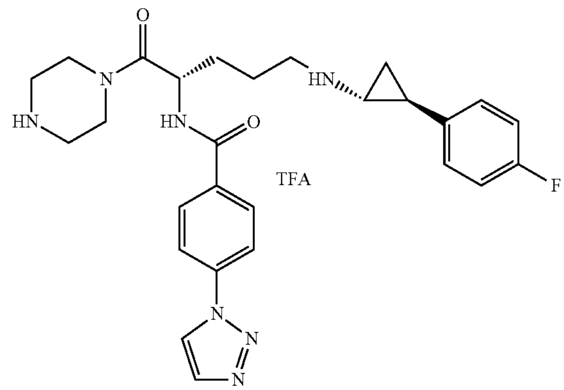 [SMILES: O=C(N[C@@H](CCCN[C@@H]1C[C@H]1c1ccc(F)cc1)C(=O)N1CCNCC1)c1ccc(-n2ccnn2)cc1] | N-[(2S)-5-[[(1R,2S)-2-(4-fluorophenyl)cyclopropyl]amino]-1-(azetidin-4-yl)-1-oxopentan-2-yl]-4-(1H-pyrazol-1-yl)benzamide trifluoroacetic acid salt |
| 25 | 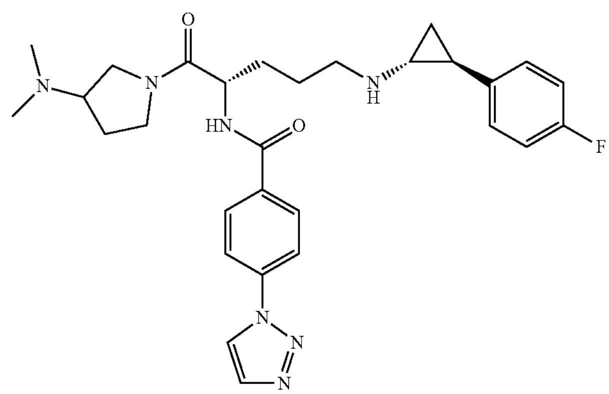 [SMILES: CN(C)C1CCN(C(=O)[C@H](CCCN[C@@H]2C[C@H]2c2ccc(F)cc2)NC(=O)c2ccc(-n3ccnn3)cc2)C1] | N-[(2S)-1-[3-(dimethylamino)pyrrolidin-1-yl]-5-[[(1R,2S)-2-(4-fluorophenyl)-cyclopropyl]amino]-1-oxopentan-2-yl]-4-(1H-1,2,3-triazol-1-yl)benzamide |
| 26 | 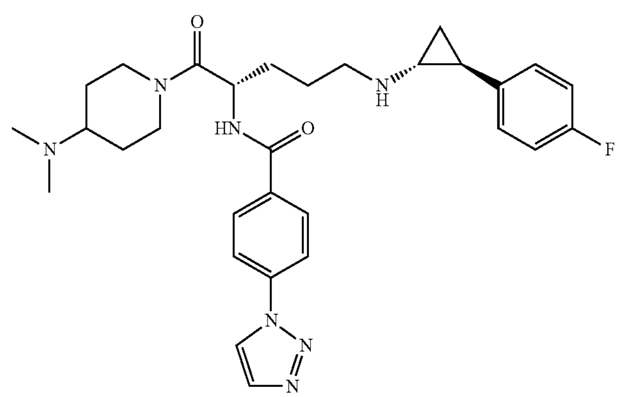 [SMILES: CN(C)C1CCN(C(=O)[C@H](CCCN[C@@H]2C[C@H]2c2ccc(F)cc2)NC(=O)c2ccc(-n3ccnn3)cc2)CC1] | N-[(2S)-1-[4-(dimethylamino)piperidin-1-yl]-5-[[(1R,2S)-2-(4-fluorophenyl)-cyclopropyl]amino]-1-oxopentan-2-yl]-4-(1H-1,2,3-triazol-1-yl)benzamide |
| 27 | 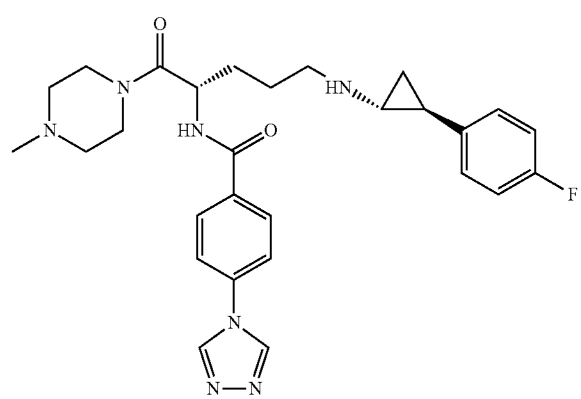 [SMILES: CN1CCN(C(=O)[C@H](CCCN[C@@H]2C[C@H]2c2ccc(F)cc2)NC(=O)c2ccc(-n3cnnc3)cc2)CC1] | N-[(2S)-5-[[(1R,2S)-2-(4-fluorophenyl)cyclopropyl]amino]-1-(4-methylpiperazin-1-yl)-1-oxopentan-2-yl]-4-(1,2,4-triazol-4-yl)benzamide |

TABLE 1-continued

Compound Examples

| Ex # | Structure | Name |
|---|---|---|
| 28 | 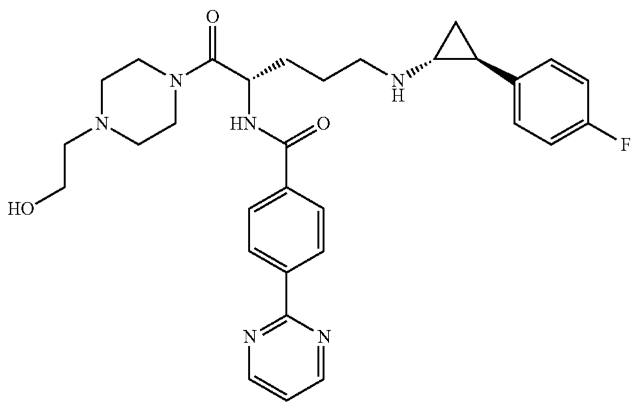 [SMILES: O=C(N[C@@H](CCCN[C@@H]1C[C@H]1c1ccc(F)cc1)C(=O)N1CCN(CCO)CC1)c1ccc(-c2ncccn2)cc1] | N-[(2S)-5-[[(1R,2S)-2-(4-Fluorophenyl)cyclopropyl]amino]-1-[4-(2-hydroxyethyl)piperazin-1-yl]-1-oxopentan-2-yl]-4-(pyrimidin-2-yl)benzamide |
| 29 | 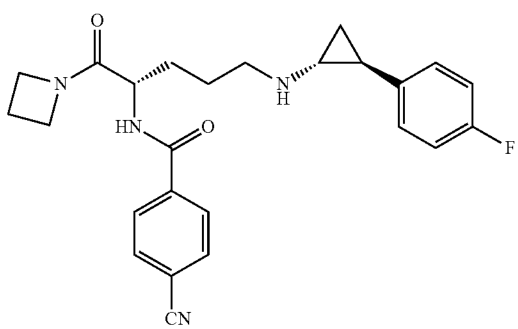 [SMILES: N#Cc1ccc(C(=O)N[C@@H](CCCN[C@@H]2C[C@H]2c2ccc(F)cc2)C(=O)N2CCC2)cc1] | N-[(2S)-5-[[(1R,2S)-2-(4-Fluorophenyl)cyclopropyl]amino]-1-(azetidin-1-yl)-1-oxopentan-2-yl]-4-cyanobenzamide |
| 30 | 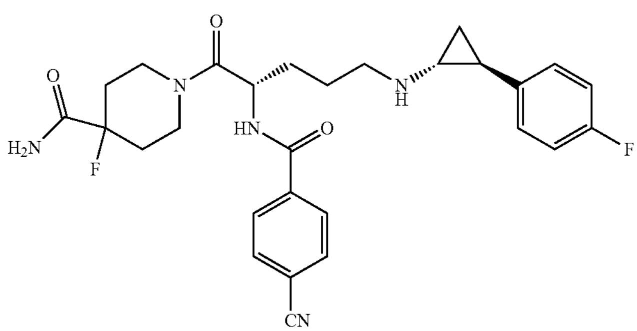 [SMILES: N#Cc1ccc(C(=O)N[C@@H](CCCN[C@@H]2C[C@H]2c2ccc(F)cc2)C(=O)N2CCC(F)(C(N)=O)CC2)cc1] | 1-((S)-2-(4-cyanobenzamido)-5-((1R,2S)-2-(4-fluorophenyl)cyclopropylamino)pentanoyl)-4-fluoropiperidine-4-carboxamide |
| 31 | 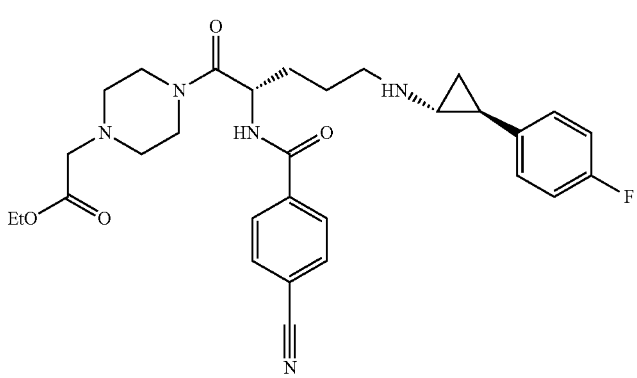 [SMILES: CCOC(=O)CN1CCN(C(=O)[C@H](CCCN[C@@H]2C[C@H]2c2ccc(F)cc2)NC(=O)c2ccc(C#N)cc2)CC1] | Ethyl 2-[4-[(2S)-2-[(4-cyanophenyl)formamido]-5-[[(1R,2S)-2-(4-fluorophenyl)cyclopropyl]amino]pentanoyl]piperazin-1-yl]acetate |

TABLE 1-continued

Compound Examples

| Ex # | Structure | Name |
|---|---|---|
| 32 | 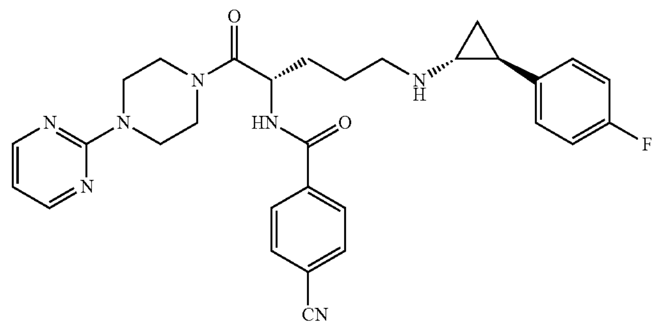 [SMILES: N#Cc1ccc(C(=O)N[C@@H](CCCN[C@@H]2C[C@H]2c2ccc(F)cc2)C(=O)N2CCN(c3ncccn3)CC2)cc1] | 4-cyano-N-[(2S)-5-[[(1R,2S)-2-(4-fluorophenyl)cyclopropyl]amino]-1-oxo-1-[4-(pyrimidin-2-yl)piperazin-1-yl]pentan-2-yl]benzamide |
| 33 | 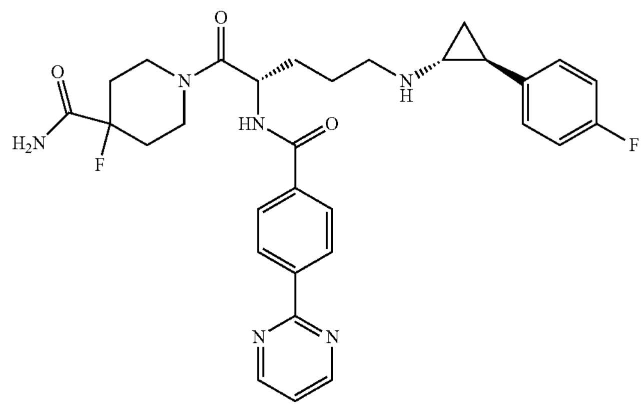 [SMILES: NC(=O)C1(F)CCN(C(=O)[C@H](CCCN[C@@H]2C[C@H]2c2ccc(F)cc2)NC(=O)c2ccc(-c3ncccn3)cc2)CC1] | 4-fluoro-1-((S)-5-((1R,2S)-2-(4-fluorophenyl)cyclopropylamino)-2-(4-(pyrimidin-2-yl)benzamido)pentanoyl)piperidine-4-carboxamide |
| 34 | 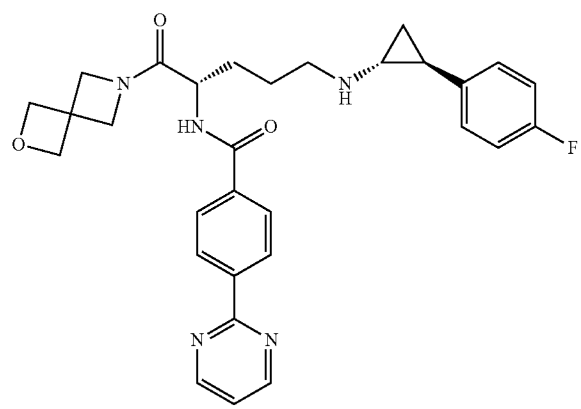 [SMILES: O=C(N[C@@H](CCCN[C@@H]1C[C@H]1c1ccc(F)cc1)C(=O)N1CC2(COC2)C1)c1ccc(-c2ncccn2)cc1] | N-[(2S)-5-[[(1R,2S)-2-(4-fluorophenyl)cyclopropyl]amino]-1-[2-oxa-6-azaspiro[3.3]heptan-6-yl]-1-oxopentan-2-yl]-4-(pyrimidin-2-yl)benzamide |
| 35 | 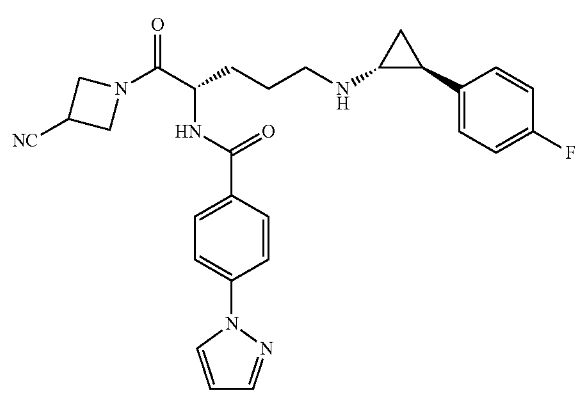 [SMILES: N#CC1CN(C(=O)[C@H](CCCN[C@@H]2C[C@H]2c2ccc(F)cc2)NC(=O)c2ccc(-n3cccn3)cc2)C1] | N-[(2S)-1-(3-cyanoazetidin-1-yl)-5-[[(1R,2S)-2-(4-fluorophenyl)cyclopropyl]amino]-1-oxopentan-2-yl]-4-(1H-pyrazol-1-yl)benzamide |

TABLE 1-continued

Compound Examples

| Ex # | Structure | Name |
|---|---|---|
| 36 | 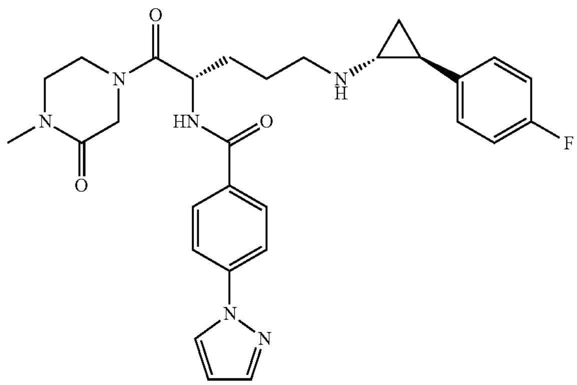 [SMILES: CN1CCN(C(=O)[C@H](CCCN[C@@H]2C[C@H]2c2ccc(F)cc2)NC(=O)c2ccc(-n3cccn3)cc2)CC1=O] | N-((S)-5-(((1R,2S)-2-(4-fluorophenyl)cyclopropylamino)-1-(4-methyl-3-oxopiperazin-1-yl)-1-oxopentan-2-yl)-4-(1H-pyrazol-1-yl)benzamide |
| 37 | 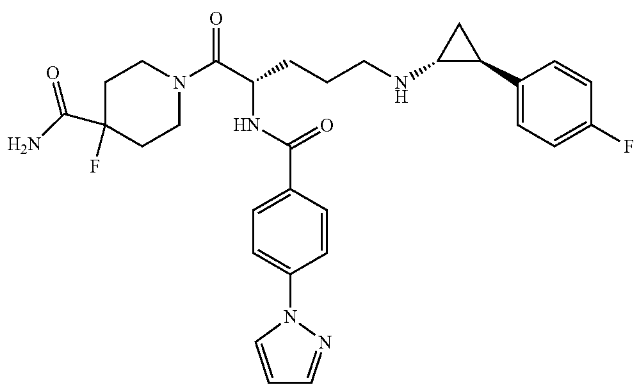 [SMILES: NC(=O)C1(F)CCN(C(=O)[C@H](CCCN[C@@H]2C[C@H]2c2ccc(F)cc2)NC(=O)c2ccc(-n3cccn3)cc2)CC1] | 1-((S)-2-(4-(1H-pyrazol-1-yl)benzamido)-5-(((1R,2S)-2-(4-fluorophenyl)cyclopropylamino)pentanoyl)-4-fluoropiperidine-4-carboxamide |
| 38 | 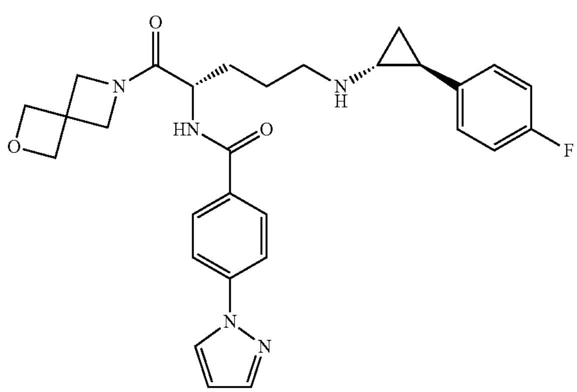 [SMILES: O=C(N[C@@H](CCCN[C@@H]1C[C@H]1c1ccc(F)cc1)C(=O)N1CC2(COC2)C1)c1ccc(-n2cccn2)cc1] | N-[(2S)-5-[[(1R,2S)-2-(4-fluorophenyl)cyclopropyl]amino]-1-[2-oxa-6-azaspiro[3.3]heptan-6-yl]-1-oxopentan-2-yl]-4-(1H-pyrazol-1-yl)benzamide |
| 39 | This example is intentionally left blank. | |
| 40 | This example is intentionally left blank. | |

TABLE 1-continued

Compound Examples

| Ex # | Structure | Name |
|---|---|---|
| 41 | 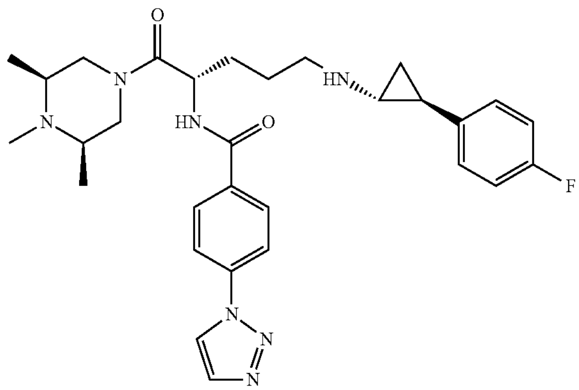 [SMILES: C[C@@H]1CN(C(=O)[C@H](CCCN[C@@H]2C[C@H]2c2ccc(F)cc2)NC(=O)c2ccc(-n3ccnn3)cc2)C[C@H](C)N1C] | N-[(2S)-5-[[(1R,2S)-2-(4-Fluorophenyl)cyclopropyl]amino]-1-oxo-1-[(3R,5S)-3,4,5-trimethylpiperazin-1-yl]pentan-2-yl]-4-(1H-1,2,3-triazol-1-yl)benzamide |
| 42 | 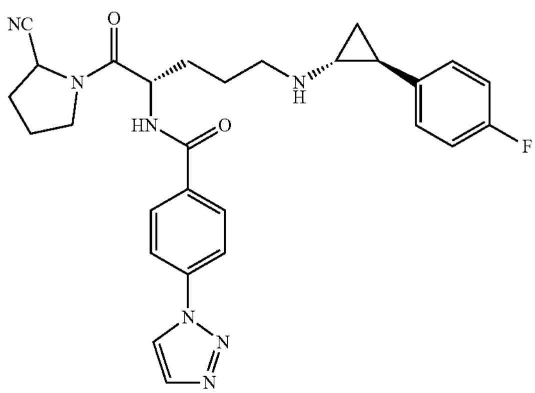 [SMILES: N#CC1CCCN1C(=O)[C@H](CCCN[C@@H]1C[C@H]1c1ccc(F)cc1)NC(=O)c1ccc(-n2ccnn2)cc1] | N-[(2S)-5-[[(1R,2S)-2-(4-fluorophenyl)cyclopropyl]amino]-1-(2-cyanopyrrolidine-1-yl)-1-oxopentan-2-yl]-4-(1H-1,2,3-triazol-1-yl)benzamide |
| 43 | 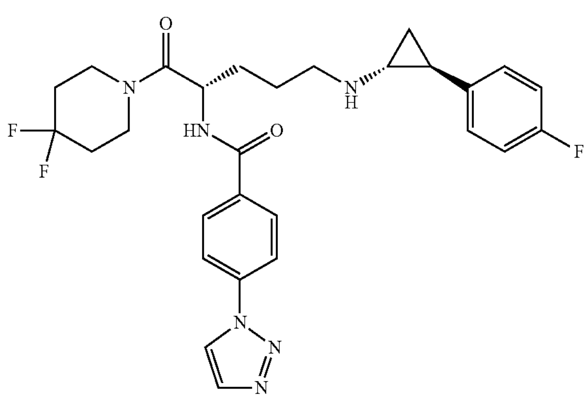 [SMILES: O=C(N[C@@H](CCCN[C@@H]1C[C@H]1c1ccc(F)cc1)C(=O)N1CCC(F)(F)CC1)c1ccc(-n2ccnn2)cc1] | N-[(2S)-1-(4,4-difluoropiperidin-1-yl)-5-[[(1R,2S)-2-(4-fluorophenyl)cyclopropyl]amino]-1-oxopentan-2-yl]-4-(1H-1,2,3-triazol-1-yl)benzamide |
| 44 | 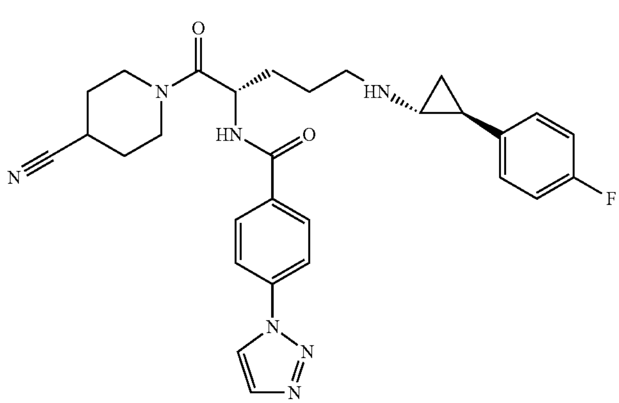 [SMILES: N#CC1CCN(C(=O)[C@H](CCCN[C@@H]2C[C@H]2c2ccc(F)cc2)NC(=O)c2ccc(-n3ccnn3)cc2)CC1] | N-[(2S)-5-[[(1R,2S)-2-(4-fluorophenyl)cyclopropyl]amino]-1-(4-cyanopiperidin-1-yl)-1-oxopentan-2-yl]-4-(1H-1,2,3-triazol-1-yl)benzamide |

TABLE 1-continued

Compound Examples

| Ex # | Structure | Name |
|---|---|---|
| 45 | 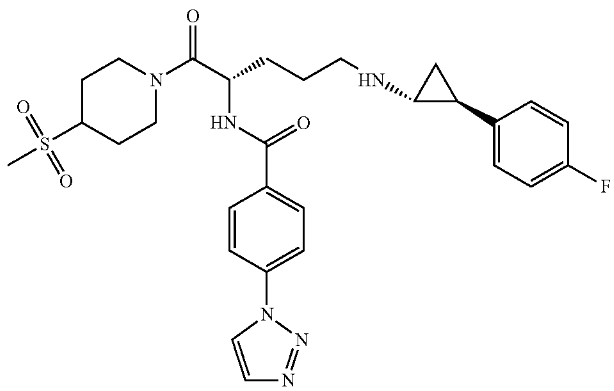 [SMILES: CS(=O)(=O)C1CCN(C(=O)[C@H](CCCN[C@@H]2C[C@H]2c2ccc(F)cc2)NC(=O)c2ccc(-n3ccnn3)cc2)CC1] | N-[(2S)-5-[[(1R,2S)-2-(4-fluorophenyl)cyclopropyl]amino]-1-(4-methanesulfonylpiperidin-1-yl)-1-oxopentan-2-yl]-4-(1H-1,2,3-triazol-1-yl)benzamide |
| 46 | 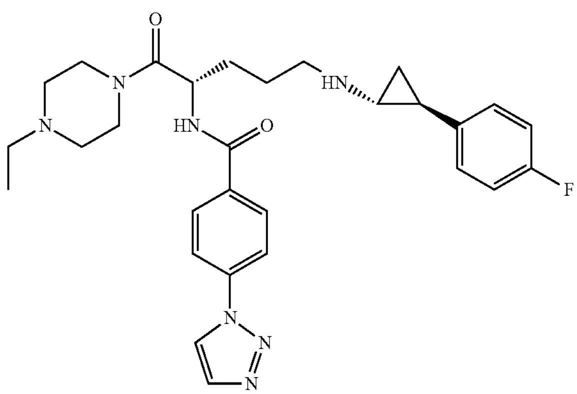 [SMILES: CCN1CCN(C(=O)[C@H](CCCN[C@@H]2C[C@H]2c2ccc(F)cc2)NC(=O)c2ccc(-n3ccnn3)cc2)CC1] | N-[(2S)-1-(4-Ethylpiperazin-1-yl)-5-[[(1R,2S)-2-(4-fluorophenyl)cyclopropyl]amino]-1-oxopentan-2-yl]-4-(1H-1,2,3-triazol-1-yl)benzamide |
| 47 | 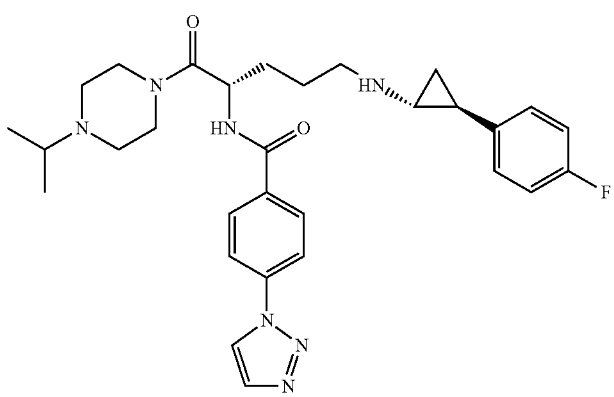 [SMILES: CC(C)N1CCN(C(=O)[C@H](CCCN[C@@H]2C[C@H]2c2ccc(F)cc2)NC(=O)c2ccc(-n3ccnn3)cc2)CC1] | N-[(2S)-5-[[(1R,2S)-2-(4-Fluorophenyl)cyclopropyl]amino]-1-oxo-1-[4-(propan-2-yl)piperazin-1-yl]pentan-2-yl]-4-(1H-1,2,3-triazol-1-yl)benzamide |
| 48 | 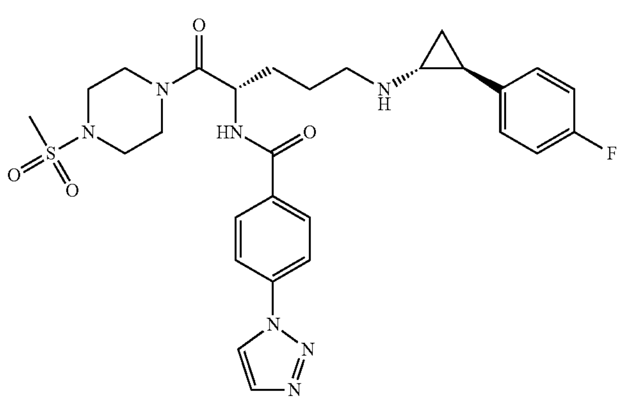 [SMILES: CS(=O)(=O)N1CCN(C(=O)[C@H](CCCN[C@@H]2C[C@H]2c2ccc(F)cc2)NC(=O)c2ccc(-n3ccnn3)cc2)CC1] | N-[(2S)-5-[[(2S)-1-(4-fluorophenyl)-1^[3]-oxiran-2-yl]amino]-1-(4-methanesulfonylpiperazin-1-yl)-1-oxopentan-2-yl]-4-(1H-1,2,3-triazol-1-yl)benzamide |

TABLE 1-continued

Compound Examples

| Ex # | Structure | Name |
|---|---|---|
| 49 | 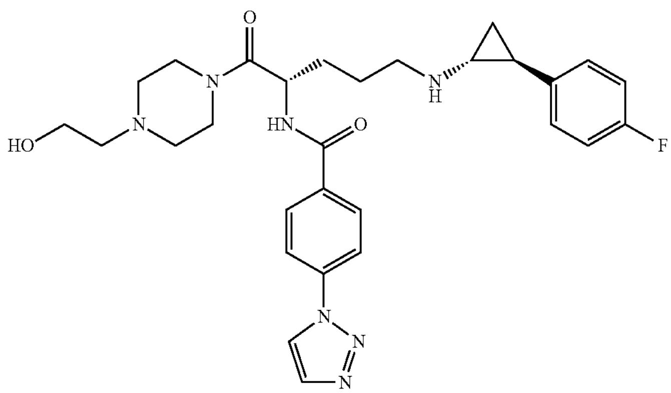 [SMILES: O=C(N[C@@H](CCCN[C@@H]1C[C@H]1c1ccc(F)cc1)C(=O)N1CCN(CCO)CC1)c1ccc(-n2ccnn2)cc1] | N-[(2S)-5-[[(1R,2S)-2-(4-Fluorophenyl)cyclopropyl]amino]-1-[4-(2-hydroxyethyl) 1H-1,2,3-triazol-1-yl]-1-oxopentan-2-yl]-4-(pyrimidin-2-yl)benzamide |
| 50 | 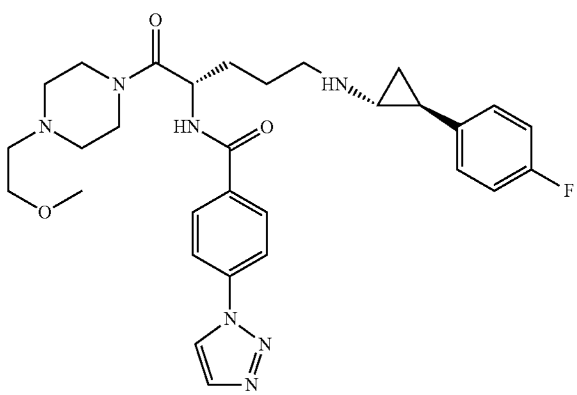 [SMILES: COCCN1CCN(C(=O)[C@H](CCCN[C@@H]2C[C@H]2c2ccc(F)cc2)NC(=O)c2ccc(-n3ccnn3)cc2)CC1] | N-[(2S)-5-[[(1R,2S)-2-(4-Fluorophenyl)cyclopropyl]amino]-1-(4-(2-methoxyethyl)-piperazin-1-yl)-1-oxopentan-2-yl]-4-(1H-1,2,3-triazol-1-yl)benzamide |
| 51 | 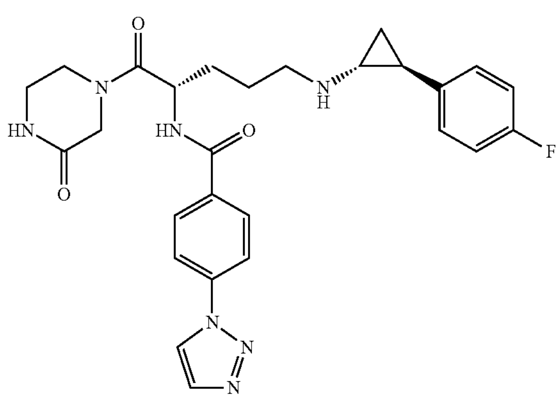 [SMILES: O=C1CN(C(=O)[C@H](CCCN[C@@H]2C[C@H]2c2ccc(F)cc2)NC(=O)c2ccc(-n3ccnn3)cc2)CCN1] | N-[(2S)-5-[[(1R,2S)-2-(4-fluorophenyl)cyclopropyl]amino]-1-(4-methyl-3-oxopiperazin-1-yl)-1-oxopentan-2-yl]-4-(1,2,3-triazol--yl)benzamide |

TABLE 1-continued

Compound Examples

| Ex # | Structure | Name |
|---|---|---|
| 52 | 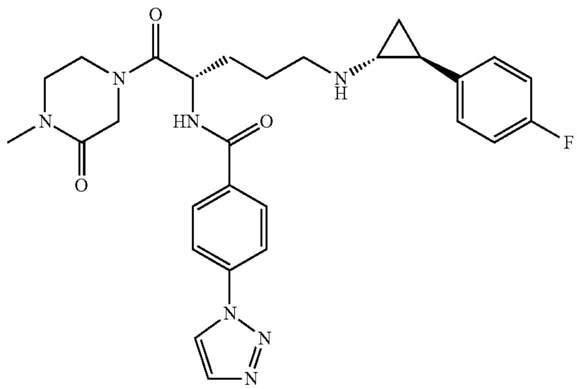 [SMILES: CN1CCN(C(=O)[C@H](CCCN[C@@H]2C[C@H]2c2ccc(F)cc2)NC(=O)c2ccc(-n3ccnn3)cc2)CC1=O] | N-[(2S)-5-[[(1R,2S)-2-(4-fluorophenyl)cyclopropyl]amino]-1-oxo-1-(3-oxopiperazin-1-yl)pentan-2-yl]-4-(1H-1,2,3-triazol-1-yl)benzamide |
| 53 | 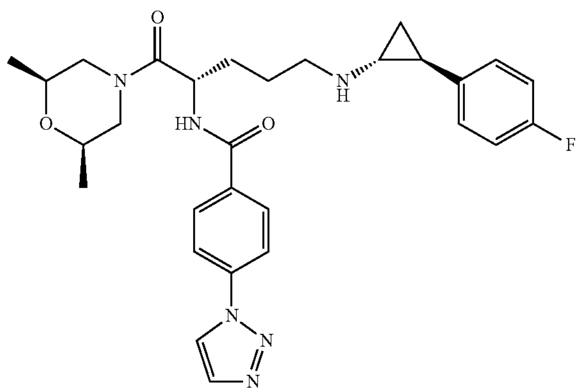 [SMILES: C[C@@H]1CN(C(=O)[C@H](CCCN[C@@H]2C[C@H]2c2ccc(F)cc2)NC(=O)c2ccc(-n3ccnn3)cc2)C[C@H](C)O1] | N-[(2S)-1-[(2R,6S)-2,6-dimethylmorpholin-4-yl]-5-[[(1R,2S)-2-(4-fluorophenyl)cyclopropyl]amino]-1-oxopentan-2-yl]-4-(1H-1,2,3-triazol-1-yl)benzamide |
| 54 | 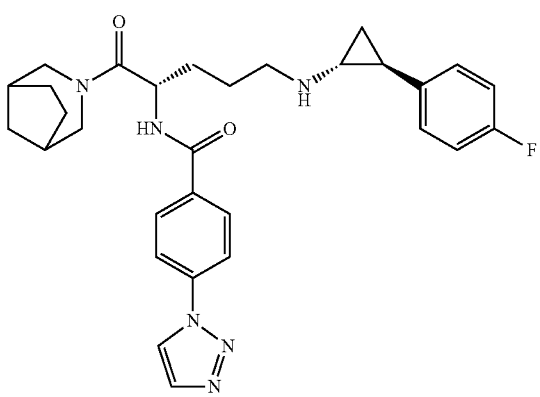 [SMILES: O=C(N[C@@H](CCCN[C@@H]1C[C@H]1c1ccc(F)cc1)C(=O)N1CC2CCC(C2)C1)c1ccc(-n2ccnn2)cc1] | N-[(2S)-1-[3-Azabicyclo[3.2.1]octan-3-yl]-5-[[(2S)-2-(4-fluorophenyl)cyclopropyl]amino]-1-oxopentan-2-yl]-4-(1H-1,2,3-triazol-1-yl)benzamide |
| 55 | 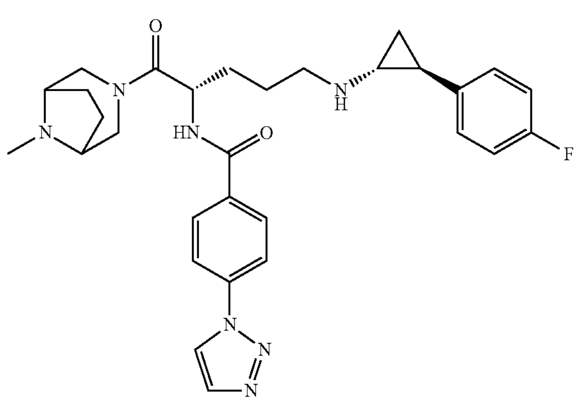 [SMILES: CN1C2CCC1CN(C(=O)[C@H](CCCN[C@@H]1C[C@H]1c1ccc(F)cc1)NC(=O)c1ccc(-n3ccnn3)cc1)C2] | N-[(2S)-5-[[(1R,2S)-2-(4-Fluorophenyl)cyclopropyl]amino]-1-(8-methyl-3,8-diazabicyclo[3.2.1]octane-1-yl)-1-oxopentan-2-yl]-4-(1H-1,2,3-triazol-1-yl)benzamide |

TABLE 1-continued

Compound Examples

| Ex # | Structure | Name |
|---|---|---|
| 56 | 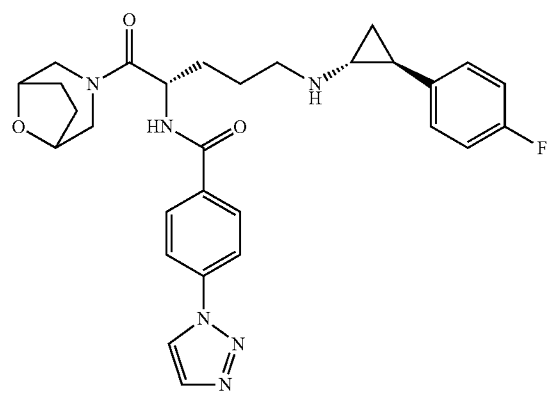 [SMILES: O=C(N[C@@H](CCCN[C@@H]1C[C@H]1c1ccc(F)cc1)C(=O)N1CC2CCC(C1)O2)c1ccc(-n2ccnn2)cc1] | N-[(2S)-5-[[(1R,2S)-2-(4-Fluorophenyl)cyclopropyl]amino]-1-(8-oxa-3-azabicyclo[3.2.1]octane-1-yl)-1-oxopentan-2-yl]-4-(1H-1,2,3-triazol-1-yl)benzamide |
| 57 | 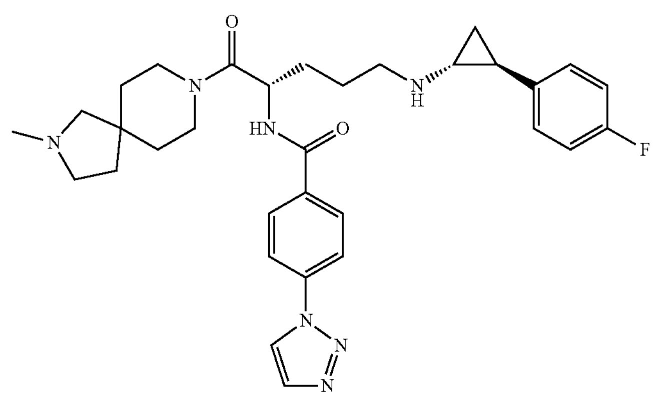 [SMILES: CN1CCC2(CCN(C(=O)[C@H](CCCN[C@@H]3C[C@H]3c3ccc(F)cc3)NC(=O)c3ccc(-n4ccnn4)cc3)CC2)C1] | N-[(2S)-5-[[(1R,2S)-2-(4-Fluorophenyl)cyclopropyl](prop-2-en-1-yl)amino]-1-(2-methyl-2,8-diazaspiro[4.5]decane-8-yl)-1-oxopentan-2-yl]-4-(1H-1,2,3-triazol-1-yl)benzamide |
| 58 | 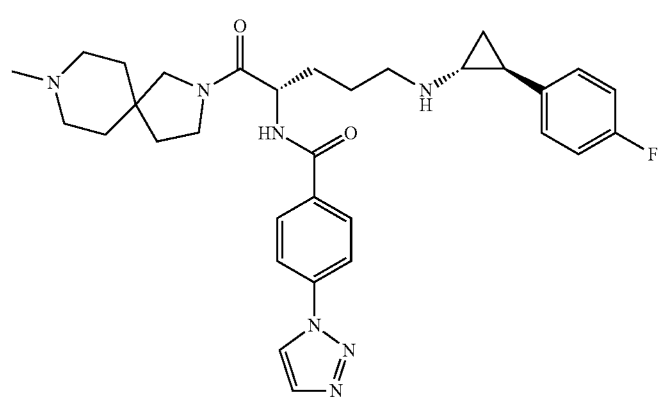 [SMILES: CN1CCC2(CC1)CCN(C(=O)[C@H](CCCN[C@@H]1C[C@H]1c1ccc(F)cc1)NC(=O)c1ccc(-n3ccnn3)cc1)C2] | N-[(2S)-5-[[(1R,2S)-2-(4-Fluorophenyl)cyclopropyl](prop-2-en-1-yl)amino]-1-(8-methyl-2,8-diazaspiro[4.5]decane-2-yl)-1-oxopentan-2-yl]-4-(1H-1,2,3-triazol-1-yl)benzamide |

TABLE 1-continued

Compound Examples

| Ex # | Structure | Name |
|---|---|---|
| 59 | 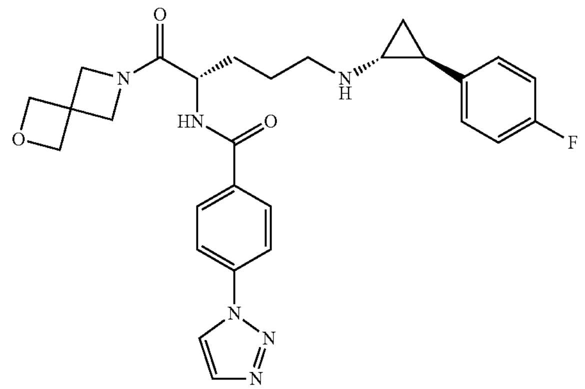 [SMILES: O=C(N[C@@H](CCCN[C@@H]1C[C@H]1c1ccc(F)cc1)C(=O)N1CC2(COC2)C1)c1ccc(-n2ccnn2)cc1] | N-((2S)-5-(((1R,2S)-2-(4-fluorophenyl)cyclopropylamino)-1-oxo-1-(2-oxa-6-azaspiro[3.3]heptan-6-yl)pentan-2-yl)-4-(1H-1,2,3-triazol-1-yl)benzamide |
| 60 | 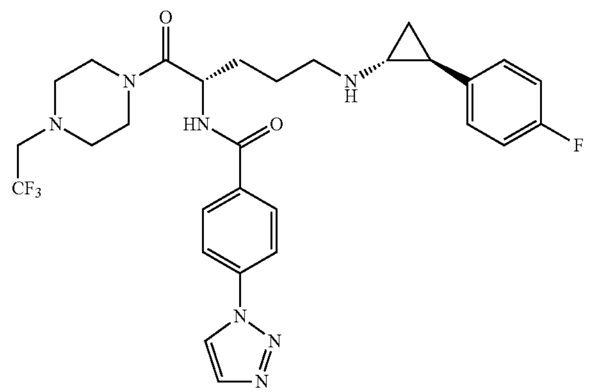 [SMILES: O=C(N[C@@H](CCCN[C@@H]1C[C@H]1c1ccc(F)cc1)C(=O)N1CCN(CC(F)(F)F)CC1)c1ccc(-n2ccnn2)cc1] | N-[(2S)-5-[[(1R,2S)-2-(4-fluorophenyl)cyclopropyl]amino]-1-oxo-1-[4-(2,2,2-trifluoroethyl)piperazin-1-yl]pentan-2-yl]-4-(1H-1,2,3-triazol-1-yl)benzamide |
| 61 | 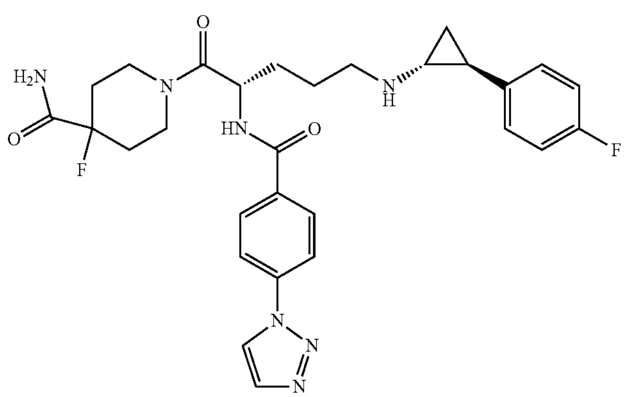 [SMILES: NC(=O)C1(F)CCN(C(=O)[C@H](CCCN[C@@H]2C[C@H]2c2ccc(F)cc2)NC(=O)c2ccc(-n3ccnn3)cc2)CC1] | 1-((S)-2-(4-(1H-1,2,3-triazol-1-yl)benzamido)-5-(((1R,2S)-2-(4-fluorophenyl)cyclopropylamino)pentanoyl)-4-fluoropiperidine-4-carboxamide |
| 62 | 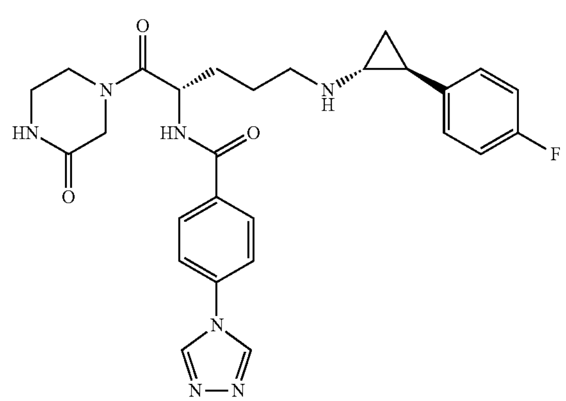 [SMILES: O=C1CN(C(=O)[C@H](CCCN[C@@H]2C[C@H]2c2ccc(F)cc2)NC(=O)c2ccc(-n3cnnc3)cc2)CCN1] | N-[(2S)-5-[[(1R,2S)-2-(4-fluorophenyl)cyclopropyl]amino]-1-oxo-1-(3-oxopiperazin-1-yl)pentan-2-yl]-4-(4H-1,2,4-triazol-4-yl)benzamide |

TABLE 1-continued

Compound Examples

| Ex # | Structure | Name |
|---|---|---|
| 63 | 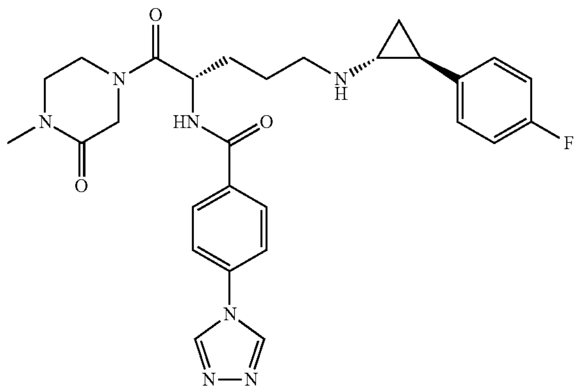 [SMILES: CN1CCN(C(=O)[C@H](CCCN[C@@H]2C[C@H]2c2ccc(F)cc2)NC(=O)c2ccc(-n3cnnc3)cc2)CC1=O] | N-[(2S)-5-[[(1R,2S)-2-(4-fluorophenyl)cyclopropyl]amino]-1-(4-methyl-3-oxopiperazin-1-yl)-1-oxopentan-2-yl]-4-(4H-1,2,4-triazol-4-yl)benzamide |
| 64 | 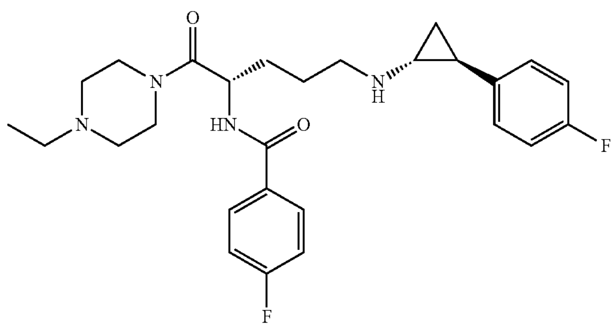 [SMILES: CCN1CCN(C(=O)[C@H](CCCN[C@@H]2C[C@H]2c2ccc(F)cc2)NC(=O)c2ccc(F)cc2)CC1] | N-[(2S)-1-(4-ethylpiperazin-1-yl)-5-[[(1R,2S)-2-(4-fluorophenyl)cyclopropyl]amino]-1-oxopentan-2-yl]-4-fluorobenzamide; trifluoroacetic acid |
| 65 | 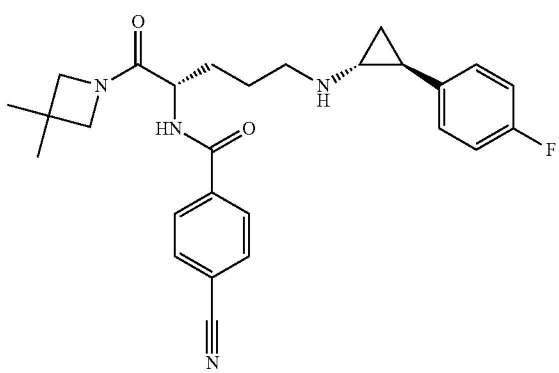 [SMILES: CC1(C)CN(C(=O)[C@H](CCCN[C@@H]2C[C@H]2c2ccc(F)cc2)NC(=O)c2ccc(C#N)cc2)C1] | 4-cyano-N-[(2S)-1-(3,3-dimethylazetidin-1-yl)-5-[[(1R,2S)-2-(4-fluorophenyl)cyclopropyl]amino]-1-oxopentan-2-yl]benzamide |
| 66 | 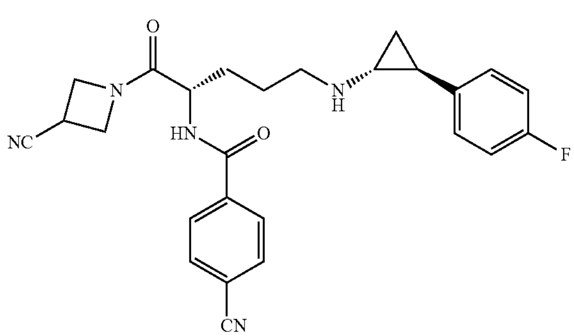 [SMILES: N#Cc1ccc(C(=O)N[C@@H](CCCN[C@@H]2C[C@H]2c2ccc(F)cc2)C(=O)N2CC(C#N)C2)cc1] | 4-cyano-N-((S)-1-(3-cyanoazetidin-1-yl)-5-((1R,2S)-2-(4-fluorophenyl)cyclopropylamino)-1-oxopentan-2-yl)benzamide |

TABLE 1-continued

Compound Examples

| Ex # | Structure | Name |
|---|---|---|
| 67 | 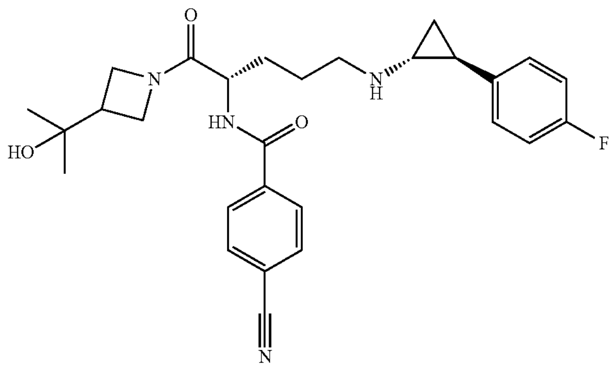 [SMILES: CC(C)(O)C1CN(C(=O)[C@H](CCCN[C@@H]2C[C@H]2c2ccc(F)cc2)NC(=O)c2ccc(C#N)cc2)C1] | 4-cyano-N-[(2S)-5-[[(1R,2S)-2-(4-fluorophenyl)cyclopropyl]amino]-1-[3-(2-hydroxypropan-2-yl)azetidin-1-yl]-1-oxopentan-2-yl]benzamide |
| 68 | 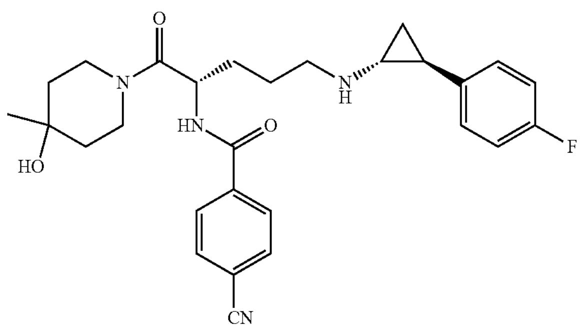 [SMILES: CC1(O)CCN(C(=O)[C@H](CCCN[C@@H]2C[C@H]2c2ccc(F)cc2)NC(=O)c2ccc(C#N)cc2)CC1] | 4-Cyano-N-[(2S)-5-[[(1R,2S)-2-(4-fluorophenyl)cyclopropyl]amino]-1-(4-hydroxy-4-methylpiperidin-1-yl)-1-oxopentan-2-yl]benzamide |
| 69 | 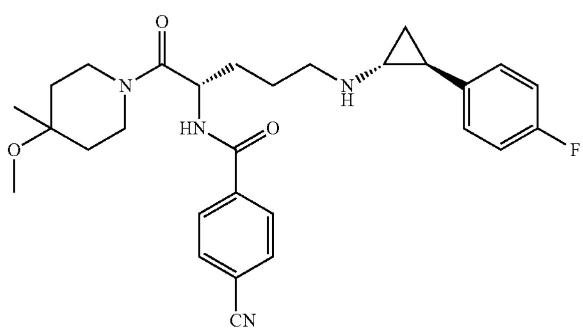 [SMILES: COC1(C)CCN(C(=O)[C@H](CCCN[C@@H]2C[C@H]2c2ccc(F)cc2)NC(=O)c2ccc(C#N)cc2)CC1] | 4-Cyano-N-[(2S)-5-[[(2S)-2-(4-fluorophenyl)cyclopropyl]amino]-1-(4-methoxy-4-methylpiperidin-1-yl)-1-oxopentan-2-yl]benzamide |
| 70 | 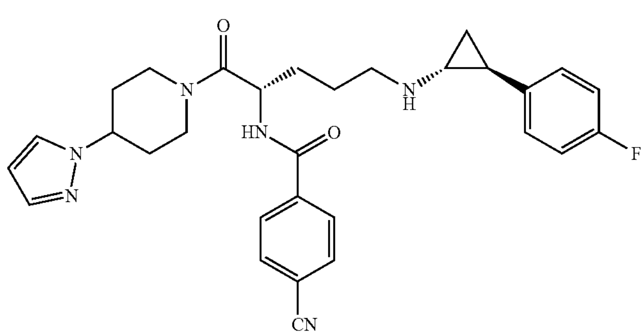 [SMILES: N#Cc1ccc(C(=O)N[C@@H](CCCN[C@@H]2C[C@H]2c2ccc(F)cc2)C(=O)N2CCC(n3cccn3)CC2)cc1] | 4-Cyano-N-[(2S)-5-[[(2S)-2-(4-fluorophenyl)cyclopropyl]amino]-1-oxo-1-[4-(1H-pyrazol-1-yl)piperidin-1-yl]pentan-2-yl]benzamide |

TABLE 1-continued

Compound Examples

| Ex # | Structure | Name |
|---|---|---|
| 71 | 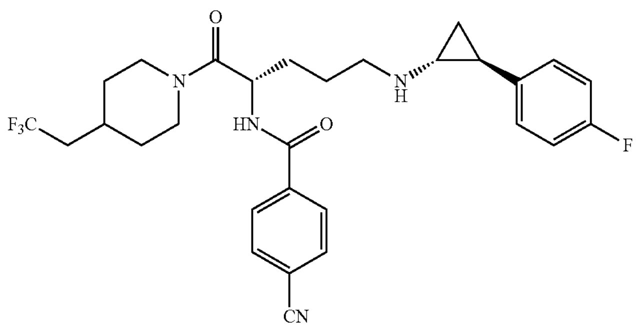 [SMILES: N#Cc1ccc(C(=O)N[C@@H](CCCN[C@@H]2C[C@H]2c2ccc(F)cc2)C(=O)N2CCC(CC(F)(F)F)CC2)cc1] | 4-cyano-N-[(2S)-5-[[(1R,2S)-2-(4-fluorophenyl)cyclopropyl]amino]-1-oxo-1-[4-(2,2,2-trifluoroethyl)piperazin-1-yl]pentan-2-yl]benzamide |
| 72 | 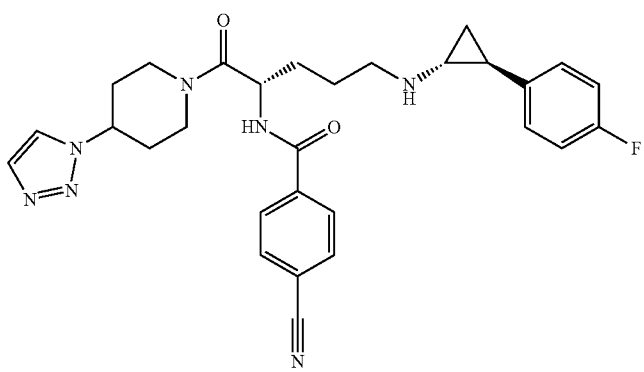 [SMILES: N#Cc1ccc(C(=O)N[C@@H](CCCN[C@@H]2C[C@H]2c2ccc(F)cc2)C(=O)N2CCC(n3ccnn3)CC2)cc1] | 4-Cyano-N-[(2S)-5-[[(1R,2S)-2-(4-fluorophenyl)cyclopropyl]amino]-1-oxo-1-[4-(1H-1,2,3-triazol-1-yl)piperidin-1-yl]pentan-2-yl]benzamide |
| 73 | 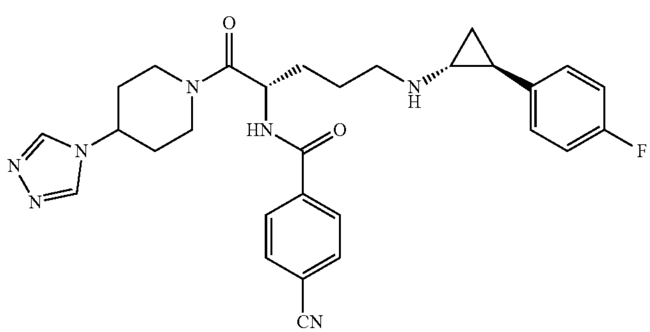 [SMILES: N#Cc1ccc(C(=O)N[C@@H](CCCN[C@@H]2C[C@H]2c2ccc(F)cc2)C(=O)N2CCC(n3cnnc3)CC2)cc1] | 4-Cyano-N-[(2S)-5-[[(2S)-2-(4-fluorophenyl)cyclopropyl](prop-2-en-1-yl)amino]-1-oxo-1-[4-(1H-1,2,4-triazol-4-yl)piperidin-1-yl]pentan-2-yl]benzamide |
| 74 | 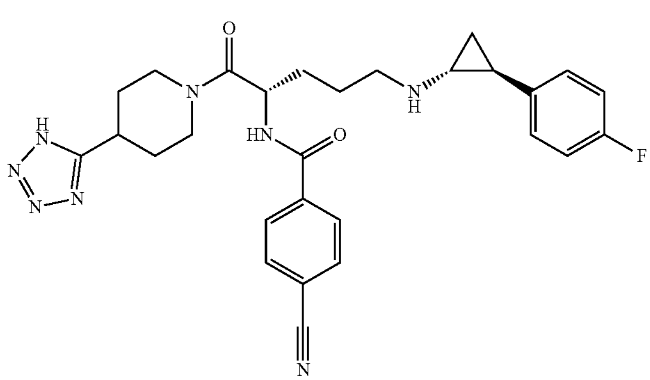 [SMILES: N#Cc1ccc(C(=O)N[C@@H](CCCN[C@@H]2C[C@H]2c2ccc(F)cc2)C(=O)N2CCC(c3nnn[nH]3)CC2)cc1] | 4-Cyano-N-[(2S)-5-[[(1R,2S)-2-(4-fluorophenyl)cyclopropyl]amino]-1-oxo-1-[4-(1H-1,2,3,4-tetrazol-5-yl)piperidin-1-yl]pentan-2-yl]benzamide |

TABLE 1-continued

Compound Examples

| Ex # | Structure | Name |
|---|---|---|
| 75 | 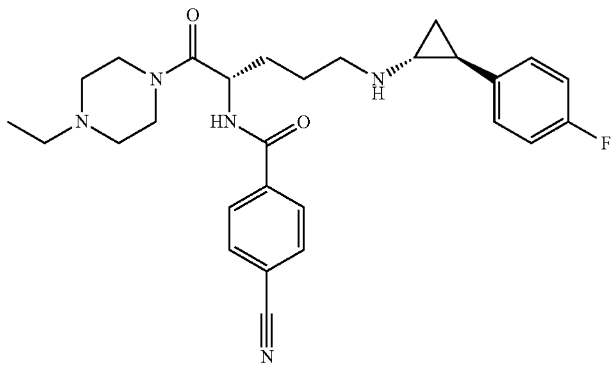 [SMILES: CCN1CCN(C(=O)[C@H](CCCN[C@@H]2C[C@H]2c2ccc(F)cc2)NC(=O)c2ccc(C#N)cc2)CC1] | 4-Cyano-N-[(2S)-1-(4-ethylpiperazin-1-yl)-5-[[(1R,2S)-2-(4-fluorophenyl)cyclopropyl]amino]-1-oxopentan-2-yl]benzamide |
| 76 | 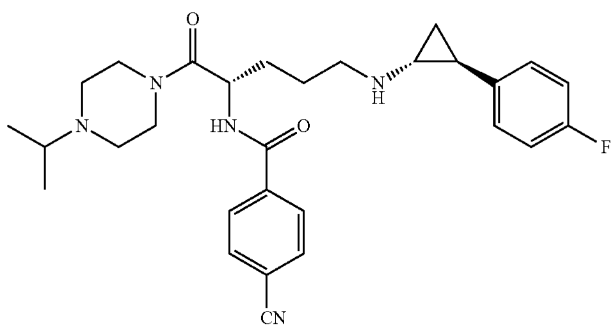 [SMILES: CC(C)N1CCN(C(=O)[C@H](CCCN[C@@H]2C[C@H]2c2ccc(F)cc2)NC(=O)c2ccc(C#N)cc2)CC1] | 4-Cyano-N-[(2S)-5-[[(2S)-2-(4-fluorophenyl)cyclopropyl]amino]-1-oxo-1-[4-(propan-2-yl)piperazin-1-yl]pentan-2-yl]benzamide |
| 77 | 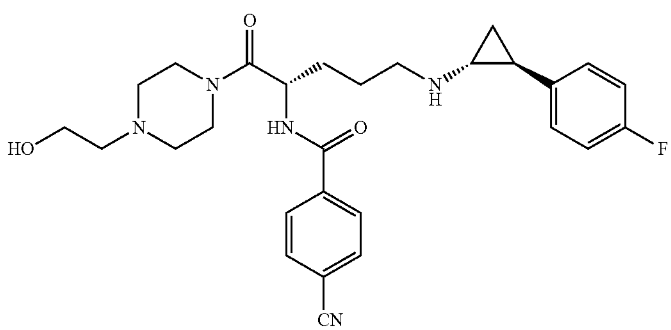 [SMILES: N#Cc1ccc(C(=O)N[C@@H](CCCN[C@@H]2C[C@H]2c2ccc(F)cc2)C(=O)N2CCN(CCO)CC2)cc1] | 4-Cyano-N-[(2S)-5-[[(1R,2S)-2-(4-fluorophenyl)cyclopropyl](prop-2-en-1-yl)amino]-1-[4-(2-hydroxyethyl)piperazin-1-yl]-1-oxopentan-2-yl]benzamide |
| 78 | 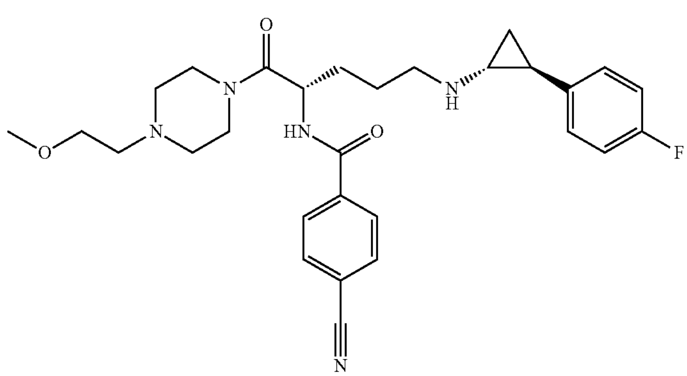 [SMILES: COCCN1CCN(C(=O)[C@H](CCCN[C@@H]2C[C@H]2c2ccc(F)cc2)NC(=O)c2ccc(C#N)cc2)CC1] | 4-Cyano-N-[(2S)-5-[[(1R,2S)-2-(4-fluorophenyl)cyclopropyl]amino]-1-[4-(2-methoxyethyl)piperazin-1-yl]-1-oxopentan-2-yl]benzamide |

TABLE 1-continued

Compound Examples

| Ex # | Structure | Name |
|---|---|---|
| 79 | 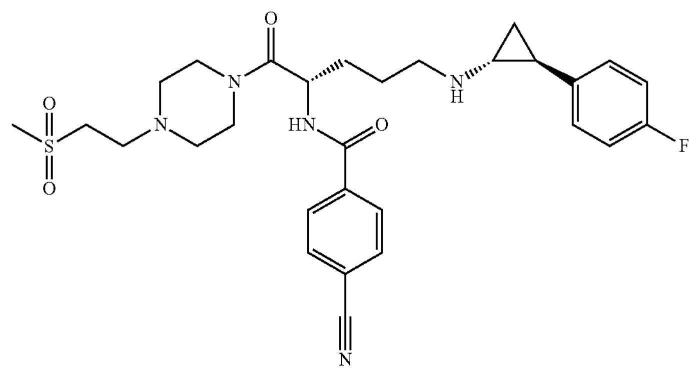 [SMILES: CS(=O)(=O)CCN1CCN(C(=O)[C@H](CCCN[C@@H]2C[C@H]2c2ccc(F)cc2)NC(=O)c2ccc(C#N)cc2)CC1] | 4-Cyano-N-[(2S)-5-[[(1R,2S)-2-(4-fluorophenyl)cyclopropyl]amino]-1-[4-(2-methanesulfonylethyl)piperazin-1-yl]-1-oxopentan-2-yl]benzamide |
| 80 | 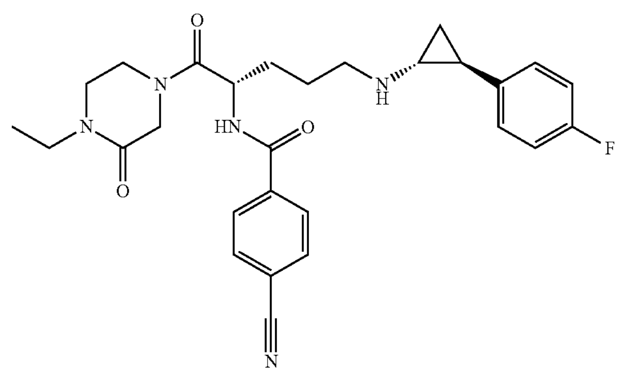 [SMILES: CCN1CCN(C(=O)[C@H](CCCN[C@@H]2C[C@H]2c2ccc(F)cc2)NC(=O)c2ccc(C#N)cc2)CC1=O] | 4-Cyano-N-[(2S)-1-(4-ethyl-3-oxopiperazin-1-yl)-5-[[(1R,2S)-2-(4-fluorophenyl)cyclopropyl]amino]-1-oxopentan-2-yl]benzamide |
| 81 | 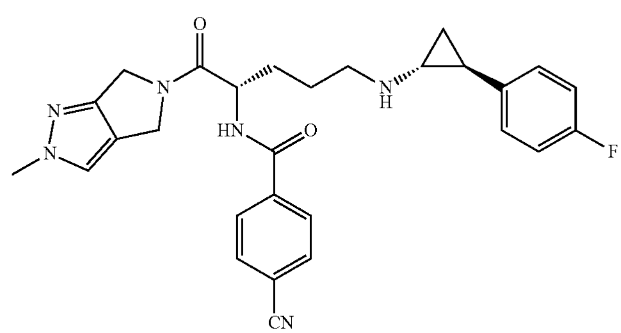 [SMILES: Cn1cc2c(n1)CN(C(=O)[C@H](CCCN[C@@H]1C[C@H]1c1ccc(F)cc1)NC(=O)c1ccc(C#N)cc1)C2] | N-[(2S)-5-[[(1R,2S)-2-(4-fluorophenyl)cyclopropyl]amino]-1-(2,4,5,6-tetrahydro-2-methyl-pyrrolo[3,4-c]pyrazol-1-yl)-1-oxopentan-2-yl]-4-cyanobenzamide |
| 82 | 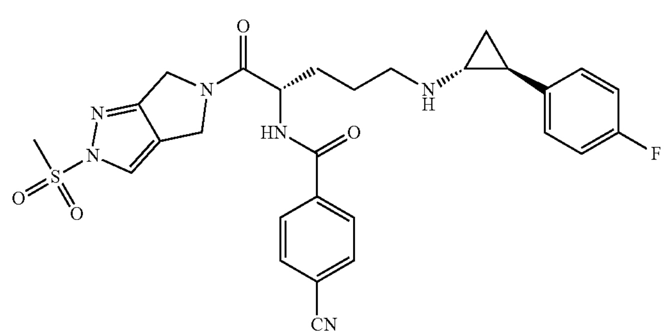 [SMILES: CS(=O)(=O)n1cc2c(n1)CN(C(=O)[C@H](CCCN[C@@H]1C[C@H]1c1ccc(F)cc1)NC(=O)c1ccc(C#N)cc1)C2] | N-[(2S)-5-[[(1R,2S)-2-(4-fluorophenyl)cyclopropyl]amino]-1-(2,4,5,6-tetrahydro-2-(methanesulfonyl)pyrrolo[3,4-c]pyrazol-1-yl)-1-oxopentan-2-yl]-4-cyanobenzamide |

TABLE 1-continued

Compound Examples

| Ex # | Structure | Name |
|---|---|---|
| 83 | 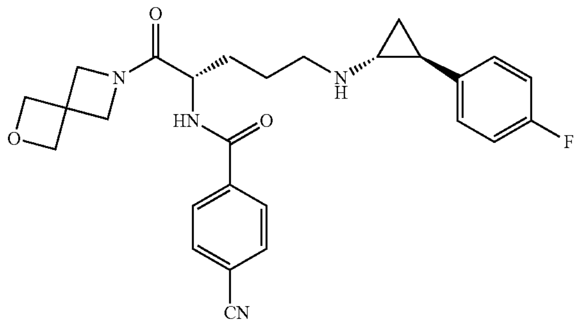 [SMILES: N#Cc1ccc(C(=O)N[C@@H](CCCN[C@@H]2C[C@H]2c2ccc(F)cc2)C(=O)N2CC3(COC3)C2)cc1] | 4-cyano-N-((2S)-5-((1R,2S)-2-(4-fluorophenyl)cyclopropylamino)-1-oxo-1-(2-oxa-6-azaspiro[3.3]heptan-6-yl)pentan-2-yl)benzamide |
| 84 | 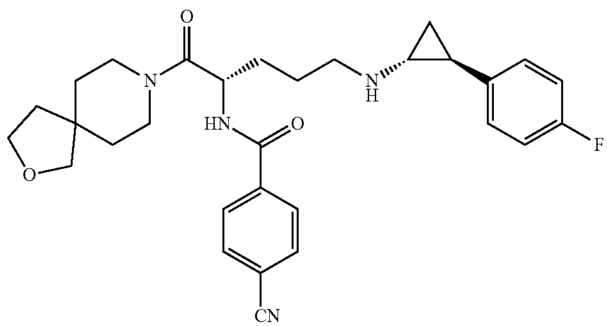 [SMILES: N#Cc1ccc(C(=O)N[C@@H](CCCN[C@@H]2C[C@H]2c2ccc(F)cc2)C(=O)N2CCC3(CCOC3)CC2)cc1] | 4-cyano-N-[(2S)-5-[[(1R,2S)-2-(4-fluorophenyl)cyclopropyl]amino]-1-[2-oxa-8-azaspiro[4.5]decan-8-yl]-1-oxopentan-2-yl]benzamide |
| 85 | 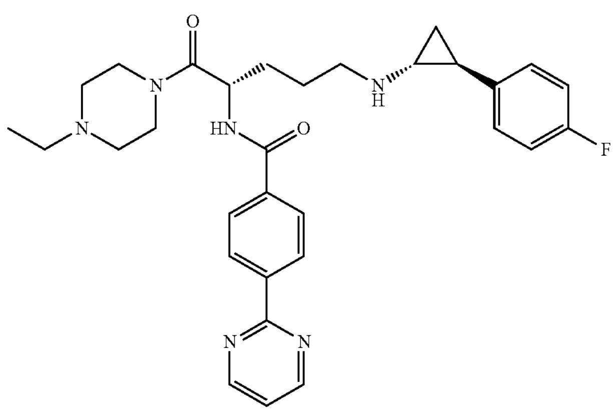 [SMILES: CCN1CCN(C(=O)[C@H](CCCN[C@@H]2C[C@H]2c2ccc(F)cc2)NC(=O)c2ccc(-c3ncccn3)cc2)CC1] | N-[(2S)-1-(4-Ethylpiperazin-1-yl)-5-[[(1R,2S)-2-(4-fluorophenyl)cyclopropyl]amino]-1-oxopentan-2-yl]-4-(pyrimidin-2-yl)benzamide |
| 86 | 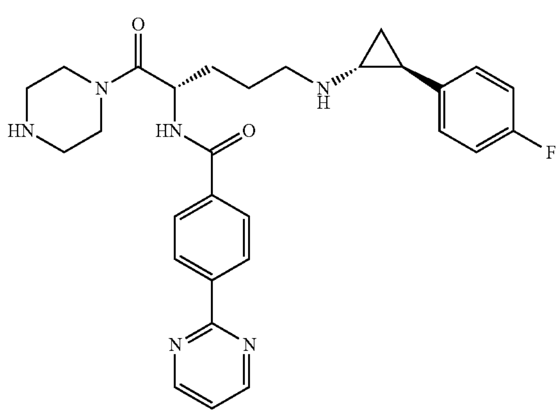 [SMILES: O=C(N[C@@H](CCCN[C@@H]1C[C@H]1c1ccc(F)cc1)C(=O)N1CCNCC1)c1ccc(-c2ncccn2)cc1] | N-[(2S)-5-[[(1R,2S)-2-(4-fluorophenyl)cyclopropyl]amino]-1-oxo-1-(piperazin-1-yl)pentan-2-yl]-4-(pyrimidin-2-yl)benzamide |
| 87 | This example is intentionally left blank. | |
| 88 | This example is intentionally left blank. | |

TABLE 1-continued

Compound Examples

| Ex # | Structure | Name |
|---|---|---|
| 89 | 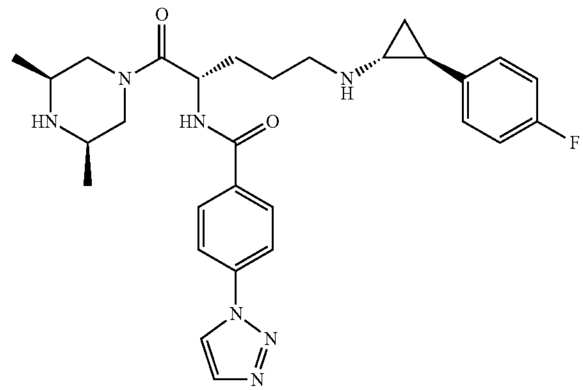 [SMILES: C[C@@H]1CN(C(=O)[C@H](CCCN[C@@H]2C[C@H]2c2ccc(F)cc2)NC(=O)c2ccc(-n3ccnn3)cc2)C[C@H](C)N1] | N-((S)-1-((3S,5R)-3,5-dimethylpiperazin-1-yl)-5-((1R,2S)-2-(4-fluorophenyl)cyclopropylamino)-1-oxopentan-2-yl)-4-(1H-1,2,3-triazol-1-yl)benzamide |
| 90 | 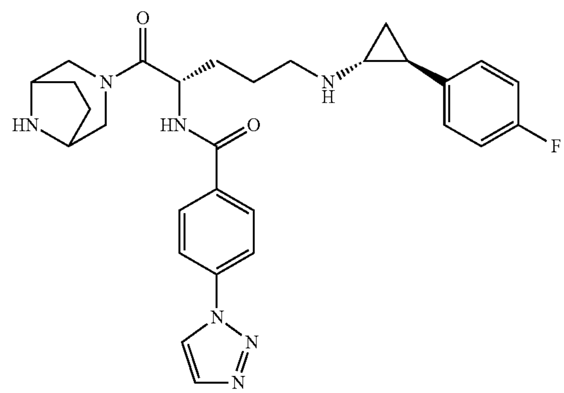 [SMILES: O=C(N[C@@H](CCCN[C@@H]1C[C@H]1c1ccc(F)cc1)C(=O)N1CC2CCC(C1)N2)c1ccc(-n2ccnn2)cc1] | N-[(2S)-5-[[(1R,2S)-2-(4-Fluorophenyl)cyclopropyl]amino]-1-(3,8-diazabicyclo[3.2.1]octane-1-yl)-1-oxopentan-2-yl]-4-(1H-1,2,3-triazol-1-yl)benzamide |
| 91 | 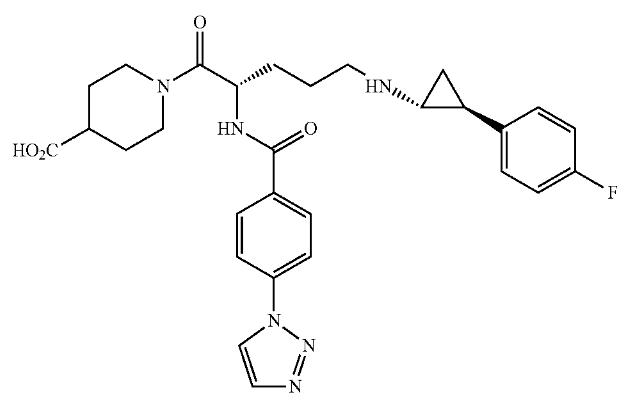 [SMILES: O=C(N[C@@H](CCCN[C@@H]1C[C@H]1c1ccc(F)cc1)C(=O)N1CCC(C(=O)O)CC1)c1ccc(-n2ccnn2)cc1] | N-[(2S)-5-[[(1R,2S)-2-(4-Fluorophenyl)cyclopropyl]amino]-1-(4-carboxypiperidin-1-yl)-1-oxopentan-2-yl]-4-(1H-1,2,3-triazol-1-yl)benzamide |
| 92 | 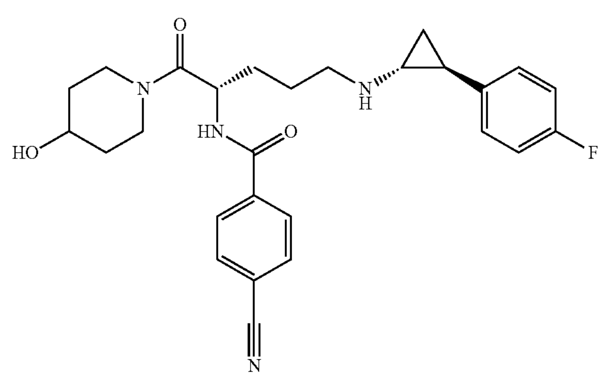 [SMILES: N#Cc1ccc(C(=O)N[C@@H](CCCN[C@@H]2C[C@H]2c2ccc(F)cc2)C(=O)N2CCC(O)CC2)cc1] | 4-Cyano-N-[(2S)-5-[[(1R,2S)-2-(4-fluorophenyl)cyclopropyl]amino]-1-(4-hydroxypiperidin-1-yl)-1-oxopentan-2-yl]benzamide |

TABLE 1-continued

Compound Examples

| Ex # | Structure | Name |
|---|---|---|
| 93 | 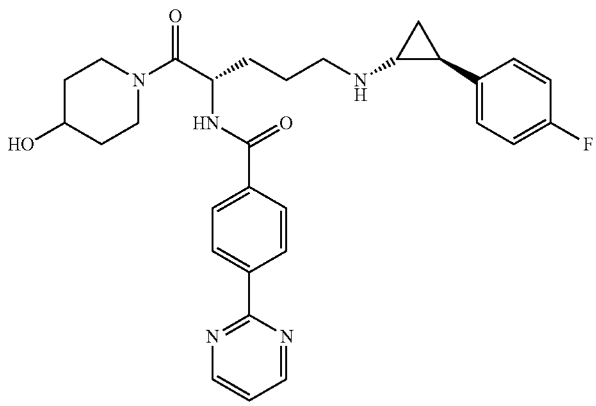 | N-[(2S)-5-[[(2S)-2-(4-Fluorophenyl)cyclopropyl]amino]-1-(4-hydroxypiperidin-1-yl)-1-oxopentan-2-yl]-4-(pyrimidin-2-yl)benzamide |
| 94 | 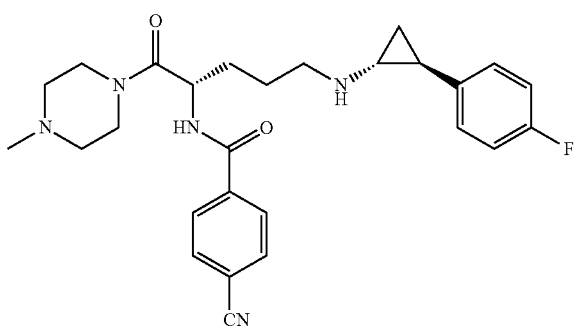 [SMILES: CN1CCN(C(=O)[C@H](CCCN[C@@H]2C[C@H]2c2ccc(F)cc2)NC(=O)c2ccc(C#N)cc2)CC1] | 4-Cyano-N-[(2S)-5-[[(1R,2S)-2-(4-fluorophenyl)cyclopropyl]amino]-1-(4-methylpiperazin-1-yl)-1-oxopentan-2-yl]benzamide |
| 95 | 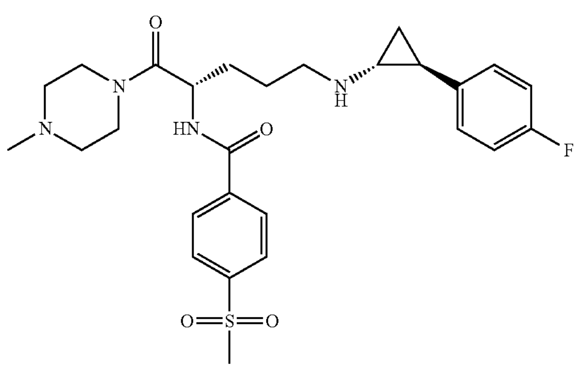 [SMILES: CN1CCN(C(=O)[C@H](CCCN[C@@H]2C[C@H]2c2ccc(F)cc2)NC(=O)c2ccc(S(C)(=O)=O)cc2)CC1] | 4-Methanesulfonyl-N-[(2S)-5-[[(1R,2S)-2-(4-fluorophenyl)cyclopropyl]amino]-1-(4-methyl-3-oxopiperazin-1-yl)-1-oxopentan-2-yl]benzamide |
| 96 | 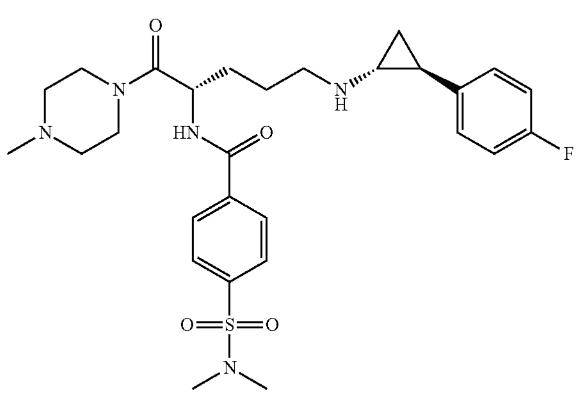 [SMILES: CN1CCN(C(=O)[C@H](CCCN[C@@H]2C[C@H]2c2ccc(F)cc2)NC(=O)c2ccc(S(=O)(=O)N(C)C)cc2)CC1] | 4-(Dimethylsulfamoyl)-N-[(2S)-5-[[(1R,2S)-2-(4-fluorophenyl)cyclopropyl]amino]-1-(4-methylpiperazin-1-yl)-1-oxopentan-2-yl]benzamide |

TABLE 1-continued

Compound Examples

| Ex # | Structure | Name |
|---|---|---|
| 97 | 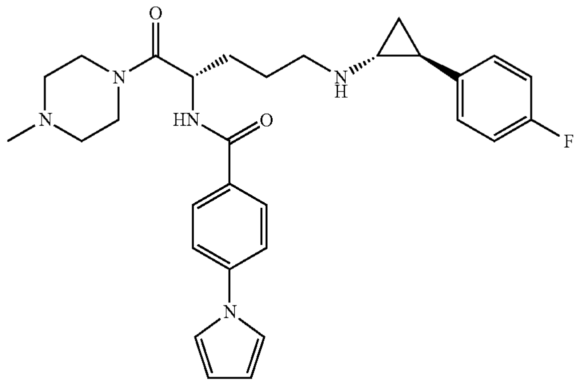 [SMILES: CN1CCN(C(=O)[C@H](CCCN[C@@H]2C[C@H]2c2ccc(F)cc2)NC(=O)c2ccc(-n3cccc3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(1-pyrrolyl)benzamide |
| 98 | 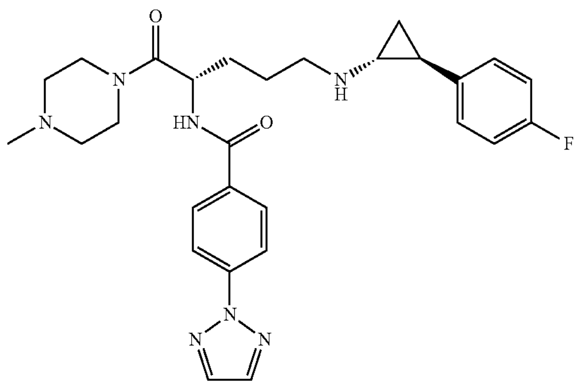 [SMILES: CN1CCN(C(=O)[C@H](CCCN[C@@H]2C[C@H]2c2ccc(F)cc2)NC(=O)c2ccc(-n3nccn3)cc2)CC1] | N-[(2S)-5-[[(1R,2S)-2-(4-fluorophenyl)cyclopropyl]amino]-1-(4-methylpiperazin-1-yl)-1-oxopentan-2-yl]-4-(2H-1,2,3-triazol-2-yl)benzamide |
| 99 | 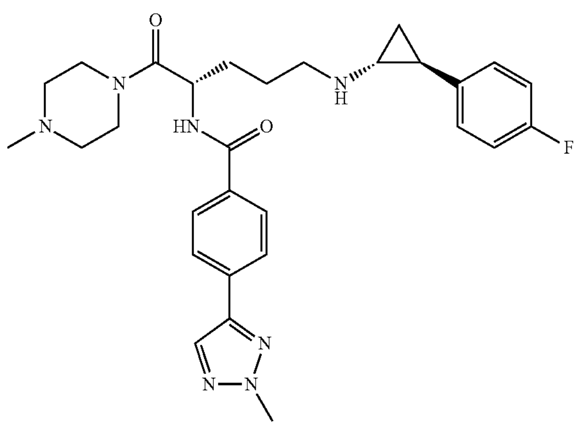 [SMILES: CN1CCN(C(=O)[C@H](CCCN[C@@H]2C[C@H]2c2ccc(F)cc2)NC(=O)c2ccc(-c3cnn(C)n3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(2-methyl-2H-1,2,3-triazol-4-yl)benzamide |
| 100 | 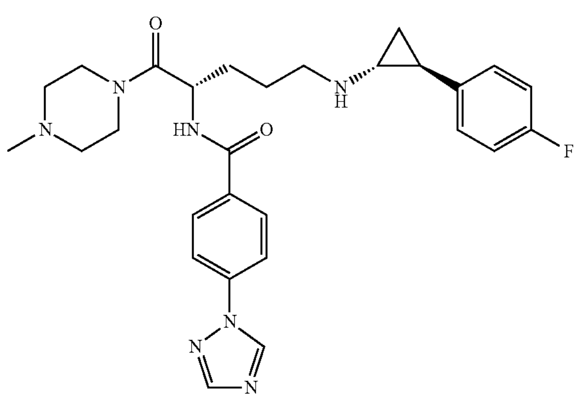 [SMILES: CN1CCN(C(=O)[C@H](CCCN[C@@H]2C[C@H]2c2ccc(F)cc2)NC(=O)c2ccc(-n3cncn3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(1H-1,2,4-triazol-1-yl)benzamide |

TABLE 1-continued

Compound Examples

| Ex # | Structure | Name |
|---|---|---|
| 101 | 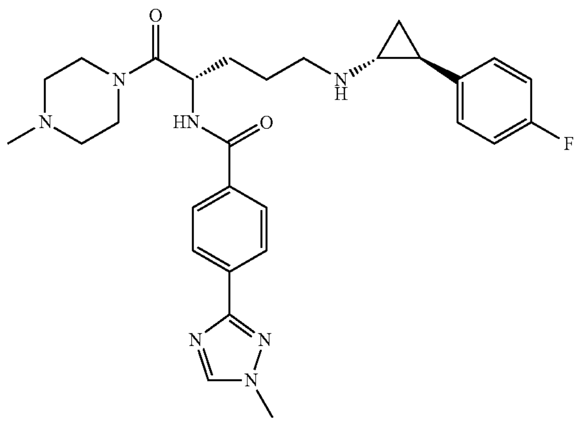 [SMILES: CN1CCN(C(=O)[C@H](CCCN[C@@H]2C[C@H]2c2ccc(F)cc2)NC(=O)c2ccc(-c3ncn(C)n3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(1-methyl-1H-1,2,4-triazol-3-yl)benzamide |
| 102 | 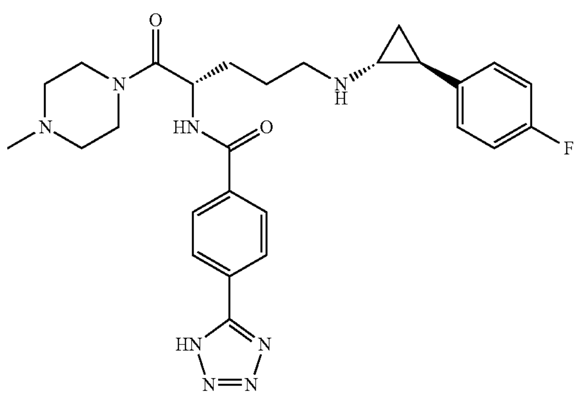 [SMILES: CN1CCN(C(=O)[C@H](CCCN[C@@H]2C[C@H]2c2ccc(F)cc2)NC(=O)c2ccc(-c3nnn[nH]3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(1H-1,2,3,4-tetrazol-5-yl)benzamide |
| 103 | 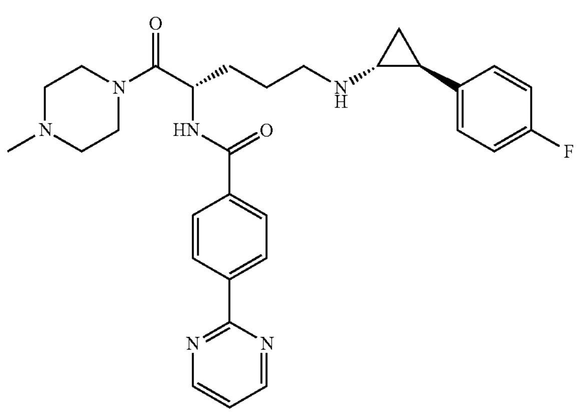 [SMILES: CN1CCN(C(=O)[C@H](CCCN[C@@H]2C[C@H]2c2ccc(F)cc2)NC(=O)c2ccc(-c3ncccn3)cc2)CC1] | N-[(2S)-5-[[(1R,2S)-2-(4-fluorophenyl)cyclopropyl]amino]-1-(4-methylpiperazin-1-yl)-1-oxopentan-2-yl]-4-(pyrimidin-2-yl)benzamide |

TABLE 1-continued

Compound Examples

| Ex # | Structure | Name |
|---|---|---|
| 104 | 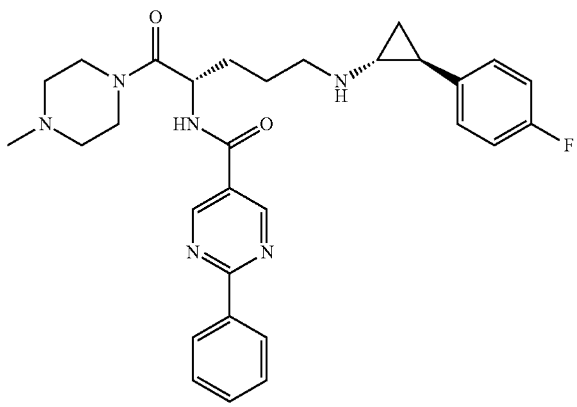 | N-[(2S)-5-[[(1R,2S)-2-(4-Fluorophenyl)cyclopropyl]amino]-1-(4-methylpiperazin-1-yl)-1-oxopentan-2-yl]-2-phenylpyrimidine-5-carboxamide |
| 105 | 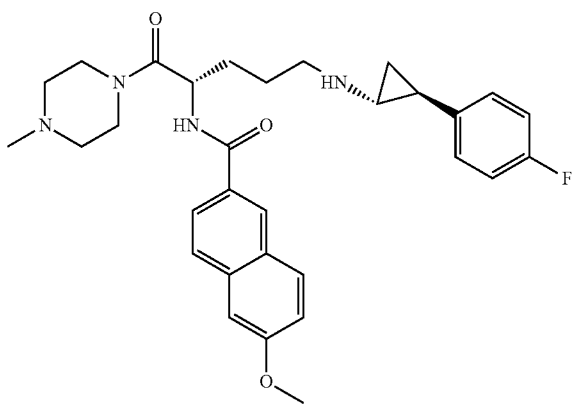 [SMILES: COc1ccc2cc(C(=O)N[C@@H](CCCN[C@@H]3C[C@H]3c3ccc(F)cc3)C(=O)N3CCN(C)CC3)ccc2c1] | N-[(2S)-5-[[(1R,2S)-2-(4-Fluorophenyl)cyclopropyl]amino]-1-(4-methylpiperazin-1-yl)-1-oxopentan-2-yl]-6-methoxynaphthalene-2-carboxamide |
| 106 | 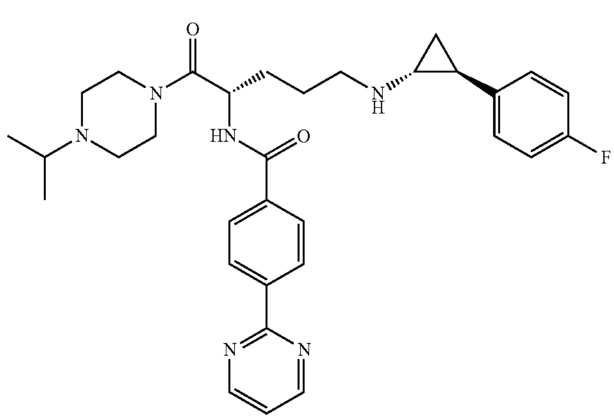 [SMILES: CC(C)N1CCN(C(=O)[C@H](CCCN[C@@H]2C[C@H]2c2ccc(F)cc2)NC(=O)c2ccc(-c3ncccn3)cc2)CC1] | N-[(2S)-5-[[(1R,2S)-2-(4-Fluorophenyl)cyclopropyl]amino]-1-oxo-1-[4-(propan-2-yl)piperazin-1-yl]pentan-2-yl]-4-(pyrimidin-2-yl)benzamide |

TABLE 1-continued

Compound Examples

| Ex # | Structure | Name |
| --- | --- | --- |
| 107 | 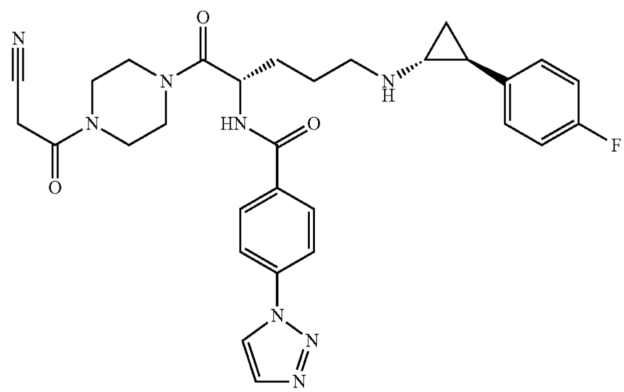 [SMILES: N#CCC(=O)N1CCN(C(=O)[C@H](CCCN[C@@H]2C[C@H]2c2ccc(F)cc2)NC(=O)c2ccc(-n3ccnn3)cc2)CC1] | N-[(2S)-1-[4-(2-Cyanoacetyl)piperazin-1-yl]-5-[[(1R,2S)-2-(4-fluorophenyl)cyclopropyl]amino]-1-oxopentan-2-yl]-4-(1H-1,2,3-triazol-1-yl)benzamide |
| 108 | 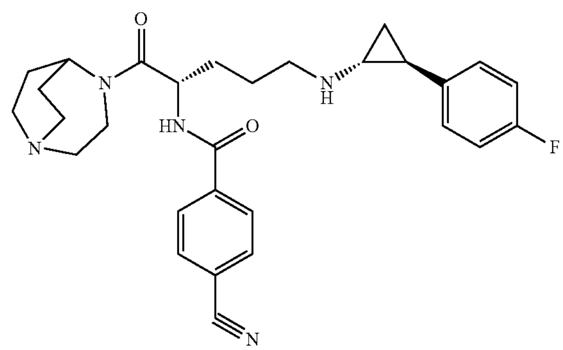 [SMILES: N#Cc1ccc(C(=O)N[C@@H](CCCN[C@@H]2C[C@H]2c2ccc(F)cc2)C(=O)N2CCN3CCC2CC3)cc1] | N-[(2S)-5-[[(1R,2S)-2-(4-Fluorophenyl)cyclopropyl]amino]-1-(1,4-diazabicyclo[3.2.2]nonane-1-yl)-1-oxopentan-2-yl]-4-cyanobenzamide |
| 109 | 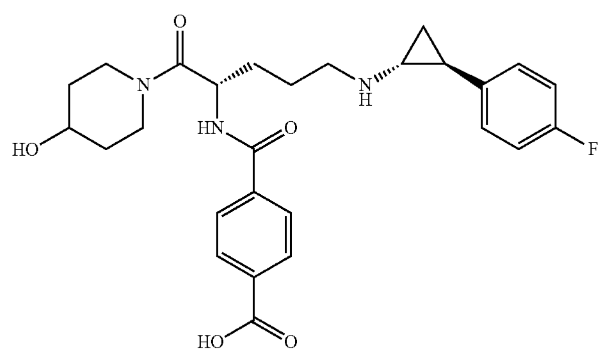 [SMILES: O=C(O)c1ccc(C(=O)N[C@@H](CCCN[C@@H]2C[C@H]2c2ccc(F)cc2)C(=O)N2CCC(O)CC2)cc1] | 4-[[(2S)-5-[[(1R,2S)-2-(4-Fluorophenyl)cyclopropyl]amino]-1-(4-hydroxypiperidin-1-yl)-1-oxopentan-2-yl]carbamoyl]benzoic acid |
| 110 | 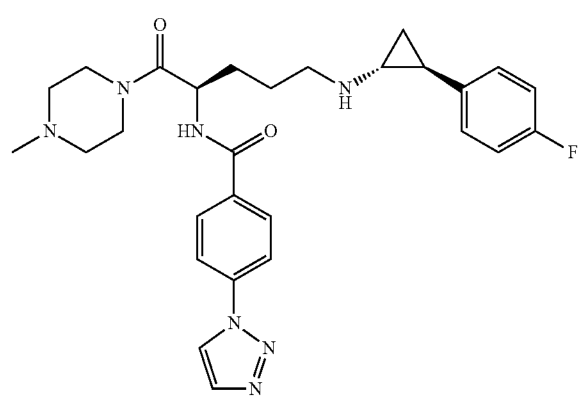 [SMILES: CN1CCN(C(=O)[C@@H](CCCN[C@@H]2C[C@H]2c2ccc(F)cc2)NC(=O)c2ccc(-n3ccnn3)cc2)CC1] | N-[(2R)-5-[[(1R,2S)-2-(4-Fluorophenyl)cyclopropyl]amino]-1-(4-methylpiperazin-1-yl)-1-oxopentan-2-yl]-4-(1H-1,2,3-triazol-1-yl)benzamide |

TABLE 1-continued

Compound Examples

| Ex # | Structure | Name |
|---|---|---|
| 111 | 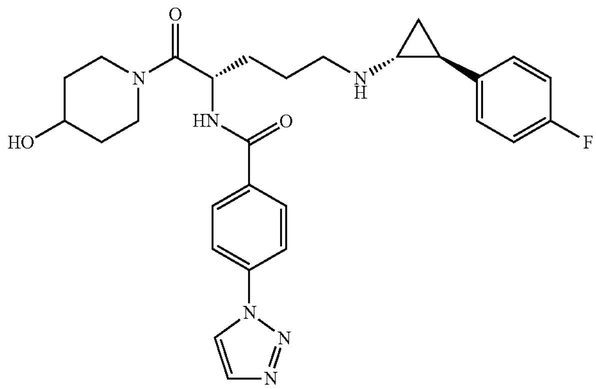 | N-[(2S)-5-[[(2S)-2-(4-fluorophenyl)cyclopropyl]amino]-1-(4-hydroxypiperidin-1-yl)-1-oxopentan-2-yl]-4-(1H-1,2,3-triazol-1-yl)benzamide |
| 112 | 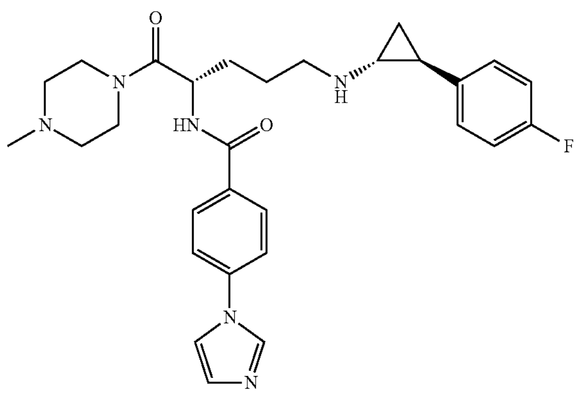 | N-((S)-5-(((1R,2S)-2-(4-fluorophenyl)cyclopropylamino)-1-(4-methylpiperazin-1-yl)-1-oxopentan-2-yl)-4-(1H-imidazol-1-yl)benzamide |
| 113 | 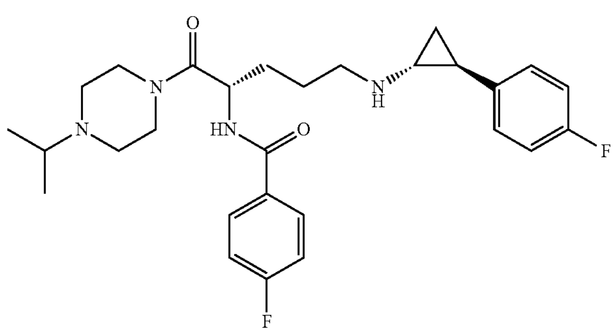 [SMILES: CC(C)N1CCN(C(=O)[C@H](CCCN[C@@H]2C[C@H]2c2ccc(F)cc2)NC(=O)c2ccc(F)cc2)CC1] | 4-Fluoro-N-[(2S)-5-[[(1R,2S)-2-(4-fluorophenyl)cyclopropyl]amino]-1-oxo-1-[4-(propan-2-yl)piperazin-1-yl]pentan-2-yl]benzamide |
| 114 | 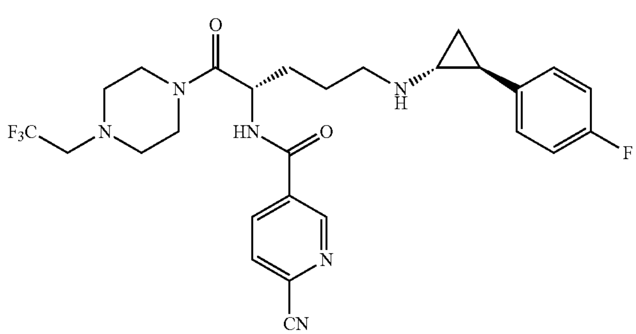 [SMILES: N#Cc1ccc(C(=O)N[C@@H](CCCN[C@@H]2C[C@H]2c2ccc(F)cc2)C(=O)N2CCN(CC(F)(F)F)CC2)cn1] | 6-cyano-N-[(2S)-5-[[(1R,2S)-2-(4-fluorophenyl)cyclopropyl]amino]-1-oxo-1-[4-(2,2,2-trifluoroethyl)piperazin-1-yl]pentan-2-yl]pyridine-3-carboxamide |

TABLE 1-continued

Compound Examples

| Ex # | Structure | Name |
|------|-----------|------|
| 115 | 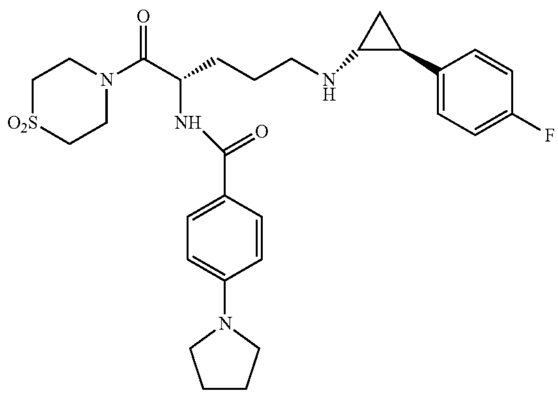 | N-[(2S)-5-[[(1R,2S)-2-(4-fluorophenyl)cyclopropyl]amino]-1-(thiomorpholine-4,4-dioxide-1-yl)-1-oxopentan-2-yl]-4-(pyrrolidin-1-yl)benzamide |
| 116 | 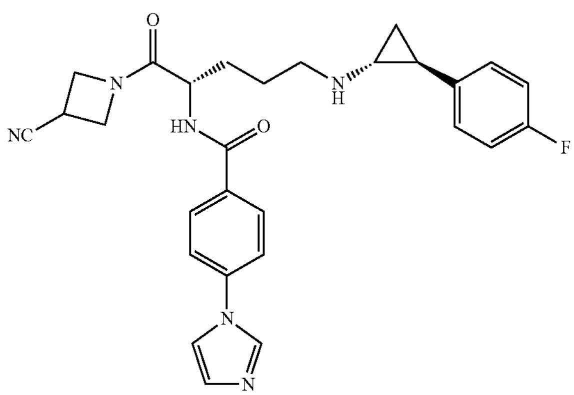 [SMILES: N#CC1CN(C(=O)[C@H](CCCN[C@@H]2C[C@H]2c2ccc(F)cc2)NC(=O)c2ccc(-n3ccnc3)cc2)C1] | N-[(2S)-1-(3-cyanoazetidin-1-yl)-5-[[(1R,2S)-2-(4-fluorophenyl)cyclopropyl]amino]-1-oxopentan-2-yl]-4-(1H-imidazol-1-yl)benzamide |
| 117 | 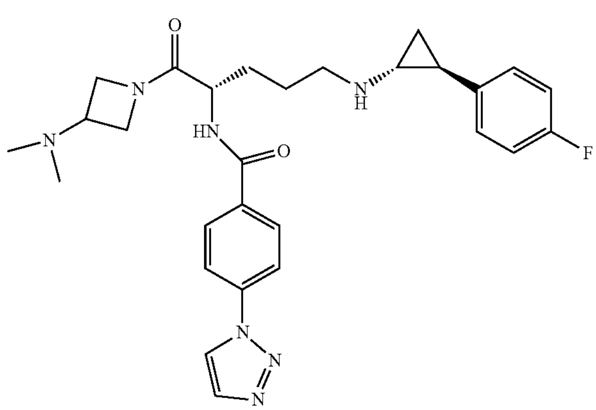 [SMILES: CN(C)C1CN(C(=O)[C@H](CCCN[C@@H]2C[C@H]2c2ccc(F)cc2)NC(=O)c2ccc(-n3ccnn3)cc2)C1] | N-[(2S)-5-[[(1R,2S)-2-(4-Fluorophenyl)cyclopropyl]amino]-1-(3-(dimethylamino)-azetidin-1-yl-1-oxopentan-2-yl]-4-(1H-1,2,3-triazol-1-yl)-benzamide |

TABLE 1-continued

Compound Examples

| Ex # | Structure | Name |
|---|---|---|
| 118 | 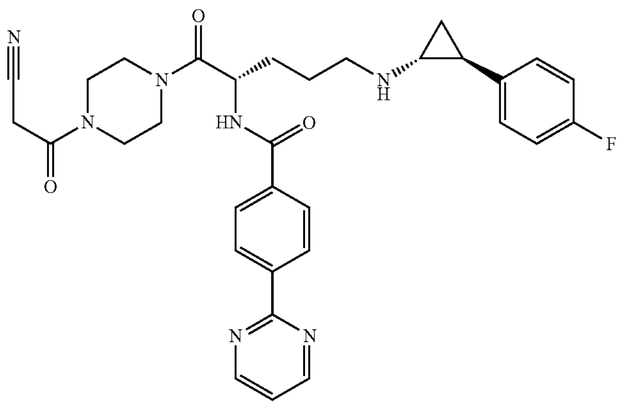 [SMILES: N#CCC(=O)N1CCN(C(=O)[C@H](CCCN[C@@H]2C[C@H]2c2ccc(F)cc2)NC(=O)c2ccc(-c3ncccn3)cc2)CC1] | N-[(2S)-1-[4-(2-Cyanoacetyl)piperazin-1-yl]-5-[[(1R,2S)-2-(4-fluorophenyl)cyclopropyl]amino]-1-oxopentan-2-yl]-4-(pyrimidin-2-yl)benzamide |
| 119 | 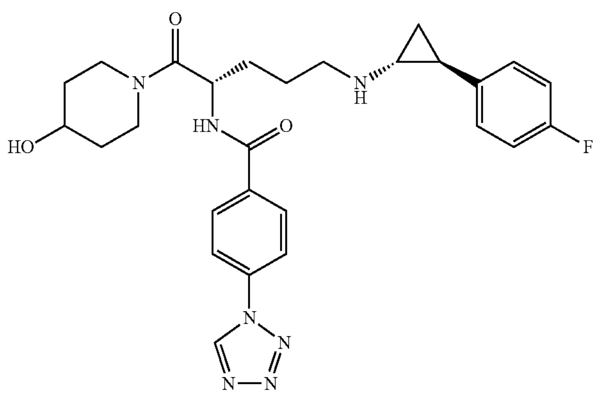 [SMILES: O=C(N[C@@H](CCCN[C@@H]1C[C@H]1c1ccc(F)cc1)C(=O)N1CCC(O)CC1)c1ccc(-n2cnnn2)cc1] | N-[(2S)-5-[[(1R,2S)-2-(4-Fluorophenyl)cyclopropyl]amino]-1-(4-hydroxypiperidin-1-yl)-1-oxopentan-2-yl]-4-(1H-1,2,3,4-tetrazol-1-yl)benzamide |
| 120 | 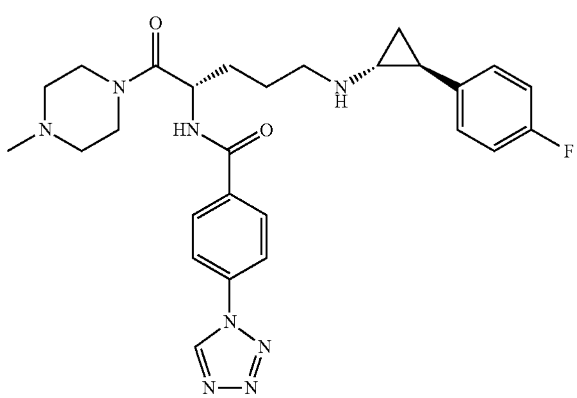 [SMILES: CN1CCN(C(=O)[C@H](CCCN[C@@H]2C[C@H]2c2ccc(F)cc2)NC(=O)c2ccc(-n3cnnn3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(1H-1,2,3,4-tetrazol-1-yl)benzamide |
| 121 | 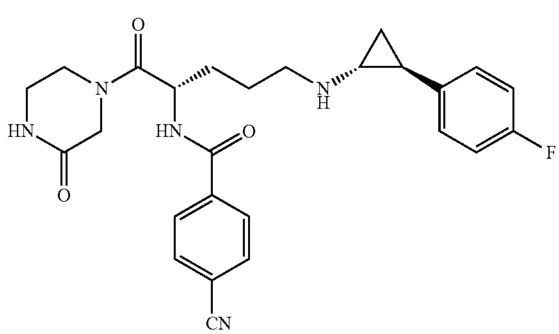 [SMILES: N#Cc1ccc(C(=O)N[C@@H](CCCN[C@@H]2C[C@H]2c2ccc(F)cc2)C(=O)N2CCNC(=O)C2)cc1] | 4-Cyano-N-[(2S)-5-[[(1R,2S)-2-(4-fluorophenyl)cyclopropyl]amino]-1-oxo-1-(3-oxopiperazin-1-yl)pentan-2-yl]benzamide |

TABLE 1-continued

Compound Examples

| Ex # | Structure | Name |
|---|---|---|
| 122 | 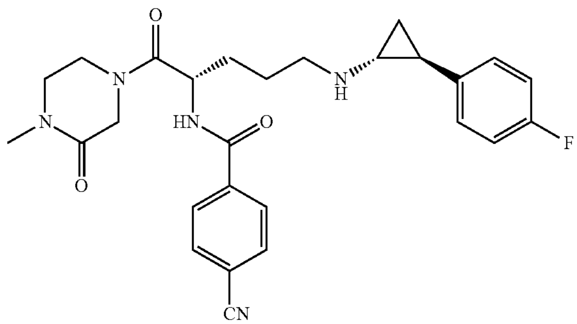 [SMILES: CN1CCN(C(=O)[C@H](CCCN[C@@H]2C[C@H]2c2ccc(F)cc2)NC(=O)c2ccc(C#N)cc2)CC1=O] | 4-Cyano-N-[(2S)-5-[[(1R,2S)-2-(4-fluorophenyl)cyclopropyl]amino]-1-(4-methyl-3-oxopiperazin-1-yl)-1-oxopentan-2-yl]benzamide |
| 123 | 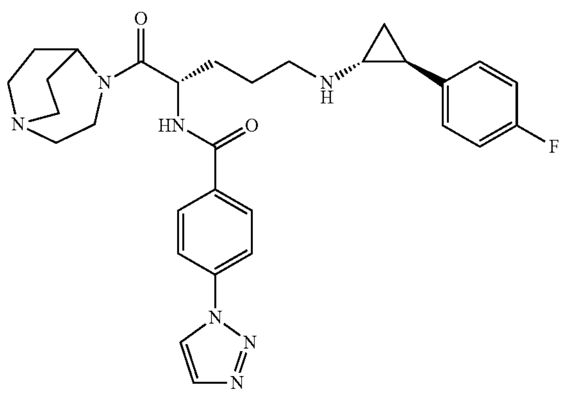 [SMILES: O=C(N[C@@H](CCCN[C@@H]1C[C@H]1c1ccc(F)cc1)C(=O)N1CCN2CCC1CC2)c1ccc(-n2ccnn2)cc1] | N-[(2S)-1-[1,4-Diazabicyclo[3.2.2]nonan-4-yl]-5-[[(1R,2S)-2-(4-fluorophenyl)cyclopropyl]amino]-1-oxopentan-2-yl]-4-(1H-1,2,3-triazol-1-yl)benzamide |
| 124 | 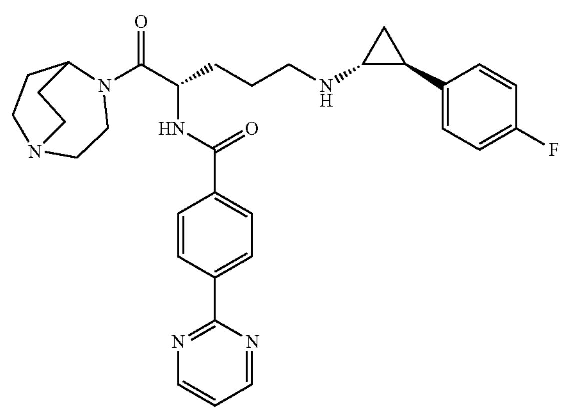 [SMILES: O=C(N[C@@H](CCCN[C@@H]1C[C@H]1c1ccc(F)cc1)C(=O)N1CCN2CCC1CC2)c1ccc(-c2ncccn2)cc1] | N-[(2S)-5-[[(1R,2S)-2-(4-Fluorophenyl)cyclopropyl]amino]-1-(1,4-diazabicyclo[3.2.2]nonane-1-yl)-1-oxopentan-2-yl]-4-(pyrimidin-2-yl)benzamide |
| 125 | 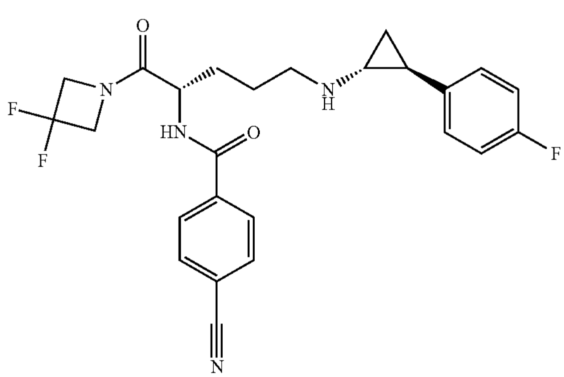 [SMILES: N#Cc1ccc(C(=O)N[C@@H](CCCN[C@@H]2C[C@H]2c2ccc(F)cc2)C(=O)N2CC(F)(F)C2)cc1] | 4-cyano-N-((S)-1-(3,3-difluoroazetidin-1-yl)-5-((1R,2S)-2-(4-fluorophenyl)cyclopropylamino)-1-oxopentan-2-yl)benzamide |

TABLE 1-continued

Compound Examples

| Ex # | Structure | Name |
|---|---|---|
| 126 | 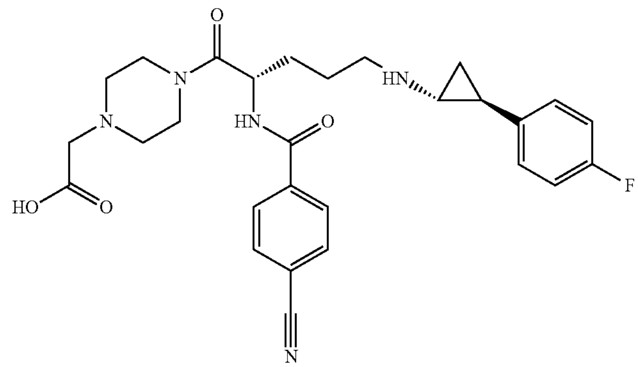 [SMILES: N#Cc1ccc(C(=O)N[C@@H](CCCN[C@@H]2C[C@H]2c2ccc(F)cc2)C(=O)N2CCN(CC(=O)O)CC2)cc1] | 2-[4-[(2S)-2-[(4-Cyanophenyl)formamido]-5-[[(1R,2S)-2-(4-fluorophenyl)cyclopropyl]amino]pentanoyl]piperazin-1-yl]acetic acid |
| 127 | 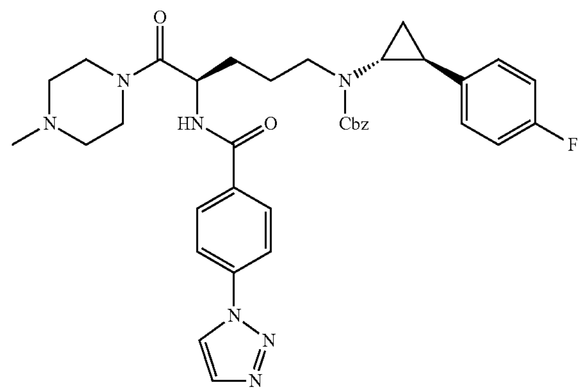 [SMILES: CN1CCN(C(=O)[C@@H](CCCN(C(=O)OCc2ccccc2)[C@@H]2C[C@H]2c2ccc(F)cc2)NC(=O)c2ccc(-n3ccnn3)cc2)CC1] | benzyl N-[(1R,2S)-2-(4-fluorophenyl)cyclopropyl]-N-[(4R)-5-(4-methylpiperazin-1-yl)-5-oxo-4-[[4-(1H-1,2,3-triazol-1-yl)phenyl]formamido]pentyl]carbamate |
| 128 | 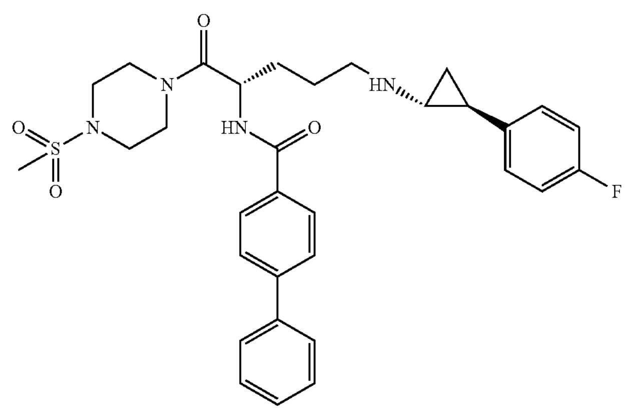 [SMILES: CS(=O)(=O)N1CCN(C(=O)[C@H](CCCN[C@@H]2C[C@H]2c2ccc(F)cc2)NC(=O)c2ccc(-c3ccccc3)cc2)CC1] | N-[(2S)-5-[[(1R,2S)-2-(4-fluorophenyl)cyclopropyl]amino]-1-(4-methanesulfonylpiperazin-1-yl)-1-oxopentan-2-yl]-4-phenylbenzamide |
| 129 | 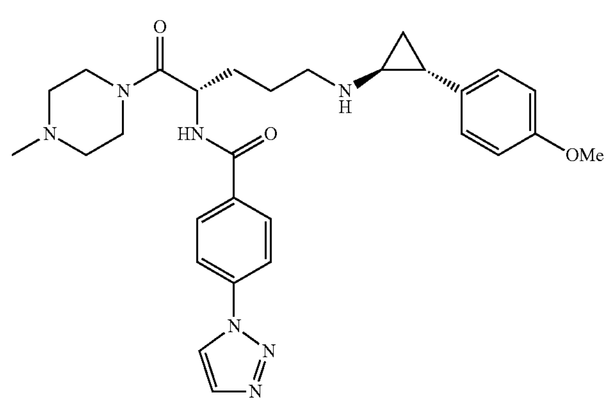 [SMILES: COc1ccc([C@H]2C[C@@H]2NCCC[C@H](NC(=O)c2ccc(-n3ccnn3)cc2)C(=O)N2CCN(C)CC2)cc1] | N-[(2S)-5-[[(1R,2S)-2-(4-methoxyphenyl)cyclopropyl]amino]-1-(4-methylpiperazin-1-yl)-1-oxopentan-2-yl]-4-(1H-1,2,3-triazol-1-yl)benzamide |

TABLE 1-continued

Compound Examples

| Ex # | Structure | Name |
|---|---|---|
| 130 | 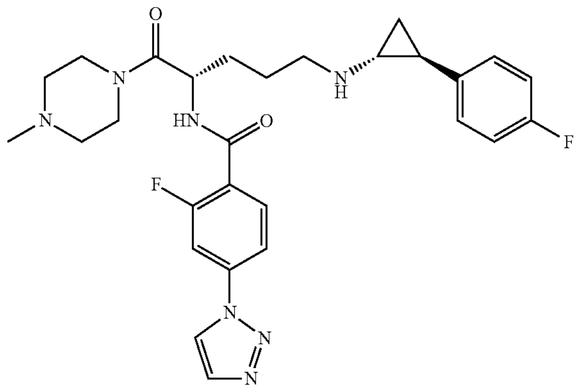 [SMILES: CN1CCN(C(=O)[C@H](CCCN[C@@H]2C[C@H]2c2ccc(F)cc2)NC(=O)c2ccc(-n3ccnn3)cc2F)CC1] | 2-Fluoro-N-[(2S)-5-[[(1R,2S)-2-(4-fluorophenyl)cyclopropyl]amino]-1-(4-methylpiperazin-1-yl)-1-oxopentan-2-yl]-4-(1H-1,2,3-triazol-1-yl)benzamide |
| 131 | 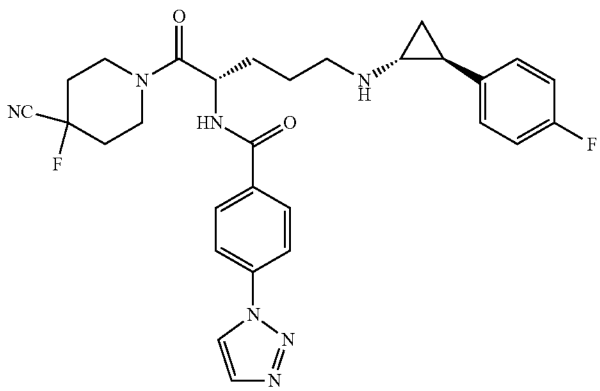 [SMILES: N#CC1(F)CCN(C(=O)[C@H](CCCN[C@@H]2C[C@H]2c2ccc(F)cc2)NC(=O)c2ccc(-n3ccnn3)cc2)CC1] | N-[(2S)-1-(4-cyano-4-fluoropiperidin-1-yl)-5-[[(1R,2S)-2-(4-fluorophenyl)cyclopropyl]amino]-1-oxopentan-2-yl]-4-(1H-1,2,3-triazol-1-yl)benzamide |
| 132 | 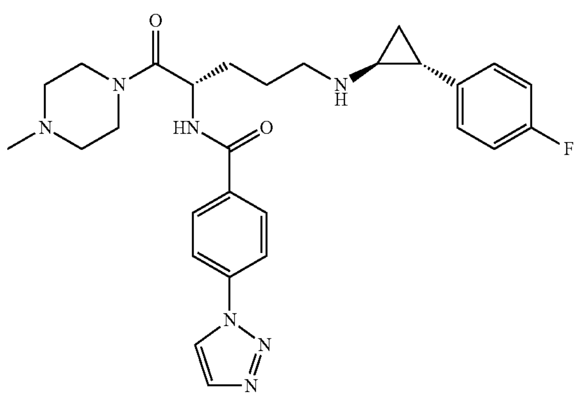 [SMILES: CN1CCN(C(=O)[C@H](CCCN[C@H]2C[C@@H]2c2ccc(F)cc2)NC(=O)c2ccc(-n3ccnn3)cc2)CC1] | N-((S)-5-((1S,2R)-2-(4-fluorophenyl)cyclopropylamino)-1-(4-methylpiperazin-1-yl)-1-oxopentan-2-yl)-4-(1H-1,2,3-triazol-1-yl)benzamide |
| 133 | 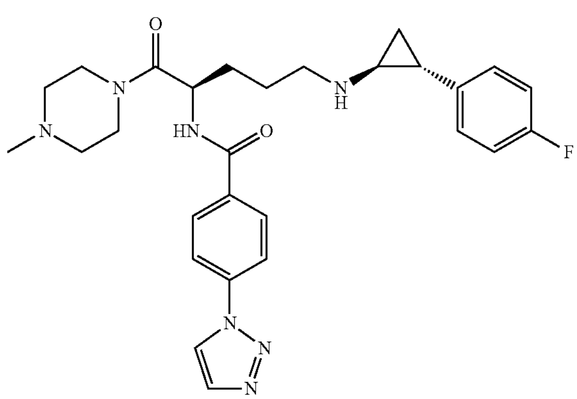 [SMILES: CN1CCN(C(=O)[C@@H](CCCN[C@H]2C[C@@H]2c2ccc(F)cc2)NC(=O)c2ccc(-n3ccnn3)cc2)CC1] | N-((R)-5-((1S,2R)-2-(4-fluorophenyl)cyclopropylamino)-1-(4-methylpiperazin-1-yl)-1-oxopentan-2-yl)-4-(1H-1,2,3-triazol-1-yl)benzamide |

TABLE 1-continued

Compound Examples

| Ex # | Structure | Name |
|---|---|---|
| 134 | 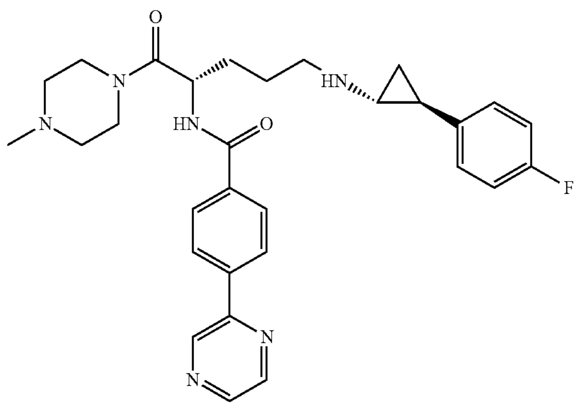 [SMILES: CN1CCN(C(=O)[C@H](CCCN[C@@H]2C[C@H]2c2ccc(F)cc2)NC(=O)c2ccc(-c3cnccn3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(pyrazin-2-yl)benzamide |
| 135 | 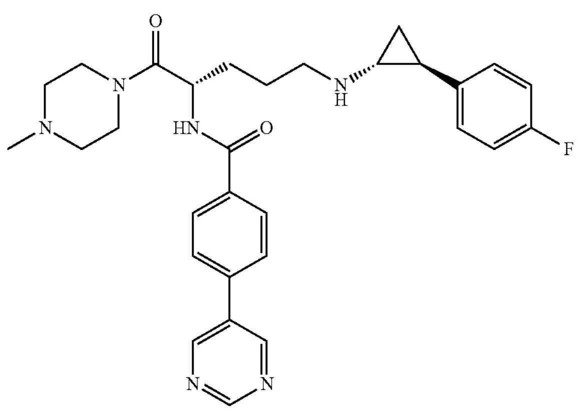 [SMILES: CN1CCN(C(=O)[C@H](CCCN[C@@H]2C[C@H]2c2ccc(F)cc2)NC(=O)c2ccc(-c3cncnc3)cc2)CC1] | N-[(2S)-5-[[(1R,2S)-2-(4-Fluorophenyl)cyclopropyl]amino]-1-(4-methylpiperazin-1-yl)-1-oxopentan-2-yl]-4-(pyrimidin-5-yl)benzamide |
| 136 | 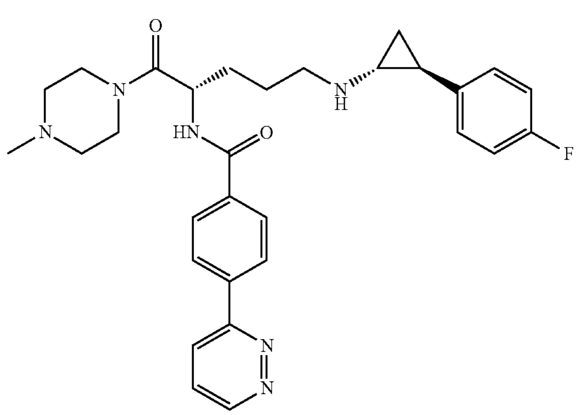 [SMILES: CN1CCN(C(=O)[C@H](CCCN[C@@H]2C[C@H]2c2ccc(F)cc2)NC(=O)c2ccc(-c3cccnn3)cc2)CC1] | N-((S)-5-((1R,2S)-2-(4-fluorophenyl)cyclopropylamino)-1-(4-methylpiperazin-1-yl)-1-oxopentan-2-yl)-4-(pyridazin-3-yl)benzamide |

TABLE 1-continued

Compound Examples

| Ex # | Structure | Name |
|---|---|---|
| 137 | 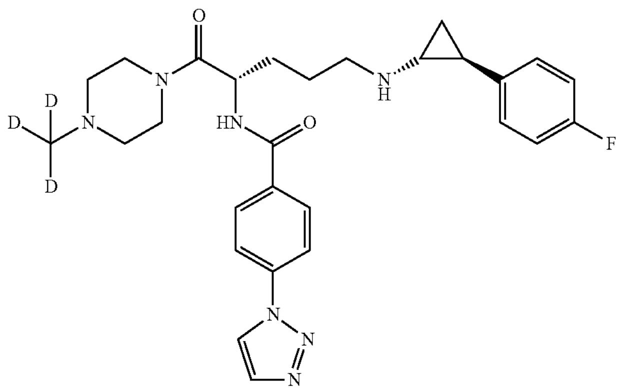 | N-[(2S)-5-[[(2S)-2-(4-Fluorophenyl)cyclopropyl]amino]-1-[4-(d₃)-methylpiperazin-1-yl]-1-oxopentan-2-yl]-4-(1H-1,2,3-triazol-1-yl)benzamide |
| 138 | 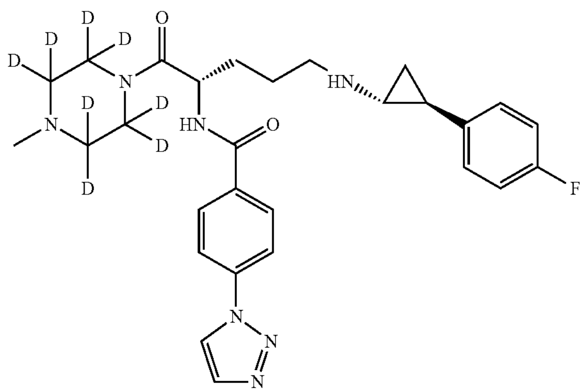 | N-[(2S)-5-[[(1R,2S)-2-(4-Fluorophenyl)cyclopropyl]amino]-1-(4-methyl-(2,2,3,3,5,5,6,6-d₈)-piperazin-1-yl)-1-oxopentan-2-yl]-4-(1H-1,2,3-triazol-1-yl)-benzamide |
| 139 | 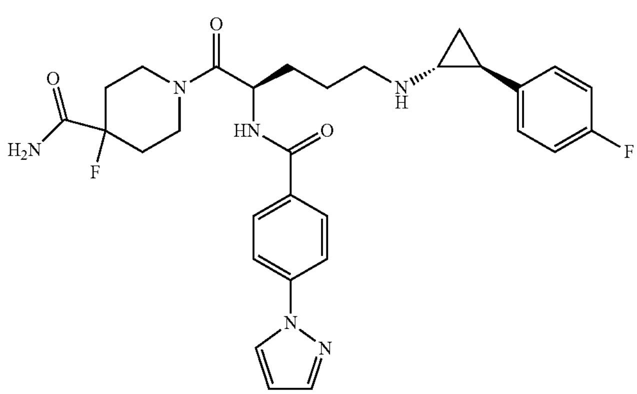 [SMILES: NC(=O)C1(F)CCN(C(=O)[C@@H](CCCN[C@@H]2C[C@H]2c2ccc(F)cc2)NC(=O)c2ccc(-n3cccn3)cc2)CC1] | 1-((R)-2-(4-(1H-pyrazol-1-yl)benzamido)-5-((1R,2S)-2-(4-fluorophenyl)cyclopropylamino)pentanoyl)-4-fluoropiperidine-4-carboxamide |
| 140 | 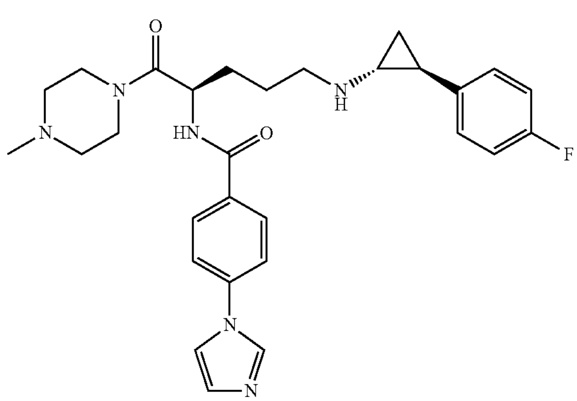 [SMILES: CN1CCN(C(=O)[C@@H](CCCN[C@@H]2C[C@H]2c2ccc(F)cc2)NC(=O)c2ccc(-n3ccnc3)cc2)CC1] | N-((R)-5-((1R,2S)-2-(4-fluorophenyl)cyclopropylamino)-1-(4-methylpiperazin-1-yl)-1-oxopentan-2-yl)-4-(1H-imidazol-1-yl)benzamide |

TABLE 1-continued

Compound Examples

| Ex # | Structure | Name |
| --- | --- | --- |
| 141 | 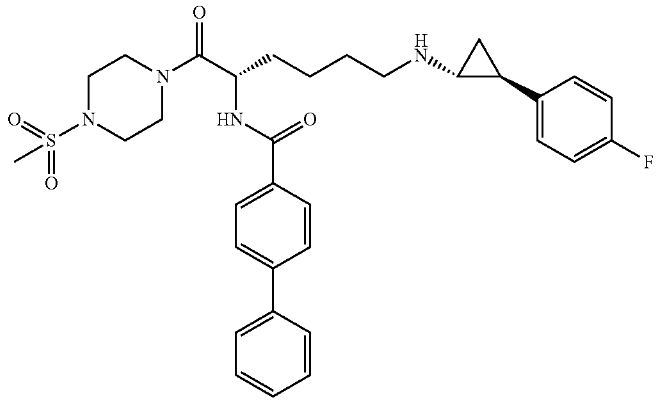 [SMILES: CS(=O)(=O)N1CCN(C(=O)[C@H](CCCCN[C@@H]2C[C@H]2c2ccc(F)cc2)NC(=O)c2ccc(-c3ccccc3)cc2)CC1] | N-((S)-6-(((1R,2S)-2-(4-fluorophenyl)cyclopropylamino)-1-(4-(methylsulfonyl)piperazin-1-yl)-1-oxohexan-2-yl)biphenyl-4-carboxamide |
| 142 | 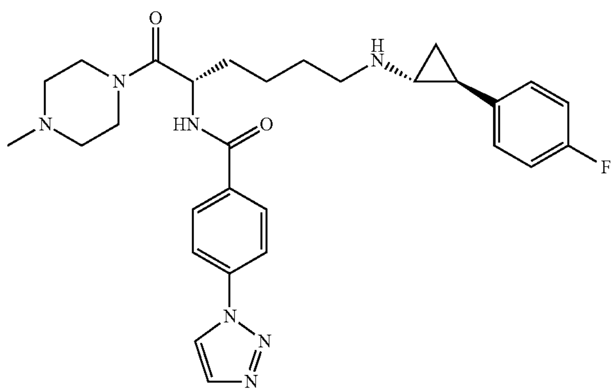 [SMILES: CN1CCN(C(=O)[C@H](CCCCN[C@@H]2C[C@H]2c2ccc(F)cc2)NC(=O)c2ccc(-n3ccnn3)cc2)CC1] | N-((S)-6-(((1R,2S)-2-(4-fluorophenyl)cyclopropylamino)-1-(4-methylpiperazin-1-yl)-1-oxohexan-2-yl)-4-(1H-1,2,3-triazol-1-yl)benzamide |
| 143 | 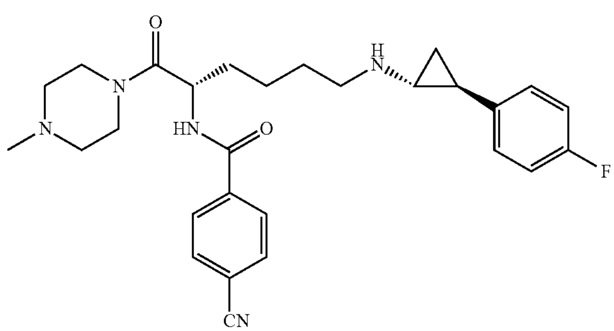 [SMILES: CN1CCN(C(=O)[C@H](CCCCN[C@@H]2C[C@H]2c2ccc(F)cc2)NC(=O)c2ccc(C#N)cc2)CC1] | 4-cyano-N-((S)-6-(((1R,2S)-2-(4-fluorophenyl)cyclopropylamino)-1-(4-methylpiperazin-1-yl)-1-oxohexan-2-yl)benzamide |
| 144 | 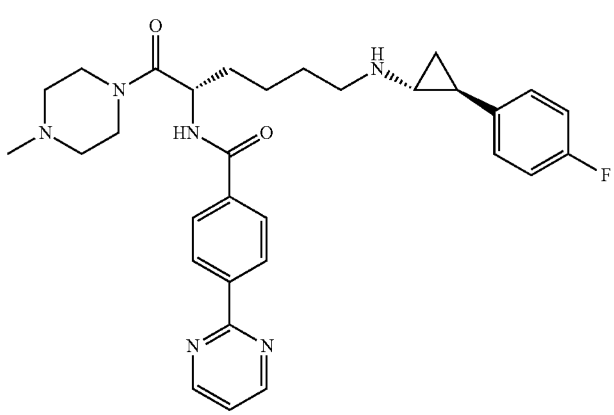 [SMILES: CN1CCN(C(=O)[C@H](CCCCN[C@@H]2C[C@H]2c2ccc(F)cc2)NC(=O)c2ccc(-c3ncccn3)cc2)CC1] | N-((S)-6-(((1R,2S)-2-(4-fluorophenyl)cyclopropylamino)-1-(4-methylpiperazin-1-yl)-1-oxohexan-2-yl)-4-(pyrimidin-2-yl)benzamide |

TABLE 1-continued

Compound Examples

| Ex # | Structure | Name |
|---|---|---|
| 145 | 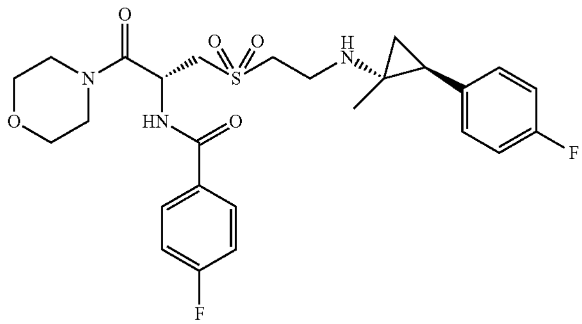 [SMILES: C[C@@]1(NCCS(=O)(=O)C[C@H](NC(=O)c2ccc(F)cc2)C(=O)N2CCOCC2)C[C@H]1c1ccc(F)cc1] | 4-fluoro-N-((R)-3-(2-((1R,2S)-2-(4-fluorophenyl)-1-methylcyclopropylamino)-ethylsulfonyl)-1-morpholino-1-oxopropan-2-yl)benzamide |
| 146 | 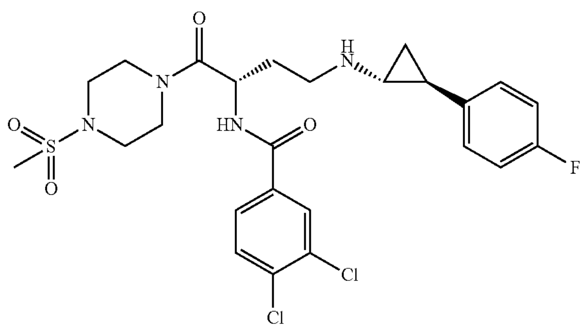 [SMILES: CS(=O)(=O)N1CCN(C(=O)[C@H](CCN[C@@H]2C[C@H]2c2ccc(F)cc2)NC(=O)c2ccc(Cl)c(Cl)c2)CC1] | 3,4-dichloro-N-((S)-4-((1R,2S)-2-(4-fluorophenyl)-cyclopropylamino)-1-(4-(methylsulfonyl)piperazin-1-yl)-1-oxobutan-2-yl)benzamide |
| 147 | 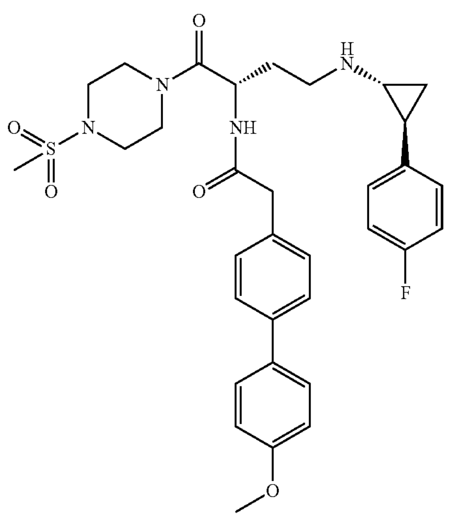 [SMILES: COc1ccc(-c2ccc(CC(=O)N[C@@H](CCN[C@@H]3C[C@H]3c3ccc(F)cc3)C(=O)N3CCN(S(C)(=O)=O)CC3)cc2)cc1] | N-((S)-4-((1R,2S)-2-(4-fluorophenyl)cyclopropylamino)-1-(4-(methylsulfonyl)piperazin-1-yl)-1-oxobutan-2-yl)-2-(4'-methoxybiphenyl-4-yl)acetamide |
| 148 | 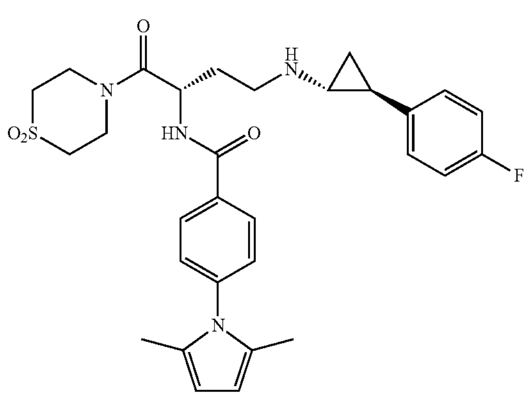 [SMILES: Cc1ccc(C)n1-c1ccc(C(=O)N[C@@H](CCN[C@@H]2C[C@H]2c2ccc(F)cc2)C(=O)N2CCS(=O)(=O)CC2)cc1] | 4-(2,5-dimethyl-1H-pyrrol-1-yl)-N-((S)-4-((1R,2S)-2-(4-fluorophenyl)cyclopropylamino)-1-oxo-1-(thiomorpholino-4,4-dioxide-1-yl)-butan-2-yl)benzamide |

TABLE 1-continued

Compound Examples

| Ex # | Structure | Name |
|---|---|---|
| 149 | 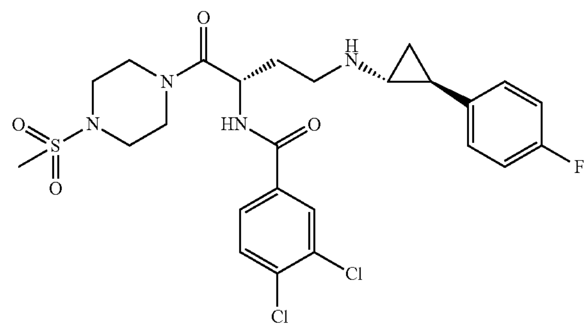 [SMILES: CS(=O)(=O)N1CCN(C(=O)[C@H](CCN[C@@H]2C[C@H]2c2ccc(F)cc2)NC(=O)c2ccc(Cl)c(Cl)c2)CC1] | 3,4-dichloro-N-((S)-4-((1R,2S)-2-(4-fluorophenyl)cyclopropylamino)-1-(4-(methylsulfonyl)piperazin-1-yl)-1-oxobutan-2-yl)benzamide |
| 150 | 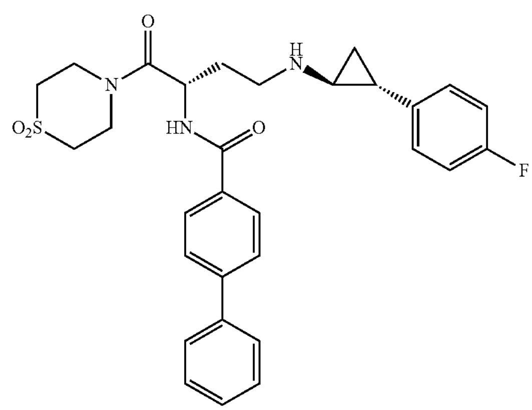 [SMILES: O=C(N[C@@H](CCN[C@H]1C[C@@H]1c1ccc(F)cc1)C(=O)N1CCS(=O)(=O)CC1)c1ccc(-c2ccccc2)cc1] | N-((S)-4-((1S,2R)-2-(4-fluorophenyl)cyclopropylamino)-1-oxo-1-(thiomorpholino-4,4-dioxide-1-yl)-butan-2-yl)biphenyl-4-carboxamide |
| 151 | 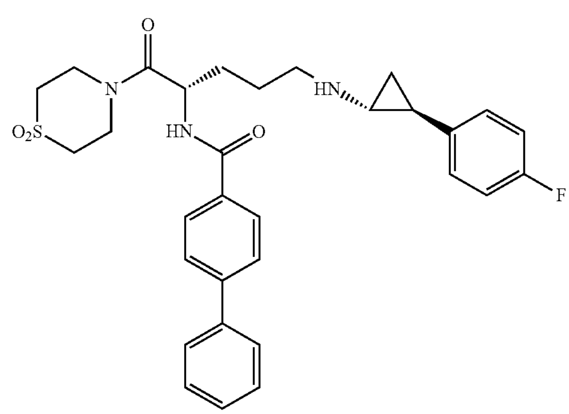 [SMILES: O=C(N[C@@H](CCCN[C@@H]1C[C@H]1c1ccc(F)cc1)C(=O)N1CCS(=O)(=O)CC1)c1ccc(-c2ccccc2)cc1] | N-((S)-5-((1R,2S)-2-(4-fluorophenyl)cyclopropylamino)-1-oxo-1-(thiomorpholino-4,4-dioxide-1-yl)-pentan-2-yl)biphenyl-4-carboxamide |

TABLE 1-continued

Compound Examples

| Ex # | Structure | Name |
| --- | --- | --- |
| 152 | 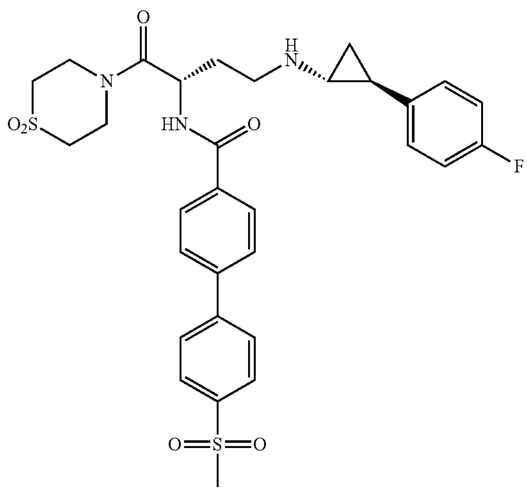 [SMILES: CS(=O)(=O)c1ccc(-c2ccc(C(=O)N[C@@H](CCN[C@@H]3C[C@H]3c3ccc(F)cc3)C(=O)N3CCS(=O)(=O)CC3)cc2)cc1] | N-((S)-4-((1R,2S)-2-(4-fluorophenyl)cyclopropylamino)-1-oxo-1-(thiomorpholino-4,4-dioxide-1-yl)-butan-2-yl)-4'-(methylsulfonyl)biphenyl-4-carboxamide |
| 153 | 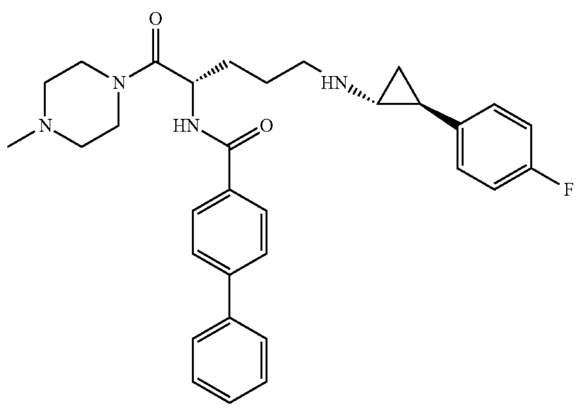 | N-((S)-5-((1R,2S)-2-(4-fluorophenyl)cyclopropylamino)-1-(4-methylpiperazin-1-yl)-1-oxopentan-2-yl)biphenyl-4-carboxamide |
| 154 | 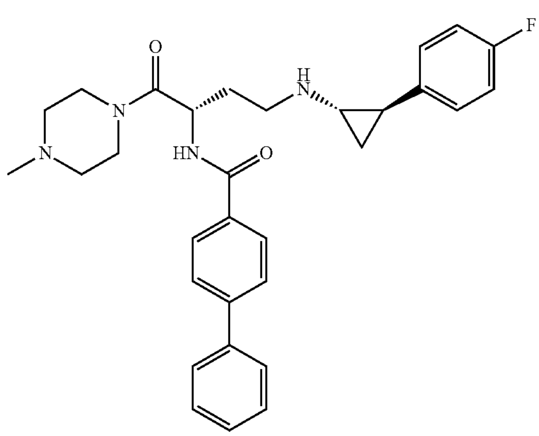 [SMILES: CN1CCN(C(=O)[C@H](CCN[C@H]2C[C@@H]2c2ccc(F)cc2)NC(=O)c2ccc(-c3ccccc3)cc2)CC1] | N-((S)-4-((1S,2R)-2-(4-fluorophenyl)cyclopropylamino)-1-(4-methylpiperazin-1-yl)-1-oxobutan-2-yl)biphenyl-4-carboxamide |

TABLE 1-continued

Compound Examples

| Ex # | Structure | Name |
|---|---|---|
| 155 | 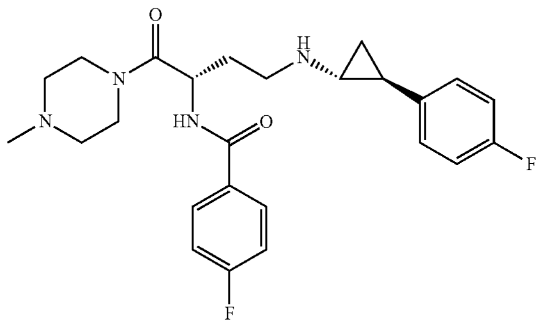 [SMILES: CN1CCN(C(=O)[C@H](CCN[C@@H]2C[C@H]2c2ccc(F)cc2)NC(=O)c2ccc(F)cc2)CC1] | 4-fluoro-N-((S)-4-((1R,2S)-2-(4-fluorophenyl)cyclopropylamino)-1-(4-methylpiperazin-1-yl)-1-oxobutan-2-yl)benzamide |
| 156 | 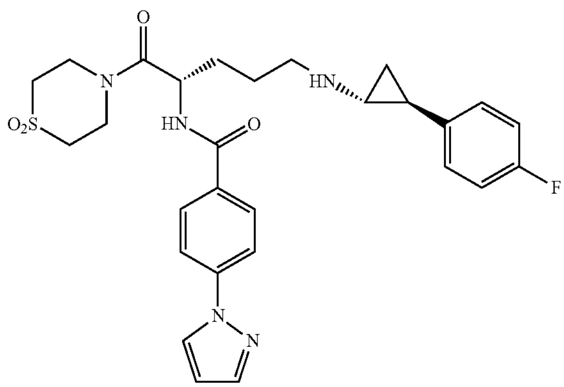 [SMILES: O=C(N[C@@H](CCCN[C@@H]1C[C@H]1c1ccc(F)cc1)C(=O)N1CCS(=O)(=O)CC1)c1ccc(-n2cccn2)cc1] | N-((S)-5-((1R,2S)-2-(4-fluorophenyl)cyclopropylamino)-1-oxo-1-(thiomorpholino-4,4-dioxide-1-yl)-pentan-2-yl)-4-(1H-pyrazol-1-yl)benzamide |
| 157 | 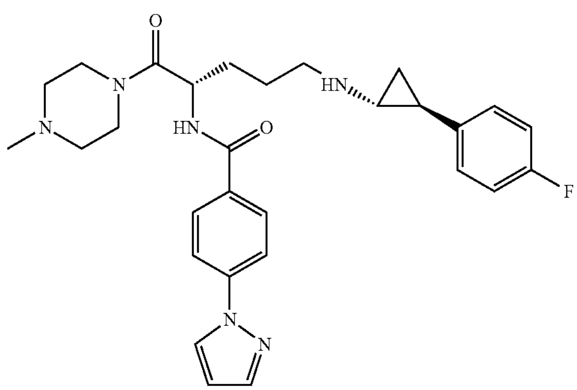 [SMILES: CN1CCN(C(=O)[C@H](CCCN[C@@H]2C[C@H]2c2ccc(F)cc2)NC(=O)c2ccc(-n3cccn3)cc2)CC1] | N-((S)-5-((1R,2S)-2-(4-fluorophenyl)cyclopropylamino)-1-(4-methylpiperazin-1-yl)-1-oxopentan-2-yl)-4-(1H-pyrazol-1-yl)benzamide |
| 158 | 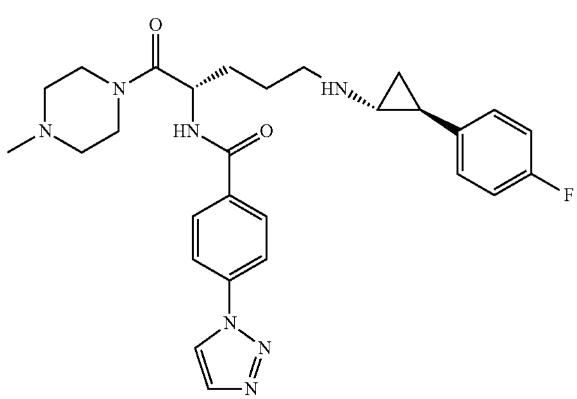 [SMILES: CN1CCN(C(=O)[C@H](CCCN[C@@H]2C[C@H]2c2ccc(F)cc2)NC(=O)c2ccc(-n3ccnn3)cc2)CC1] | N-((S)-5-((1R,2S)-2-(4-fluorophenyl)cyclopropylamino)-1-(4-methylpiperazin-1-yl)-1-oxopentan-2-yl)-4-(1H-1,2,3-triazol-1-yl)benzamide |

TABLE 1-continued

Compound Examples

| Ex # | Structure | Name |
|---|---|---|
| 159 | 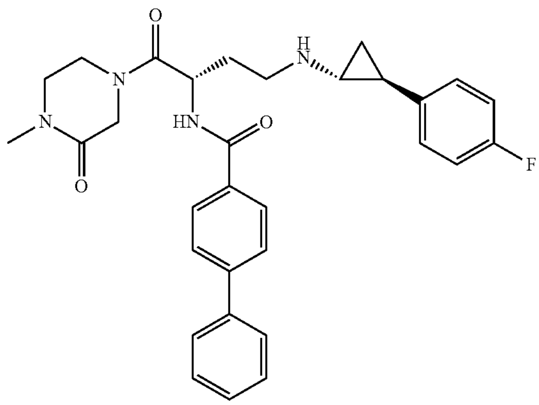 [SMILES: CN1CCN(C(=O)[C@H](CCN[C@@H]2C[C@H]2c2ccc(F)cc2)NC(=O)c2ccc(-c3ccccc3)cc2)CC1=O] | N-((S)-4-((1R,2S)-2-(4-fluorophenyl)cyclopropylamino)-1-(4-methyl-3-oxopiperazin-1-yl)-1-oxobutan-2-yl)biphenyl-4-carboxamide |
| 160 | 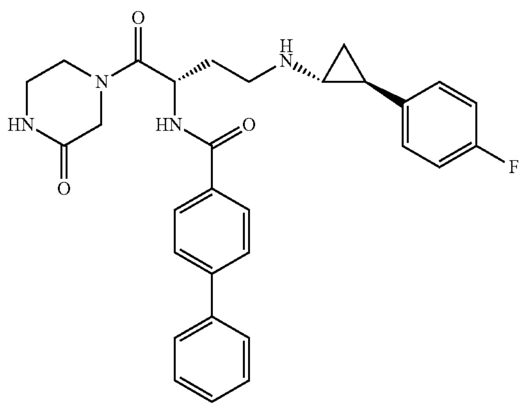 [SMILES: O=C1CN(C(=O)[C@H](CCN[C@@H]2C[C@H]2c2ccc(F)cc2)NC(=O)c2ccc(-c3ccccc3)cc2)CCN1] | N-((S)-4-((1R,2S)-2-(4-fluorophenyl)cyclopropylamino)-1-oxo-1-(3-oxopiperazin-1-yl)butan-2-yl)biphenyl-4-carboxamide |
| 161 | 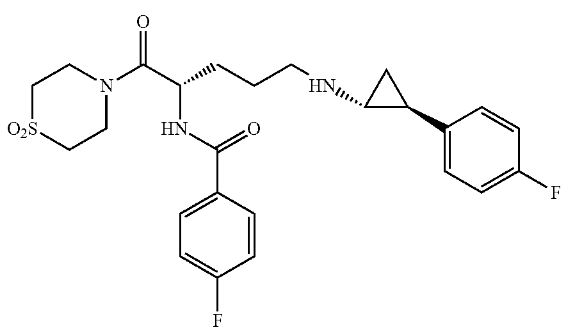 [SMILES: O=C(N[C@@H](CCCN[C@@H]1C[C@H]1c1ccc(F)cc1)C(=O)N1CCS(=O)(=O)CC1)c1ccc(F)cc1] | 4-fluoro-N-((S)-5-((1R,2S)-2-(4-fluorophenyl)cyclopropylamino)-1-oxo-1-(thiomorpholino-4,4-dioxide-1-yl)-pentan-2-yl)benzamide |
| 162 | 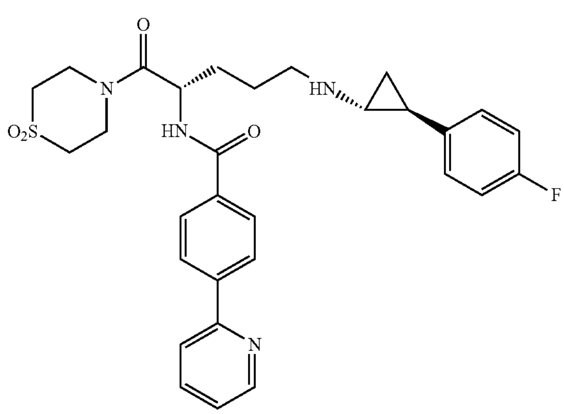 [SMILES: O=C(N[C@@H](CCCN[C@@H]1C[C@H]1c1ccc(F)cc1)C(=O)N1CCS(=O)(=O)CC1)c1ccc(-c2ccccn2)cc1] | N-((S)-5-((1R,2S)-2-(4-fluorophenyl)cyclopropylamino)-1-oxo-1-(thiomorpholino-4,4-dioxide-1-yl)-pentan-2-yl)-4-(pyridin-2-yl)benzamide |

TABLE 1-continued

Compound Examples

| Ex # | Structure | Name |
|---|---|---|
| 163 | 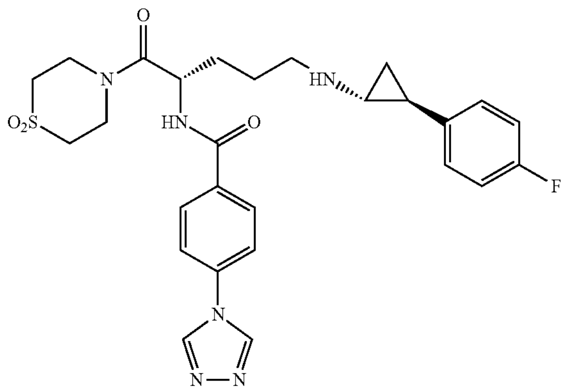 [SMILES: O=C(N[C@@H](CCCN[C@@H]1C[C@H]1c1ccc(F)cc1)C(=O)N1CCS(=O)(=O)CC1)c1ccc(-n2cnnc2)cc1] | N-((S)-5-(((1R,2S)-2-(4-fluorophenyl)cyclopropylamino)-1-oxo-1-(thiomorpholino-4,4-dioxide-1-yl)-pentan-2-yl)-4-(4H-1,2,4-triazol-4-yl)benzamide |
| 164 | 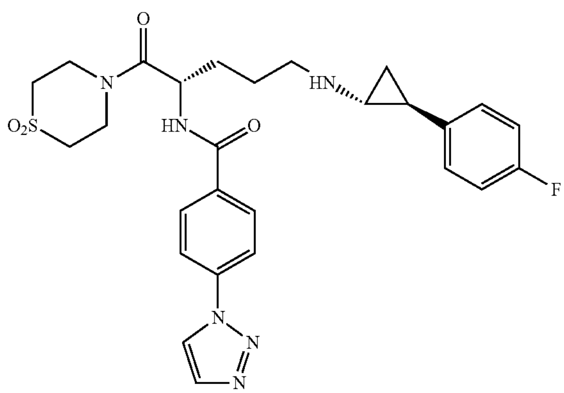 | N-((S)-5-(((1R,2S)-2-(4-fluorophenyl)cyclopropylamino)-1-oxo-1-(thiomorpholino-4,4-dioxide-1-yl)-pentan-2-yl)-4-(1H-1,2,3-triazol-1-yl)benzamide |
| 165 | 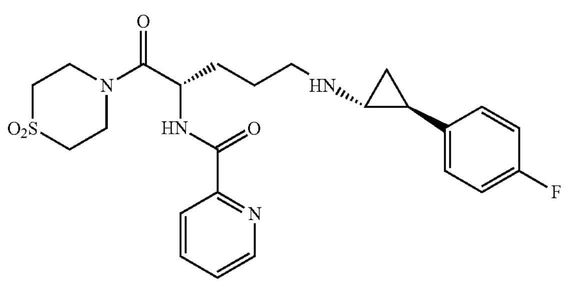 [SMILES: O=C(N[C@@H](CCCN[C@@H]1C[C@H]1c1ccc(F)cc1)C(=O)N1CCS(=O)(=O)CC1)c1ccccn1] | N-((S)-5-(((1R,2S)-2-(4-fluorophenyl)cyclopropylamino)-1-oxo-1-(thiomorpholino-4,4-dioxide-1-yl)-pentan-2-yl)picolinamide |
| 166 | 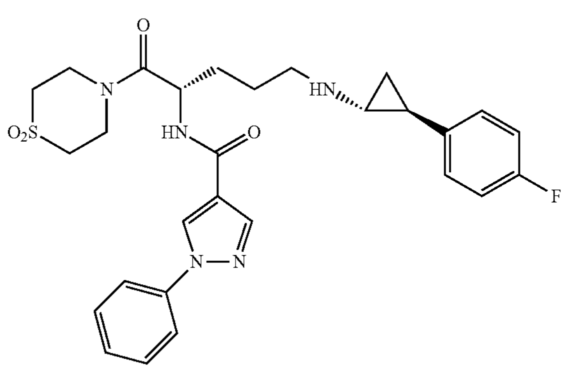 [SMILES: O=C(N[C@@H](CCCN[C@@H]1C[C@H]1c1ccc(F)cc1)C(=O)N1CCS(=O)(=O)CC1)c1cnn(-c2ccccc2)c1] | N-((S)-5-(((1R,2S)-2-(4-fluorophenyl)cyclopropylamino)-1-oxo-1-(thiomorpholino-4,4-dioxide-1-yl)-pentan-2-yl)-1-phenyl-1H-pyrazole-4-carboxamide |

TABLE 1-continued

Compound Examples

| Ex # | Structure | Name |
|---|---|---|
| 167 | 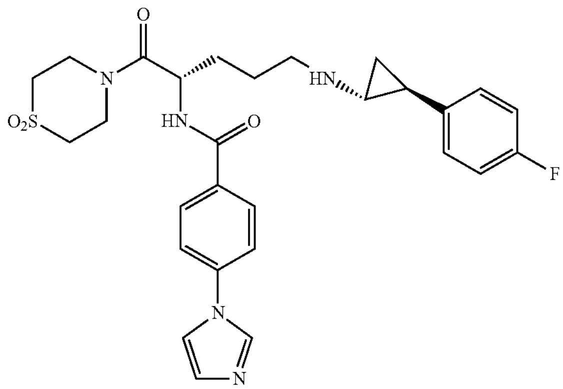 [SMILES: O=C(N[C@@H](CCCN[C@@H]1C[C@H]1c1ccc(F)cc1)C(=O)N1CCS(=O)(=O)CC1)c1ccc(-n2ccnc2)cc1] | N-((S)-5-(((1R,2S)-2-(4-fluorophenyl)cyclopropylamino)-1-oxo-1-(thiomorpholino-4,4-dioxide-1-yl)-pentan-2-yl)-4-(1H-imidazol-1-yl)benzamide |
| 168 | 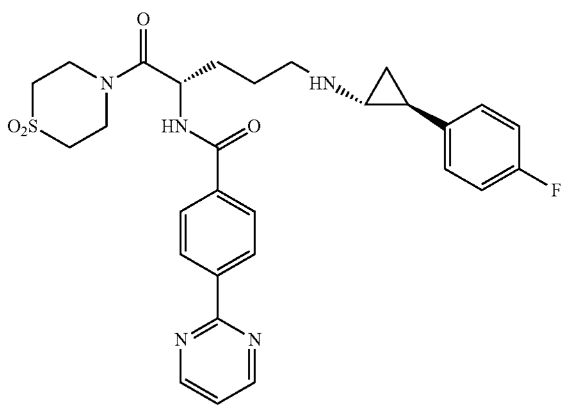 [SMILES: O=C(N[C@@H](CCCN[C@@H]1C[C@H]1c1ccc(F)cc1)C(=O)N1CCS(=O)(=O)CC1)c1ccc(-c2ncccn2)cc1] | N-((S)-5-(((1R,2S)-2-(4-fluorophenyl)cyclopropylamino)-1-oxo-1-(thiomorpholino-4,4-dioxide-1-yl)-pentan-2-yl)-4-(pyrimidin-2-yl)benzamide |
| 169 | 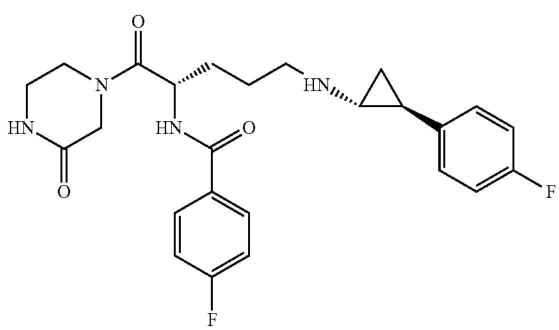 [SMILES: O=C1CN(C(=O)[C@H](CCCN[C@@H]2C[C@H]2c2ccc(F)cc2)NC(=O)c2ccc(F)cc2)CCN1] | 4-fluoro-N-((S)-5-(((1R,2S)-2-(4-fluorophenyl)cyclopropylamino)-1-oxo-1-(3-oxopiperazin-1-yl)pentan-2-yl)benzamide |
| 170 | 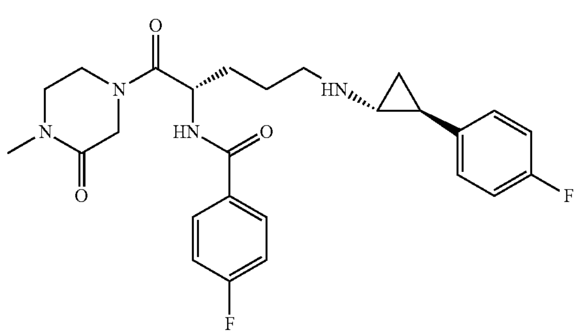 [SMILES: CN1CCN(C(=O)[C@H](CCCN[C@@H]2C[C@H]2c2ccc(F)cc2)NC(=O)c2ccc(F)cc2)CC1=O] | 4-fluoro-N-((S)-5-(((1R,2S)-2-(4-fluorophenyl)cyclopropylamino)-1-(4-methyl-3-oxopiperazin-1-yl)-1-oxopentan-2-yl)benzamide |

TABLE 1-continued

Compound Examples

| Ex # | Structure | Name |
|---|---|---|
| 171 | 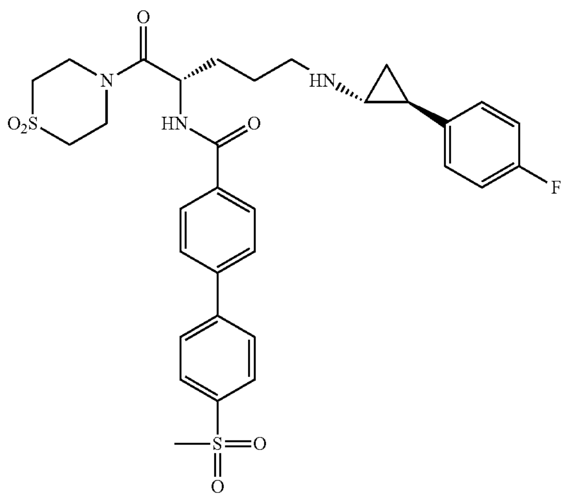 [SMILES: CS(=O)(=O)c1ccc(-c2ccc(C(=O)N[C@@H](CCCN[C@@H]3C[C@H]3c3ccc(F)cc3)C(=O)N3CCS(=O)(=O)CC3)cc2)cc1] | N-((S)-5-(((1R,2S)-2-(4-fluorophenyl)cyclopropylamino)-1-oxo-1-(thiomorpholino-4,4-dioxide-1-yl)-pentan-2-yl)-4'-(methylsulfonyl)biphenyl-4-carboxamide |
| 172 | 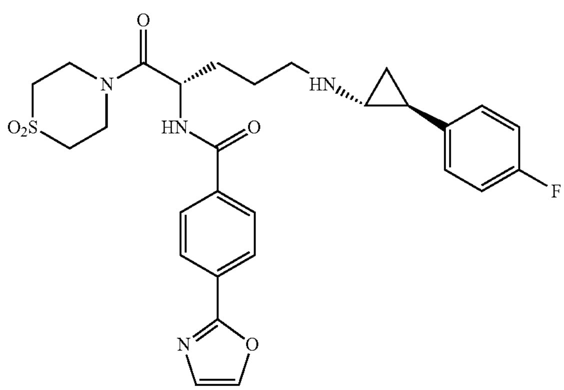 [SMILES: O=C(N[C@@H](CCCN[C@@H]1C[C@H]1c1ccc(F)cc1)C(=O)N1CCS(=O)(=O)CC1)c1ccc(-c2ncco2)cc1] | N-((S)-5-(((1R,2S)-2-(4-fluorophenyl)cyclopropylamino)-1-oxo-1-(thiomorpholino-4,4-dioxide-1-yl)-pentan-2-yl)-4-(oxazol-2-yl)benzamide |
| 173 | 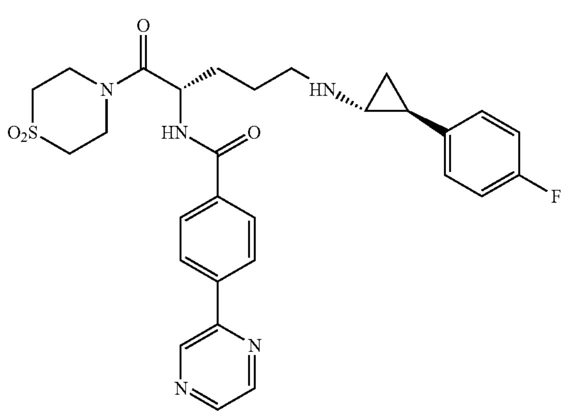 | N-((S)-5-(((1R,2S)-2-(4-fluorophenyl)cyclopropylamino)-1-oxo-1-(thiomorpholino-4,4-dioxide-1-yl)-pentan-2-yl)-4-(pyrazin-2-yl)benzamide |

TABLE 1-continued

Compound Examples

| Ex # | Structure | Name |
|---|---|---|
| 174 | 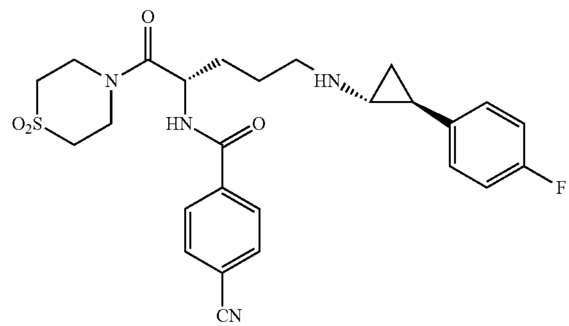 [SMILES: N#Cc1ccc(C(=O)N[C@@H](CCCN[C@@H]2C[C@H]2c2ccc(F)cc2)C(=O)N2CCS(=O)(=O)CC2)cc1] | 4-cyano-N-((S)-5-((1R,2S)-2-(4-fluorophenyl)cyclopropylamino)-1-oxo-1-(thiomorpholino-4,4-dioxide-1-yl)-pentan-2-yl)benzamide |
| 175 | 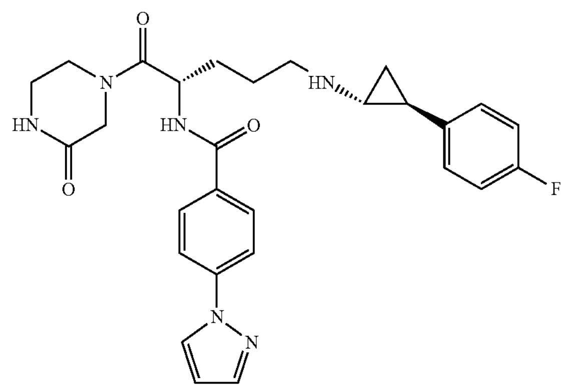 [SMILES: O=C1CN(C(=O)[C@H](CCCN[C@@H]2C[C@H]2c2ccc(F)cc2)NC(=O)c2ccc(-n3cccn3)cc2)CCN1] | N-((S)-5-((1R,2S)-2-(4-fluorophenyl)cyclopropylamino)-1-oxo-1-(3-oxopiperazin-1-yl)pentan-2-yl)-4-(1H-pyrazol-1-yl)benzamide |
| 176 | 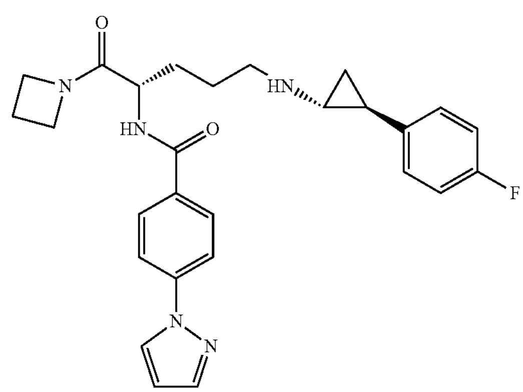 [SMILES: O=C(N[C@@H](CCCN[C@@H]1C[C@H]1c1ccc(F)cc1)C(=O)N1CCC1)c1ccc(-n2cccn2)cc1] | N-((S)-1-(azetidin-1-yl)-5-((1R,2S)-2-(4-fluorophenyl)cyclopropylamino)-1-oxopentan-2-yl)-4-(1H-pyrazol-1-yl)benzamide |
| 177 | 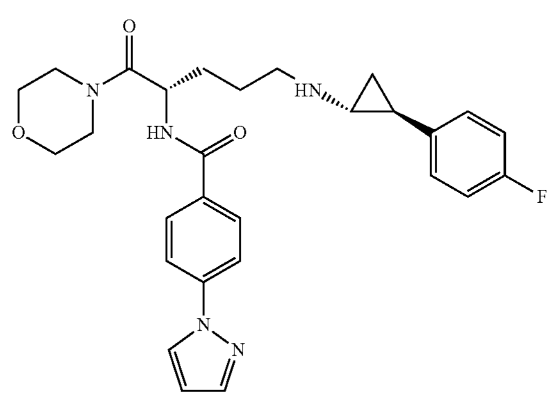 [SMILES: O=C(N[C@@H](CCCN[C@@H]1C[C@H]1c1ccc(F)cc1)C(=O)N1CCOCC1)c1ccc(-n2cccn2)cc1] | N-((S)-5-((1R,2S)-2-(4-fluorophenyl)cyclopropylamino)-1-morpholino-1-oxopentan-2-yl)-4-(1H-pyrazol-1-yl)benzamide |

TABLE 1-continued

Compound Examples

| Ex # | Structure | Name |
|---|---|---|
| 178 | 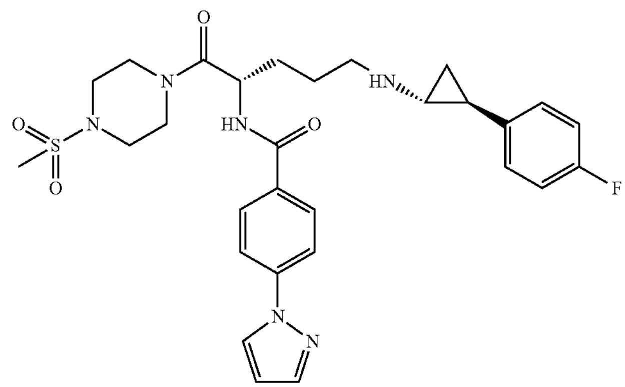 [SMILES: CS(=O)(=O)N1CCN(C(=O)[C@H](CCCN[C@@H]2C[C@H]2c2ccc(F)cc2)NC(=O)c2ccc(-n3cccn3)cc2)CC1] | N-((S)-5-(((1R,2S)-2-(4-fluorophenyl)cyclopropylamino)-1-(4-(methylsulfonyl)piperazin-1-yl)-1-oxopentan-2-yl)-4-(1H-pyrazol-1-yl)benzamide |
| 179 | 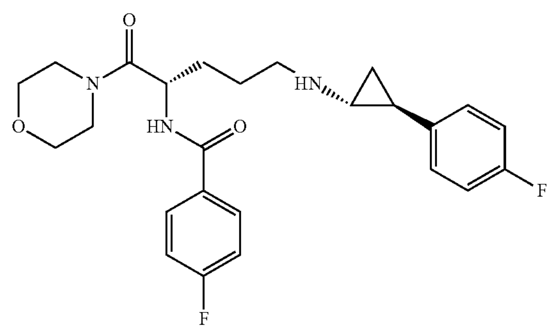 [SMILES: O=C(N[C@@H](CCCN[C@@H]1C[C@H]1c1ccc(F)cc1)C(=O)N1CCOCC1)c1ccc(F)cc1] | 4-fluoro-N-((S)-5-(((1R,2S)-2-(4-fluorophenyl)cyclopropylamino)-1-morpholino-1-oxopentan-2-yl)benzamide |
| 180 | 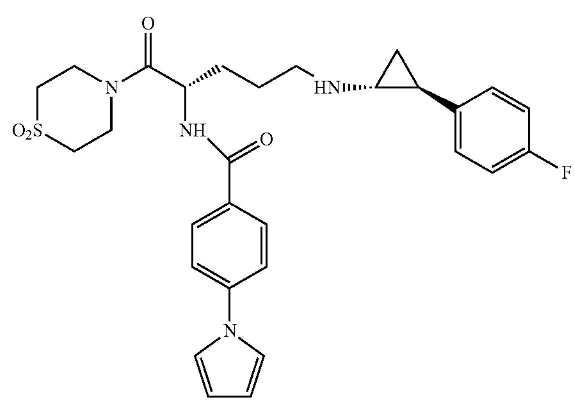 [SMILES: O=C(N[C@@H](CCCN[C@@H]1C[C@H]1c1ccc(F)cc1)C(=O)N1CCS(=O)(=O)CC1)c1ccc(-n2cccc2)cc1] | N-((S)-5-(((1R,2S)-2-(4-fluorophenyl)cyclopropylamino)-1-oxo-1-(thiomorpholino-4,4-dioxide-1-yl)-pentan-2-yl)-4-(1H-pyrrol-1-yl)benzamide |
| 181 | 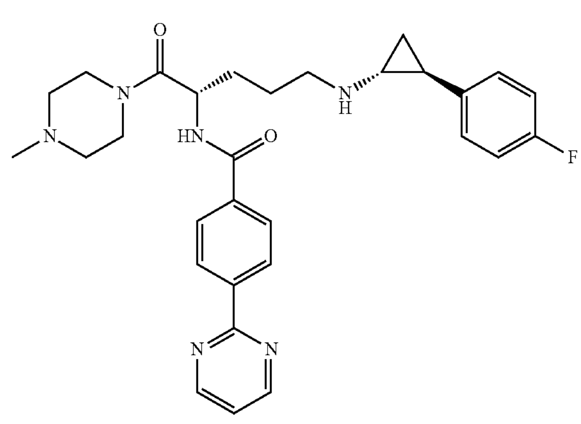 [SMILES: CN1CCN(C(=O)[C@H](CCCN[C@@H]2C[C@H]2c2ccc(F)cc2)NC(=O)c2ccc(-c3ncccn3)cc2)CC1] | N-((S)-5-(((1R,2S)-2-(4-fluorophenyl)cyclopropylamino)-1-(4-methylpiperazin-1-yl)-1-oxopentan-2-yl)-4-(pyrimidin-2-yl)benzamide |

TABLE 1-continued

Compound Examples

| Ex # | Structure | Name |
|---|---|---|
| 182 | 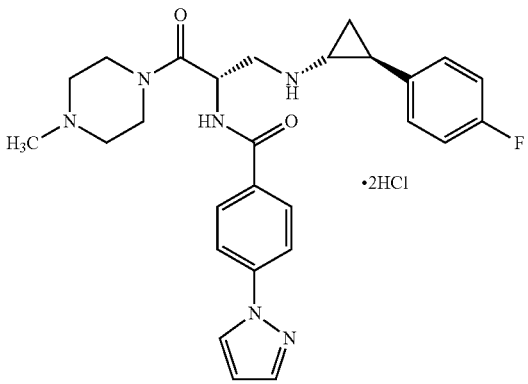 | N-((S)-3-((1R,2S)-2-(4-fluorophenyl)cyclopropylamino)-1-(4-methylpiperazin-1-yl)-1-oxopropan-2-yl)-4-(1H-pyrazol-1-yl)benzamide dihydrochloride salt |
| 183 | 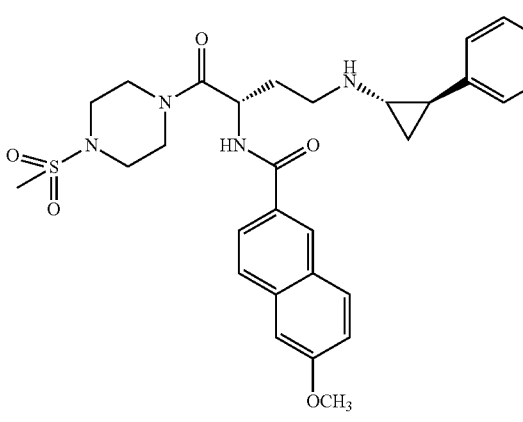 | N-((S)-4-((1S,2R)-2-(4-fluorophenyl)cyclopropylamino)-1-(4-(methylsulfonyl)piperazin-1-yl)-1-oxobutan-2-yl)-6-methoxy-2-naphthamide |
| 184 | 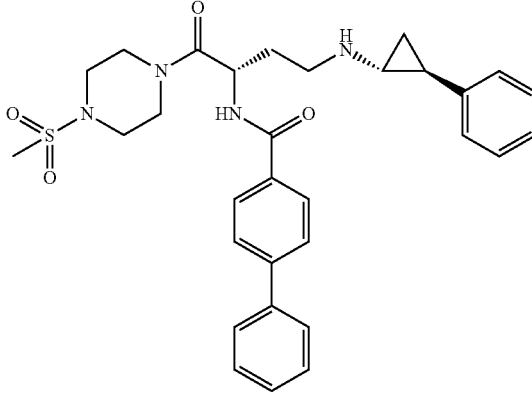 | N-((S)-4-((1R,2S)-2-(4-fluorophenyl)cyclopropylamino)-1-(4-(methylsulfonyl)piperazin-1-yl)-1-oxobutan-2-yl)biphenyl-4-carboxamide |
| 185 | 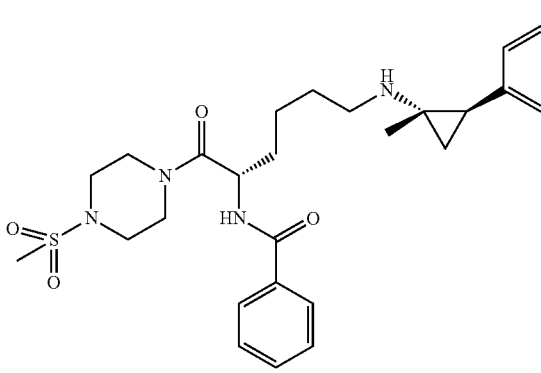 | N-((S)-6-((1S,2R)-2-(4-fluorophenyl)-1-methylcyclopropylamino)-1-(4-(methylsulfonyl)piperazin-1-yl)-1-oxohexan-2-yl)benzamide |

TABLE 1-continued

Compound Examples

| Ex # | Structure | Name |
|---|---|---|
| 186 | 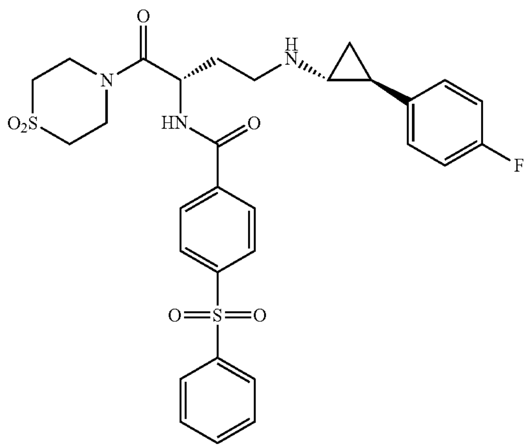 [SMILES: O=C(N[C@@H](CCN[C@@H]1C[C@H]1c1ccc(F)cc1)C(=O)N1CCS(=O)(=O)CC1)c1ccc(S(=O)(=O)c2ccccc2)cc1] | N-((S)-4-((1R,2S)-2-(4-fluorophenyl)cyclopropylamino)-1-oxo-1-(thiomorpholino-4,4-dioxide-1-yl)-butan-2-yl)-4-(phenylsulfonyl)benzamide |
| 187 | 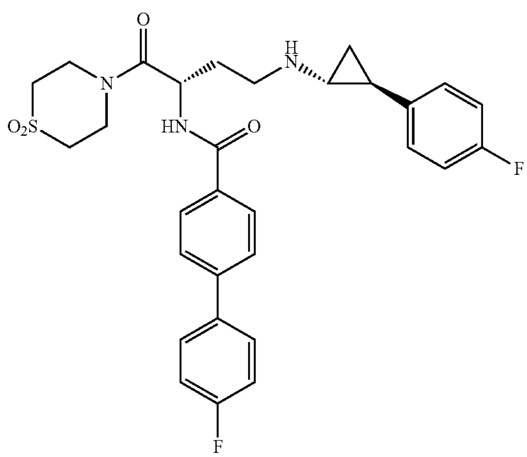 [SMILES: O=C(N[C@@H](CCN[C@@H]1C[C@H]1c1ccc(F)cc1)C(=O)N1CCS(=O)(=O)CC1)c1ccc(-c2ccc(F)cc2)cc1] | 4'-fluoro-N-((S)-4-((1R,2S)-2-(4-fluorophenyl)cyclopropylamino)-1-oxo-1-(thiomorpholino-4,4-dioxide-1-yl)-butan-2-yl)biphenyl-4-carboxamide |
| 188 | 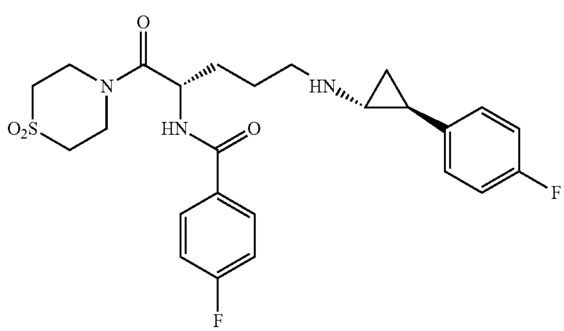 [SMILES: O=C(N[C@@H](CCCN[C@@H]1C[C@H]1c1ccc(F)cc1)C(=O)N1CCS(=O)(=O)CC1)c1ccc(F)cc1] | N-((S)-1-(azetidin-1-yl)-5-((1R,2S)-2-(4-fluorophenyl)cyclopropylamino)-1-oxopentan-2-yl)-4-fluorobenzamide |

Also provided herein is salt of a compound as disclosed herein, or a polymorph or solvate thereof.

In certain embodiments, the salt has Formula VI:

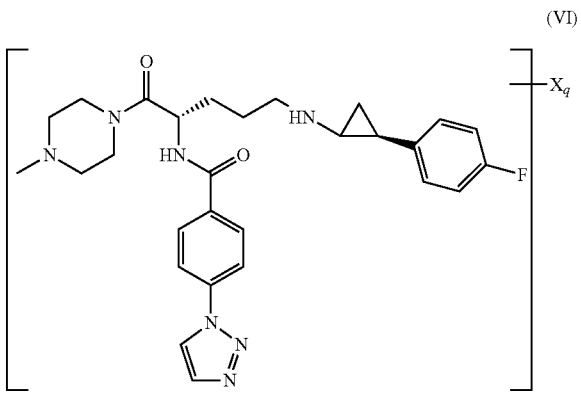

(VI)

or a polymorph or solvate thereof, wherein:

X is chosen from tosylate, sulfate, tartrate, oxalate, besylate, fumarate, citric, esylate, and malate; and q is an integer chosen from 1 and 2.

In certain embodiments, X is tosylate.

In certain embodiments, q is 2.

Provided herein is N—((S)-5-(((1R,2S)-2-(4-fluorophenyl)cyclopropylamino)-1-(4-methylpiperazin-1-yl)-1-oxopentan-2-yl)-4-(1H-1,2,3-triazol-1-yl)benzamide bis-tosylate, or a polymorph thereof. Also provided herein is N—((S)-5-(((1R,2S)-2-(4-fluorophenyl)cyclopropylamino)-1-(4-methylpiperazin-1-yl)-1-oxopentan-2-yl)-4-(1H-1,2,3-triazol-1-yl)benzamide bis-tosylate Form 2.

Also provided herein is a tosylate salt of a compound as disclosed herein, or a polymorph or solvate thereof. Also provided herein is a bis-tosylate salt of a compound as disclosed herein, or a polymorph or solvate thereof.

Also provided herein is a compound, or a salt, polymorph, or solvate thereof, as disclosed herein is provided for use as a medicament. Also provided herein is a compound as disclosed herein, or a salt, polymorph, or solvate thereof, for use in the manufacture of a medicament for the prevention or treatment of a KDM1A-mediated disease.

Also provided herein is a compound as disclosed herein is for use in the manufacture of a medicament for the prevention or treatment of a disease or condition chosen from sickle cell disease, thalassemia major, and other beta-hemoglobinopathies.

Also provided herein is a pharmaceutical composition is provided which comprises a compound as disclosed herein, together with a pharmaceutically acceptable carrier.

In certain embodiments, the pharmaceutical composition is formulated for oral administration.

In certain embodiments, the pharmaceutical composition additionally comprises another therapeutic agent.

Also provided herein is a method of inhibiting KDM1A is provided, comprising contacting KDM1A with a compound as disclosed herein.

Also provided herein is a method of treatment of a KDM1A-mediated disease comprising the administration of a therapeutically effective amount of a compound as disclosed herein, or a salt, polymorph, or solvate thereof, to a patient in need thereof.

In certain embodiments, the disease is cancer.

In certain embodiments, the cancer is chosen from Ewing's sarcoma, multiple myeloma, T-cell leukemia, Wilm's tumor, small-cell lung cancer, bladder cancer, prostate cancer, breast cancer, head/neck cancer, colon cancer, and ovarian cancer.

In certain embodiments, the disease is a myeloid disease.

In certain embodiments, the myeloid disease is chosen from myelofibrosis, polycythemia vera, essential thrombocythemia, myelodysplastic syndrome (MDS), acute myelogenous leukemia (AML), and chronic myelogenous leukemia (CML).

In certain embodiments, the disease is an inflammatory disease.

In certain embodiments, the inflammatory disease is chosen from inflammatory bowel disease, rheumatoid arthritis, or systemic lupus erythematosus.

Also provided herein is a method of treatment of a globin-mediated disease comprising the administration of a therapeutically effective amount of a compound as disclosed herein, or a salt, polymorph, or solvate thereof, to a patient in need thereof.

Also provided herein is a method for achieving an effect in a patient is provided; comprising the administration of a therapeutically effective amount of a compound as disclosed herein; wherein the effect is chosen from an elevation of red blood cell count, an elevation of the red blood cell count of red cells containing fetal hemoglobin, an elevation in the total concentration of fetal hemoglobin in red cells, an elevation in the total concentration of fetal hemoglobin in reticulocytes, an increase in the transcription of the gamma globin gene in bone marrow-derived red cell precursors, e.g., pro-erythroblasts, a reduction in the number of sickle cell crises a patient experiences over a unit period of time, a halt to or prevention of tissue damage e.g. in the heart, spleen, brain or kidney caused by sickling cells, a reduction in the proportion of red cells that undergo sickling under physiological conditions of relative hypoxia as measured using patient blood in an in vitro assay, an increase in the amount of histone 3 lysine methylation at lysine position 4 (H3K4me1 and H3K4me2), and/or a decrease in the amount of histone 3 methylation at lysine position 9 (H3K9me1 or H3K4me2) near or at the gamma globin promoter as assayed by ChIP using cells derived from a treated patient.

Also provided herein is a method of inhibiting at least one KDM1A function is provided; comprising the step of contacting KDM1A with a compound as disclosed herein; wherein the inhibition is measured by phenotype of red cells or their precursors either cultured or in vivo in humans or mouse or transgenic mice containing the human beta globin locus or portions thereof, the ability of cancer cells to proliferate, the expression of specific genes known to be regulated by KDM1A activity such as gamma globin, a change in the histone methylation states, a change in the methylation state of proteins known to be demethylated by KDM1A such as G9a or SUV39H1, expression of KDM1A-regulated genes, or binding of KDM1A with a natural binding partner such as CoREST, DNMT1 or HDACs.

Inhibition of KDM1A (LSD1) activity alone may be sufficient therapy for the treatment of some diseases; for other such as cancer, combination therapies are often additive or synergistic in their therapeutic effects and may even be necessary to achieve the full clinical benefit desired. There is specific scientific evidence to rationalize the combination of an inhibitor of KDM1A with all-trans retinoic acid (ATRA), arsenic trioxide, inhibitors of DNA methyltransferases such as 5'-azacytidine or 5'-aza 2'-deoxycytidine, inhibitors of NFκB signaling such as sulindac or conventional anti-neoplastic agents such as anthracyclines or nucleoside analogues such as cytosine arabinoside. Likewise, agents that induce leukemia stem cells into the cell cycle (G-CSF, GM-CSF, stem cell factor, thrombopoietin (TPO)) or agents that negate the contributory role cytokines (TPO, CCL3(MIP-1)) play in remodeling the niche of cancer stem cells may be useful as part of a combination including an LSD1 inhibitor.

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% from the specified amount.

A "therapeutically effective amount" of a drug is an amount of drug or its pharmaceutically acceptable salt that eliminates, alleviates, or provides relief of the symptoms of the disease for which it is administered.

A "subject in need thereof" is a human or non-human animal that exhibits one or more symptoms or indicia of a disease.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.). When n is set at 0 in the context of "0 carbon atoms", it is intended to indicate a bond or null.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, hydroxyalkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "amino acid", as used herein, alone or in combination, refers to a —NHCHRC(O)O— group, which may be attached to the parent molecular moiety to give either an N-terminus or C-terminus amino acid, wherein R is independently chosen from hydrogen, alkyl, aryl, heteroaryl, heterocycloalkyl, aminoalkyl, amido, amidoalkyl, carboxyl, carboxylalkyl, guanidinealkyl, hydroxyl, thiol, and thioalkyl, any of which themselves may be optionally substituted. The term C-terminus, as used herein, alone or in combination, refers to the parent molecular moiety being bound to the amino acid at the amino group, to give an amide as described herein, with the carboxyl group unbound, resulting in a terminal carboxyl group, or the corresponding carboxylate anion. The term N-terminus, as used herein, alone or in combination, refers to the parent molecular moiety being bound to the amino acid at the carboxyl group, to give an ester as described herein, with the amino group unbound resulting in a terminal secondary amine, or the corresponding ammonium cation. In other words, C-terminus refers to —NHCHRC(O)OH or to —NHCHRC(O)O$^-$ and N-terminus refers to H$_2$NCHRC(O)O— or to H$_3$N$^+$CHRC(O)O—.

The term "aminoalkyl," as used herein, alone or in combination, refers to an amino group as defined herein linked through an alkyl group to the parent moiety.

The term "aryl", as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C$_6$H$_4$=derived from benzene. Examples include benzothiophene and benzimidazole.

The term "biphenyl" as used herein refers to two phenyl groups connected at one carbon site on each ring.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "guanidine", as used herein, alone or in combination, refers to —NHC(=NH)NH$_2$, or the corresponding guanidinium cation.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogen atoms are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furanyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuranyl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl, azepinyl, diazepinyl, benzazepinyl, and the like. Exemplary tricyclic heterocyclic groups include carbazolyl, benzidolyl, phenanthrolinyl, dibenzofuranyl, acridinyl, phenanthridinyl, xanthenyl and the like.

The term "heteroarylalkyl" as used herein alone or as part of another group refers to alkyl groups as defined above having a heteroaryl substituent.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, imidazolidinyl, isoindolinyl, morpholinyl, oxazolidinyl, isoxazolidinyl, piperidinyl, piperazinyl, methylpiperazinyl, N-methylpiperazinyl, pyrrolidinyl, pyrazolidinyl, tetrahydrofuranyl, tetrahydropyridinyl, thiomorpholinyl, thiazolidinyl, diazepanyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "hydroxamic acid", as used herein, alone or in combination, refers to —C(=O)NHOH, wherein the parent molecular moiety is attached to the hydroxamic acid group by means of the carbon atom.

The phrase "in the main chain" refers to the longest contiguous or adjacent chain of carbon atoms starting at the point of attachment of a group to the compounds of any one of the formulas disclosed herein. The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate," as used herein, alone or in combination, refers to a —P(=O)(OR)$_2$ group, wherein R is chosen from alkyl and aryl. The term "phosphonic acid", as used herein, alone or in combination, refers to a —P(=O)(OH)$_2$ group.

The terms "sulfonate," "sulfonic acid," and "sulfonic," as used herein, alone or in combination, refer to the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a $X_3CO$— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. Similarly, when a designation such as "n" which may be chosen from a group or range of integers is designated to be 0, then the group which it designates is either absent, if in a terminal position, or condenses to form a bond, if it falls between two other groups.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

When the construction

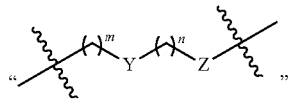

as used herein, the alkylene groups enclosed by ( )$_m$ and ( )$_n$ may be m or n carbons long.

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reaction of the appropriate compound, in the form of the free base, with the appropriate acid.

The compounds disclosed herein can exist as polymorphs and other distinct solid forms such as solvates, hydrates, and the like. A compound may be a polymorph, solvate, or hydrate of a salt or of the free base or acid.

While it may be possible for the compounds disclosed herein to be administered as the raw chemical, it is also possible to present them as pharmaceutical formulations (equivalently, "pharmaceutical compositions"). Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, intraadiposal, intraarterial, intracranial, intralesional, intranasal, intraocular, intrapericardial, intraperitoneal, intrapleural, intraprostatical, intrarectal, intrathecal, intratracheal, intratumoral, intraumbilical, intravaginal, intravesicular, intravitreal, and intramedullary), intraperitoneal, rectal, topical (including, without limitation, dermal, buccal, sublingual, vaginal, rectal, nasal, otic, and ocular), local, mucosal, sublingual, subcutaneous, transmucosal, transdermal, transbuccal, transdermal, and vaginal; liposomal, in cremes, in lipid compositions, via a catheter, via a lavage, via continuous infusion, via infusion, via inhalation, via injection, via local delivery, via localized perfusion, bathing target cells directly, or any combination thereof. Administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound disclosed herein or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as hard or soft capsules, wafers, cachets or tablets each containing a predetermined amount of the active ingredient; as a powder or granules; as a syrup, elixir, solution, or a suspension in an aqueous liquid or a non-aqueous liquid; or as an oil-in-water liquid emulsion, a water-in-oil liquid emulsion, or a compound dispersed in a liposome. The active ingredient may also be presented as a bolus, electuary or paste.

Pharmaceutical preparations that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide delayed, slowed, or controlled release or absorption of the active ingredient therein. Compositions may further comprise an agent that enhances solubility or dispersability. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Depending on the route of administration, the compounds, or granules or particles thereof, may be coated in a material to protect the compounds from the action of acids and other natural conditions that may inactivate the compounds.

The compounds may be formulated for parenteral administration by injection, e.g., by bolus injection or continuous infusion, either to the body or to the site of a disease or wound. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. To administer the therapeutic compound by other than parenteral administration, it may be necessary to coat the compound with, or co-administer the compound with a material to prevent its inactivation (for example, via liposomal formulation).

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations disclosed herein may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations disclosed herein including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenan, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected because of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

In certain topical embodiments, formulations are prepared using a buffering system that maintains the formulation at a pH of about 4.5 to a pH of about 8. In further embodiments, the pH is from 7 to 8.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. Several optional ingredients can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, galactomannan polymers (such as guar and derivatives thereof), and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example, a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

The therapeutic compound may also be administered intraspinally or intracerebrally. Dispersions for these types of administrations can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and required other ingredients to be pharmacologically sound. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

It should be understood that in addition to the ingredients particularly mentioned above, the formulations described above may include other agents conventional in the art having regard to the type of formulation in question, for example, those suitable for oral administration may include flavoring agents.

Compounds may be administered at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

Preferred unit dosage formulations are those containing an effective dose, as herein below recited, or an appropriate fraction thereof, of the active ingredient. In certain embodiments, a formulation disclosed herein is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

The amount of active ingredient that may be combined with the carrier materials to produce a single dosage form will vary depending upon the host treated and the particular mode of administration. Similarly, the precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Alternatively, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). There is even the possibility that two compounds, one of the compounds described herein and a second compound may together achieve the desired therapeutic effect that neither alone could achieve. Alternatively, by way of example only, the benefit experienced by a patient may be increased by administering one of the compounds described herein with another therapeutic agent (which also includes a therapeutic regimen) that also has therapeutic benefit. By way of example only, in a treatment for acute myelogenous leukemia or sickle cell anemia involving administration of one of the compounds described herein, increased therapeutic benefit may result by also providing the patient with another therapeutic agent for sickle cell anemia or for acute myelogenous leukemia. In any case, regardless of the disease, disorder or condition being treated, the overall benefit experienced by the patient may simply be additive of the two therapeutic agents or the two agents may have synergistic therapeutic effects in a patient.

Effective combination therapy may be achieved with a single composition or pharmacological formulation that includes both agents, or with two distinct compositions or formulations, at the same time, wherein one composition includes a compound of the present disclosure, and the other includes the second agent(s). Alternatively, the therapy may precede or follow the other agent treatment by intervals ranging from minutes to months. Administration of the compounds of the present disclosure to a patient will follow general protocols for the administration of pharmaceuticals, taking into account the toxicity, if any, of the drug. It is expected that the treatment cycles would be repeated as necessary.

Specific, non-limiting examples of possible combination therapies include use of certain compounds of the invention with the following agents and classes of agents: agents that inhibit DNA methyltransferases such as decitabine or 5'-azacytadine; agents that inhibit the activity of histone deacetylases, histone de-sumoylases, histone de-ubiquitinases, or histone phosphatases such as hydroxyurea; antisense RNAs that might inhibit the expression of other components of the protein complex bound at the DR site in the gamma globin promoter; agents that inhibit the action of Klf1 or the expression of KLF1; agents that inhibit the action of Bcl11a or the expression of BCL11A; and agents that inhibit cell cycle progression such as hydroxyurea, ara-C or daunorubicin; agents that induce differentiation in leukemic cells such as all-trans retinoic acid (ATRA).

Thus, in another aspect, the present invention provides methods for treating diseases or disorders in a human or animal subject in need of such treatment comprising administering to said subject an amount of a compound disclosed herein effective to reduce or prevent said disorder in the subject, optionally in combination with at least one additional agent for the treatment of said disorder that is known in the art.

Used either as a monotherapy or in combination with other agents, the compounds disclosed herein are useful in the prevention and/or treatment of beta-hemoglobinopathies such as thalassemia major, sickle cell disease, hemoglobin E/thalassemia, and thalassemia *intermedia*.

The compounds disclosed herein can be used in the treatment of diseases in which an increase in transcription through the manipulation of epigenetic regulatory factors such as inhibition of KDM1A would be beneficial to the patient. This applies to diseases including but not limited to loss of function mutations, mutations resulting in haploinsufficiency, deletions and duplications of genetic material or epigenetic regulatory mechanisms have altered the normal expression pattern of a gene or genes that has the effect of altering the dose of a gene product(s). Such diseases may include diseases both acquired and hereditary in which the expression of, for example, cytokines affecting immune function, are altered, X-linked mental retardation and other forms of compromised cognitive or motor function such as Alzheimer and Parkinson disease whether they are the acquired or hereditary forms, lipid disorders such as elevated cholesterol, low density lipoprotein, very low density lipoprotein or triglycerides, both type one and type two diabetes, and Mendelian genetic diseases.

Other disorders or conditions that can be advantageously treated by the compounds disclosed herein include inflammation and inflammatory conditions. Inflammatory conditions include, without limitation: arthritis, including subtypes and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritus and vitiligo. In addition, compounds of invention are also useful in organ transplant patients either alone or in combination with conventional immunomodulators.

Autoimmune disorders may be ameliorated by the treatment with compounds disclosed herein. Autoimmune disorders include Crohn's disease, ulcerative colitis, dermatitis, dermatomyositis, diabetes mellitus type 1, Goodpasture's syndrome, Graves' disease, Guillain-Barré syndrome (GBS), autoimmune encephalomyelitis, Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis, Sjögren's syndrome, scleroderma, temporal arteritis (also known as "giant cell arteritis"), vasculitis, and Wegener's granulomatosis.

The compounds disclosed herein are also useful for the treatment of organ and tissue injury associated with severe burns, sepsis, trauma, wounds, and hemorrhage- or resuscitation-induced hypotension, and also in such diseases as vascular diseases, migraine headaches, periarteritis *nodosa*, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, swelling occurring after injury, ischemias including myocardial ischemia, cardiovascular ischemia, and ischemia secondary to cardiac arrest, and the like.

The compounds disclosed herein are also useful for the treatment of certain diseases and disorders of the nervous system. Central nervous system disorders in KDM1A inhibition is useful include cortical dementias including Alzheimer's disease, central nervous system damage resulting from stroke, ischemias including cerebral ischemia (both focal ischemia, thrombotic stroke and global ischemia (for example, secondary to cardiac arrest), and trauma. Neurodegenerative disorders in which KDM1A inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen-induced convulsions and toxicity, dementia e.g., pre-senile dementia, and AIDS-related dementia, cachexia, Sydenham's chorea, Huntington's disease, Parkinson's Disease, amyotrophic lateral sclerosis (ALS), Korsakoffs disease, cognitive disorders relating to a cerebral vessel disorder, hypersensitivity, sleeping disorders, schizophrenia, depression, depression or other symptoms associated with Premenstrual Syndrome (PMS), and anxiety.

Still other disorders or conditions advantageously treated by the compounds disclosed herein include the prevention or treatment of hyperproliferative diseases, especially cancers, either alone or in combination with standards of care especially those agents that target tumor growth by re-instating tumor suppressor genes in the malignant cells. Hematological and non-hematological malignancies which may be treated or prevented include but are not limited to multiple myeloma, acute and chronic leukemias and hematopoietic proliferative and neoplastic disorders including Myelodysplastic Syndrome (MDS), Acute Myelogenous Leukemia (AML), Acute Lymphocytic Leukemia (ALL), Chronic Lymphocytic Leukemia (CLL), and Chronic Myelogenous Leukemia (CML), lymphomas, including Hodgkin's lymphoma and non-Hodgkin's lymphoma (low, intermediate, and high grade), as well as solid tumors and malignancies of the brain, head and neck, breast, lung (including non-small-cell lung cancer), reproductive tract, upper digestive tract, pancreas, liver, renal system, bladder, prostate and colorectal. The present compounds and methods can also be used to treat fibrosis, such as that which occurs with radiation therapy. The present compounds and methods can be used to treat subjects having or prevent the progression of adenomatous polyps, including those with familial adenomatous polyposis (FAP) or sarcoidosis. Non-cancerous proliferative disorders additionally include psoriasis, eczema, and dermatitis.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds disclosed herein may also be used to prevent tissue damage when therapeutically combined with antibacterial or antiviral agents.

The compounds disclosed herein are also useful for the treatment of treat metabolic disorders. KDM1A, using flavin adenosine dinucleotide (FAD) as a cofactor, epigenetically regulates energy-expenditure genes in adipocytes depending on the cellular FAD availability. Additionally, loss of KDM1A function induces a number of regulators of energy expenditure and mitochondrial metabolism resulting in the activation of mitochondrial respiration. Furthermore, in the adipose tissues from mice fed a high-fat diet, expression of KDM1A-target genes is reduced.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL-less than 40 mg/dL; pro-thrombotic state (e.g., high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels often for decades before overt diabetes develops. Eventually the beta cells of the pancreas are unable to overcome insulin resistance through hypersecretion. Glucose levels rise and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with type 2 diabetes includes increased serum very-low-density lipoprotein (VLDL) cholesterol and triglyceride levels and, sometimes, a decreased low-density lipoprotein (LDL) cholesterol level. Insulin resistance has been found in persons with low levels of high-density lipoprotein HDL). Insulin levels have also been linked to VLDL synthesis and plasma triglyceride levels.

Specific metabolic diseases and symptoms to be treated by the compounds, compositions, and methods disclosed herein are those mediated at least in part by KDM1A. Accordingly, disclosed herein are methods: for treating insulin resistance in a subject; for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; for inducing mitochondrial respiration in a subject; or for treating disease; all comprising the administration of a therapeutic amount of a compound as described herein, to a patient in need thereof. In further embodiments, the disease to be treated may be a metabolic disease. In further embodiment, the metabolic disease may be selected from the group consisting of: obesity, diabetes mellitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be selected from the group consisting of: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Methods

General Synthetic Methods for Preparing Compounds

The following invention is further illustrated by the following Examples.

In the Examples below and throughout the disclosure, the following abbreviations may be used: PTFE=polytetrafluoroethylene; RM=Reaction Mixture; RH=Relative Humidity; RT=Room Temperature; SM=Starting Material; MeCN=acetonitrile; ClPh=chlorophenol; DCE=dichloroethane; DCM=dichloromethane; DIPE=di-isopropylether; DMA=dimethyl acetamide; DMF=dimethyl formamide; DMSO=dimethylsulfoxide; Et$_2$O=diethyl ether; EtOAc=ethyl acetate; EtOH=ethanol; H$_2$O=water; IPA=propan-2-ol; i-PrOAc=iso-propyl acetate; MEK=methyl ethyl ketone; MeOH=methanol; MIBK=methyl isobutyl ketone; MTBE=methyl tert-butyl ether; n-BuOAc=n-butyl acetate; n-BuOH=n-butanol; NMP=n-methyl pyrrolidone; n-PrOH=n-propanol; s-BuOAc=s-butyl acetate; t-BuOH=t-butanol; TFA=trifluoro acetic acid; THF=tetrahydrofuran; TMP=2,2,4-trimethylpentane; $^1$H-NMR=Proton Nuclear magnetic Resonance; DSC=Differential Scanning Calorimetry; DVS=Dynamic Vapour Sorption; GVS=Gravimetric Vapour Sorption; HPLC=High Performance Liquid Chromatography; HS=Head Space; HSM=Hot Stage Microscopy; IC=Ion Chromatography; IDR=Intrinsic Dissolution Rate; KF=Karl-Fisher; MAS=Magic Angle Spinning; MDSC=Modulated Differential Scanning Calorimetry; PLM=Polarised Light Microscopy; PVM=Particle Vision and Measurement; SCXRD=Single Crystal X-Ray Diffraction; SS-NMR=Solid State Nuclear Magnetic Resonance; TGA=Thermal Gravimetric Analysis; UV=UltraViolet VH-XRPD=Variable Humidity X-Ray Powder Diffraction; VT-XRPD=Variable Temperature X-Ray Powder Diffraction; and XRPD=X-Ray Powder Diffraction. Other abbreviations may be used and will be familiar in context to those of skill in the art.

Example 1

Scheme 1

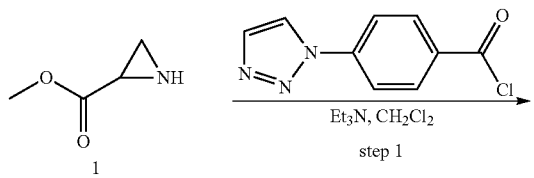

153
-continued

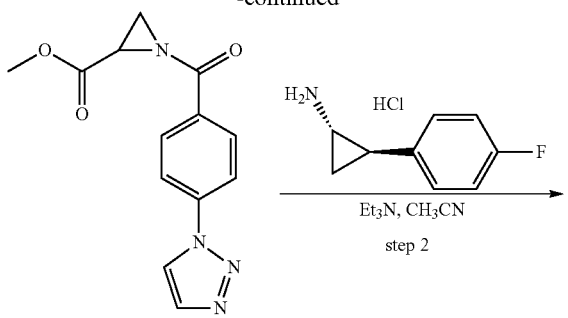

2

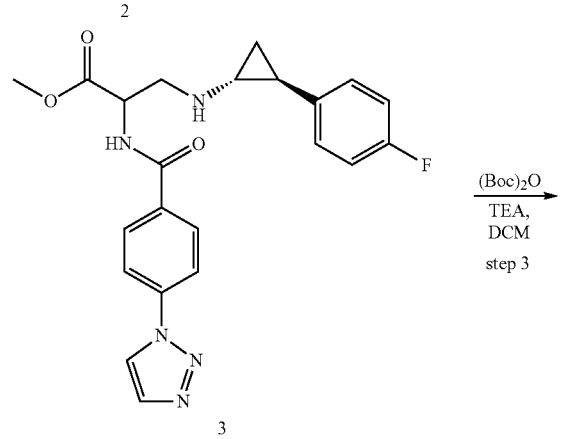

3

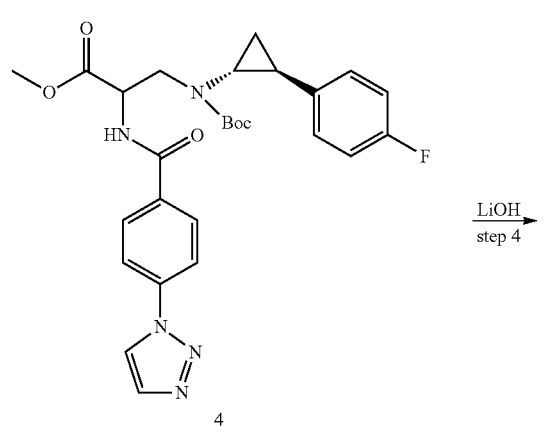

4

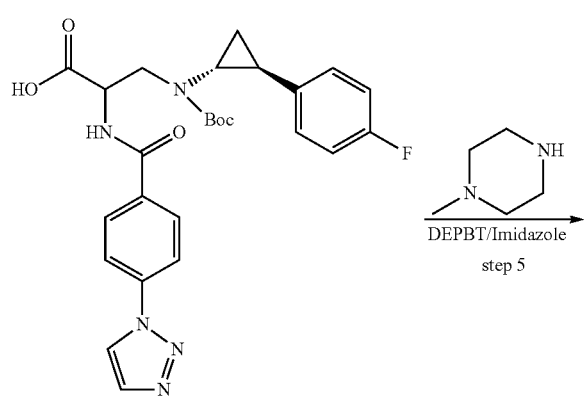

5

154
-continued

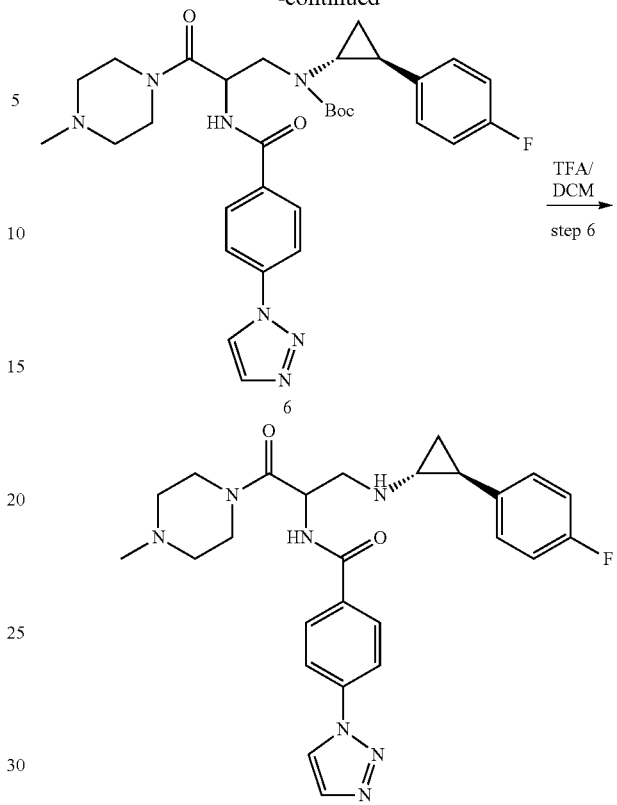

Synthesis of 1

4-(1H-1,2,3-triazolyl-1-yl)benzoyl Chloride (201)

In a 100-mL round-bottom flask were combined a solution of 4-(1H-1,2,3-triazol-1-yl)benzoic acid (1.2 g, 6.34 mmol, 1.00 equiv) in thionyl chloride (20 mL). The resulting solution was stirred for 1 h at 80° C., then concentrated under vacuum, affording 1.2 g (78%) of the product (as its hydrochloride salt) as an off-white solid.

1-(4-(1H-1,2,3-triazol-1-yl)benzoyl-2-carbomethoxy Aziridine (203)

In a 250-mL round-bottom flask were added a solution of methyl aziridine-2-carboxylate (1 g, 9.89 mmol, 1.00 equiv) in CH$_2$Cl$_2$ (80 mL) and Et$_3$N (3 g, 29.65 mmol, 3.00 equiv), followed by the addition of a solution of 4-(1H-1,2,3-triazol-1-yl)benzoyl chloride (2.3 g, 11.08 mmol, 1.12 equiv) in CH$_2$Cl$_2$ (20 mL) dropwise with stirring at 0° C. The resulting solution was stirred for 1 h at 25° C., then washed with 1×50 mL of water and 1×50 mL of brine, dried over Na$_2$SO$_4$, and concentrated under vacuum. The residue was applied onto a silica gel column with ethyl acetate/petroleum ether (1:3). This resulted in 2.5 g (93%) of the product as a white solid.

Methyl 3-[[(1R,2S)-2-(4-fluorophenyl)cyclopropyl]amino]-2-[[4-(1H-1,2,3-triazol-1-yl)phenyl]formamido]propanoate In a 50-mL round-bottom flask were combined the compound produced in the previous step (1.5 g, 5.51 mmol, 1.00 equiv), CH₃CN (20 mL), (1S,2R)-2-(4-fluorophenyl)cyclopropan-1-amine hydrochloride (2.6 g, 13.86 mmol, 2.50 equiv) and Et₃N (1.4 g, 13.84 mmol, 2.48 equiv). The resulting solution was stirred for 16 h at 80° C. in an oil bath, then diluted with 50 ml of EtOAc, washed with 1×30 mL of water and 1×30 mL of brine, dried over Na₂SO₄ and concentrated under vacuum. The residue was applied onto a silica gel column with EtOAc/petroleum ether (2:1), affording 1 g (43%) of PH-IMA-2013-003-362-11 as an off-white solid.

Methyl 3-[[(1R,2S)-2-(4-fluorophenyl)cyclopropyl](tert-butoxycarbonyl)amino]-2-[[4-(1H-1,2,3-triazol-1-yl)phenyl]formamido]propanoate (204)

In a 50-mL round-bottom flask were combined the compound produced in the previous step (1 g, 2.36 mmol, 1.00 equiv), CH₂Cl₂ (20 mL), Et₃N (500 mg, 4.94 mmol, 2.09 equiv) and di-tert-butyl dicarbonate (780 mg, 3.57 mmol, 1.51 equiv). The resulting solution was stirred for 16 h at 25° C. The resulting mixture was washed with 1×30 mL of water and 1×30 mL of brine, dried over Na₂SO₄, and concentrated under vacuum. The residue was applied onto a silica gel column with EtOAc/petroleum ether (1:2), affording 600 mg (49%) of PH-IMA-2013-003-362-12 as a white solid.

3-[[(1R,2S)-2-(4-Fluorophenyl)cyclopropyl](tert-butoxycarbonyl)amino]-2-[[4-(1H-1,2,3-triazol-1-yl)phenyl]formamido]propanoic Acid (205)

Into a 50-mL round-bottom flask was added a solution of the compound produced in the previous step (600 mg, 1.15 mmol, 1.00 equiv) in THF (25 mL), followed by LiOH (41 mg, 1.71 mmol, 1.49 equiv) in water (6 mL). The resulting solution was stirred for 2 h at 25° C. The pH value of the solution was adjusted to 5 with HCl (2 M). The resulting solution was extracted with 2×30 mL of EtOAc, and the organic layers were combined and washed with 1×30 mL of brine, dried over anhydrous Na₂SO₄, and concentrated under vacuum, affording 580 mg (99%) of the product as a white solid.

N-[3-[[(1R,2S)-2-(4-Fluorophenyl)cyclopropyl](tert-butoxycarbonyl)amino]-1-(4-methylpiperazin-1-yl)-1-oxopropan-2-yl]-4-(1H-1,2,3-triazol-1-yl)benzamide (206)

In a 100-mL round-bottom flask were combined the compound from the previous step (580 mg, 1.14 mmol, 1.00 equiv), THF (40 mL), and 3-(diethoxyphosphoryloxy)-1,2,3-benzotriazin-4(3H)-one ("DEPBT") (530 mg, 1.77 mmol, 1.56 equiv), followed by the addition of imidazole (120 mg, 1.76 mmol, 1.55 equiv) at 0° C. The mixture was stirred for 40 min. To this was added a solution of 1-methylpiperazine (180 mg, 1.80 mmol, 1.58 equiv) in THF (10 mL) dropwise with stirring at 0° C. The resulting solution was stirred for 16 h at 25° C., diluted with 50 mL of EtOAc, then washed with 1×50 mL of sat.NaHCO₃ and 1×50 mL of brine. The organic layers were dried over Na₂SO₄ and concentrated under vacuum, affording 600 mg (89%) of the product as light yellow oil.

N-[3-[[(1R,2S)-2-(4-Fluorophenyl)cyclopropyl]amino]-1-(4-methylpiperazin-1-yl)-1-oxopropan-2-yl]-4-(1H-1,2,3-triazol-1-yl)benzamide (1)

In a 50-mL round-bottom flask were combined the compound from the previous step (600 mg, 1.01 mmol, 1.00 equiv), CH₂Cl₂ (20 mL) and CF₃COOH (4 mL). The resulting solution was stirred for 2 h at 25° C. The pH value of the solution was adjusted to 9 with sat. NaHCO₃. The resulting solution was extracted with 3×30 mL of EtOAc and the organic layers were combined and washed with 1×50 mL of brine. The organic layers was dried over Na₂SO₄ and concentrated under vacuum. The crude product (5 mL) was purified by Prep-HPLC with the following conditions (2#-AnalyseHPLC-SHIMADZU(HPLC-10)): Column, XBridge C18 OBD Prep Column, 100? 10 am, 19 mm×250 mm; mobile phase, Waters (10 MMOL/L NH4HCO3) and ACN—Waters (20.0% ACN—Waters up to 60.0% in 6 min); Detector, uv 254/220 nm. 150 mL product was obtained. This resulted in 330 mg (66%) of 1 as a white solid.

Example 4

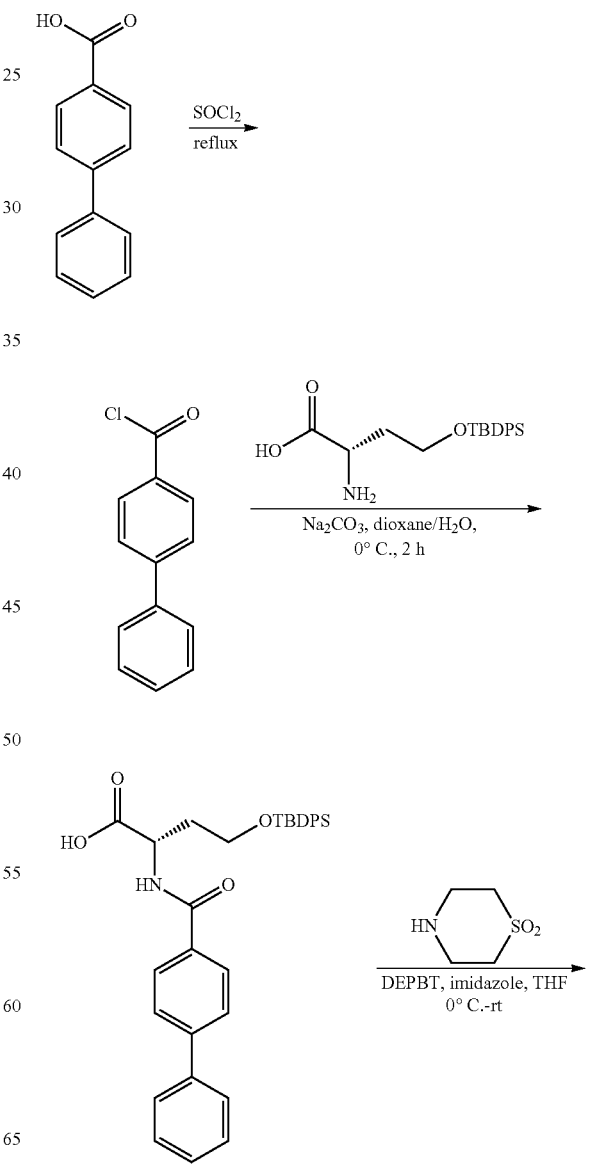

Scheme 2

157

-continued

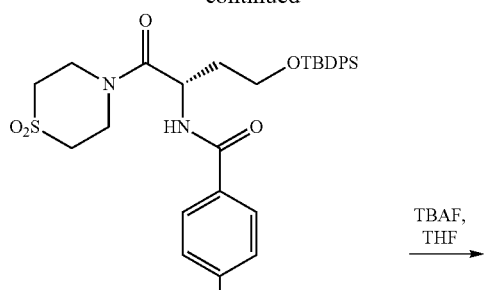

TBAF, THF →

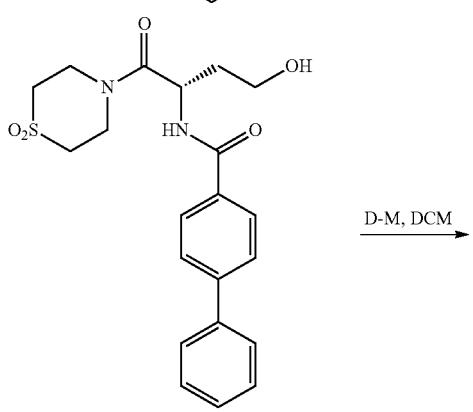

D-M, DCM →

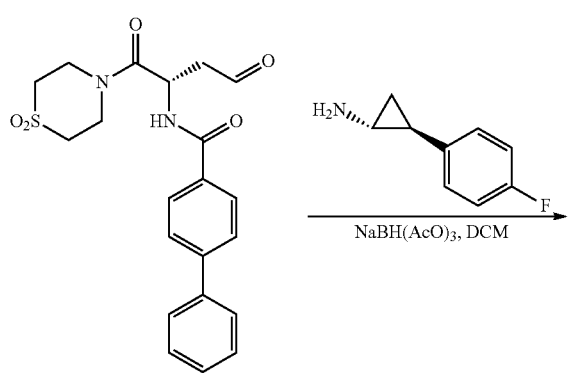

NaBH(AcO)₃, DCM →

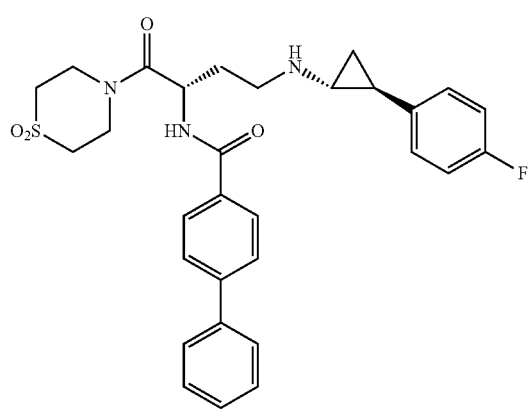

158

Synthesis of 4

4-phenylbenzoyl Chloride

Into a 250-mL round-bottom flask were combined 4-phenylbenzoic acid (15 g, 75.67 mmol, 1.00 equiv) and thionyl chloride (30 mL). The resulting solution was stirred for 16 h at 80° C. in an oil bath, then concentrated under vacuum, resulting in 15 g (91%) of the product as an off-white solid.

(2S)-2-[(4-(phenyl)phenyl)formamido]-4-[(tert-butyldiphenylsilyl)oxy]butanoic Acid The method used to prepare 203 was used with (2S)-2-amino-4-[(tert-butyldiphenylsilyl)oxy]butanoic acid (6.8 g, 19.02 mmol, 1.00 equiv) and 4-phenylbenzoyl chloride (5 g, 23.08 mmol, 1.20 equiv), affording 8 g (78%) of PH-IMA-2013-003-174-2 as a yellow oil.

N-[1-(thiomorpholine-1,1-dioxide-4-yl)-1-oxo-4-((tert-butyldiphenylsilyl)oxy)-butan-2-yl]-4-phenylbenzamide The method used to prepare 206 was used with the compound from the previous step (5 g, 9.29 mmol, 1.00 equiv) and and thiomorpholine-1,1-dioxide hydrochloride (2.4 g, 13.98 mmol, 1.50 equiv) to afford 5 g (83.3%) of the product as a off-white solid.

(3S)-4-(thiomorpholine-1,1-dioxide-4-yl)-4-oxo-3-[4-(phenyl)phenyl)formamido]-1-butanol (207)

In a 250-mL round-bottom flaskwere combined the compound from the previous step (22 g, 33.59 mmol, 1.00 equiv) and THF (150 ml). Bu₄NF (66 mL, 66 mmol, 1.0 M in THF) was added dropwise with stirring at 0° C. The resulting solution was stirred for 16 h at 25° C., concentrated under vacuum, diluted with 100 mL of EtOAc, and washed with 4×100 mL of water and 2×100 mL of brine. The combined organic layers was dried over Na₂SO₄ and applied onto a silica gel column with EtOAc to afford 10 g (71%) of the product as a off-white solid.

(3S)-4-(thiomorpholine-1,1-dioxide-4-yl)-4-oxo-3-[4-(phenyl)phenyl)formamido]-1-butanal (208)

In a 500-mL flask purged and maintained with an inert atmosphere of nitrogen were combined the compound produced in the previous step (10 g, 24.01 mmol, 1.00 equiv) in CH₂Cl₂ (250 ml). This was followed by the addition of Dess-Martin periodinane (20.4 g, 48.11 mmol, 2.00 equiv), in portions at 0° C. The resulting solution was stirred for 1 h at 25° C., then filtered out over diatomaceous earth, concentrated under reduced pressure, diluted with 30 mL CH₂Cl₂, and applied onto a silica gel column with EtOAc/petroleum ether (1:1) to afford 9 g (90%) of the product as a white solid.

N-[(2S)-4-[[(1R,2S)-2-(4-fluorophenyl)cyclopropyl]amino]-1-(thiomorpholine-1,1-dioxide-4-yl)-1-oxobutan-2-yl]-4-phenylbenzamide (4)

In a 50-mL flask purged and maintained with an inert atmosphere of nitrogen was combined a solution of the compound from the previous step (450 mg, 1.09 mmol, 1.00 equiv), CH₂Cl₂ (10 ml), and (1R,2S)-2-(4-fluorophenyl)cyclopropan-1-amine (30 mg, 0.39 mmol, 1.20 equiv). This was followed by the addition of NaBH(AcO)₃ (552 mg, 2.60 mmol, 2.40 equiv), in portions at 0° C. The resulting solution was stirred for 10 min at 25° C. The reaction was then quenched by the addition of 5 mL of water. The resulting solution was extracted with 3×10 mL of CH₂Cl₂, and the organic layers were combined, dried over Na₂SO₄, concentrated under reduced pressure, and purified with Prep-HPLC to afford 223.9 mg (38%) of the product as a white solid.

Example 12

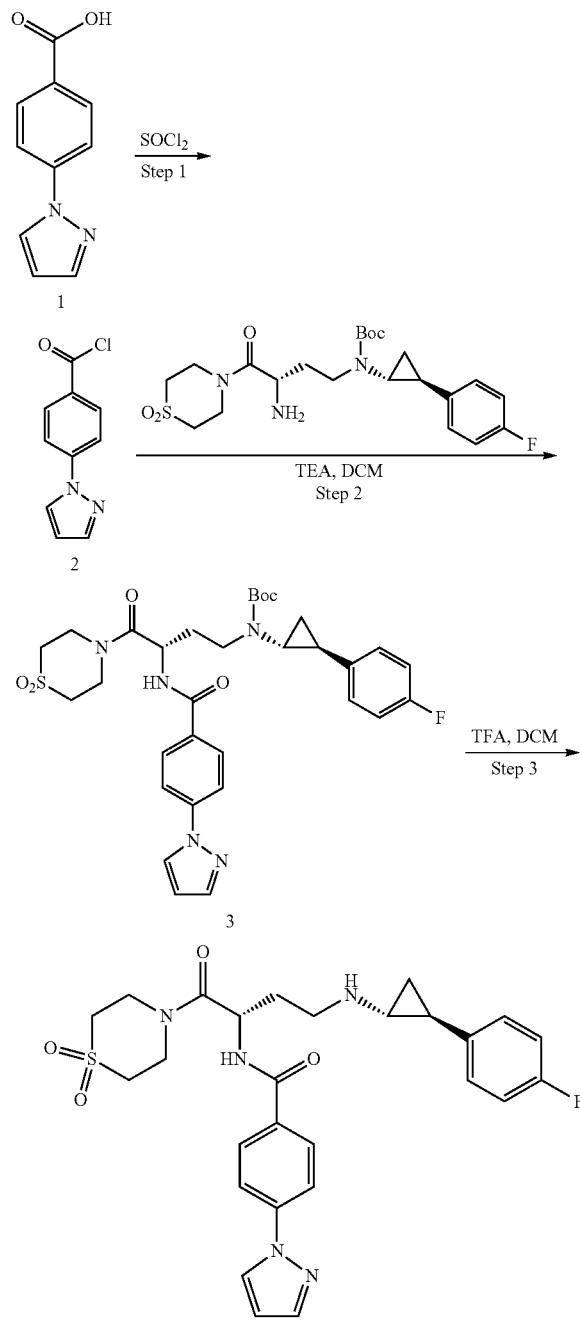

Synthesis of 12

4-(1H-Pyrazol-1-yl)benzoyl Chloride

The method used to prepare 201 was used with 4-(1H-pyrazol-1-yl)benzoic acid (100 mg, 0.53 mmol), affording 110 mg (crude) of 4-(1H-pyrazol-1-yl)benzoyl chloride as a yellow solid.

tert-Butyl N-[(3S)-4-(thiomorpholine-1,1-dioxide-4-yl)-4-oxo-3-[[4-(1H-pyrazol-1-yl)phenyl]formamido]butyl]-N-[(1R,2S)-2-(4-fluorophenyl)cyclopropyl]carbamate The method used to prepare 203 was used. with tert-butyl N-[(3S)-3-amino-4-(thiomorpholine-1,1-dioxide-4-yl)-4-oxobutyl]-N-[(1R,2S)-2-(4-fluorophenyl)cyclopropyl]carbamate (227 mg, 0.48 mmol, 1.00 equiv) and 4-(1H-pyrazol-1-yl)benzoyl chloride (110 mg, 0.53 mmol, 1.10 equiv), affording 150 mg (49%) of the product as a yellow oil.

N-[(2S)-4-[[(1R,2S)-2-(4-Fluorophenyl)cyclopropyl]amino]-1-(thiomorpholine-1,1-dioxide-4-yl)-1-oxobutan-2-yl]-4-(1H-pyrazol-1-yl)benzamide In a 50-mL round-bottom flask was combined the compound from the previous step (150 mg, 0.23 mmol, 1.00 equiv), CF₃COOH (1 mL), and CH₂Cl₂ (10 mL). The solution was stirred for 12 h at room temperature, then concentrated under reduced pressure and purified by Prep-HPLC, affording 63.1 mg (42%) of 12 trifluoroacetic acid salt as a white solid.

Example 20

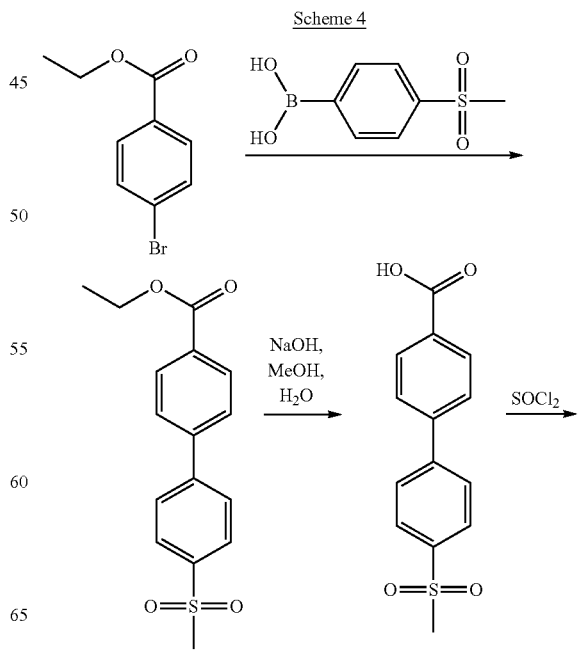

161

-continued

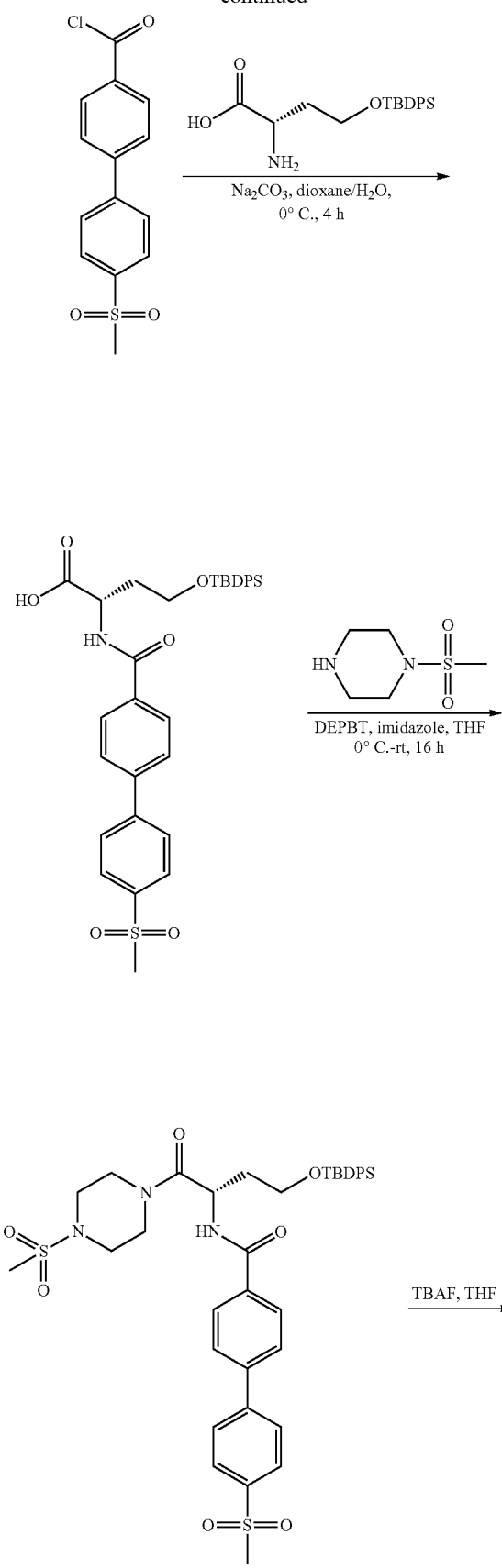

162

-continued

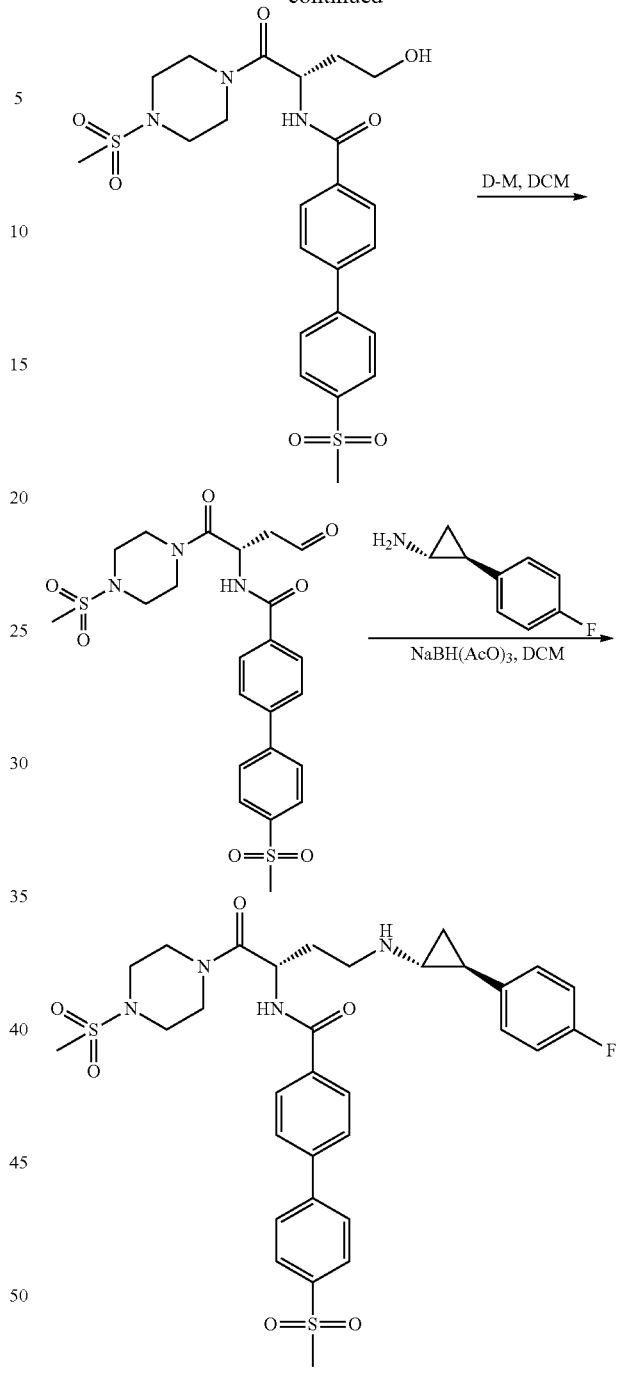

Synthesis of 20

Ethyl 4-methanesulfonylphenyl Benzoate

In a 500-mL round-bottom flask purged and maintained with an inert atmosphere of nitrogen were combined a solution of ethyl 4-bromobenzoate (5 g, 21.83 mmol, 1.00 equiv) in dioxane (200 mL), (4-methanesulfonylphenyl) boronic acid (5.2 g, 26.00 mmol, 1.19 equiv), and a solution of $K_2CO_3$ (6 g, 43.41 mmol, 1.99 equiv) in water (20 mL), Pd(PPh$_3$)$_4$ (2.5 g). The resulting solution was stirred for 16 h at 100° C. in an oil bath, then cooled to room temperature, diluted with 500 mL of H₂O, and extracted with 3×200 mL of EtOAc. The organic layers were combined, washed with 1×500 mL of brine, dried over Na₂SO₄ and concentrated under reduced pressure. The crude product was purified by re-crystallization from EtOAc to afford 6 g of the product as a white solid.

4-Methanesulfonylphenyl Benzoic Acid (209)

In a 250-mL round-bottom flask were combined the product from the previous reaction (9 g, 29.57 mmol, 1.00 equiv), methanol (150 mL), NaOH (3 g, 75.00 mmol, 2.54 equiv). The resulting solution was stirred for 5 h at 25° C., then concentrated under vacuum and diluted with 200 mL of H₂O. The pH value of the aqueous was adjusted to 2 with HCl (2 M). The solids that formed were collected by filtration and dried in an oven, affording 6 g (73%) of the product as a white solid.

4-Methanesulfonylphenyl Benzoyl Chloride

The method used to prepare 201 was used with the compound from the previous step (5 g, 18.10 mmol), affording 5 g (94%) of the product as a light yellow solid.

N—((S)-4-(((1R,2S)-2-(4-fluorophenyl)cyclopropy-lamino)-1-(4-(methylsulfonyl)piperazin-1-yl)-1-oxobutan-2-yl)-4'-(methylsulfonyl)biphenyl-4-Car-boxamide The remainder of the synthesis proceeded as for Scheme 2.

Example 21

Scheme 5

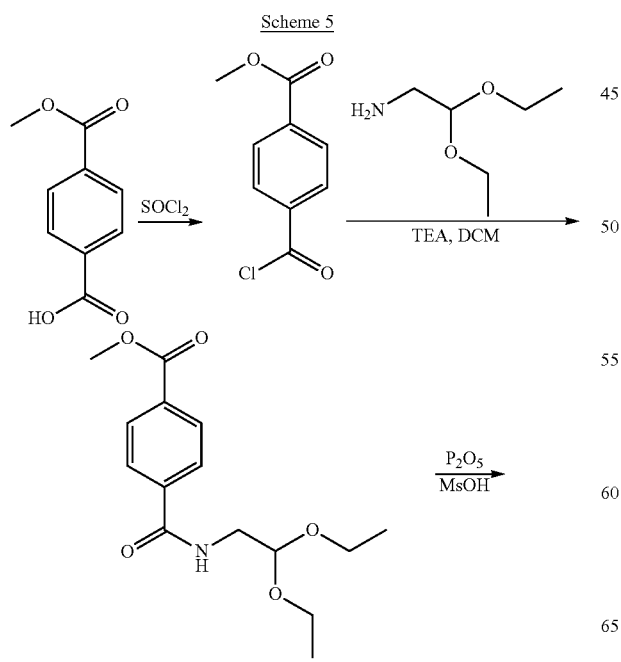

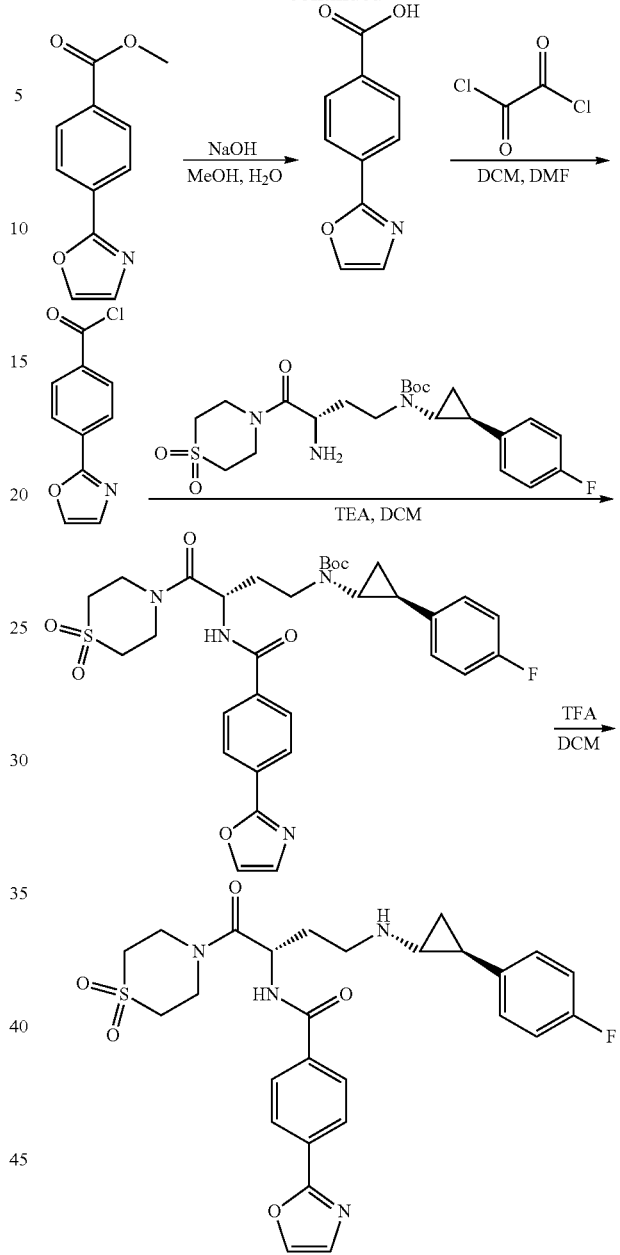

Synthesis of 21

4-(Methoxycarbonyl)Benzoyl Chloride

The method used to prepare 201 was used with 4-(methoxycarbonyl)benzoic acid (2 g, 11.10 mmol) to afford 2.2 g (100%) of the product as a yellow solid.

N-(2,2-Diethoxyethyl)-4-(methoxycarbonyl)Benzamide

The method used to prepare 203 was used with the compound from the previous step and 2,2-diethoxyethan-1-amine (1.22 g, 9.16 mmol) to afford 3 g (92%) of the product as a yellow solid.

165
Methyl 4-(oxazol-2-yl)-Benzoate

Into a 500-mL round-bottom flask purged and maintained with an inert atmosphere of nitrogen was placed the product from the previous step (3 g, 10.16 mmol, 1.00 equiv), methanesulfonic acid (150 mL), phosphorus pentoxide (8.52 g, 59.18 mmol, 5.00 equiv). The resulting solution was stirred for 2 h at 140° C. in an oil bath, cooled to room temperature, and extracted with 3×150 mL of EtOAc The organic layers were combined, dried over $Na_2SO_4$, concentrated under reduced pressure, and applied onto a silica gel column with EtOAc/petroleum ether (1:1), affording 1.5 g (73%) of the product as a yellow solid.

166
4-(Oxazol-2-yl)-benzoic Acid

The method used to prepare 209 was used with the product from the previous step (1.5 g, 7.38 mmol, 1.00 equiv) to afford 1.2 g (86%) of the product as a yellow solid.

N—((S)-4-((1R,2S)-2-(4-Fluorophenyl)cyclopropylamino)-1-(thiomorpholine-1,1-dioxide-4-yl)-1-oxobutan-2-yl)-4-(oxazol-2-yl)phenyl-4-carboxamide The remainder of the synthesis proceeded as for Scheme 2.

Example 23

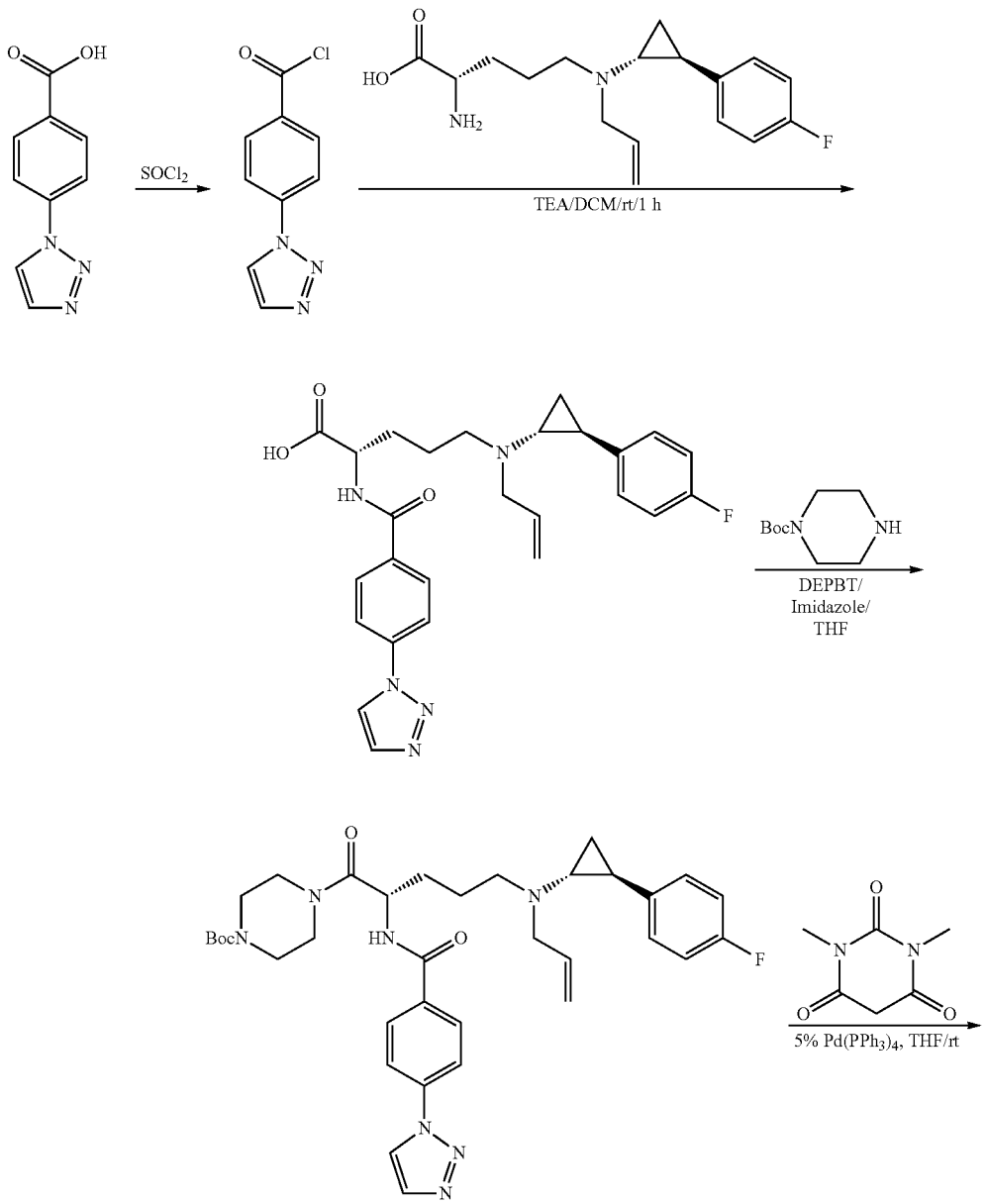

Scheme 6

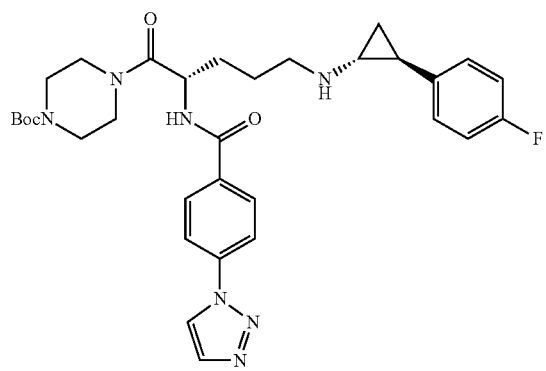
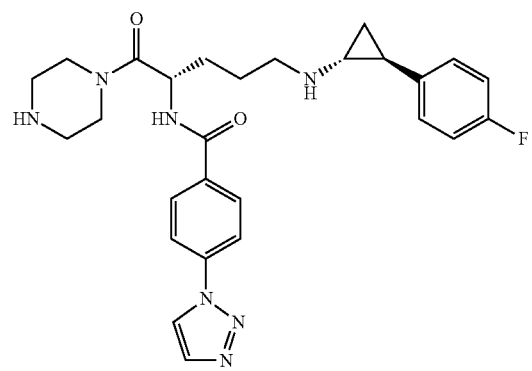

Synthesis of 23

(2S)-5-[[(1R,2S)-2-(4-fluorophenyl)cyclopropyl](propen-3-yl)amino]-2-[[4-(1H-1,2,3-triazol-1-yl)phenyl]formamido]pentanoic Acid The method used to prepare 203 was used with (2S)-5-[[(1R,2S)-2-(4-fluorophenyl)cyclopropyl](prop-2-en-1-yl)amino]-2-aminopentanoic acid (800 mg, 2.61 mmol, 1.00 equiv) and 4-(1H-1,2,3-triazol-1-yl)benzoyl chloride (800 mg, 3.85 mmol, 1.50 equiv) to afford 550 mg (44%) of the product as a yellow solid.

N-[(2S)-1-(4-(tert-butyloxycarbonyl)piperazin-1-yl)-5-[[(1R,2S)-2-(4-fluorophenyl)cyclopropyl](prop-2-en-1-yl)amino]-1-oxopentan-2-yl]-4-(1H-1,2,3-triazol-1-yl)benzamide The method used to prepare 206 was used with the compound from the previous step (250 mg, 0.52 mmol, 1.00 equiv) and 4-(tert-butyloxycarbonyl)piperazine (148 mg, 0.79 mmol, 1.50 equiv) to afford 210 mg (62%) of the product as a yellow solid.

N-[(2S)-1-(4-(tert-butyloxycarbonyl)piperazin-1-yl)-5-[[(1R,2S)-2-(4-fluorophenyl)cyclopropyl]amino]-1-oxopentan-2-yl]-4-(1H-1,2,3-triazol-1-yl)benzamide (210)

Into a 100-mL round-bottom flask purged and maintained with an inert atmosphere of nitrogen, was the compound from the previous step (210 mg, 0.32 mmol, 1.00 equiv), THF (30 mL), barbituric acid (127 mg, 0.81 mmol, 2.50 equiv), and tetrakis(triphenylphosphine)-palladium (94 mg, 0.08 mmol, 0.25 equiv). The resulting solution was stirred for 2 h at 50° C. in an oil bath, then concentrated under reduced pressure, applied onto a silica gel column with $CH_2Cl_2$/methanol (10:1), affording 150 mg (76%) of the product as a yellow solid.

N-[(2S)-5-[[(1R,2S)-2-(4-fluorophenyl)cyclopropyl]amino]-1-oxo-1-(1H-1,2,3-triazol-1-yl)pentan-2-yl]-4-(pyrimidin-2-yl)benzamide Trifluoroacetic Acid Salt The procedure used to prepare 1 was used with the compound produced in the previous step (150 mg, 0.25 mmol, 1.00 equiv) to afford 53.2 mg (43%) of the product as an off-white solid.

Example 35

Scheme 7

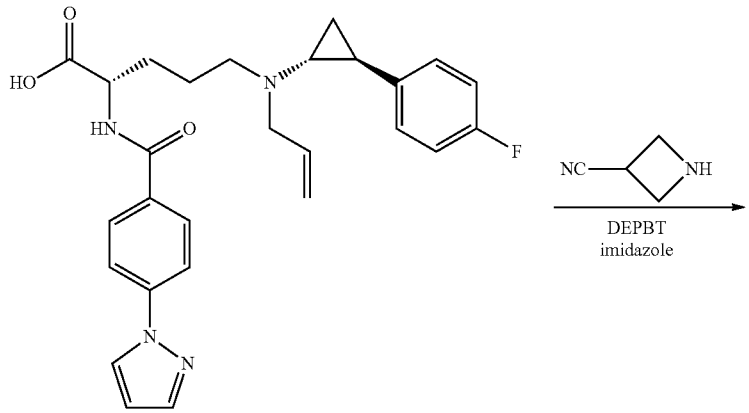

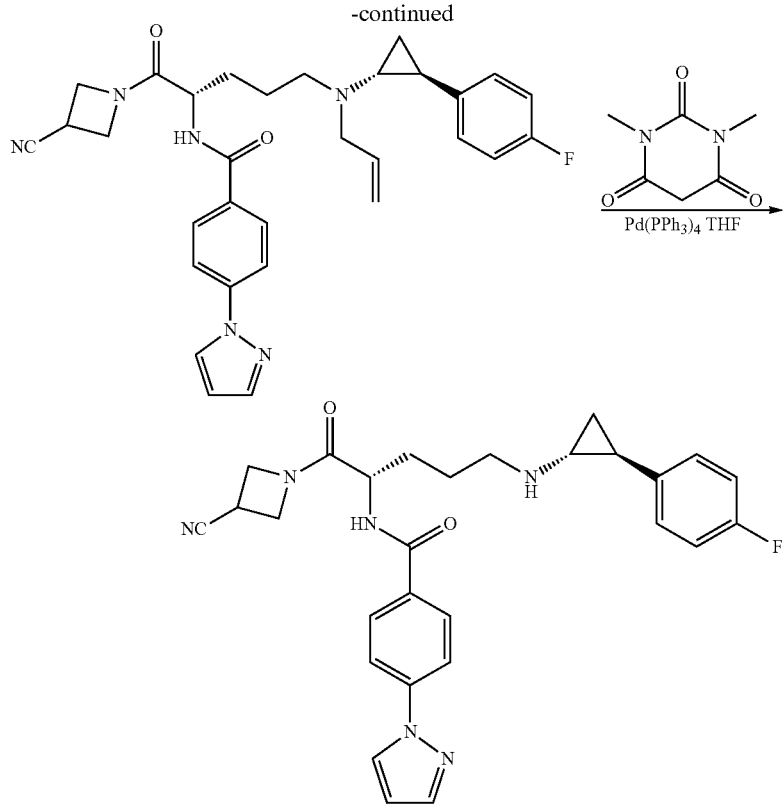

Synthesis of 35

N-[(2S)-1-(3-cyanoazetidin-1-yl)-5-[[(1R,2S)-2-(4-fluorophenyl)cyclopropyl](prop-2-en-1-yl)amino]-1-oxopentan-2-yl]-4-(1H-pyrazol-1-yl)benzamide The method used to prepare 206 was used with (2S)-5-[[(1R,2S)-2-(4-fluorophenyl)cyclopropyl](prop-2-en-1-yl)amino]-2-[[4-(1H-pyrazol-1-yl)phenyl]-formamido]pentanoic acid (400 mg, 0.84 mmol, 1.00 equiv) and azetidine-3-carbonitrile to afford 301 mg (66%) of the product as a light yellow oil.

N-[(2S)-1-(3-cyanoazetidin-1-yl)-5-[[(1R,2S)-2-(4-fluorophenyl)cyclopropyl]amino]-1-oxopentan-2-yl]-4-(1H-pyrazol-1-yl)benzamide(35)

The method used to prepare 210 was used with the compound produced in the previous step (301 mg, 0.56 mmol, 1.00 equiv) to afford 72.1 mg (26%) of 35 as an off-white solid.

Example 86

Scheme 8

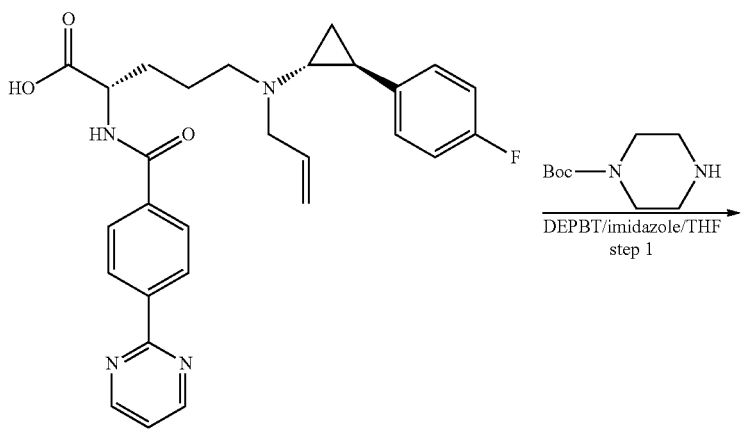

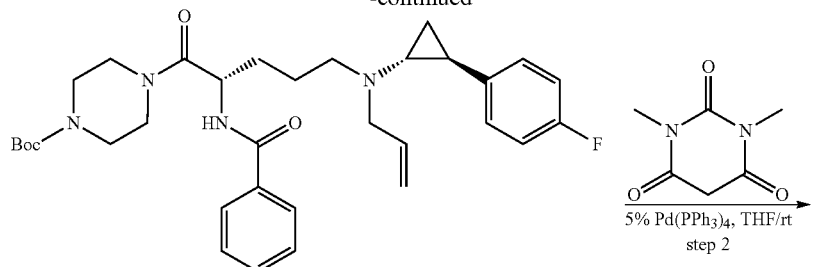

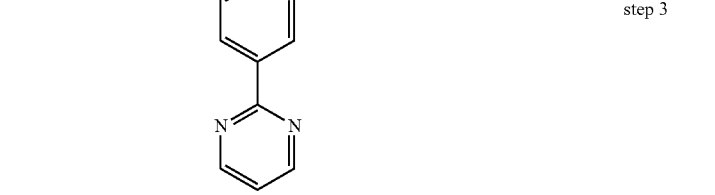

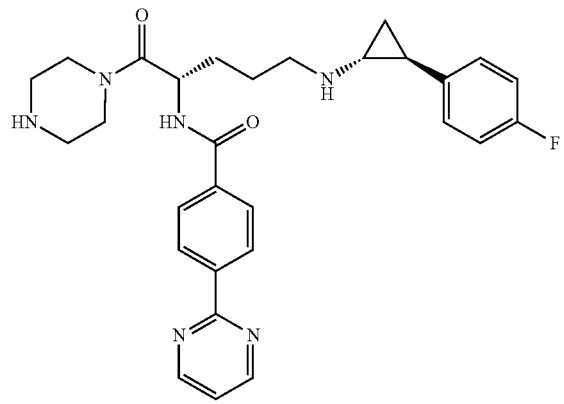

Synthesis of 86

N-[(2S)-1-(4-(tert-butyloxycarbonyl)piperazin-1-yl)-5-[[(1R,2S)-2-(4-fluorophenyl)cyclopropyl](prop-2-en-1-yl)amino]-1-oxopentan-2-yl]-4-(pyrimidin-2-yl)benzamide The method used to prepare 206 was used with (2S)-5-[[(1R,2S)-2-(4-fluorophenyl)cyclopropyl](prop-2-en-1-yl)amino]-2-[[4-(pyrimidin-2-yl)phenyl]formamido]pentanoic acid (250 mg, 0.51 mmol, 1.00 equiv) and 1-tert-butyl-1^3,3,6-oxadiazocan-2-one (143 mg, 0.76 mmol, 1.50 equiv) to afford 280 mg (66%) of the product as a yellow solid.

N-[(2S)-1-(4-(tert-butyloxycarbonyl)piperazin-1-yl)-5-[[(1R,2S)-2-(4-fluorophenyl)cyclopropyl]amino]-1-oxopentan-2-yl]-4-(pyrimidin-2-yl)benzamide The method used to prepare 210 was used with the compound produced in the previous step (280 mg, 0.43 mmol) to afford 0.2 g (76%) of the product as a yellow solid.

N-[(2S)-5-[[(1R,2S)-2-(4-fluorophenyl)cyclopropyl]amino]-1-oxo-1-(piperazin-1-yl)pentan-2-yl]-4-(pyrimidin-2-yl)benzamide Trifluoroacetic Acid Salt (86)

The method used to prepare 1 was used with the compound produced in the previous step (200 mg, 0.32 mmol) to afford 70 mg (34%) of 86 as a white solid.

Example 91
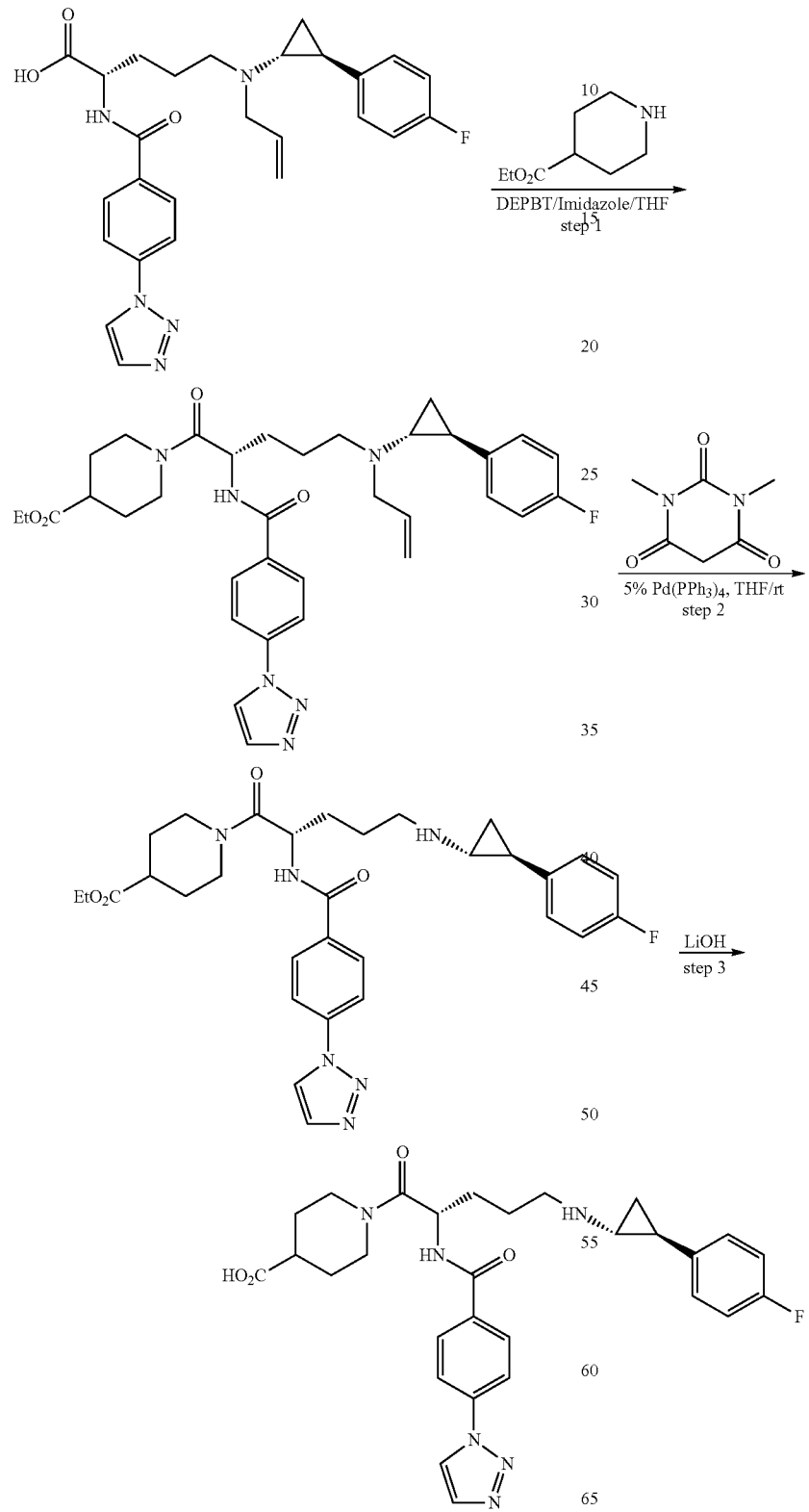

Synthesis of 91

N-[(2S)-5-[[(1R,2S)-2-(4-Fluorophenyl)cyclopropyl](prop-2-en-1-yl)amino]-1-(4-carboethoxypiperidin-1-yl)-1-oxopentan-2-yl]-4-(1H-1,2,3-triazol-1-yl)benzamide The method used to prepare 206 was used with (2S)-5-[[(1R,2S)-2-(4-fluorophenyl)cyclopropyl](prop-2-en-1-yl)amino]-2-[[4-(1H-1,2,3-triazol-1-yl)phenyl]-formamido]pentanoic acid (200 mg, 0.42 mmol, 1.00 equiv) and methyl piperidine-4-carboxylate (80 mg, 0.56 mmol, 1.33 equiv) to afford 180 mg (71%) of the product as a colorless oil.

N-[(2S)-5-[[(1R,2S)-2-(4-fluorophenyl)cyclopropyl]amino]-1-(4-carboethoxypiperidin-1-yl)-1-oxopentan-2-yl]-4-(1H-1,2,3-triazol-1-yl)benzamide The method used to prepare 210 was used with the compound produced in the previous step (180 mg, 0.30 mmol) to afford 100 mg (60%) of the product as an orange oil.

N-[(2S)-5-[[(1R,2S)-2-(4-Fluorophenyl)cyclopropyl]amino]-1-(4-carboxypiperidin-1-yl)-1-oxopentan-2-yl]-4-(1H-1,2,3-triazol-1-yl)benzamide (91)

In a 50-mL round-bottom flask were combined the compound from the previous step (100 mg, 0.17 mmol, 1.00 equiv) in THF (20 mL) and LiOH (20 mg, 0.84 mmol, 4.82 equiv) in water (5 mL). The resulting solution was stirred for 16 h at 25° C., then concentrated under vacuum. The crude product was purified by Prep-HPLC, affording 52.9 mg (46%) of the product as a light yellow solid.

Example 92

Scheme 10

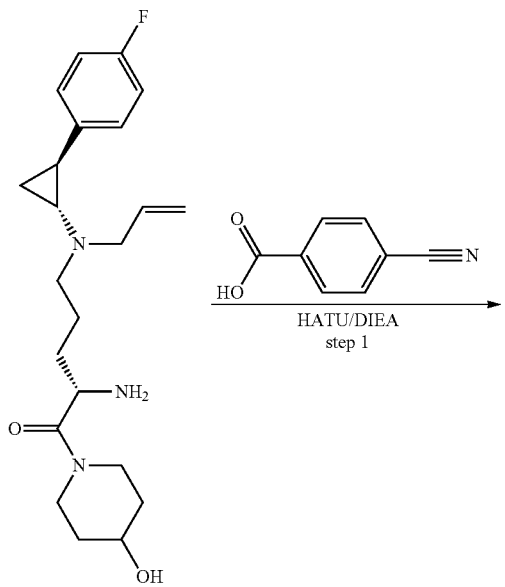

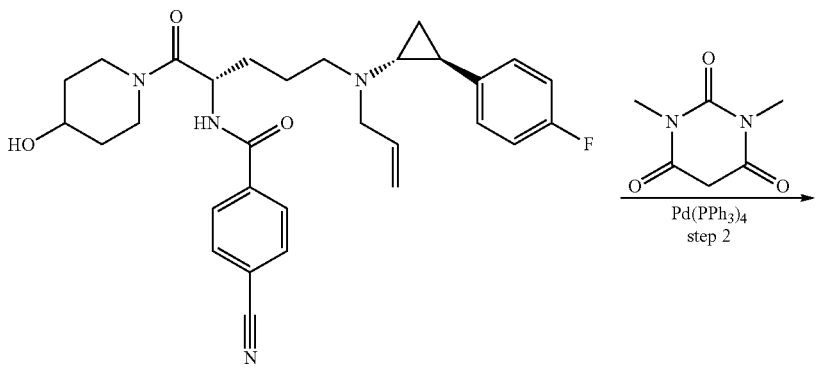

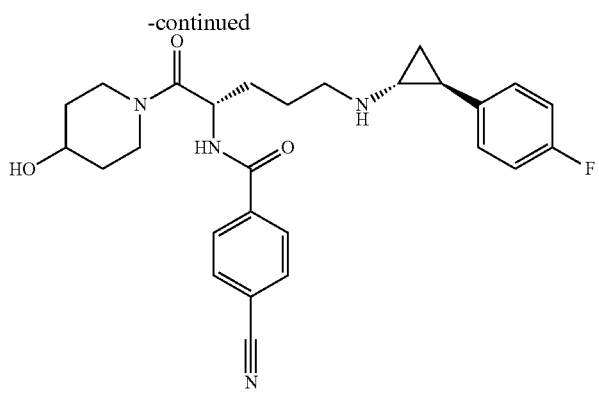

Synthesis of 92

4-Cyano-N-[(2S)-5-[[(1R,2S)-2-(4-fluorophenyl)cyclopropyl](prop-2-en-1-yl)amino]-1-(4-hydroxypiperidin-1-yl)-1-oxopentan-2-yl]benzamide (211)

In a 100-mL round-bottom flask were combined a solution of 4-cyanobenzoic acid (136.7 mg, 0.93 mmol, 1.20 equiv) $CH_2Cl_2$ (20 mL), i-$Pr_2NEt$ (298 mg, 2.31 mmol, 3.00 equiv), and 1-[bis(dimethylamino)methylene]-1H-1,2,3-triazolo[4,5-b]pyridinium 3-oxide hexafluorophosphate ("HATU") (439 mg, 1.15 mmol, 1.50 equiv), The mixture was stirred for 1h, then a solution of (2S)-2-amino-5-[[(1R,2S)-2-(4-fluorophenyl)cyclopropyl](prop-2-en-1-yl)-amino]-1-(4-hydroxypiperidin-1-yl)pentan-1-one (300 mg, 0.77 mmol, 1.00 equiv) in $CH_2Cl_2$ (5 mL) was added. The resulting solution was stirred for 60 min at 25° C., then concentrated under vacuum and applied onto a silica gel column with $CH_2Cl_2$/methanol (10:1), affording 480 mg (120%) of the product as a light yellow liquid.

4-Cyano-N-[(2S)-5-[[(1R,2S)-2-(4-fluorophenyl)cyclopropyl]amino]-1-(4-hydroxypiperidin-1-yl)-1-oxopentan-2-yl]benzamide (92)

The method used to prepare 210 was used with the compound produced in the previous step (480 mg, 0.93 mmol) to afford 46.7 mg (11%) of 92 as a light yellow solid.

Example 109

Scheme 11

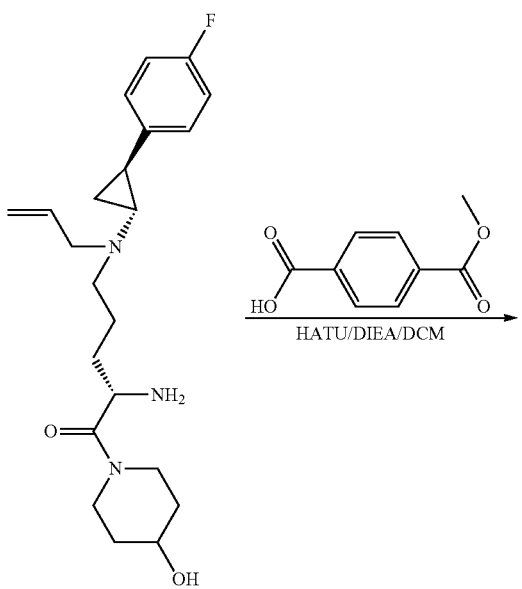

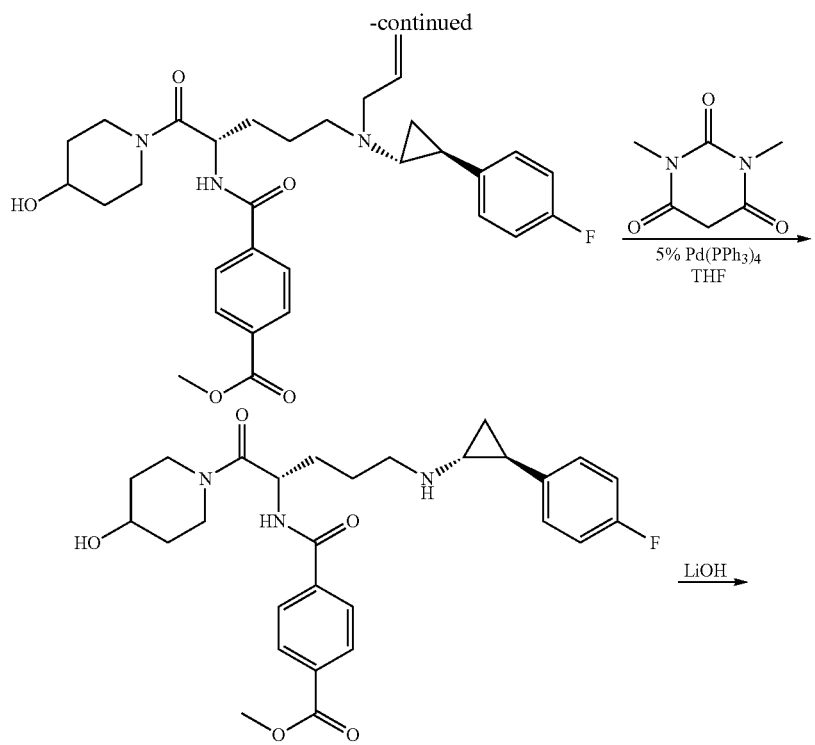

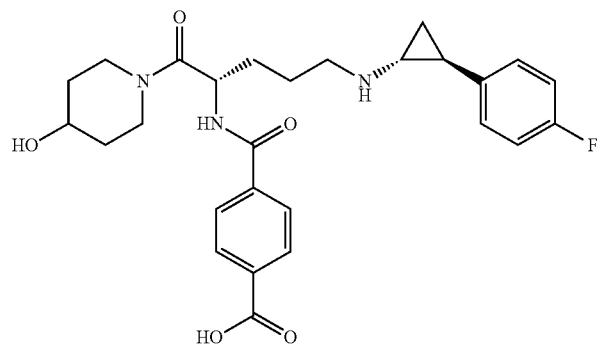

Synthesis of 109

Methyl 4-[[(2S)-5-[[(1R,2S)-2-(4-fluorophenyl)cyclopropyl](prop-2-en-1-yl)amino]-1-(4-hydroxypiperidin-1-yl)-1-oxopentan-2-yl]carbamoyl]benzoate The method used to prepare 211 was used with 4-(methoxycarbonyl)benzoic acid (231.4 mg, 1.28 mmol, 1.00 equiv) and (2S)-2-amino-5-[[(1R,2S)-2-(4-fluorophenyl)cyclopropyl](prop-2-en-1-yl)amino]-1-(4-hydroxypiperidin-1-yl)pentan-1-one (500 mg, 1.28 mmol, 1.00 equiv) to afford 420 mg (59%) of the product as a light yellow oil.

Methyl 4-[[(2S)-5-[[(1R,2S)-2-(4-fluorophenyl)cyclopropyl]amino]-1-(4-hydroxypiperidin-1-yl)-1-oxopentan-2-yl]carbamoyl]benzoate (109)

The method used to prepare 210 was used with the compound produced in the previous step (420 mg, 0.76 mmol) to afford 650 mg (99%) of the product as an orange oil.

4-[[(2S)-5-[[(1R,2S)-2-(4-Fluorophenyl)cyclopropyl]amino]-1-(4-hydroxypiperidin-1-yl)-1-oxopentan-2-yl]carbamoyl]benzoic acid (109)

In a 100-mL round-bottom flask were combined the compound from the previous step (650 mg, 1.27 mmol, 1.00 equiv), LiOH (60 mg, 2.51 mmol, 2.00 equiv), methanol (20 mL), and water (13 mL). The resulting solution was stirred for 3 h at room temperature. The resulting mixture was concentrated under vacuum. The crude product was purified by Prep-HPLC to afford 45.1 mg (7%) of the product as an orange solid.

Example 109
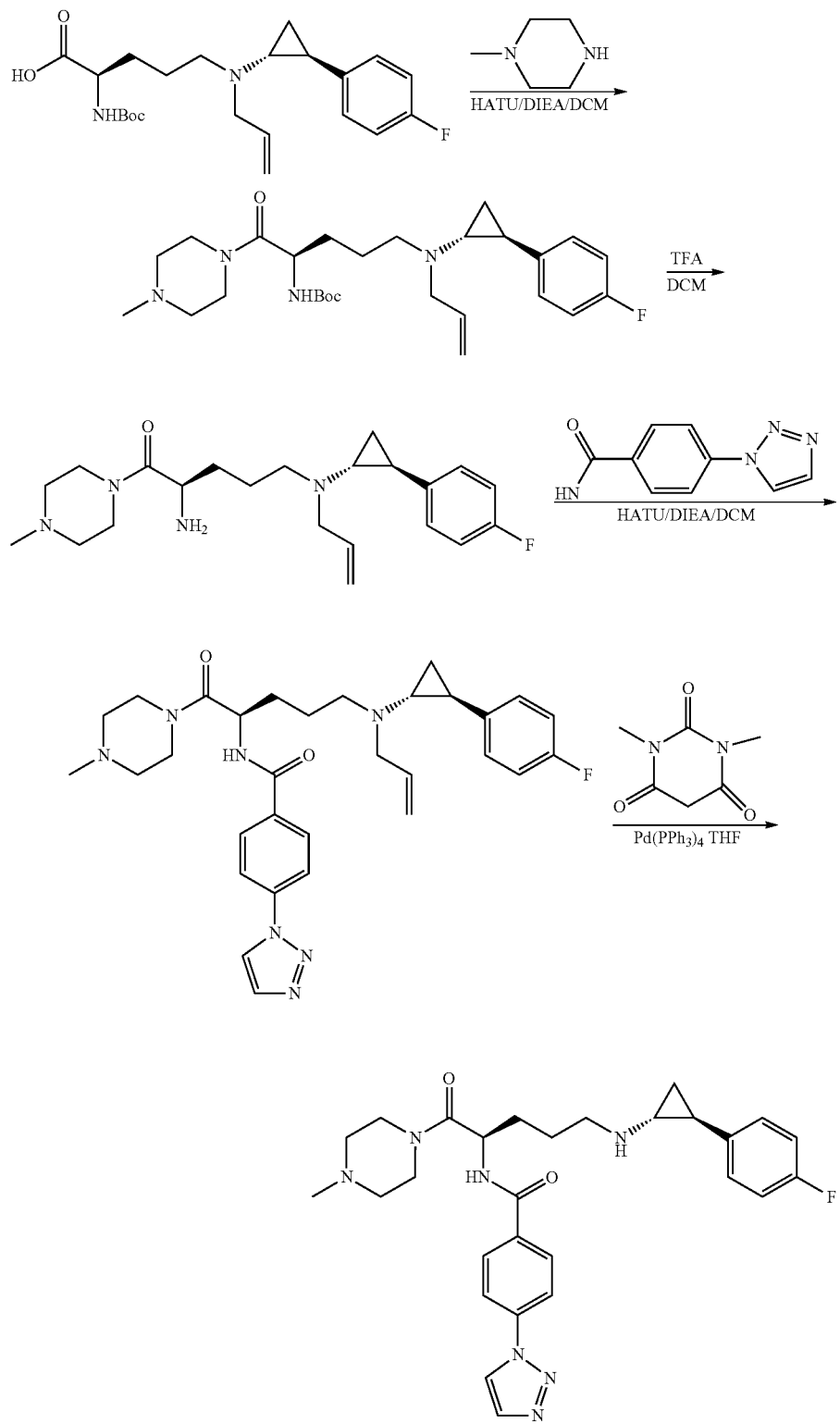
Scheme 12

183
Synthesis of 110

N-[(2R)-5-[[(1R,2S)-2-(4-Fluorophenyl)cyclopropyl](prop-2-en-1-yl)amino]-1-(4-methylpiperazin-1-yl)-1-oxopentan-2-yl]carbamate The method used to prepare 211 was used with 2-[[(tert-butoxy)carbonyl]amino]-5-[[2-(4-fluorophenyl)cyclopropyl](prop-2-en-1-yl)amino]pentanoic acid (1 g, 2.46 mmol, 1.00 equiv) and 1-methylpiperazine (500 mg, 4.99 mmol, 2.00 equiv) to afford in 1.1 g (95%) of the product as off-white oil.

4-(1H-1,2,3-Triazol-1-yl)benzoic acid (926 mg, 4.90 mmol) (2R)-2-amino-5-[[(1R,2S)-2-(4-fluorophenyl)cyclopropyl](prop-2-en-1-yl)amino]-1-(4-methylpiperazin-1-yl)pentan-1-one The procedure used to prepare 1 was used with the compound produced in the previous step (2.4 g, 4.91 mmol) to afford 1.8 g (95%) of the product as off-white oil.

184

N-[(2R)-5-[[(1R,2S)-2-(4-Fluorophenyl)cyclopropyl](prop-2-en-1-yl)amino]-1-(4-methylpiperazin-1-yl)-1-oxopentan-2-yl]-4-(1H-1,2,3-triazol-1-yl)benzamide The method used to prepare 211 was used with the compound produced in the previous step (1.9 g, 4.89 mmol, 1.00 equiv) to afford 1.2 g (44%) of the product as off-white oil.

N-[(2R)-5-[[(1R,2S)-2-(4-Fluorophenyl)cyclopropyl]amino]-1-(4-methylpiperazin-1-yl)-1-oxopentan-2-yl]-4-(1H-1,2,3-triazol-1-yl)benzamide (110)

The method used to prepare 210 was used with the compound produced in the previous step (1.2 g, 2.14 mmol) to afford 15.1 mg (1%) of 110 as a white solid.

Example 111

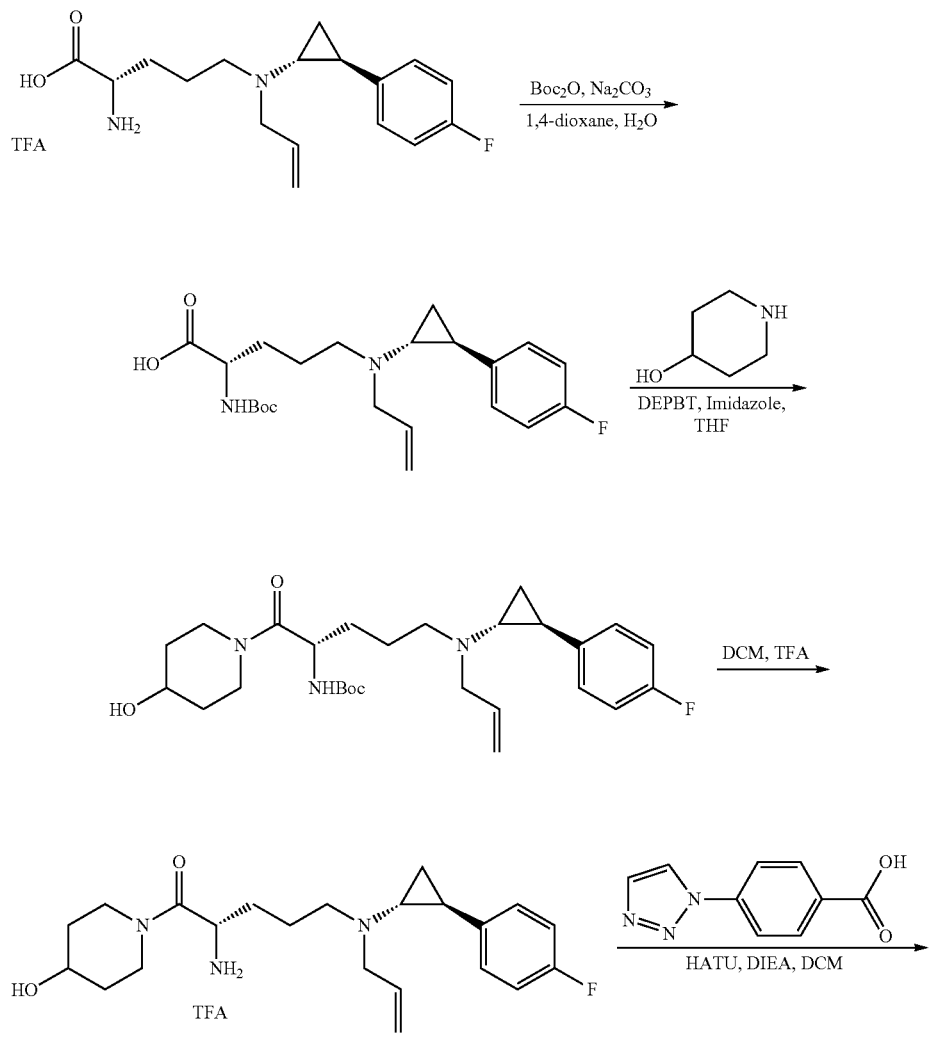

Scheme 13

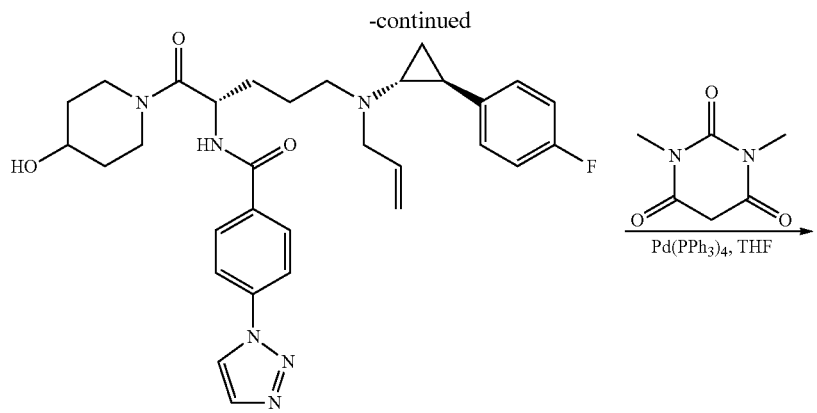

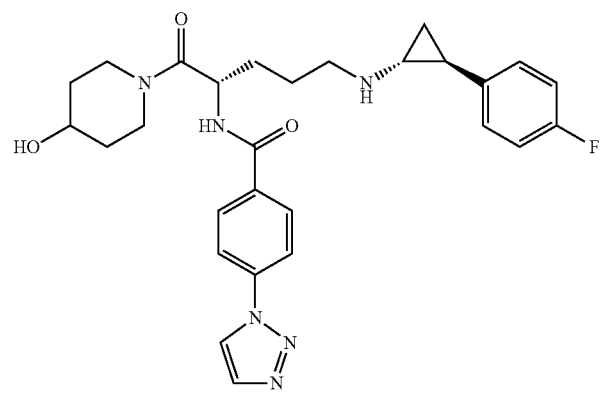

Synthesis of 111

(2S)-2-[[(tert-Butoxy)carbonyl]amino]-5-[[(2S)-2-(4-fluorophenyl)cyclopropyl](prop-2-en-1-yl)amino]pentanoic Acid In a 250-mL round-bottom flask were combined (2S)-2-amino-5-[[(2S)-2-(4-fluorophenyl)cyclopropyl](prop-2-en-1-yl)amino]pentanoic acid; $CF_3COOH$ (2 g, 4.76 mmol, 1.00 equiv), 1,4-dioxane (100 mL), $Boc_2O$ (1.44 g, 6.60 mmol, 1.39 equiv), and a solution of $Na_2CO_3$ (1.4 g, 13.21 mmol, 2.78 equiv) in $H_2O$ (25 mL). The resulting solution was stirred for 1 h at room temperature, concentrated under vacuum, diluted with 40 mL of DMF and applied onto a C18 column with $MeCN/H_2O$ (1:1), affording 1.8 g (93%) of the product as light yellow oil.

tert-Butyl N-[(2S)-5-[[(2S)-2-(4-fluorophenyl)cyclopropyl](prop-2-en-1-yl)amino]-1-(4-hydroxypiperidin-1-yl)-1-oxopentan-2-yl]carbamate The method used to prepare 206 was used with (2S)-2-[[(tert-butoxy)carbonyl]amino]-5-[[(2S)-2-(4-fluorophenyl)-cyclopropyl](prop-2-en-1-yl)amino]pentanoic acid (900 mg, 2.21 mmol, 1.00 equiv) and piperidin-4-ol (335 mg, 3.31 mmol, 1.50 equiv) to afford 1.2 g (98%) of the product as light yellow oil.

(2S)-2-Amino-5-[[(2S)-2-(4-fluorophenyl)cyclopropyl](prop-2-en-1-yl)amino]-1-(4-hydroxypiperidin-1-yl)pentan-1-one; Trifluoroacetic Acid Salt The method used to prepare 1 was used with the compound produced in the previous step (1.2 g, 2.45 mmol, 1.00 equiv) to afford 880 mg (71%) of the product as a yellow oil.

N-[(2S)-5-[[(2S)-2-(4-Fluorophenyl)cyclopropyl](prop-2-en-1-yl)amino]-1-(4-hydroxypiperidin-1-yl)-1-oxopentan-2-yl]-4-(1H-1,2,3-triazol-1-yl)benzamide The method used to prepare 211 was used with the compound produced in the previous step (400 g, 794.39 mmol, 1.00 equiv), and 4-(1H-1,2,3-triazol-1-yl)benzoic acid (205 mg, 1.08 mmol) to afford 300 mg of the product as a yellow solid.

N-[(2S)-5-[[(2S)-2-(4-fluorophenyl)cyclopropyl]amino]-1-(4-hydroxypiperidin-1-yl)-1-oxopentan-2-yl]-4-(1H-1,2,3-triazol-1-yl)benzamide (111)

The method used to prepare 210 was used with the compound produced in the previous step (300 mg, 0.54 mmol) to afford (23%) of 111 as an off-white solid.

Example 117
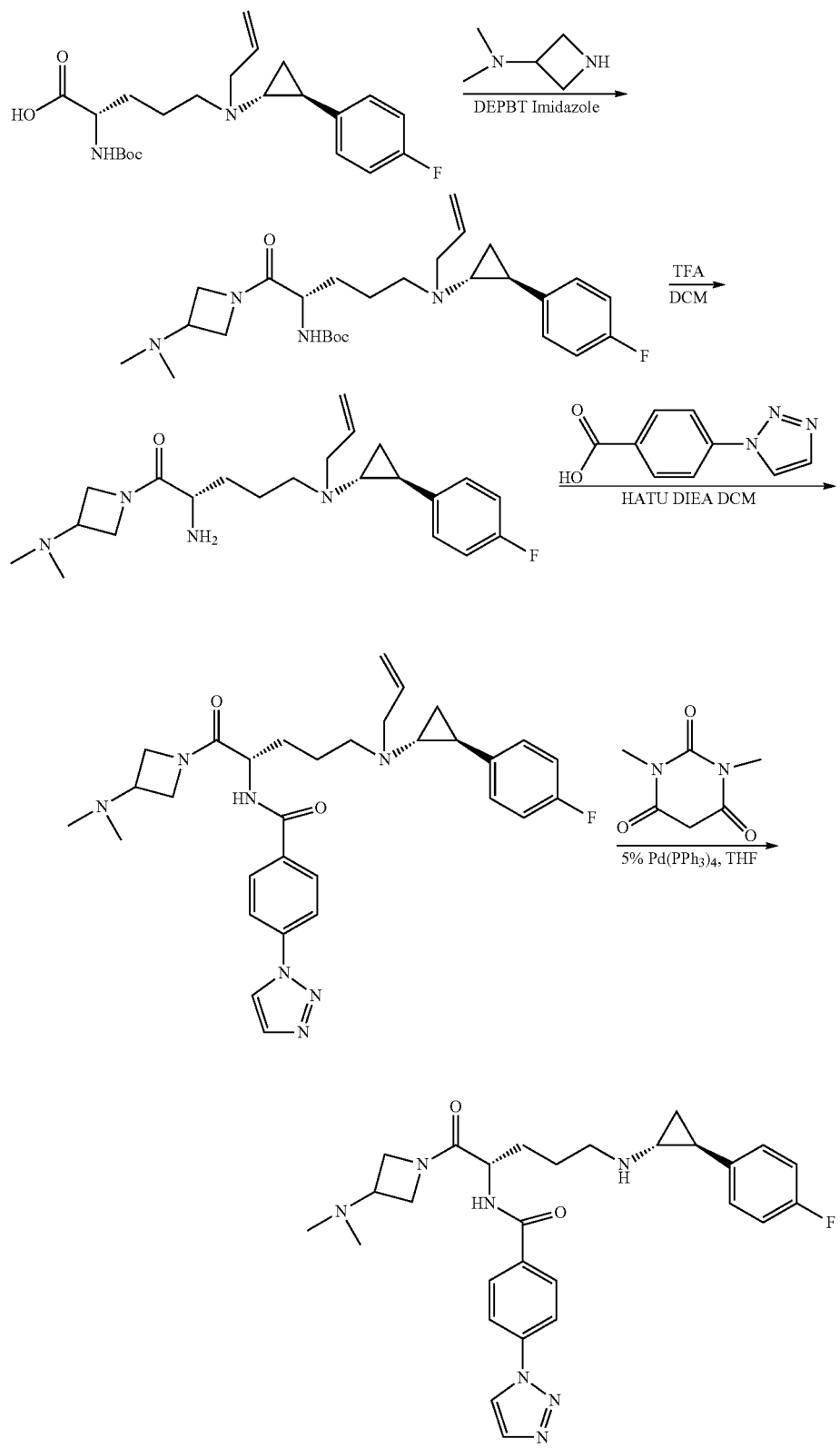

189

Synthesis of 117 tert-Butyl N-[(2R)-5-[[(2S)-2-(4-fluorophenyl)cyclopropyl](prop-2-en-1-yl)amino]-1-oxo-1-(3-(dimethylamino)-azetidin-1-yl)-pentan-2-yl]carbamate The method used to prepare 206 was used with (2S)-2-[[(tert-butoxy)carbonyl]amino]-5-[[(1R,2S)-2-(4-fluorophenyl)cyclopropyl](prop-2-en-1-yl)amino]pentanoic acid (400 mg, 0.98 mmol, 1.00 equiv) and N,N-dimethylazetidin-3-amine (147.9 mg, 1.48 mmol, 1.50 equiv) to afford 490 mg (99%) of the product as an off-white solid.

1-Oxo-1-(3-(dimethylamino)-azetidin-1-yl)-(2R)-2-amino-5-[[(2S)-2-(4-fluorophenyl)cyclopropyl](prop-2-en-1-yl)amino]-pentane The procedure used to prepare 1 was used with the compound produced in the previous step (490 mg, 1.00 mmol, 1.00 equiv) to afford 470 mg (99%) of the product as a light yellow solid.

190

N-[(2S)-5-[[(1R,2S)-2-(4-Fluorophenyl)cyclopropyl](prop-2-en-1-yl)amino]-1-(3-(dimethylamino)-azetidin-1-yl-1-oxopentan-2-yl]-4-(1H-1,2,3-triazol-1-yl)-benzamide The method used to prepare 211 was used with the compound produced in the previous step (470 mg, 1.21 mmol, 1.00 equiv). to afford 608 mg (90%) of the product as a light yellow solid.

N-[(2S)-5-[[(1R,2S)-2-(4-Fluorophenyl)cyclopropyl]amino]-1-(3-(dimethylamino)-azetidin-1-yl-1-oxopentan-2-yl]-4-(1H-1,2,3-triazol-1-yl)-benzamide (117)

The method used to prepare 210 was used with the compound produced in the previous step (978 mg, 1.75 mmol, 1.00 equiv) to afford 61.0 mg (7%) of 117 as an off-white solid.

Example 126

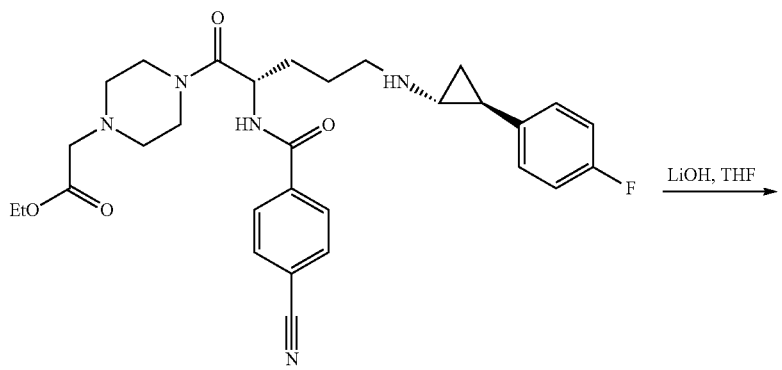

Scheme 15

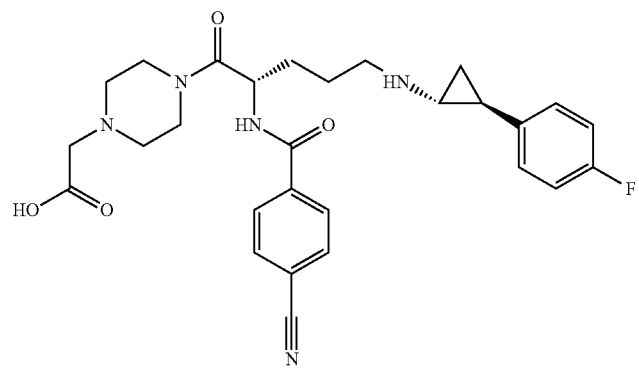

Synthesis of 126

2-[4-[(2S)-2-[(4-Cyanophenyl)formamido]-5-[[(1R, 2S)-2-(4-fluorophenyl)-cyclopropyl]amino]pentanoyl]piperazin-1-yl]acetate (126)

In a 100-mL round-bottom flask were combined a solution of ethyl 2-[4-[(2S)-2-[(4-cyanophenyl)formamido]-5-[[(1R, 2S)-2-(4-fluorophenyl)cyclopropyl]amino]pentanoyl]piperazin-1-yl]acetate (150 mg, 0.27 mmol, 1.00 equiv) in THF (20 mL) and a solution of LiOH (13.1 mg, 0.55 mmol, 2.00 equiv) in water (5 mL). The resulting solution was stirred for 2 h at 25° C. The pH value of the solution was adjusted to 3-4 with aqueous HCl (2 M). The resulting mixture was concentrated under vacuum. The residue was applied onto a reverse-phase silica gel column with MeCN/H$_2$O (1:10) The crude product (5 mL) was purified by Prep-HPLC to afford 108 mg (64%) of 126 as a light yellow solid.

Example 127

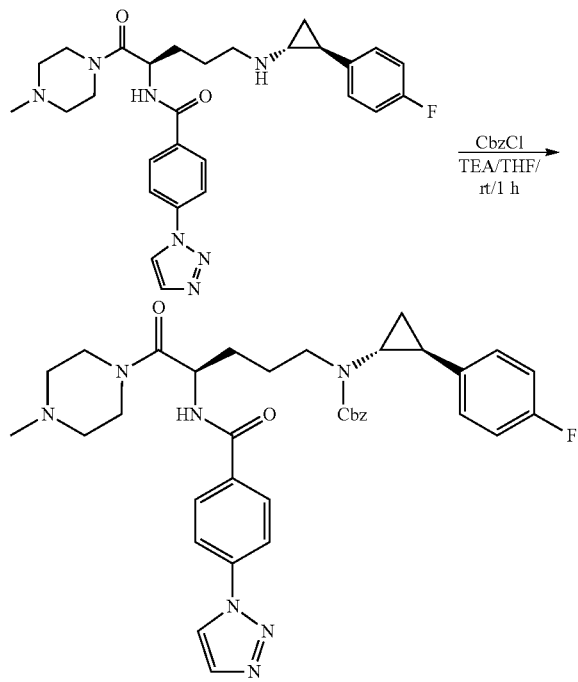

Synthesis of 127

N-Benzyl N-[(1R,2S)-2-(4-fluorophenyl)cyclopropyl]-N-[(4R)-5-(4-methylpiperazin-1-yl)-5-oxo-4-[[4-(1H-1,2,3-triazol-1-yl)phenyl]formamido]pentyl]carbamate (127)

In a 50-mL round-bottom flask purged and maintained with an inert atmosphere of nitrogen was combined a solution of N-[(2R)-5-[[(1R,2S)-2-(4-fluorophenyl)cyclopropyl]amino]-1-(4-methylpiperazin-1-yl)-1-oxopentan-2-yl]-4-(1H-1,2,3-triazol-1-yl)benzamide (40 mg, 0.08 mmol, 1.00 equiv) in tetrahydrofuran (5 mL), TEA (23 mg, 0.23 mmol, 3.00 equiv), CbzCl (19.7 mg, 0.12 mmol, 1.50 equiv).

The resulting solution was stirred for 1 h at room temperature, and was then quenched by the addition of 15 mL of water/ice, extracted with 3×20 mL of EtOAc. The organic layers were combined, washed with 3×20 mL of brine, dried over Na$_2$SO$_4$ and concentrated under vacuum. The residue was applied onto a silica gel column with dichloromethane/methanol (20:1) to afford 49.5 mg (98%) of 127 as an off-white solid.

Example 128

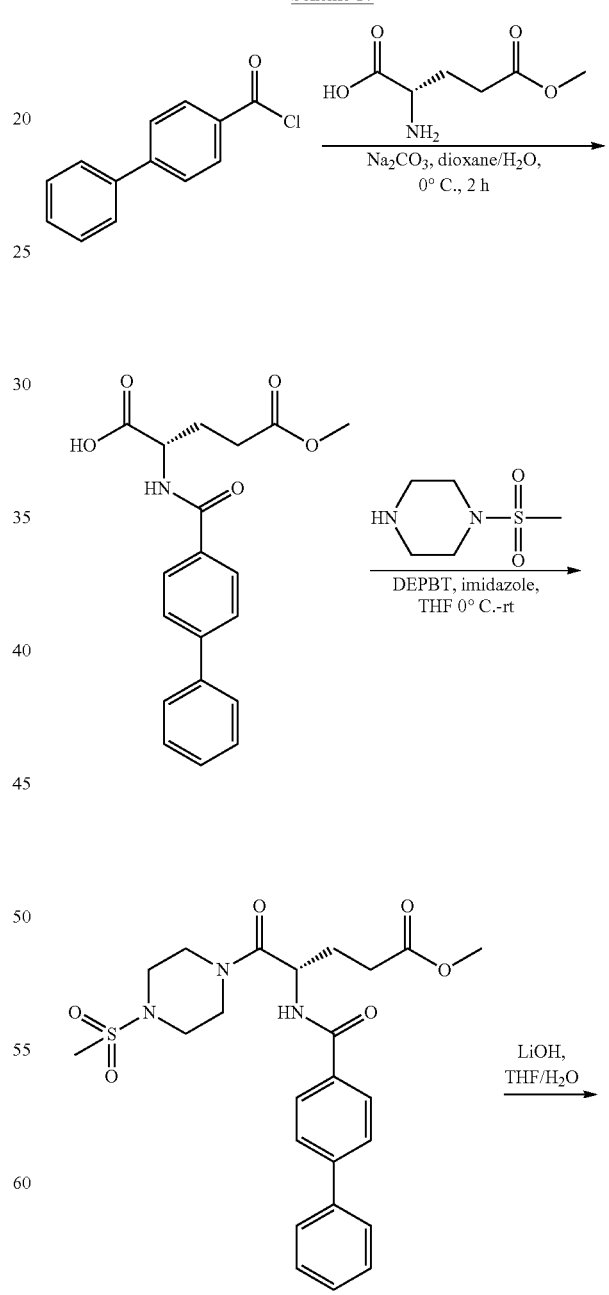

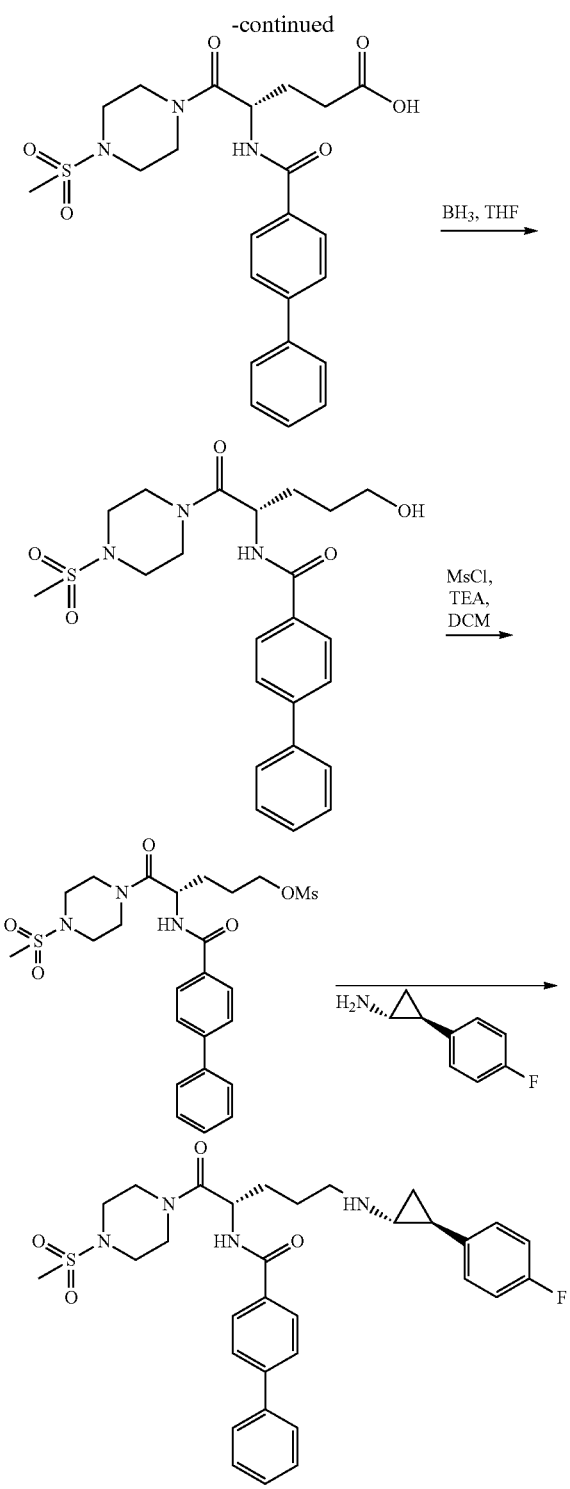

Synthesis of 128

(2S)-5-Methoxy-5-oxo-2-[(4-phenylphenyl)formamido]pentanoic Acid

The method used to prepare 203 was used with (2S)-2-amino-5-methoxy-5-oxopentanoic acid (4.9 g, 30.41 mmol, 1.00 equiv) and 4-phenylbenzoyl chloride (5 g, 23.08 mmol, 0.76 equiv) to afford 4 g (39%) of the product as a white solid.

Methyl (4S)-5-(4-methanesulfonylpiperazin-1-yl)-5-oxo-4-[(4-phenylphenyl)formamido]pentanoate The method used to prepare 206 was used with (2S)-5-methoxy-5-oxo-2-[(4-phenylphenyl)formamido]pentanoic acid (2 g, 5.86 mmol, 1.00 equiv) and 1-methanesulfonylpiperazine (1.15 g, 7.00 mmol, 1.20 equiv) to afford 2.5 g (88%) of the product as an off-white solid (4S)-5-(4-Methanesulfonylpiperazin-1-yl)-5-oxo-4-[(4-phenylphenyl)formamido]pentanoic Acid Into a 250-mL round-bottom flask, were combined the compound from the previous step (1 g, 2.05 mmol, 1.00 equiv), LiOH (73 mg, 3.05 mmol, 1.49 equiv), and THF/H$_2$O (50/12 mL). The resulting solution was stirred for 1 h at room temperature. The pH value of the solution was adjusted to 2 with HCl (2 M). The resulting solution was extracted with 3×30 mL of EtOAc, and the organic layers were combined and dried over Na$_2$SO$_4$ and concentrated under vacuum, affording 700 mg (72%) of the product as an off-white solid.

(4S)-5-(4-Methanesulfonylpiperazin-1-yl)-5-oxo-4-[(4-phenylphenyl)formamido]-1-pentanol (202)

Into a 100-mL round-bottom flask were combined a solution of the compound from the previous step (700 mg, 1.48 mmol, 1.00 equiv) in THF (10 mL) and BH$_3$ (1 M in THF) (2.2 mL). The resulting solution was stirred for 2 h at room temperature. The reaction was then quenched by the addition of 20 mL of water, then extracted with 3×20 mL of EtOAc. The organic layers were combined, dried over Na$_2$SO$_4$, and concentrated under vacuum. The residue was applied onto a silica gel column with EtOAc/petroleum ether (1:1) to afford 400 mg (59%) of the product as a yellow oil.

(4S)-5-(4-Methanesulfonylpiperazin-1-yl)-5-oxo-4-[(4-phenylphenyl)formamido]pentyl Methanesulfonate In a 50-mL round-bottom flask were combined a solution of the compound from the previous step (300 mg, 0.65 mmol, 1.00 equiv) and Et$_3$N (132 mg, 1.30 mmol, 2.00 equiv) in CH$_2$Cl$_2$ (5 mL). This was followed by the addition of methanesulfonyl chloride (90 mg, 0.78 mmol, 1.20 equiv) dropwise with stirring at 0° C. The resulting solution was stirred for 30 min at room temperature. The reaction was then quenched by the addition of 10 mL of water. The resulting solution was extracted with 3×10 mL of CH$_2$Cl$_2$, and the organic layers were combined and dried over anhydrous Na$_2$SO$_4$ and concentrated under vacuum. The residue was applied onto a silica gel column with EtOAc/petroleum ether (1:2) to afford 200 mg (57%) of the product as an off-white solid.

N-[(2S)-5-[[(1R,2S)-2-(4-fluorophenyl)cyclopropyl]amino]-1-(4-methanesulfonylpiperazin-1-yl)-1-oxopentan-2-yl]-4-phenylbenzamide (128)

Into a 50-mL round-bottom flask purged and maintained with an inert atmosphere of nitrogen were combined the compound from the previous step (200 mg, 0.37 mmol, 1.00 equiv), iPr₂NEt (96 mg, 0.74 mmol, 2.00 equiv), KI (62 mg), (1R,2S)-2-(4-fluorophenyl)cyclopropan-1-amine (62 mg, 0.41 mmol, 1.10 equiv) and CH₃CN (10 mL). The resulting solution was stirred for 12 h at 50° C. in an oil bath. The reaction was then quenched by the addition of 10 mL of water. The resulting solution was extracted with 3×10 mL of EtOAc, and the organic layers were combined and dried over anhydrous Na₂SO₄ and concentrated under vacuum. The crude product was purified by Prep-HPLC, affording 12.7 mg (6%) of 128 as an off-white solid.

Example 129

Scheme 18

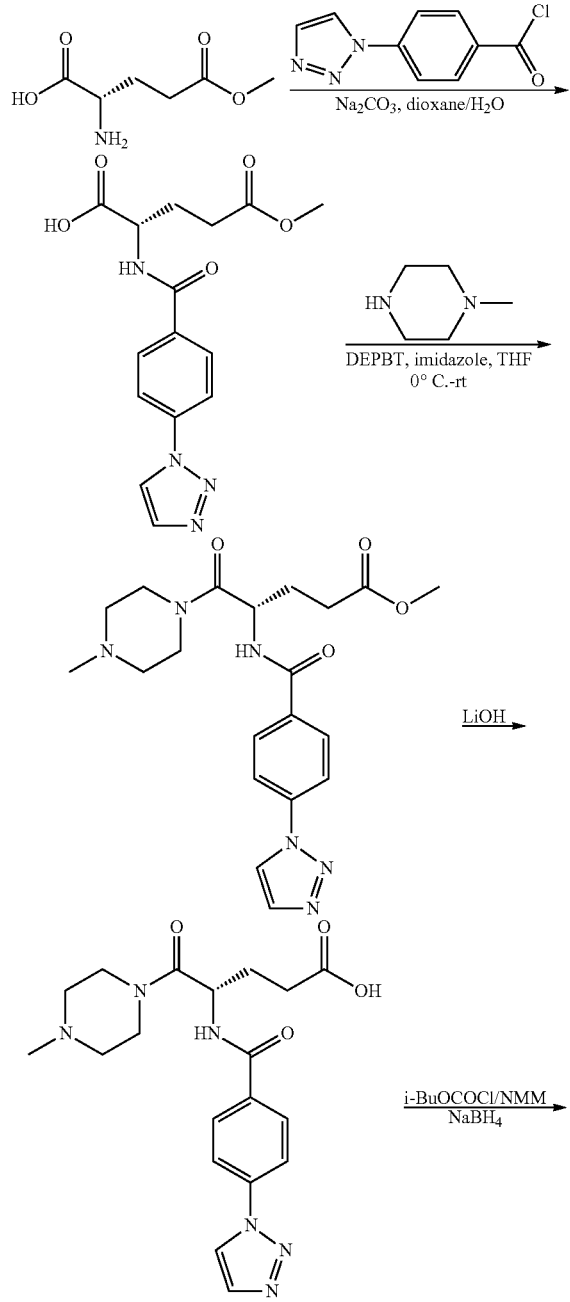

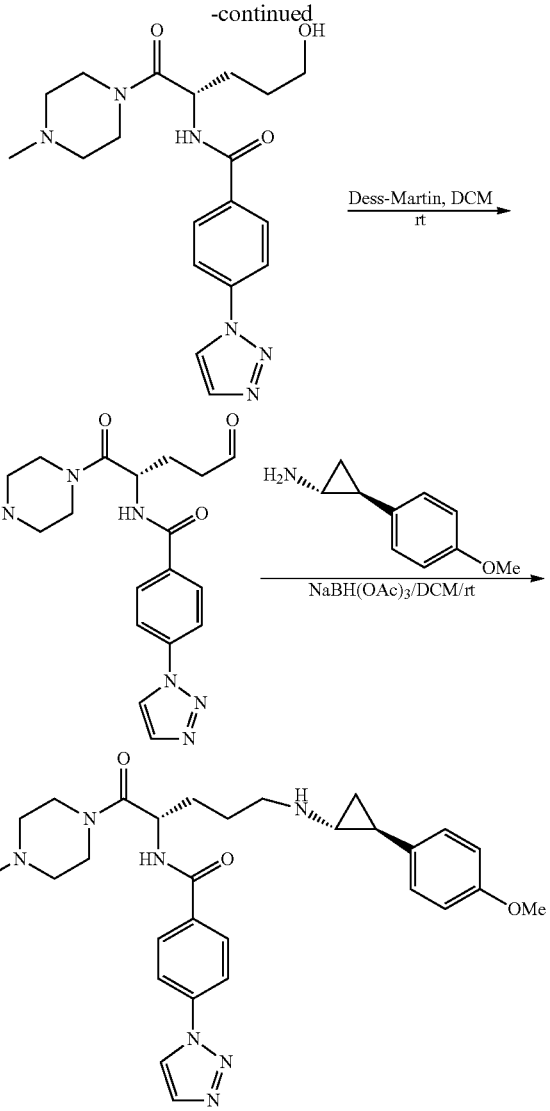

Synthesis of 129

(2S)-5-Methoxy-5-oxo-2-[[4-(1H-1,2,3-triazol-1-yl)phenyl]]-pentanoic Acid

The method used to prepare 203 was used with (2S)-2-amino-5-methoxy-5-oxopentanoic acid (3 g, 18.63 mmol, 1.00 equiv), and 4-(1H-1,2,3-triazol-1-yl)benzoyl chloride (4.65 g, 22.36 mmol, 1.20 equiv) to afford 2.5 g (40%) of the product as a yellow oil.

Methyl (4S)-5-(4-methylpiperazin-1-yl)-5-oxo-4-[[4-(1H-1,2,3-triazol-1-yl)phenyl]formamido]-pentanoate The method used to prepare 206 was used with the compound produced in the previous step (2.5 g, 7.53 mmol, 1.00 equiv) in and 1-methylpiperazine (1.13 g, 11.30 mmol, 1.50 equiv) to afford 2 g (64%) of the product as a yellow oil.

(4S)-5-(4-Methylpiperazin-1-yl)-5-oxo-4-[[4-(1H-1,2,3-triazol-1-yl)phenyl]formamido]-pentanoic Acid The method to prepare 205 was used with the compound produced in the previous step (2 g, 4.83 mmol) to afford 1.8 g (93%) of the product as an off-white solid.

(4S)-5-(4-Methylpiperazin-1-yl)-5-oxo-4-[[4-(1H-1,2,3-triazol-1-yl)phenyl]formamido]-1-pentanol In a 100-mL round-bottom flask were combined a solution of the product from the previous step (1.6 g, 4.00 mmol, 1.00 equiv) in THF (20 mL), N-methyl morpholine (983 mg, 8.40 mmol, 2.10 equiv), and tert-butyl chloroformate (1151 mg, 8.40 mmol, 2.10 equiv). The resulting mixture was stirred for 2 h at −20 degrees, then NaBH$_4$ (1.52 g, 40.0 mmol, 10.00 equiv) in methanol (10 mL) was added. The resulting solution was stirred for 2 h at −20° C. in a liquid nitrogen bath. The resulting mixture was concentrated under vacuum. The residue was applied onto a silica gel column with ethyl acetate/petroleum ether (10:1), affording 450 mg (29%) of the product as an off-white solid.

(4S)-5-(4-Methylpiperazin-1-yl)-5-oxo-4-[[4-(1H-1,2,3-triazol-1-yl)phenyl]formamido]-pentanal The method used to prepare 208 was used with the compound produced in the previous step (200 mg, 0.52 mmol, 1.00 equiv) to afford 150 mg (75%) of the product as an off-white solid.

n

N-[(2S)-5-[[(1R,2S)-2-(4-methoxyphenyl)cyclopropyl]amino]-1-(4-methylpiperazin-1-yl)-1-oxopentan-2-yl]-4-(1H-1,2,3-triazol-1-yl)benzamide (129)

In a 25-mL round-bottom flask were combined solution of the compound from the previous step (150 mg, 0.391 mmol, 1.00 equiv), (1R,2S)-2-(4-methoxyphenyl)cyclopropanamine (76 mg, 0.47 mmol, 1.20 equiv), NaBH(OAc)$_3$ (199 mg, 0.94 mmol, 2.40 equiv) and CH$_2$Cl$_2$ (20 mL). The resulting solution was stirred for 10 min at 25° C., then diluted with 30 mL of H$_2$O and extracted with 2×20 mL of CH$_2$Cl$_2$. The organic layers were combined, dried over Na$_2$SO$_4$, and concentrated under vacuum. The crude product was purified by Prep-HPLC, affording 5.9 mg (2.8%) of 129 as an off-white solid.

Example 130

Scheme 19

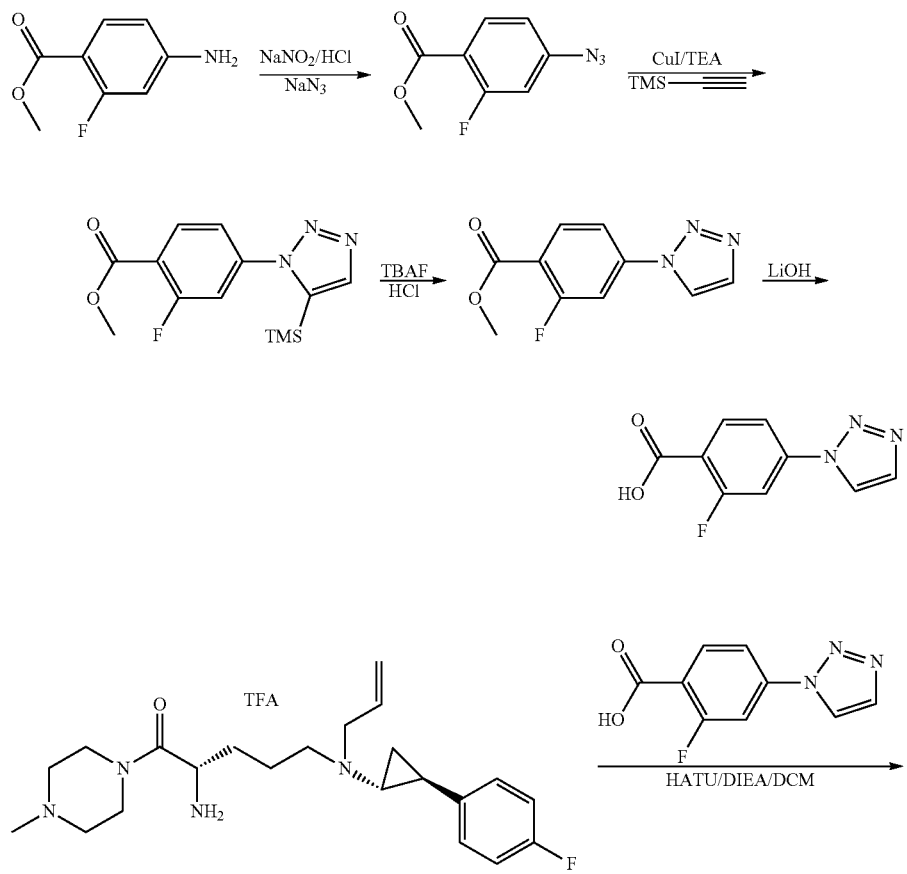

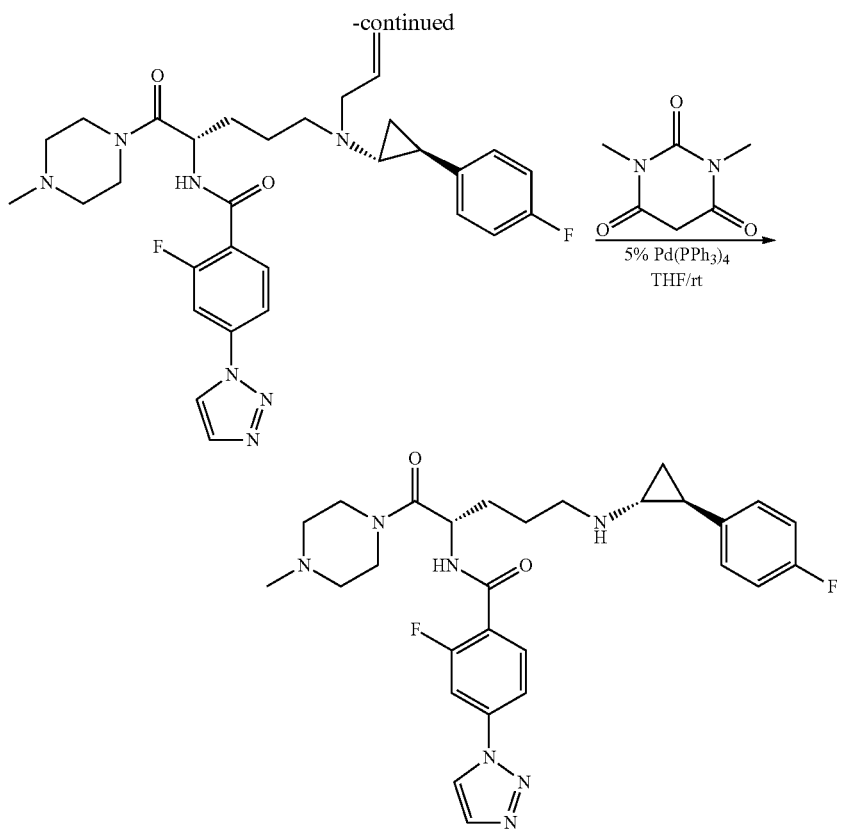

Synthesis of 130

Methyl 4-azido-2-fluorobenzoate

Into a 100-mL round-bottom flask purged and maintained with an inert atmosphere of nitrogen, was placed a solution of methyl 4-amino-2-fluorobenzoate (1 g, 5.91 mmol, 1.00 equiv) in hydrogen chloride (5 mL), a solution of NaNO$_2$ (407 mg, 5.90 mmol, 1.00 equiv) in water (5 mL), a solution of NaN$_3$ (575 mg, 8.85 mmol, 1.50 equiv) in water (5 mL). The resulting solution was stirred for 15 min at 0° C. The solids were filtered out. The resulting mixture was concentrated under vacuum. The residue was applied onto a silica gel column with ethyl acetate/petroleum ether (1:1). This resulted in 800 mg (69%) of the product as a yellow solid.

Methyl 2-fluoro-4-[5-(trimethylsilyl)-1H-1,2,3-triazol-1-yl]benzoate

Into a 100-mL round-bottom flask purged and maintained with an inert atmosphere of nitrogen, was placed a solution of methyl 4-azido-2-fluorobenzoate (800 mg, 4.10 mmol, 1.00 equiv) in methanol (20 mL), ethynyltrimethylsilane (603 mg, 6.14 mmol, 1.50 equiv), CuI (1.2 g, 6.30 mmol, 1.50 equiv), TEA (1.2 g, 11.88 mmol, 3.00 equiv). The resulting solution was stirred for 16 h at room temperature. The reaction was then quenched by the addition of 50 mL of water/ice. The resulting solution was extracted with 3×50 mL of ethyl acetate and the organic layers combined and concentrated under vacuum. The residue was applied onto a silica gel column with ethyl acetate/petroleum ether (1:1). This resulted in 700 mg (58%) of the product as a yellow solid.

Methyl 2-fluoro-4-(1H-1,2,3-triazol-1-yl)benzoate

Into a 100-mL round-bottom flask purged and maintained with an inert atmosphere of nitrogen, was placed a solution of methyl 2-fluoro-4-[5-(trimethylsilyl)-1H-1,2,3-triazol-1-yl]benzoate (700 mg, 2.39 mmol, 1.00 equiv) in tetrahydrofuran (10 mL), TBAF (1.25 g, 4.78 mmol, 2.00 equiv), AcOH (144 mg, 2.40 mmol, 1.00 equiv). The resulting solution was stirred for 2 days at room temperature. The reaction was then quenched by the addition of 50 mL of water/ice. The resulting solution was extracted with 3×50 mL of ethyl acetate and the organic layers combined and concentrated under vacuum. The residue was applied onto a silica gel column with dichloromethane/methanol (100:1). This resulted in 550 mg (crude) of the product as a yellow solid.

2-fluoro-4-(1h-1,2,3-triazol-1-yl)benzoic acid

The procedure used to prepare 205 was used with the compound produced in the previous step to afford 450 mg (87%) of the product as a light yellow solid

2-Fluoro-N-[(2S)-5-[[(1R,2S)-2-(4-fluorophenyl)cyclopropyl](prop-2-en-1-yl)amino]-1-(4-methylpiperazin-1-yl)-1-oxopentan-2-yl]-4-(1H-1,2,3-triazol-1-yl)benzamide The method used to prepare 211 was used with the compound produced in the previous step (160 mg, 0.77 mmol, 1.00 equiv) and (2S)-2-amino-5-[[(1R,2S)-2-(4-fluorophenyl)cyclopropyl](prop-2-en-1-yl)amino]-1-(4-methylpiperazin-1-yl)pentan-1-one (300 mg, 0.77 mmol, 1.00 equiv) to afford 250 mg (56%) of the product as a yellow solid.

2-Fluoro-N-[(2S)-5-[[(1R,2S)-2-(4-fluorophenyl)cyclopropyl]amino]-1-(4-methylpiperazin-1-yl)-1-oxopentan-2-yl]-4-(1H-1,2,3-triazol-1-yl)benzamide (130)
The method used to prepare 210 was used with the compound produced in the previous step (250 mg, 0.43 mmol) to afford 33.2 mg (14%) of 130 as a light brown solid.
Example 131
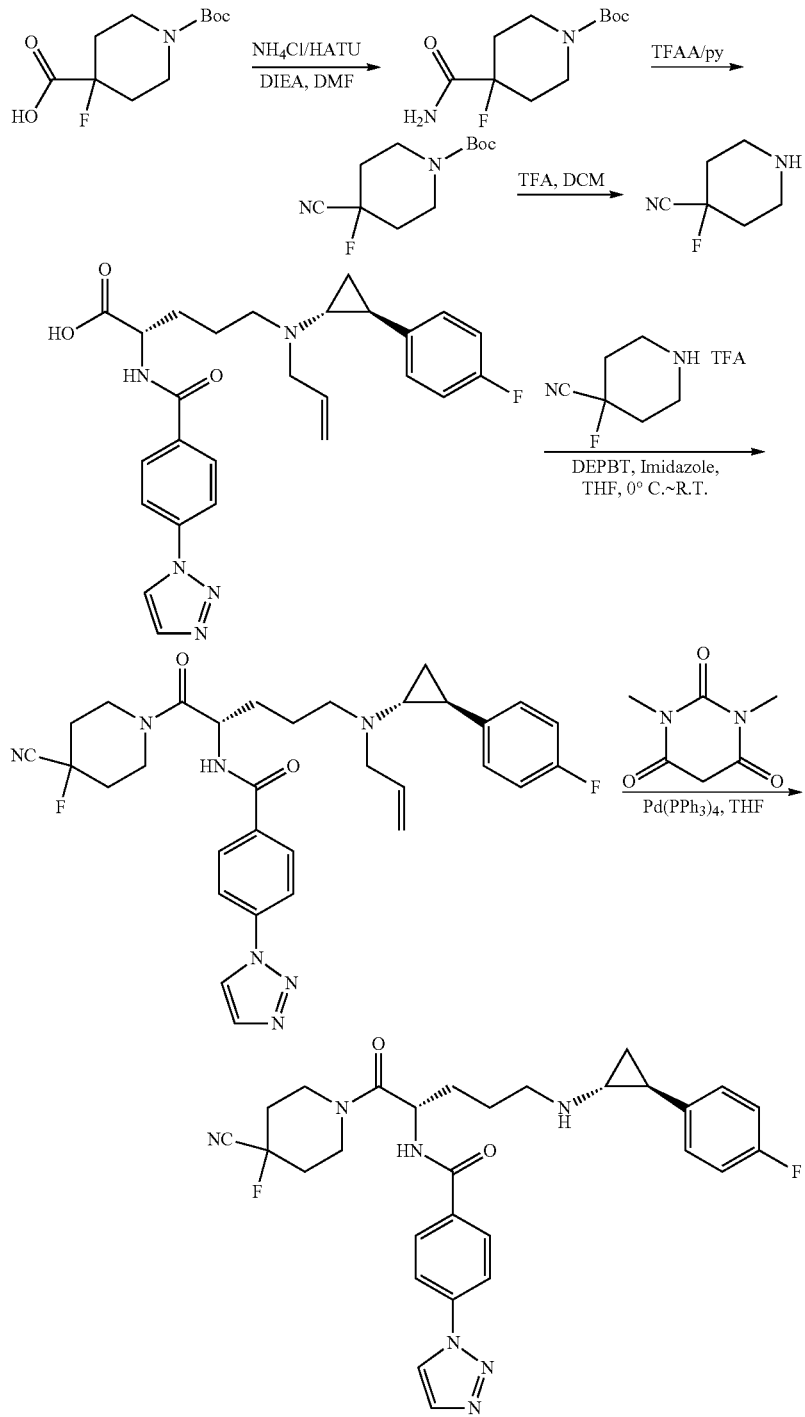

Synthesis of 131 tert-Butyl 4-carbamoyl-4-fluoropiperidine-1-carboxylate

In a 250-mL round-bottom flask were combined 1-[(tert-butoxy)carbonyl]-4-fluoropiperidine-4-carboxylic acid (3 g, 12.13 mmol, 1.00 equiv), DMF (50 mL), NH4Cl (1.75 g, 32.72 mmol, 1.50 equiv), HATU (9.23 g, 24.27 mmol, 2.00 equiv), and iPr2NEt (3.13 g, 24.22 mmol, 2.00 equiv). The resulting solution was stirred overnight at 25° C. The resulting solution was extracted with 200 mL of EtOAc and the organic layers were combined, washed with 5×50 mL of H2O, then applied onto a silica gel column with ethyl acetate/petroleum ether, affording 2.7 g (90%) of the product as a white solid.

tert-butyl 4-cyano-4-fluoropiperidine-1-carboxylate

In a 250-mL round-bottom flask were combined the compound from the previous step (1.6 g, 6.50 mmol, 1.00 equiv), pyridine (15 mL), TFAA (10 mL), and THF (30 mL). The resulting solution was stirred for 1 h at 0° C. in a water/ice bath. The crude product (50 mL) was purified by Flash-Prep-HPLC with the following conditions (IntelFlash-1): Column, C18 silica gel; mobile phase, MeCN/H2O=0/100 increasing to MeCN/H2O=50/50 within 30 min; Detector, UV 254 nm. 10 mL product was obtained, affording 1.2 g (81%) of the product as a white solid.

4-Fluoropiperidine-4-carbonitrile

In a 250-mL round-bottom flask were combined the compound from the previous step (800 mg, 3.50 mmol, 1.00 equiv), CF3COOH (1 mL), and CH2Cl2 (5 mL). The resulting solution was stirred for 1 h at 25° C., then concentrated under vacuum to afford 350 mg (78%) of the product as a white solid.

N-[(2S)-1-(4-Cyano-4-fluoropiperidin-1-yl)-1-oxo-5-[[(1R,2S)-2-phenylcyclopropyl](prop-2-en-1-yl)amino]pentan-2-yl]-4-(1H-1,2,3-triazol-1-yl)benzamide The method used to prepare 206 was used with (2S)-5-[[(1R,2S)-2-(4-fluorophenyl)cyclopropyl](prop-2-en-1-yl)amino]-2-[[4-(1H-1,2,3-triazol-1-yl)phenyl]formamido]pentanoic acid (700 mg, 1.47 mmol, 1.00 equiv) and 4-fluoropiperidine-4-carbonitrile (350 mg, 2.73 mmol, 2.00 equiv) to afford 816 mg (98%) of the product as a yellow oil.

N-[(2S)-1-(4-Cyano-4-fluoropiperidin-1-yl)-5-[[(1R,2S)-2-(4-fluorophenyl)cyclopropyl]amino]-1-oxo-pentan-2-yl]-4-(1H-1,2,3-triazol-1-yl)benzamide (131)

The method used to prepare 210 was used with the compound from the previous step to afford 40.7 mg (5%) of the product as a white solid.

Example 132

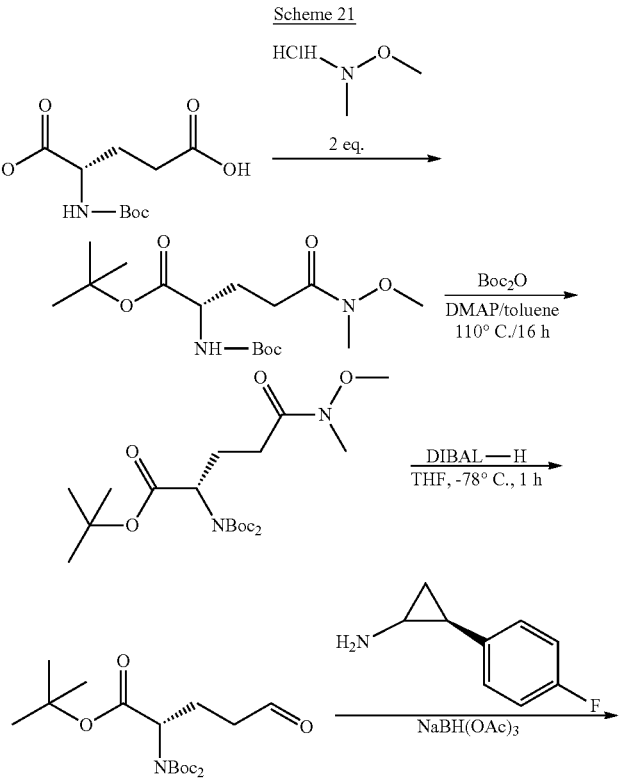

Scheme 21

-continued
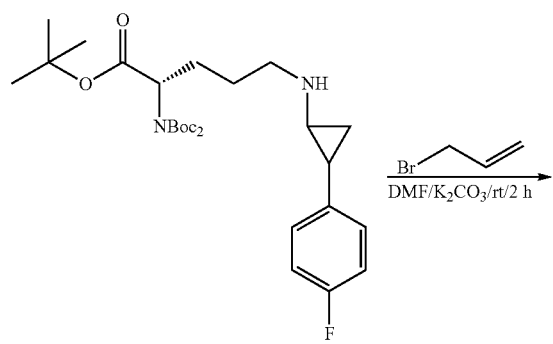
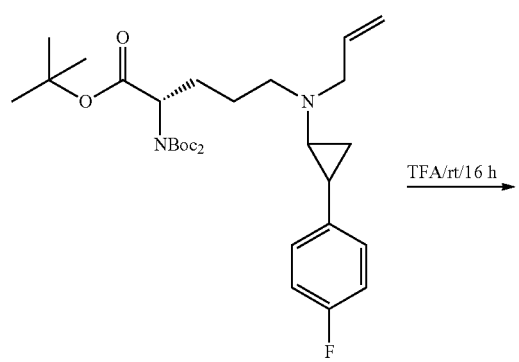
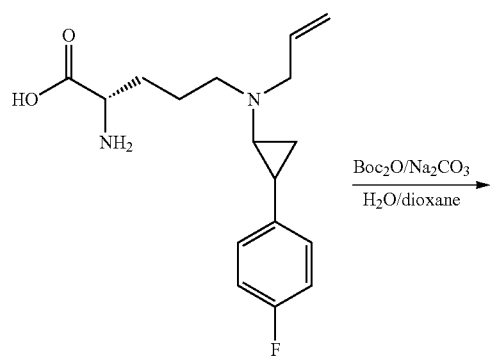
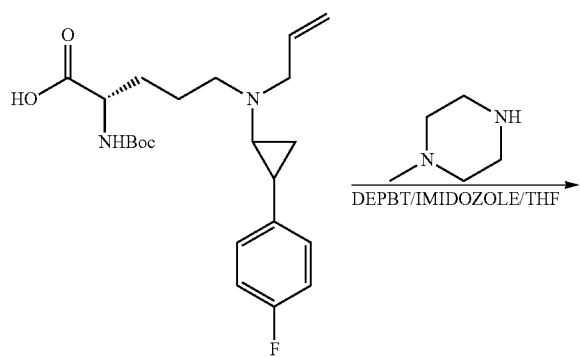

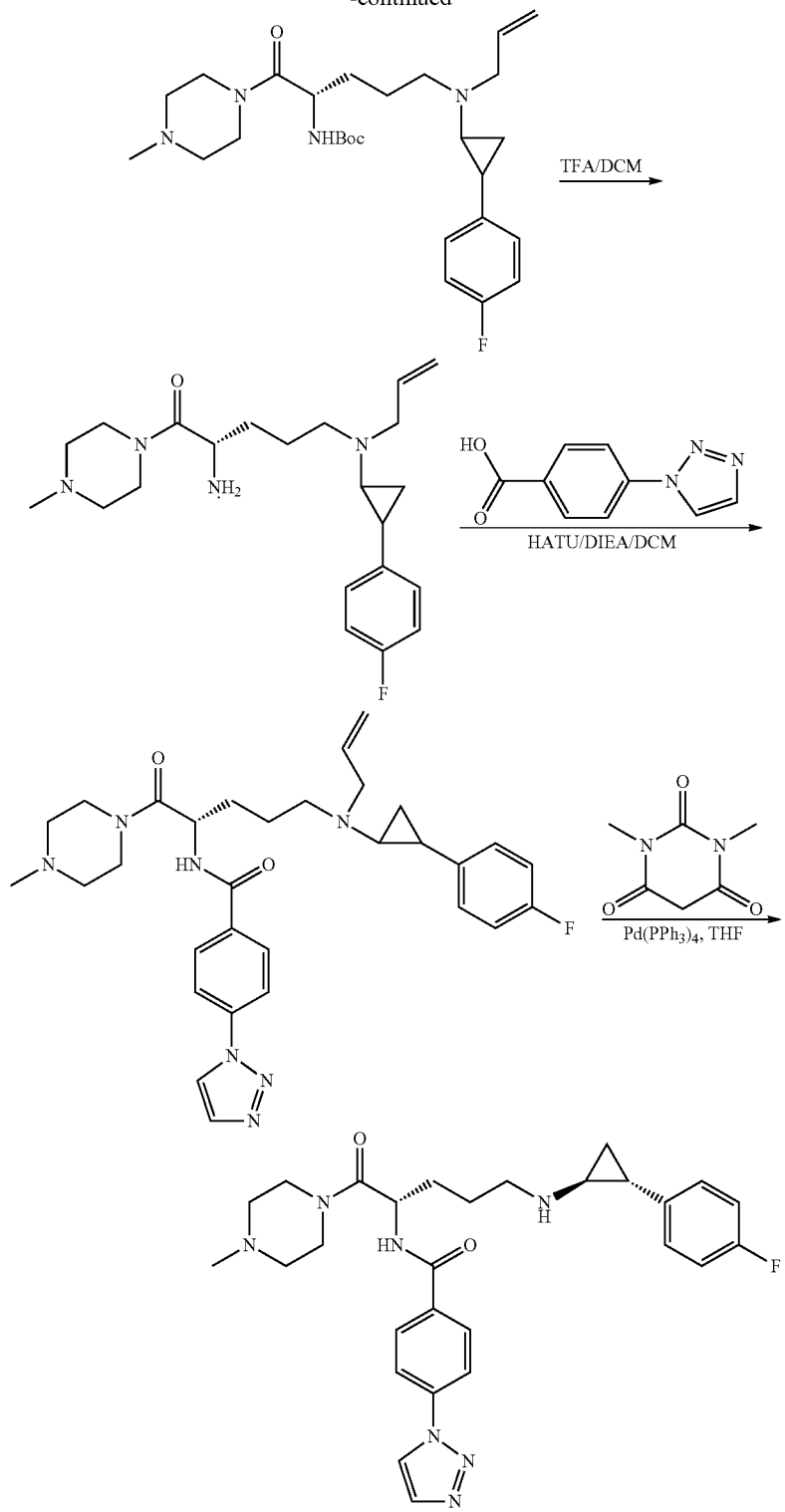

Synthesis of 132

(4S)—N-Methyl-N-methoxy-5-(tert-butoxy)-4-[(tert-butoxycarbonyl)amino]-5-oxopentanamide In a 1-L round-bottom flask were combined a solution of (4S)-5-(tert-butoxy)-4-[[(tert-butoxy)carbonyl] amino]-5-oxopentanoic acid (20.0 g, 65.93 mmol, 1.00 equiv) in $CH_2Cl_2$ (200 mL), EDCI (18.9 g, 98.59 mmol, 1.50 equiv), HOBT (13.4 g, 98.80 mmol, 1.50 equiv), methoxy(methyl) amine hydrochloride (9.7 g, 98.94 mmol, 1.50 equiv), and $Et_3N$ (20.0 g, 197.65 mmol, 3.00 equiv). The resulting solution was stirred for 3 h at 25° C. The then washed with 3×100 mL of $H_2O$, dried over $Na_2SO_4$, concentrated under vacuum, then applied onto a silica gel column with EtOAc/petroleum ether (1:3) to afford 22.1 g (96%) of the product as a light yellow oil.

(4S)—N-Methyl-N-methoxy-5-(tert-butoxy)-4-[di(tert-butoxycarbonyl)amino]-5-oxopentanamide The method used to prepare 204 was used with the compound from the previous step (19.1 g, 54.99 mmol, 1.00 equiv) to afford 23.6 g (96%) of the product as a light yellow oil.

(4S)-5-(tert-Butyloxy)-4-[di(tert-butoxycarbonyl)amino]-5-oxopentanal

Into a 500-mL 3-necked round-bottom flask purged and maintained with an inert atmosphere of nitrogen were combined a solution of the compound from the previous step (6 g, 13.42 mmol, 1.00 equiv) in THF (50 mL), followed by the addition of disobutyl aluminium hydride (30 mL, 2.50 equiv) dropwise with stirring at −78° C. in 30 min. The resulting solution was stirred for 30 min at −78° C., then quenched by the addition of 50 mL $NH_4Cl$(aq). The resulting solution was extracted with 3×100 mL of EtOAc. The organic layers were combined, dried over $Na_2SO_4$ and concentrated under vacuum, affording 6.3 g (crude) of the product as a light yellow oil.

tert-Butyl (2S)-5-[[(1R,2S)-2-(4-fluorophenyl)cyclopropyl]amino]-2-[di(tert-butoxycarbonyl)amino]pentanoate Into a 500-mL round-bottom flask purged and maintained with an inert atmosphere of nitrogen were combined the compound from the previous step (6.3 g, 16.26 mmol, 1.00 equiv), 2-(4-fluorophenyl)cyclopropan-1-amine hydrochloride (2.45 g, 13.06 mmol, 0.80 equiv), $NaBH(OAc)_3$ (8.25 g, 38.93 mmol, 2.40 equiv), and methanol (150 mL). The resulting solution was stirred for 30 min at 25° C. The resulting mixture was concentrated under vacuum, then diluted with 100 mL EtOAc. The resulting mixture was washed with 3×20 mL of $H_2O$, dried and concentrated under vacuum. The residue was applied onto a silica gel column with EtOAc/petroleum ether (1:4), affording 3.1 g (36%) of the product as a light yellow oil.

tert-Butyl (2S)-5-[[(1R,2S)-2-(4-fluorophenyl)cyclopropyl](propen-2-yl)amino]-2-[di(tert-butoxycarbonyl)amino]pentanoate Into a 500-mL round-bottom flask purged and maintained with an inert atmosphere of nitrogen were combined a solution of the compound from the previous step (3.1 g, 5.93 mmol, 1.00 equiv) in DMF (10 mL), $K_2CO_3$ (2.45 g, 17.78 mmol, 3.00 equiv), and 3-bromoprop-1-ene (1.43 g, 11.85 mmol, 2.00 equiv). The resulting solution was stirred for 2 h at 25° C. The resulting solution was diluted with 50 mL of EtOAc, then washed with 3×5 mL of $H_2O$, dried over $Na_2SO_4$, and concentrated under vacuum. The residue was applied onto a silica gel column with EtOAc/petroleum ether (1:7) to afford 3 g (90%) of the product as a light yellow oil.

(2S)-5-[[(1R,2S)-2-(4-Fluorophenyl)cyclopropyl](propen-2-yl)amino]-2-aminopentanoic Acid In a 500-mL round-bottom flask were combined the compound from the previous step (3 g, 43.01 mmol, 1.00 equiv) and $CF_3COOH$ (10 mL). The resulting solution was stirred for 16 h at 25° C. then concentrated under vacuum. The crude product was purified by Flash-Prep-HPLC with $CH_3CN:H_2O$ (1:100-15:1) to afford 2 g (83%) of the product as a light yellow solid.

(2S)-5-[(1R,2S)-2-(4-Fluorophenyl)cyclopropyl](propen-2-yl)amino]-2-[(tert-butoxycarbonyl)amino]pentanoic Acid Into a 500-mL round-bottom flask, was placed a solution of the compound from the previous step (2 g, 6.51 mmol, 1.00 equiv) in dioxane (20 mL), $(Boc)_2O$ (2.13 g, 9.77 mmol, 1.50 equiv), $Na_2CO_3$ (2.07 g, 19.54 mmol, 3.0 equiv) in $H_2O$ (20 ml). The resulting solution was stirred for 2 h at room temperature. The solid was removed by filtration, and the resulting solution was concentrated under vacuum. The crude product was purified by flash with $CH_3CN:H_2O$ (1:100-1:1) to afford 2.3 g (86%) of the product as a yellow oil.

(2S)-2-[(tert-butoxycarbonyl)amino]-5-[[(1R,2S)-2-(4-Fluorophenyl)cyclopropyl](propen-2-yl)amino]-1-(4-methylpiperazin-1-yl)-1-oxopentane The method used to prepare 206 was used with the compound from the previous step (2.3 g, 5.67 mmol, 1.00 equiv) and N-methylpiperazine (850 mg, 8.50 mmol, 1.5 equiv) to afford 2.3 g (83%) of PH-IMA-2013-003-384-8 as a yellow oil.

(2S)-2-[(tert-butoxycarbonyl)amino]-5-[[(1R,2S)-2-(4-Fluorophenyl)cyclopropyl](propen-2-yl)amino]-1-(4-methylpiperazin-1-yl)-1-oxopentane The method used to prepare 211 was used with the compound from the previous step to afford 1.8 g of the product as a yellow oil.

(2S)—N-[5-[[(1R,2S)-2-(4-Fluorophenyl)cyclopropyl](propen-2-yl)amino]-1-(4-methylpiperazin-1-yl)-1-oxopentan-2-yl]-4-(1H-1,2,3-triazol-1-yl)benzamide The method used to prepare 211 was used with the compound from the previous step (1.8 g, 4.63 mmol, 1.0 equiv) and 4-(1H-1,2,3-triazol-1-yl)benzoic acid (875 mg, 4.63 mmol, 1.0 equiv) to afford 1.7 g (66%) of the product as a yellow solid.

(2S)—N-[5-[[(1R,2S)-2-(4-Fluorophenyl)cyclopropyl] amino]-1-(4-methylpiperazin-1-yl)-1-oxopentan-2-yl]-4-(1H-1,2,3-triazol-1-yl)benzamide(132)

The method used to prepare 210 was used with the compound from the previous step to afford 281.8 mg (18%) of 132 as a light-yellow solid.

Example 134
Scheme 22
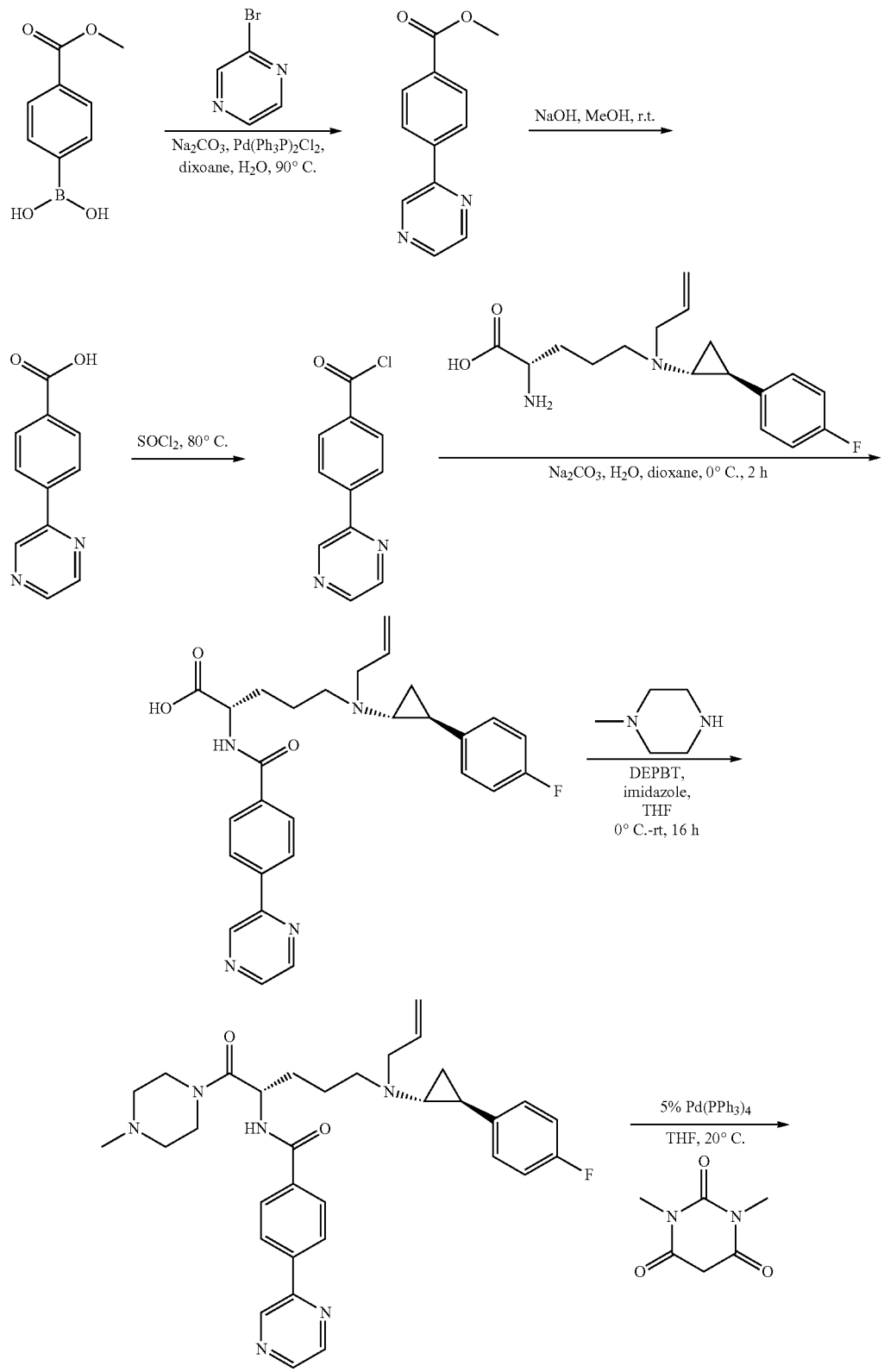

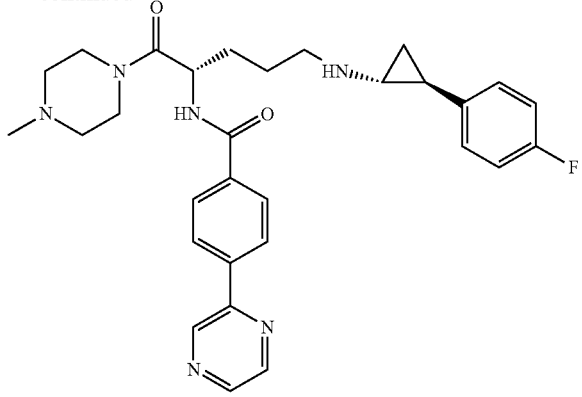

Synthesis of 134

Methyl 4-(2-pyrazinyl) Benzoate

In a 250-mL Round-Bottom Flask Purged and maintained with an inert atmosphere of nitrogen were combined a solution of [4-(methoxycarbonyl)phenyl]boronic acid (1 g, 5.56 mmol, 1.20 equiv) in 1,4-dioxane (30 mL), 2-bromopyrazine (800 mg, 5.03 mmol, 1.00 equiv), a solution of $Na_2CO_3$ (1.5 g, 14.15 mmol, 3.00 equiv) in water (30 mL), and $Pd(Ph_3P)_2Cl_2$ (330 mg, 0.47 mmol, 0.10 equiv). The resulting solution was stirred for 16 h at 90° C. in an oil bath. The solids were filtered out. The resulting solution was extracted with 3×30 mL of EtOAc, and the organic layers combined and concentrated under vacuum. This resulted in 0.8 g (74%) of the product as a white solid.

4-(2-Pyrazinyl) Benzoic Acid

In a 100-mL round-bottom flask were combined a solution of methyl 4-(pyrazin-2-yl)benzoate (800 mg, 3.73 mmol, 1.00 equiv) in methanol (20 mL), a solution of NaOH (150 mg, 3.75 mmol, 1.00 equiv) in water (20 mL). The resulting solution was stirred for 16 h at 80° C. in an oil bath. The pH value of the solution was adjusted to 7 with HCl (1M). The solids were collected by filtration. The resulting mixture was concentrated under vacuum. This resulted in 0.65 g (87%) of the product as a white solid.

4-(2-Pyrazinyl)-benzoyl Chloride

In a 100-mL round-bottom flask were combined 4-(pyrazin-2-yl)benzoic acid (650 mg, 3.25 mmol, 1.00 equiv) and thionyl chloride (20 mL). The resulting solution was stirred for 16 h at 80° C. in an oil bath. The resulting mixture was concentrated under vacuum. This resulted in 0.7 g (99%) of the product as a light yellow solid.

(2S)-5-[[(1R,2S)-2-(4-Fluorophenyl)cyclopropyl](prop-2-en-1-yl)amino]-2-[[4-(2-pyrazinyl)phenyl]formamido]pentanoic Acid The method used to prepare 203 was used with the compound produced in the previous step (500 mg, 1.63 mmol, 1.00 equiv) and 4-(pyridin-2-yl)benzoyl chloride (393 mg, 1.81 mmol, 1.10 equiv), to afford 360 mg (45%) of the product as a yellow solid.

N-[(2S)-5-[[(1R,2S)-2-(4-Fluorophenyl)cyclopropyl](prop-2-en-1-yl)amino]-1-(4-methylpiperazin-1-yl)-1-oxopentan-2-yl]-4-(pyrazin-2-yl)benzamide The method used to prepare 206 was used with the compound produced in the previous step (360 mg, 0.74 mmol, 1.00 equiv) and 1-methylpiperazine (111 mg, 1.11 mmol, 1.50 equiv) to afford 300 mg (71%) of the product as a yellow solid.

N-[(2S)-5-[[(1R,2S)-2-(4-Fluorophenyl)cyclopropyl]amino]-1-(4-methylpiperazin-1-yl)-1-oxopentan-2-yl]-4-(pyrazin-2-yl)benzamide (134)

The method used to prepare 210 was used with the compound produced in the previous step (300 mg, 0.53 mmol, 1.00 equiv), affording 88.8 mg (32%) of the product as an off-white solid.

Example 135

Scheme 23

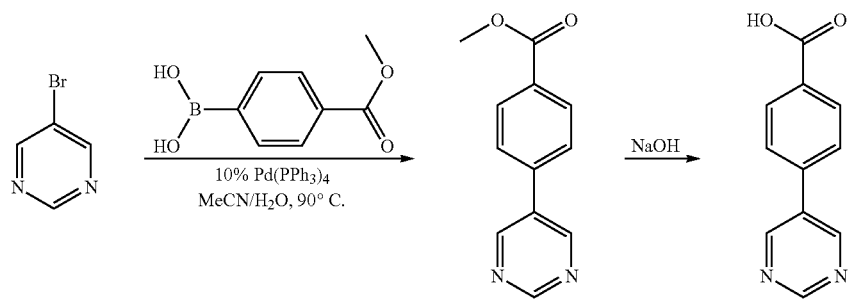

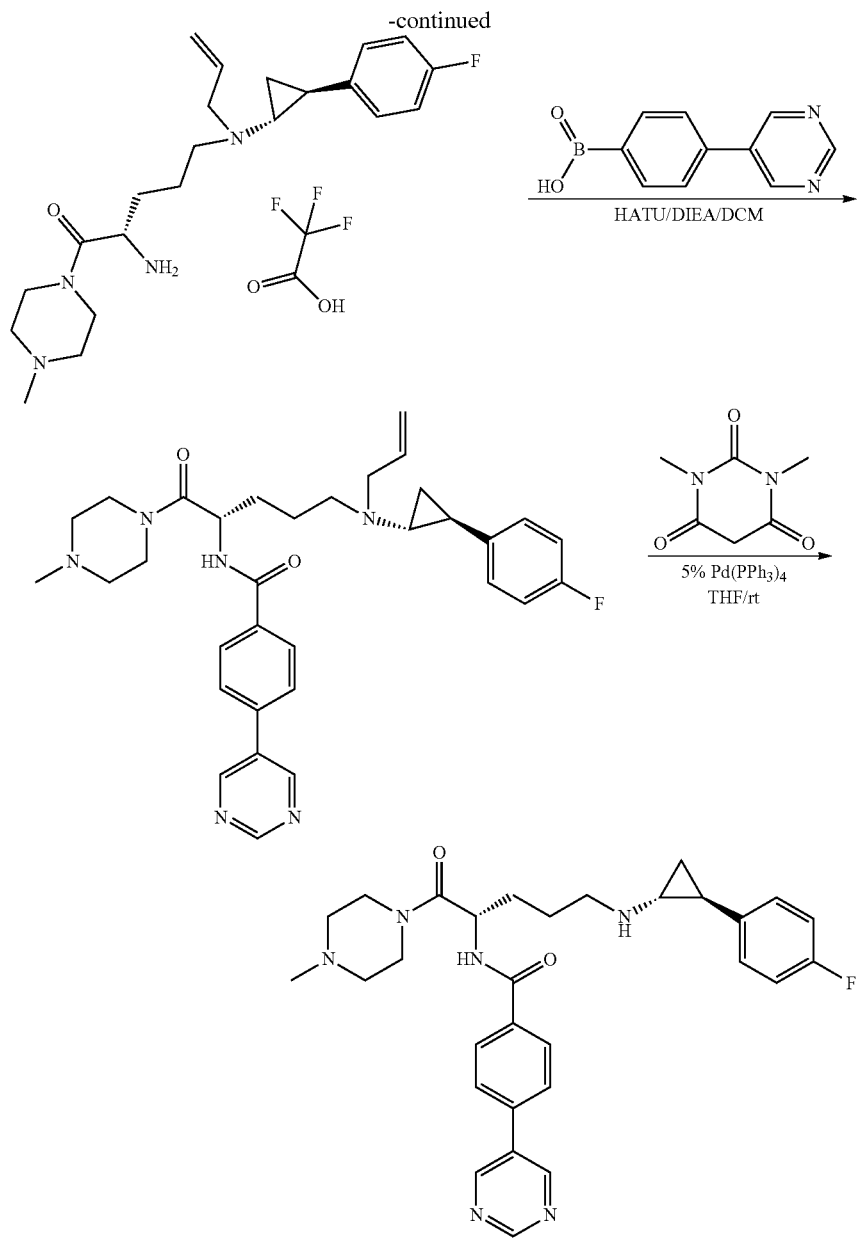

Synthesis of 135

Methyl 4-(pyrimidin-5-yl)benzoate

In a 250-mL round-bottom flask purged and maintained with an inert atmosphere of nitrogen were combined solution of 5-bromopyrimidine (2.2 g, 13.84 mmol, 1.10 equiv) in MeCN (60 mL). This was followed by the addition of [4-(methoxycarbonyl)phenyl]boronic acid (2.26 g, 12.56 mmol, 1.00 equiv), in portions. To this was added a solution of Na$_2$CO$_3$ (2.9 g, 27.36 mmol, 2.00 equiv) in water (30 mL) dropwise with stirring at room temperature in 2 min. To the mixture was added Pd(PPh$_3$)$_4$ (1.45 g, 1.25 mmol, 0.10 equiv), in portions. The resulting solution was stirred for 4 h at 90° C. The solids were removed by filtration. The resulting mixture was concentrated under vacuum. The residue was applied onto a silica gel column with ethyl acetate/petroleum ether (1:1). This resulted in 1.31 g (49%) of the product as a yellow solid.

4-(Pyrimidin-5-yl)benzoic Acid

The method used to prepare 209 was used with the compound produced in the previous step (1.31 g, 6.12 mmol, 1.00 equiv) to afford 0.7 g (57%) of as a white solid.

N-[(2S)-5-[[(1R,2S)-2-(4-Fluorophenyl)cyclopropyl] (prop-2-en-1-yl)amino]-1-(4-methylpiperazin-1-yl)-1-oxopentan-2-yl]-4-(pyrimidin-5-yl)benzamide The method used to prepare 211 was used with the compound produced in the previous step (250 mg, 0.50 mmol, 1.00 equiv) to afford (70%) of as a yellow foam.

N-[(2S)-5-[[(1R,2S)-2-(4-Fluorophenyl)cyclopropyl]amino]-1-(4-methylpiperazin-1-yl)-1-oxopentan-2-yl]-4-(pyrimidin-5-yl)benzamide (135)
The method used to prepare 210 was used with the compound produced in the previous step (200 mg, 0.35 mmol) to afford 15 mg (8%) of 135 as an off-white solid.
Example 137
Scheme 24
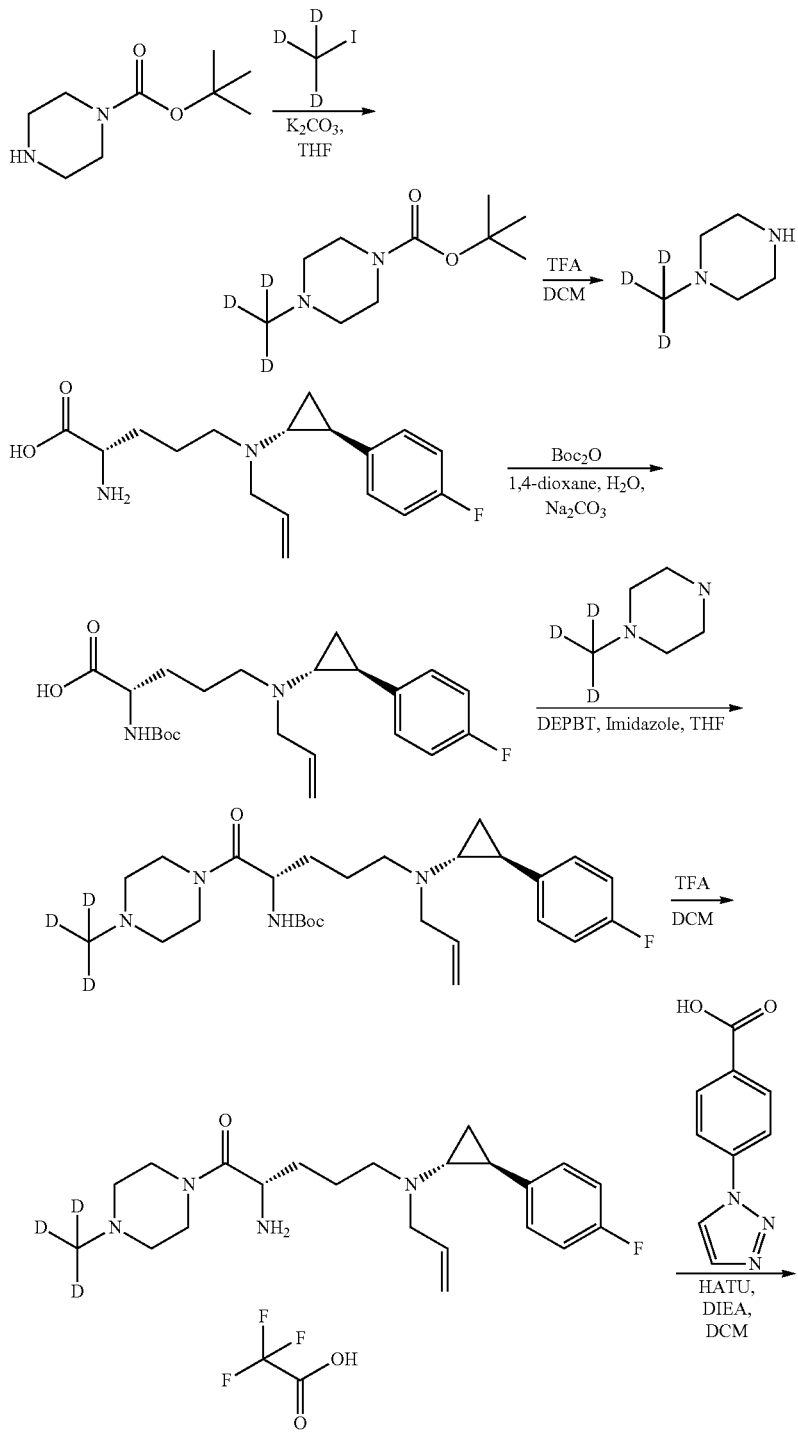

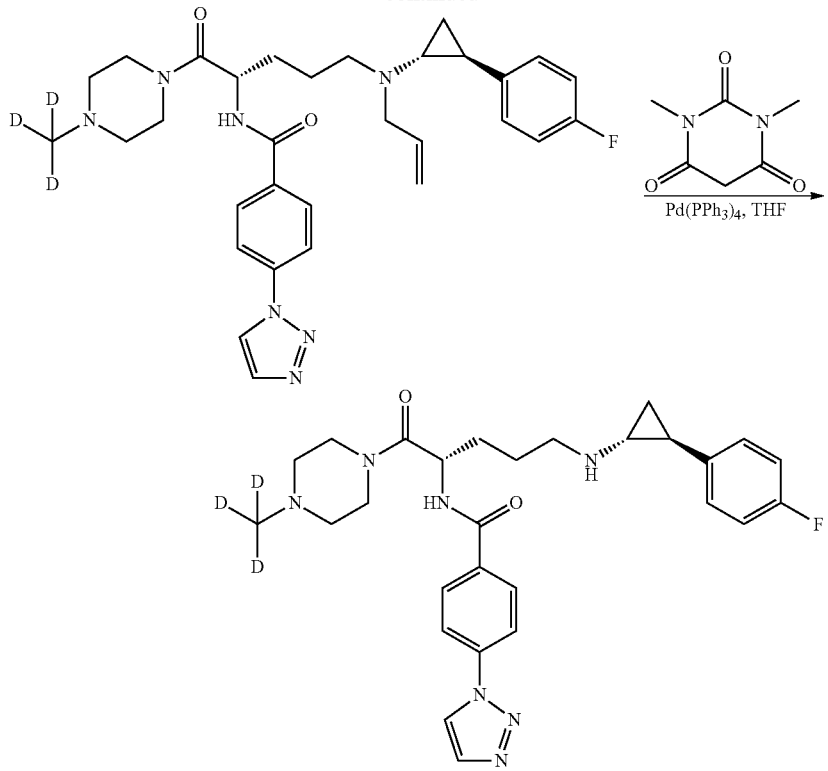

Synthesis of 137 tert-Butyl 4-(d₃)-methylpiperazine-1-carboxylate

In a 100-mL round-bottom flask were combined tert-butyl piperazine-1-carboxylate (1 g, 5.37 mmol, 1.00 equiv), $K_2CO_3$ (2.23 g, 16.13 mmol, 3.01 equiv) and THF (40 mL). The resulting solution was stirred for 1 h at room temperature. This was followed by the addition of iodomethane-$d_3$ (780 mg, 5.38 mmol, 1.00 equiv) dropwise with stirring at −12° C. The resulting solution was stirred overnight at room temperature. The solids were removed by filtration, and the crude product was purified by Prep-HPLC. The resulting solution was extracted with 3×30 mL of 5:1 $CH_2Cl_2$:MeOH, and the organic layers were combined and concentrated under vacuum, affording 500 mg (46%) of the product as a colorless oil.

1-(d₃)-Methylpiperazine

The method used to prepare 1 was used with the compound produced in the previous step (500 mg, 2.46 mmol, 1.00 equiv) to afford 250 mg (99%) of the product as a colorless oil.

(2S)-2-[[(tert-Butoxy)carbonyl]amino]-5-[[(2S)-2-(4-fluorophenyl)cyclopropyl](prop-2-en-1-yl)amino]pentanoic Acid The method used to prepare 204 was used with (2S)-2-amino-5-[[(2S)-2-(4-fluorophenyl)cyclopropyl](prop-2-en-1-yl)amino]pentanoic acid (1.29 g, 4.21 mmol, 1.00 equiv), 1,4-dioxane (50 mL), affording 1.3 g (76%) of the product as a white solid.

tert-Butyl N-[(2S)-5-[[(2S)-2-(4-fluorophenyl)cyclopropyl](prop-2-en-1-yl)amino]-1-[4-(d₃)-methylpiperazin-1-yl]-1-oxopentan-2-yl]carbamate The method used to prepare 206 was used with the compound produced in the previous step (1.075 g, 2.64 mmol, 1.00 equiv) and 1-(d₃)-methylpiperazine (300 mg, 2.91 mmol, 1.10 equiv) to afford 650 mg (50%) of the product as a yellow oil.

(2S)-2-amino-5-[[(2S)-2-(4-fluorophenyl)cyclopropyl](prop-2-en-1-yl)amino]-1-[4-(d₃)-methylpiperazin-1-yl]pentan-1-one; Trifluoroacetic Acid Salt The method used to prepare 1 was used with the compound produced in the previous step (650 mg, 1.32 mmol, 1.00 equiv), to afford 710 mg (96%) of as a yellow oil.

N-[(2S)-5-[[(2S)-2-(4-Fluorophenyl)cyclopropyl](prop-2-en-1-yl)amino]-1-[4-(d₃)-methylpiperazin-1-yl]-1-oxopentan-2-yl]-4-(1H-1,2,3-triazol-1-yl)benzamide The method used to prepare 211 was used with the compound produced in the previous step and 4-(1H-1,2,3-triazol-1-yl)benzoic acid (231 mg, 1.22 mmol, 1.23 equiv) to afford 700 mg (96%) of the product as light yellow oil.

N-[(2S)-5-[[(2S)-2-(4-Fluorophenyl)cyclopropyl]amino]-1-[4-(d₃)-methylpiperazin-1-yl]-1-oxopentan-2-yl]-4-(1H-1,2,3-triazol-1-yl)benzamide (137)

The method used to prepare 210 was used with the compound produced in the previous step (850 mg, 1.51 mmol) to afford 112.2 mg (14%) of 137 as a light yellow solid.

Example 138
Scheme 25
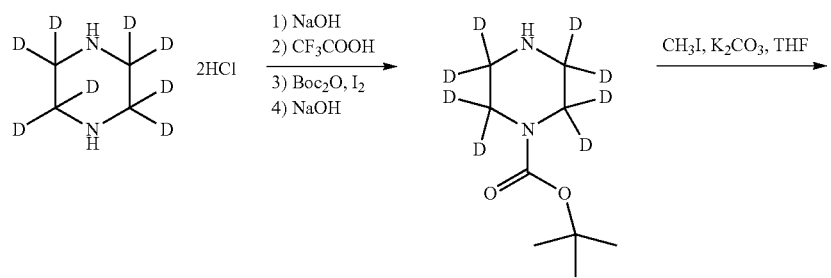
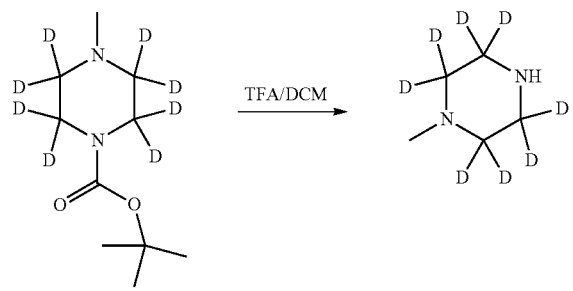
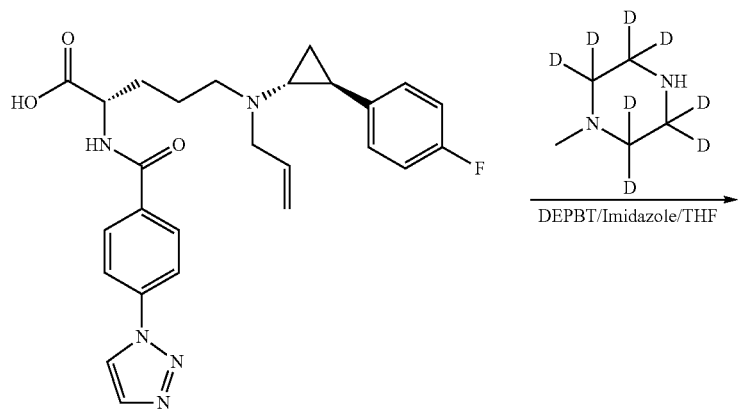
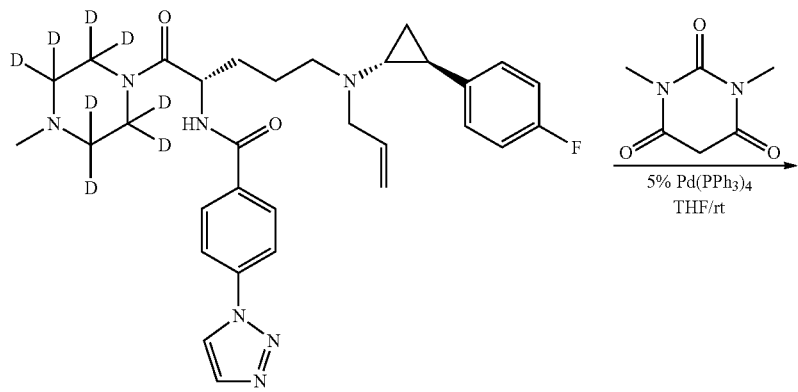

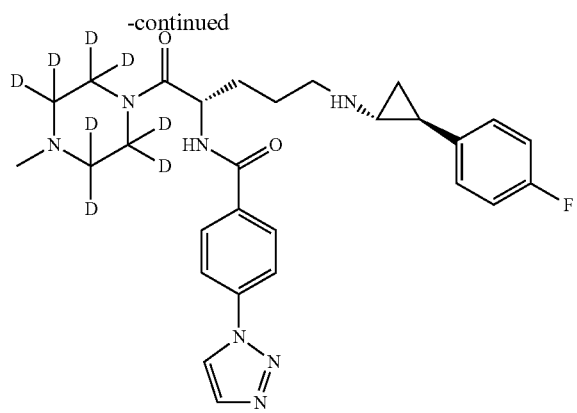

Synthesis of 138

1-(tert-Butoxycarbonyl)-(2,2,3,3,5,5,6,6-$d_8$)piperazine

Into a 250-mL round-bottom flask was added a solution of (2,2,3,3,5,5,6,6-$d_8$)piperazine dihydrochloride (1 g, 5.98 mmol, 1.00 equiv) in methanol (10 mL), followed by the addition of a solution of NaOH (480 mg, 12.00 mmol, 2.00 equiv) in methanol (10 mL). The mixture was stirred for 30 min, then $CF_3COOH$ (682 mg, 5.98 mmol, 1.00 equiv) was added. The reaction mixture was stirred for an additional 15 min, then water (20 mL) was added. The solution was stirred for 30 min, then a solution of $Boc_2O$ (1.3 g, 5.96 mmol, 1.00 equiv) and 12 (152 mg, 0.60 mmol, 0.10 equiv) in methanol (40 mL) was added. The resulting solution was stirred for 3 h at 25° C., then concentrated under vacuum. The pH value of the solution was adjusted to 11 with NaOH (20%). The solids were removed by filtration, and the resulting solution was extracted with 3×30 mL of EtOAc. The organic layers were combined, washed with 1×50 mL of brine, then dried over $Na_2SO_4$. The resulting solution was concentrated under vacuum to afford 1 g (86%) of the product as off-white solid.

1-(tert-Butoxycarbonyl)-4-methyl-(2,2,3,3,5,5,6,6-$d_8$)piperazine

In a 100-mL round-bottom flask was combined the compound from the previous step (1 g, 5.15 mmol, 1.00 equiv), THF (30 mL), and $K_2CO_3$ (2.14 g, 15.48 mmol, 3.01 equiv). The mixture was stirred for 1h, then a solution of $CH_3I$ (730 mg, 5.14 mmol, 1.00 equiv) in THF (10 mL) was added dropwise with stirring at −12° C. The resulting solution was stirred for 16 h at 25° C. The solids that formed were removed by filtration. The resulting solution was concentrated under vacuum, diluted with 50 mL of $H_2O$, and extracted with 3×30 mL of EtOAc. The organic layers were combined, washed with 1×50 mL of brine, dried over $Na_2SO_4$, and concentrated under reduced pressure to afford 500 mg (47%) of the product as a light yellow oil.

1-Methyl-(2,2,3,3,5,5,6,6-$d_8$)piperazine

The procedure used to prepare 1 was used with the compound produced in the previous step (500 mg, 2.40 mmol, 1.00 equiv) to afford 200 mg (37%) of PH-IMA-2013-003-336-3 as a light yellow solid.

N-[(2S)-5-[[(1R,2S)-2-(4-Fluorophenyl)cyclopropyl] (prop-2-en-1-yl)amino]-1-(4-methyl-(2,2,3,3,5,5,6,6-$d_8$)-piperazin-1-yl)-1-oxopentan-2-yl]-4-(1H-1,2,3-triazol-1-yl)-benzamide The method used to prepare 206 was used with the compound produced in the previous step and (2S)-5-[[(1R,2S)-2-(4-fluorophenyl)cyclopropyl](prop-2-en-1-yl)amino]-2-[[4-(1H-1,2,3-triazol-1-yl)phenyl]formamido] pentanoic acid (300 mg, 0.63 mmol, 1.00 equiv) to afford 150 mg (42%) of the product as a colorless oil.

N-[(2S)-5-[[(1R,2S)-2-(4-Fluorophenyl)cyclopropyl] amino]-1-(4-methyl-(2,2,3,3,5,5,6,6-$d_8$)-piperazin-1-yl)-1-oxopentan-2-yl]-4-(1H-1,2,3-triazol-1-yl)-benzamide (138)

The method used to prepare 210 was used with the compound produced in the previous step (150 mg, 0.26 mmol) to afford 65.7 mg (47%) of 138 as a white solid.

Example 142

Scheme 26

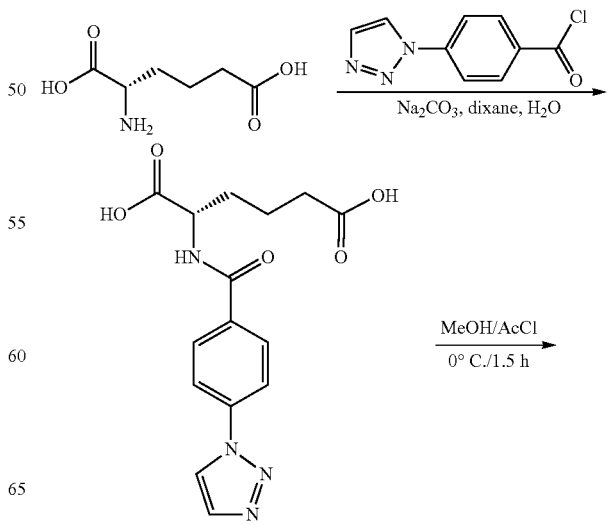

225
-continued

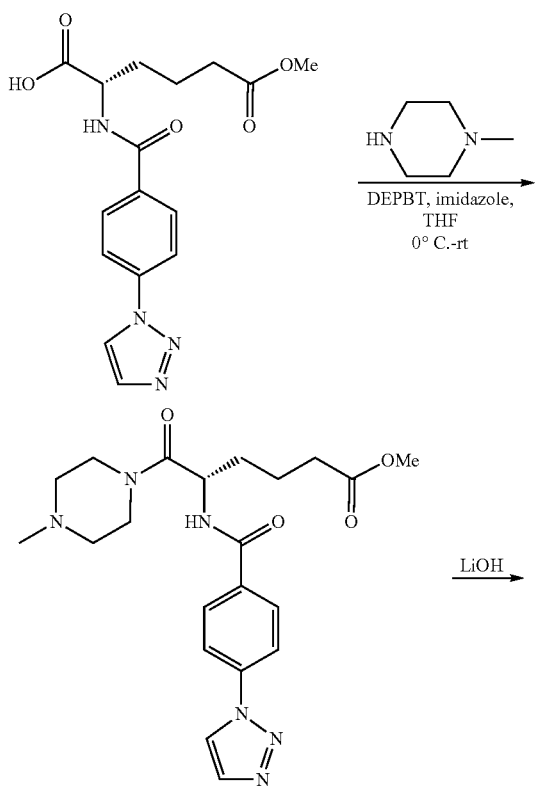

226
-continued

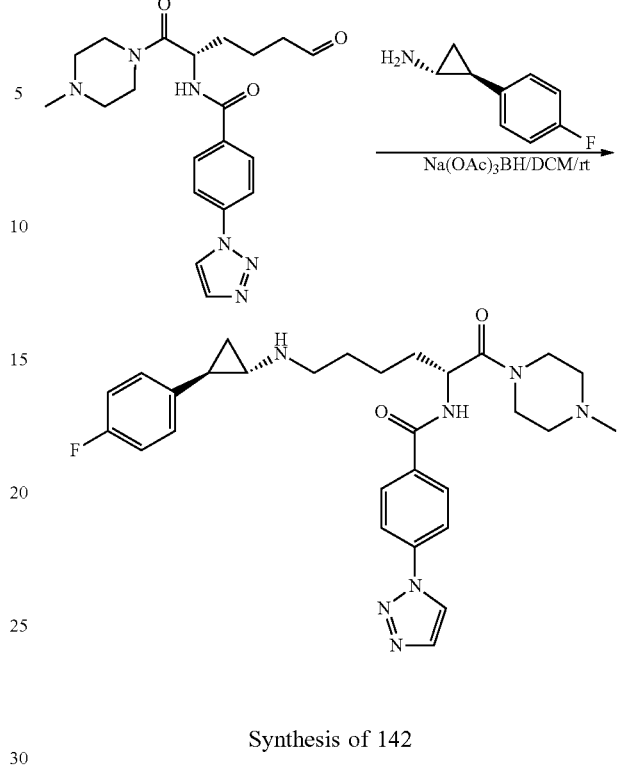

Synthesis of 142

(2S)-2-[(4-(1H-1,2,3-Triazol-1-yl)phenyl)formamido]-hexanedioic Acid

In a 500-mL round-bottom flask were combined a solution of (2S)-2-aminohexanedioic acid (3 g, 18.62 mmol, 1.00 equiv) in water (50 mL) and dioxane (50 mL), a solution of $Na_2CO_3$ (5.9 g, 55.67 mmol, 2.99 equiv) in $H_2O$ (50 mL). A solution of 4-(1H-1,2,3-triazol-1-yl)benzoyl chloride (4.26 g, 20.52 mmol, 1.10 equiv) in dioxane (50 mL) was then added dropwise. The resulting solution was stirred for 1 h at 25° C. The pH value of the solution was adjusted to 2 with HCl (2 M). The resulting solution was extracted with 3×150 mL of EtOAc, and the organic layers were combined, washed with 1×300 mL of brine, dried over $Na_2SO_4$, concentrated under vacuum, and applied onto a silica gel column with $CH_2Cl_2$/methanol to afford 4.5 g the product as a off-white solid.

(2S)-6-Methoxy-6-oxo-2-[(4-(1H-1,2,3-triazol-1-yl)phenyl)formamido]-hexanoic Acid In a 100-mL round-bottom flask was added a solution of (2S)-2-[(4-(1H-1,2,3-triazol-1-yl)phenyl)formamido]-hexanedioic acid (2500 mg, 7.52 mmol, 1.00 equiv) in methanol (40 mL), followed by the dropwise addition of AcCl (700 mg) with stirring at 0° C. The resulting solution was stirred for 100 min at 0° C. The pH value of the solution was adjusted to 9 with sat. $NaHCO_3$. The resulting solution was extracted with 2×20 mL of EtOAc and the aqueous layers were combined. HCl (2 M) was employed to adjust the pH to 2. The resulting solution was extracted with 3×50 mL of EtOAc, and the organic layers were combined, washed with 1×50 mL of brine, dried over $Na_2SO_4$, and concentrated under vacuum, affording 1.5 g (58%) of the product as a colorless oil.

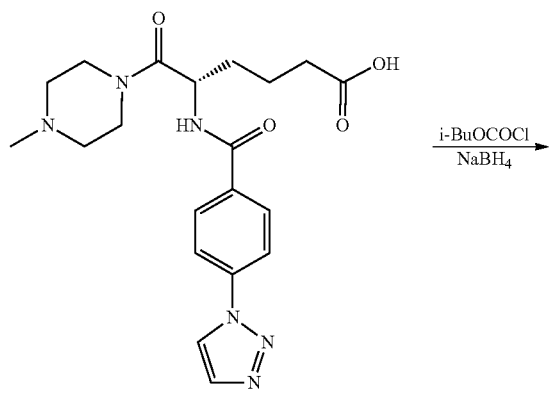

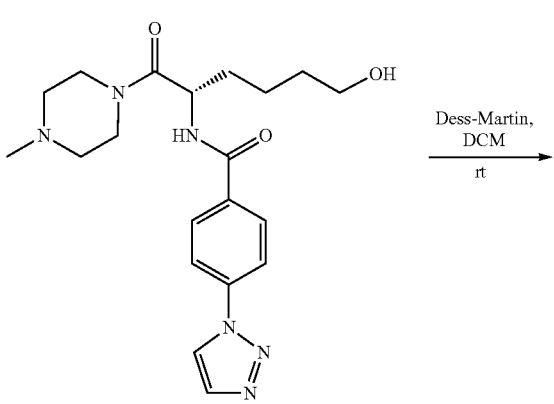

Methyl (5S)-6-(4-methylpiperazin-1-yl)-6-oxo-5-[4-(1H-1,2,3-triazol-1-yl)phenyl)formamido]hexanoate The method used to prepare 206 was used with the compound from the previous step (1.5 g, 4.33 mmol, 1.00 equiv) and 1-methylpiperazine (500 mg, 4.99 mmol, 1.73 equiv) to afford 1 g (54%) of the product as a colorless oil

(5S)-6-(4-Methylpiperazin-1-yl)-6-oxo-5-[4-(1H-1,2,3-triazol-1-yl)phenyl)formamido]hexanoic Acid The method used to prepare 205 was used with the compound from the previous step (1 g, 2.33 mmol) to afford 950 mg (98%) of the product as a colorless oil

(5S)-6-(4-Methylpiperazin-1-yl)-6-oxo-5-[4-(1H-1,2,3-triazol-1-yl)phenyl)formamido]hexanol(212)

In a 100-mL round-bottom flask were combined the product from the previous step (980 mg, 2.36 mmol, 1.00 equiv),), N-methylmorpholine (500 mg, 4.94 mmol, 2.09 equiv), and THF (50 mL), followed by the addition of i-BuOCOCl (500 mg, 3.65 mmol, 1.54 equiv) dropwise with stirring at −20° C. The mixture was stirred for 2h at −20° C. To this was added a solution of NaBH$_4$ (1 g, 26.43 mmol, 11.18 equiv) in methanol (20 mL) dropwise with stirring at −20° C. The resulting solution was stirred for 2 h at 25° C., concentrated under vacuum, and applied onto a silica gel column with CH$_2$Cl$_2$/methanol (5:1), to afford 300 mg (32%) of the product as a colorless oil.

(5S)-6-(4-Methylpiperazin-1-yl)-6-oxo-5-[4-(1H-1,2,3-triazol-1-yl)phenyl)formamido]hexanal The method used to prepare 208 was used with the compound from the previous step (300 mg, 0.75 mmol, 1.00 equiv) to afford 200 mg (67%) of the product as off-white solid.

N-[(2S)-6-[[(1R,2S)-2-(4-fluorophenyl)cyclopropyl]amino]-1-(4-methylpiperazin-1-yl)-1-oxohexan-2-yl]-4-(1H-1,2,3-triazol-1-yl)benzamide (142)

The method used to prepare 4 was used with the compound from the previous step (200 mg, 0.50 mmol, 1.00 equiv) and (1R,2S)-2-(4-fluorophenyl)cyclopropan-1-amine (76 mg, 0.50 mmol, 1.00 equiv) to afford 21.4 mg (7%) of 142 as a colorless oil.

Example 143

Scheme 27

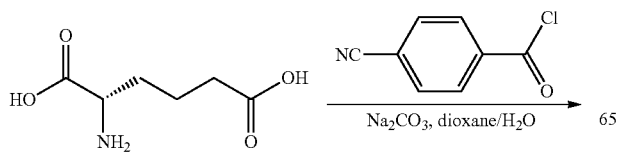

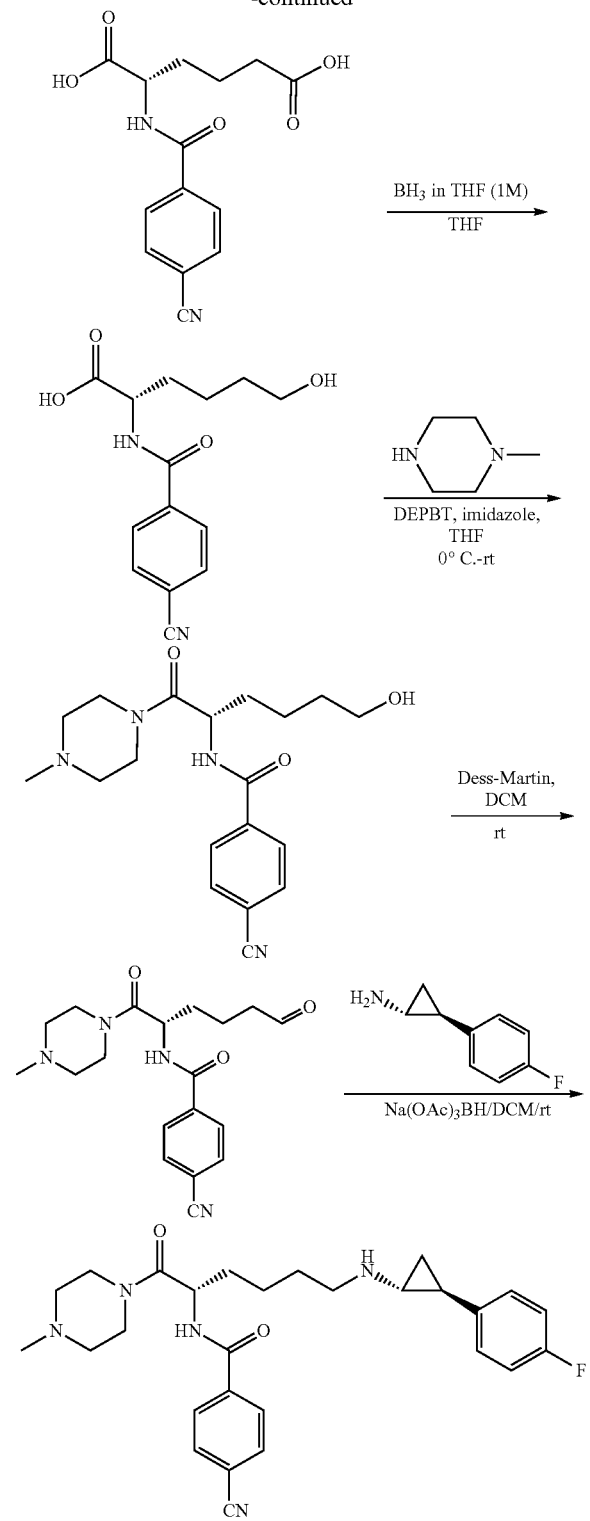

Synthesis of 143

(2S)-2-[(4-Cyanophenyl)formamido]-hexanedioic Acid

The method used to prepare 203 was used with (2S)-2-aminohexanedioic acid (5 g, 31.03 mmol, 1.00 equiv) and 4-cyanobenzoyl chloride (5.2 g, 31.41 mmol, 1.01 equiv) to afford 7 g (78%) of the product as a colorless oil.

(2S)-2-[(4-Cyanophenyl)formamido]-6-hydroxy-hexanoic Acid

In a 250-mL 3-necked round-bottom flask purged and maintained with an inert atmosphere of nitrogen were combined the product from the previous step (2 g, 6.89 mmol) and THF (100 mL), followed by the dropwise addition of BH₃ (17 mL, 1 M in THF) with stirring at 0° C. The resulting solution was stirred for 2 h at 0° C. The reaction was then quenched by the addition of 5 mL of methanol. The resulting mixture was concentrated under reduced pressure, diluted with 50 mL of sat Na₂CO₃, and washed with 3×30 mL of EtOAc. The aqueous layers were combined and and adjusted to pH 2 with HCl (2 M). The resulting solution was extracted with 3×50 mL of EtOAc, and the organic layers were combined, washed with 1×50 mL of brine, dried over Na₂SO₄, and concentrated under reduced pressure, affording 1 g (53%) of the product as a colorless oil.

(5S)-6-(4-Methylpiperazin-1-yl)-6-oxo-5-[(4-cyanophenyl)formamido]hexanol

The method used to prepare 206 was used with (2S)-2-[4-cyanophenyl)formamido]-6-hydroxyhexanoic acid (1 g, 3.62 mmol, 1.00 equiv) and 1-methylpiperazine (540 mg, 5.39 mmol, 1.49 equiv) to afford 1 g (77%) of the product as a colorless oil.

(5S)-6-(4-Methylpiperazin-1-yl)-6-oxo-5-[(4-cyanophenyl)formamido]hexanal

The method used to prepare 208 was used with (5S)-6-(4-methylpiperazin-1-yl)-6-oxo-5-[(4-cyanophenyl)formamido]hexanol (500 mg, 1.39 mmol) to afford 450 mg (91%) of the product as off-white solid N-[(2S)-6-[[(1R,2S)-2-(4-fluorophenyl)cyclopropyl]amino]-1-(4-methylpiperazin-1-yl)-1-oxohexan-2-yl]-4-cyanobenzamide (142)

The method used to prepare 4 was used with (5S)-6-(4-methylpiperazin-1-yl)-6-oxo-5-[(4-cyanophenyl)formamido]hexanal (450 mg, 1.26 mmol, 1.00 equiv) and (1R,2S)-2-(4-fluorophenyl)cyclopropan-1-amine (250 mg, 1.65 mmol, 1.31 equiv) to afford 174.1 mg (28%) of the product as a white solid.

Example 144

Scheme 28

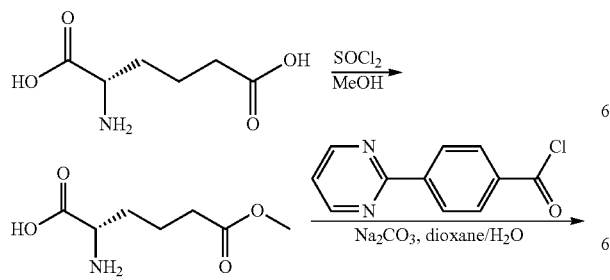

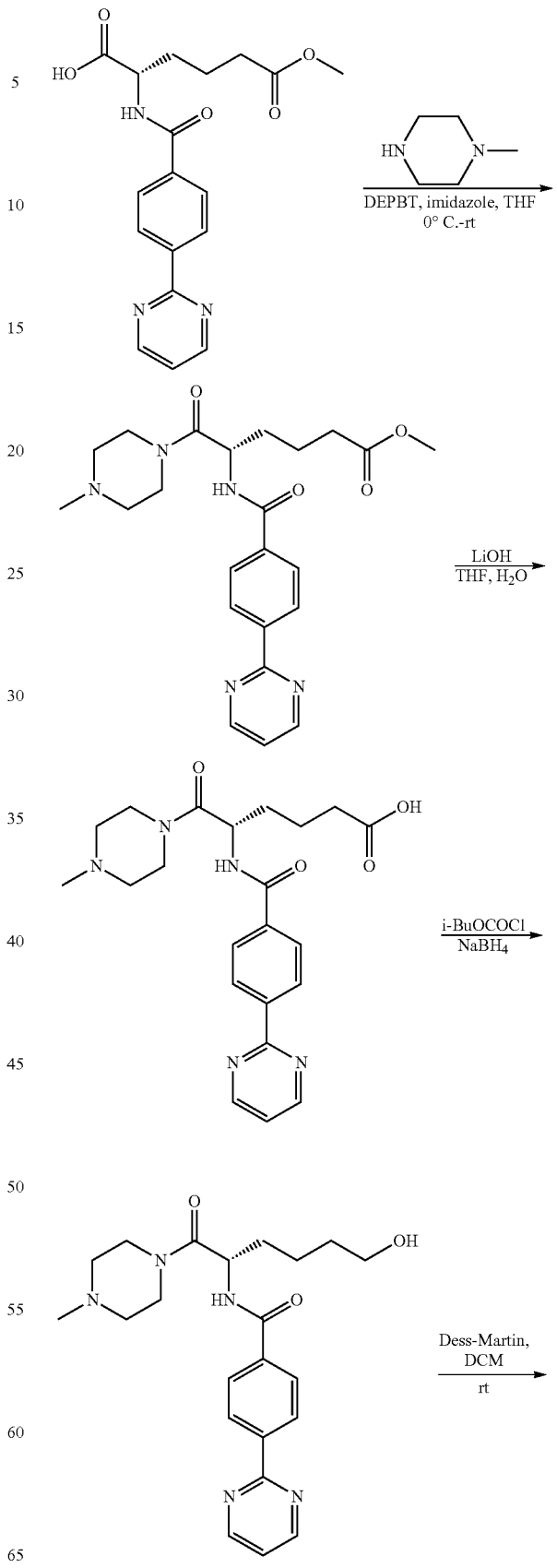

-continued

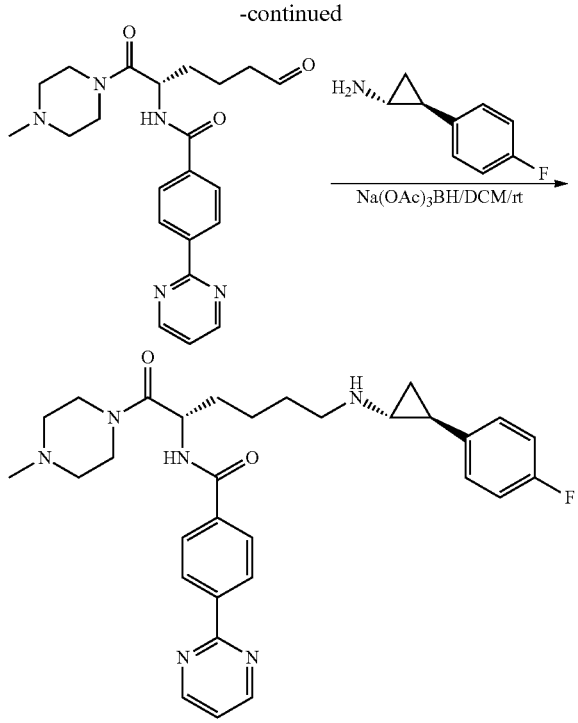

Synthesis of 144

(2S)-2-Amino-6-methoxy-6-oxo-hexanoic acid

In a 250-mL round-bottom flask were combined a solution of thionyl chloride (6.2 mL) in methanol (40 mL) and (2S)-2-aminohexanedioic acid (10 g, 62.05 mmol, 1.00 equiv). The resulting solution was stirred for 10 min at 0° C. in a water/ice bath. The reaction mixture was then poured into Et$_2$O (200 mL) and stirred for 10 min. The solid that formed was collected by filtration, affording 10 g (92%) of the product as a white solid (2S)-6-Methoxy-6-oxo-2-[(4-(pyrimidin-2-yl)phenyl)formamido]-hexanoic Acid The method used to prepare 203 was used with (2S)-2-amino-6-methoxy-6-oxo-hexanoic acid (3 g, 14.17 mmol, 1.00 equiv) and 4-(pyrimidin-2-yl)benzoyl chloride (3 g, 13.72 mmol, 0.97 equiv) to afford 3 g (59%) of the product as an off-white solid.

Methyl (5S)-6-(4-methylpiperazin-1-yl)-6-oxo-5-[4-(pyrimidin-2-yl)phenyl)formamido]hexanoate The method used to prepare 206 was used with (2S)-6-methoxy-6-oxo-2-[(4-(pyrimidin-2-yl)phenyl)formamido]-hexanoic acid (3 g, 8.39 mmol, 1.00 equiv) and 1-methyl-piperazine (1.3 g, 12.98 mmol, 1.55 equiv) to afford 1 g (27%) of the product as a colorless oil.

(5S)-6-(4-Methylpiperazin-1-yl)-6-oxo-5-[4-(pyrimidin-2-yl)phenyl)formamido]hexanoic Acid The method used to prepare 205 was used with methyl (5S)-6-(4-methylpiperazin-1-yl)-6-oxo-5-[4-(pyrimidin-2-yl)phenyl)formamido]hexanoate (1 g, 2.28 mmol, 1.00 equiv) to afford 600 mg (62%) of the product as a colorless oil.

(5S)-6-(4-Methylpiperazin-1-yl)-6-oxo-5-[4-(pyrimidin-2-yl)phenyl)formamido]hexanol The method used to prepare 212 was used with (5S)-6-(4-Methylpiperazin-1-yl)-6-oxo-5-[4-(pyrimidin-2-yl)phenyl)formamido]hexanoic acid (600 mg, 1.41 mmol, 1.00 equiv) to afford 300 mg (52%) of the product as a colorless oil.

(5S)-6-(4-Methylpiperazin-1-yl)-6-oxo-5-[4-(pyrimidin-2-yl)phenyl)formamido]hexanal The method used to prepare 208 was used with (5S)-6-(4-methylpiperazin-1-yl)-6-oxo-5-[4-(pyrimidin-2-yl)phenyl)formamido]hexanol (300 mg, 0.73 mmol) to afford 150 mg (50%) of the product as off-white solid.

N-[(2S)-6-[[(1R,2S)-2-(4-fluorophenyl)cyclopropyl]amino]-1-(4-methylpiperazin-1-yl)-1-oxohexan-2-yl]-4-(pyrimidin-2-yl)benzamide (144)

The method used to prepare 4 was used with (5S)-6-(4-methylpiperazin-1-yl)-6-oxo-5-[4-(pyrimidin-2-yl)phenyl)formamido]hexanal (150 mg, 0.37 mmol, 1.00 equiv) and (1S,2R)-2-(4-fluorophenyl)cyclopropan-1-amine (80 mg, 0.53 mmol, 1.44 equiv) to afford 9.2 mg (5%) of 144 as a light yellow semi-solid.

Example 145

Scheme 29

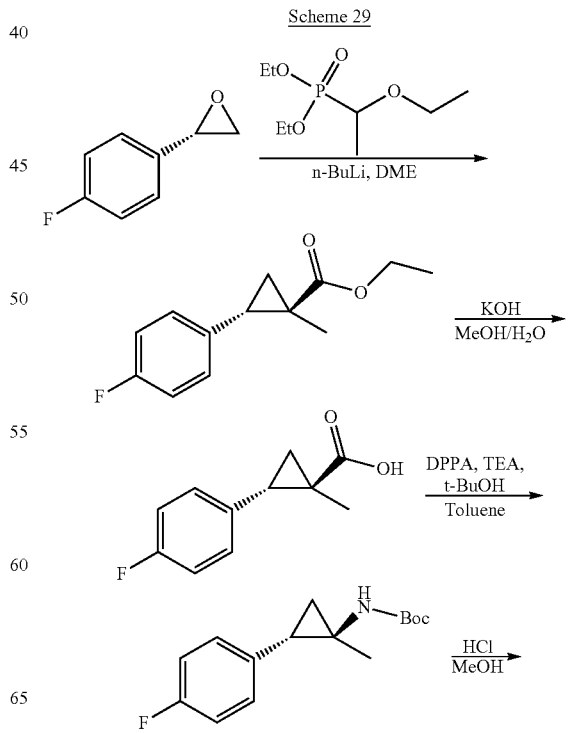

233
-continued

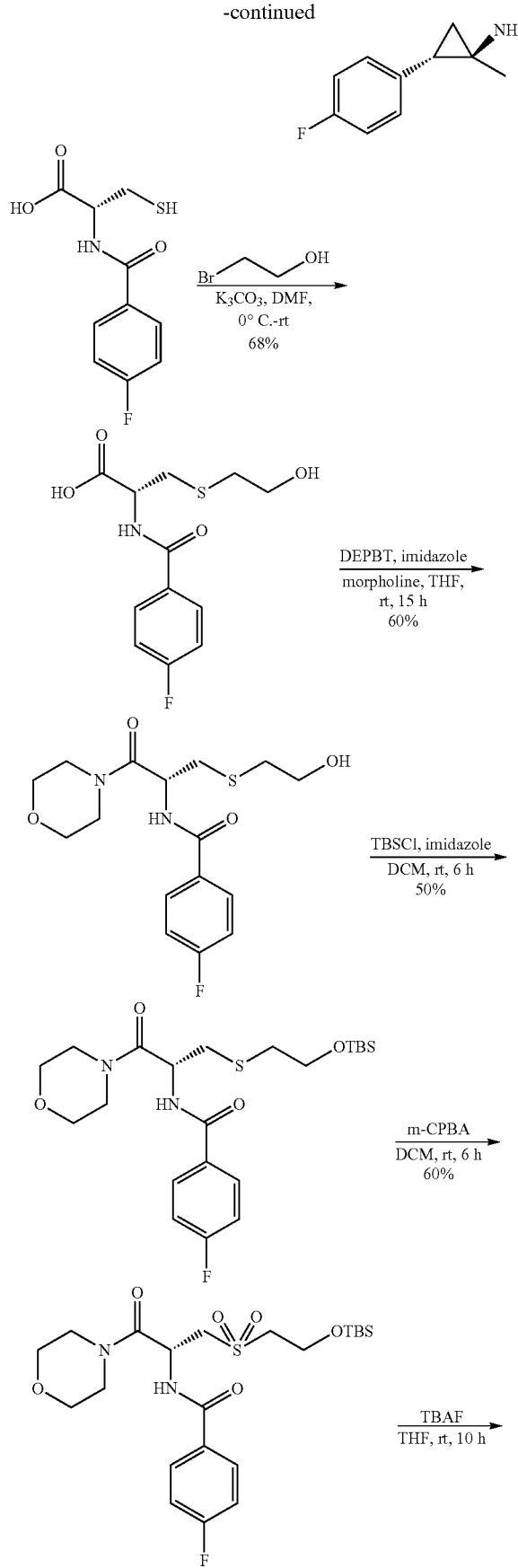

234
-continued

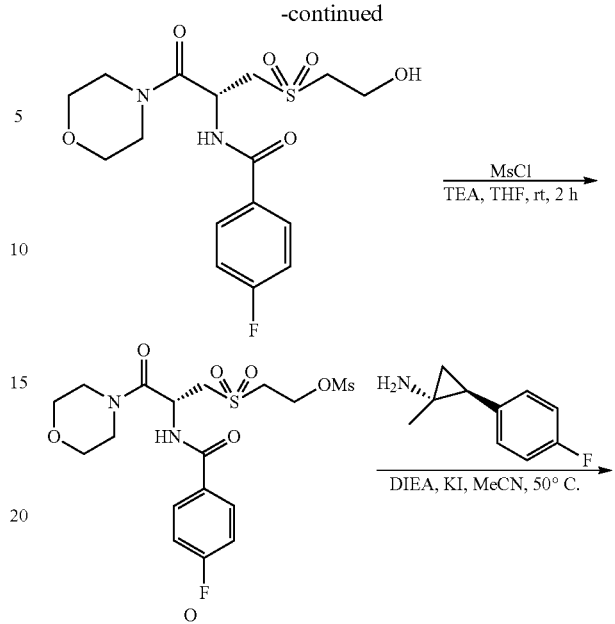

Synthesis of 145

(2R)-2-[(4-Fluorophenyl)formamido]-3-[(2-hydroxyethyl)sulfanyl]propanoic Acid

In a 250-mL round-bottom flask was placed a solution of (2R)-2-[(4-fluorophenyl)formamido]-3-mercaptopropanoic acid (5 g, 20.55 mmol) in N,N-dimethylformamide (50 mL) and $K_2CO_3$ (5.7 g, 40.94 mmol), followed by the addition of a solution of 2-bromoethanol (2.8 g, 22.41 mmol) in N,N-dimethylformamide (20 mL) dropwise with stirring at 0° C. The resulting solution was stirred for 5 h at room temperature, then diluted with 200 mL of $H_2O$. The pH of the solution was adjusted to 3 with HCl (2 M). The resulting solution was extracted with 2×200 mL of EtOAc, and the organic layers were combined, dried over $Na_2SO_4$ and concentrated under vacuum. The residue was applied onto a silica gel column with $CH_2Cl_2$/methanol (20:1), affording 4 g (68%) of the product as a yellow oil.

4-Fluoro-N-[(2R)-3-[(2-hydroxyethyl)sulfanyl]-1-(morpholin-4-yl)-1-oxopropan-2-yl]benzamide In a 250-mL round-bottom flask were combined a solution of (2R)-2-[(4-fluorophenyl)formamido]-3-[(2-hydroxyethyl)sulfanyl]propanoic acid (4 g, 13.92 mmol, 1.00 equiv) in THF (50 mL), DEPBT (6.25 g, 20.90 mmol, 1.50 equiv) and imidazole (1.42 g, 20.88 mmol, 1.50 equiv). The mixture was stirred for 30 min at 0° C., then morpholine (1.2 g, 13.77 mmol, 0.99 equiv) was added. The resulting solution was stirred for 12 h at room temperature, diluted with 200 mL of EtOAc, and washed with 1×100 mL of brine. The organic layers were dried over Na$_2$SO$_4$ and concentrated under vacuum. The residue was applied onto a silica gel column with EtOAc/petroleum ether (1:10), affording 3 g (60%) of the product as a yellow oil.

N-[(2R)-3-([2-[(tert-Butyldimethylsilyl)oxy]ethyl]sulfanyl)-1-(morpholin-4-yl)-1-oxopropan-2-yl]-4-fluorobenzamide In a 250-mL round-bottom flask were combined a solution of 4-fluoro-N-[(2R)-3-[(2-hydroxyethyl)sulfanyl]-1-(morpholin-4-yl)-1-oxopropan-2-yl]benzamide (3 g, 8.42 mmol, 1.00 equiv) in CH$_2$Cl$_2$ (30 mL) and imidazole (1.14 g, 16.76 mmol, 1.99 equiv). followed by the addition of TBSCl (1.9 g, 12.58 mmol, 1.49 equiv), dropwise at 0° C. The resulting solution was stirred for 6 h at room temperature. The reaction was then quenched by the addition of 50 mL of water. The resulting solution was extracted with 2×100 mL of CH$_2$Cl$_2$ and the organic layers were combined and dried over anhydrous Na$_2$SO$_4$ and concentrated under vacuum. The residue was applied onto a silica gel column with ethyl acetate/petroleum ether (1:30). This resulted in 2 g (50%) of the product as a white solid.

N-[(2R)-3-([2-[(tert-Butyldimethylsilyl)oxy]ethyl]sulfonyl)-1-(morpholin-4-yl)-1-oxopropan-2-yl]-4-fluorobenzamide In a 250-mL round-bottom flask were combined a solution of N-[(2R)-3-([2-[(tert-butyldimethylsilyl)oxy]ethyl]sulfanyl)-1-(morpholin-4-yl)-1-oxopropan-2-yl]-4-fluorobenzamide (2 g, 4.25 mmol, 1.00 equiv) in CH$_2$Cl$_2$ (20 mL) and m-CPBA (1.84 g, 10.66 mmol, 2.51 equiv). The resulting solution was stirred for 6 h at room temperature, then diluted with 50 mL of CH$_2$Cl$_2$. The resulting mixture was washed with 1×50 mL of saturated Na$_2$CO$_3$, then with 1×50 mL of brine. The organic layers were dried over anhydrous Na$_2$SO$_4$ and concentrated under vacuum. The residue was applied onto a silica gel column with EtOAc/petroleum ether (1:30), affording 1.3 g (61%) of the product as a white solid.

4-Fluoro-N-[(2R)-3-[(2-hydroxyethane)sulfonyl]-1-(morpholin-4-yl)-1-oxopropan-2-yl]benzamide In a 50-mL round-bottom flask were combined a solution of N-[(2R)-3-([2-[(tert-butyldimethylsilyl)oxy]ethyl]sulfonyl)-1-(morpholin-4-yl)-1-oxopropan-2-yl]-4-fluorobenzamide (500 mg, 0.99 mmol, 1.00 equiv) in THF (10 mL) and Bu$_4$NF (2M) (1.5 mL). The resulting solution was stirred for 10 h at room temperature, then diluted with 50 mL of EtOAc. The resulting mixture was washed with 2×10 mL of brine, dried over anhydrous Na$_2$SO$_4$, and concentrated under vacuum. The residue was applied onto a silica gel column with EtOAc/petroleum ether (1:20), affording 300 mg (78%) of the product as a yellow oil.

2-[[(2R)-2-[(4-Fluorophenyl)formamido]-3-(morpholin-4-yl)-3-oxopropyl]sulfonyl]ethyl Methanesulfonate In a 50-mL round-bottom flask were combined a solution of 4-fluoro-N-[(2R)-3-[(2-hydroxyethyl)sulfonyl]-1-(morpholin-4-yl)-1-oxopropan-2-yl]benzamide (300 mg, 0.77 mmol, 1.00 equiv) in THF (5 mL) and Et$_3$N (156 mg, 1.54 mmol, 2.00 equiv). This was followed by the addition of methanesulfonyl chloride (134 mg, 1.17 mmol, 1.51 equiv) dropwise with stirring at 0° C. The resulting solution was stirred for 2 h at room temperature. The reaction was then quenched by the addition of 10 mL of water. The resulting solution was extracted with 3×10 mL of ethyl acetate. The combined organic layers were dried over Na$_2$SO$_4$ and concentrated under vacuum. The residue was applied onto a silica gel column with EtOAc/petroleum ether (1:50), affording 200 mg (56%) of the product as a white solid.

Ethyl (1R)-2-(4-fluorophenyl)-1-methylcyclopropane-1-carboxylate

In a 100-mL 3-necked round-bottom flask purged and maintained with an inert atmosphere of nitrogen were combined a solution of ethyl 2-(diethoxyphosphoryl)propanoate (3.45 g, 14.48 mmol, 2.00 equiv) in ethylene glycol dimethyl ether (20 mL), followed by the addition of n-BuLi (2.5M) (5.8 mL) dropwise with stirring at 0° C. The resulting solution was stirred for 30 min at room temperature. To this was added 2-(4-fluorophenyl)oxirane (1 g, 7.24 mmol, 1.00 equiv). The resulting solution was allowed to react, with stirring, for an additional 12 h while the temperature was maintained at 80° C. in an oil bath. The reaction mixture was cooled to room temperature and then quenched by the addition of 20 mL of water. The resulting solution was extracted with 3×50 mL of EtOAc, and the organic layers were combined, dried over anhydrous Na$_2$SO$_4$, concentrated under vacuum. The residue was applied onto a silica gel column with EtOAc/petroleum ether (1:100), affording 1 g (62%) of the product as a yellow oil.

(1R)-2-(4-Fluorophenyl)-1-methylcyclopropane-1-carboxylic Acid

In a 50-mL round-bottom flask were combined a solution of ethyl (1R)-2-(4-fluorophenyl)-1-methylcyclopropane-1-carboxylate (1 g, 4.50 mmol, 1.00 equiv) in methanol/H$_2$O (10/2 mL) and KOH (1.26 g, 22.46 mmol, 4.99 equiv). The resulting solution was stirred for 10 h at room temperature, and then diluted with 20 mL of H$_2$O. The pH value of the solution was adjusted to 2 with HCl (2 M). The resulting solution was extracted with 3×20 mL of EtOAc, and the organic layers were combined, dried over anhydrous Na$_2$SO$_4$, and concentrated under vacuum, affording 800 mg (92%) of the product as a yellow oil.

tert-Butyl N-[(1R)-2-(4-fluorophenyl)-1-methylcyclopropyl]carbamate

In a 50-mL 3-necked round-bottom flask purged and maintained with an inert atmosphere of nitrogen were combined a solution of (1R)-2-(4-fluorophenyl)-1-methylcyclopropane-1-carboxylic acid (400 mg, 2.06 mmol, 1.00 equiv) in toluene (10 mL), diphenylphosphoryl azide (680 mg, 2.47 mmol, 1.20 equiv), and Et$_3$N (312 mg, 3.08 mmol, 1.50 equiv). The resulting solution was stirred for 30 min at 90° C. in an oil bath. tert-Butanol (2 mL) was then added. The resulting solution was allowed to react, with stirring, for an additional 12 h while the temperature was maintained at 90° C. in an oil bath. The reaction mixture was cooled to room temperature, then diluted with 50 mL of EtOAc. The resulting mixture was washed with 30 mL of H$_2$O, dried over anhydrous Na$_2$SO$_4$, then concentrated under vacuum. The residue was applied onto a silica gel column with EtOAc/petroleum ether (1:100), affording 350 mg (64%) of the product as a yellow oil.

(1R,2S)-2-(4-Fluorophenyl)-1-methylcyclopropan-1-amine

Into a 50-mL round-bottom flask was added a solution of tert-butyl N-[(1R,2S)-2-(4-fluorophenyl)-1-methylcyclopropyl]carbamate (350 mg, 1.32 mmol, 1.00 equiv) in methanol(HCl) (10 mL). The resulting solution was stirred for 2 h at room temperature, then diluted with 10 mL of H$_2$O. The pH value of the solution was adjusted to 9 with saturated Na$_2$CO$_3$. The resulting solution was extracted with 3×10 mL of EtOAc, and the organic layers were combined and dried over anhydrous Na$_2$SO$_4$ and concentrated under vacuum, affording 200 mg (92%) of the product as a yellow oil.

4-Fluoro-N-[(2R)-3-[(2-[[(1R,2S)-2-(4-fluorophenyl)-1-methylcyclopropyl]amino]ethane)sulfonyl]-1-(morpholin-4-yl)-1-oxopropan-2-yl]benzamide (145)

In a 25-mL round-bottom flask purged and maintained with an inert atmosphere of nitrogen were combined a solution of 2-[[(2R)-2-[(4-fluorophenyl)formamido]-3-(morpholin-4-yl)-3-oxopropane]sulfonyl]ethyl methanesulfonate (200 mg, 0.43 mmol, 1.00 equiv) in MeCN (10 mL), i-Pr$_2$NEt, (110 mg, 0.85 mmol, 1.99 equiv), KI (71 mg, 0.43 mmol, 1.00 equiv), and (1R,2S)-2-(4-fluorophenyl)-1-methylcyclopropan-1-amine (71 mg, 0.43 mmol, 1.00 equiv). The resulting solution was stirred for 12 h at 50° C. in an oil bath, and then diluted with 30 mL of EtOAc. The resulting mixture was washed with 1×20 mL of H$_2$O, dried over Na$_2$SO$_4$, then concentrated under vacuum. The crude product was purified by HPLC, affording 64.3 mg (28%) of the product as a white solid.

Example 146

Scheme 30

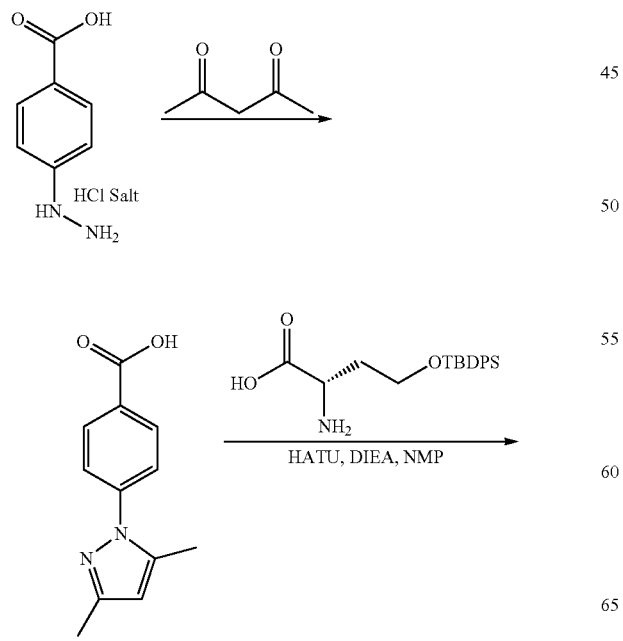

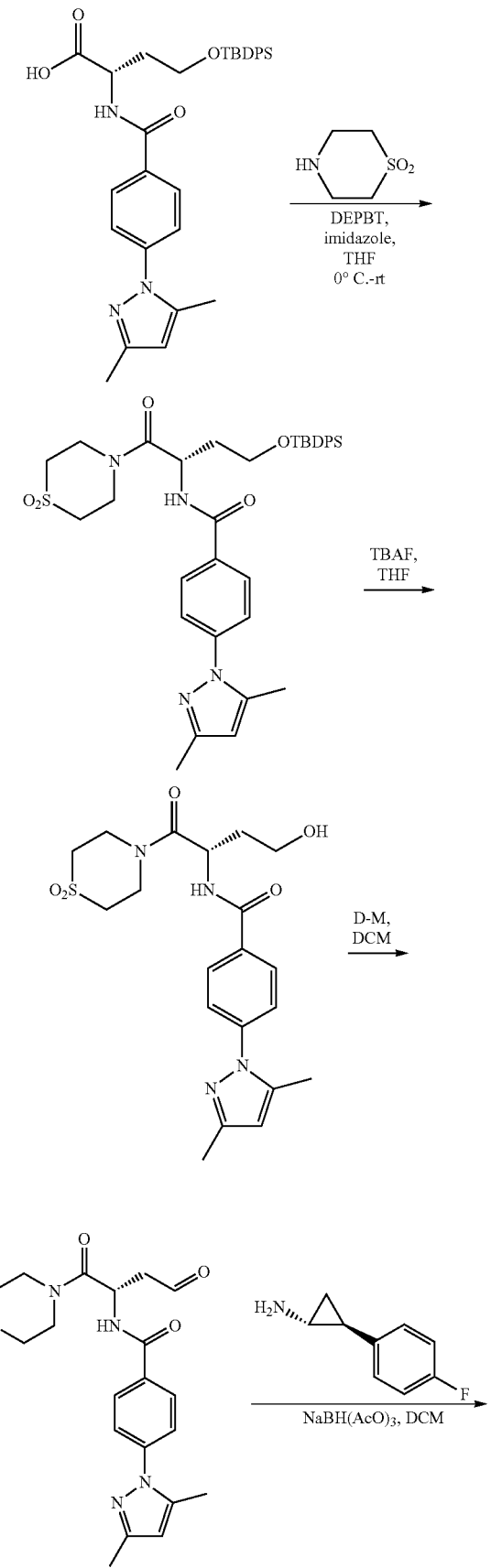

239
-continued

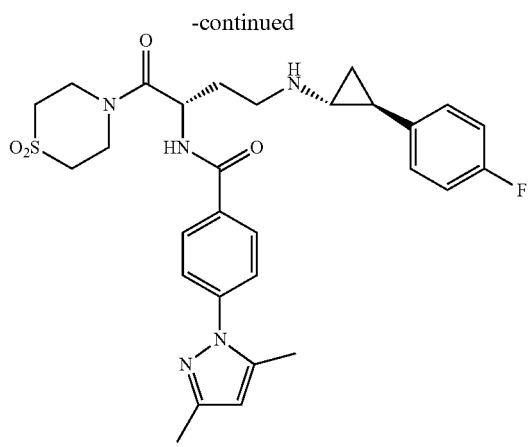

Synthesis of 146

4-(3,5-dimethylpyrazol-1-yl)benzoic Acid

In a 250-mL round-bottom flask were combined 4-hydrazinylbenzoic acid (8.8 g, 57.84 mmol, 1.00 equiv), AcOH (100 mL), and pentane-2,4-dione (5.8 g, 57.93 mmol, 1.00 equiv). The resulting solution was stirred for 16 h at 118° C. in an oil bath, and concentrated under vacuum. The resulting solid was washed with 3×100 mL of EtOAc and dried under vacuum, affording 9.2 g (74%) of the product as a light-brown solid.

(2S)-2-[(4-(3,5-dimethylpyrazol-1-yl)phenyl)formamido]-4-[(tert-butyldiphenylsilyl)oxy]butanoic Acid The method used to prepare 211 was used with the compound from the previous step (5 g, 23.12 mmol, 1.50 equiv) and (2S)-2-amino-4-[(tert-butyldiphenylsilyl)oxy] butanoic acid (5.52 g, 15.44 mmol, 1.00 equiv) to afford 1 g (12%) of the product as a yellow solid.

(2S)—N-[1-(thiomorpholine-1,1-dioxide-4-yl)-1-oxo-4-((tert-butyldiphenylsilyl)oxy)-butan-2-yl]-4-(4-(3,5-dimethylpyrazol-1-yl)benzamide The method used to prepare 206 was used with the compound produced in the previous step (5 g, 9.00 mmol, 1.00 equiv) and thiomorpholine-1,1-dioxide (1.46 g, 10.8 mmol, 1.20 equiv) to afford 1 g (17%) of the product as a yellow oil.

(3S)-4-(thiomorpholine-1,1-dioxide-4-yl)-4-oxo-3-[[4-(3,5-dimethylpyrazol-1-yl)phenyl]formamido]-butanol The method used to prepare 207 was used with the compound from the previous step (1 g, 1.49 mmol, 1.00 equiv) to afford 300 mg (46%) of the product as a yellow oil.

(3S)-4-(thiomorpholine-1,1-dioxide-4-yl)-4-oxo-3-[[4-(3,5-dimethylpyrazol-1-yl)phenyl]formamido]-butanal The method used to prepare 208 was used with the compound from the previous step (50 mg, 0.11 mmol, 1.00 equiv) to afford 45 mg (91%) of the product as a light yellow solid.

240

N-[(2S)-4-[[(1R,2S)-2-(4-fluorophenyl)cyclopropyl]amino]-1-(thiomorpholine-1,1-dioxide-4-yl)-1-oxobutan-2-yl]-4-(3,5-dimethylpyrazol-1-yl)benzamide (146)

The method used to prepare 4 was used with the compound from the previous step (45 mg, 0.10 mmol, 1.00 equiv) and (1R,2S)-2-(4-fluorophenyl)cyclopropan-1-amine (19 mg, 0.125 mmol, 1.20 equiv) to afford 11.7 mg (20%) of 146 as a white solid.

Example 148

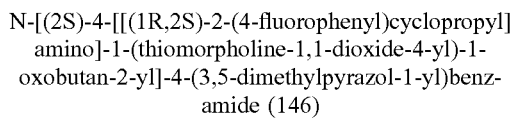

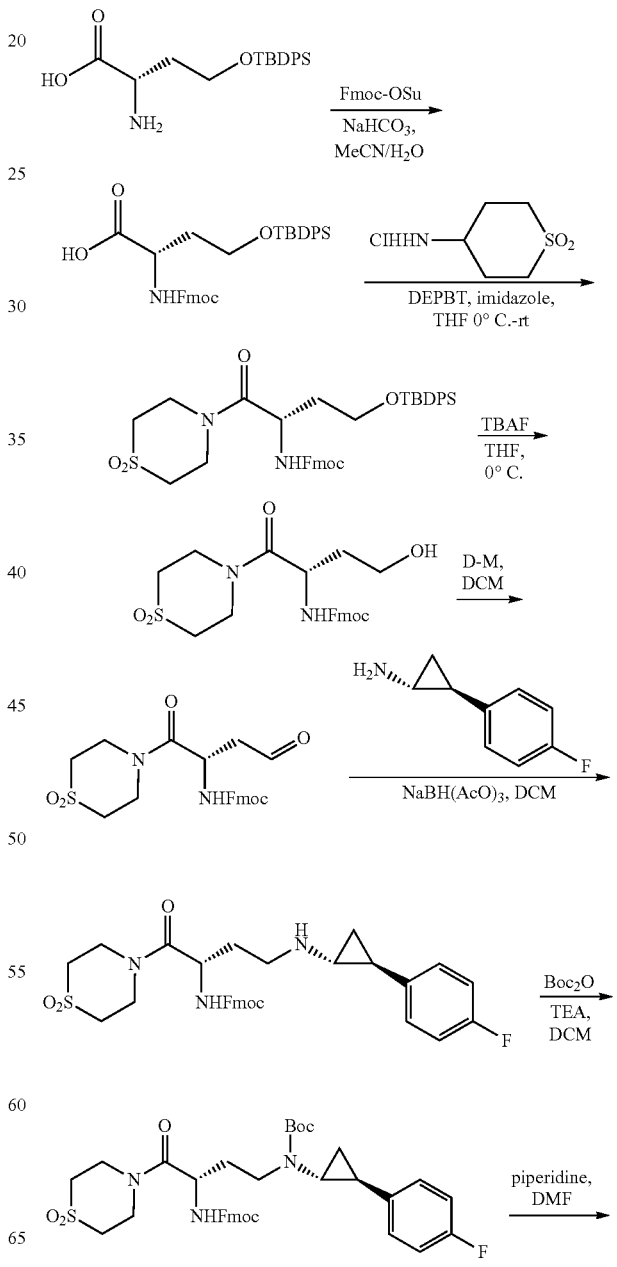

241
-continued

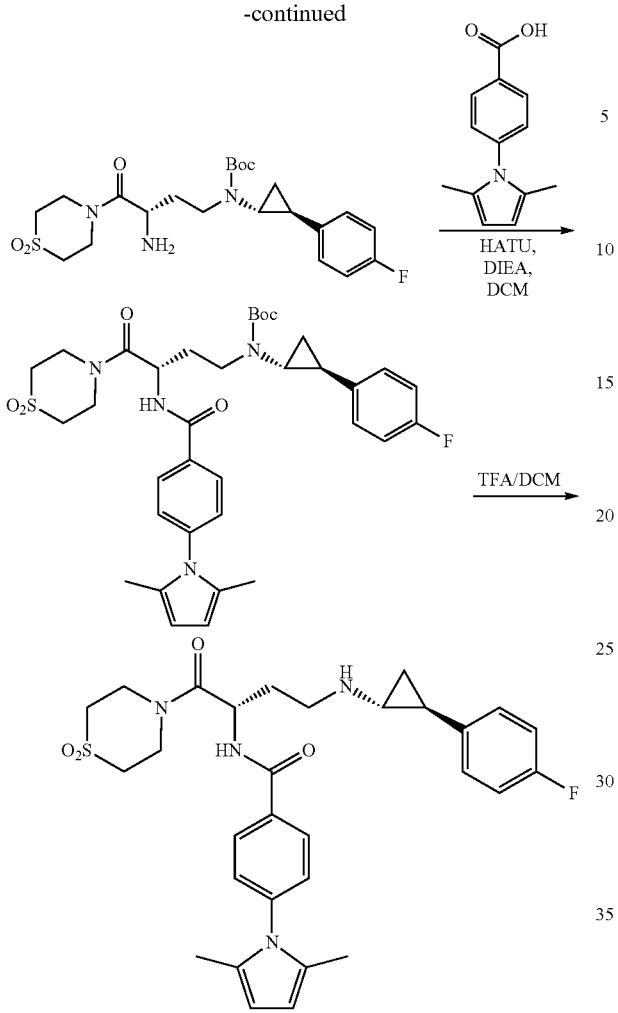

Synthesis of 148

(2S)-4-[(tert-Butyldiphenylsilyl)oxy]-2-[[(9H-fluoren-9-ylmethoxy)carbonyl]amino]butanoic Acid In a 1000-mL round-bottom flask purged and maintained with an inert atmosphere of nitrogen, was combined a solution of (2S)-2-amino-4-[(tert-butyldiphenylsilyl)oxy] butanoic acid (10 g, 27.97 mmol, 1.00 equiv) in MeCN (300 mL), 5% aqueous NaHCO$_3$ (300 mL), and Fmoc-OSu (10.4 g, 30.86 mmol, 1.10 equiv). The resulting solution was stirred for 12 h at room temperature. The pH value of the solution was adjusted to 3 with HCl (2 M). The resulting solution was extracted with 3×200 mL of EtOAc. The organic layers were combined, dried over Na$_2$SO$_4$, concentrated under reduced pressure, and applied onto a silica gel column with EtOAc/petroleum ether (1:1), to afford 11 g (68%) of the product as a yellow solid.

9H-Fluoren-9-ylmethyl N-[(2S)-4-[(tert-butyldiphenylsilyl)oxy]-1-(thiomorpholine-1,1-dioxide-4-yl)-1-oxobutan-2-yl]carbamate The procedure of 206 was used with the compound from the previous step and thiomorpholine-1,1-dioxide (3.9 g, 22.59 mmol, 1.19 equiv) to afford 9 g (68%) of the product as a yellow solid.

242

(3S)-4-(thiomorpholine-1,1-dioxide-4-yl)-4-oxo-3-[((9H-fluoren-9-ylmethyl)oxycarbonyl)amino]-1-butanol The method used to prepare 207 was used with the compound from the previous step (5 g, 7.17 mmol, 1.00 equiv) to afford 1.7 g of the product as an off-white solid.

(3S)-4-(thiomorpholine-1,1-dioxide-4-yl)-4-oxo-3-[((9H-fluoren-9-ylmethyl)oxycarbonyl)amino]-1-butanal The method used to prepare 208 was used with the compound from the previous step (1.7 g, 3.71 mmol) to afford 1.2 g (71%) of the product as a yellow solid.

9H-fluoren-9-ylmethyl N-[(2R)-1-(thiomorpholine-1,1-dioxide-4-yl)-4-[[(1R,2S)-2-(4-fluorophenyl) cyclopropyl]amino]-1-oxobutan-2-yl]carbamate The method used to prepare 4 was used with the compound from the previous step (1.2 g, 2.63 mmol, 1.00 equiv) and (1R,2S)-2-(4-fluorophenyl)cyclopropan-1-amine (476 mg, 3.15 mmol, 1.20 afford 1.4 g (90%) of the product as a yellow solid.

tert-Butyl N-[(3R)-4-(thiomorpholine-1,1-dioxide-4-yl)-3-[[(9H-fluoren-9-ylmethoxy)carbonyl]amino]-4-oxobutyl]-N-[(1R,2S)-2-(4-fluorophenyl)cyclopropyl]carbamate The method used to prepare 204 was used with the product from the previous reaction (1.4 g, 2.37 mmol, 1.00 equiv) to afford 1.5 g (92%) of the product as a yellow solid.

tert-Butyl N-[(3S)-3-amino-4-(thiomorpholine-1,1-dioxide-4-yl)-4-oxobutyl]-N-[(1R,2S)-2-(4-fluorophenyl)cyclopropyl]carbamate In a 100-mL round-bottom flask was combined the compound from the previous step (1.5 g, 2.17 mmol, 1.00 equiv), piperidine (5 mL), and DMF (20 mL). The resulting solution was stirred for 12 h at room temperature, then diluted with 100 mL of H$_2$O. The solids that formed were removed by filtration. The resulting solution was extracted with 3×20 mL of EtOAc, and the organic layers were combined, dried over Na$_2$SO$_4$, and concentrated under reduced pressure, affording 800 mg (79%) of the product as a yellow oil.

tert-Butyl N-[(3S)-3-[[4-(2,5-dimethyl-1H-pyrrol-1-yl)phenyl]formamido]-4-(thiomorpholine-1,1-dioxide-4-yl)-4-oxobutyl]-N-[(1R,2S)-2-(4-fluorophenyl) cyclopropyl]carbamate The method used to prepare 211 was used with the product from the previous step (397 mg, 0.85 mmol, 1.00 equiv) and 4-(2,5-dimethyl-1H-pyrrol-1-yl)benzoic acid (200 mg, 0.93 mmol, 1.10 equiv) to afford 200 mg (35%) of the product as a yellow oil.

4-(2,5-Dimethyl-1H-pyrrol-1-yl)-N-[(2S)-1-(thiomorpholine-1,1-dioxide-4-yl)-4-[[(1R,2S)-2-(4-fluorophenyl)cyclopropyl]amino]-1-oxobutan-2-yl]benzamide, Trifluoroacetic Acid Salt The method used to prepare 1 was used with the product from the previous step (120 mg, 0.18 mmol, 1.00 equiv) to afford 12 mg (10%) of the product as a light yellow solid.

Example 150

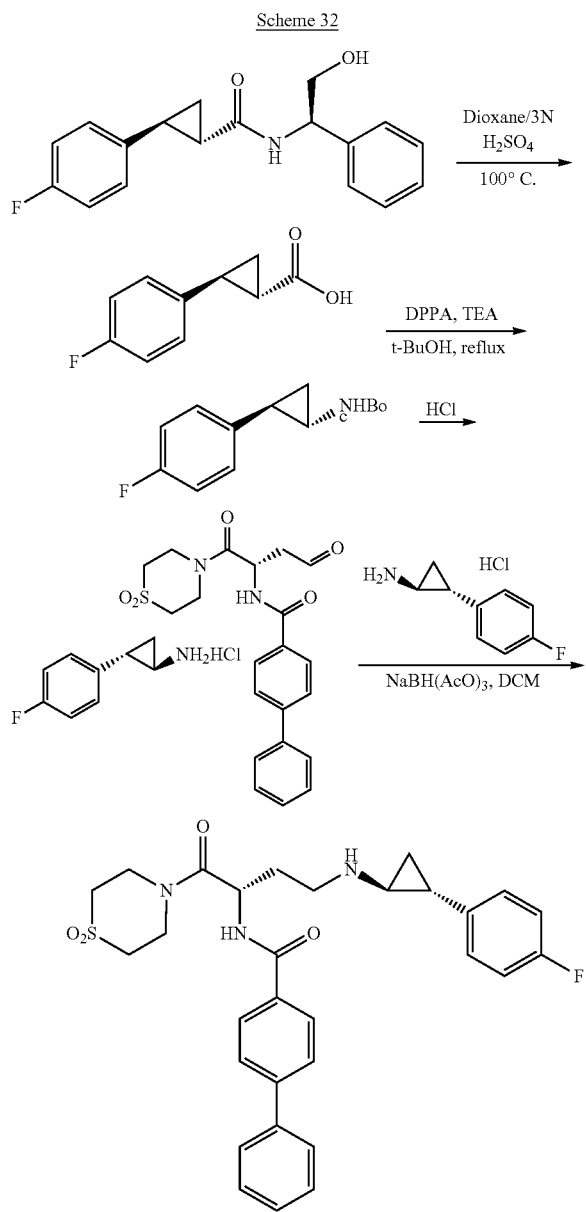

(1R,2S)-2-(4-fluorophenyl)cyclopropanecarboxylic Acid

Into a 250-mL round-bottom flask, was placed a solution of (1R)—N-(2-hydroxy-1-phenylethyl)-2-(4-fluorophenyl)-1-methylcyclopropane-1-carboxamide (5 g, 16.70 mmol, 1.00 equiv) in dioxane (100 ml) and $H_2SO_4$ (30 mL). The resulting solution was stirred for 16 h at 100° C. in an oil bath. The resulting solution was then diluted with 300 mL of $CH_2Cl_2$ The combined organic layers were washed with 2×200 mL of $H_2O$ and 1×500 mL of brine, dried over $Na_2SO_4$, and concentrated under reduced pressure to afford 2 g (66%) of the product as a colorless oil.

N-(tert-butoxycarbonyl)-(1R,2S)-2-(4-fluorophenyl)cyclopropyl]amine

In a 250-mL round-bottom flask purged and maintained with an inert atmosphere of nitrogen was combined a solution of the compound from the above step (2 g, 11.10 mmol, 1.00 equiv) in toluene (100 mL). Then DPPA (4.6 g, 16.72 mmol, 1.51 equiv) and $Et_3N$ (1.7 g, 16.80 mmol, 1.51 equiv) were added at room temperature. The reaction mixture was stirred at 110° C. in an oil bath. After 30 min, the reaction mixture was cooled to 90° C. Then t-BuOH (20 mL) was added to the solution. The resulting solution was stirred for 5 h at 90° C., then extracted with 3×100 mL of EtOAc. The combined organic layers were washed with brine, dried over $Na_2SO_4$, concentrated under reduced pressure, and applied onto a silica gel column with EtOAc/petroleum ether (1:10) to afford 2 g (72%) of the product as a white solid.

(1R,2S)-2-(4-Fluorophenyl)cyclopropyl]amine

In a 100-mL round-bottom flask were combined a solution of the compound from the previous step (2 g, 7.93 mmol) and HCl/MeOH (50 mL). The resulting solution was stirred for 1 h at room temperature. The reaction mixture was then concentrated under reduced pressure, affording 1.4 g (92%) of the product as a colorless oil.

N-[(2S)-4-[[(1R,2S)-2-(4-fluorophenyl)cyclopropyl]amino]-1-(thiomorpholine-1,1-dioxide-4-yl)-1-oxobutan-2-yl]-4-phenylbenzamide The method used to prepare 4 was used with the product from the above reaction (137 mg, 0.72 mmol, 1.50 equiv) and (3S)-4-(thiomorpholine-1,1-dioxide-4-yl)-4-oxo-3-[4-(phenyl)phenyl]formamido]-1-butanal (200 mg, 0.48 mmol, 1.00 equiv) to afford 106.9 mg (34.4%) of the product as a white solid.

Example 152

Scheme 33

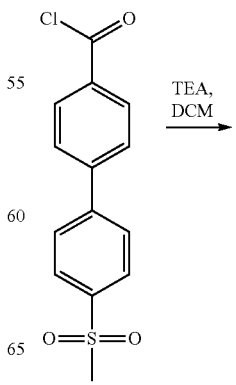

245
-continued

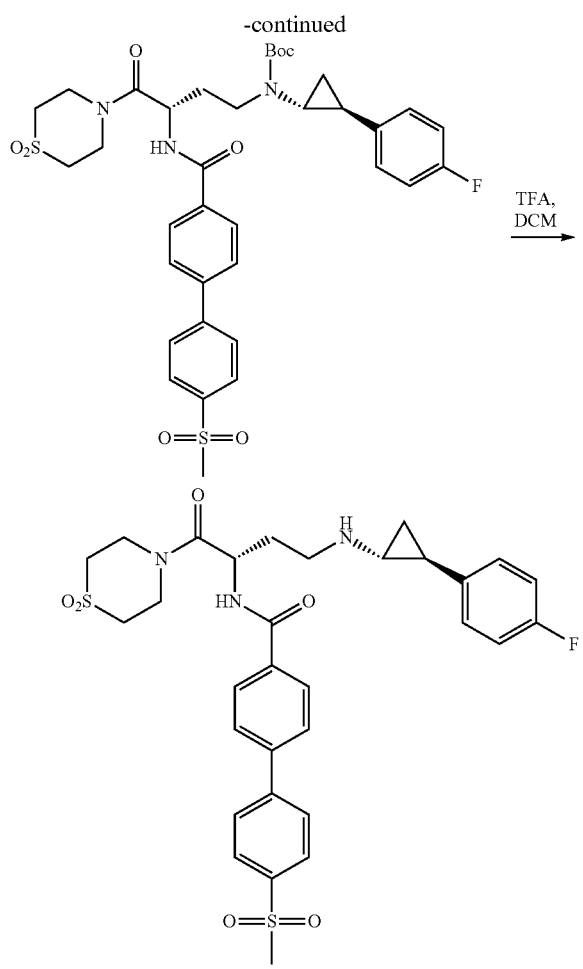

246
Synthesis of 152 tert-Butyl N-[(3S)-4-(thiomorpholin-1,1-dioxide-4-yl)-3-[[4-(4-methanesulfonylphenyl)phenyl]formamido]-4-oxobutyl]-N-[(1R,2S)-2-(4-fluorophenyl)cyclopropyl]carbamate Into a 100-mL round-bottom flask purged and maintained with an inert atmosphere of nitrogen were combined tert-butyl N-[(3S)-3-amino-4-(thiomorpholin-1,1-dioxide-4-yl)-4-oxobutyl]-N-[(1R,2S)-2-(4-fluorophenyl)cyclopropyl]-carbamate (100 mg, 0.21 mmol, 1.00 equiv), $Et_3N$ (43 mg, 0.42 mmol, 2.00 equiv), $CH_2Cl_2$ (10 mL), followed by the dropwise addition of a solution of 4-(4-methanesulfonylphenyl)benzoyl chloride (70 mg, 0.24 mmol, 1.12 equiv) in $CH_2Cl_2$ (5 mL) dropwise with stirring. The resulting solution was stirred for 2 h at room temperature, then quenched by the addition of 10 mL of water. The resulting solution was extracted with 3×10 mL of $CH_2Cl_2$. The combined organic layers were dried $Na_2SO_4$, concentrated under reduced pressure, and applied onto a silica gel column with EtOAc/petroleum ether (1:5) to afford 100 mg (65%) of the product as a yellow oil.

N-[(2S)-1-(thiomorpholin-1,1-dioxide-4-yl)-4-[[(1R,2S)-2-(4-fluorophenyl)cyclopropyl]amino]-1-oxobutan-2-yl]-4-(4-methanesulfonylphenyl)benzamide Trifluoroacetic Acid Salt In a 50-mL round-bottom flask were combined the compound from the previous step (100 mg, 0.14 mmol, 1.00 equiv), $CF_3COOH$ (1 mL) and $CH_2Cl_2$ (10 mL). The resulting solution was stirred for 2 h at room temperature, then concentrated under reduced pressure. The crude product was purified by Prep-HPLC, affording 51.5 mg (52%) of the product as a white solid.

Example 158

Scheme 34 (a)

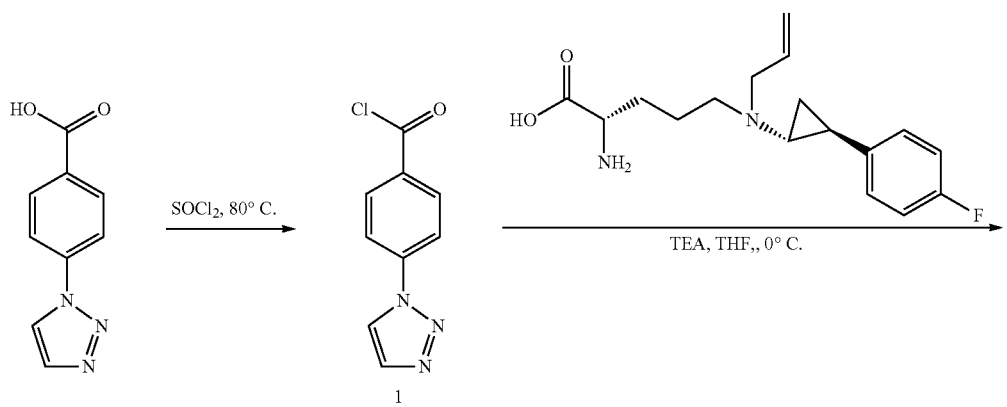

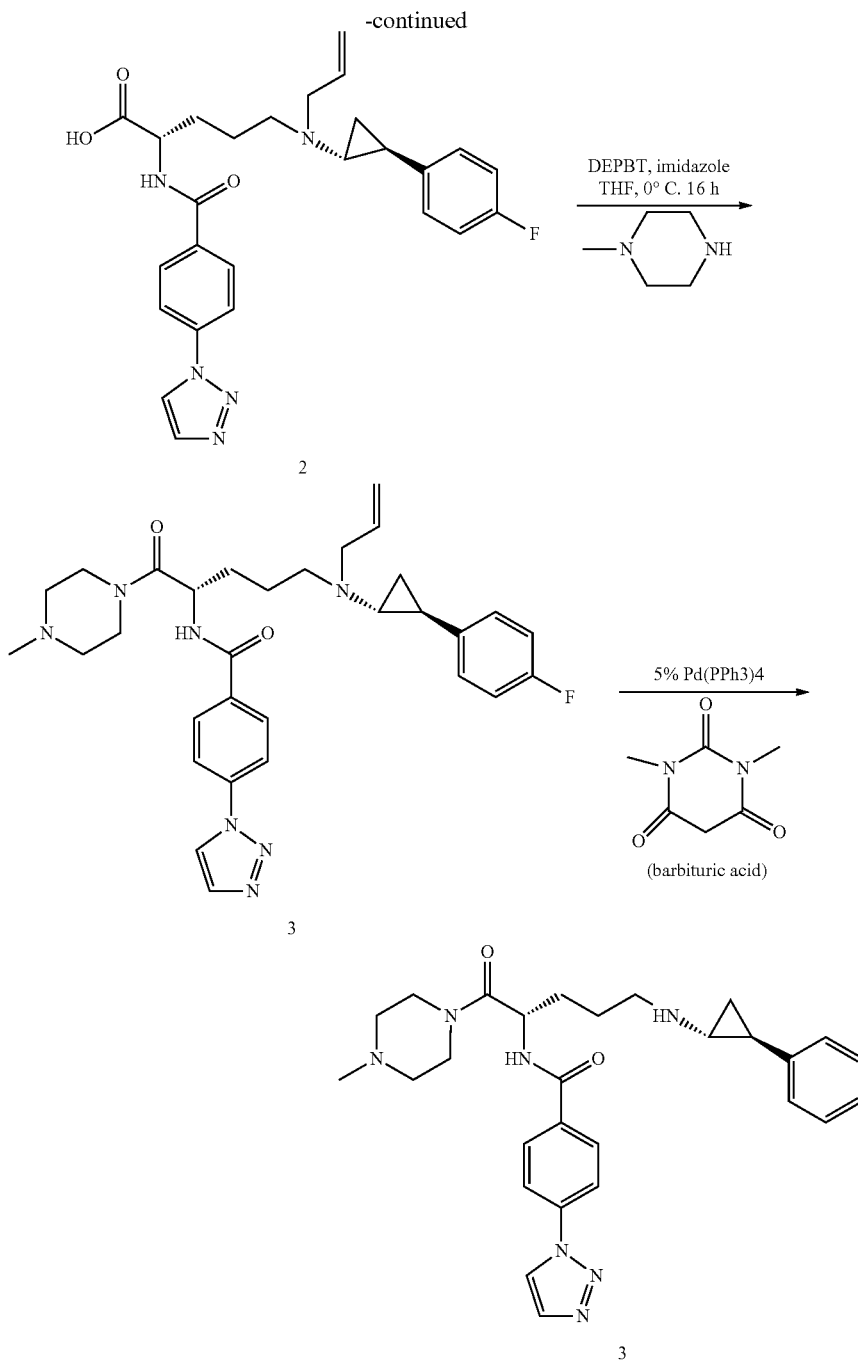

Synthesis of 158

4-(1H-1,2,3-triazolyl-1-yl)benzoyl Chloride (1)

In a 100-mL round-bottom flask were combined 4-(1H-1,2,3-triazol-1-yl)benzoic acid (1 g, 5.29 mmol, 1.00 equiv) and thionyl chloride (20 mL). The resulting solution was stirred for 16 h at 80° C. in an oil bath. The resulting mixture was then concentrated under reduced pressure, affording 1 g (91%) of intermediate (1) as a yellow solid.

(2S)-5-[[(1R,2S)-2-(4-fluorophenyl)cyclopropyl] (propen-3-yl)amino]-2-[[4-(1H-1,2,3-triazol-1-yl) phenyl]formamido]pentanoic Acid (2)

In a 100-mL round-bottom flask were combined (2S)-2-amino-5-[(1R,2S)-2-(4-fluorophenyl)cyclopropyl](prop-2-en-1-yl)aminopentanoic acid (500 mg, 1.63 mmol, 1.00 equiv), Et$_3$N (494 mg, 4.88 mmol, 3.00 equiv) and THF (20 mL). This was followed by the addition of a solution of intermediate (1) from the previous step (1 g, 4.82 mmol, 2.95 equiv) in THF (20 mL) dropwise with stirring at 0° C. in 30 min. The resulting solution was stirred for 1 h at 0° C. in an ice/salt bath, then concentrated under reduced pressure, and applied onto a silica gel column with $CH_2Cl_2$/methanol (10:1). The collected fractions were combined and concentrated under reduced pressure, affording 400 mg (51%) of intermediate (2) as a off-white solid.

N-[(2S)-1-(4-(methyl)piperazin-1-yl)-5-[[(1R,2S)-2-(4-fluorophenyl)-cyclopropyl](prop-2-en-1-yl) amino]-1-oxopentan-2-yl]-4-(1H-1,2,3-triazol-1-yl) benzamide (3)

In a 100-mL round-bottom flask were combined intermediate (2) from the previous step (400 mg, 0.84 mmol, 1.00 equiv), DEPBT (375 mg, 1.25 mmol, 1.50 equiv), and THF (20 mL), followed by the addition of imidazole (85 mg, 1.25 mmol, 1.50 equiv). The mixture was stirred for 30 min at 0° C., at which point 1-methylpiperazine (127 mg, 1.27 mmol, 1.50 equiv) was added dropwise with stirring at 0° C. in 3 min. The resulting solution was stirred for 16 h at 20° C., then concentrated under reduced pressure. The residue was applied onto a silica gel column with $CH_2Cl_2$/methanol (10:1). The collected fractions were combined and concentrated under vacuum, affordin 300 mg (64%) of intermediate (3) as a yellow solid.

N-[(2S)-1-(4-(methyl)piperazin-1-yl)-5-[[(1R,2S)-2-(4-fluorophenyl)-cyclopropyl]amino]-1-oxopentan-2-yl]-4-(1H-1,2,3-triazol-1-yl)benzamide (3)

Into a 100-mL round-bottom flask purged and maintained with an inert atmosphere of nitrogen, was placed N-[(2S)-5-[[(1R,2S)-2-(4-fluorophenyl)cyclopropyl](prop-2-en-1-yl)amino]-1-(4-methylpiperazin-1-yl)-1-oxopentan-2-yl]-4-(1H-1,2,3-triazol-1-yl)benzamide (300 mg, 0.54 mmol, 1.00 equiv), 1,3-dimethyl-1,3-diazinane-2,4,6-trione (210 mg, 1.34 mmol, 2.50 equiv), $Pd(PPh_3)_4$ (155 mg, 0.13 mmol, 0.25 equiv). The resulting solution was stirred for 2 h at 45° C. in an oil bath. The resulting mixture was concentrated under vacuum. The crude product (10 mL) was purified by Flash-Prep-HPLC. This resulted in 65 mg (23%) of Example 158 as a yellow solid.

Alternatively, Example 158 and its bis-tosylate salt may be prepared by the following method.

Scheme 34 (b)

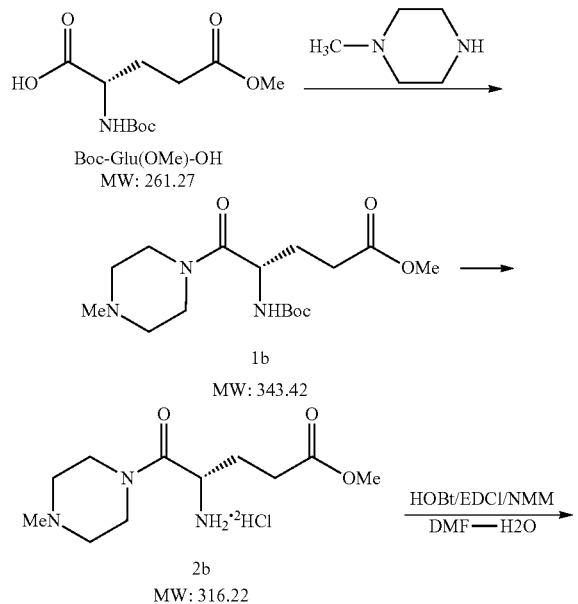

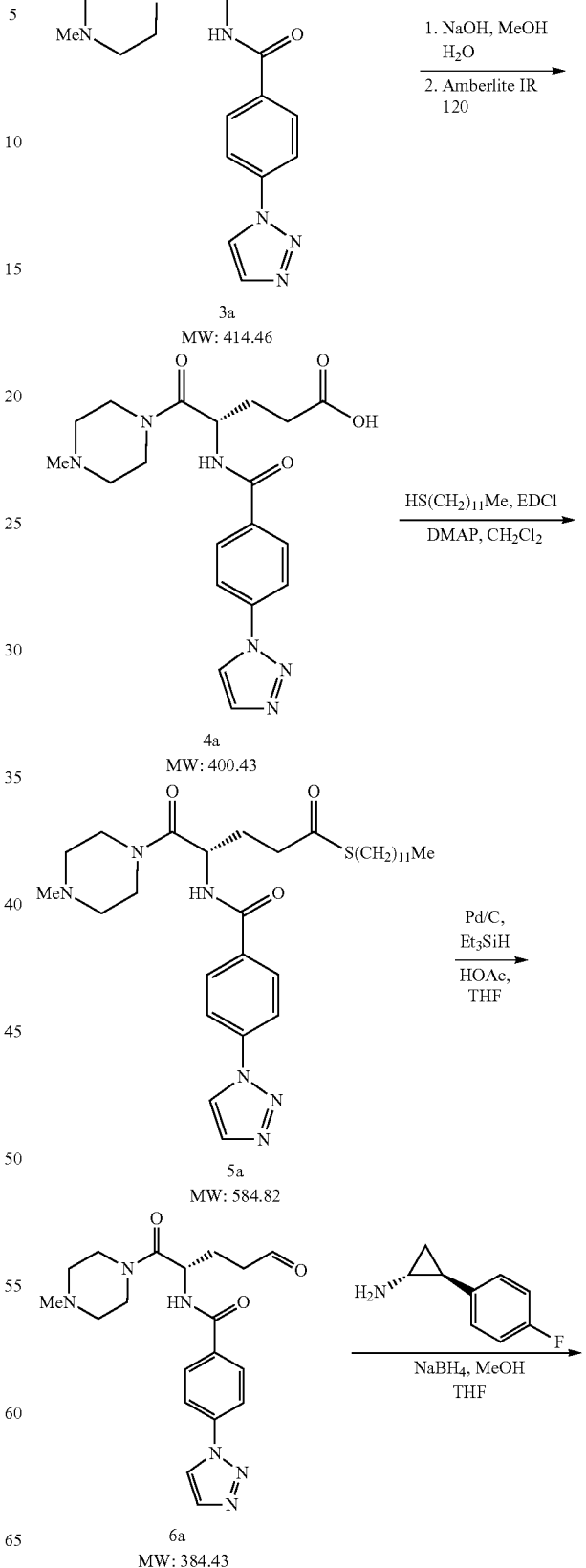

251
-continued
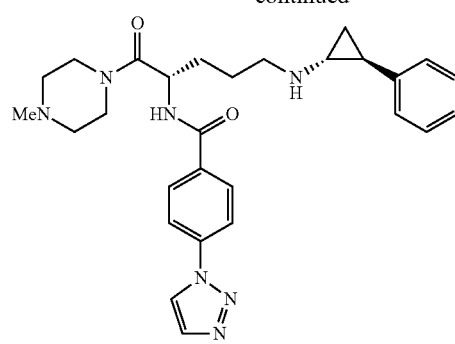
MW: 519.61
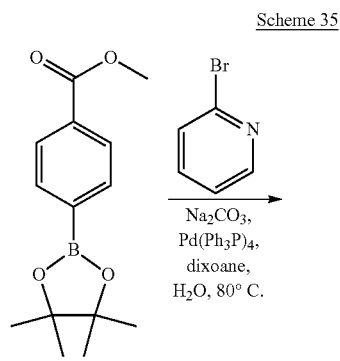
MW: 864.02
Scheme 35
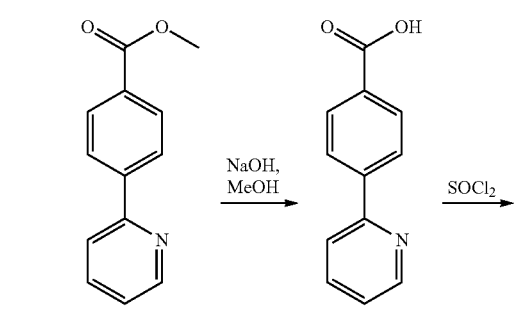
252
-continued
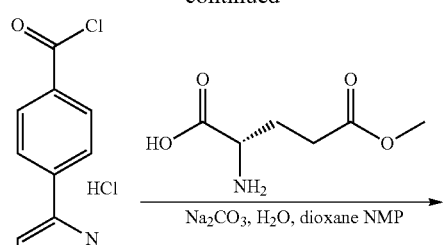
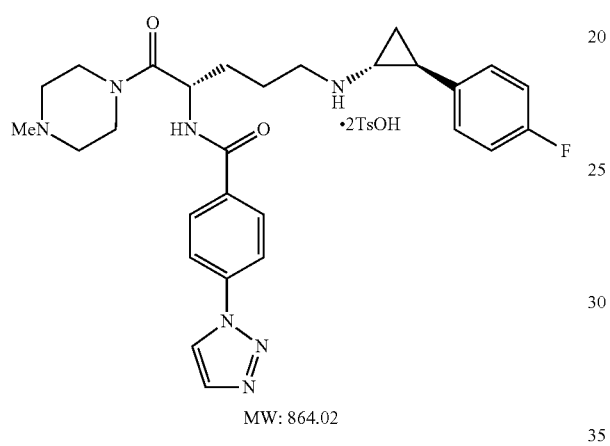
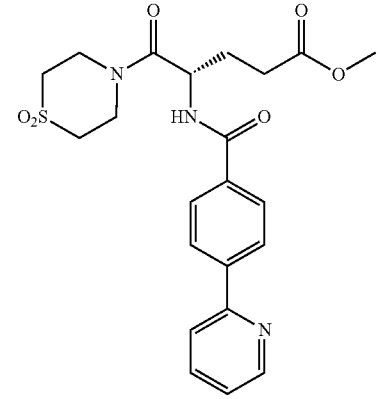
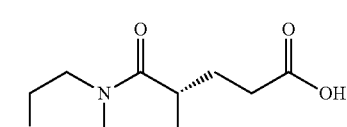

-continued

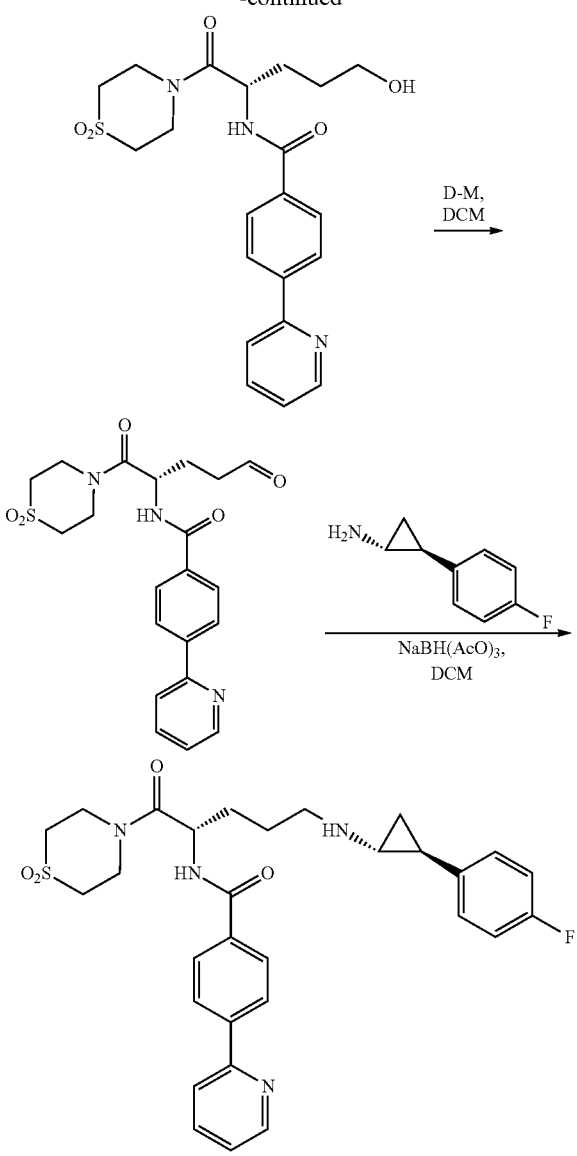

Synthesis of 162

Methyl 4-(pyridin-2-yl)benzoate

In a 250-mL round-bottom flask purged and maintained with an inert atmosphere of nitrogen was combined a solution of methyl 4-(4,4,5,5-tetramethyl-1,3,2-dioxaborolan-2-yl)benzoate (5 g, 0.019 mol, 1.00 equiv) in dioxane (50 mL), $Na_2CO_3$ (6.04 g, 0.057 mol, 3.00 equiv), 2-bromopyridine (4.5 g, 0.028 mol, 1.50 equiv), and $Pd(Ph_3P)_4$ (1.1 g, 0.001 mmol, 0.05 equiv). The resulting solution was stirred for 16 h at 80° C. The resulting solution was quenched by water/ice and extracted with 3×50 ml EtOAc. The combined organic layers were washed with brine, dried over $Na_2SO_4$, concentrated under reduced pressure, and purified by flash chromatography with EtOAc/petroleum ether (1:5) to afford 3.5 g (86%) of the product as a light yellow solid.

4-(Pyridin-2-yl)benzoic Acid

The method used to prepare 209 was used with the compound from the previous step (3.5 g, 0.016 mol, 1.00 equiv) in MeOH (50 mL) to afford 3 g (92%) of the product as a off-white solid.

4-(Pyridin-2-yl)benzoyl Chloride

The method used to prepare 201 was used with the compound from the previous reaction (3 g, 0.015 mol, 1.00 equiv). The crude product was used for the next step without further purification.

(S)-5-Methoxy-5-oxo-2-(4-(pyridin-2-yl)benzamido)
pentanoic Acid

Into a 250-mL round-bottom flask purged and maintained with an inert atmosphere of nitrogen, was placed a solution of (2S)-2-amino-5-methoxy-5-oxopentanoic acid (2 g, 12.41 mmol, 1.00 equiv) in dioxane (25 mL), a solution of $Na_2CO_3$ (3.94 g, 37.17 mmol, 3.00 equiv) in water (50 mL). Then 4-(pyridin-2-yl)benzoyl chloride (crude) in N-methyl-2-pyrrolidone (100 ml) was added dropwise at 0° C. The resulting solution was stirred for 1 h at 0° C. The pH value of the solution was adjusted to 6 with HCl (1 M). The resulting mixture was concentrated under reduced pressure. The residue was purified by reverse phase flash chromatography with $CH_3CN/H_2O$ (1%-20%), affording 1.9 g (45%) of the product as a light yellow solid.

Methyl (4S)-5-oxo-5-[1-(thiomorpholine-1,1-dioxide-4-yl)]-4-[(4-(2-pyridyl)phenyl)formamido]pentanoate The method used to prepare 206 was used with the product from the previous step (1.9 g, 5.56 mmol, 1.00 equiv) and thiomorpholine-1,1-dioxide (1.13 g, 8.34 mmol, 1.50 equiv), to afford 1.4 g (55%) of the product as a brown solid.

(4S)-5-Oxo-5-[1-(thiomorpholine-1,1-dioxide-4-yl)]-
4-[(4-(2-pyridyl)phenyl)formamido]pentanoic Acid The procedure used to prepare 205 was used with the compound from the previous step (1.4 g, 3.04 mmol, 1.00 equiv) to afford 1.2 g (89%) of the product as an off-white solid.

(4S)-5-Oxo-5-[1-(thiomorpholine-1,1-dioxide-4-yl)]-
4-[(4-(2-pyridyl)phenyl)formamido]pentanol The method used to prepare 212 was used with the product from the previous step (800 mg, 1.8 mmol, 1.00 equiv) to afford 550 mg (71%) of the product as a brown solid.

(4S)-5-Oxo-5-[1-(thiomorpholine-1,1-dioxide-4-yl)]-
4-[(4-(2-pyridyl)phenyl)formamido]pentanal The method used to prepare 208 was used with the compound from the previous step (550 mg, 1.27 mmol, 1.00 equiv) to afford 350 mg (64%) of the product as a off-white solid.

[(2S)-1-(Thiomorpholine-1,1-dioxide-4-yl)-5-[[(1R,2S)-2-(4-fluorophenyl)-cyclopropyl]amino]-1-oxo-pentan-2-yl] 4-(pyridin-2-yl)-benzamide
The method used to prepare 4 was used with the compound from the previous step (350 mg, 0.82 mmol, 1.00 equiv) and (1R,2S)-2-(4-fluorophenyl)cyclopropan-1-amine hydrochloride salt (231 mg, 1.23 mmol, 1.50 equiv) to afford 61.9 mg (13.4%) of the product as a white solid.
Example 163
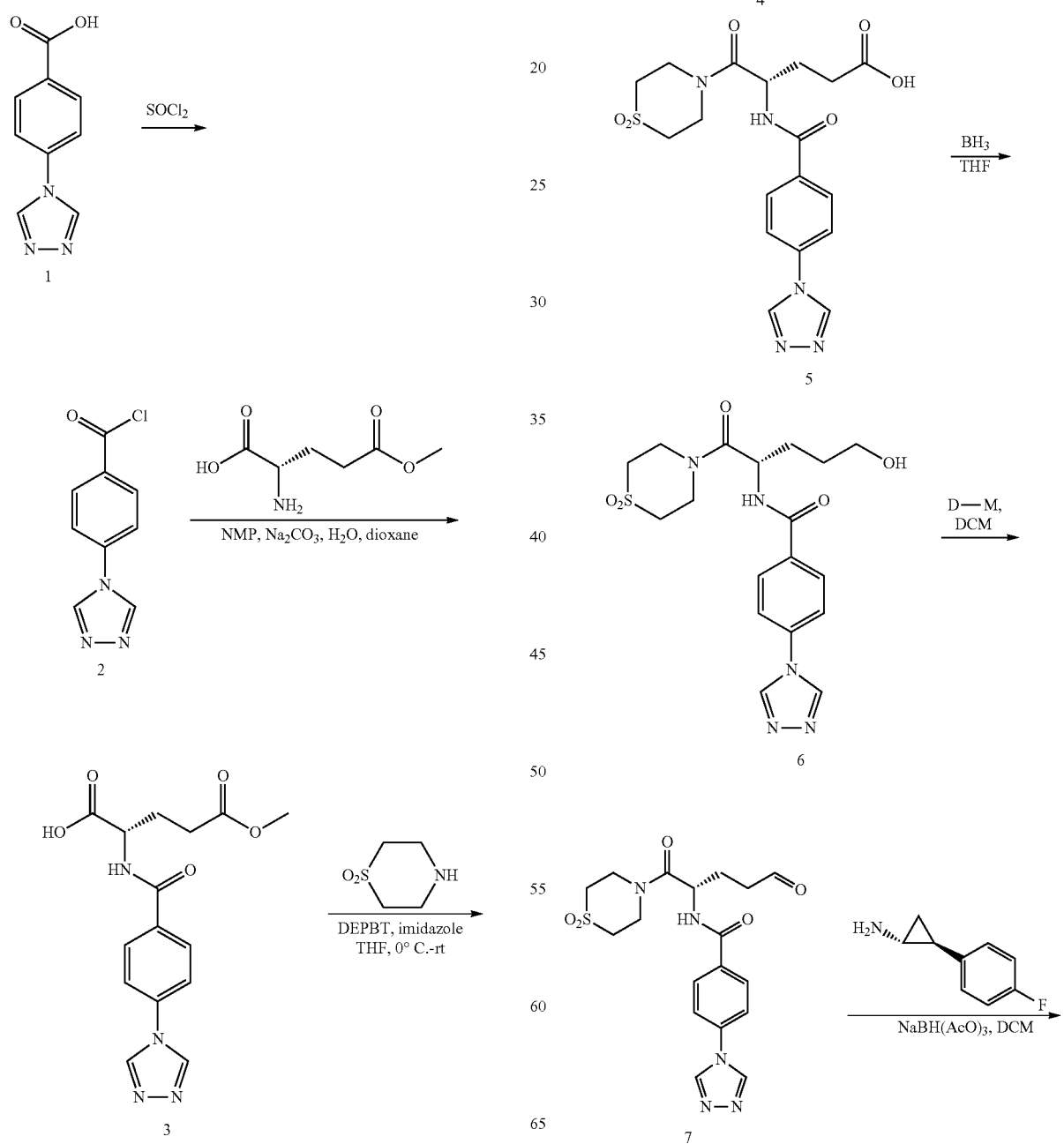

257
-continued

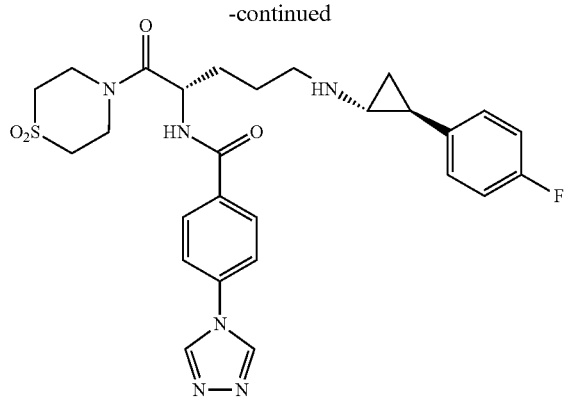

Synthesis of 163

4-(4H-1,2,4-Triazol-4-yl)benzoyl Chloride

The method used to prepare 201 was used with 4-(4H-1,2,4-triazol-4-yl)benzoic acid (2 g, 10.57 mmol, 1.00 equiv) to afford 2 g (91%) of the product as a white solid.

(2S)-5-Methoxy-5-oxo-2-[[4-(4H-1,2,4-triazol-4-yl)phenyl]formamido]pentanoic Acid In a 500-mL round-bottom flask were combined (2S)-2-amino-5-methoxy-5-oxopentanoic acid (1.55 g, 9.62 mmol, 1.00 equiv), dioxane (100 mL), water (100 mL), and Na$_2$CO$_3$ (3.06 g, 28.87 mmol, 3.00 equiv), followed by the dropwise addition of a solution of 4-(4H-1,2,4-triazol-4-yl)benzoyl chloride (2 g, 9.63 mmol, 1.00 equiv) in NMP (50 mL) dropwise with stirring at 0° C. The resulting solution was stirred for 2 h at room temperature, then concentrated under vacuum and purified by Prep-HPLC to afford 2 g (63%) of the product as a yellow solid.

Methyl (4S)-5-(thiomorpholine-1,1-dioxide-4-yl)-5-oxo-4-[[4-(4H-1,2,4-triazol-4-yl)phenyl]formamido]pentanoate The method used to prepare 206 was used with the product from the previous step (2 g, 6.02 mmol, 1.00 equiv) and thiomorpholine-1,1-dioxide (1.22 g, 8.96 mmol, 1.49 equiv) to afford 1.4 g (52%) of the product as a yellow oil.

(4S)-5-(Thiomorpholine-1,1-dioxide-4-yl)-5-oxo-4-[[4-(4H-1,2,4-triazol-4-yl)phenyl]formamido] pentanoic Acid The method used to prepare 205 was used with the compound from the previous step (1.4 g, 3.11 mmol, 1.00 equiv) to afford 1 g (74%) of the product as a white solid.

(4S)-5-(Thiomorpholine-1,1-dioxide-4-yl)-5-oxo-4-[[4-(4H-1,2,4-triazol-4-yl)phenyl]formamido] pentanol The method used to prepare 202 was used with the compound from the previous step (900 mg, 2.07 mmol, 1.00 equiv) to afford 450 mg (52%) of the product as a yellow oil.

258

(4S)-5-(Thiomorpholine-1,1-dioxide-4-yl)-5-oxo-4-[[4-(4H-1,2,4-triazol-4-yl)phenyl]formamido] pentanal The method used to prepare 208 was used with the compound from the previous step (450 mg, 1.07 mmol, 1.00 equiv) to afford 300 mg (67%) of the product as a yellow oil.

N-[(2S)-1-(Thiomorpholine-1,1-dioxide-4-yl)-5-[[(1R,2S)-2-(4-fluorophenyl)cyclopropyl]amino]-1-oxopentan-2-yl]-4-(4H-1,2,4-triazol-4-yl)benzamide The method used to prepare 4 was used with the product from the previous step (300 mg, 0.72 mmol, 1.00 equiv) to afford 17 mg (4%) of the product as an off-white solid.

Example 164

Scheme 37

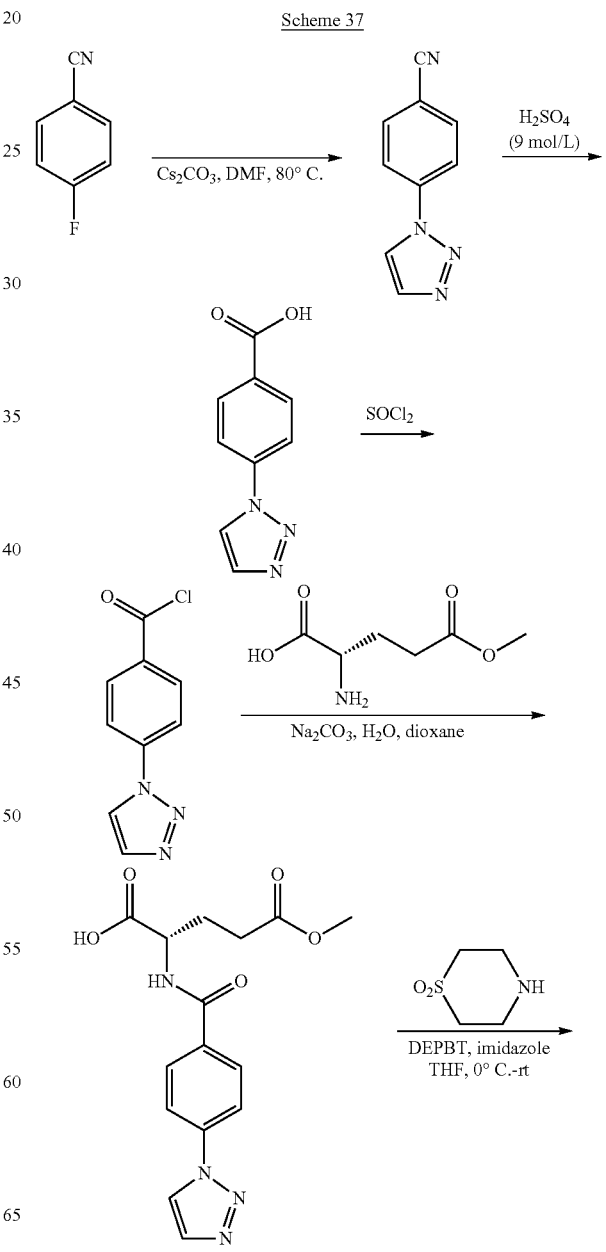

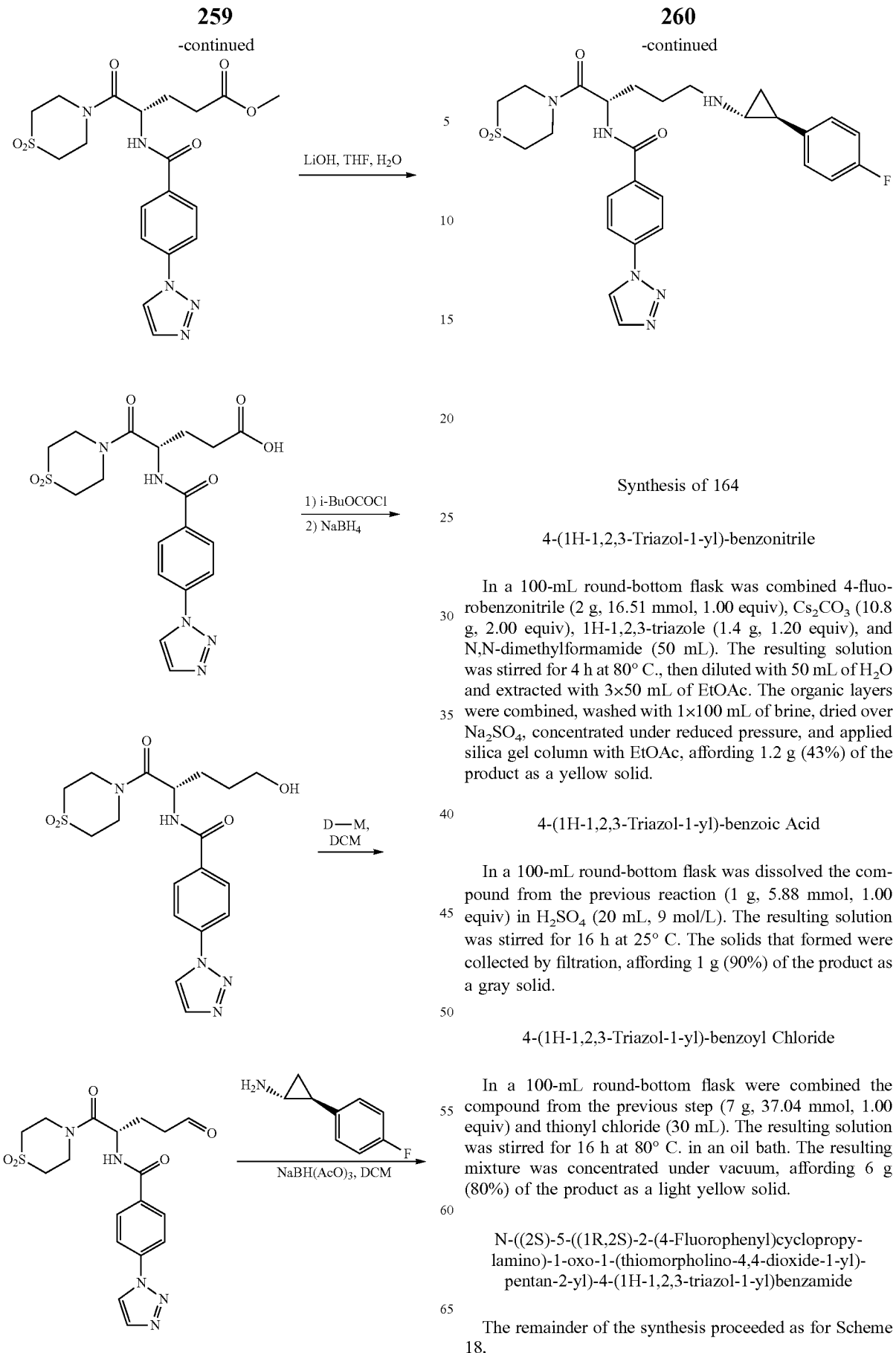

Synthesis of 164

4-(1H-1,2,3-Triazol-1-yl)-benzonitrile

In a 100-mL round-bottom flask was combined 4-fluorobenzonitrile (2 g, 16.51 mmol, 1.00 equiv), $Cs_2CO_3$ (10.8 g, 2.00 equiv), 1H-1,2,3-triazole (1.4 g, 1.20 equiv), and N,N-dimethylformamide (50 mL). The resulting solution was stirred for 4 h at 80° C., then diluted with 50 mL of $H_2O$ and extracted with 3×50 mL of EtOAc. The organic layers were combined, washed with 1×100 mL of brine, dried over $Na_2SO_4$, concentrated under reduced pressure, and applied silica gel column with EtOAc, affording 1.2 g (43%) of the product as a yellow solid.

4-(1H-1,2,3-Triazol-1-yl)-benzoic Acid

In a 100-mL round-bottom flask was dissolved the compound from the previous reaction (1 g, 5.88 mmol, 1.00 equiv) in $H_2SO_4$ (20 mL, 9 mol/L). The resulting solution was stirred for 16 h at 25° C. The solids that formed were collected by filtration, affording 1 g (90%) of the product as a gray solid.

4-(1H-1,2,3-Triazol-1-yl)-benzoyl Chloride

In a 100-mL round-bottom flask were combined the compound from the previous step (7 g, 37.04 mmol, 1.00 equiv) and thionyl chloride (30 mL). The resulting solution was stirred for 16 h at 80° C. in an oil bath. The resulting mixture was concentrated under vacuum, affording 6 g (80%) of the product as a light yellow solid.

N-((2S)-5-((1R,2S)-2-(4-Fluorophenyl)cyclopropylamino)-1-oxo-1-(thiomorpholino-4,4-dioxide-1-yl)-pentan-2-yl)-4-(1H-1,2,3-triazol-1-yl)benzamide The remainder of the synthesis proceeded as for Scheme 18, Example 166
Scheme 38
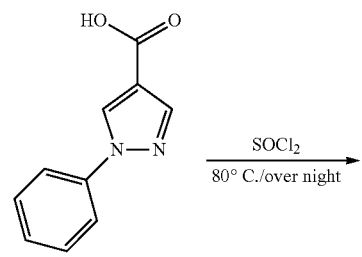
SOCl₂
80° C./over night
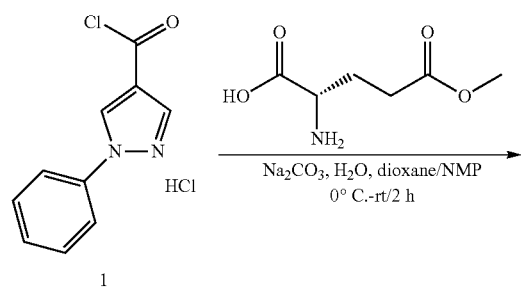
Na₂CO₃, H₂O, dioxane/NMP
0° C.-rt/2 h
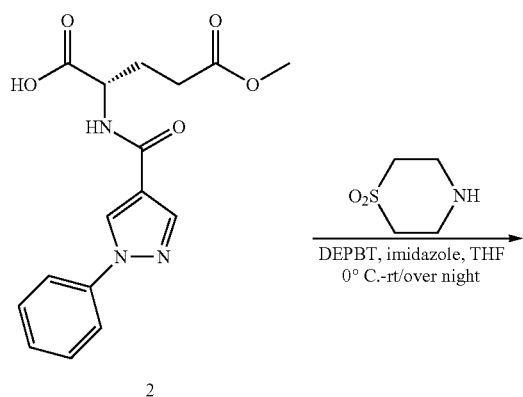
DEPBT, imidazole, THF
0° C.-rt/over night
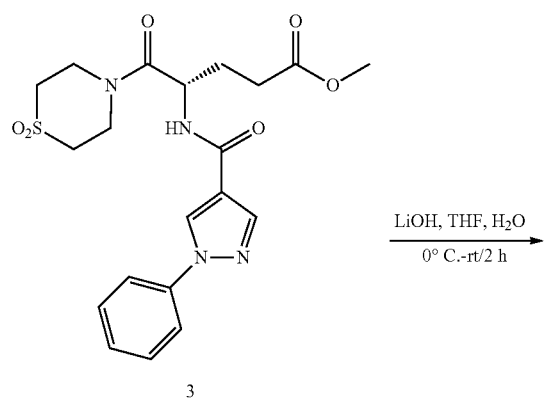
LiOH, THF, H₂O
0° C.-rt/2 h
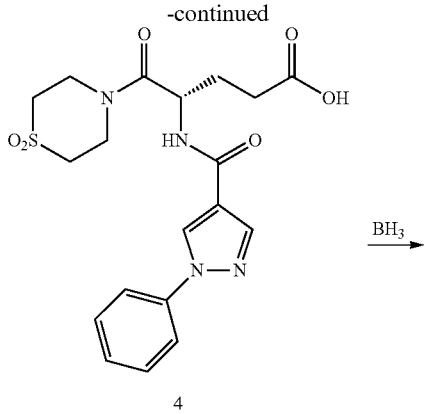
BH₃
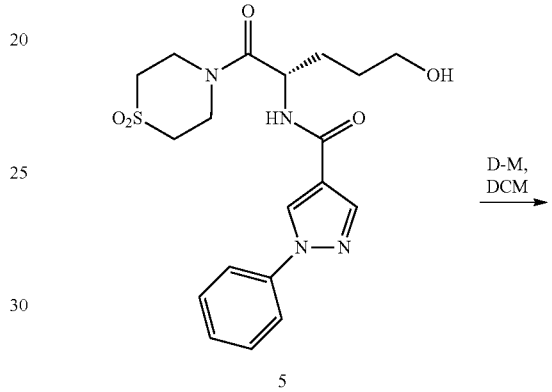
D-M,
DCM
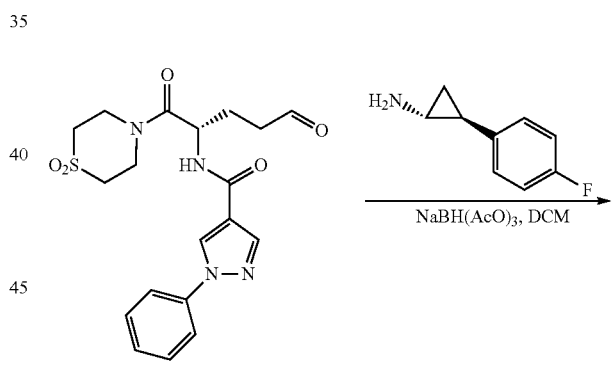
NaBH(AcO)₃, DCM
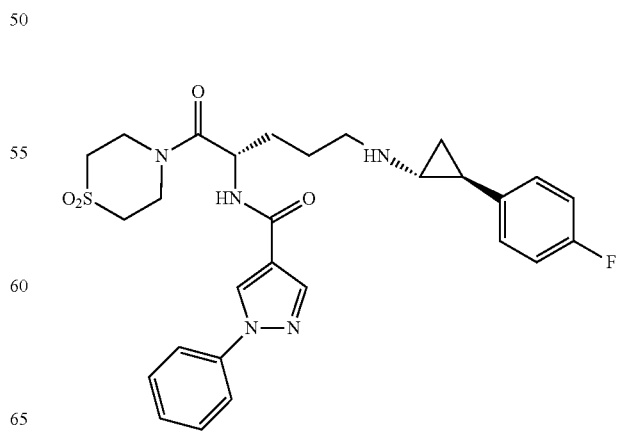

Synthesis of 166

1-Phenyl-1H-pyrazole-4-carbonyl Chloride Hydrochloride

The method used to prepare 201 was used with 1-phenyl-1H-pyrazole-4-carboxylic acid (5 g, 26.57 mmol, 1.00 equiv) to afford 5 g (77%) crude of the product as a yellow solid.

(2S)-5-Methoxy-5-oxo-2-[(1-phenyl-1H-pyrazol-4-yl)formamido]pentanoic Acid

The method used to prepare 203 was used with (2S)-2-amino-5-methoxy-5-oxopentanoic acid (2.76 g, 17.13 mmol, 1.00 equiv) and 1-phenyl-1H-pyrazole-4-carbonyl chloride hydrochloride (5 g, 20.57 mmol, 1.20 equiv) to afford 2.7 g (48%) of the product as an off-white solid.

Methyl (4S)-5-(thiomorpholin-1,1-dioxide-4-yl)-5-oxo-4-[(1-phenyl-1H-pyrazol-4-yl)formamido]pentanoate The method used to prepare 206 was used with the compound from the previous step (2.7 g, 8.15 mmol, 1.00 equiv) and thiomorpholine-1,1-dioxide (1.34 g, 9.84 mmol, 1.21 equiv) to afford 1.8 g (49%) of the product as an off-white solid.

(4S)-5-(Thiomorpholin-1,1-dioxide-4-yl)-5-oxo-4-[(1-phenyl-1H-pyrazol-4-yl)formamido]pentanoic Acid The method used to prepare 205 was used with the compound from the previous step (1.8 g, 4.01 mmol) to afford 1.22 g (70%) of the product as an off-white solid.

(3S)-4-(Thiomorpholine-1,1-dioxide-4-yl)-4-oxo-3-[4-(1H-pyrazol-1-yl)phenyl)formamido]-1-butanol The method to prepare 202 was used with the compound from the previous step to afford 0.8 g (68%) of the product as an off-white solid.

(3S)-4-(Thiomorpholine-1,1-dioxide-4-yl)-4-oxo-3-[4-(1H-pyrazol-1-yl)phenyl)formamido]-1-butanal The method used to prepare 208 was used with the compound from the previous step (800 mg, 1.90 mmol, 1.00 equiv) to afford 480 mg (60%) of the product as a off-white solid.

N-[(2S)-1-(Thiomorpholine-1,1-dioxide-4-yl)-5-[[(1R,2S)-2-(4-fluorophenyl)cyclopropyl]amino]-1-oxopentan-2-yl]-1-phenyl-1H-pyrazole-4-carboxamide The method used to prepare 4 was used with the compound from the previous reaction (480 mg, 1.15 mmol, 1.00 equiv) and (1R,2S)-2-(4-fluorophenyl)cyclopropan-1-amine (208 mg, 1.38 mmol, 1.20 equiv) to afford 33.5 mg (5%) of the product as a white solid.

Example 168

Scheme 39

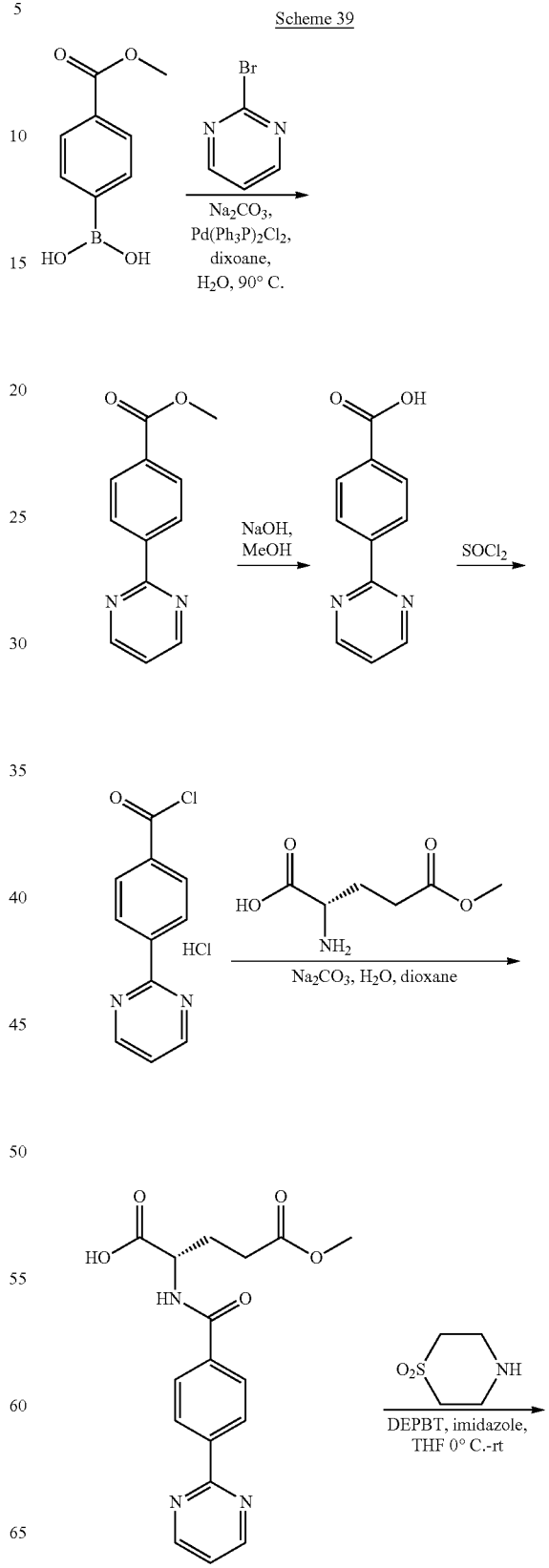

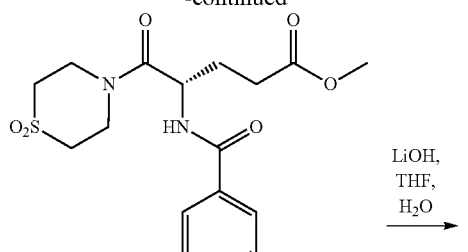

LiOH,
THF,
H₂O
→

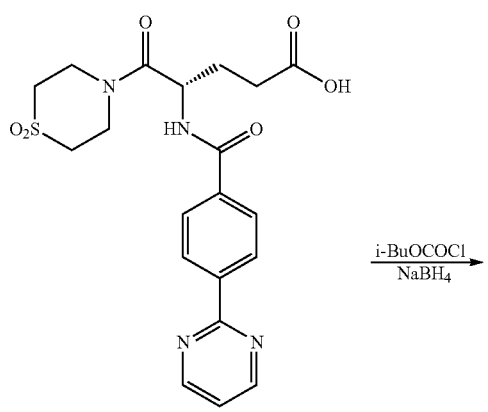

i-BuOCOCl
NaBH₄
→

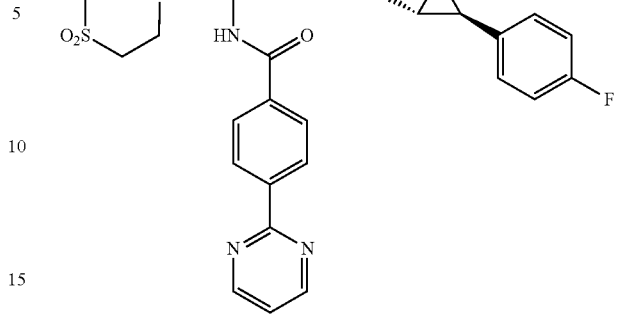

Synthesis of 168

Methyl 4-(pyrimidin-2-yl)benzoate

In a 250-mL round-bottom flask were combined [4-(methoxycarbonyl)phenyl]boronic acid (5 g, 27.78 mmol, 1.00 equiv), dixoane (100 mL), 2-bromopyrimidine (5.3 g, 33.34 mmol, 1.20 equiv), Na₂CO₃ (5.89 g, 55.57 mmol, 2.00 equiv), water (10 mL), and Pd(Ph₃P)₂Cl₂ (3.2 g, 2.77 mmol, 0.10 equiv). The resulting solution was stirred for 16 h at 80° C. The solids that formed were removed by filtration. The resulting solution was extracted with 3×50 mL of EtOAc. The organic layers were combined and applied onto a silica gel column with CH₂Cl₂/methanol (10:1) to afford 4.4 g (74%) of the product as a light yellow solid.

4-(Pyrimidin-2-yl)benzoic Acid

In a 250-mL round-bottom flask were combined the compound from the previous step (4.4 g, 20.54 mmol, 1.00 equiv), NaOH (2.4 g, 60.00 mmol, 2.92 equiv), and methanol (50 mL). The resulting solution was stirred for 2 h at room temperature. The pH value of the solution was adjusted to 7 with HCl (1 M). The solids that formed were collected by filtration, affording 3.15 g (77%) of the product as a light yellow solid.

4-(Pyrimidin-2-yl)benzoyl Chloride

The method used to prepare 201 was used with the compound from the previous step (3.15 g, 15.73 mmol, 1.00 equiv) affording 3.20 g (80%) of crude 4-(pyrimidin-2-yl)benzoyl chloride hydrochloride as a light yellow solid.

(2S)-5-Methoxy-5-oxo-2-[[4-(pyrimidin-2-yl)phenyl]formamido]pentanoic Acid

The method used to prepare 203 was used with the compound from the previous step (1.68 g, 10.42 mmol, 0.83 equiv) and 4-(pyrimidin-2-yl)benzoyl chloride hydrochloride (3.20 g, 12.54 mmol, 1.00 equiv) to afford 1.75 g (41%) of the product as a off-white solid.

Methyl (4S)-5-(thiomorpholine-1,1-dioxide-4-yl)-5-oxo-4-[[4-(pyrimidin-2-yl)phenyl]formamido]pentanoate The method used to prepare 206 was used with the compound from the previous step (1.7 g, 4.95 mmol, 1.00

D-M,
DCM
→

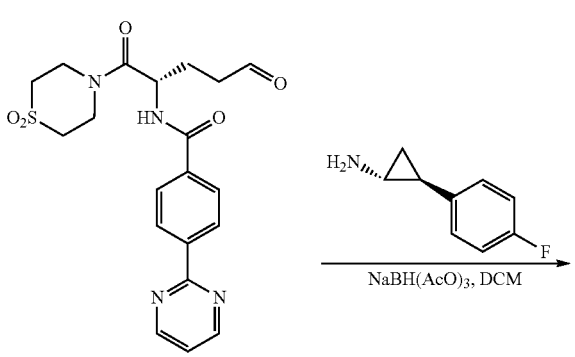

NaBH(AcO)₃, DCM
→ equiv) and thiomorpholine-1,1-dioxide (800 mg, 5.87 mmol, 1.19 equiv), to afford 1.35 g (59%) of the product as a light yellow solid.

(4S)-5-(thiomorpholine-1,1-dioxide-4-yl)-5-oxo-4-[[4-(pyrimidin-2-yl)phenyl]formamido]pentanoic Acid The method used to prepare 205 was used with the product from the previous step (1.35 g, 2.93 mmol, 1.00 equiv) to afford 0.98 g (75%) of the product as a off-white solid.

(4S)-5-(thiomorpholine-1,1-dioxide-4-yl)-5-oxo-4-[[4-(pyrimidin-2-yl)phenyl]formamido]pentanol The method used to prepare 212 was used with the compound from the previous step (980 mg, 2.19 mmol, 1.00 equiv), to afford 710 mg (75%) of the product as a solid.

(4S)-5-(thiomorpholine-1,1-dioxide-4-yl)-5-oxo-4-[[4-(pyrimidin-2-yl)phenyl]formamido]pentanal The method used to prepare 208 was used with the compound from the previous step (710 mg, 1.64 mmol, 1.00 equiv) to afford (72%) of the product as a white solid.

N-[(2S)-1 (thiomorpholine-1,1-dioxide-4-yl)-5-[[(1R,2S)-2-(4-fluorophenyl)cyclopropyl]amino]-1-oxopentan-2-yl]-4-(pyrimidin-2-yl)benzamide The method that was used to prepare 4 was used with the compound from the previous step (510 mg, 1.18 mmol, 1.00 equiv) to afford 59.9 mg (9%) of the product as a off-white solid.

Example 180

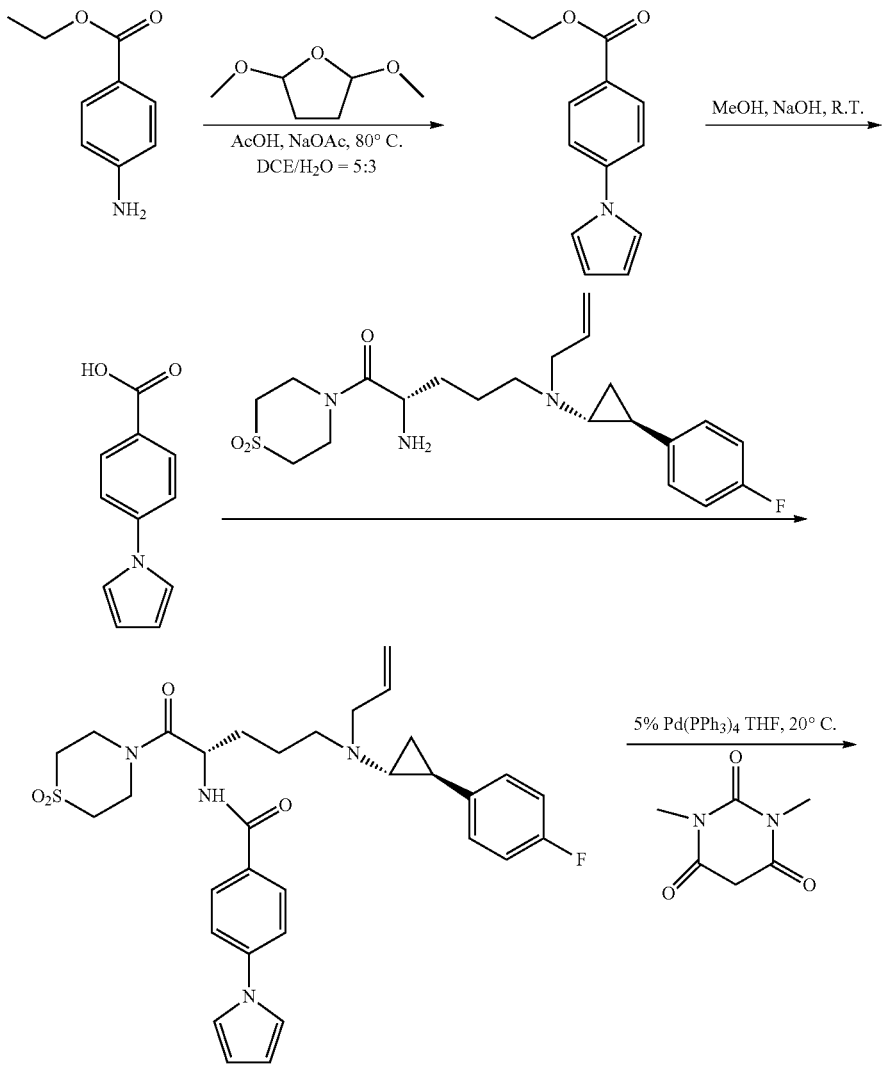

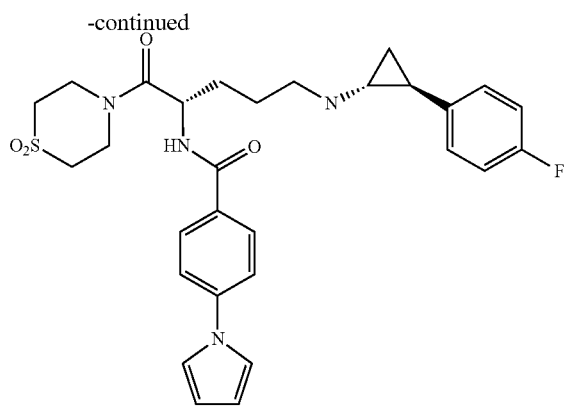

Synthesis of 180

Ethyl 4-(1H-pyrrol-1-yl) benzoate

In a 250-mL round-bottom flask was combined a solution of ethyl 4-aminobenzoate (4 g, 24.21 mmol, 1.00 equiv) in CH$_2$Cl$_2$ (100 mL), a solution of AcOH (300 mg, 5.00 mmol, 0.20 equiv) in water (30 mL), NaOAc (2 g, 24.39 mmol, 1.00 equiv), and 2,5-dimethoxyoxolane (4.8 g, 36.32 mmol, 1.50 equiv). The resulting solution was stirred for 16 h at 90° C. in an oil bath. The resulting mixture was concentrated under vacuum, affording 3.5 g (67%) of the product as an off-white solid.

4-(1H-Pyrrol-1-yl) benzoic Acid

In a 250-mL round-bottom flask was combined the compound from the previous step (3.5 g, 16.26 mmol, 1.00 equiv), methanol (100 mL), and NaOH (1.3 g, 32.50 mmol, 2.00 equiv). The resulting solution was stirred for 16 h at 50° C. in an oil bath. The pH value of the solution was adjusted to 7 with HCl (1 M). The solids that formed were collected by filtration, affording 3 g (99%) of the product as a white solid.

N-[(2S)-5-[[(1R,2S)-2-(4-fluorophenyl)cyclopropyl](propen-3-yl)amino]-1-(thiomorpholine-1,1-dioxide-4-yl)-1-oxopentan-2-yl]-4-(1H-pyrrol-1-yl)benzamide The procedure of 211 was used with the compound from the previous step (100 mg, 0.53 mmol, 1.50 equiv) and (2S)-2-amino-5-[[(1R,2S)-2-(4-fluorophenyl)cyclopropyl](prop-2-en-1-yl)amino]-1-(thiomorpholine-1,1-dioxide-4-yl)pentan-1-one (150 mg, 0.35 mmol, 1.00 equiv), affording 150 mg (72%) of the product as a yellow solid.

N-[(2S)-5-[[(1R,2S)-2-(4-fluorophenyl)cyclopropyl]amino]-1-(thiomorpholine-1,1-dioxide-4-yl)-1-oxopentan-2-yl]-4-(1H-pyrrol-1-yl)benzamide The method to prepare 210 was used with the compound from the previous step to afford 41.5 mg (30%) of the product as a light yellow solid.

Example 181

Scheme 41

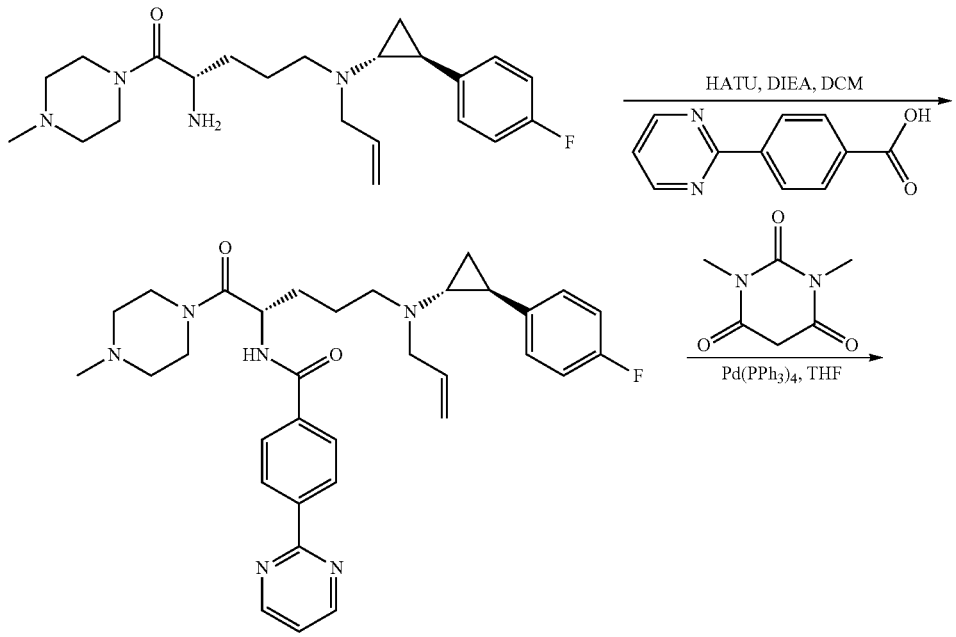

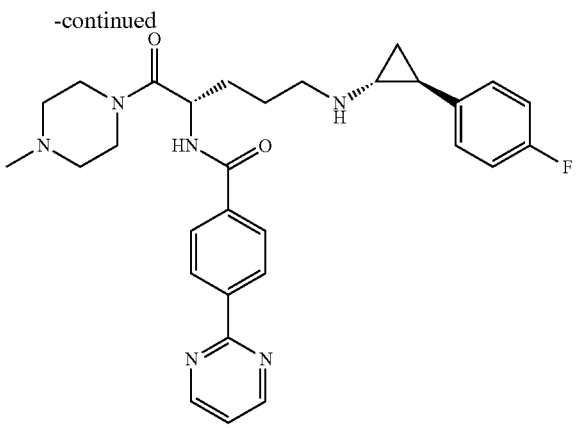

Into a 250-mL round-bottom flask, was placed (2S)-2-amino-5-[[(1R,2S)-2-(4-fluorophenyl)cyclopropyl](prop-2-en-1-yl)amino]-1-(4-methylpiperazin-1-yl)pentan-1-one (1.04 g, 2.68 mmol, 1.00 equiv), dichloromethane (50 mL), HATU (1.71 g, 4.50 mmol, 1.68 equiv), DIEA (1.16 g, 8.98 mmol, 3.35 equiv). This was followed by the addition of a solution of 4-(pyrimidin-2-yl)benzoic acid (450 mg, 2.25 mmol, 0.84 equiv) in $CH_2Cl_2$ (5 mL) dropwise with stirring at 0° C. The resulting solution was stirred overnight at room temperature. The resulting mixture was concentrated under vacuum. The resulting solution was extracted with 3×50 mL of EtOAc and the organic layers combined. This resulted in 0.52 g (34%) of N-[(2S)-5-[[(1R,2S)-2-(4-fluorophenyl)cyclopropyl](prop-2-en-1-yl)amino]-1-(4-methylpiperazin-1-yl)-1-oxopentan-2-yl]-4-(pyrimidin-2-yl)benzamide as a red solid.

Into a 100-mL round-bottom flask purged and maintained with an inert atmosphere of nitrogen, was placed N-[(2S)-5-[[(1R,2S)-2-(4-fluorophenyl)cyclopropyl](prop-2-en-1-yl)amino]-1-(4-methylpiperazin-1-yl)-1-oxopentan-2-yl]-4-(pyrimidin-2-yl)benzamide (520 mg, 0.91 mmol, 1.00 equiv), THF (15 mL), 1,3-dimethyl-1,3-diazinane-2,4,6-trione (426 mg, 2.73 mmol, 2.99 equiv), $Pd(PPh_3)_4$ (210 mg, 0.18 mmol, 0.20 equiv). The resulting solution was stirred for 2 h at 50° C. in an oil bath. The solids were filtered out. The resulting solution was extracted with 3×50 mL of EtOAc and the organic layers were combined and concentrated under vacuum. The mixture was dried over $Na_2SO_4$. The crude product was purified by Prep-HPLC. This resulted in 180.9 mg (37%) of N-[(2S)-5-[[(1R,2S)-2-(4-fluorophenyl)cyclopropyl]amino]-1-(4-methylpiperazin-1-yl)-1-oxopentan-2-yl]-4-(pyrimidin-2-yl)benzamide as a light yellow solid.

Example 182

Scheme 42

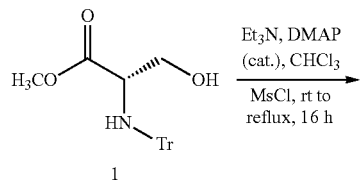

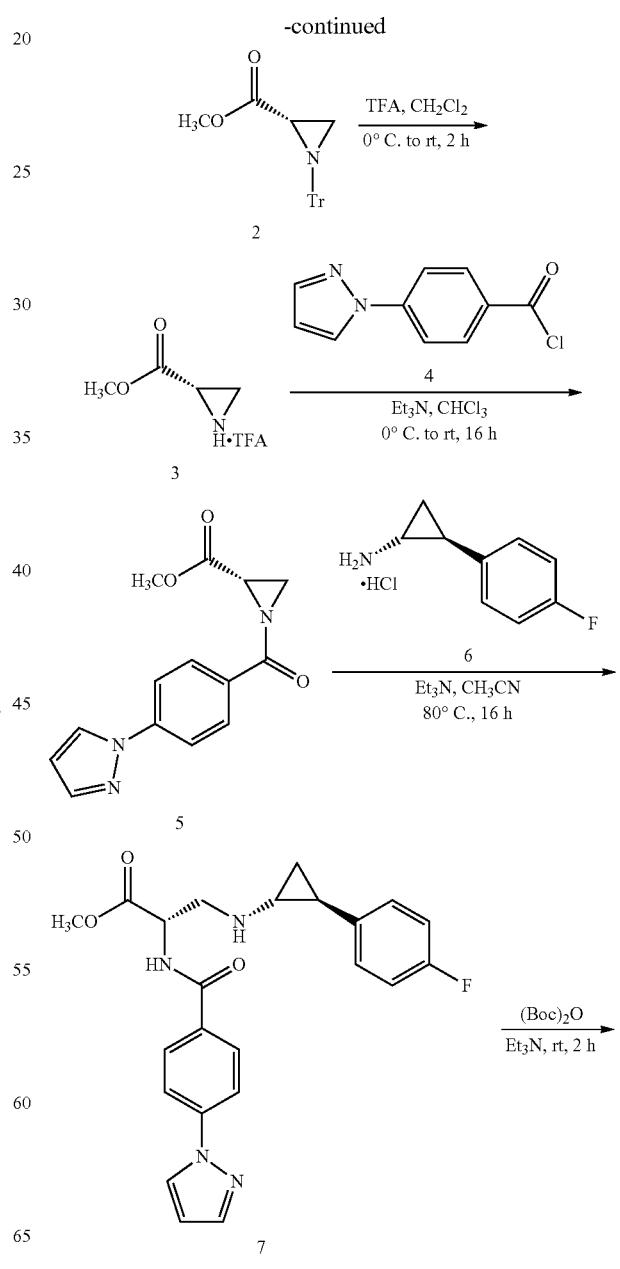

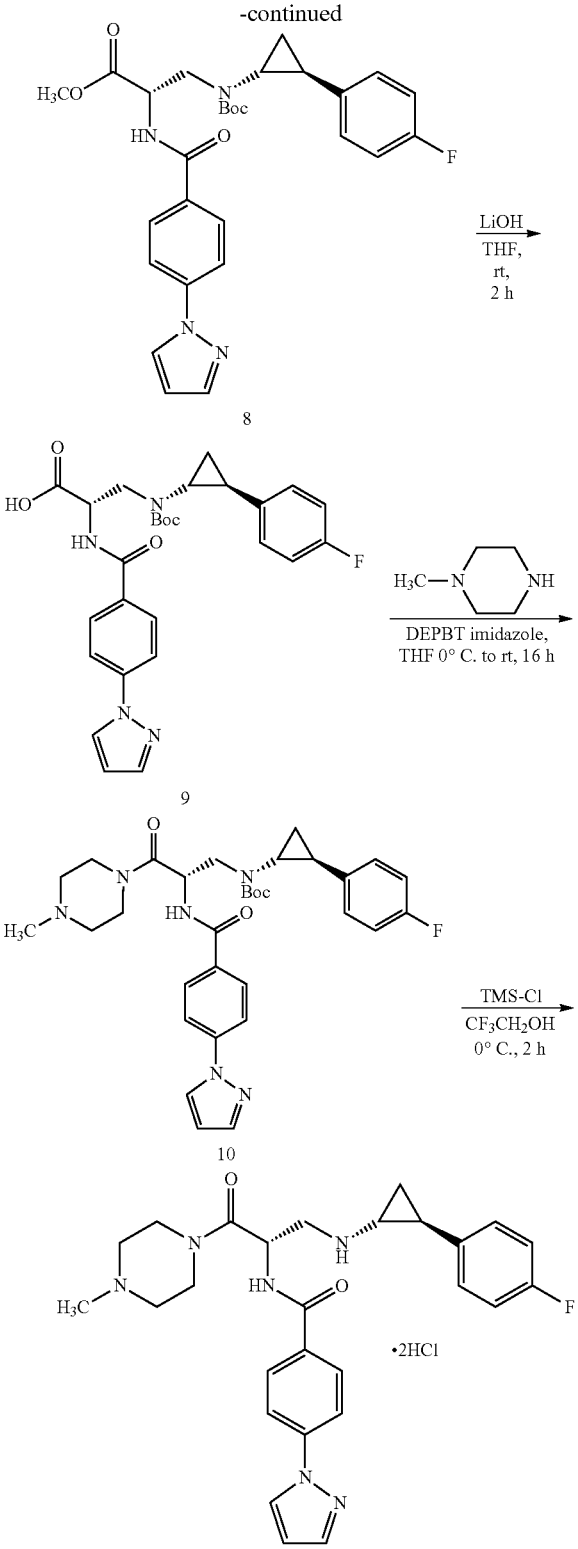

Synthesis of 182

(S)-methyl 1-tritylaziridine-2-carboxylate [2]

To a solution of (S)-methyl 3-hydroxy-2-(tritylamino) propanoate (1, 2.00 g, 5.54 mmol) in chloroform (30 mL) was added with triethylamine (2.08 mL, 14.95 mmol) and dimethylaminopyridine (67 mg, 0.55 mmol) followed by methanesulfonyl chloride (888 mg, 7.75 mmol). The reaction mixture was stirred under nitrogen atmosphere at 65° C. for 16 h. After this time, the reaction was cooled to room temperature and diluted with water (50 mL). The layers were separated and the aqueous layer was extracted with ethyl acetate (2×100 mL). The combined organic layers were washed with brine (100 mL), dried over anhydrous sodium sulfate and concentrated under reduced pressure. The resulting residue was recrystallized from ethanol to afford 2 (1.20 g, 63%) as an off-white solid.

(S)-methyl aziridine-2-carboxylate Trifluoroacetic Acid Salt [3]

To a stirred solution of 2 (1.00 g, 2.91 mmol) in a mixture of methanol (3.0 mL) and chloroform (3.0 mL) at 0° C. was added trifluoroacetic acid (2.1 mL). The mixture was stirred under nitrogen atmosphere at room temperature for 2 h. After this time, the reaction mixture was concentrated under reduced pressure to afford crude 3 (600 mg) as a colorless liquid, which was used without further purification.

4-(1H-pyrazol-1-yl)benzoyl Chloride[4]

To a solution of 4-(1H-pyrazol-1-yl)benzoic acid (400 mg, 2.12 mmol) in methylene chloride (8.0 mL) was added oxalyl chloride (270 mg, 2.12 mmol) followed by dimethylformamide (0.05 mL). The reaction mixture was stirred under nitrogen atmosphere at room temperature for 2 h. After this time, the reaction mixture was concentrated under reduced pressure to afford crude 4 (400 mg, IN-MRG-K-163-1) as an off white solid, which was used without further purification.

(S)-methyl 1-[4-(1H-pyrazol-1-yl)benzoyl]aziridine-2-carboxylate [5]

To a solution of 3 (600 mg, 3.03 mmol) in chloroform (10 mL) was added 4 (756 mg, 3.63 mmol), followed by triethylamine (1.0 mL, 7.57 mmol) and the reaction mixture was stirred under nitrogen atmosphere at room temperature for 16 h. After this time, the reaction mixture was diluted with water (10 mL). The layers were separated and the aqueous layer was extracted with chloroform (2×20 mL). The combined organic layers were washed with brine (20 mL), dried over anhydrous sodium sulfate and concentrated under reduced pressure. The resulting residue was purified by chromatography (silica gel, CH$_3$OH/CH$_2$Cl$_2$, gradient) to afford 5 [480 mg, 60% for two steps] as an off white solid.

(S)-methyl 2-[4-(1H-pyrazol-1-yl)benzamido]-3-{[(1R,2S)-2-(4-fluorophenyl)cyclopropyl]amino}propanoate [7]

To a solution of 5 (450 mg, 1.66 mmol) in acetonitrile (10 mL) was added 6 (776 mg, 4.15 mmol) followed by triethylamine (0.6 mL, 4.15 mmol). The reaction mixture was stirred under nitrogen atmosphere at 80° C. for 16 h. After this time, the reaction mixture was cooled and diluted with water (10 mL). The layers were separated and the aqueous layer was extracted with ethyl acetate (2×20 mL). The combined organic layers were washed with brine (10 mL), dried over anhydrous sodium sulfate and concentrated under reduced pressure. The resulting residue was purified by MS-triggered preparative HPLC to afford 7•TFA (100 mg, 14%) as a brown red gum. MS-triggered Preparative HPLC purifications were performed using a Sunfire C18 column, OBD, 10μ (30×250 mm) with UV detection at 220 nm using a solvent gradient program (15% to 55% acetonitrile/water with 0.1% trifluoroacetic acid).

(S)-methyl 2-[4-(1H-pyrazol-1-yl)benzamido]-3-[(tertbutoxycarbonyl)[(1R,2S)-2-(4-fluorophenyl)cyclopropyl]amino]propanoate [8]

To a solution of 7 (100 mg, 0.23 mmol) in methylene chloride (5.0 mL) was added Boc anhydride (0.7 mL, 0.35 mmol) followed by triethylamine (0.06 mL, 0.47 mmol). The reaction mixture was stirred under nitrogen atmosphere at room temperature for 2 h. After this time, the reaction mixture was diluted with water (5.0 mL). The layers were separated and the aqueous layer was extracted with chloroform (2×10 mL). The combined organic layers were washed with brine (5.0 mL), dried over anhydrous sodium sulfate and concentrated under reduced pressure. The resulting residue was purified by chromatography (silica gel, EtOAc/hexanes, gradient) to afford 8 (60 mg, 48%) as an off white solid.

(S)-2-[4-(1H-pyrazol-1-yl)benzamido]-3-[(tert-butoxycarbonyl)[(1R,2S)-2-(4-fluorophenyl)cyclopropyl]amino]propanoic Acid [9]

To a solution of 8 (60 mg, 0.11 mmol) in a mixture of tetrahydrofuran (2.0 mL) and water (1.0 mL) was added lithium hydroxide monohydrate (8.9 mg, 0.17 mmol). The reaction mixture was stirred at room temperature for 2 h. After this time, the reaction mixture was diluted with water (5 mL) and acidified with 2 N aqueous HCl to pH 5. The mixture was extracted with ethyl acetate (2×10 mL). The combined organic layers were washed with brine (10 mL), dried over anhydrous Na$_2$SO$_4$ and concentrated under reduced pressure to afford 9 (50 mg, 86%) as an off white solid.

tert-butyl [(S)-2-[4-(1H-pyrazol-1-yl)benzamido]-3-(4-methylpiperazin-1-yl)-3-oxopropyl][(1R,2S)-2-(4-fluorophenyl)cyclopropyl]carbamate [10]

To a solution of 9 (50 mg, 0.09 mmol) in tetrahydrofuran (3.0 mL) was added (3-(diethoxyphosphoryloxy)-1,2,3-benzotriazin-4(3H)-one) (DEPBT, 44 mg, 0.14 mmol) followed by imidazole (10 mg, 0.147 mmol). The reaction mixture was stirred under nitrogen atmosphere at 0° C. for 40 min. After this time, 1-methylpiperazine (15 mg, 0.14 mmol) was added at 0° C. The reaction was warmed to room temperature and stirred under nitrogen atmosphere for 16 h. After this time, the reaction mixture was filtered through diatomaceous earth and rinsed with ethyl acetate (10 mL). The filtrate was washed with brine (5.0 mL), dried over anhydrous sodium sulfate and concentrated under reduced pressure. The resulting residue was purified by chromatography (silica gel, CH$_3$OH/CH$_2$Cl$_2$, gradient) to afford 10 (30 mg, 51%) as an off white solid.

N—[(S)-3-{[(1R,2S)-2-(4-fluorophenyl)cyclopropyl]amino}-1-(4-methylpiperazin-1-yl)-1-oxopropan-2-yl]-4-(1H-pyrazol-1-yl)benzamide Hydrochloride Salt To a solution of 10 (30 mg, 0.05 mmol) in trifluoroethanol (3.0 mL) was added chlorotrimethylsilane (0.1 mL). The reaction mixture was stirred under nitrogen atmosphere at 0° C. for 2 h. After this time, the reaction mixture was concentrated under reduced pressure. The resulting residue was triturated with methyl tert-butyl ether and pentanes to afford the product (20 mg, 71%) as a hygroscopic off white solid.

Example 186

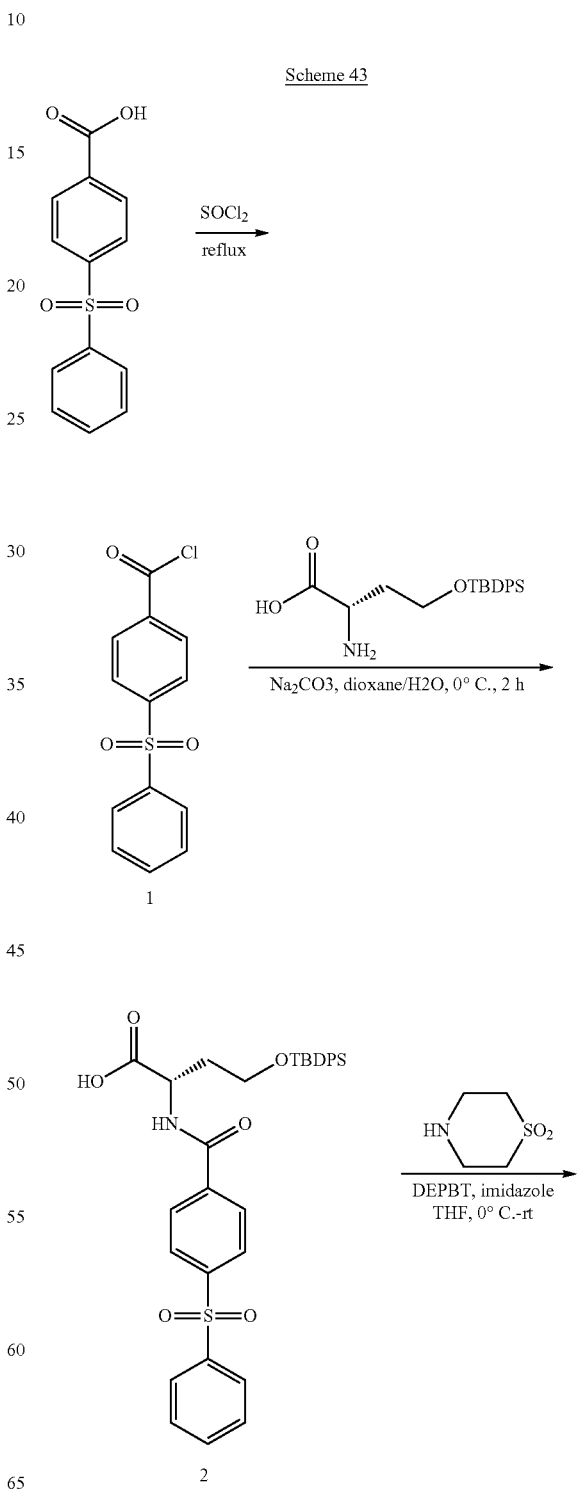

277
-continued

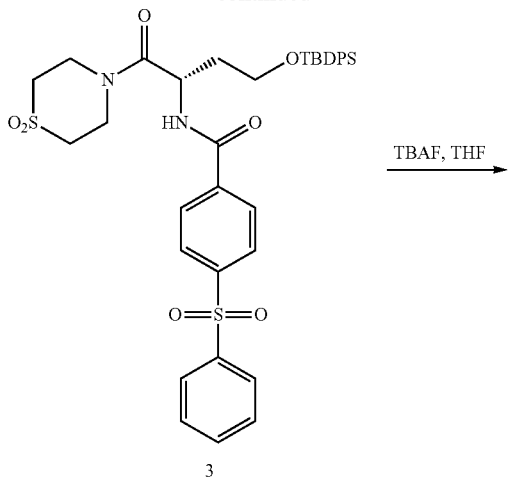

3

TBAF, THF →

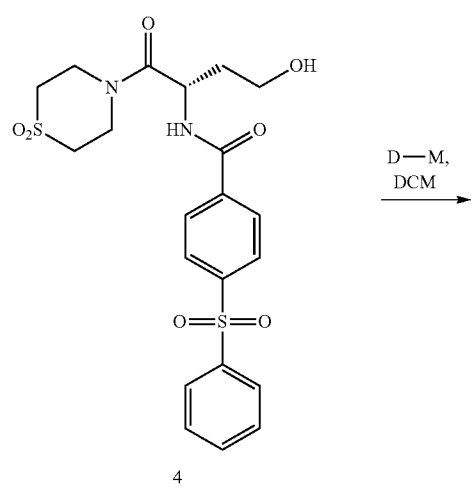

4

D—M, DCM →

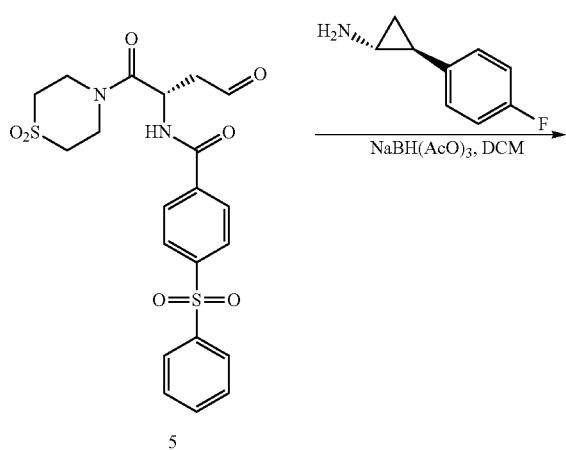

5

NaBH(AcO)₃, DCM →

278
-continued

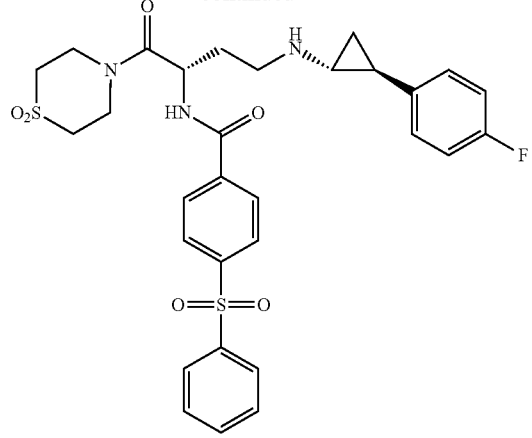

Synthesis of 186

Into a 250-mL round-bottom flask, was placed 4-(phenylsulfonyl)benzoic acid (2 g, 7.63 mmol, 1.00 equiv), sulfurooyl dichloride (20 mL). The resulting solution was stirred for 16 h at 80° C. in an oil bath. The resulting mixture was concentrated under vacuum. This resulted in 2 g (93%) of (1) as a off-white solid.

Into a 1000-mL round-bottom flask, was placed a solution of (2S)-2-amino-4-[(tert-butyldiphenylsilyl)oxy]butanoic acid (2.12 g, 5.93 mmol, 1.00 equiv) in H₂O (50 ml), dioxane (50 mL), a solution of sodium carbonate (1.89 g, 17.79 mmol, 3 equiv) in water (20 mL). This was followed by the addition of a solution of (1) (2 g, 7.12 mmol, 1.20 equiv) in dioxane (40 mL) dropwise with stirring at 0° C. The resulting solution was stirred for 1 h at 0° C. in a water/ice bath. The pH value of the solution was adjusted to 2 with hydrogen chloride (2 mol/L). The resulting solution was extracted with 3×100 mL of ethyl acetate and the organic layers combined. The resulting mixture was washed with 1×100 mL of brine. The mixture was dried over anhydrous sodium sulfate. The resulting mixture was concentrated under vacuum. The resulting mixture was washed with 20 mL of DCM. The solids were filtered out. This resulted in 3 g (70%) of (2) as yellow oil.

Into a 100-mL 3-necked round-bottom flask, was placed a solution of (2) (3 g, 4.98 mmol, 1.00 equiv) in tetrahydrofuran (100 mL), DEPBT (2235 mg, 7.48 mmol, 1.50 equiv). This was followed by the addition of imidazole (508 mg, 7.48 mmol, 1.50 equiv), stirred for 40 mins at 0° C. To this was added a solution of Thiomorpholine-1,1-dioxide (807 mg, 5.98 mmol, 1.20 equiv) in tetrahydrofuran (10 mL) dropwise with stirring at 0° C. The resulting solution was stirred for 16 h at 25° C. The solids were filtered out. The resulting mixture was concentrated under vacuum. The resulting solution was diluted with 100 mL of H₂O. The resulting solution was extracted with 3×100 mL of ethyl acetate and the organic layers combined and dried over anhydrous sodium sulfate. The residue was applied onto a silica gel column with ethyl acetate/petroleum ether (1:3). The collected fractions were combined and concentrated under vacuum. This resulted in 2.5 g (70%) of (3) as yellow oil.

Into a 50-mL round-bottom flask, was placed a solution of (3) (1500 mg, 2.09 mmol, 1.00 equiv) in tetrahydrofuran (30 mL), TBAF (4.2 mL, 2.00 equiv). The resulting solution was stirred for 16 h at 25° C. The resulting mixture was concentrated under vacuum. The resulting solution was diluted with 50 mL of H₂O. The resulting solution was extracted with 3×50 mL of ethyl acetate and the organic layers combined and dried over anhydrous sodium sulfate. The residue was applied onto a silica gel column with ethyl acetate. The collected fractions were combined and concentrated under vacuum. This resulted in 700 mg (70%) of (4) as yellow oil.

Into a 25-mL round-bottom flask, was placed a solution of (4) (200 mg, 0.42 mmol, 1.00 equiv) in dichloromethane (20 mL), Dess-Martin (353 mg, 0.83 mmol, 2.00 equiv). The resulting solution was stirred for 30 min at 25° C. The residue was applied onto a silica gel column with ethyl acetate. The collected fractions were combined and concentrated under vacuum. This resulted in 150 mg (75%) of (5) as a light yellow solid.

Into a 25-mL round-bottom flask, was placed a solution of (5) (150 mg, 0.31 mmol, 1.00 equiv) in dichloromethane (20 mL), (1R,2S)-2-(4-fluorophenyl)cyclopropan-1-amine (57 mg, 0.38 mmol, 1.20 equiv), NaBH(AcO)$_3$ (159 mg, 0.75 mmol, 2.40 equiv). The resulting solution was stirred for 10 min at 25° C. The resulting solution was diluted with 30 mL of H$_2$O. The resulting solution was extracted with 2×20 mL of dichloromethane and the organic layers combined and dried over anhydrous sodium sulfate and concentrated under vacuum. The crude product was purified by Prep-HPLC. This resulted in 19.2 mg (10%) of N—((S)-4-((1R,2S)-2-(4-fluorophenyl)cyclopropylamino)-1-oxo-1-(thiomorpholino-4,4-dioxide-1-yl)-butan-2-yl)-4-(phenylsulfonyl)benzamide as a white solid.

Example 187

Scheme 44

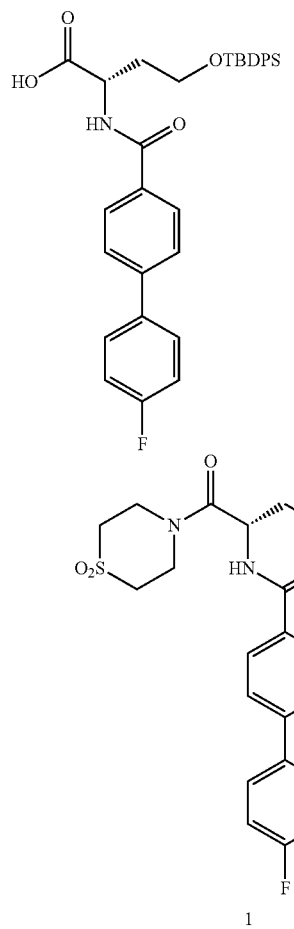

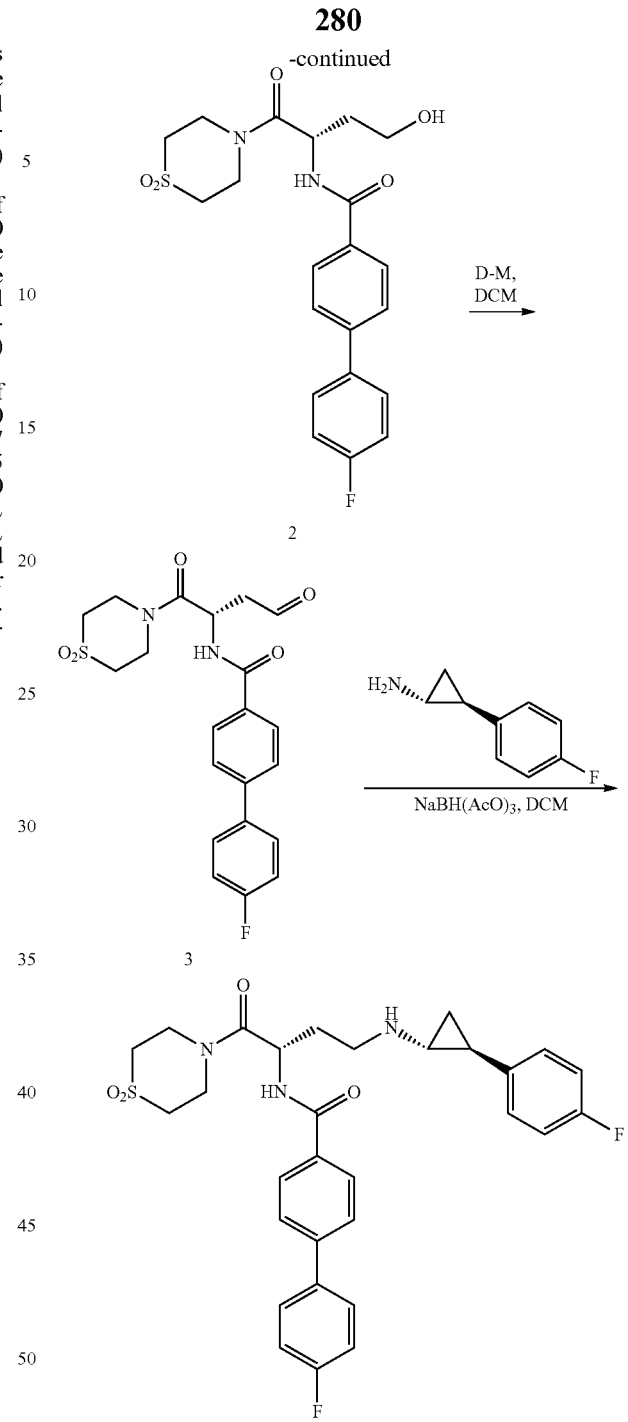

Synthesis of 187

Into a 250-mL round-bottom flask, was placed a solution of (2S)-4-[(tert-butyldiphenylsilyl)oxy]-2-[[4-(4-fluorophenyl)phenyl]formamido]butanoic acid (2 g, 3.60 mmol, 1.00 equiv) in tetrahydrofuran (50 mL), DEPBT (1.62 g, 5.41 mmol, 1.50 equiv). This was followed by the addition of imidazole (370 mg, 5.44 mmol, 1.50 equiv). stirred for 40 min at 0° C. To this was added a solution of thiomorpholine-1,1-dioxide (890 mg, 6.58 mmol, 1.50 equiv) in tetrahydrofuran (20 mL) dropwise with stirring at 0° C. in 30 min. The resulting solution was stirred for 16 h at 25° C. The resulting mixture was concentrated under vacuum. The resulting solution was diluted with 50 mL of H₂O. The resulting solution was extracted with 3×50 mL of ethyl acetate and the organic layers combined. The residue was applied onto a silica gel column with ethyl acetate/petroleum ether (1:1). This resulted in 2 g (82%) of (1) as a off-white solid.

Into a 100-mL round-bottom flask, was placed a solution of N-[(2S)-4-[(tert-butyldiphenylsilyl)oxy]-1-oxo-1-(thiomorpholine-1,1-dioxide-4-yl]-butan-2-yl]-4-(4-fluorophenyl)-benzamide (2 g, 2.97 mmol, 1.00 equiv) in tetrahydrofuran (10 mL), TBAF (6 mL, 2.00 equiv). The resulting solution was stirred for 16 h at 25° C. The resulting mixture was concentrated under vacuum. The residue was applied onto a silica gel column with ethyl acetate. This resulted in 1 g (77%) of (2) as a off-white solid.

Into a 50-mL round-bottom flask, was placed a solution of 4-(4-fluorophenyl)-N-[(2S)-4-hydroxy-1-oxo-1-(thiomorpholine-1,1-dioxide-4-yl)-butan-2-yl]benzamide (200 mg, 0.46 mmol, 1.00 equiv) in dichloromethane (10 mL), Dess-Martin (389 mg, 0.92 mmol, 2.00 equiv). The resulting solution was stirred for 1 h at 25° C. The residue was applied onto a silica gel column with ethyl acetate. The collected fractions were combined and concentrated under vacuum. This resulted in 150 mg (75%) of (3) as yellow oil.

Into a 50-mL round-bottom flask, was placed a solution of N-[(2S)-1,4-dioxo-1-(thiomorpholine-1,1-dioxide-4-yl)-butan-2-yl]-4-(4-fluorophenyl)benzamide (150 mg, 0.35 mmol, 1.00 equiv) in dichloromethane (15 mL), (1R,2S)-2-(4-fluorophenyl)cyclopropan-1-amine (63.2 mg, 0.42 mmol, 1.20 equiv), NaBH(AcO)₃ (147 mg, 0.69 mmol, 2.00 equiv). The resulting solution was stirred for 10 min at 28° C. The resulting mixture was concentrated under vacuum. The crude product was purified by Prep-HPLC. This resulted in 37.1 mg (19%) of 4'-fluoro-N—((S)-4-((1R,2S)-2-(4-fluorophenyl)cyclopropylamino)-1-oxo-1-(thiomorpholino-4,4-dioxide-1-yl)-butan-2-yl)biphenyl-4-carboxamide as a white solid.

Example 188

Scheme 45

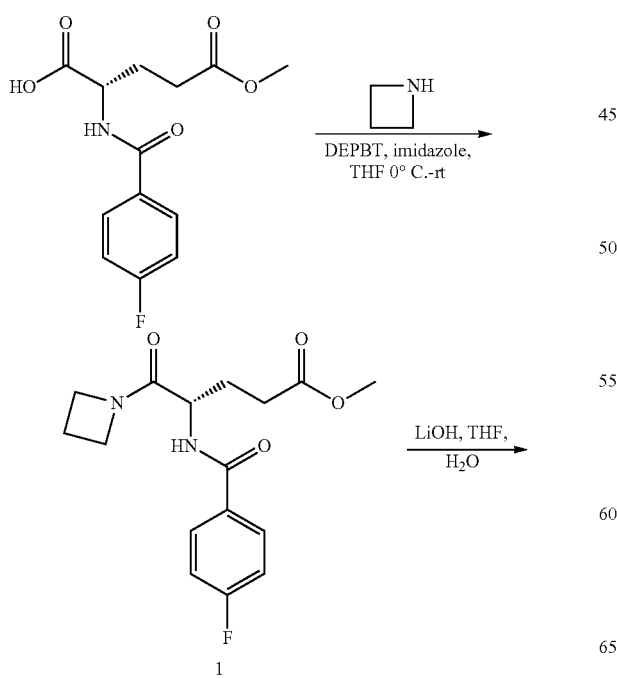

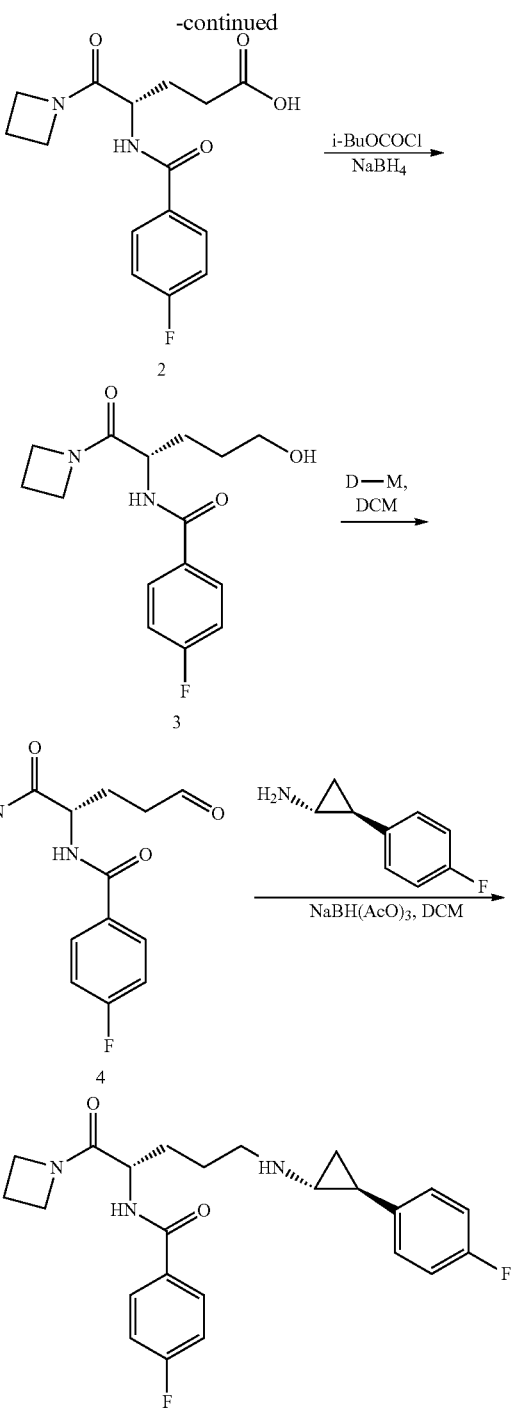

Synthesis of 188

Into a 500-mL round-bottom flask, was placed a solution of (2S)-2-[(4-fluorophenyl)formamido]-5-methoxy-5-oxopentanoic acid (3.4 g, 12.00 mmol, 1.00 equiv) in tetrahydrofuran (200 mL), DEPBT (5.4 g, 1.50 equiv). This was followed by the addition of imidazole (1.2 g, 1.50 equiv). stirred for 40 min at 0° C. To this was added azetidine (1.1 g, 19.27 mmol, 1.50 equiv) dropwise with stirring at 0° C. in 10 min. The resulting solution was stirred for 16 h at 20° C. The resulting mixture was concentrated under vacuum. The residue was applied onto a silica gel column with ethyl acetate/petroleum ether (10:1). The collected fractions were combined and concentrated under vacuum. This resulted in 3.5 g (90%) of PH-(1) as yellow oil.

Into a 250-mL round-bottom flask, was placed a solution of methyl (4S)-5-(azetidin-1-yl)-4-[(4-fluorophenyl)formamido]-5-oxopentanoate (2 g, 6.20 mmol, 1.00 equiv) in tetrahydrofuran (100 mL), a solution of lithiumol (270 mg, 11.27 mmol, 1.80 equiv) in water (20 mL). The resulting solution was stirred for 2 h at 20° C. The resulting mixture was concentrated under vacuum. This resulted in 1.5 g (78%) of (2) as a light yellow solid. Into a 100-mL round-bottom flask, was placed a solution of (4S)-5-(azetidin-1-yl)-4-[(4-fluorophenyl)formamido]-5-oxopentanoic acid (500 mg, 1.62 mmol, 1.00 equiv) in tetrahydrofuran (20 mL). This was followed by the addition of NMM (350 mg, 3.46 mmol, 2.10 equiv). stirred for 40 min at 0 degrees. To this was added chloro(2-methylpropoxy)methanone (470 mg, 3.44 mmol, 2.10 equiv). stirred for 60 min at −20° C. To the mixture was added NaBH$_4$ (650 mg, 17.18 mmol, 10.00 equiv), methanol (5 mL). The resulting solution was stirred for 1 h at 30° C. in an oil bath. The residue was applied onto a silica gel column with ethyl acetate/petroleum ether (10:1). The collected fractions were combined and concentrated under vacuum. This resulted in 350 mg (73%) of (3) as yellow oil.

Into a 100-mL round-bottom flask, was placed a solution of N-[(2S)-1-(azetidin-1-yl)-5-hydroxy-1-oxopentan-2-yl]-4-fluorobenzamide (350 mg, 1.19 mmol, 1.00 equiv) in dichloromethane (20 mL), Dess-Martin (1 g, 2.36 mmol, 2.00 equiv). The resulting solution was stirred for 60 min at 30° C. in an oil bath. The residue was applied onto a silica gel column with ethyl acetate/petroleum ether (10:1). The collected fractions were combined and concentrated under vacuum. This resulted in 230 mg (66%) of (4) as yellow oil.

Into a 100-mL round-bottom flask, was placed a solution of N-[(2S)-1-(azetidin-1-yl)-1,5-dioxopentan-2-yl]-4-fluorobenzamide (230 mg, 0.79 mmol, 1.00 equiv) in dichloromethane (20 mL), (1R,2S)-2-(4-fluorophenyl)cyclopropan-1-amine (176 mg, 1.16 mmol, 1.20 equiv), NaBH(AcO)$_3$ (422 mg, 2.40 equiv). The resulting solution was stirred for 5 min at 20° C. The resulting mixture was concentrated under vacuum. The crude product (1 mL) was purified by Flash-Prep-HPLC. This resulted in 86 mg (26%) of N—((S)-1-(azetidin-1-yl)-5-((1R,2S)-2-(4-fluorophenyl)cyclopropylamino)-1-oxopentan-2-yl)-4-fluorobenzamide as a off-white solid.

The following table discloses physical data for compounds; examples not listed above were synthesized according to the methods disclosed above, form example according to the identified scheme. Such compounds may also be synthesized by those of skill in the art according to methods known in the art.

TABLE 2

Physical Data and Synthetic Methods

| Ex # | Scheme | MS | 1H NMR |
|---|---|---|---|
| 1 | 1 | 492 [M + H]$^+$ | (300 MHz, CD$_3$OD-d$_4$) δ ppm: 8.61 (d, J = 1.3 Hz, 1H), 8.06 (d, J = 8.6 Hz, 2H), 8.02-7.94 (m, 2H), 7.90 (d, J = 1.3 Hz, 1H), 7.06 (ddt, J = 8.0, 5.3, 2.7 Hz, 2H), 6.93 (t, J = 8.8 Hz, 2H), 5.33-5.17 (m, 1H), 3.78-3.41 (m, 4H), 3.07 (dd, J = 6.9, 5.4 Hz, 2H), 2.55-2.28 (m, 5H), 2.26 (s, 3H), 1.90 (ddt, J = 9.1, 5.9, 2.8 Hz, 1H), 1.15-0.87 (m, 2H). |
| 2 | 1 | 503 (M + 1) | (400 MHz, Methanol-d$_4$) δ 8.88 (d, J = 4.9 Hz, 2H), 8.55-8.47 (m, 2H), 8.04-7.96 (m, 2H), 7.40 (t, J = 4.9 Hz, 1H), 7.10 (ddd, J = 8.2, 5.2, 2.5 Hz, 2H), 6.96 (td, J = 8.8, 1.6 Hz, 2H), 5.34-5.23 (m, 1H), 3.71 (s, 2H), 3.64 (d, J = 16.6 Hz, 1H), 3.59-3.51 (m, 3H), 3.18-3.02 (m, 2H), 2.54-2.31 (m, 5H), 2.29 (s, 3H), 1.93 (ddt, J = 9.4, 6.2, 3.4 Hz, 1H), 1.16-0.95 (m, 2H). |
| 3 | 1 | 450 [M + H]$^+$ | (300 MHz, CD$_3$OD-d$_4$) δ ppm: 8.03-7.92 (m, 2H), 7.87-7.76 (m, 2H), 7.05 (ddd, J = 8.4, 5.3, 2.6 Hz, 2H), 6.98-6.86 (m, 2H), 5.30-5.11 (m, 1H), 3.73-3.42 (m, 4H), 3.05 (dd, J = 7.2, 5.4 Hz, 2H), 2.49-2.28 (m, 5H), 2.25 (s, 3H), 1.89 (dt, J = 9.3, 4.4 Hz, 1H), 1.15-0.88 (m, 2H). |
| 4 | 2 | 550 [M + H]$^+$ | (300 MHz, MeOD-d$_4$) δ ppm: 8.01(m, 2H), 7.81-7.77(m, 2H), 7.71-7.66(m, 2H), 7.50-7.45(m, 2H), 7.42-7.38(m, 1H), 7.22-7.17(m, 2H), 7.10-7.01(m, 2H), 5.28-5.20(m, 1H), 4.39-4.31(m, 1H), 4.19-4.10(m, 1H), 3.78-3.98(m, 2H), 3.36-3.32(m, 2H), 3.21-3.11(m, 4H), 3.05-2.98(m, 1H), 2.57-2.51(m, 1H), 2.39-2.22(m, 1H), 2.21-2.11(m, 1H), 1.57-1.49(m, 1H), 1.42-1.37(m, 1H) |
| 5 | 2 | 515 [M + H]$^+$ | (300 MHz, Methanol-d$_4$) δ 7.97-7.88 (m, 2H), 7.72-7.63 (m, 4H), 7.47-7.33 (m, 4H), 7.05-7.00(m, 2H), 6.93-6.88 (m, 2H), 5.14-5.10 (m, 1H), 3.75-3.50 (m, 4H), 2.84-2.79 (m, 2H), 2.44-2.40 (m, 4H), 2.32-2.25 (m, 4H), 2.09-1.85 (m, 3H), 1.05-1.00 (m, 1H), 0.97-0.93 (m, 1H) |
| 6 | 2 | [M + H]+472 | (300 MHz, MeOD): δ d7.88~7.90(d, J = 6.0 Hz, 2H), 7.62~7.71(m, 4H), 7.41~7.46(t, J = 7.35 Hz, 2H), 7.35~7.37(m, 1H), 7.00~7.05(m, 2H), 6.88~6.93(t, J = 8.7 Hz, 2H), 4.61~4.66(m, 1H), 4.47~4.49(m, 1H), 4.29~4.31(m, 1H), 4.00~4.05(m, 2H), 2.81~2.85(t, J = 6.9 Hz, 2H), 2.26~2.34(m, 3H), 1.88~2.01(m, 3H), 0.93~1.06(m, 2H). |
| 7 | 2 | 597 [M + H]$^+$ | (300 MHz, MeOD-d$_4$) δ ppm: 8.00-7.92(m, 2H), 7.79-7.68(m, 4H), 7.29-7.20 (m, 4H), 7.07-6.98 (m, 2H), 5.23-5.19 (m, 1H), 3.98-3.87 (m, 1H), 3.86-3.72(m, 1H), 3.69- |

TABLE 2-continued

Physical Data and Synthetic Methods

| Ex # | Scheme | MS | 1H NMR |
|---|---|---|---|
| | | | 3.59 (m, 2H), 3.37 (m, 4H), 3.26-3.10 (m, 2H), 3.02-2.95 (m, 1H), 2.82(s, 3H), 2.57-2.49 (m, 1H), 2.39-2.25 (m, 1H), 2.21-2.09 (m, 1H), 1.55-1.47(m, 1H), 1.42-1.35(m, 1H) |
| 8 | 2 | 550 [M + H]$^+$ | (300 MHz, Methanol-d$_4$) δ 8.15-8.14 (m, 1H), 7.89-.786 (m, 2H), 7.70-7.68 (m, 2H), 7.63-7.59 (m, 1H), 7.51-7.47 (m, 2H), 7.42-7.41 (m, 2H), 7.23-7.20 (m, 2H), 7.06-7.02 (m, 2H), 5.28-5.24 (m, 1H), 4.39-4.34 (m, 1H), 4.21-4.13 (m, 1H), 3.96-3.81 (m, 2H), 3.37-3.32 (m, 2H), 3.19-3.16 (m, 4H), 3.02-3.00 (m, 1H), 2.52-2.49 (m, 1H), 2.38-2.31 (m, 1H), 2.26-2.18 (m, 1H), 1.55-1.52 (m, 1H), 1.41-1.39 (m, 1H) |
| 9 | 2 | [M + H]+540 | (300 MHz, DMSO): 8.44 (d, J = 8 Hz, 2H), 7.70-7.51 (m, 4H), 7.50-7.40 (m, 2H), 7.40-7.28 (m, 3H), 7.08-6.96 (m, 4H), 4.90-4.70 (m, 1H), 3.75-3.45 (m, 6H), 3.20-2.95 (m, 4H), 2.88 (s, 3H), 2.60-2.55 (m, 2H), 2.20~2.05 (m, 1H), 1.82-1.65 (m, 3H), 0.95-0.70 (m, 2H) |
| 10 | 2 | 567 [M + H]$^+$ | (300 MHz, Methanol-d$_4$) δ 7.78-7.75 (m, 4H), 7.44-7.40 (m, 3H), 6.95-6.85 (m, 4H), 4.92-4.81(m, 1H), 3.90-3.68 (m, 4H), 3.54-3.36 (m, 2H), 3.23-3.11 (m, 2H), 3.03-2.86 (m, 2H), 2.68-2.63 (m, 5H), 2.11-2.07 (m, 1H), 1.88-1.73 (m, 3H), 0.93-0.88 (m, 1H), 0.86-0.79 (m, 1H) |
| 11 | 2 | 479 [M + H]$^+$ | (300 MHz, MeOD-d$_4$) δ ppm: 9.34 (s, 1H), 9.00 (s, 1H), 8.23-8.10 (m, 2H), 8.05-7.90 (m, 1H), 7.90-7.72 (m, 1H), 7.30-7.12 (m, 2H), 7.12-6.93 (m, 2H), 5.40-5.18 (m, 1H), 4.00-3.80 (m, 2H), 3.80-3.60 (m, 2H), 3.45-3.35 (m, 4H), 3.30-3.18 (m, 2H), 3.10-2.98 (m, 1H), 2.86 (s, 3H), 2.62-2.50 (m, 1H), 2.58-2.15 (m, 2H), 1.65-1.50 (m, 1H), 150-1.31(m, 1H) |
| 12 | 3 | [M + H]$^+$ 540 | (300 MHz, MeOD-d$_4$) δ ppm: 8.31 (s, 1H), 8.05-7.84 (m, 4H), 7.75 (d, J = 1.7 Hz, 1H), 7.23-7.12 (m, 2H), 7.08-6.94 (m, 2H), 6.50-6.62 (m, 1H), 5.20-5.30 (m, 1H), 4.42-4.25 (m, 1H), 4.20-4.01 (m, 1H), 3.98-3.72 (m, 2H), 3.29-3.35 (m, 2H), 3.10-3.20 (m, 4H), 3.05-2.97 (m, 1H), 2.58-2.42 (m, 1H), 2.39-2.05 (m, 2H), 1.58-1.42 (m, 1H), 1.42-1.30 (m, 1H). |
| 13 | 2 | 548[M + H]$^+$ | (300 MHz, CD$_3$OD-d$_4$) δ ppm: 7.91-7.82 (m, 2H), 7.45-7.40 (m, 2H), 7.23-7.15 (m, , 1H), 7.10-7.00 (m, 6H), 7.00-6.88 (m, 2H), 5.15-5.10 (m, 1H), 4.55-4.28 (m, 2H), 4.01-3.85 (m, 1H), 3.75-3.60 (m, 1H), 3.45-3.35(m, 1H), 3.25-3.05 (m, 3H), 3.95-3.75 (m, 2H), 3.35-3.21 (m, 1H), 2.11-1.85 (m, 3H), 1.12-0.85 (m, 2H) |
| 14 | 2 | 553 [M + H]$^+$ | (400 MHz, Methanol-d$_4$) δ 8.47-8.23 (m, 1H), 8.08-7.52 (m, 2H), 7.75-7.68 (m, 1H), 7.63-7.49(m, 3H), 7.08-6.91 (m, 4H), 5.31-5.29 (M, 1H), 4.13-3.89 (m, 2H), 3.87-3.71 (m, 1H), 3.64-3.47 (m, 2H), 3.26-3.16 (m, 1H), 2.95-2.80 (m, 6H), 2.37-2.31 (m, 1H), 2.24-.86 (m, 4H), 1.12-1.01(m, 1H), 1.00-0.88 (m, 1H) |
| 15 | 2 | 583 [M + H]$^+$ | (400 MHz, MeOD-d$_4$) δ ppm: 8.44 (s, 1H), 8.22-7.71 (m, 4H), 7.73-7.42 (m, 2H), 7.25 (dd, J = 8.3, 5.1 Hz, 1H), 7.20-6.77 (m, 3H), 4.77 (t, J = 9.4 Hz, 1H), 3.95 (s, 1H), 3.63-3.47 (m, 2H), 3.25-2.70 (m, 3H), 2.64-2.44 (m, 1H), 2.35 (dq, J = 9.2, 4.8, 4.2 Hz, 1H), 2.24-1.85 (m, 2H), 1.62-0.90 (m, 2H). |
| 16 | 2 | [M + H]+540 | (300 MHz, MeOD): 8.10-7.95 (m, 2H), 7.92-7.75 (m, 2H), 7.10-6.90 (m, 4H), 5.20-5.10 (m, 1H), 4.08~3.88 (m, 2H), 3.85-3.68 (m, 1H), 3.65~3.50 (m, 2H), 3.26-3.10 (m, 1H), 2.95~2.81 (m, 5H), 2.40~2.30(m, 1H), 2.20~1.90(m, 3H), 1.15~1.00 (m, 1H), 1.00~0.92 (m, 1H). |
| 17 | 2 | 579 [M + H]$^+$ | (300 MHz, Methanol-d$_4$) δ 8.11-8.10 (m, 1H), 7.84-.781 (m, 2H), 7.65-7.62 (m, 2H), 7.58-7.52 (m, 1H), 7.46-7.41 (m, 2H), 7.37-7.33 (m, 1H), 7.18-7.13 (m, 2H), 7.01-6.95 (m, 2H), 5.20-5.16 (m, 1H), 3.91-3.73 (m, 2H), 3.63-3.55 (m, 2H), 3.41-3.29 (m, 3H), 3.26-3.21 (m, 1H), 3.20-3.09 (m, 2H), 2.98-2.94 (m, 1H), 2.78 (s, 3H), 2.53-2.44 (m, 1H), 2.37-2.10 (m, 2H), 1.51-1.48 (m, 1H), 1.37-1.33(m, 1H) |
| 18 | 2 | 591[M + H]$^+$ | (400 MHz, MeOD-d$_4$) δ ppm: 7.98 (dd, J = 8.2, 1.4 Hz, 2H), 7.78 (d, J = 8.0 Hz, 2H), 7.69 (d, J = 7.5 Hz, 2H), 7.49 (t, J = 7.5 Hz, 1H), 7.45-7.38 (m, 1H), 7.12 (d, J = 8.2 Hz, 2H), 6.87 (d, J = 8.4 Hz, 2H), 5.22 (dd, J = 8.1, 5.4 Hz, 1H), 4.93 (s, 1H), 3.90 (d, J = 13.3 Hz, 1H), 3.77 (d, J = 1.3 Hz, 4H), 3.65 (dd, J = 13.1, 6.6 Hz, 2H), 3.36 (s, 3H), 3.19 (q, J = 10.0 Hz, 2H), 2.95 (dt, J = 7.9, 4.0 Hz, 1H), 2.85 (s, 3H), 2.48 (ddd, J = 10.3, 6.6, 3.5 Hz, |

TABLE 2-continued

Physical Data and Synthetic Methods

| Ex # | Scheme | MS | 1H NMR |
|---|---|---|---|
| | | | 1H), 2.33 (dq, J = 13.8, 7.3 Hz, 1H), 2.20 (dq, J = 14.4, 7.3 Hz, 1H), 1.50 (ddd, J = 10.7, 6.7, 4.4 Hz, 1H), 1.35 (q, J = 7.1 Hz, 1H). |
| 19 | 2 | 562 [M + H]+ | (300 MHz, Methanol-d4) δ 7.9-7.88 (m, 2H), 7.71-764 (m, 4H), 7.46-7.43 (m, 2H), 7.41-7.35 (m, 2H), 6.95-6.92 (m, 2H), 6.76-6.73 (m, 2H), 5.14-5.09 (m, 1H), 4.45-4.27 (m, 2H), 3.93-3.84 (m, 1H), 3.72-3.61 (m, 4H), 3.45-3.33 (m, 1H), 3.19-3.04 (m, 3H), 2.88-2.83 (m, 2H), 2.25-2.22 (m, 1H), 2.02-1.96 (m, 2H), 1.84-1.81 (m, 1H), 1.00-0.93 (m, 1H), 0.91-0.88 (m, 1H) |
| 20 | 4 | 657 [M + H]+ | (400 MHz, MeOD-d4) δ ppm: 8.09 (d, J = 8.1 Hz, 2H), 8.06-8.02 (m, 2H), 7.97 (d, J = 8.2 Hz, 2H), 7.88 (d, J = 8.0 Hz, 2H), 7.23 (dd, J = 8.5, 5.4 Hz, 2H), 7.06 (t, J = 8.7 Hz, 2H), 5.24 (dd, J = 8.0, 5.5 Hz, 1H), 3.90 (s, 1H), 3.79 (s, 1H), 3.67 (d, J = 12.2 Hz, 2H), 3.36 (d, J = 11.8 Hz, 4H), 3.20 (s, 5H), 3.02 (dt, J = 7.9, 4.0 Hz, 1H), 2.86 (s, 3H), 2.55 (d, J = 9.1 Hz, 1H), 2.41-2.27 (m, 1H), 2.27-2.12 (m, 1H), 1.56 (dt, J = 10.8, 5.5 Hz, 1H), 1.41 (q, J = 7.2 Hz, 1H). |
| 21 | 5 | 541 [M + H]+ | (400 MHz, MeOD-d4) δ ppm: 8.25-8.15 (m, 2H), 8.15-8.00 (m, 3H), 7.42-7.37 (m, 1H), 7.28-7.15 (m, 1H), 7.10-7.00 (m, 2H), 5.30-5.20 (m, 1H), 4.48-4.29 (m, 1H), 4.25-4.10 (m, 1H), 4.00-3.85 (m, 2H), 3.42-3.37 (m, 2H), 3.27-3.12 (m, 4H), 3.12-2.92 (m, 1H), 2.60-2.50 (m, 1H), 2.45-2.30 (m, 1H), 2.30-2.17 (m, 1H), 1.60-1.50 (m, 1H), 1.50-1.40 (m, 1H) |
| 22 | 4 | [M + H]+ 555 | (300 MHz, MeOD-d4): δ ppm 8.10-7.90 (m, 2H), 7.82-7.70 (m, 2H), 7.22-7.15 (m, , 2H), 7.05-6.85 (m, 2H), 5.30-5.15 (m, 1H), 4.55-4.25 (m, 1H), 4.25-4.03 (m, 1H), 4.05-3.70 (m, 2H), 3.35-3.30 (m, 2H), 3.25-3.05 (m, 4H), 3.05-2.88 (m, 1H), 2.60-2.45 (m, 1H), 2.45-2.05 (m, 2H), 1.70-1.50 (m, 1H), 1.45-1.29 (m, 1H). |
| 23 | 6 | 506 [M + H]+ | (400 MHz, MeOD-d4) δ ppm: 8.64 (d, J = 1.2 Hz, 1H), 8.10-7.96 (m, 4H), 7.93 (d, J = 1.2 Hz, 1H), 7.04 (m, 2H), 6.98-6.87 (m, 2H), 5.06 (m, 1H), 3.68 (m, 3H), 3.55-3.44 (m, 1H), 2.96-2.70 (m, 6H), 2.28 (m, 1H), 1.95-1.75 (m, 3H), 1.66 (m, 2H), 1.09-0.91 (m, 2H). |
| 24 | 6 | [M + H]+477 | (300 MHz, CD3OD)δ ppm: 8.62 (s, 1H), 7.96-8.15(m, 4H), 7.85-7.96 (m, 1H), 7.08-7.24 (m, 2H), 6.90-7.08 (m, 2H), 4.56-4.75 (m, 1H), 4.39-4.52 (m, 1H), 4.18-4.38(m, 1H), 3.86-4.12 (m, 2H), 3.18-3.25 (m, 2H), 2.90-3.00 (m, 1H), 2.38-2.40(m, 1H), 2.23-2.40 (m, 2H), 1.70-2.00 (m, 4H), 1.40-1.54 (m, 1H), 1.20-1.40 (m, 1H). |
| 25 | 6 | 534 [M + H] | (400 MHz, MeOD-d4) δ ppm: 8.64(s, 1H), 8.09-8.01 m, 4H), 7.94(s, 1H), 7.20-7.17(m, 2H), 7.04-6.99(m, 2H), 4.90-4.87(m, 1H), 4.16-3.87(m, 3H), 3.82-3.69(m, 1H), 3.1-3.42(m, 1H), 3.27-3.22(m, 2H), 2.99-2.94(m, 7H), 2.58-2.43(m, 2H), 2.37-2.15(m, 1H), 2.01-1.82(m, 4H), 1.50-1.47(m, 1H), 1.39-1.35(m, 1H) |
| 26 | 6 | 548 [M + H] | (300 MHz, MeOD-d4) δ ppm: 8.61 (s, 1H), 8.10-7.88 (m, 5H), 7.15 (m, 2H), 6.97 (m, 2H), 5.09 (s, 1H), 4.75-4.63 (m, 1H), 4.29 (m, 1H), 3.47 (m, 1H), 3.21 (m, 4H), 2.98-2.85 (m, 6H), 2.71 (m, 1H), 2.47 (m, 1H), 2.13 (m, 2H), 1.93-1.72 (m, 5H), 1.61 (m, 1H), 1.48 (m, 1H), 1.31 (m, 1H). |
| 27 | 6 | 520 [M + H]+ | (400 MHz, MeOD-d4) δ ppm: 9.21 (s, 2H), 8.10 (d, J = 8.3 Hz, 2H), 7.90-7.78 (m, 2H), 7.28-7.16 (m, 2H), 7.09-6.98 (m, 2H), 5.12 (dd, J = 8.2, 5.2 Hz, 1H), 4.60 (d, J = 78.2 Hz, 2H), 3.59 (s, 3H), 3.31-3.04 (m, 4H), 3.03-2.87 (m, 4H), 2.50 (ddd, J = 10.3, 6.6, 3.5 Hz, 1H), 1.95 (dddd, J = 28.6, 20.2, 15.7, 8.6 Hz, 4H), 1.51 (ddd, J = 10.7, 6.9, 4.4 Hz, 1H), 1.38 (q, J = 7.1 Hz, 1H). |
| 28 | 6 | [M + H]+ 561 | (300 MHz, MeOD-d4): δ ppm 8.85 (d, J = 4.9 Hz, 2H), 8.52-8.42 (m, 2H), 7.98-7.89 (m, 2H), 7.37 (t, J = 4.9 Hz, 1H), 7.07-6.83 (m, 4H), 5.08-5.04 (m, 1H), 3.76-3.51 (m, 6H), 2.78-2.72 (m, 2H), 2.60-2.50 (m, 6H), 2.30-2.19 (m, 1H), 1.93-1.74 (m, 3H), 1.68-1.62 (m, 2H), 1.07-0.86 (m, 2H) |
| 29 | 6 | 435 [M + H] | (400 MHz, MeOD-d4) δ ppm: 8.31 (d, J = 2.6 Hz, 1H), 8.00-7.81 (m, 4H), 7.75 (d, J = 1.7 Hz, 1H), 7.22-7.11 (m, 2H), 7.07-6.94 (m, 2H), 6.55 (dd, J = 2.6, 1.8 Hz, 1H), 4.65 (t, J = 6.8 Hz, 1H), 4.35 (dq, J = 39.0, 8.3 Hz, 2H), 4.13-3.91 (m, 2H), 3.22 (t, J = 7.3 Hz, 2H), 2.93 (dt, J = 8.0, 4.1 Hz, 1H), 2.49-2.23 (m, 3H), 1.84 (q, J = 11.1, 8.9 Hz, 4H), 1.51-1.27 (m, 2H) |

TABLE 2-continued

Physical Data and Synthetic Methods

| Ex # | Scheme | MS | 1H NMR |
|---|---|---|---|
| 30 | 6 | 524 [M + H] | (400 MHz, MeOD-$d_4$) δ ppm: 7.96-7.94(d, J = 8 Hz, 2H), 7.83-7.81(d, J = 8 Hz, 2H), 7.05-7.02(m, 2H), 6.94-6.90(m, 2H), 5.10-5.07(m, 1H), 4.51-4.42(m, 1H), 4.17-4.10(m, 1H), 3.51-3.40(m, 1H), 3.09-2.95(m, 1H), 2.78-2.72(m, 2H), 2.30-1.75(m, 8H), 1.69-1.57(m, 2H), 1.05-0.92(m, 2H), |
| 31 | 6 | 550 [M + H] | (400 MHz, MeOD-$d_4$) δ ppm: 8.02-7.95 (d, J = 8.4 Hz, 2H), 7.89-7.81 (d, J = 8.4 Hz, 2H), 7.23-7.13 (m, 2H), 7.07-6.97 (m, 2H), 5.09 (m, 1H), 4.29 (m, 2H), 4.03 (m, 4H), 3.87 (s, 1H), 3.71 (s, 1H), 3.50-3.17 (m, 6H), 2.93 (m, 1H), 2.46 (m, 1H), 2.00-1.80 (m, 4H), 1.48 (m, 1H), 1.34 (m, 4H) |
| 32 | 6 | 542[M + H]$^+$ | (300 MHz, Methanol-d4) δ 8.33 (d, J = 4.8 Hz, 2H), 8.00-7.91 (m, 2H), 7.87-7.77 (m, 2H), 7.15 (ddd, J = 8.5, 5.2, 2.6 Hz, 2H), 7.06-6.91 (m, 2H), 6.62 (t, J = 4.8 Hz, 1H), 5.13 (dd, J = 7.7, 5.3 Hz, 1H), 3.75 (m, 8H), 3.28-3.15 (m, 2H), 2.92 (dt, J = 7.9, 4.1 Hz, 1H), 2.41 (ddd, J = 10.4, 6.6, 3.6 Hz, 1H), 2.05-1.74 (m, 4H), 1.50-1.27 (m, 2H) |
| 33 | 6 | 577 [M + H]$^+$ | (400 MHz, MeOD-$d_4$) δ ppm: 8.88-8.87(m, 2H), 8.51-8.49(m, 2H), 7.97-7.95(m, 2H), 7.41-7.38(m, 1H), 7.05-7.02(m, 2H), 6.93-6.89(m, 2H), 5.13-5.10(m, 1H), 4.53-4.42(m, 1H), 4.19-4.12(m, 1H), 3.53-3.41(m, 1H), 3.12-2.95(m, 1H), 2.78-2.72(m, 2H), 2.30-1.76(m, 8H), 1.71-1.61(m, 2H), 1.05-1.01(m, 1H), 0.97-0.92(m, 1H) |
| 34 | 6 | 530 [M + H]$^+$ | $^1$H NMR (300 MHz, Methanol-$d_4$) δ 8.80 (d, J = 4.8 Hz, 2H), 8.50 (d, J = 8.4 Hz, 2H), 7.98 (d, J = 8.1 Hz, 2H), 7.41 (t, J = 4.8 Hz, 1H), 7.11-6.86 (m, 4H), 4.85-4.80 (m, 4H), 4.75-4.62 (m, 1H), 4.60-4.44 (m, 2H), 4.28-4.10 (m, 2H), 2.81-2.75 (m, 2H), 2.40-2.20 (m, 1H), 1.95-1.83 (m, 3H), 1.75-1.60 (m, 2H), 1.10-0.95 (m, 3H). |
| 35 | 7 | 501[M + H]$^+$ | (300 MHz, MeOD-$d_4$) δ ppm: 8.42-8.22(d, J = 2.1 Hz, 1H), 8.11-7.91 (m, 2H), 7.91-7.81 (m, 2H), 7.81-7.69 (m, 1H), 7.18-7.08 (m, 2H), 7.08-6.88 (m, 2H), 6.81-6.52 (m, 1H), 4.85-4.45 (m, 3H), 4.45-4.05 (m, 2H), 3.96-3.61 (m, 1H), 2.91-2.78 (m, 2H), 2.41-2.21 (m, 1H), 1.95-1.71 (m, 3H), 1.46-1.71 (m, 2H), 1.15-0.85 (m, 2H), |
| 36 | 7 | 533 (M + 1) | (CD$_3$OD, ppm): 8.36(s, 1H), 8.07-7.95 (m, 2H), 7.95-7.87 (m, 2H), 7.87-7.75 (m, 1H), 7.30-7.15 (m, 2H), 7.12-7.00 (m, 2H), 6.59 (s, 1H), 5.05-5.20 (m, 1H), 4.20-4.50 (m, 2H), 3.72-4.20 (m, 3H), 3.41-3.58 (m, 2H), 3.15-3.28 (m, 2H), 2.90-3.05 (m, 4H), 2.43-2.53 (m, 1H), 1.80-2.10 (m, 1H), 1.45-1.52 (m, 1H), 1.35-1.44 (m, 1H) |
| 37 | 7 | 565 [M + H]$^+$ | (400 MHz, MeOD-$d_4$) δ ppm: 8.32(s, 1H), 7.99-7.97(d, J = 14.4 Hz, 2H), 7.87-7.85(d, 2H), 7.76(s, 1H), 7.06-7.02(m, 2H), 6.94-6.89(m, 2H), 6.57-6.55(m, 1H), 5.12-5.08(m, 1H), 4.19-4.12(m, 1H), 3.57-3.41(m, 1H), 3.12-2.95(m, 1H), 2.80-2.72(m, 2H), 2.29-1.76(m, 8H), 1.71-1.61(m, 2H), 1.06-1.01(m, 1H), 0.97-0.93(m, 1H), |
| 38 | 7 | 518 [M + H]$^+$ | (300 MHz, Methanol-$d_4$) δ 8.34(s, 1H), 8.05-7.70(m, 5H), 7.10-6.90 (m, 4H), 6.57 (d, J = 1.8 Hz, 1H), 4.87-4.80 (m, 3H), 4.70-4.60 (m, 1H), 4.60-4.55 (m, 2H), 4.28-4.20 (m, 1H), 4.20-4.08 (m, 1H), 2.82-2.72 (m, 2H), 2.35-2.25 (m, 1H), 2.00-1.75 (m, 3H), 1.75-1.60 (m, 2H), 1.35-1.25 (m, 1H), 1.10-1.00 (m, 3H). |
| 41 | 7 | 548 (M + 1) | (CD$_3$OD, ppm): 8.64 (s, 1H), 7.88-8.15 (m, 5H), 7.01-7.12 (m, 2H), 6.85-6.99 (m, 2H), 5.05-5.18 (m, 1H), 4.28-4.45 (m, 1H), 3.95-4.11 (m, 1H), 2.95-3.10 (m, 1H), 2.71-2.85 (m, 2H), 2.42-2.65 (m, 1H), 2.11-2.38 (m, 6H), 1.80-1.98 (m, 3H), 1.55-1.71 (m, 2H), 1.27-1.36 (m, 2H), 1.12-1.22 (m, 6H), 0.85-1.10 (m, 3H). |
| 42 | 7 | 516 [M + H]$^+$ | (400 MHz, MeOD-$d_4$) δ ppm: 8.63(s, 1H), 8.08-8.04 (m, 2H), 8.00-7.93(m, 2H), 7.93(s, 1H), 7.07-7.02(m, 2H), 6.94-6.90(m, 2H), 4.83-4.72(m, 1H), 4.02-3.50(m, 2H), 2.82-2.77(m, 2H), 2.41-2.07(m, 5H), 2.02-1.60(m, 5H), 1.06-1.03(m, 1H), 0.97-0.95(m, 1H) |
| 43 | 7 | [M + H]$^+$ 541 | (400 MHz, Methanol-$d_4$) δ 8.64 (s, 1H), 8.10-8.02 (m, 2H), 8.02-7.98 (m, 2H), 7.97-7.91 (m, 1H), 7.11-7.03 (m, 2H), 7.00-6.88 (m, 2H), 5.14-5.06 (m, 1H), 4.10-3.90 (m, 2H), 3.78-3.62 (m, 1H), 3.58-3.42 (m, 1H), 2.86-2.70 (m, 2H), 2.36-2.26 (m, 1H), 2.25-1.80 (m, 7H), 1.80-1.61 (m, 2H), 1.15-1.03 (m, 1H), 1.00-0.89 (m, 1H). |

TABLE 2-continued

Physical Data and Synthetic Methods

| Ex # | Scheme | MS | 1H NMR |
|---|---|---|---|
| 44 | 7 | 530 [M + H]+ | (300 MHz, MeOD-$d_4$) δ ppm: 8.60 (m, 1H), 8.11-7.93 (m, 4H), 7.90 (m, 1H), 7.13-6.72 (m, 4H), 5.04 (m, 1H), 4.11-3.75 (m, 4H), 3.15-2.75 (m, 1H), 2.75 (m, 2H), 2.25 (m, 1H), 2.18-1.75 (m, 7H), 1.64 (m, 2H), 1.05-0.97 (m, 2H). |
| 45 | 7 | 583 [M + H]+ | (300 MHz, MeOD-$d_4$) δ ppm: 8.61 (s, 1H), 8.11-7.93 (m, 4H), 7.90 (d, J = 1.2 Hz, 1H), 7.02 (m, 2H), 6.90 (m, 2H), 5.07 (m, 1H), 4.64 (m, 1H), 4.32 (m, 1H), 3.40-3.38 (m, 1H), 3.20-3.15 (m, 1H), 2.91-2.76 (m, 6H), 2.28-2.05(m, 3H), 2.05-1.76 (m, 7H), 1.20-0.78 (m, 2H). |
| 46 | 7 | 534 (M + 1) | (CD$_3$OD, ppm): 8.64 (d, J = 1.2 Hz, 1H), 8.10-8.05 (m, 2H), 8.05-8.00 (m, 2H), 7..98-7.87 (m, 1H), 7.10-7.00 (m, 2H), 6.95-6.86 (m, 2H), 5.15-5.00 (m, 1H), 3.90-3.62 (m, 3H), 3.60-3.50 (m, 1H), 2.85-2.70 (m, 2H), 2.65-2.40 (m, 6H), 2.35-2.27 (m, 1H), 2.00-1.60 (m, 5H), 1.35-0.85 (m, 7H) |
| 47 | 7 | 548 (M + 1) | (CD$_3$OD, ppm): 8.64 (s, 1H), 8.12-8.05 (m, 2H), 8.05-8.00 (m, 2H), 8.00-7.95 (m, 1H), 7.10-7.02 (m, 2H), 7.00-6.85 (m, 2H), 5.14-5.00 (m, 1H), 3.86-3.60 (m, 3H), 3.60-3.50 (m, 1H), 2.90-2.70 (m, 3H), 2.70-2.0 (m, 4H), 2.35-2.20 (m, 1H), 1.98-1.76 (m, 3H), 1.75-1.55 (m, 2H), 1.20-1.00 (m, 7H), 1.00-0.90 (m, 1H) |
| 48 | 7 | 584 (M + 1) | (CD$_3$OD, ppm): 8.63 (s, 1H), 7.88-8.11 (m, 5H), 7.00-7.10 (m, 2H), 6.88-6.98 (m, 2H), 5.00-5.14 (m, 1H), 3.85-4.02 (m, 2H), 3.63-3.78 (m, 1H), 3.45-3.60 (m, 1H), 3.37-3.45 (m, 1H), 3.10-3.20 (m, 1H), 2.98-3.05 (m, 2H), 2.69-2.92 (m, 5H), 2.22-2.38 (m, 1H), 1.79-1.98 (m, 3H), 1.60-1.79 (m, 2H), 0.91-1.10 (m, 2H). |
| 49 | 7 | 550 [M + H]+ | (400 MHz, MeOD-$d_4$) δ ppm: 8.62 (d, J = 1.2 Hz, 1H), 8.10-7.88 (m, 5H), 7.22-7.10 (m, 2H), 6.99 (m, 2H), 5.10 (m, 1H), 3.75 (m, 6H), 3.21 (m, 2H), 3.10-2.89 (m, 7H), 2.43 (m, 1H), 1.99-1.80 (m, 4H), 1.51-1.23 (m, 2H) |
| 50 | 7 | 564 [M + H]+ | (300 MHz, MeOD-$d_4$) δ ppm: 8.61 (s, 1H), 8.15-7.95 (m, 4H), 7.91 (d, J = 1.2 Hz, 1H), 7.15 (m, 2H), 7.07-6.85 (m, 2H), 5.08 (m, 1H), 4.30-3.78 (m, 3H), 3.71 (m, 2H), 3.38 (m, 9H), 3.25 (m, 3H), 2.91 (m, 1H), 2.45 (m, 1H), 2.08-1.63 (m, 4H), 1.51-1.18 (m, 2H). |
| 51 | 7 | 520 [M + H]+ | (300 MHz, MeOD-$d_4$) δ ppm: 8.31 (d, J = 2.6 Hz, 1H), 8.00-7.81 (m, 4H), 7.75 (d, J = 1.7 Hz, 1H), 7.22-7.11 (m, 2H), 7.07-6.94 (m, 2H), 6.55 (dd, J = 2.6, 1.8 Hz, 1H), 4.65 (t, J = 6.8 Hz, 1H), 4.35 (dq, J = 39.0, 8.3 Hz, 2H), 4.13-3.91 (m, 2H), 3.22 (t, J = 7.3 Hz, 2H), 2.93 (dt, J = 8.0, 4.1 Hz, 1H), 2.49-2.23 (m, 3H), 1.84 (q, J = 11.1, 8.9 Hz, 4H), 1.51-1.27 (m, 2H). |
| 52 | 7 | 534 [M + H]+ | (300 MHz, MeOD-$d_4$) δ ppm: 8.31 (d, J = 2.6 Hz, 1H), 8.00-7.81 (m, 4H), 7.75 (d, J = 1.7 Hz, 1H), 7.22-7.11 (m, 2H), 7.07-6.94 (m, 2H), 6.55 (dd, J = 2.6, 1.8 Hz, 1H), 4.65 (t, J = 6.8 Hz, 1H), 4.35 (dq, J = 39.0, 8.3 Hz, 2H), 4.13-3.91 (m, 2H), 3.22 (t, J = 7.3 Hz, 2H), 2.93 (dt, J = 8.0, 4.1 Hz, 1H), 2.49-2.23 (m, 3H), 1.84 (q, J = 11.1, 8.9 Hz, 4H), 1.51-1.27 (m, 2H). |
| 53 | 7 | 535[M + H]+ | (400 MHz, Methanol-$d_4$) δ 8.66 (d, J = 1.3 Hz, 1H), 8.12-7.99 (m, 5H), 7.96 (d, J = 1.2 Hz, 1H), 7.07 (dd, J = 8.2, 5.1 Hz, 3H), 6.95 (t, J = 8.8 Hz, 3H), 5.18-5.05 (s, 1H), 4.50-4.32 (m, 1H), 4.19-3.97 (m, 1H), 3.76-3.50 (m, 2H), 3.00-2.75 (m, 3H), 2.46-2.30 (m, 2H), 2.00-1.60 (m, 5H), 1.30-0.95 (m, 8H), 1.08 (s, 1H). |
| 54 | 7 | 531 (M + 1) | (400 MHz, Methanol-$d_4$) δ 8.64 (d, J = 1.2 Hz, 2H), 8.11-7.96 (m, 8H), 7.93 (d, J = 1.2 Hz, 2H), 7.05 (ddd, J = 8.8, 5.3, 2.0 Hz, 4H), 6.93 (ddd, J = 9.5, 7.7, 1.4 Hz, 4H), 4.99 (dd, J = 8.4, 5.8 Hz, 1H), 4.38 (s, 1H), 4.09 (s, 1H), 3.99-3.91 (m, 1H), 3.63 (d, J = 10.4 Hz, 1H), 3.52-3.43 (m, 1H), 3.36 (d, J = 2.6 Hz, 1H), 2.84-2.68 (m, 4H), 2.28 (dtd, J = 7.6, 4.7, 3.2 Hz, 2H), 2.06-1.94 (m, 3H), 1.95-1.59 (m, 26H), 1.10-0.91 (m, 4H) |
| 55 | 7 | 546 [M + H]+ | (300 MHz, MeOD-$d_4$) δ ppm: 8.68-8.53 (m, 1H), 8.14-7.90 (m, 5H), 7.01 (ddt, J = 8.3, 4.8, 2.4 Hz, 2H), 6.93-6.74 (m, 2H), 5.00 (ddd, J = 21.2, 8.5, 5.5 Hz, 1H), 4.22-3.66 (m, 2H), 3.52-3.32 (m, 1H), 3.22 (s, 2H), 3.02-2.80 (m, 1H), 2.79-2.64 (m, 2H), 2.33-2.19 (m, 4H), 2.13-1.92 (m, 2H), 1.91-1.67 (m, 4H), 1.67-1.36 (m, 3H), 1.06-0.89 (m, 2H). |
| 56 | 7 | 533 [M + H]+ | (300 MHz, MeOD-$d_4$) δ ppm: 8.66 (d, J = 1.2 Hz, 1H), 8.11-7.92 (m, 4H), 7.92 (s, 1H), 7.07-6.98 (m, 2H), |

TABLE 2-continued

Physical Data and Synthetic Methods

| Ex # | Scheme | MS | 1H NMR |
|---|---|---|---|
| | | | 6.93-6.79 (m, 2H), 4.97 (ddd, J = 25.1, 8.4, 5.5 Hz, 1H), 4.36 (dd, J = 8.1, 5.2 Hz, 2H), 4.19-3.69 (m, 2H), 3.49-3.34 (m, 1H), 2.92 (td, J = 13.9, 2.5 Hz, 1H), 2.80-2.61 (m, 2H), 2.24 (ddd, J = 7.6, 4.6, 3.2 Hz, 1H), 2.06-1.73 (m, 6H), 1.64 (m, 3H), 1.12-0.77 (m, 2H). |
| 57 | 7 | 574 [M + H]$^+$ | (300 MHz, MeOD-d$_4$) δ ppm: 8.61 (d, J = 1.3 Hz, 1H), 8.16-7.79 (m, 5H), 7.12-6.74 (m, 4H), 5.06 (dd, J = 8.5, 5.3 Hz, 1H), 3.83-3.30 (m, 4H), 2.73 (tt, J = 8.2, 4.1 Hz, 2H), 2.62 (t, J = 7.0 Hz, 2H), 2.54-2.38 (m, 2H), 2.32 (d, J = 4.6 Hz, 3H), 2.30-2.18 (m, 1H), 1.94-1.48 (m, 11H), 1.07-0.73 (m, 2H). |
| 58 | 7 | 574 [M + H]$^+$ | (300 MHz, MeOD-d$_4$) δ ppm: 8.61 (d, J = 1.3 Hz, 1H), 8.15-7.52 (m, 5H), 7.12-6.69 (m, 4H), 4.81-4.67 (m, 1H), 4.00-3.31 (m, 3H), 3.40-3.30 (m, 1H), 3.25-3.18 (m, 1H), 2.75 (t, J = 7.2 Hz, 2H), 2.42 (d, J = 47.9 Hz, 4H), 2.26 (t, J = 2.7 Hz, 4H), 1.96-1.49 (m, 11H), 1.11-0.84 (m, 2H). |
| 59 | 7 | 520[M + H]$^+$ | (400 MHz, MeOD-d$_4$) δ 8.07 (s, 1H), 8.10-7.90 (m, 5H), 7.10-6.85 (m, 4H), 4.87 (s, 4H), 4.72-4.65 (m, 1H), 4.55-4.45 (m, 2H), 4.25-4.10 (m, 2H), 3.80-3.70 (m, 2H), 2.35- |
| 60 | 7 | 588 [M + H]$^+$ | (300 MHz, MeOD-d$_4$) δ ppm: 8.64 (s, 1H), 8.16-7.79 (m, 5H), 7.12-6.74 (m, 4H), 5.06 (m, 1H), 3.83-3.45 (m, 4H), 3.19-3.02 (m, 2H), 2.89-2.60 (m, 6H), 2.35-2.20 (m, 1H), 2.00-1.50 (m, 5H), 1.10-0.90 (m, 2H). |
| 61 | 7 | 566[M + H]$^+$ | (400 MHz, Methanol-d$_4$) δ 8.54 (s, 1H), 8.05-7.80 (m, 5H), 7.05-6.80 (m, 4H), 5.10-4.90 (m, 1H), 4.45-4.35 (m, 1H), 4.18-4.05 (m, 1H), 3.55-3.30 (m, 1H), 3.00-2.85 (m, 1H), 2.90-2.60 (m, 2H), 2.25-1.50 (m, 10H), 1.00-0.80 (m, 2H). |
| 62 | 7 | [M + H]$^+$ 520 | (300 MHz, MeOD-d$_4$): δ ppm 9.07 (s, 2H), 8.07-7.98 (m, 2H), 7.80-7.70 (m, 2H), 7.08-6.80 (m, 4H), 5.15-4.95 (m, 1H), 4.50-4.26 (m, 1H), 4.10-3.95 (m, 1H), 3.90-3.80(m, 1H), 3.40-3.20 (m, 3H), 2.78-2.74 (m, 2H), 2.32-2.28 (m, 1H), 1.94-1.77 (m, 3H), 1.70-1.60 (m, 2H), 1.07-0.88 (m, 2H) |
| 63 | 7 | [M + H]$^+$ 534 | (300 MHz, MeOD-d$_4$): δ ppm 9.07 (s, 2H), 8.07-7.98 (m, 2H), 7.85-7.70 (m, 2H), 7.08-6.84 (m, 4H), 5.09-4.95 (m, 1H), 4.35-3.75 (m, 4H), 3.46-3.38 (m, 2H), 3.22-3.15 (m, 2H), 2.95-2.90 (m, 4H), 2.44-2.40 (m, 1H), 1.90-1.83 (m, 4H), 1.47-1.32 (m, 2H) |
| 64 | 7 | 485 | (300 MHz, MeOD-d$_4$): δ ppm 7.95-7.83 (m, 2H), 7.25-7.08 (m, 4H), 7.06-6.91 (m, 2H), 5.06-50.2(m, 1H), 4.70-4.40(m, 2H), 3.60-3.55 (m, 4H), 3.28-3.11 (m, 4H), 3.18-3.05(m, 2H), 2.92-2.88(m, 1H), 2.46-2.42 (m, 1H), 1.90-1.82 (m, 4H), 1.52-1.25 (m, 5H) |
| 65 | 7 | [M + H]$^+$ 463 | (400 MHz, Methanol-d$_4$) δ 8.05-7.95 (m, 2H), 7.89-7.77(m, 2H), 7.11-7.00 (m, 2H), 7.00-6.88 (m, 2H), 4.70-4.56 (m, 1H), 4.23-4.10 (m, 1H), 4.00-3.90 (m, 1H), 3.78-3.70 (m, 1H), 3.69-3.60 (m, 1H), 2.85-2.67 (m, 2H), 2.34-2.22 (m, 1H), 1.95-1.80 (m, 3H), 1.78-7.50 (m, 2H), 1.30 (s, 6H), 1.11-1.00 (m, 1H), 1.00-0.89 (m, 1H). |
| 66 | 7 | 460 [M + H]$^+$ | (400 MHz, MeOD-d$_4$) δ ppm: 7.98 (m, 2H), 7.86 (m, 2H), 7.19 (m, 2H), 7.03 (m, 2H), 4.74 (m, 1H), 4.65-4.54 (m, 2H), 4.41-4.09 (m, 2H), 3.75 (m, 1H), 3.25 (m, 2H), 2.95 (m, 1H), 2.45 (m, 1H), 1.95 (m, 1H), 1.83 (m, 3H), 1.47-1.37 (m, 2H) |
| 67 | 7 | [M + H]$^+$ 493 | (400 MHz, Methanol-d$_4$) δ 8.05-7.93 (m, 2H), 7.89-7.77(m, 2H), 7.11-7.00 (m, 2H), 7.00-6.88 (m, 2H), 4.68-4.50 (m, 1H), 4.50-4.30 (m, 1H), 4.30-4.16 (m, 1H), 4.10-3.88 (m, 2H), 2.86-2.65 (m, 3H), 2.36-2.21 (m, 1H), 1.98-1.76 (m, 3H), 1.76-1.53 (m, 2H), 1.25-1.11 (m, 6H), 1.11-1.00 (m, 1H), 1.00-0.89 (m, 1H). |
| 68 | 7 | 493 (M + 1) | (CD$_3$OD, ppm): 8.10-7.97 (m, 2H), 7.97-7.80 (m, 2H), 7.01-7.15 (m, 2H), 6.84-7.01 (m, 2H), 5.02-5.15 (m, 1H), 3.99-4.26 (m, 1H), 3.72-3.98 (m, 1H), 3.45-3.72 (m, 1H), 3.10-3.30 (m, 1H), 2.64-2.88 (m, 2H), 2.22-2.36 (m, 1H), 1.44-1.96 (m, 9H), 1.19-1.38 (m, 3H), 0.92-1.11 (m, 2H). |
| 69 | 7 | 507 (M + 1) | (400 MHz, Methanol-d$_4$) δ 8.03-7.93 (m, 2H), 7.87-7.78 (m, 2H), 7.09-6.99 (m, 2H), 6.98-6.87 (m, 2H), 5.05 (dd, J = 8.7, 5.2 Hz, 1H), 4.19 (d, J = 13.2 Hz, 1H), 3.89-3.73 (m, 1H), 3.54-3.36 (m, 1H), 3.22 (d, J = 2.8 Hz, 3H), 2.99 (td, J = 12.6, 2.8 Hz, 1H), 2.82-2.67 (m, 2H), 2.26 (ddd, J = 7.5, 4.4, 3.4 Hz, 1H), 1.93-1.73 (m, 5H), 1.72-1.35 (m, 4H), 1.18 (d, J = 9.1 Hz, 3H), 1.08-0.90 (m, 2H). |

TABLE 2-continued

Physical Data and Synthetic Methods

| Ex # | Scheme | MS | 1H NMR |
|---|---|---|---|
| 70 | 7 | 529 (M + 1) | (400 MHz, Methanol-$d_4$) δ 7.99 (dd, J = 8.4, 2.6 Hz, 2H), 7.87-7.79 (m, 2H), 7.69 (dd, J = 8.4, 2.4 Hz, 1H), 7.49 (dd, J = 14.3, 1.9 Hz, 1H), 7.09-7.00 (m, 2H), 6.93 (td, J = 8.7, 6.7 Hz, 2H), 6.29 (dt, J = 6.0, 2.1 Hz, 1H), 5.10 (dt, J = 9.6, 4.9 Hz, 1H), 4.64 (t, J = 15.6 Hz, 1H), 4.53-4.43 (m, 1H), 4.28 (s, 1H), 3.44-3.30 (m, 1H), 2.97-2.71 (m, 3H), 2.29 (dt, J = 7.1, 3.7 Hz, 1H), 2.24-1.78 (m, 8H), 1.67 (t, J = 10.0 Hz, 2H), 1.09-0.92 (m, 2H). |
| 71 | 7 | 546[M + H]$^+$ | (300 MHz, Methanol-$d_4$) δ 8.03-7.78 (m, 4H), 7.15-6.86 (m, 4H), 5.10-5.00 (m, 1H), 3.85-3.60 (m, 3H), 3.60-3.50 (m, 1H), 3.20-2.10 (m, 2H), 2.80-2.50 (m, 6H), 2.38-2.18 (m, 1H), 2.00-1.78 (m, 3H), 1.75-1.52 (m, 2H), 1.10-0.85 (m, 2H). |
| 72 | 7 | [M + H]$^+$ 530 | (400 MHz, Methanol-$d_4$) δ 8.10-8.03 (m, 1H), 8.03-7.94 (m, 2H), 7.90-7.80 (m, 2H), 7.80-7.70 (m, 1H), 7.10-7.00(m, 2H), 7.00-6.81 (m, 2H), 5.15-5.02 (m, 1H), 4.80-4.51 (m, 1H), 4.40-4.20 (m, 1H), 350-3.48 (m, 1H), 3.18-2.88 (m, 1H), 2.87-2.66 (m, 2H), 2.39-2.10 (m, 4H), 2.10-1.78 (m, 4H), 1.78-1.67 (m, 2H), 1.10-0.87 (m, 2H). |
| 73 | 7 | 571 [M + H]$^+$ | (400 MHz, MeOD-$d_4$) δ ppm: 8.67 (d, J = 7.2 Hz, 2H), 8.01-7.96 (m, 2H), 7.85 (d, J = 8.4 Hz, 2H), 7.05-7.03(m, 2H), 6.96-6.91(m, 2H), 5.11-5.04(m, 1H), 4.71-4.63(m, 1H), 4.61-4.50(m, 1H), 4.39-4.26(m, 1H), 3.31-3.30(m, 1H), 2.91-2.75(m, 3H), 2.32-2.09(m, 4H), 1.96-1.83(m, 4H), 1.71-1.61(m, 2H), 1.10-1.03(m, 1H), 0.98-0.96(m, 1H) |
| 74 | 7 | [M + H]$^+$ 531; | (300 MHz, Methanol-$d_4$) δ 8.02-7.90 (m, 2H), 7.90-7.86 (m, 2H), 7.26-7.18 (m, 2H), 7.10-6.96 (m, 2H), 5.22-5.18 (m, 1H), 4.75-4.55 (m, 1H), 4.55-4.40 (m, 1H), 4.30-4.10 (m, 1H), 3.25-3.23 (m, 1H), 3.12-2.90 (m, 3H), 2.50-2.41 (m, 1H), 2.28-2.10 (m, 2H), 2.10-2.00 (m, 6H), 1.55-1.35 (m, 2H). |
| 75 | 7 | [M + H]$^+$ 492 | (300 MHz, Methanol-$d_4$) δ 8.00-7.90 (m, 2H), 7.90-7.74 (m, 2H), 7.11-7.00 (m, 2H), 7.00-6.82 (m, 2H), 5.10-4.95 (m, 1H), 3.85-4.42 (m, 4H), 2.83-2.66 (m, 2H), 2.66-2.33 (m, 6H), 2.33-2.15 (m, 1H), 1.94-1.71 (m, 3H), 1.71-1.48 (m, 2H), 1.20-1.05 (m, 3H), 1.05-0.80 (m, 2H). |
| 76 | 7 | 506.25 (M + 1) | (300 MHz, Methanol-$d_4$) δ 7.94 (d, J = 8.2 Hz, 2H), 7.80 (d, J = 8.2 Hz, 2H), 7.07-6.84 (m, 4H), 5.01 (dd, J = 8.6, 5.3 Hz, 1H), 3.73-3.59 (m, 4H), 2.78-2.47 (m, 7H), 2.24 (dt, J = 7.6, 4.1 Hz, 1H), 1.92-1.72 (m, 3H), 1.66-1.55 (m, 2H), 1.09-0.86 (m, 8H). |
| 77 | 7 | 508 [M + H]$^+$ | (400 MHz, MeOD-$d_4$) δ ppm: 7.97 (d, J = 8.3 Hz, 2H), 7.83 (d, J = 8.3 Hz, 2H), 7.13-6.99 (m, 2H), 6.98-6.88 (m, 2H), 5.04 (m, 1H), 3.81-3.60 (m, 5H), 3.60-3.49 (m, 1H), 2.75 (m, 2H), 2.55 (m, 6H), 2.27 (m, 1H), 1.94-1.72 (m, 3H), 1.63 (m, 2H), 1.08-0.91 (m, 2H). |
| 78 | 7 | [M + H]$^+$ 522 | (400 MHz, Methanol-$d_4$) δ 8.02-7.90 (m, 2H), 7.88-7.74 (m, 2H), 7.14-7.00 (m, 2H), 7.00-6.86(m, 2H), 5.02-5.10(m, 1H), 3.82-3.62 (m, 3H), 3.62-3.51(m, 3H), 3.47-3.43 (m, 3H), 2.81-2.68 (m, 2H), 2.67-2.43 (m, 6H), 2.35-2.21 (m, 1H), 1.96-1.78 (m, 3H), 1.72-1.58 (m, 2H), 1.01-1.00(m, 1H), 1.00-0.90(m, 1H). |
| 79 | 7 | [M + H]$^+$ 570 | (300 MHz, Methanol-$d_4$) δ 8.02-7.90 (m, 2H), 7.90-7.80 (m, 2H), 7.13-7.00 (m, 2H), 7.00-6.86(m, 2H), 5.00-5.15(m, 1H), 3.86-3.45 (m, 5H), 3.45-3.36 (m, 1H), 3.07 (s, 3H), 2.96-2.76 (m, 4H), 2.68-2.20 (m, 5H), 2.08-1.80 (m, 3H), 1.80-1.50 (m, 2H), 1.25-0.92 (m, 2H). |
| 80 | 7 | [M + H]$^+$ 506 | (400 MHz, Methanol-$d_4$) δ 8.20-7.90 (m, 2H), 7.90-7.68 (m, 2H), 7.20-7.02 (m, 2H), 7.02-6.80 (m, 2H), 5.20-5.00 (m, 1H), 4.40-4.28 (m, 1H), 4.28-4.00 (m, 1H), 4.01-3.70 (m, 2H), 3.65-3.42 (m, 4H), 3.00-2.85 (m, 2H), 2.58-2.25 (m, 1H), 2.07-1.80 (m, 3H), 1.80-1.55 (m, 2H), 1.17 (t, J = 7.2 Hz, 3H), 1.20-1.09(m, 1H), 1.09-1.00 (m, 1H). |
| 81 | 7 | 501 [M + H]$^+$ | (300 MHz, MeOD-$d_4$) δ ppm: 7.96 (d, J = 8.5, Hz, 2H), 7.80 (d, J = 8.5 Hz, 2H), 7.49-7.24 (m, 1H), 7.13-6.95 (m, 2H), 6.93-6.81 (m, 2H), 5.15-4.90 (m, 1H), 4.79-4.31 (m, 4H), 3.94-3.70 (m, 3H), 2.77 (t, J = 7.1 Hz, 2H), 2.25 (m, 1H), 2.01-1.77 (m, 3H), 1.68 (m, 2H), 1.13-0.78 (m, 2H). |
| 82 | 7 | 565 [M + H]$^+$ | (400 MHz, MeOD-$d_4$) δ ppm: 8.05-7.95 (m, 3H), 7.87-7.79 (m, 2H), 7.04 (m, 2H), 6.97-6.86 (m, 2H), 5.11 (m, 1H), 4.87-4.64 (m, 2H), 4.51-4.48 (m, 2H), 3.40 (s, 3H), 2.84-2.74 (m, 2H), 2.29 (m, 1H), 2.00-1.83 (m, 3H), 1.70 (m, 2H), 1.10-0.91 (m, 2H). |

TABLE 2-continued

Physical Data and Synthetic Methods

| Ex # | Scheme | MS | 1H NMR |
|---|---|---|---|
| 83 | 7 | 477 [M + H]+ | (400 MHz, MeOD-d4) δ ppm: 8.02-7.95 (m, 2H), 7.86-7.75 (m, 2H), 7.15-7.00 (m, 2H), 7.00-6.89 (m, 2H), 4.85-4.75(m, 4H), 4.75-4.65 (m, 1H), 4.55-4.40 (m, 2H), 4.25-4.05 (m, 2H), 2.85-2.70 (m, 2H), 2.35-2.20 (m, 1H), 21.95-1.52 (m, 5H), 1.10-0.95(m, 2H). |
| 84 | 7 | 519[M + H]+ | (400 MHz, Methanol-d4) δ 8.00-7.80(m, 4H), 7.15-7.25(m, 2H), 7.0-7.1(m, 2H), 5.1-5.2(m, 1H), 3.85-3.95(m, 2H), 3.85-3.45(m, 5H), 3.33-3.21(m, 3H), 300-2.92(m, 1H), 2.4-2.5(m, 1H), 1.9-2.0(m, 1H), 1.75-1.9(m, 5H), 1.5-1.75(m, 4H), 1.35-1.55(m, 2H). |
| 85 | 7 | [M + H]+ 545 | (300 MHz, MeOD-d4): δ ppm 8.85 (d, J = 4.9 Hz, 2H), 8.52-8.42 (m, 2H), 7.98-7.89 (m, 2H), 7.37 (t, J = 4.9 Hz, 1H), 7.05-7.00 (m, 2H), 6.95-6.83 (m, 2H), 5.06-5.02(m, 1H), 3.78-3.62 (m, 4H), 3.56-3.50 (m, 1H), 2.76-2.72 (m, 2H), 2.48-2.44(m, 6H), 2.28-2.22(m, 1H), 1.93-1.75 (m, 3H), 1.68-1.64(m, 2H), 1.15-0.86 (m, 5H). |
| 86 | 8 | 517 (M + 1) | (CD3OD, ppm): 8.87 (d, 2H), 8.49 (d, 2H), 7.95 (d, 2H), 7.40 (t, 1H), 7.09-7.22 (m, 2H), 6.91-7.08 (m, 2H), 5.00-5.20 (m, 2H), 3.94-4.18 (m, 2H), 3.55-3.90 (m, 2H), 3.11-3.28 (m, 6H), 2.84-2.98 (m, 1H), 2.32-2.52 (m, 1H) 1.73-2.00 (m, 4H), 1.29-1.41 (m, 2H). |
| 89 | 8 | 534 [M + H]+ | (400 MHz, MeOD-d4) δ ppm: 8.64 (s, 1H), 8.10-7.91 (m, 5H), 7.05 (m, 2H), 6.92 (m, 2H), 5.14-5.03 (m, 1H), 4.42 (m, 1H), 4.04 (m, 1H), 2.85-2.69 (m, 5H), 2.32-2.20 (m, 2H), 1.94-1.76 (m, 3H), 1.71-1.62 (m, 2H), 1.17-0.91 (m, 8H). |
| 90 | 8 | 532 [M + H]+ | (300 MHz, MeOD-d4) δ ppm: 8.69-8.51 (m, 1H), 8.13-7.93 (m, 4H), 7.95-7.85 (m, 1H), 7.05-6.96 (m, 2H), 6.96-6.83 (m, 2H), 4.93 (t, J = 7.2 Hz, 1H), 4.58-4.26 (m, 2H), 3.20-2.61 (m, 6H), 2.24 (dd, J = 7.7, 4.4 Hz, 1H), 2.18-1.73 (m, 7H), 1.65 (t, J = 13.4 Hz, 2H), 1.06-0.79 (m, 2H). |
| 91 | 9 | 549 [M + H]+ | (300 MHz, MeOD-d4) δ ppm: 8.61 (s, 1H), 8.07-7.96 (m, 4H), 7.91 (s, 1H), 7.16 (m, 2H), 6.99 (m, 2H), 5.11 (m, 1H), 4.45-4.18 (m, 1H), 4.03-3.97 (m, 1H), 3.40-2.78 (m, 5H), 2.63-2.42 (m, 2H), 1.94 1.25 (m, 10H). |
| 92 | 10 | [M + H]+ 479 | (400 MHz, Methanol-d4) δ ppm: 8.02-7.90 (d, J = 2.8 Hz, 2H), 7.90-7.80 (d, J = 2.8 Hz, 2H), 7.26-7.10 (m, 2H), 7.07-6.96 (m, 2H), 5.18-5.06 (m, 1H), 4.30-3.80 (m, 3H), 3.58-3.36 (m, 1H), 3.30-3.16 (m, 2H), 3.16-2.85 (m, 2H), 2.60-2.46 (m, 1H), 2.05-1.75 (m, 6H), 1.62-1.30 (m, 4H). |
| 93 | 10 | 532.3 (M + 1) | (400 MHz, Methanol-d4) δ 8.88 (d, J = 4.9 Hz, 2H), 8.50 (d, J = 8.3 Hz, 2H), 7.96 (dd, J = 8.5, 1.7 Hz, 2H), 7.40 (t, J = 4.9 Hz, 1H), 7.04 (ddd, J = 8.6, 5.2, 2.6 Hz, 2H), 6.97-6.85 (m, 2H), 5.11 (dt, J = 8.7, 4.5 Hz, 1H), 4.17 (d, J = 12.9 Hz, 1H), 4.06-3.96 (m, 1H), 3.97-3.79 (m, 2H), 3.08 (ddd, J = 13.4, 10.2, 3.2 Hz, 1H), 2.83-2.72 (m, 2H), 2.28 (dd, J = 6.8, 3.8 Hz, 1H), 1.92-1.78 (m, 6H), 1.74-1.52 (m, 3H), 1.46 (td, J = 10.1, 9.4, 5.0 Hz, 1H), 1.09-0.91 (m, 2H). |
| 94 | 10 | [M + H]+ 478 | (300 MHz, MeOD-d4): δ7.99-7.89 (m, 2H), 7.84-7.75 (m, 2H), 7.07-6.84 (m, 4H), 5.03-4.95 (m, 1H), 3.81-3.47 (m, 4H), 2.75-2.70 (m, 2H), 2.53-2.18 (m, 8H), 1.92-1.67 (m, 3H), 1.62-1.57 (m, 2H), 1.07-0.86 (m, 2H). |
| 95 | 10 | 531 [M + H]+ | (300 MHz, MeOD-d4) δ ppm: 8.04 (s, 4H), 7.33-7.07 (m, 2H), 7.07-6.85 (m, 2H), 5.07 (t, J = 6.6 Hz, 1H), 4.40-3.60 (m, 3H), 3.22 (d, J = 13.0 Hz, 7H), 3.14 (s, 3H), 2.90 (s, 4H), 2.52-2.24 (m, 1H), 1.87 (q, J = 11.0 Hz, 4H), 1.59-1.34 (m, 1H), 1.30 (dd, J = 15.7, 8.6 Hz, 1H). |
| 96 | 10 | 560 (M + 1) | (CD3OD, ppm): 7.97-8.12 (m, 2H), 7.74-7.97 (m, 2H), 6.98-7.13 (m, 2H), 6.84-6.98 (m, 2H), 4.96-5.12 (m, 1H), 3.42-3.85 (m, 4H), 2.60-2.80 (m, 8H), 2.34-2.60 (m, 4H), 2.12-2.34 (m, 4H), 1.72-1.93 (m, 3H), 1.50-1.72 (m, 2H), 0.97-1.05 (m, 2H) |
| 97 | 10 | 518 [M + H]+ | (400 MHz, MeOD-d4) δ ppm: 7.97-7.89 (m, 2H), 7.62-7.53 (m, 2H), 7.29 (t, J = 2.2 Hz, 2H), 7.10-7.00 (m, 2H), 6.98-6.87 (m, 2H), 6.32 (t, J = 2.2 Hz, 2H), 5.06 (m, 1H), 3.78 (m, 2H), 3.66 (m, 1H), 3.58 (m, 1H), 2.84-2.69 (m, 2H), 2.55-2.37 (m, 4H), 2.34-2.23 (m, 4H), 1.94-1.73 (m, 3H), 1.66 (m, 2H), 1.09-0.91 (m, 2H). |

TABLE 2-continued

Physical Data and Synthetic Methods

| Ex # | Scheme | MS | 1H NMR |
|---|---|---|---|
| 98 | 10 | 520 (M + 1) | (CD$_3$OD, ppm): 8.26-8.11 (m, 2H), 8.10-7.91 (m, 4H), 7.13-7.00 (m, 2H), 7.00-6.81 (m, 2H), 5.13-4.98 (m, 1H), 3.81-3.68 (m, 2H), 3.61-3.51 (m, 1H), 2.85-2.68 (m, 2H), 2.60-2.38 (m, 4H), 2.38-2.18 (m, 4H), 1.99-1.77 (m, 3H), 1.77-1.60 (m, 2H), 1.36-1.28 (m, 1H), 1.08-0.93 (m, 2H). |
| 99 | 10 | 534 (M + 1) | (CD$_3$OD, ppm): 8.07 (s, 1H), 7.91 (s, 4H), 7.09-6.99 (m, 2H), 6.99-6.88 (m, 2H), 5.12-5.02 (m, 1H), 4.28 (s, 3H), 3.85-3.65 (m, 3H), 3.58-3.48 (m, 1H), 2.82-2.72 (m, 2H), 2.58-2.40 (m, 4H), 2.37-2.28 (s, 3H), 2.37-2.27 (m, 1H), 1.97-1.77 (m, 3H), 1.77-1.59 (m, 2H), 1.08-0.91 (m, 2H). |
| 100 | 10 | 520 [M + H]$^+$ | (400 MHz, MeOD-d$_4$) δ ppm: 9.20(s, 1H), 8.20 (s, 1H), 8.04-8.01(m, 2H), 7.96-7.94(m, 2H), 7.05-7.02(m, 2H), 6.94-6.89(m, 2H), 5.08-5.04(m, 1H), 3.81-3.62(m, 3H), 3.59-3.51(m, 1H), 2.78-2.73(m, 2H), 2.55-2.36(m, 4H), 2.29-2.25(m, 4H), 1.89-1.86(m, 3H), 1.66-1.65(m, 2H), 1.04-1.02(m, 1H), 0.96-0.94(m, 1H) |
| 101 | 10 | 534 (M + 1) | (CD$_3$OD, ppm): 8.48 (s, 1H), 8.13 (m, 2H), 7.94 (m, 2H), 7.15-7.01 (m, 2H), 6.99-6.86 (m, 2H), 5.13-5.02 (m, 1H), 4.02 (s, 3H), 3.90-3.48 (m, 5H), 2.85-2.68 (m, 2H), 2.60-2.38 (m, 4H), 2.38-2.28 (m, 4H), 2.00-1.60 (m, 5H), 1.12-0.88 (m, 2H). |
| 102 | 10 | [M + H]$^+$ 521 | (300 MHz, Methanol-d$_4$) δ 8.20-8.10 (m, 2H), 8.10-7.95 (m, 2H), 7.28-7.10(m, 2H), 7.10-6.86(m, 2H), 5.14-5.06(m, 1H), 4.48-3.60(m, 3H), 3.56-3.31(m, 3H), 3.26-3.06(m, 3H), 2.99-2.88(m, 4H), 2.53-2.40(m, 1H), 2.03-1.78(m, 4H), 1.53-1.40(m, 1H), 1.40-1.25(m, 2H). |
| 103 | 10 | 531 [M + H]$^+$ | (400 MHz, MeOD-d$_4$) δ ppm: 8.85(s, 2H), 8.48(d, J = 8.4 Hz, 2H), 8.05-7.90 (m, 2H), 7.55-7.40 (m, 1H), 7.10-6.98 (m, 2H), 6.98-6.80 (m, 2H), 5.15-5.00 (m, 1H), 3.88-3.45 (m, 4H), 2.88-2.70 (m, 2H), 2.60-2.35 (m, 4H), 2.35-2.20 (m, 4H), 1.96-1.75 (m, 3H), 1.75-1.62 (m, 2H), 1.10-0.88 (m, 2H) |
| 104 | 10 | 531 (M + 1) | (CD$_3$OD, ppm): 9.18 (s, 1H), 8.47 (dd, 2H), 7.45-7.61 (m, 3H), 6.69-7.11 (m, 2H), 6.78-6.99 (m, 2H), 5.01-5.12 (m, 1H), 3.58-3.88 (m, 3H), 3.47-3.56 (m, 1H), 2.72-2.93 (m, 2H), 2.34-2.58 (m, 5H), 2.19-2.33 (m, 3H), 1.92-2.05 (m, 1H), 1.74-1.92 (m, 2H), 1.55-1.74 (m, 2H), 0.97-1.15 (m, 2H). |
| 105 | 10 | 533 [M + H]$^+$ | (400 MHz, MeOD-d$_4$) δ ppm: 8.36-8.31 (m, 1H), 7.89-7.79 (m, 3H), 7.30 (m, 1H), 7.20 (m, 1H), 7.07-6.97 (m, 2H), 6.95-6.84 (m, 2H), 5.10 (m, 1H), 3.94 (s, 3H), 3.86-3.60 (m, 3H), 3.54 (m, 1H), 2.85-2.69 (m, 2H), 2.56-2.35 (m, 4H), 2.33-2.22 (m, 4H), 1.97-1.76 (m, 3H), 1.67 (m, 2H), 1.08-0.89 (m, 2H). |
| 106 | 10 | 559 (M + 1) | (CD$_3$OD, ppm): 8.85 (d, 2H), 8.48 (d, J = 8.4 Hz, 2H), 7.95 (d, J = 8.7 Hz, 2H), 7.45 (dd, J = 4.8 Hz, 5.1 Hz, 1H), 7.14-6.96 (m, 2H), 6.96-6380 (m, 2H), 5.20-5.00 (m, 1H), 3.90-3.45 (m, 4H), 2.85-2.66 (m, 3H), 2.66-2.40 (m, 4H), 2.38-2.12 (m, 1H), 2.00-1.75 (m, 3H), 1.75-1.46 (m, 2H), 1.15-0.80 (m, 7H). |
| 107 | 10 | 574 (M + 1) | (CD$_3$OD, ppm): 8.64 (s, 1H), 7.91-8.12 (m, 5H), 7.01-7.11 (m, 2H), 6.89-7.00 (m, 2H), 5.03-5.12 (m, 1H), 3.44-3.99 (m, 9H), 2.71-2.85 (m, 2H), 2.25-2.38 (m, 1H), 1.82-1.98 (m, 3H), 1.62-1.76 (m, 2H), 1.27-1.38 (m, 1H), 0.92-1.11 (m, 2H). |
| 108 | 10 | 504 [M + H]$^+$ | (300 MHz, MeOD-d$_4$) δ ppm: 8.04-7.91 (m, 2H), 7.80 (d, J = 8.3 Hz, 2H), 7.08-6.96 (m, 2H), 6.95-6.85 (m, 2H), 5.00 (dd, J = 8.6, 5.5 Hz, 1H), 4.53-4.35 (m, 1H), 3.98 (ddt, J = 64.0, 15.0, 5.1 Hz, 1H), 3.78-3.41 (m, 1H), 3.11-2.90 (m, 6H), 2.81-2.64 (m, 2H), 2.24 (dt, J = 6.8, 3.5 Hz, 1H), 2.08-1.52 (m, 9H), 0.96 (ddt, J = 23.4, 7.0, 5.4 Hz, 2H). |
| 109 | 11 | 498 [M + H]$^+$ | (400 MHz, MeOD-d$_4$) δ ppm: 8.11-8.09 (m, 2H), 7.92-7.89 (m, 2H), 7.18-7.16 (m, 2H), 7.03-6.99 (m, 2H), 5.14 (m, 1H), 4.22-3.88 (m, 3H), 3.45 (m, 1H), 3.27-3.18 (m, 5H), 2.93 (m, 1H), 2.45 (m, 1H), 1.83-1.82 (m, 6H), 1.45 (m, 4H) |
| 110 | 12 | 520 [M + H]$^+$ | (400 MHz, MeOD-d$_4$) δ ppm: δ 8.64 (m, 1H), 8.10-7.96 (m, 4H), 7.93 (m, 1H), 7.09-7.01 (m, 2H), 6.96-6.86 (m, 2H), 5.07 (m, 1H), 3.77 (m, 2H), 3.67 (m, 1H), 3.54 (m, 1H), 2.81 (m, 2H), 2.55-2.38 (m, 4H), 2.32 (m, 4H), 1.95-1.68 (m, 4H), 1.36-1.26 (m, 1H), 1.12-0.94 (m, 2H). |
| 111 | 13 | 521 (M + 1) | (400 MHz, Methanol-d$_4$) δ 8.63 (d, J = 1.3 Hz, 1H), 8.07-8.05 (d, J = 7.2 Hz, 2H), 8.00-7.98 (d, J = 7.2 Hz, 2H), 7.93 (d, J = 1.2 Hz, 1H), 7.09-7.00 (m, 2H), 6.98- |

TABLE 2-continued

Physical Data and Synthetic Methods

| Ex # | Scheme | MS | 1H NMR |
|---|---|---|---|
| | | | 6.87 (m, 2H), 5.11 (m, 1H), 4.16-3.80 (m, 3H), 3.39-3.31 (m, 1H), 2.77 (m, 2H), 2.27 (m, 1H), 2.05-1.81 (m, 6H), 1.75-1.43 (m, 4H), 1.09-0.91 (m, 2H). |
| 112 | 13 | 519 [M + H]$^+$ | (400 MHz, MeOD-d$_4$) δ ppm: δ 8.26 (s, 1H), 8.01 (d, J = 2 Hz, 2H), 7.68(d, J = 2 Hz, 2H), 7.67(s, 1H), 7.18 (m, 1H), 7.10-7.00 (m, 2H), 6.99-6.87 (m, 2H), 5.06 (m, 1H), 3.85-3.62 (m, 3H), 3.54 (m, 1H), 2.85-2.69 (m, 2H), 2.56-2.38 (m, 4H), 2.34-2.23 (m, 4H), 1.89-1.70 (m, 3H), 1.60-1.56 (m, 2H), 1.09-0.91 (m, 2H). |
| 113 | 13 | 499.4 (M + 1) | (CD$_3$OD, ppm): 7.95-7.88 (m, 2H), 7.25-7.10 (m, 2H), 7.10-6.98 (m, 2H), 6.98-6.82 (m, 2H), 5.10-4.95 (m, 1H), 3.87-3.40 (m, 4H), 2.80-2.63 (m, 3H), 2.63-2.46 (m, 4H), 2.28-2.15 (m, 1H), 1.91-1.70 (m, 3H), 1.70-1.52 (m, 2H), 1.10-0.90 (m, 7H). |
| 114 | 13 | 547 [M + H]$^+$ | (400 MHz, MeOD-d$_4$) δ ppm: 9.20 (d, J = 1.6 Hz, 1H), 8.37 (dd, J = 2.4 Hz, 6 Hz, 1H), 8.00-7.90(m, 1H), 7.20-7.00(m, 2H), 7.00-6.89 (m, 2H), 5.15-5.05 (m, 1H), 3.80-3.50 (m, 4H), 3.20-3.05 (m, 2H), 2.85-2.60 (m, 6H), 2.30-2.20 (m, 1H), 2.00-1.78 (m, 3H), 1.78-1.60 (m, 2H), 1.10-0.95 (m, 2H). |
| 115 | 13 | 557 [M + H]$^+$ | (400 MHz, MeOD-d$_4$) δ ppm: 7.77-7.68 (m, 2H), 7.22-7.12 (m, 2H), 7.06-6.95 (m, 2H), 6.62-6.53 (m, 2H), 5.10 (m, 1H), 4.43 (m, 1H), 4.22 (m, 1H), 3.88 (m, 1H), 3.73-3.63 (m, 1H), 3.38-3.10 (m, 10H), 2.92 (m, 1H), 2.44 (m, 1H), 2.11-1.99 (m, 4H), 2.00-1.75 (m, 4H), 1.45 (m, 1H), 1.39-1.29 (m, 1H). |
| 116 | 13 | 501[M + H]$^+$ | (400 MHz, Methanol-d$_4$) δ 8.26 (s, 1H), 8.05-7.98 (m, 2H), 7.75-7.65 (m, 3H), 7.19 (s, 1H), 7.10-7.00 (m, 2H), 7.00-6.90 (m, 2H), 4.90-4.10 (m, 5H), 3.88-3.76 (m, 1H), 2.85-2.70 (m, 2H), 2.36-2.21 (m, 1H), 2.00-1.55 (m, 5H), 1.15-0.95 (m, 2H). |
| 117 | 14 | 520[M + H]$^+$ | (400 MHz, MeOD-d$_4$) δ ppm: δ 8.64 (s, 1H), 8.11-7.96 (m, 4H), 7.93 (m, 1H), 7.05 (m, 2H), 6.98-6.88 (m, 2H), 4.68-3.75 (m, 5H), 3.27-3.16 (m, 1H), 2.78 (m, 2H), 2.28 (m, 1H), 2.21 (d, J = 5.9 Hz, 6H), 1.95-1.79 (m, 3H), 1.66 (m, 2H), 1.09-0.91 (m, 2H). |
| 118 | 14 | 584 (M + 1) | (CD$_3$OD, ppm): 8.69-8.91 (m, 2H), 8.38-8.45 (m, 2H), 7.89-8.00 (m, 2H), 7.33-7.44 (m, 1H), 6.98-7.07 (m, 2H), 6.79-6.96 (m, 2H), 4.96-5.12 (m, 1H), 3.73-3.95 (m, 3H), 3.44-3.58 (m, 4H), 2.68-2.72 (m, 2H), 2.18-2.31 (m, 1H), 1.77-1.93 (m, 3H), 1.57-1.71 (m, 2H), 0.80-1.08 (m, 3H) |
| 119 | 14 | 522[M + H]$^+$ | (400 MHz, MeOD-d$_4$) δ ppm: 9.85(s, 1H), 8.10-8.08 (m, 2H), 8.01-7.99 (m, 2H), 7.07-7.03 (m, 2H), 6.94-6.90 (m, 2H), 5.12 (m, 1H), 4.09 (m, 3H), 3.55-3.04 (m, 3H), 2.91 (m, 2H), 2.32 (m, 1H), 2.03-1.40 (m, 9H), 1.02 (m, 2H). |
| 120 | 14 | [M + H]$^+$ 521 | (300 MHz, MeOD-d$_4$): δ9.82 (s, 1H), 8.11-7.92 (m, 4H), 7.08-6.83 (m, 4H), 5.10-5.03 (m, 1H), 3.79-3.57 (m, 4H), 2.78-2.72 (m, 2H), 2.53-2.19 (m, 8H), 1.93-1.74 (m, 3H), 1.68-1.62(m, 2H), 1.08-0.87 (m, 2H). |
| 121 | 14 | 478 [M + H]$^+$ | (400 MHz, MeOD-d$_4$) δ ppm: 8.05-7.90 (m, 2H), 7.90-7.70 (m, 2H), 7.10-7.00 (m, 2H), 7.00-6.86 (m, 2H), 5.05-4.90 (m, 1H), 4.50-4.25(m, 1H), 4.10-3.90 (m, 1H), 3.90-3.62 (m, 1H), 3.45-3.37 (m, 1H), 3.37-3.30 (m, 1H), 3.28-3.18 (m, 1H), 2.80-2.60 (m, 2H), 2.30-2.18 (m, 1H), 1.95-1.50 (m, 5H), 1.10-0.85 (m, 2H) |
| 122 | 14 | 478 [M + H]$^+$ | (400 MHz, MeOD-d$_4$) δ ppm: 9.20-8.85(m, 1H), 8.20-8.00 (m, 2H), 8.00-7.96 (m, 2H), 7.15-6.88 (m, 4H), 5.05-4.65 (m, 1H), 4.26-3.80 (m, 3H), 3.75-3.60 (m, 1H), 3.45-3.38 (m, 1H), 3.30-3.20 (m, 1H), 2.95-2.80 (m, 3H), 2.70-2.58 (m, 2H), 2.20-2.12 (m, 1H), 1.90-1.67 (m, 3H), 1.60-1.36 (m, 2H), 1.00-0.80 (m, 2H) |
| 123 | 14 | 546 [M + H]$^+$ | (400 MHz, MeOD-d$_4$) δ ppm: 8.64 (s 1H), 8.11-7.91 (m, 5H), 7.04 (m, H), 6.98-6.87 (m, 2H), 5.11-5.00 (m, 1H), 4.54 (m, 1H), 4.01-3.51(m, 1H), 3.02 (m, 6H), 2.78 (m, 2H), 2.28 (m, 1H), 2.04-1.60 (m, 9H), 1.00 (m, 2H). |
| 124 | 14 | 557 [M + H]$^+$ | (300 MHz, MeOD-d$_4$) δ ppm: 8.86 (dd, J = 4.9, 1.1 Hz, 2H), 8.47 (dd, J = 8.4, 1.7 Hz, 2H), 7.94 (d, J = 8.4 Hz, 2H), 7.37 (t, J = 4.9 Hz, 1H), 7.02 (d, J = 8.6, 5.4 Hz, 2H), 6.89 (t, J = 8.5 Hz, 2H), 5.05 (dd, J = 8.3, 5.2 Hz, 1H), 4.47 (d, J = 27.3 Hz, 1H), 4.16-3.82 (m, 1H), 3.81-3.47 (m, 1H), 3.02 (dq, J = 13.2, 6.4 Hz, 6H), 2.84-2.70 (m, 2H), 2.26 (dd, J = 7.1, 3.9 Hz, 1H), 2.10-1.56 (m, 9H), 1.10-0.84 (m, 2H) |

TABLE 2-continued

Physical Data and Synthetic Methods

| Ex # | Scheme | MS | 1H NMR |
|---|---|---|---|
| 125 | 14 | 463 [M + H]$^+$ | (400 MHz, MeOD-d$_4$) δ 7.98 (d, J = 4.8 Hz, 2H), 7.83 (d, J = 2 Hz, 2H), 7.10-7.00 (m, 2H), 7.00-6.90 (m, 2H), 4.96-4.90 (m, 1H), 4.77-4.62 (m, 1H), 4.80-4.65 (m, 1H), 4.60-4.45 (m, 2H), 4.45-4.20 (m, 2H), 2.85-2.72 (m, 2H), 2.35-2.22 (m, 1H), 2.00-1.75 (m, 3H), 1.70-1.58 (m, 2H), 1.10-0.90 (m, 2H) |
| 126 | 15 | 522 [M + H]$^+$ | (400 MHz, MeOD-d$_4$) δ ppm: 8.03-7.95 (d, J = 4.8 Hz, 2H), 7.89-7.81 (d, J = 4.8 Hz, 2H), 7.23-7.13 (m, 2H), 7.07-6.96 (m, 2H), 5.08 (m, 1H), 4.09 (m, 4H), 3.91 (m, 1H), 3.74 (m, 1H), 3.40 (m, 3H), 3.25 (m, 3H), 2.93 (m, 1H), 2.47 (m, 1H), 2.00-1.77 (m, 4H), 1.48 (m, 1H), 1.35 (m, 1H). |
| 127 | 16 | [M + H]$^+$ 654; | (400 MHz, Methanol-d$_4$) δ 8.64 (s, 1H), 8.10-7.99(m, 4H), 7.99-7.92 (m, 1H), 7.39-7.22 (m, 5H), 7.15-6.90 (m, 2H), 6.90-6.75 (m, 2H), 5.21-5.13 (m, 3H), 3.78-3.52 (m, 6H), 3.49-3.40 (m, 1H), 2.75-2.64 (m, 1H), 2.55-2.40 (m, 4H), 2.40-2.25 (m, 3H), 2.25-2.10 (m, 1H), 1.93-65 (m, 4H), 1.52-1.10 (m, 3H). |
| 128 | 17 | [M + H]$^+$593 | (300 MHz, MeOD-d$_4$) δ ppm: 7.89~7.87(m, 2H), 7.70~7.62(m, 4H), 7.46~7.35(m, 3H), 7.04~6.99(m, 2H), 6.89~6.86(, .2H), 5.07~5.02(m, 1H), 3.92~3.86(m, 1H), 3.72~3.65(m, 1H), 3.51~3.45(m, 1H), 3.38~3.32(m, 2H), 3.28~3.25(m, 1H), 3.18~3.07(m, 1H), 2.83(s, 3H), 2.77~2.72(m, 2H), 2.26~2.24(m, 1H), 1.89~1.82(m, 3H), 1.66~1.64(m, 2H), 1.03~0.92(m, 2H). |
| 129 | 18 | 532 [M + H]$^+$ | (400 MHz, Methanol-d$_4$) δ 8.63 (s, 1H), 8.06-8.03 (m, 2H), 8.03-7.98 (m, 2H), 7.97-7.93(m, 1H), 6.96-6.94 (m, 2H), 6.76-6.74 (m, 2H), 5.08-5.07 (m, 1H), 3.76-3.63 (m, 6H), 3.57-3.51 (m, 1H), 2.80-2.74 (m, 2H), 2.56-2.38 (m, 4H), 2.31 (s, 3H), 2.26-2.20 (m, 1H), 1.89-1.81 (m, 3H), 1.72-1.64 (m, 2H), 0.99-0.89 (m, 2H) |
| 130 | 19 | [M + H]$^+$ 538 | (400 MHz, Methanol-d$_4$) δ 8.67 (s, 1H), 7.99-7.82 (m, 4H), 7.05 (ddd, J = 8.4, 5.3, 2.6 Hz, 2H), 6.98-6.86 (m, 2H), 5.10 (m, 1H), 3.83-3.50 (m, 4H), 2.84-2.68 (m, 2H), 2.56-2.36 (m, 4H), 2.59 (s, 3H) 2.25-2.23 (m, 1H), 1.97-1.79 (m, 2H), 1.79-1.70 (m, 1H), 1.69-1.60 (m, 2H), 1.08-0.91 (m, 2H). |
| 131 | 20 | 548[M + H]$^+$ | (400 MHz, Methanol-d$_4$) δ 8.66 (s, 1H), 8.12-7.99 (m, 4H), 7.96 (s, 1H), 7.15-7.02(m, 2H), 7.02-6.88 (m, 2H), 5.17-5.01 (s, 1H), 4.20-3.63 (m, 3H), 3.48-3.36 (m, 1H), 2.78 (s, 2H), 2.51-2.10 (s, 5H), 1.98-1.79 (m, 3H), 1.79-1.51 (m, 2H), 1.12-0.89 (m, 2H) |
| 132 | 21 | 520 [M + H]$^+$ | (400 MHz, MeOD-d$_4$) δ ppm: 8.65(s, 1H), 8.06-8.01 (m, 2H), 7.98-7.93(m, 2H), 7.93(s, 1H), 7.05-7.01(m, 2H), 6.92-6.87(m, 2H), 5.08-5.05(m, 1H), 3.81-3.62(m, 3H), 3.57-3.50(m, 1H), 2.78-2.75(m, 2H), 2.55-2.49(m, 4H), 2.35-2.26(m, 4H), 1.89-1.86(m, 3H), 1.84-1.82(m, 2H), 1.04-1.02(m, 1H), 0.96-0.95(m, 1H) |
| 133 | 21 | 520 [M + H]$^+$ | (400 MHz, MeOD-d$_4$) δ ppm: 8.65(s, 1H), 8.15-7.94 (m, 5H), 7.11-7.05(m, 2H), 6.96-6.87(m, 2H), 5.15-5.05(m, 1H), 3.87-3.47(m, 4H), 2.87-2.72(m, 2H), 2.55-2.40(m, 4H), 2.35-2.32(m, 3H), 2.32-2.27 (m, 1H), 1.99-1.76(m, 3H), 1.76-1.52 (m, 2H), 1.14-1.02(m, 1H), 1.02-0.91(m, 1H) |
| 134 | 22 | 531 [M + H]$^+$ | (400 MHz, MeOD-d$_4$) δ ppm: 9.19 (d, J = 1.6 Hz, 1H), 8.73 (dd, J = 2.5, 1.5 Hz, 1H), 8.60 (d, J = 2.5 Hz, 1H), 8.26-8.18 (m, 2H), 8.05-7.98 (m, 2H), 7.23-7.13 (m, 2H), 7.07-6.94 (m, 2H), 5.12 (m, 1H), 4.68-4.48 (m, 2H), 3.57 (s, 3H), 3.36-3.20 (m, 2H), 3.13 (m, 3H), 2.98-2.89 (m, 4H), 2.47 (m, 1H), 2.03-1.80 (m, 4H), 1.49 (m, 1H), 1.35 (m, 1H). |
| 135 | 23 | 531 (M + 1) | (CD$_3$OD, ppm): 9.20 (s, 1H), 9.13 (s, 2H), 8.02 (d, J = 6.3 Hz, 2H), 7.84 (d, J = 6.9 Hz, 2H), 7.12-7.00 (m, 2H), 700-6.86 (m, 2H), 5.15-5.05 (m, 1H), 3.86-3.52 (m, 4H), 2.85-2.73 (m, 2H), 2.55-2.45 (m, 3H), 2.30 (s, 3H), 2.30-2.22 (m, 1H), 1.92-1.85 (m, 2H), 1.80-1.60 (m, 2H), 1.40-0.90 (m, 4H). |
| 136 | 23 | 531 [M + H]$^+$ | (400 MHz, MeOD-d$_4$) δ ppm: 9.21-9.20(m, 1H), 8.28-8.21(m, 3H), 8.05-8.03(m, 2H), 7.87-7.83(m, 1H), 7.08-7.05(m, 2H), 6.96-6.92(m, 2H), 5.10-5.09(m, 1H), 3.85-3.52(m, 4H), 2.80-2.78(m, 2H), 2.54-2.43(m, 4H), 2.33 (s, 3H), 2.30-2.29(m, 1H), 1.94-1.82(m, 3H), 1.73-1.65(m, 2H), 1.07-1.05(m, 1H), 0.98-0.97(m, 1H), |
| 137 | 24 | 523.3 (M + 1) | (400 MHz, Methanol-d$_4$) δ 8.64 (d, J = 1.3 Hz, 1H), 8.11-7.91 (m, 5H), 7.04 (ddd, J = 8.5, 5.3, 2.6 Hz, 2H), 6.97-6.86 (m, 2H), 5.07 (dd, J = 8.7, 5.2 Hz, 1H), 3.87-3.40 |

TABLE 2-continued

Physical Data and Synthetic Methods

| Ex # | Scheme | MS | 1H NMR |
|---|---|---|---|
| | | | (m, 4H), 2.77 (ddd, J = 11.4, 8.6, 5.1 Hz, 2H), 2.59-2.35 (m, 4H), 2.27 (ddd, J = 7.5, 4.4, 3.3 Hz, 1H), 1.85 (dddd, J = 28.2, 14.0, 7.4, 4.4 Hz, 3H), 1.74-1.59 (m, 2H), 1.08-0.90 (m, 2H). |
| 138 | 25 | 528 [M + H]$^+$ | (300 MHz, MeOD-d$_4$) δ ppm: 8.60 (s, 1H), 8.17-7.84 (m, 5H), 7.11-7.01 (m, 2H), 6.95-6.77 (m, 2H), 5.03 (m, 1H), 2.75 (m, 2H), 2.38-2.10 (m, 4H), 1.95-1.67 (m, 3H), 1.70-1.58 (m, 2H), 1.14-0.80 (m, 2H). |
| 139 | | 565 [M + H]$^+$ | (400 MHz, MeOD-d$_4$) δ ppm: δ8.33(s, 1H), 7.99-7.96(d, J = 8.8 Hz, 2H), 7.87-7.85(d, 2H), 7.76(s, 1H), 7.05-7.02(m, 2H), 6.92-6.87(m, 2H), 6.57-6.56(m, 1H), 5.14-5.11(m, 1H), 4.19-4.16(m, 1H), 3.57-3.41(m, 1H), 3.12-2.95(m, 1H), 2.80-2.72(m, 2H), 2.29-1.78(m, 8H), 1.71-1.61(m, 2H), 1.06-1.01(m, 1H), 0.96-0.92(m, 1H). |
| 140 | | 519 [M + H]$^+$ | (400 MHz, MeOD-d$_4$) δ ppm: δ 8.25 (s, 1H), 8.01 (d, J = 2 Hz, 2H), 7.68(d, J = 2 Hz, 2H), 7.67(s, 1H), 7.18 (m, 1H), 7.10-7.00 (m, 2H), 6.99-6.87 (m, 2H), 5.08 (m, 1H), 3.85-3.62 (m, 3H), 3.54 (m, 1H), 2.85-2.69 (m, 2H), 2.56-2.38 (m, 4H), 2.34-2.23 (m, 4H), 1.89-1.70 (m, 3H), 1.60-1.56 (m, 2H), 1.09-0.91 (m, 2H). |
| 141 | 2 | 607[M + H]$^+$ | (400 MHz, Methanol-d4) δ 7.96 (dd, J = 8.5, 1.8 Hz, 2H), 7.76 (d, J = 8.1 Hz, 2H), 7.73-7.66 (m, 2H), 7.49 (t, J = 7.6 Hz, 2H), 7.41 (t, J = 7.3 Hz, 1H), 7.26-7.19 (m, 2H), 7.10-7.02 (m, 2H), 5.11 (dd, J = 8.6, 5.5 Hz, 1H), 4.01 (dd, J = 26.1, 13.6 Hz, 2H), 3.66 (t, J = 11.0 Hz, 1H), 3.56-3.36 (m, 3H), 3.22 (t, J = 7.8 Hz, 3H), 3.18-3.08 (m, 1H), 2.97 (dt, J = 7.8, 4.0 Hz, 1H), 2.88 (s, 3H), 2.47 (ddd, J = 10.4, 6.7, 3.6 Hz, 1H), 1.86 (dtt, J = 39.1, 16.6, 7.5 Hz, 4H), 1.68-1.43 (m, 3H), 1.39 (q, J = 7.1 Hz, 1H). |
| 142 | 26 | 534 [M + H]$^+$ | (400 MHz, CD$_3$OD-d$_4$) δ ppm: 8.67 (d, J = 1.2 Hz, 1H), 8.18-8.01 (m, 4H), 7.96 (d, J = 1.3 Hz, 1H), 7.29-7.15 (m, 2H), 7.13-6.97 (m, 2H), 5.06 (m, 1H), 4.8-4.3(m, 2H), 3.9-2.9 (m, 12H), 2.50 (m, 1H), 2.03-1.71 (m, 4H), 1.69-1.33 (m, 4H). |
| 143 | 27 | 492 [M + H]$^+$ | (300 MHz, CD$_3$OD-d$_4$) δ ppm: 8.02-7.88 (d, J = 11.6 Hz, 2H), 7.88-7.70 (d, J = 11.6 Hz, 2H), 7.07-6.81 (m, 4H), 4.99 (m, 1H), 3.73-3.69 (m, 2H), 3.64-3.38 (m, 2H), 2.68 (t, J = 7.1 Hz, 2H), 2.57-2.34 (m, 4H), 2.30-2.16 (m, 4H), 1.97-1.67 (m, 3H), 1.49-1.3 (m, 4H), 1.08-0.82 (m, 2H). |
| 144 | 28 | 545 [M + H]$^+$ | (300 MHz, CD$_3$OD-d$_4$) δ ppm: 8.85 (d, J = 4.9 Hz, 2H), 8.48 (d, J = 8.3 Hz, 2H), 7.94 (d, J = 8.3 Hz, 2H), 7.38 (t, J = 4.9 Hz, 1H), 7.03 (t, J = 8.7 Hz, 2H), 6.91 (t, J = 8.7 Hz, 2H), 5.03 (m, 1H), 4.60-4.55 (m, 2H), 3.82-3.44 (m, 4H), 2.72 (t, J = 7.1 Hz, 2H), 2.49-2.30(m, 4H), 2.29 (m, 4H), 1.98-1.73 (m, 3H), 1.67-1.35 (m, 4H), 1.12-0.86 (m, 2H). |
| 145 | 29 | [M + H]+ 536 | (400 MHz, CDCl$_3$): δ7.87~7.82 (m, 2H), 7.17~7.07 (m, 4H), 6.99~6.95 (m, 2H), 5.70~5.65 (m, 1H), 3.81~3.64 (m, 10H), 3.42~3.50 (m, 1H), 3.39~3.33 (m, 3H), 2.22~2.30 (m, 1H), 1.10~1.20 (m, 1H), 1.00 (s, 3H), 0.90~0.87 (m, 1H) |
| 146 | 30 | 568 [M + H]$^+$ | (300 MHz, MeOD-d$_4$) δ ppm: 8.00-7.91(m, 2H), 7.62-7.48(m, 2H), 7.12-7.00(m, 2H), 7.00-6.81 (m, 2H), 6.09 (s, 1H), 5.18-5.08 (m, 1H), 4.50-4.28 (m, 2H), 4.00-3.81 (m, 1H), 3.78-3.59 (m, 1H), 3.58-3.36 (m, 1H), 3.21-3.03 (m, 3H), 2.91-2.78 (m, 2H), 2.34-2.25 (m, 4H), 2.10-1.94 (m, 2H), 1.94-1.80 (m, 1H), 1.10-0.90(m, 2H) |
| 147 | 2 | 515 [M + H]$^+$ | (300 MHz, Methanol-d$_4$) δ 8.07-7.91 (m, 6H), 7.58 (m, 3H), 7.06-6.83 (m, 4H), 5.08 (dd, J = 8.5, 5.3 Hz, 1H), 4.36 (m, 2H), 3.89 (m, 2H), 3.66 (s, 1H), 3.39 (s, 1H), 3.10 (s, 3H), 2.81 (t, J = 6.7 Hz, 2H), 2.25 (dd, J = 7.2, 3.9 Hz, 1H), 2.04-1.87 (m, 2H), 1.06-0.87 (m, 2H) |
| 148 | 31 | [M + H]+567 | (300 MHz, CD$_3$OD): δ(ppm): 7.98-7.96 (d, 1H, J = 6 HZ), 7.34~7.32 (d, 2H, J = 6 Hz), 7.19-7.15 (t, 2H, J = 6 Hz), 7.04-7.00 (t, 2H, J = 6 Hz), 5.81 (s, 2H), 5.24-5.19 (m, 1H), 4.35-4.27 (m, 1H), 4.16-4.05 (m, 1H), 3.87-3.85 (m, 2H), 3.33-3.28 (m, 2H), 3.16-3.10 (m, 4H), 2.99-2.95 (m, 1H), 2.48-2.43 (m, 1H), 2.29-2.10 (m, 2H), 1.98 (s, 6H), 1.50-1.40 (m, 1H), 1.38-1.33 (m, 1H) |
| 150 | 32 | 550 [M + H]$^+$ | (400 MHz, MeOD-d$_4$) δ ppm: 8.05-7.94 (m, 2H), 7.85-7.75 (m, 2H), 7.74-7.64 (m, 2H), 7.55-7.46 (m, 2H), 7.46-7.39 (m, 1H), 7.30-7.18 (m, 2H), 7.11-7.01 (m, 2H), 5.27 (dd, J = 8.0, 5.5 Hz, 1H), 4.40 (d, J = 14.6 Hz, 1H), 4.16 (d, J = 15.3 Hz, 1H), 3.89 (dd, J = 22.3, 16.0 |

TABLE 2-continued

Physical Data and Synthetic Methods

| Ex # | Scheme | MS | 1H NMR |
|---|---|---|---|
| | | | Hz, 2H), 3.44-3.35 (m, 2H), 3.19 (d, J = 6.1 Hz, 4H), 3.02 (dt, J = 7.9, 4.0 Hz, 1H), 2.54 (ddd, J = 10.3, 6.7, 3.6 Hz, 1H), 2.35 (dq, J = 14.0, 6.9 Hz, 1H), 2.29-2.15 (m, 1H), 1.55 (ddd, J = 10.7, 6.9, 4.4 Hz, 1H), 1.42 (q, J = 7.1 Hz, 1H) |
| 151 | 17 | 564 [M + H]$^+$ | (300 MHz, MeOD-d$_4$) δ ppm: 7.92 (s, 2H), 7.67 (dd, J = 17.5, 8.3 Hz, 4H), 7.51-7.30 (m, 3H), 7.07 (s, 2H), 6.93 (q, J = 9.0, 8.0 Hz, 2H), 5.07 (s, 1H), 4.51-4.23 (m, 2H), 3.94 (s, 1H), 3.67 (s, 1H), 3.36 (s, 1H), 3.16 (d, J = 18.6 Hz, 3H), 2.91 (s, 2H), 2.47 (s, 1H), 2.07 (d, J = 9.2 Hz, 1H), 1.89 (s, 2H), 1.71 (d, J = 10.8 Hz, 2H), 1.12 (d, J = 32.7 Hz, 2H). |
| 152 | 33 | [M + H]$^+$ 628; | (300 MHz, CD$_3$OD-d$_4$) 8.04-7.83 (m, 8H), 7.23-7.18 (m, 2H), 7.06-7.00 (m, 2H), 5.27-5.22 (m, 1H), 4.42-4.35 (m, 1H), 4.19-4.12 (m, 1H), 3.95-3.80 (m, 2H), 3.36-3.30 (m, 2H), 3.19-3.14 (m, 7H), 3.03-2.97 (m, 1H), 2.55-2.48 (m, 1H), 2.38-2.15 (m, 2H), 1.58-1.51 (m, 1H), 2.41-1.32 (m, 1H) |
| 153 | 17 | 529 [M + H]$^+$ | (400 MHz, MeOD-d$_4$) δ ppm: 7.99-7.92 (m, 2H), 7.80-7.72 (m, 2H), 7.69 (dd, J = 7.5, 1.6 Hz, 2H), 7.49 (t, J = 7.6 Hz, 2H), 7.41 (t, J = 7.3 Hz, 1H), 7.11-7.02 (m, 2H), 6.94 (t, J = 8.8 Hz, 2H), 5.10 (dd, J = 8.7, 5.2 Hz, 1H), 3.81 (d, J = 15.7 Hz, 2H), 3.69 (s, 1H), 3.53 (d, J = 24.1 Hz, 1H), 2.79 (dp, J = 11.8, 5.1 Hz, 2H), 2.60-2.37 (m, 4H), 2.34 (s, 2H), 2.30 (dt, J = 7.7, 4.1 Hz, 1H), 1.98-1.78 (m, 3H), 1.69 (q, J = 8.0 Hz, 2H), 1.06 (dt, J = 9.6, 4.9 Hz, 1H), 0.98 (q, J = 6.1 Hz, 1H) |
| 155 | 2 | 457 [M + H]$^+$ | (300 MHz, MeOD-d$_4$) δ ppm: 7.96-7.93(m, 2H), 7.24-7.17(m, 4H), 7.04-7.00(m, 2H), 5.19-5.15(m, 1H), 3.31(m, 10H), 2.98-2.92(m, 4H), 2.52-2.50(m, 1H), 2.30-2.20(m, 1H), 2.19-2.17(m, 1H), 1.55-1.51(m, 1H), 1.49-1.35(m, 1H) |
| 156 | 18 | [M + H]+554 | (300 MHz, CD$_3$OD-d4) δ (ppm): 8.31 (d, J = 2.6 Hz, 1H), 8.01-7.82 (m, 4H), 7.76-7.74(m, 1H), 7.22-7.10 (m, 2H), 7.06-6.92 (m, 2H), 6.56-6.54 (m, 1H), 5.14-5.12 (m, 1H), 4.42-4.38 (m, 1H), 4.32-4.24 (m, 1H), 3.92-3.88 (m, 1H), 3.75-3.65 (m, 1H), 3.29-3.08 (m, 5H), 2.92-2.82 (m, 1H), 2.46-2.42 (m, 1H), 1.99-1.78 (m, 4H), 1.51-1.27 (m, 2H) |
| 157 | 7 | 519 [M + H]$^+$ | (400 MHz, MeOD-d$_4$) δ ppm: 8.36 (d, J = 2.6 Hz, 1H), 8.08-7.98 (m, 2H), 7.97-7.88 (m, 2H), 7.80 (d, J = 1.7 Hz, 1H), 7.30-7.16 (m, 2H), 7.11-6.98 (m, 2H), 6.60 (t, J = 2.2 Hz, 1H), 5.12 (dd, J = 8.2, 5.2 Hz, 1H), 4.60 (d, J = 85.5 Hz, 2H), 3.59 (s, 3H), 3.31-3.03 (m, 4H), 3.03-2.83 (m, 4H), 2.50 (ddd, J = 10.3, 6.6, 3.6 Hz, 1H), 2.09-1.72 (m, 4H), 1.51 (ddd, J = 10.8, 6.9, 4.4 Hz, 1H), 1.43-1.31 (m, 1H). |
| 158 | 7; 34(a); 34(b) | 520 [M + H]$^+$ | (300 MHz, MeOD-d$_4$) δ ppm: 8.61(s, 1H), 8.04-7.95(q, 4H), 7.90(s, 1H), 7.04-7.00(m, 2H), 6.99-6.86(m, 2H), 5.09-5.05(m, 1H), 3.80-3.61(m, 3H), 3.59-3.49(m, 1H), 2.80-2.70(m, 2H), 2.51-2.30(m, 4H), 2.30-2.18(m, 4H), 1.87-1.80(m, 3H), 1.65-1.62(m, 2H), 1.02-0.91(m, 2H) |
| 159 | 2 | 529 [M + H]$^+$ | (400 MHz, MeOD-d$_4$) δ ppm: 7.95 (d, J = 7.8 Hz, 2H), 7.75 (d, J = 7.9 Hz, 2H), 7.72-7.66 (m, 2H), 7.49 (t, J = 7.6 Hz, 2H), 7.40 (t, J = 7.4 Hz, 1H), 7.12-7.04 (m, 2H), 6.96 (t, J = 8.7 Hz, 2H), 5.19 (s, 1H), 5.07 (s, 1H), 4.58-4.25 (m, 2H), 4.10 (d, J = 18.4 Hz, 2H), 3.91 (s, 2H), 3.55 (s, 1H), 3.46 (s, 1H), 2.88 (t, J = 6.9 Hz, 2H), 2.33 (s, 1H), 2.17-1.87 (m, 4H), 1.09 (dt, J = 9.6, 4.9 Hz, 1H), 0.99 (t, J = 6.0 Hz, 1H) |
| 160 | 2 | 515 [M + H]$^+$ | (300 MHz, Methanol-d$_4$) δ 7.98-7.88 (m, 2H), 7.78-7.59 (m, 4H), 7.51-7.31 (m, 3H), 7.17 (ddd, J = 8.2, 5.2, 2.6 Hz, 2H), 7.08-6.94 (m, 2H), 5.20 (t, J = 6.7 Hz, 1H), 4.33-4.16 (m, 1H), 4.07 (d, J = 18.5 Hz, 1H), 3.87-3.66 (m, 2H), 3.32 (m, 4H), 2.97 (dt, J = 7.9, 4.1 Hz, 1H), 2.57-2.48 (m, 1H), 2.36-2.24 (m, 1H), 2.16 (dt, J = 14.0, 7.1 Hz, 1H), 1.50 (dt, J = 10.9, 5.9 Hz, 1H), 1.35 (q, J = 7.0 Hz, 1H) |
| 161 | 17 | 506 [M + H]$^+$ | (300 MHz, MeOD-d$_4$) δ ppm: 7.92-7.90(m, 2H), 7.23-7.17(m, 4H), 7.04-7.00(m, 2H), 5.12-5.09(m, 1H), 4.48-4.40(m, 1H), 4.31-4.21(m, 1H), 3.92-3.83(m, 1H), 3.72-3.67(m, 1H), 3.28-3.09(m, 6H), 2.95-2.93(m, 1H), 2.44(m, 1H), 1.90-1.82(m, 4H), 1.47-1.44(m, 1H), 1.37-1.35(m, 1H) |
| 162 | 35 | :[M + H]$^+$565 | (300 MHz, MeOD-d4) δ ppm: 8.70-8.58 (m, 1H), 8.15-8.00 (m, 2H), 8.00-7.80 (m, 4H), 7.60-7.42 (m, 1H), |

TABLE 2-continued

Physical Data and Synthetic Methods

| Ex # | Scheme | MS | 1H NMR |
|---|---|---|---|
| | | | 7.10-6.96 (m, 2H), 6.96-6.80 (m, 2H), 5.15-5.00 (m, 1H), 4.60-4.20 (m, 2H), 4.03-3.82 (m, 1H), 3.72-3.56 (m, 1H), 3.48-3.35 (m, 1H), 3.23-3.02 (m, 3H), 2.85-2.65 (m, 2H), 2.35-2.20 (m, 1H), 2.00-1.80 (m, 3H), 1.78-1.50 (m, 2H), 1.05-0.88 (m, 2H) |
| 163 | 36 | [M + H]+555 | (300 MHz, Methanol-d$_4$): δ(ppm): 9.06 (s, 2H), 8.09-7.98 (m, 2H), 7.79-7.69 (m, 2H), 7.02 (dd, J = 8.7, 5.4 Hz, 2H), 6.90 (t, J = 8.8 Hz, 2H), 5.08-4.96 (m, 1H), 4.48-4.35(m, 2H), 3.92-3.81 (m, 1H), 3.68-3.63 (m, 1H), 3.42-3.35(m, 1H), 3.15-3.08 (m, 3H), 2.75 (t, J = 7.1 Hz, 2H), 2.30-2.20 (m, 1H), 1.89-1.82 (m, 3H), 1.64-1.55 (m, 2H), 1.08-0.89 (m, 2H) |
| 164 | 37 | 555 [M + H]+ | (300 MHz, Methanol-d$_4$) δ 8.61 (d, J = 1.3 Hz, 1H), 8.11-7.87 (m, 5H), 7.02 (ddd, J = 8.3, 5.4, 2.6 Hz, 2H), 6.97-6.83 (m, 2H), 5.09-4.97 (m, 1H), 4.42 (d, J = 18.0 Hz, 1H), 4.32 (s, 1H), 3.93 (t, J = 12.6 Hz, 1H), 3.64 (s, 1H), 3.41 (d, J = 12.3 Hz, 1H), 3.11 (m, 3H), 2.75 (t, J = 7.4 Hz, 2H), 2.26 (ddd, J = 7.5, 4.4, 3.3 Hz, 1H), 1.94-1.79 (m, 3H), 1.65 (t, J = 8.4 Hz, 2H), 1.08-0.87 (m, 2H) |
| 165 | 18 | 489 [M + H]+ | (300 MHz, CD3OD-d$_4$) δ(ppm): 8.62 (ddt, J = 4.8, 1.8, 1.0 Hz, 1H), 8.07 (dq, J = 7.9, 1.0 Hz, 1H), 7.95 (tt, J = 7.5, 1.4 Hz, 1H), 7.56 (ddt, J = 7.4, 4.9, 1.2 Hz, 1H), 7.21-7.08 (m, 2H), 6.98 (ddd, J = 8.7, 7.8, 1.2 Hz, 2H), 5.14 (dd, J = 7.6, 5.0 Hz, 1H), 4.45 (d, J = 14.8 Hz, 1H), 4.21 (d, J = 15.6 Hz, 1H), 3.87 (t, J = 12.6 Hz, 1H), 3.65 (t, J = 11.5 Hz, 1H), 3.27-3.02 (m, 6H), 2.89 (p, J = 4.0 Hz, 1H), 2.47-2.37 (m, 1H), 2.09-1.70 (m, 4H), 1.49-1.25 (m, 2H) |
| 166 | 38 | 554 [M + H]+ | (300 MHz, DMSO-d$_6$) δ 9.02 (s, 1H), 8.48 (d, J = 7.8 Hz, 1H), 8.22 (s, 1H), 7.89-7.80 (m, 2H), 7.53 (t, J = 7.9 Hz, 2H), 7.36 (dd, J = 8.2, 6.5 Hz, 1H), 7.11-6.94 (m, 4H), 4.92 (d, J = 7.4 Hz, 1H), 4.11 (s, 2H), 3.88 (s, 1H), 3.64 (s, 1H), 3.27 (s, 2H), 3.15 (s, 1H), 3.02 (d, J = 10.6 Hz, 1H), 2.62 (t, J = 6.5 Hz, 2H), 2.17 (s, 1H), 1.73 (dd, J = 24.5, 12.1 Hz, 3H), 1.49 (d, J = 10.2 Hz, 2H), 0.90 (p, J = 6.5, 5.5 Hz, 2H) |
| 167 | 2 | [M + H]+554 | (300 MHz, Methanol-d4) δ 8.24 (s, 1H), 8.05-7.94 (m, 2H), 7.73-7.61 (m, 3H), 7.16 (s, 1H), 7.08-6.97 (m, 2H), 6.98-6.84 (m, 2H), 5.08-4.97 (m, 1H), 4.45-4.28 (m, 2H), 3.95-3.87 (m, 1H), 3.64-3.55 (m, 1H), 3.40-3.32 (m, 1H), 3.26-3.08 (m, 3H), 2.77 (t, J = 7.0 Hz, 2H), 2.28 (dt, J = 7.5, 3.9 Hz, 1H), 1.90-1.85 (m, 3H), 1.65-1.57 (m, 2H), 1.10-0.89 (m, 2H) |
| 168 | 39 | 566 [M + H]+ | (400 MHz, DMSO-d$_6$) δ ppm: 9.00-8.90 (d, 2H), 8.90-8.80 (d, 1H), 8.50-8.40 (d, 2H), 8.10-8.00 (d, 2H), 7.50 (t, 1H), 7.10-6.90 (m, 4H), 5.00-4.80 (dd, 1H), 4.25-4.05 (m, 2H), 4.00-3.80 (m, 1H), 3.70-3.50 (t, 1H), 3.30-3.25 (m, 2H), 3.25-3.10 (m, 1H), 3.10-2.95 (m, 1H), 2.70-2.60 (m, 2H), 2.40-2.30 (m, 1H), 2.20-2.10 (m, 1H), 1.95-1.65 (m, 3H), 1.65-1.40 (m, 2H), 1.00-0.80 (m, 2H) |
| 169 | 18 | 471 [M + H]+ | (400 MHz, MeOD-d$_4$) δ ppm: 7.91-7.88(m, 2H), 7.23-7.17(m, 4H), 7.04-7.00(m, 2H), 5.13-5.00(m, 1H), 4.38-4.00(m, 2H), 3.97-3.70(m, 2H), 3.40-3.30(m, 2H), 3.30-3.19(m, 2H), 3.00-2.91(m, 2H), 2.57-2.43(m, 1H), 2.10-1.73(m, 4H), 1.60-1.28(m, 2H) |
| 170 | 18 | 485 [M + H]+ | (400 MHz, MeOD-d$_4$) δ ppm: 7.88-7.85(m, 2H), 7.20-7.13(m, 4H), 7.01-6.96(m, 2H), 5.13-4.91(m, 1H), 4.45-3.71(m, 4H), 3.51-3.35(m, 2H), 3.11-3.31(m, 2H), 3.00-2.95(m, 4H), 2.57-2.43(m, 1H), 2.10-1.63(m, 4H), 1.45-1.40(m, 1H), 1.36-1.31(m, 1H) |
| 171 | 18 | 642 [M + H]+ | $^1$H NMR (300 MHz, MeOD-d$_4$) δ ppm: 8.08 (d, J = 8.3 Hz, 2H), 8.04-7.92 (m, 4H), 7.85 (d, J = 8.3 Hz, 2H), 7.20 (dd, J = 8.6, 5.2 Hz, 2H), 7.03 (t, J = 8.7 Hz, 2H), 5.18 (s, 1H), 4.43 (s, 2H), 4.26 (s, 2H), 3.95 (s, 2H), 3.72 (s, 2H), 3.18 (s, 5H), 3.01-2.93 (m, 1H), 2.45 (s, 1H), 2.07-1.76 (m, 5H), 1.54-1.33 (m, 3H). |
| 172 | 18 | 566 [M + H]+ | (400 MHz, MeOD-d$_4$) δ ppm: 9.20(s, 1H), 8.69(s, 1H), 8.57-8.56(m, 1H), 8.27-8.18(m, 2H), 8.05-7.95 (m, 2H), 7.22-7.12(m, 2H), 7.05-6.93(m, 2H), 5.22-5.10(m, 1H), 4.50-4.41(m, 1H), 4.32-4.21(m, 1H), 3.99-3.86(m, 1H), 3.79-3.66(m, 1H), 3.39-3.02 (m, 6H), 3.00-2.81(m, 1H), 2.50-2.41(m, 1H), 2.00-1.79(m, 4H), 1.52-1.41(m, 1H), 1.41-1.31(m, 1H) |
| 173 | 34 | 566 [M + H]+ | (400 MHz, MeOD-d$_4$) δ ppm: 9.20(s, 1H), 8.69(s, 1H), 8.57-8.56(m, 1H), 8.27-8.18(m, 2H), 8.05-7.95 (m, 2H), |

TABLE 2-continued

Physical Data and Synthetic Methods

| Ex # | Scheme | MS | 1H NMR |
|---|---|---|---|
| | | | 7.22-7.12 (m, 2H), 7.05-6.93 (m, 2H), 5.22-5.10(m, 1H), 4.50-4.41(m, 1H), 4.32-4.21(m, 1H), 3.99-3.86(m, 1H), 3.79-3.66(m, 1H), 3.39-3.02 (m, 6H), 3.00-2.81(m, 1H), 2.50-2.41(m, 1H), 2.00-1.79(m, 4H), 1.52-1.41(m, 1H), 1.41-1.31(m, 1H) |
| 174 | 18 | [M + H]$^+$513 | (300 MHz, DMSO-d6) δ ppm: 8.00-7.90 (m, 2H), 7.900-7.730 (m, 2H), 7.36-7.11 (m, 2H), 7.10-6.90 (m, 2H), 5.21-5.02 (m, 1H), 4.54-4.32 (m, 1H), 4.32-4.15 (m, 1H), 4.00-3.80 (m, 1H), 3.78-3.52 (m, 1H), 3.31-3.30 (m, 1H), 3.25-3.19 (m, 2H), 3.19-3.05 (m, 3H), 2.99-2.88 (m, 1H), 2.49-2.36 (m, 1H), 2.05-1.76 (m, 4H), 1.55-1.25 (m, 2H) |
| 175 | 7 | 519 [M + 1]$^+$ | (CD$_3$OD, ppm): 8.60 (s, 1H), 8.00-8.10 (m, 2H), 7.88-7.99 (m, 2H), 7.79-7.80 (m, 1H), 7.18-7.28 (m, 2H), 7.00-7.10 (m, 2H), 6.59 (s, 1H), 5.05-5.20 (m, 1H), 4.20-4.50 (m, 1H), 4.05-4.18 (m, 1H), 3.70-4.00 (m, 2H), 3.38-3.42 (m, 1H), 3.21-3.28 (m, 2H), 2.91-3.01 (m, 1H), 2.43-2.47 (m, 1H), 1.81-2.17 (m, 4H), 1.45-1.52 (m, 1H), 1.35-1.44 (m, 1H) |
| 176 | 7 | 477 [M + H]$^+$ | (300 MHz, MeOD-d$_4$) δ ppm: 8.31 (d, J = 2.6 Hz, 1H), 8.00-7.81 (m, 4H), 7.75 (d, J = 1.7 Hz, 1H), 7.22-7.11 (m, 2H), 7.07-6.94 (m, 2H), 6.55 (dd, J = 2.6, 1.8 Hz, 1H), 4.65 (t, J = 6.8 Hz, 1H), 4.35 (dq, J = 39.0, 8.3 Hz, 2H), 4.13-3.91 (m, 2H), 3.22 (t, J = 7.3 Hz, 2H), 2.93 (dt, J = 8.0, 4.1 Hz, 1H), 2.49-2.23 (m, 3H), 1.84 (q, J = 11.1, 8.9 Hz, 4H), 1.51-1.27 (m, 2H). |
| 177 | 7 | [M + H]$^+$506 | (300 MHz, DMSO-d6)δ ppm: 9.11-8.12 (m, 3H), 8.62 (d, J = 2.7 Hz, 1H), 8.11-8.01(m, 2H), 7.81 (d, J = 1.5 Hz, 1H), 7.31-7.20 (m, 2H), 7.20-7.05 (m, 2H), 6.70-6.50 (m, 1H), 5.02-4.82 (m, 1H), 3.78-3.36 (m, 8H), 3.22-3.03 (m, 2H), 3.00-2.87 (m, 1H), 2.46-2.32 (m, 1H), 1.96-1.51(m, 4H), 1.50-1.35 (m, 1H), 1.35-1.22 (m, 1H). |
| 178 | 7 | 583 [M + H]$^+$ | (400 MHz, MeOD-d$_4$) δ ppm: 8.37 (d, J = 2.6 Hz, 1H), 8.08-7.98 (m, 2H), 7.98-7.88 (m, 2H), 7.80 (d, J = 1.8 Hz, 1H), 7.27-7.17 (m, 2H), 7.11-6.99 (m, 2H), 6.60 (t, J = 2.2 Hz, 1H), 5.16 (dd, J = 8.2, 5.1 Hz, 1H), 3.99 (d, J = 13.3 Hz, 1H), 3.92 (d, J = 13.3 Hz, 1H), 3.65 (t, J = 10.7 Hz, 1H), 3.53 (dd, J = 12.9, 8.5 Hz, 1H), 3.39 (d, J = 3.9 Hz, 2H), 3.31-3.11 (m, 4H), 2.97 (dt, J = 7.9, 4.0 Hz, 1H), 2.87 (s, 3H), 2.47 (ddd, J = 10.3, 6.7, 3.7 Hz, 1H), 2.06-1.75 (m, 4H), 1.48 (ddd, J = 10.8, 6.9, 4.4 Hz, 1H), 1.39 (q, J = 7.1 Hz, 1H). |
| 179 | 18 | 458 [M + H]$^+$ | (400 MHz, DMSO-d$_6$) δ ppm: 8.70-8.60 (d, 1H), 8.05-7.90 (dd, 2H), 7.35-7.20 (t, 2H), 7.05-6.95 (m, 4H), 4.92-4.75 (m, 1H), 3.60-3.50 (m, 6H), 3.50-3.40 (m, 2H), 2.70-2.60 (t, 2H), 2.45-2.25 (m, 1H), 2.20-2.10 (m, 1H), 1.85-1.60 (m, 3H), 1.55-1.40 (m, 1H), 1.00-0.80 (m, 2H) |
| 180 | 40 | 553 [M + H]$^+$ | (300 MHz, MeOD-d$_4$) δ ppm: 7.92-7.90(d, J = 4.8 Hz, 2H), 7.56-7.54(d, J = 4.8 Hz, 2H), 7.25-7.24(t, J = 2.1 Hz, 2H), 7.04-6.99(m, 2H), 6.93-6.87(m, 2H), 6.30-6.28(t, J = 2.1 Hz, 2H), 5.03-4.99(m, 1H), 4.55-4.25(m, 1H), 3.995-3.86(m, 1H), 3.72-3.58(m, 1H), 3.48-3.33(m, 1H), 3.18-3.07(m, 3H), 2.76-2.72(m, 2H), 2.26-2.24(m, 1H), 1.89-1.82(m, 3H), 1.65-1.63(m, 2H), 1.02-0.91(m, 2H) |
| 181 | 41 | 531 [M + H]$^+$ | $^1$H NMR (400 MHz, MeOD-d$_4$) δ ppm: 8.85(s, 2H), 8.48(d, J = 8.4 Hz, 2H), 8.05-7.90 (m, 2H), 7.55-7.40 (m, 1H), 7.10-6.98 (m, 2H), 6.98-6.80 (m, 2H), 5.15-5.00 (m, 1H), 3.88-3.45 (m, 4H), 2.88-2.70 (m, 2H), 2.60-2.35 (m, 4H), 2.35-2.20 (m, 4H), 1.96-1.75 (m, 3H), 1.75-1.62 (m, 2H), 1.10-0.88 (m, 2H) |
| 182 | 42 | 491 | $^1$H NMR (300 MHz, DMSO-d$_6$): □ 10.9-10.7 (m, 1H), 9.77-9.39 (m, 2H), 9.15 (d, J = 7.8 Hz, 1H), 8.64 (d, J = 2.8 Hz, 1H), 8.07-7.97 (m, 4H), 7.81 (app s, 1H), 7.27-7.11 (m, 4H), 6.61 (t, J = 2.1 Hz, 1H), 5.37 (t, J = 6.0 Hz, 1H), 4.44-4.30 (m, 2H), 3.51-3.45 (m, 4H), 3.02-2.92 (m, 3H), 2.77 (s, 3H), 2.75-2.59 (m, 2H), 1.63-1.57 (m, 1H), 1.30-1.23 (m, 2H) |
| 183 | 2 | 583 | |
| 184 | 32 | 579 | |
| 185 | 2 | 545 | |
| 186 | 43 | 515 [M + H]$^+$ | $^1$H NMR (300 MHz, Methanol-d$_4$) δ 8.07-7.91 (m, 6H), 7.58 (m, 3H), 7.06-6.83 (m, 4H), 5.08 (dd, J = 8.5, 5.3 Hz, 1H), 4.36 (m, 2H), 3.89 (m, 2H), 3.66 (s, 1H), 3.39 (s, 1H), 3.10 (s, 3H), 2.81 (t, J = 6.7 Hz, 2H), 2.25 (dd, J = 7.2, 3.9 Hz, 1H), 2.04-1.87 (m, 2H), 1.06-0.87 (m, 2H) |
| 187 | 44 | 568 [M + H]$^+$ | $^1$H NMR (300 MHz, MeOD-d$_4$) δ ppm: 7.98-7.92(m, 2H), 7.75-7.68(m, 4H), 7.29-7.20 (m, 2H), 7.10-7.05 (m, |

TABLE 2-continued

Physical Data and Synthetic Methods

| Ex # | Scheme | MS | 1H NMR |
|---|---|---|---|
| | | | 2H), 6.98-6.90 (m, 2H), 5.19-5.13 (m, 1H), 4.52-4.32 (m, 2H), 4.00-3.91(m, 1H), 3.76-3.65 (m, 1H), 3.50-3.38 (m, 1H), 3.22-3.11 (m, 3H), 2.91-2.85(m, 2H), 2.35-2.30 (m, 1H), 2.16-1.86 (m, 3H), 1.09-0.93(m, 2H) |
| 188 | 45 | 428 [M + H]$^+$ | $^1$H NMR (400 MHz, MeOD-d$_4$) δ ppm: 7.93-7.89(m, 2H), 7.25-7.20(m, 4H), 7.07-7.01(m, 2H), 4.70-4.61(m, 1H), 4.50-4.41(m, 1H), 4.40-4.29(m, 1H), 4.18-4.00(m, 2H), 3.30-3.21(m, 2H), 3.18-2.90(m, 1H), 2.55-2.45(m, 1H), 2.38-2.20(m, 2H), 2.00-1.74(m, 4H), 1.60-1.50(m, 1H), 1.41-1.35(m, 1H) |

The invention is further illustrated by the following examples, which may not have been made yet or tested. The methods exemplified below may also be extrapolated to compounds disclosed herein which may not yet have not been made or tested. A variety of stereochemical arrangements are shown below and are meant to demonstrate that all racemic, (R), (S), cis, and trans isomers are contemplated.

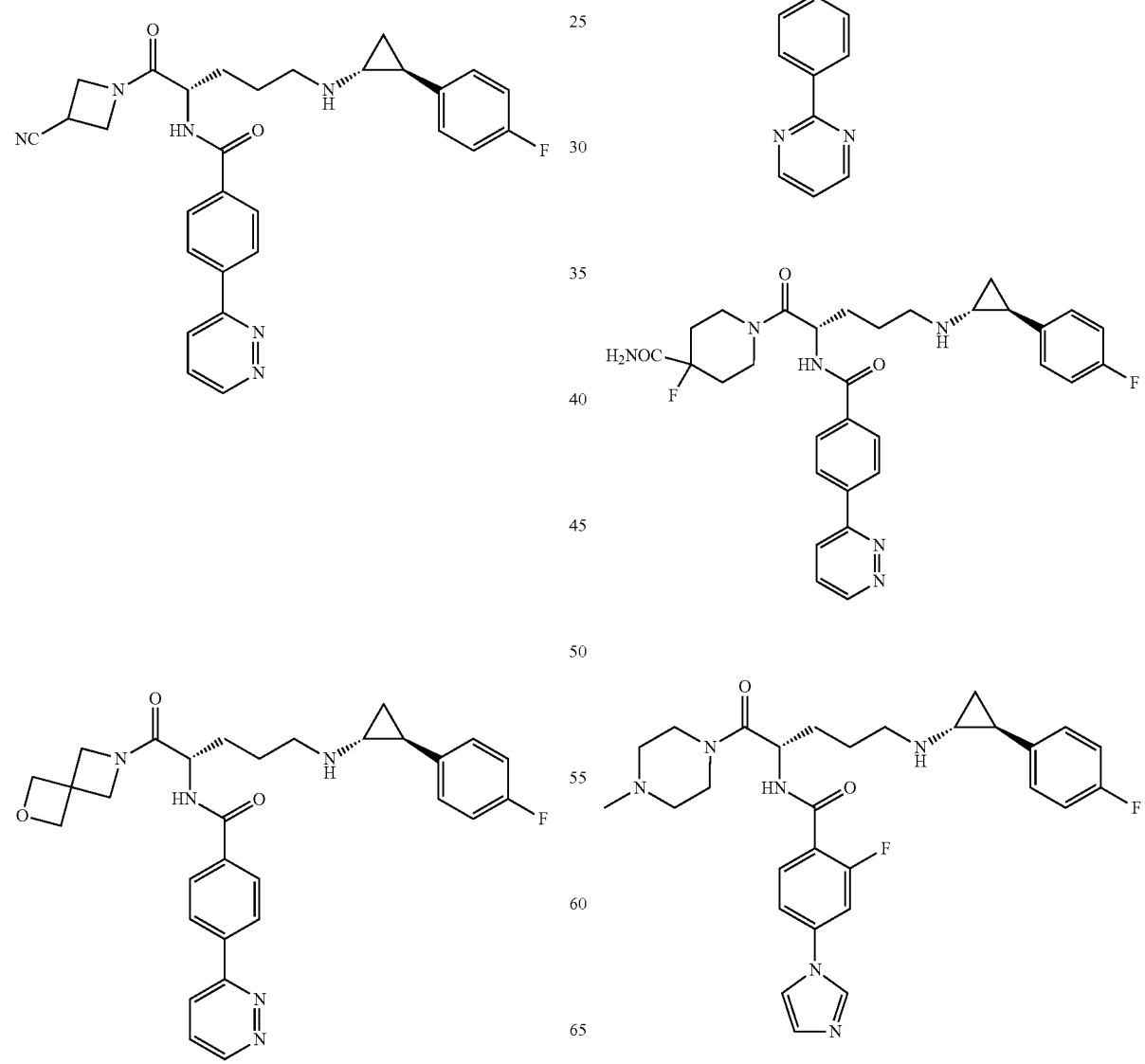

315
-continued
316
-continued
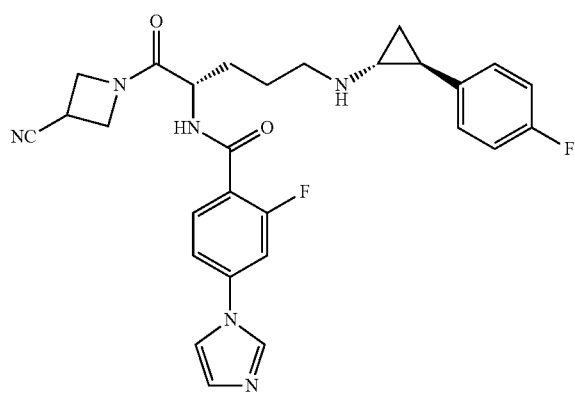
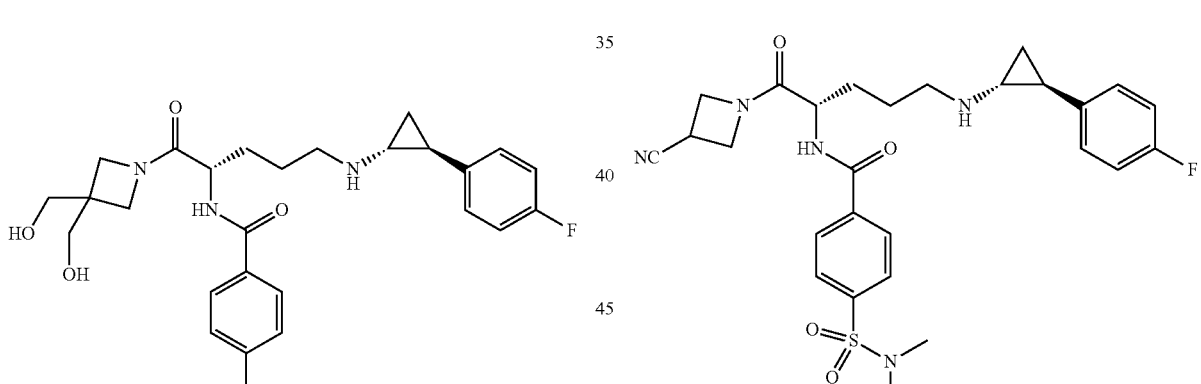
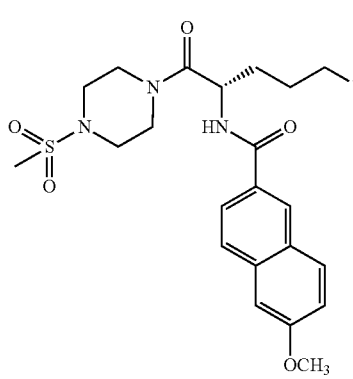
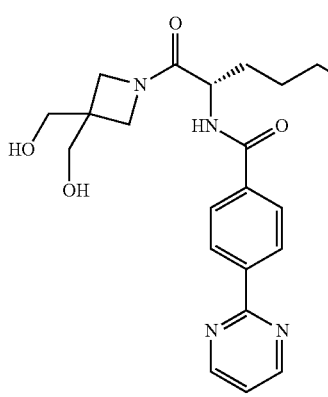
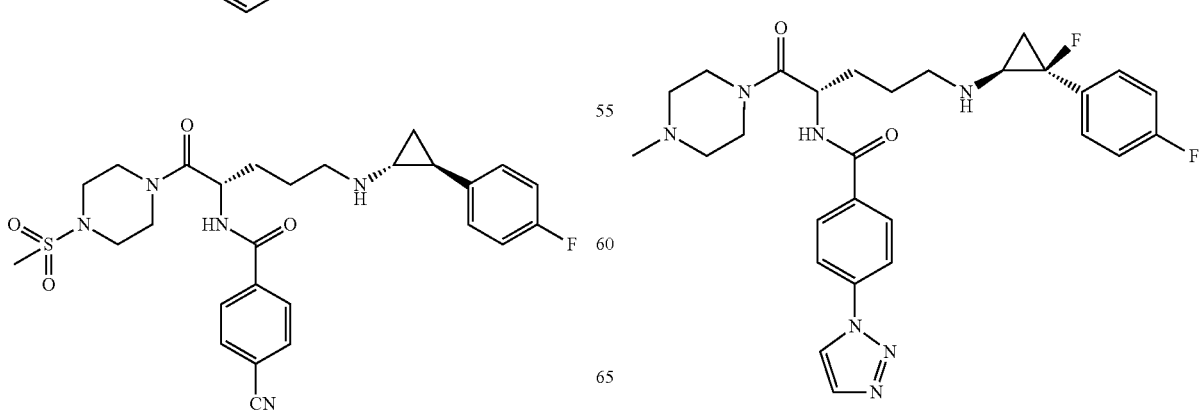
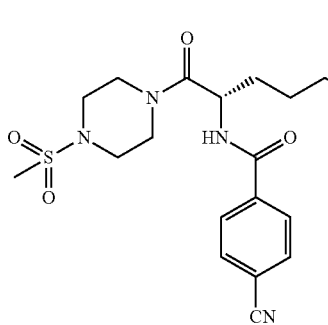

317
-continued
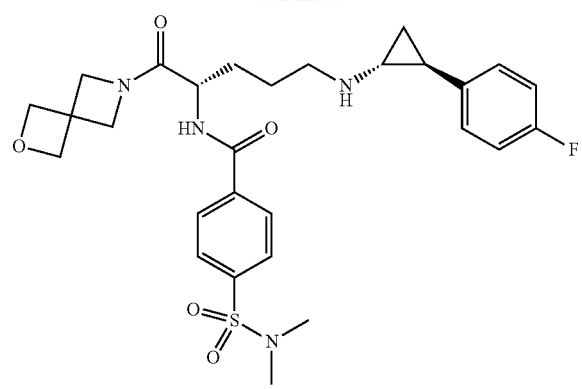
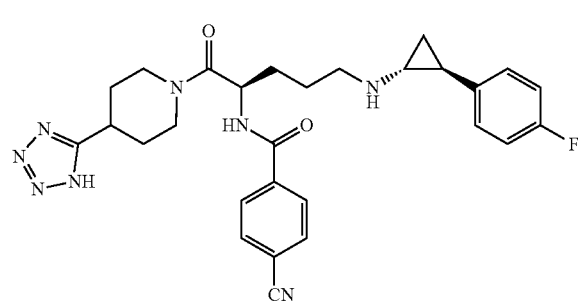
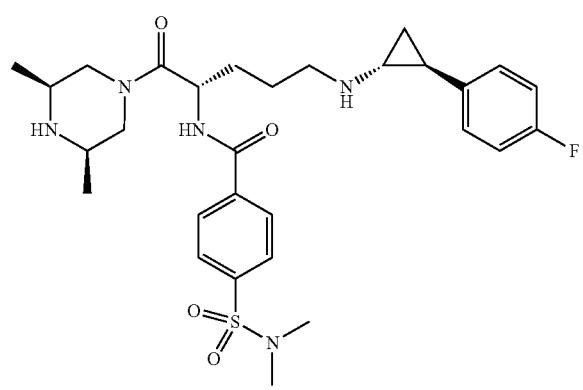
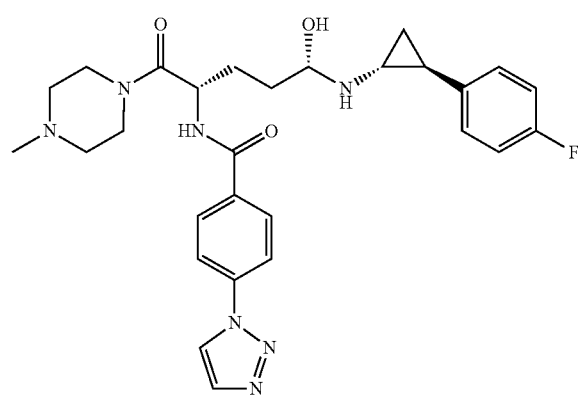
318
-continued
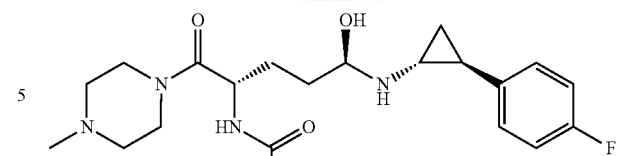
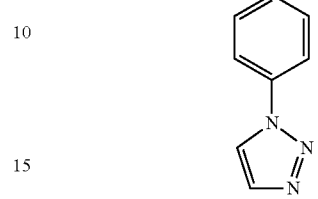
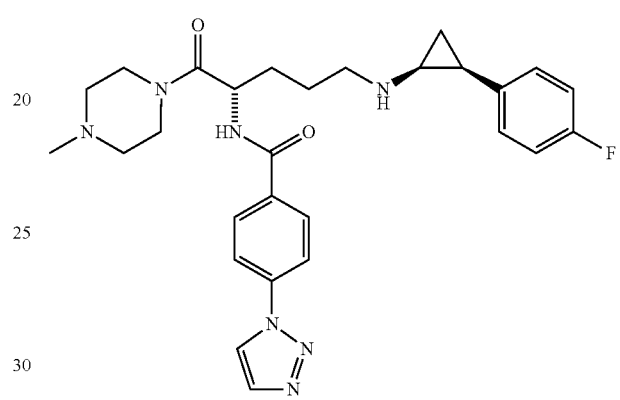
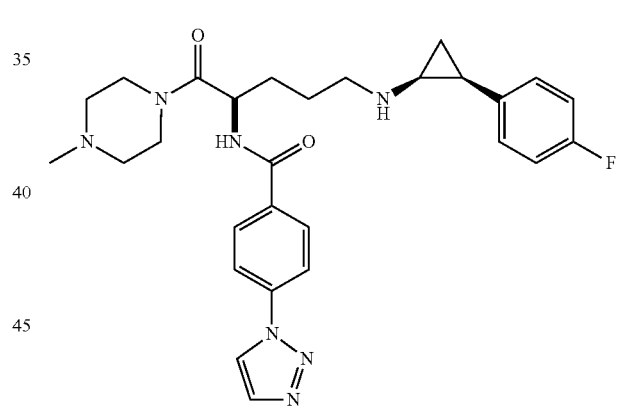
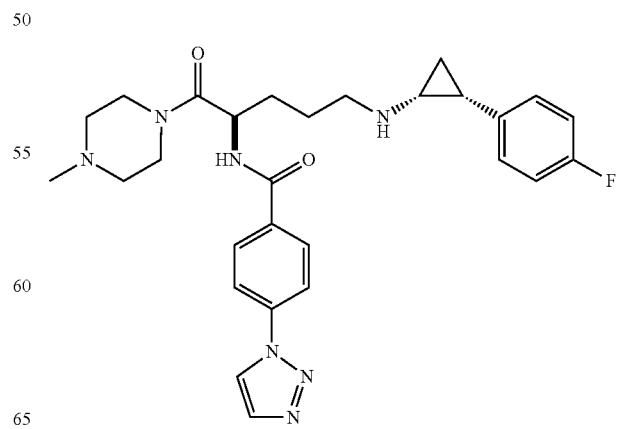

319
-continued
320
-continued
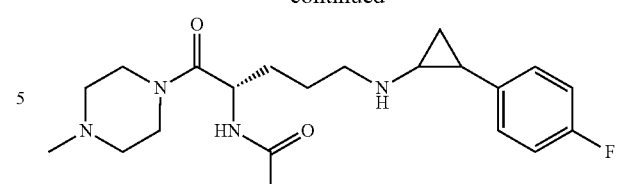
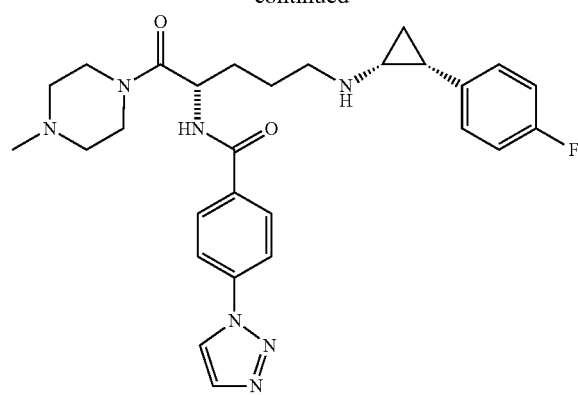
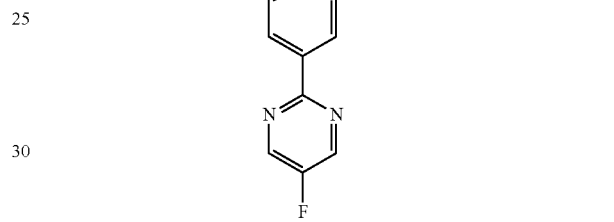
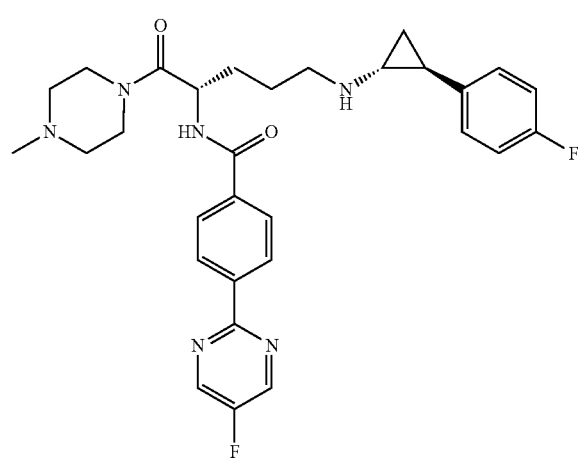
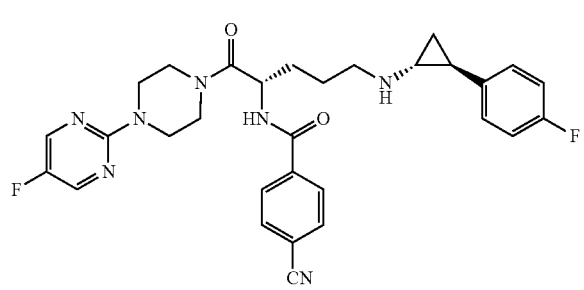
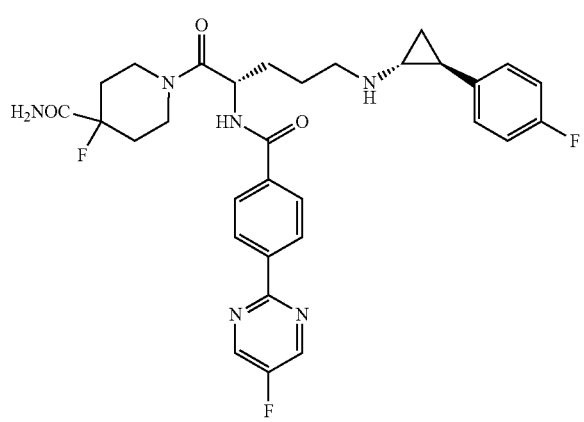
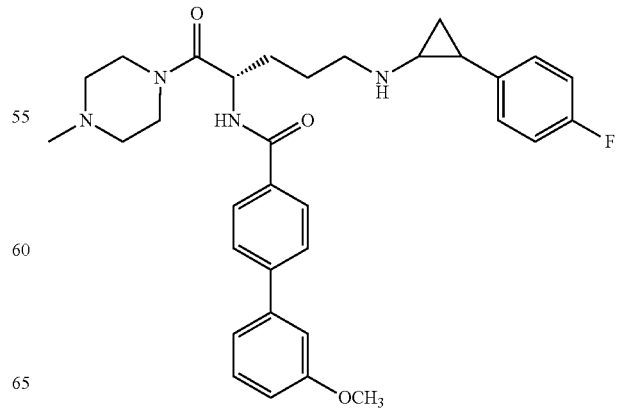

321
-continued
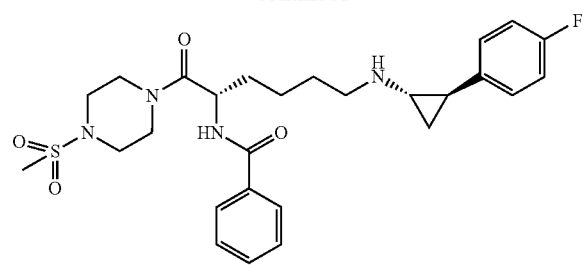
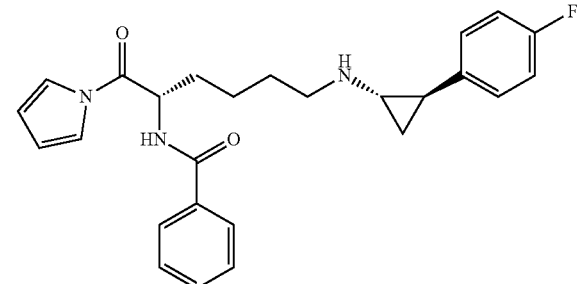
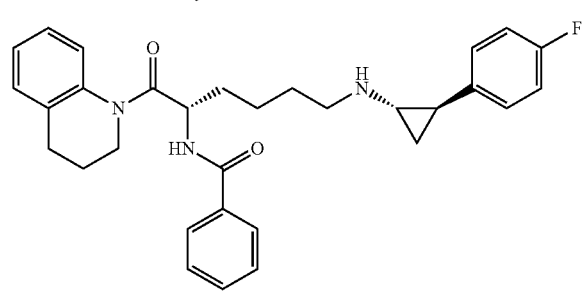
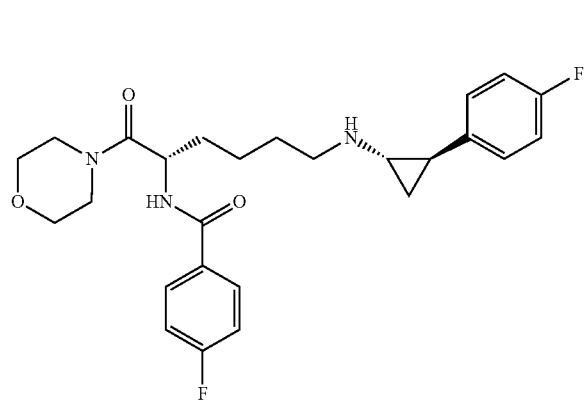
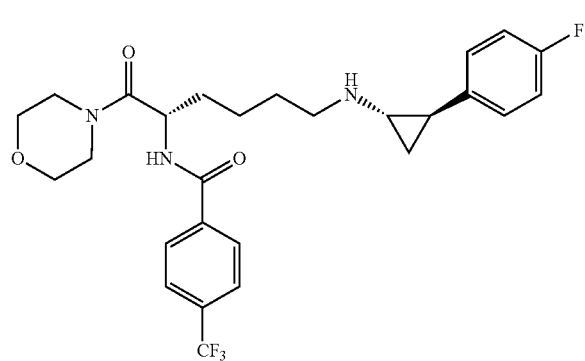
322
-continued
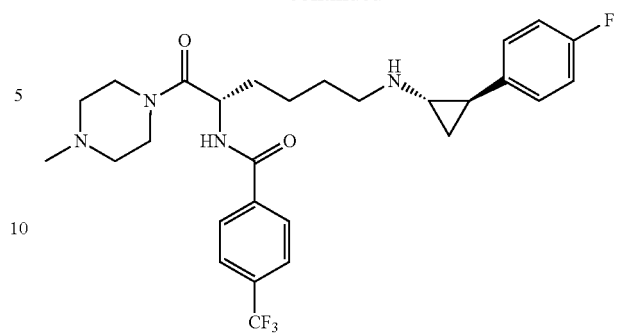
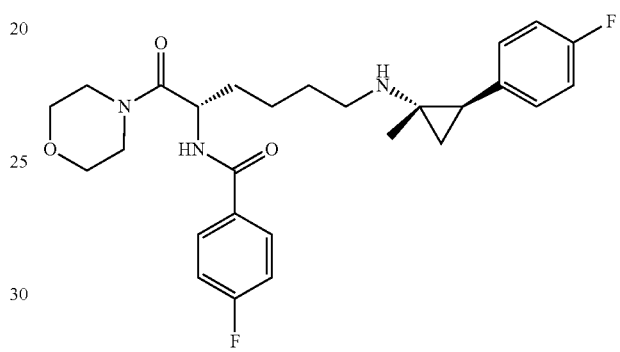
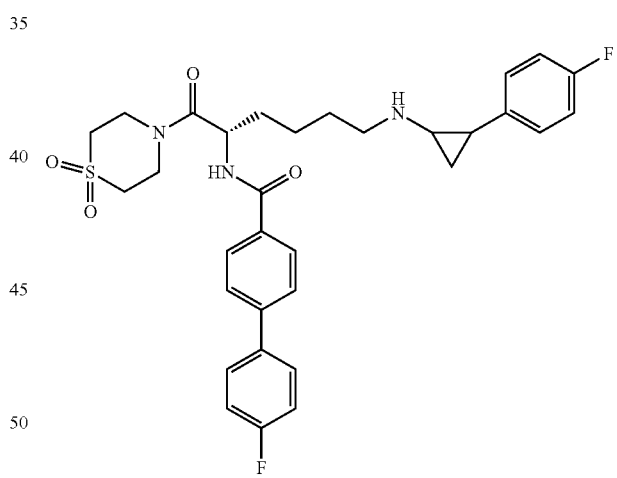
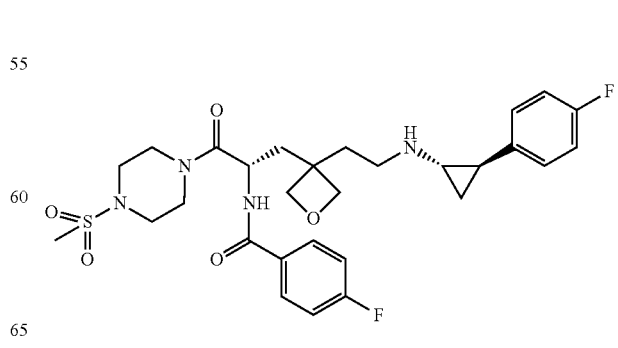

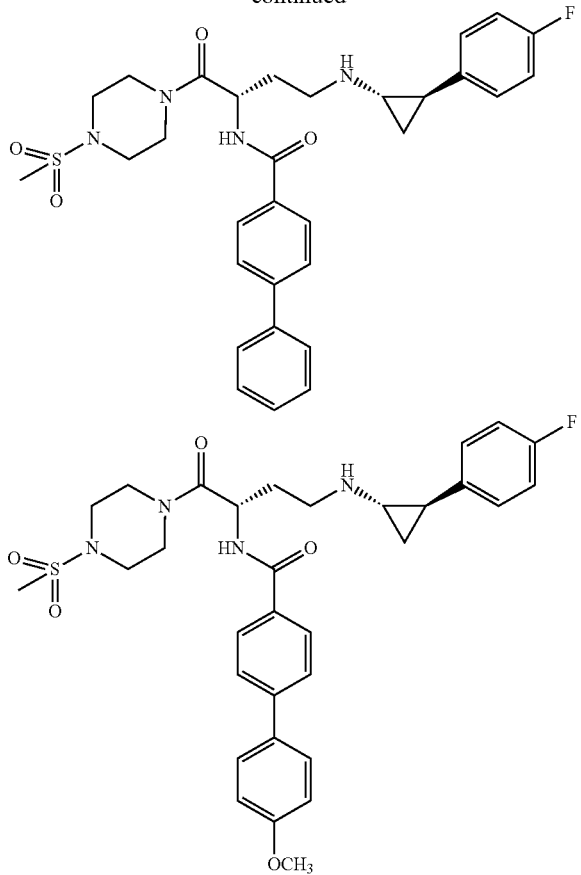

Salts and Polymorphs

Example 1 free base form is an unstable, amorphous and hygroscopic material that deliquesces when subjected to high humidity, and degrades at ambient conditions over time. Various lots of Example 1 were analyzed by HPLC shortly after synthesis (analysis from 1-24 hours post-synthesis) and re-tested for purity a unit of time later. Results are given in Table 3.

TABLE 3

| Lot | Initial Purity | Re-Test Purity | Time Between Tests |
|---|---|---|---|
| 1 | 93% | 82% | 49 days |
| 2 | 81% | 72% | 16 days |

In the salt and polymorph experiments below, the following counterions form the following salts and are abbreviated as follows: 2,5-dihydroxybenzoic acid-dihydroxybenzoate—DHBA; adipic acid-adipate salt—ADA; benzenesulfonic acid-benzenesulfonate or besylate salt—BSA; benzoic acid-benzoate salt—BA; caprylic acid-caprylate—CYA; citric acid-citrate—CA; D-glucuronic acid-glucuronate—GA; ethanesulfonic acid-ethanesulfonate or esylate—ESA; fumaric acid-fumarate—FUA; galactaric acid-galactarate—GA; glycolic acid-glycolate—GLYA; hippuric acid-hippurate—HPA; hydrochloric acid-hydrochloride—HCl; ketoglutaric acid-ketoglutarate—KGA; L-ascorbic acid-ascorbate salt—ASBA; L-aspartic acid-aspartate—ASP; L-glutamic acid-glutamate—GLU; L-lactic acid-lactate—LA; L-malic acid-malate—MA; L-tartaric acid-tartrate—TAR; maleic acid-maleate—MEA; malonic acid-malonate—MLNA; nicotinic acid-nicotinate—NA; orotic acid-orotate—ORA; oxalic acid-oxalate—OXA; phosphoric acid-phosphorate—PHOA; propionic acid-propionate—PROA; p-toluene sulfonic acid (monohydrate)-tosylate—pTSA; succinic acid-succinate—SUCA; sulfuric acid-sulfate —SUL or $SO_4$; and thiocyanic acid-thiocyanate—TCA. Salts may form between counterions in stoichiometric ratios, for example 1:1 (a mono-salt) or 2:1 (a bis-salt).

Preparation of Salts of Example 1

Salt forms were prepared from a diverse range of solvent and techniques including cooling, maturation, evaporation and anti-solvent addition. The possibility of forming mono and bis salts was also investigated for a number of the counter-ions.

Solvents.

Example 1 was treated with increasing volumes of solvent (2-propanol (IPA), acetone, methylethyl ketone, ethyl acetate, tetrahydrofuran, acetonitrile, 1,4-dioxane, 90:10 IPA:water, 90:10 THF:water, tert-butylmethyl ether (MTBE), and n-heptane) until the material fully dissolved or until a maximum of 100 vol. had been used. After each addition of solvent, the system was stirred at 25° C. for 10 min before the addition of a new aliquot of solvent. Example 1 was readily soluble in 2-propanol (IPA), acetone, methylethyl ketone, ethyl acetate, tetrahydrofuran, acetonitrile, 1,4-dioxane, 90:10 IPA:water, and 90:10 THF:water, dissolving readily in 10 vol. solvent. MTBE and n-heptane were identified as anti-solvents when Example 1 was not soluble in 100 vol. solvent.

Hydrochloride Salt.

Solutions of Example 1 were treated with neat HCl (37 wt % (12M), 4.8 µL). The samples were then stirred at 25° C. for 1 hour. The solutions were cooled in the fridge (ca. 4° C.) for 24 hours. If no suspension was obtained the samples were then matured at ambient/50° C. in 8-hour cycles for 4 days (Section 8.11). Any solids obtained were analyzed by XRPD. On addition of HCl to solutions of Example 1 in various solvents, many samples formed a precipitate, which after further stirring became a gum. Analysis of these solids by XRPD found all to be amorphous. Results are given in Table 4.

TABLE 4

| Solvent | Obs. on addition of 1 eq HCl | Obs. after 1 hour | Obs. after cooling in fridge | Obs. after maturation for 4 days | XRPD |
|---|---|---|---|---|---|
| 2-Propanol | precipitate | clear solution | clear solution | orange solution | — |
| Acetone | precipitate | gum | gum | gum | amorphous |
| Methylethyl Ketone | precipitate | gum | gum | sticky solid | amorphous |

TABLE 4-continued

| Solvent | Obs. on addition of 1 eq HCl | Obs. after 1 hour | Obs. after cooling in fridge | Obs. after maturation for 4 days | XRPD |
|---|---|---|---|---|---|
| Ethyl Acetate | precipitate | gum | gum | sticky solid | amorphous |
| Tetrahydrofuran | precipitate | gum | gum | sticky solid | amorphous |
| Acetonitrile | precipitate | clear solution | oil | sticky solid | amorphous |
| 1,4-Dioxane | precipitate | gum | gum | sticky solid | amorphous |
| 90:10 IPA:water | vapour evolved | clear solution | clear solution | orange solution | — |
| 90:10 THF:water | clear solution | clear solution | clear solution | orange oil | — |
| tert-Butylmethyl Ether | cloudy solution | white precipitate and undissolved solid | — | — | amorphous |
| n-Heptane | no change on addition (white gum) | solid dissolving | gum | orange oil | — |

First Salt Experiments.

Several salt experiments were undertaken in order to determine if a stable, non-hygroscopic crystalline form of Example 1 could be identified. Salts with varying crystallinity were isolated from HCl, phosphoric, sulfuric, L-tartaric, fumaric, p-toluenesulfonic and oxalic acid. In general, the crystallinity of the solids isolated was poor.

Salt Experiment 1.

Example 1 was dissolved in solvent (240 mg in 2.4 mL, 10 volumes) to form stock solutions and then dispensed into vials (400 µL/~40 mg per vial). The solutions were treated with 1 equivalent of counterions (for hydrochloric acid (HCl), sulfuric acid ($H_2SO_4$ or "$SO_4$"), methanesulfonic acid (mesylate or "MSA"), phosphoric acid ($H_3PO_4$ or "PHOA"), and L-tartaric acid (TAR), 77 µL for 1M; for fumaric acid (FUA), 154 µL for 0.5M) using stock solutions. The solutions/suspensions were then cooled down to 0° C. at 0.2° C./min and stirred at 0° C. overnight. The resulting solids were analyzed by XRPD and those that were amorphous or poorly crystalline were then matured for 5 days. If after cooling to 0° C. a clear solution or gum was obtained, the mother liquors were removed from the vials, split in two and anti-solvent (MTBE or heptane, 400 µl) added to each of the aliquots. After anti-solvent addition, the samples were matured for 5 days. After maturation, clear solutions and gums were allowed to evaporate at ambient conditions. Suspensions were filtered, air-dried and characterized by XRPD. Any resulting crystalline solids were characterized by high resolution XRPD, 1H NMR, HPLC and one week storage at 40° C. and 75% RH.

Crystalline solids were isolated from the experiments involving sulfuric, phosphoric, L-tartaric acid in IPA. A further weakly crystalline solid was also found from fumaric acid in ethyl acetate. All other solids were found to be amorphous, although some of these showed peak shifts by NMR, which is indicative of salt formation. Results are given in Table 5.

TABLE 5

| Ex. | Counter-ion | Solv. | XRPD | Anti-solv. | Obs. on add'n of antisolv. | Obs. after maturation | XRPD | High-Res XRPD | NMR |
|---|---|---|---|---|---|---|---|---|---|
| S1 | HCl | IPA | — | MTBE | susp. | gum | Am | — | — |
| S2 | | | | Heptane | oil | gum | | — | — |
| S3 | $SO_4$ | IPA | WC | — | — | sticky solid | Partially crystalline Sulf pattern 1 | Partially crystalline Sulf pattern 1 | peak shifts, ~2.4 eq IPA |
| S4 | MSA | IPA | — | MTBE | susp. | gum | Am | — | — |
| S5 | | | | Heptane | gum | gum | — | — | — |
| S6 | PHOA | IPA | Am | — | — | white solid | Partially crystalline PHOA pattern 1 | Am | no peak shifts, ~0.4 eq IPA |
| S7 | TAR | IPA | Am | — | — | white solid | Am | Crystalline TAR Form 1 | Peak shifts, ~0.7 eq acid, ~0.2 eq IPA |
| S8 | FUA | IPA | —* | — | — | sticky solid | Am | — | — |
| S9 | HCl | THF | — | MTBE | susp. | gum | — | — | — |
| S10 | | | | Heptane | susp. | gum | — | — | — |
| S11 | $SO_4$ | THF | Am | — | — | white solid | Am | Am | Peak shifts, ~0.3 eq THF |

TABLE 5-continued

| Ex. | Counter-ion | Solv. | XRPD | Anti-solv. | Obs. on add'n of antisolv. | Obs. after maturation | XRPD | High-Res XRPD | NMR |
|---|---|---|---|---|---|---|---|---|---|
| S12 | MSA | THF | — | MTBE | susp. | gum | Am | — | — |
| S13 | | | | Heptane | gum | gum | — | — | — |
| S14 | PHOA | THF | Am | — | — | white solid | Am | Am | no peak shifts, ~4.6 eq THF |
| S15 | TAR | THF | Am | — | — | white solid | Am | Am | Peak shifts, ~1.4 eq acid, ~0.9 eq THF |
| S16 | FUA | THF | Am | — | — | white solid | Am | — | — |
| S17 | HCl | EtAc | — | MTBE | sol'n | gum | — | — | — |
| S18 | | | | Heptane | sol'n | gum | — | — | — |
| S19 | SO$_4$ | EtAc | Am | — | — | white solid | Am | Am | peak shifts, ~3.9 eq EtOAc |
| S20 | MSA | EtAc | — | MTBE | sol'n | gum | Am | — | — |
| S21 | | | | Heptane | gum | gum | — | — | — |
| S22 | PHOA | EtAc | Am | — | — | white solid | Am | Am | no peaks shifts, ~0.7 eq EtOAc |
| S23 | TAR | EtAc | Am | — | — | white solid | Am | Am | Peak shifts, ~1 eq acid, ~0.4 eq EtOAc |
| S24 | FUA | EtAc | WC | — | — | white solid | WC | WC FUA pattern 1 | Peak shifts, ~0.8 eq acid, ~0.2 eq EtOAc |

EtAC = Ethyl Acetate;
Am = amorphous;
WC = weakly crystalline;
solv. = solvent;
sol'n = solution;
susp. = suspension;
*= some ppt upon warming.

Of the 16 solids obtained, four were found to be partially crystalline: sulfuric, phosphoric, L-tartaric acid in IPA. A further weakly crystalline solid was also found from fumaric acid in ethyl acetate. All other solids were found to be amorphous. All samples analyzed by XRPD were placed into storage at 40° C. and 75% RH for one week. However, after one day all samples except the tartrate had deliquesced and were therefore not characterized further. The tartrate was analyzed by XRPD after one week at 40° C. and 75% RH and no change in form was observed, and it was further analyzed by TGA and DSC. The thermal analysis showed an initial weight loss in the TGA which corresponded to a broad endotherm in the DSC. These are likely due to the loss of IPA and water from the sample. The purity of the sample by HPLC was 89.7% compared to 93.6%1 for the input Example 1.

Experiment 2.

Example 1 was dissolved in methyethyl ketone (MEK) or acetonitrile (MeCN) (20 mg in 200 al, 10 vol) at ambient conditions. The solutions were then heated to 50° C., treated with 1.1 or 2.1 eq of acid and stirred at this temperature for 1 hour. The resulting solutions/suspensions were then cooled down to 5° C. at 0.1° C./min and held overnight. Any solids obtained were analyzed by XRPD and those that were amorphous or poorly crystalline were then matured between 50° C./ambient on an 8-hour cycle. Any clear solutions were left to evaporate slowly at ambient conditions. If the samples evaporated to form gums, these were dissolved in IPA (10 vol, 200 μL) and matured. Any solutions with gums present were also matured between 50° C./ambient on an 8 hour cycle. Any resulting crystalline solids were characterized by high resolution XRPD, NMR, HPLC, IC (for inorganic counter-ions) and one week storage at 40° C. and 75% RH. Table 4 shows the experimental conditions tested.

TABLE 6

| Counter-ion/Coformer | Conc. | Sol-vent | Vol for 1.1 eq (μL) | Vol for 2.1 eq (μL) |
|---|---|---|---|---|
| Hydrochloric acid - HCl | 1.0M | THF | 43 | 81 |
| Sulfuric acid - SO$_4$ | 1.0M | THF | 43 | 81 |
| p-Toluene sulfonic acid monohydrate-pTSA | 1.0M | THF | 43 | 81 |
| Oxalic acid - OXA | 1.0M | THF | 43 | 81 |
| Maleic acid - MEA | 1.0M | THF | 43 | 81 |
| Ketoglutaric acid - KGA | 1.0M | THF | 43 | 81 |
| 2,5-Dihydroxybenzoic acid - DHBA | 1.0M | THF | 43 | 81 |
| Fumaric acid - FUA | 0.5M | MeOH:THF 1:1 | 85 | 162 |
| Galactaric acid - GA | 1.0M | THF | 43 | 81 |
| L-Ascorbic acid - ASBA | 0.5M | THF | 85 | 162 |
| Benzoic acid - BA | 1.0M | THF | 43 | 81 |
| Succinic acid - SUCA | 1.0M | THF | 43 | 81 |
| L-Tartaric acid - TAR | 1.0M | THF | 43 | 81 |

The following experiments were done in MEK at 1:1 eq.

TABLE 7a

| Ex. | Counter-ion | Obs. on add addition | Obs. on cooling to 5° C. | XRPD | Appearance after evap. | Maturation length | Appearance after maturation | XRPD after maturation |
|---|---|---|---|---|---|---|---|---|
| S25 | HCl | ppt | gum | — | — | 6 days | gum | — |
| S26 | SO₄ | gum | ppt/gum | Am | — | 6 days | ppt | Sulf pattern 2 |
| S27 | pTSA | ppt | clear sol'n | — | gum | 8 days | clear sol'n | — |
| S28 | OXA | gum | ppt | Am | — | 6 days | ppt | OXA Form 1 |
| S29 | MEA | ppt | gum | — | — | 6 days | gum | — |
| S30 | KGA | ppt | gum | — | — | 6 days | gum | — |
| S31 | DHBA | clear sol'n | clear sol'n | — | gum | 8 days | gum | — |
| S32 | FUA | ppt then redissolve | gum | — | — | 6 days | gum | — |
| S33 | GA | ppt | ppt | GA | — | 6 days | ppt | GA |
| S34 | ASBA | ppt | gum | — | — | 6 days | clear sol'n | — |
| S35 | BA | clear sol'n | clear sol'n | — | gum | 8 days | ppt | WC * |
| S36 | SUCA | clear sol'n | clear sol'n | — | gum | 8 days | ppt | WC * |
| S37 | TAR | clear sol'n | ppt | Am | — | 6 days | paste | Am |

Am = amorphous;
WC = WC;
ppt = precipitate;
sol'n = solution;
* = some ppt upon warming.

The following experiments were done in MEK at 2:1 eq.

TABLE 7b

| Ex. | Counter-ion | Obs. on acid addition | Obs. on cooling to 5° C. | XRPD | Appearance after evap. | Maturation length | Appearance after maturation | XRPD after maturation |
|---|---|---|---|---|---|---|---|---|
| S38 | HCl | ppt | gum | — | — | 6 days | gum | — |
| S39 | SO₄ | gum | ppt/gum | Am | — | 6 days | gum | — |
| S40 | pTSA | ppt | ppt | pTSA Form 1 | — | — | — | — |
| S41 | OXA | gum | ppt | Am | — | 6 days | paste | deliquesced on frit |
| S42 | MEA | ppt | gum | — | — | 6 days | gum | — |
| S43 | KGA | gum | gum | — | — | 6 days | gum | — |
| S44 | DHBA | clear sol'n | clear sol'n | — | gum | 8 days | gum | — |
| S45 | FUA | ppt then redissolve | clear sol'n | — | gum | 8 days | gum | — |
| S46 | GA | ppt | ppt | GA | — | 6 days | paste | Galactaric acid |
| S47 | ASBA | ppt | cloudy sol'n and pink gum | paste - WC | — | 6 days | clear sol'n and red gum | — |
| S48 | BA | clear sol'n | clear sol'n | — | gum | 8 days | ppt | WC * |
| S49 | SUCA | clear sol'n | clear sol'n | — | gum | 8 days | clear sol'n | — |
| S50 | TAR | clear sol'n | ppt | Am | — | 6 days | paste | WC |

Am = amorphous;
WC = WC;
ppt = precipitate;
sol'n = solution;
* = some ppt upon warming.

The following experiments were done in MeCN at 1:1 eq.

TABLE 7c

| Ex. | Counter-ion | Obs. on acid addition | Obs. on cooling to 5° C. | XRPD | Appearance after evap. | Maturation length | Appearance after maturation | XRPD after maturation |
|---|---|---|---|---|---|---|---|---|
| S51 | HCl | ppt | gum | — | — | 4 days | gum | — |
| S52 | SO₄ | gum | ppt | WC | — | 4 days | ppt | Sulf pattern 3 |
| S53 | pTSA | clear sol'n | clear sol'n | — | gum | 8 days | clear sol'n | — |
| S54 | OXA | gum | ppt/gum | WC | — | 4 days | ppt | OXA Form 1 |
| S55 | MEA | clear sol'n | clear sol'n | — | gum | 8 days | gum | — |

TABLE 7c-continued

| Ex. | Counter-ion | Obs. on acid addition | Obs. on cooling to 5° C. | XRPD | Appearance after evap. | Maturation length | Appearance after maturation | XRPD after maturation |
|---|---|---|---|---|---|---|---|---|
| S56 | KGA | ppt | gum | — | — | 4 days | gum | — |
| S57 | DHBA | cloudy sol'n | gum | — | — | 4 days | clear sol'n | — |
| S58 | FUA | ppt | gum | — | — | 4 days | gum | — |
| S59 | GA | ppt | ppt | GA | — | 4 days | paste | GA |
| S60 | ASBA | cloudy sol'n | red gum | — | — | 4 days | red sol'n and gum | — |
| S61 | BA | clear sol'n | clear sol'n | — | gum | 8 days | clear sol'n | — |
| S62 | SUCA | clear sol'n | clear sol'n | — | gum | 8 days | ppt | WC * |
| S63 | TAR | gum | gum | — | — | 4 days | paste | Am |

Am = amorphous;
WC = WC;
ppt = precipitate;
sol'n = solution;
* = some ppt upon warming.

The following experiments were done in MeCN at 2:1 eq.

TABLE 7d

| Ex. | Counter-ion | Obs. on acid addition | Obs. on cooling to 5° C. | XRPD | Appearance after evap. | Maturation length | Appearance after maturation | XRPD after maturation |
|---|---|---|---|---|---|---|---|---|
| S64 | HCl | ppt | gum | — | — | 4 days | gum | — |
| S65 | SO$_4$ | gum | ppt/gum | Am | — | 4 days | gum | — |
| S66 | pTSA | clear sol'n | ppt | pTSA Form 2 | — | — | — | — |
| S67 | OXA | gum | ppt | Am | — | 4 days | paste | Am |
| S68 | MEA | clear sol'n | oil | — | — | 4 days | clear sol'n | — |
| S69 | KGA | ppt | gum | — | — | 4 days | gum | — |
| S70 | DHBA | ppt | gum | — | — | 4 days | clear sol'n | — |
| S71 | FUA | ppt | gum | — | — | 4 days | gum | — |
| S72 | GA | ppt | ppt | GA | — | 4 days | paste | GA |
| S73 | ASBA | cloudy sol'n | red sol'n and gum | — | — | 4 days | red sol'n | — |
| S74 | BA | clear sol'n | clear sol'n | — | gum | 8 days | ppt | WC * |
| S75 | SUCA | clear sol'n | clear sol'n | — | gum | 8 days | clear sol'n | — |
| S76 | TAR | gum | gum/paste | Am | — | 4 days | paste | Am |

Am = amorphous;
WC = WC;
ppt = precipitate;
sol'n = solution;
* = some ppt upon warming.

In total 10 solids were obtained from cooling in MEK. One of these using 2.1 eq p-toluene sulphonic acid monohydrate was found to be crystalline (pTSA Form 1) and another from ascorbic acid was a paste that was weakly crystalline. The solid obtained from galactaric acid was consistent with the reference diffractogram for this counter-ion. All other solids from cooling were amorphous. After maturation, crystalline solids were found in samples from 1.1 eq additions of sulphuric acid (Sulf pattern 1) and oxalic acid (OXA Form 1).

After cooling seven solids were isolated from MeCN and analyzed by XRPD. The solid from 2.1 eq of toluene sulphonic acid monohydrate was found to be crystalline and displayed a different XRPD diffractogram (pTSA Form 2) to the reference pattern for the acid and the other tosylate solid obtained from the MEK experiment (pTSA Pattern 1). Samples from 1.1 equivalent addition of sulphuric acid and oxalic acid were found to be weakly crystalline, with crystallinity improving after maturation. The diffractogram for the sulphate (Sulf Pattern 3) was different to those previously observed in the initial experiment and in MEK (Sulf Pattern 1 and 2 respectively). All other solids obtained after cooling and maturation were amorphous.

Clear solutions that were obtained on cooling in MEK and MeCN were left to evaporate and resulted in gums. These were re-dissolved in IPA and matured. After maturation, some of the samples yielded solids. However, all of these solids had the same XRPD pattern, despite having different counter-ions (benzoic and succinic acid) and acid equivalents added. $^1$H NMR confirmed all of these samples had degraded to the same crystalline product, with trace amounts of the counter-ion present. The degradation of these samples is probably caused by the amount of further treatment (at elevated temperature) these samples underwent after the initial cooling. If salt formation was incomplete, the presence of amorphous free base, which is known to be unstable, may also have contributed to the degradation to an unknown crystalline compound.

Example 1 and S36 (succinate from MEK at 1:1 eq) were characterized by a range of 1D and 2D NMR experiments to further understand this degradation. Due to the small amount of S36 isolated, the $^{13}$C NMR spectra could not be fully assigned. It was clear that the phenyl ring with the fluoride has been lost. The main degradation product is most likely the primary amine after loss of this ring.

Characterization of Salts.

Crystalline and partially crystalline salts were characterized further using a range of techniques.

Tosylates.

Initial HPLC analysis on both tosylate salts indicated that salt formation has increased the purity to 88.0% and 90.6% compared to Example 1 which had a purity of 81.4%. Of the two forms found, pTSA Form 2 is the more stable. The other salt, pTSA Form 1, becomes amorphous upon isolation and also converts to pTSA Form 2 after storage at 40° C. and 75% RH. Results are shown below in Table 8.

TABLE 8

|  | S40 | S66 |
| --- | --- | --- |
| Salt | Tosylate from MEK 2:1 | Tosylate from MeCN 2:1 |
| High-Res XRPD | pTSA Form 1, Amorphous, after isolating solid | pTSA Form 2 |
| $^1$H-NMR (DMSO-$_{d6}$) | Peak shifts to free base ~2 eq acid | Peak shifts to free base ~2 eq acid |
| HPLC (Purity % AUC) | 88.0* | 90.6* |
| Storage at 40° C. and 75% RH | Change to pTSA Form 2 | No change: pTSA Form 2 |

*tosylate peak not integrated

Sulfates.

Both sulfates were found to have different XRPD diffractograms (Sulf pattern 2 and 3) which were not consistent with the sulfate obtained in the initial salt experiment which deliquesced on storage at 40° C. and 75% RH (Sulf pattern 1). After storage at 40° C. and 75% RH, both solids displayed the same diffractogram, Sulf pattern 2. Results are shown below in Table 9.

TABLE 9

|  | S26 | S52 |
| --- | --- | --- |
| Salt | Sulfate from MEK 1:1 | Sulfate from MeCN 1:1 |
| High Resolution XRPD | Weakly crystalline Sulf pattern 2, possible reduction in crystallinity after isolating solid | Weakly crystalline, Sulf pattern 3 |
| $^1$H-NMR (DMSO-$_{d6}$) | Peak shifts to free base | Peak shifts to free base |
| HPLC (Purity %, AUC) | 81.4 | 84.0 |
| Storage at 40° C. and 75% RH | No change in form Sulf pattern 2 Increased crystallinity | Change in form Sulf pattern 2 |
| IC | 1:0.99 | 1:0.98 |

Oxalates.

Both oxalates display the same XRPD diffractogram (OXA pattern1), although as with the other salts, the solid from MEK loses some crystallinity on isolation. After storage at 40° C. and 75% RH, both oxalates changed to the same form (OXA Form 2). Results are shown below in Table 10.

TABLE 10

| Technique | S28 | S54 |
| --- | --- | --- |
| Salt | Oxalate from MEK 1:1 | Oxalate from MeCN 1:1 |
| High Resolution XRPD | Weakly crystalline OXA Form 1, possible reduction in crystallinity after isolating solid | OXA Form 1 |
| 1H-NMR (DMSO-d6) | Peak shifts to free base ~0.2 eq MEK | Peak shifts to free base ~0.3 eq MeCN |
| HPLC (Purity %, AUC) | 84.9 | 85.5 |
| Storage at 40° C. and 75% RH | Change in form OXA Form 2 | Change in form OXA Form 2 |
| Thermal analysis of sample from storage at 40° C. and 75% RH (OXA Form 2) | DSC: Broad endotherm onset 28° C. (183.6 J/g)* | TGA: 5 wt % loss 30-140° C.* |
| IC | 1:1.04 | 1:0.97 |

*Owing to sample availability DSC and TGA could not be performed on both samples Scale-Up.

The three most crystalline salt forms, the mono tartrate (TAR Form 1), mono oxalate (OXA Form 1), and bis tosylate (pTSA Form 2) were selected for scale up and further characterisation. This included a preliminary polymorphism assessment.

Tartrates.

TAR Form 1 was not obtained on scale up. Instead, a new solvated form, TAR Form 2, was isolated. This form was found to be unstable to humidity with a loss of crystallinity, conversion to a new form (TAR Form 3) and a significant drop in purity observed.

In the first experiment, Example 1 was dissolved in IPA (100 mg in 1 mL, 10 vol) at ambient conditions. The solution was then heated to 50° C., treated with 1.1 eq of L-tartaric acid (1M in THF, 212 µL) and stirred at 50° C. for 1 hour. The resulting suspension was then cooled down to 5° C. at 0.1° C./min overnight. XRPD showed only amorphous solids which were then matured between 50° C./ambient on an 8-hour cycle for 7 days. $^1$H NMR (DMSO-d6) showed only Peak shifts to free base (~0.5 eq IPA). A crystalline tartrate was not obtained in this experiment even after further maturation. Analysis of the amorphous tartrate by DSC indicated no evidence of crystallization.

In the second experiment, Example 1 was dissolved in IPA (10 vol., 500 mg in 5 mL) at ambient conditions. The solution was then stirred at 25° C. and treated with 1.1 eq of L-tartaric acid (1030 µL, 1 M in THF). The sample was then stirred for 1 hour at 25° C., cooled to 0° C. at 0.2° C./min and left at 0° C. overnight. Any solids obtained were analyzed by XRPD and then matured between 50° C./ambient on an 8 hour cycle for 2 days. Aliquots of the sample were taken and analyzed by XRPD during maturation to monitor crystallinity. The sample remained low in crystallinity and was seeded with crystalline tartrate salt (S7) after 2 days. The seeded sample was returned to maturation for a further 4 days before the bulk sample was filtered and dried under vacuum at ambient conditions overnight. Any resulting crystalline solids were characterized.

The tartrate was found to be weakly crystalline after cooling, with no improvement seen after 2 days maturation. The sample was seeded to aid the formation of crystalline material but after a further 4 days maturation XRPD analysis showed the sample to be amorphous. After isolation and drying, high-resolution XRPD showed the sample to have crystallised to a new form, TAR Form 2.

The tartrate salt contained ~1 eq of IPA by $^1$H NMR, and this coupled with the new XRPD (TAR Form 2) diffractogram confirmed a different form, most likely solvated, had been obtained. Upon heating to a point after the first weight loss in the TGA (75° C.) and analysing by XRPD, a mixture of TAR Form 1 and 2 was observed. $^1$H NMR of this material showed a decrease in the amount of IPA present. VT-XRPD indicated that the sample changed again at 120° C., which corresponds to the end of the broad endotherm in the DSC. Other complex thermal behaviour was noted in an exotherm before degradation. GVS showed the tartrate to be very hygroscopic taking up ~30% w/w water, with decreased crystallinity and a change in form noted by XPPD post GVS. Both storage conditions resulted in changes in crystallinity and form but storage at 40° C. and 75% RH also caused a significant loss in purity (>30%). Results from this experiment are shown below in Table 12.

Tosylates.

The bis tosylate, pTSA Form 2, was successfully scaled up and displayed the best solid state properties of all the salts investigated. This form is believed to be a channel hydrate as water can be taken up and lost from the structure without changing the crystalline form. The only other crystalline form of the tosylate observed during the study, pTSA Form 1, converted to pTSA Form 2 on storage at elevated temperature and humidity. Limited stability studies on the tosylate indicated it had improved chemical stability over the free form. The bis-tosylate salt had higher purity than the corresponding free base.

In the first experiment, Example 1 was dissolved in MEK or MeCN (100 mg in 1 mL, 10 vol) at ambient conditions. The solutions were then heated to 50° C., treated with 2.1 eq of p-toluene sulfonic acid monohydrate (1M in THF, 405 µL) and stirred constant temperature for 1 hour. The resulting suspensions were then cooled down to 5° C. at 0.1° C./min overnight. Any solids obtained were analyzed by XRPD and those that were amorphous or weakly crystalline were then matured between 50° C./ambient on an 8-hour cycle for 7 days. Any resulting crystalline solids were characterized by high resolution XRPD, $^1$H NMR, HPLC, TGA, DSC and one week storage at 40° C. and 75% RH. After cooling the tosylates, the solids displayed the same XRPD diffractograms, pTSA Forms 1 and 2, as observed previously. However, after further maturation to try and improve the crystallinity, both tosylate salts were consistent with pTSA Form 2 by XRPD. This salt was found to be a bis tosylate with higher purity than the free base in both instances, although the solid from MeCN was notably better. Results are shown below in Table 11.

TABLE 11

| Salt | Tosylate from MEK | Tosylate from MeCN |
| --- | --- | --- |
| High Resolution XRPD | pTSA Form 2 | pTSA Form 2 |
| 1H-NMR (DMSO-d6) | Peak shifts to free base ~2 eq acid | Peak shifts to free base ~2 eq acid |
| HPLC (Purity %, AUC) | 84.5 | 93.9 |
| Storage at 40° C. and 75% RH | No change in form pTSA Form 2 | No change in form pTSA Form 2 |
| DSC | Broad endotherm onset 28° C. (98.0 J/g) Endotherm onset 155° C. (12.3 J/g) followed by exotherm | Broad endotherm onset 28° C. (100.1 J/g) Endotherm onset 168° C. (38.1 J/g) followed by exotherm |

TABLE 11-continued

| Salt | Tosylate from MEK | Tosylate from MeCN |
| --- | --- | --- |
| TGA | 2.3 wt % loss 30-60° C. | 3 wt % loss 30-70° C. |
| VT-XRPD | — | No change in form of sample up to 170° C. |

The first weight loss in the TGA of the tosylate salt corresponds to a broad endotherm in the DSC. Based on the $^1$H NMR, which showed no significant amounts of residual solvent, this suggested that pTSA Form 2, is a hydrated form. Variable temperature XRPD (VT-XRPD) of tosylate showed no change to the crystalline form of the material up to 170° C., after which the sample melts. This indicates that pTSA Form 2 could be a channel hydrate in which the water can move in an out of the structure without affecting the crystalline lattice.

In the second experiment, Example 1 was dissolved in acetonitrile (10 vol., 500 mg in 5 mL) at ambient conditions. The solution was then stirred at 50° C. and treated with 2.1 eq of p-toluenesulfonic acid monohydrate (2060 µL, 1 M in THF). The sample was then stirred for 1 hour at 50° C., cooled to 5° C. at 0.1° C./min and left at 5° C. overnight. Any solids obtained were analyzed by XRPD and then matured between 50° C./ambient on an 8 hour cycle for 1 day. Aliquots of the sample were taken and analyzed by XRPD during maturation to monitor crystallinity. No notable change in crystallinity was observed between the XRPD diffractograms pre and post maturation. The bulk sample was filtered and dried under vacuum at ambient conditions overnight. Any resulting crystalline solids were characterized. Although the tosylate was crystalline after cooling, it was matured to see if any increase in crystallinity would be obtained. The sample was removed from maturation after 1 day when no change to the sample was seen by XRPD.

The XRPD diffractogram of the tosylate was found to be consistent with pTSA Form 2, as expected. Weight loss in the TGA corresponding to the broad endotherm in the DSC, indicated this is a hydrated form. This is further supported by the $^1$H NMR which showed no significant amounts of residual solvent. The sample displays a melt, endotherm (onset 170° C.) in the DSC. GVS of the material shows the sample to have a fully reversible uptake and loss of water, only taking up ~5% w/w water over a full cycle. No change in form was observed. Storage at both 40° C. and 75% RH and 25° C. and 95% RH showed no changes in the form or purity of the sample. Results from this experiment are shown below in Table 12.

Oxalates.

A new form of the oxalate was also obtained on scale up. This material, named OXA Form 3, was very similar to OXA Form 1 isolated in the initial experiment. OXA Form 3 is believed to be a hydrate form that readily converts to a higher hydrate on exposure to humidity. This higher hydrate, OXA Form 2, is hygroscopic but stable to elevated humidity. This form was also obtained by maturation of OXA Form 3 in THF:Water (95:5) in the polymorphism assessment.

Example 1 was dissolved in acetonitrile (10 vol., 500 mg in 5 mL) at ambient conditions. The solution was then stirred at 50° C. and treated with 1.1 eq of oxalic acid (1030 µL, 1 M in THF). The sample was then stirred for 1 hour at 50° C., cooled to 5° C. at 0.1° C./min and left at 5° C. overnight. Any solids obtained were analyzed by XRPD and then matured between 50° C./ambient on an 8 hour cycle for 2 days. Aliquots of the sample were taken and analyzed by XRPD during maturation to monitor crystallinity. No notable change in crystallinity was observed between the XRPD diffractograms pre and post maturation. The bulk sample was filtered and dried under vacuum at ambient conditions overnight. Any resulting crystalline solids were characterized. Although the oxalate was crystalline after cooling, it was matured to see if any increase in crystallinity would be obtained. The samples were removed from maturation after 2 days, when no change to the sample was seen by XRPD.

The oxalate was found to have an XRPD diffractogram that was similar to OXA Form 1 with some differences. OXA Form 3 it may be a more crystalline sample of OXA Form 1. The broad endotherm in the DSC and first weight loss in the TGA, suggest the oxalate is a hydrated form. The form of oxalate was found to be unchanged by temperatures up to 140° C., suggesting the water is in channels and not bound within the crystal structure. As with the tartrate, the oxalate displayed an exotherm before degradation in the DSC. Although the form of oxalate is not changed by temperatures, it is by humidity. Storage at both 40° C. and 75% RH and 25° C. and 95% RH changed the form of the material to OXA Form 2, with no affect on the purity of the samples. OXA Form 2 is likely to be a higher hydrated form. GVS shows the sample to be hygroscopic taking up ~12% w/w water during a full cycle, post GVS XRPD shows a change in form to OXA Form 2 post GVS. Results from this experiment are shown below in Table 12.

Results from the larger scale-up experiments above are shown below in Table 12.

TABLE 12

| High Res XRPD | TAR Form 2 (Amorphous before isolation) | pTSA Form 2 | OXA Form 3* |
|---|---|---|---|
| ¹H-NMR (DMSO-d6) | Peaks shifts to free base ~1 eq acid ~1 eq IPA | Peak shifts to free base ~2 eq acid | Peak shifts to free base trace MeCN |
| HPLC (Purity %, AUC) | 97.3 | 97.5 | 97.7 |
| PLM | Agglomerated particles Small amount of birefringence | Lath shaped particles Birefringence | Agglomerated particles Birefringence |
| DSC | Broad endotherm onset 46° C. (155.5 J/g) Endotherm onset 124° C. (3.8 J/g) followed by exotherm onset 130° C. (70.2 J/g) | Broad endotherm onset 29° C. (97.9 J/g) Endotherm onset 170° C. (46.3 J/g) | Broad endotherm onset 34° C. (117.1 J/g) Endotherm onset 115° C. (1.1 J/g) Exotherm onset 155° C. (30.7 J/g) |
| TGA | 4.4 wt % loss 30-70° C. 1.5 wt % loss 110-130° C. | 2.9 wt % loss 40-80° C. | 4.4 wt % loss 40-80° C. |
| XRPD after first TGA weight loss | Isotherm at 75° C. Mixture of forms TAR Form 1 and 2 NMR: ~0.15 eq IPA | Isotherm at 100° C. No change in form | Isotherm at 100° C. No change in form |
| Karl Fischer | 7.0% | 4.6% | 7.5% |
| GVS | Very hygroscopic Reversible after 1st uptake ~30% w/w water uptake between 0 and 90% RH High res XRPD: Change in form TAR Form 3 Decreased crystallinity | Fully reversible ~5% w/w water uptake between 0 and 90% RH ~4% w/w water uptake between 0 and 30% RH High res XRPD: No change in form pTSA Form 2 | Hygroscopic Reversible after 1st uptake ~12% w/w water uptake between 0 and 90% RH High res XRPD: Change in form OXA Form 2 |
| Storage @ 40° C./75% RH | Change in formTAR Form 3 Decreased crystallinity Purity: 64.2% | No change in form pTSA Form 2 Purity: 97.4% | Change in form OXA Form 2 Purity: 97.8% |
| Storage @ 25° C./95% RH | Change in form TAR Form 3 Decreased crystallinity Purity: 95.7% | No change in form pTSA Form 2 Purity: 97.5% | Change in form OXA Form 2 Purity: 97.9% |
| VT-XRPD | Change in form at 120° C. TAR pattern 4 Sample melted at 140° C. | No change in form on heating♦. | No change in form of sample up to 140° C. |
| IC | 1:1.00 | 1:2.1 | 1:1.03 |
| Yield | ~580 mg, ~92% | ~620 mg, ~93% | ~500 mg, ~86% |
| Kinetic Solubility SGF 2 hours | >23.2 mg/ml at pH 2.1 | 16.5 mg/ml at pH 1.3 | >25.6 mg/ml at pH 1.6 |

*Similar to QXA pattern1,
♦Analysis performed on earlier batch

Amorphous Example 1 (10 mg) was treated with increasing volumes of solvent at 25° C. with stirring (Table #). Clear solutions were observed in most cases. For those instances where dissolution was not observed, the samples were placed at 50° C. for 10 minutes. To all samples still in suspension, a further 10 volumes of solvents were added and the sample placed at 25° C. The temperature was then once again increased to 50° C. and maintained until the end of the experiment. Further solvent was added until the material fully dissolved or until a maximum of 70 volumes had been used. Hydrochloric acid was then added (1.1 equivalents) to all samples. A cooling ramp was set to 5° C. at 0.1° C./min and the solutions or oils were stirred at this temperature overnight, yielding oils or solutions.

Solutions were evaporated to dryness (ambient conditions), or treated with anti-solvent (TBME, 150 μL, stirring at 25° C.). Any oils or gums were subjected to sonication, followed by maturation between ambient and 50° C. for ca. 4 hours at each temperature (Section 7.7). Oils were subsequently treated with anti-solvent and matured further at the above conditions. Results are shown below in Table 13.

TABLE 13

| Solvent | 10 vol 25° C. | 10 vol 50° C. | 20 vol 25° C. | 20 vol 50° C. | 40 vol 50° C. | 70 vol 50° C. | Add'n of HCl | At 5° C. | Further work | Results | Further work | Results |
|---|---|---|---|---|---|---|---|---|---|---|---|---|
| Diethyl ether | oil | oil | oil | oil | oil | oil | oil + turbid | oil | SON + MAT | oil | AS + MAT | oil |
| Dimethyl sulfoxide | # | | | | | | sol'n | sol'n | Evap. (glass slide) | sol'n | AS + STIR | oil |
| Propyl acetate | # | | | | | | turbid | oil | SON + MAT | oil | AS + MAT | oil |
| Methyl acetate | # | | | | | | turbid | oil | SON + MAT | oil | AS + MAT | oil |
| Isopropyl acetate | # | | | | | | turbid | oil | SON + MAT | oil | AS + MAT | oil |
| MIBK | # | | | | | | turbid | oil | SON + MAT | oil | AS + MAT | oil |
| MEK | # | | | | | | turbid | oil | SON + MAT | oil | AS + MAT | oil |
| 1-Butanol | # | | | | | | sol'n | sol'n | Evap. | oil + sol'n | AS + STIR | oil |
| 2-Propanol | # | | | | | | sol'n | sol'n | AS + STIR | oil + sol'n | AS + STIR | oil |
| 1-Propanol | # | | | | | | sol'n | sol'n | Slow Evap. | oil | AS + STIR | oil |
| Water | x | x | x | oil | oil | oil | oil, turned into sol'n | sol'n | Evap. | sol'n | Evap. (glass slide) | oil |
| Acetone | # | | | | | | turbid | oil | SON + MAT | oil | AS + MAT | oil |
| Ethanol | # | | | | | | sol'n | sol'n | AS + STIR | oil + sol'n | AS + STIR | oil |
| Anisole | # | | | | | | turbid | oil | SON + MAT | oil | AS + MAT | oil |
| Methanol | # | | | | | | sol'n | sol'n | AS + STIR | oil + sol'n | AS + STIR | oil |
| Cyclohexane | oil | oil | oil | oil | oil | oil | oil + ppt | oil | SON + MAT | oil | AS + MAT | oil |
| Toluene | # | | | | | | turbid | oil | SON + MAT | oil | AS + MAT | oil |
| Acetonitrile | # | | | | | | sol'n | oil | SON + MAT | oil | AS + MAT | oil |
| Dichloromethane | # | | | | | | turbid | oil | SON + MAT | oil | AS + MAT | oil |
| IPA:Water (85:15) | # | | | | | | sol'n | sol'n | Slow Evap. | oil | AS + STIR | oil |
| MeOH:Water (85:15) | # | | | | | | sol'n | sol'n | Slow Evap. | oil | AS + STIR | oil |
| EtOH:Water (85:15) | # | | | | | | sol'n | sol'n | Slow Evap. | oil | AS + STIR | oil |
| Acetone:Water (95:5) | # | | | | | | sol'n | sol'n | Slow Evap. | oil | AS + STIR | oil |
| Acetone:Water (90:10) | # | | | | | | sol'n | sol'n | Slow Evap. | oil | AS + STIR | oil |

# = clear solution;
x = suspension;
sol'n—solution;
SON = sonication 30 min;
MAT = maturation ambient- 50° C., 4 h each, 4 days;
STIR = constant 25° C.;
AS = anti-solvent addition TBME 150 μL;

Dissolution of amorphous Example 1 was observed in most solvents at 25° C. (10 volumes). Exceptions were water, diethyl ether and cyclohexane, where oils eventually formed. No solids were obtained after the addition of hydrochloric acid. Turbidity was observed in most instances upon addition of the acid, but oils were observed after the cooling ramp, and also after subsequent sonication, anti-solvent addition with stirring and/or maturation.

Second Salt Experiments.

Amorphous Example 1 was dissolved in 1-propanol, acetone or isopropyl acetate (1380 mg in 13.8 mL, 10 volumes) at 25° C. The equivalent to 30 mg Example 1 (300 µL) was pipetted into vials, which were then placed at 50° C. The selected acids were added at 50° C. The temperature was maintained for 1 hour and a cooling ramp to 5° C. at 0.1° C./min was set up overnight.

Any precipitates observed were filtered and analyzed by XRPD. The remaining oils or solutions were subjected to anti-solvent additions. TBME (10 volumes) was used as anti-solvent for the 1-propanol experiments. n-Heptane (10 volumes) was the anti-solvent added to the acetone experiments, and hexane (7 volumes) was added to the isopropyl acetate experiment. The samples, where applicable, were further treated by maturation, cooling or evaporation. Finally, all oils and gums were dried under vacuum at room temperature over one week. Further solvent (IPA/5% water, nitromethane or toluene, 8 volumes) was added. Further maturation between ambient conditions and 50° C. was set up, 4 hours at each temperature, for a total of 11 days.

Crystalline or partially crystalline materials were isolated for sulfate, benzenesulfonate, oxalate, fumarate, L-malate, citrate and ethanesulfonate salts. Oxalate salts were not characterized owing to the fact that these salts were reported in the previous salt selection project.

A number of different XRPD patterns were observed for the attempted sulfate salts, including one (SUL3) observed in the experiment above. One form of benzenesulfonate salt was observed in three instances, from 1-propanol and acetone. One form of fumarate salt was observed from IPAc/TBME, independent of the amount of acid used. Another poorly crystalline fumarate, denoted as FUA2, was observed after maturation in IPA/5% water. Finally, partially crystalline L-malate, citrate and ethanesulfonate salts were observed. The results are summarised in Tables 12a-12c.

Results from salt experiments performed in 1-propanol are given below in Table 14a.

TABLE 14a

| Ex. | Counter-ionr | Eq · s | Obs. on add'n | Obs after 1 h | Obs at 5° C. | TBME add'n | XRPD | Procedure | Obs. After Previous Procedure | Maturation in IPA/5% water |
|---|---|---|---|---|---|---|---|---|---|---|
| S77 | HCl | 1.1 | sol'n | sol'n | sol'n | oil | n/a | evap. | oil | oil |
| S78 | HCl | 2.2 | sol'n | sol'n | sol'n | oil | n/a | evap. | oil | oil |
| S79 | SUL | 1.1 | ppt | ppt | ppt | n/a | SUL3* | n/a | n/a | n/a |
| S80 | SUL | 2.2 | ppt | ppt | ppt | n/a | Mainly amorphous | n/a | n/a | n/a |
| S81 | SUL | 0.6 | ppt | ppt | ppt | n/a | SUL4# | n/a | n/a | n/a |
| S82 | TCA | 1.1 | turbid | turbid | turbid | turbid | n/a | evap. | oil | oil |
| S83 | TCA | 2.2 | turbid | turbid | turbid | turbid | n/a | evap. | oil | oil |
| S84 | BSA | 1 | sol'n | sol'n | sol'n | ppt | Deliquesced | n/a | n/a | n/a |
| S85 | BSA | 2 | sol'n | sol'n | ppt | n/a | BSA1 LC# | n/a | n/a | n/a |
| S86 | OXA | 1.1 | ppt | ppt | ppt | n/a | OXA1* | n/a | n/a | n/a |
| S87 | OXA | 2.2 | ppt | ppt | ppt | n/a | gel | maturation 25-5° C. | oil | oil |
| S88 | OXA | 0.6 | ppt | ppt | ppt | n/a | deliquesced | n/a | n/a | n/a |
| S89 | ASP | 1.1 | soln/acid | turbid/acid | ppt | n/a | insuff. | evap. | insuff. | n/a |
| S90 | ASP | 2.2 | soln/acid | soln/acid | turbid | ppt | insuff. | evap. | insuff. | n/a |
| S91 | ASP | 0.6 | soln/acid | soln/acid | turbid/oil | ppt | evap. | insuff. | insuff. | n/a |
| S92 | MEA | 1.1 | sol'n | sol'n | sol'n | oil | n/a | evap. | oil | oil |
| S93 | MEA | 2.2 | sol'n | sol'n | oil | oil | n/a | evap. | oil | oil |
| S94 | PHOA | 1.1 | ppt | ppt | ppt | n/a | deliquesced | n/a | n/a | n/a |
| S95 | PHOA | 2.2 | ppt | ppt | ppt | n/a | amorphous | n/a | n/a | n/a |
| S96 | ESA | 1 | sol'n | sol'n | sol'n | sol'n | n/a | −20° C. | sol'n | oil |
| S97 | ESA | 2 | sol'n | sol'n | sol'n | ppt | deliquesced | n/a | n/a | n/a |
| S98 | GLU | 1.1 | soln/acid | turbid/acid | ppt | n/a | insuff. | evap. | insuff. | n/a |
| S99 | GLU | 2.2 | soln/acid | soln/acid | turbid | ppt | insuff. | evap. | insuff. | n/a |
| S100 | GLU | 0.6 | soln/acid | soln/acid | turbid | ppt | n/a | evap. | insuff. | n/a |
| S101 | MLNA | 1.1 | sol'n | sol'n | oil | oil | n/a | evap. | oil | oil |
| S102 | MLNA | 2.2 | sol'n | sol'n | oil | oil | n/a | evap. | oil | oil |
| S103 | FUA | 1.1 | sol'n | sol'n | sol'n | oil | n/a | evap. | oil | oil |
| S104 | FUA | 2.2 | sol'n | sol'n | sol'n | oil | n/a | evap. | oil | FUA2 LC# |
| S105 | FUA | 0.6 | sol'n | sol'n | sol'n | oil | n/a | evap. | oil | oil |

TABLE 14a-continued

| Ex. | Counter-ionr | Eq · s | Obs. on add'n | Obs after 1 h | Obs at 5° C. | TBME add'n | XRPD | Procedure | Obs. After Previous Procedure | Maturation in IPA/5% water |
|---|---|---|---|---|---|---|---|---|---|---|
| S106 | CA | 1.1 | ppt | ppt | ppt | n/a | deli-quesced& | n/a | n/a | n/a |
| S107 | CA | 2.2 | ppt | ppt | ppt | n/a | deli-quesced& | n/a | n/a | n/a |
| S108 | GA | 1.1 | sol'n | sol'n | sol'n | sol'n | n/a | −20° C. | sol'n | n/a |
| S109 | GA | 2.2 | sol'n | sol'n | sol'n | sol'n | n/a | −20° C. | sol'n | n/a |
| S110 | MA | 1.1 | ppt | sol'n | oil | ppt | insuff. | evap. | insuff. | n/a |
| S111 | MA | 2.2 | ppt | ppt | gum | ppt | insuff. | evap. | insuff. | n/a |
| S112 | HPA | 1.1 | sol'n | sol'n | gum | oil | n/a | evap. | insuff. | n/a |
| S113 | HPA | 2.2 | sol'n | sol'n | sol'n | sol'n | n/a | −20° C. | sol'n | oil |
| S114 | GLYA | 1.1 | sol'n | sol'n | sol'n | sol'n | n/a | −20° C. | sol'n | oil |
| S115 | GLYA | 2.2 | sol'n | sol'n | sol'n | sol'n | n/a | −20° C. | sol'n | oil |
| S116 | LA | 1.1 | sol'n | sol'n | sol'n | sol'n | n/a | −20° C. | sol'n | oil |
| S117 | LA | 2.2 | sol'n | sol'n | sol'n | sol'n | n/a | −20° C. | sol'n | oil |
| S118 | ADA | 1.1 | sol'n | sol'n | sol'n | sol'n | n/a | −20° C. | sol'n | oil |
| S119 | NA | 1.1 | soln/acid | turbid/acid | turbid/acid | sol'n | n/a | −20° C. | sol'n oil | |
| S120 | PROA | 1.1 | sol'n | sol'n | sol'n | sol'n | n/a | −20° C. | sol'n | oil |
| S121 | CYA | 1.1 | sol'n | sol'n | sol'n | sol'n | n/a | −20° C. | sol'n | oil |
| S122 | ORA | 1.1 | soln/acid | turbid/acid | turbid/acid | turbid/ppt | insuff. | evap. | insuff. | n/a |
| S123 | GLU | 1.1 | soln/acid | turbid/acid | ppt | n/a | insuff. | evap. | insuff. | n/a | ppt = precipitate;
sol'n = solution;
−20° C. = placed in freezer;
acid = where acid was added as neat solid, acid particles were observed as opposed to precipitation of further solid;
= new crystalline or partially crystalline solids;
insuff. = insufficient material for analysis;
LC = low crystallinity;
* = crystalline or partially crystalline solids previously observed;
& = analyzed by XRPD although evidence of deliquescence was observed.

Results from salt experiments performed in acetone are given below in Table 14b.

TABLE 14b

| Ex. | Counter-ion | Eq · s | Obs. on add'n | Obs after 1 h | Obs at 5° C. | TBME add'n | XRPD | Procedure | Obs. After Previous Procedure | Maturation in Nitro-methane |
|---|---|---|---|---|---|---|---|---|---|---|
| S124 | HCl | 1.1 | turbid | oil | oil | oil | n/a | maturation | oil | oil |
| S125 | HCl | 2.2 | ppt | oil | oil | oil | n/a | maturation | oil | oil |
| S126 | SUL | 1.1 | ppt | ppt | ppt | n/a | SUL5# | n/a | n/a | n/a |
| S127 | SUL | 2.2 | ppt | ppt | ppt | n/a | Deli-quesced* | n/a | n/a | n/a |
| S128 | SUL | 0.6 | ppt | ppt | ppt | n/a | Mainly amorphous | n/a | n/a | n/a |
| S129 | TCA | 1.1 | ppt | ppt | turbid | turbid | n/a | maturation | oil | oil |
| S130 | TCA | 2.2 | ppt | ppt | turbid | turbid | n/a | maturation | oil | oil |
| S131 | BSA | 1 | sol'n | sol'n | sol'n | ppt | n/a | BSA1 LC# | n/a | n/a | n/a |
| S132 | BSA | 2 | turbid | turbid | turbid | ppt | n/a | BSA1 LC# | n/a | n/a | n/a |
| S133 | OXA | 1.1 | oil | ppt | ppt | n/a | OXA1* | n/a | n/a | n/a |
| S134 | OXA | 2.2 | oil | ppt | ppt | n/a | n/a (gel) | maturation | gel | oil |
| S135 | OXA | 0.6 | ppt | ppt | ppt | n/a | OXA1* | n/a | n/a | n/a |
| S136 | ASP | ### | oln/acid | urbid | urbid | turbid | insuff. | maturation | oil turbid | |
| S137 | ASP | 2.2 | soln/acid | turbid | turbid | turbid | insuff. | evap. | turbid | oil |
| S138 | ASP | 0.6 | soln/acid | turbid | turbid | turbid | insuff. | evap. | turbid | oil |
| S139 | MEA | 1.1 | sol'n | sol'n | sol'n | oil | n/a | maturation | oil | oil |
| S140 | MEA | 2.2 | turbid | turbid | sol'n | oil | n/a | maturation | oil | oil |
| S141 | PHOA | 1.1 | ppt | ppt | ppt | n/a | amorphous | n/a | n/a | n/a |
| S142 | PHOA | 2.2 | ppt | ppt | ppt | n/a | amorphous | n/a | n/a | n/a |
| S143 | ESA | 1 | sol'n | sol'n | sol'n | oil | n/a | matu-ration | oil | oil |
| S144 | ESA | 2 | turbid | turbid | ppt | n/a | Deliquesced | n/a | n/a | n/a |
| S145 | GLU | 1.1 | soln/acid | turbid | turbid | turbid | n/a | maturation | turbid | oil |

TABLE 14b-continued

| Ex. | Counter-ion | Eq · s | Obs. on add'n | Obs after 1 h | Obs at 5° C. | TBME add'n | XRPD | Procedure | Obs. After Previous Procedure | Maturation in Nitro-methane |
|---|---|---|---|---|---|---|---|---|---|---|
| S146 | GLU | 2.2 | soln/acid | turbid | turbid | turbid | n/a | maturation | turbid | oil |
| S147 | GLU | 0.6 | soln/acid | turbid | turbid | turbid | n/a | maturation | turbid | oil |
| S148 | MLNA | 1.1 | turbid | turbid | oil | oil | n/a | maturation | oil | oil |
| S149 | MLNA | 2.2 | turbid | oil | oil | oil | n/a | maturation | oil | oil |
| S150 | FUA | 1.1 | sol'n | sol'n | sol'n | oil | n/a | maturation | oil | oil |
| S151 | FUA | 2.2 | sol'n | sol'n | sol'n | oil | n/a | maturation | oil | Amorphous solid |
| S152 | FUA | 0.6 | sol'n | sol'n | sol'n | oil | n/a | maturation | oil | oil |
| S153 | CA | 1.1 | ppt | oil | oil | oil | n/a | maturation | oil | oil |
| S154 | CA | 2.2 | ppt | gum | gum | oil | n/a | maturation | oil | oil |
| S155 | GA | 1.1 | sol'n | sol'n | sol'n | sol'n | n/a | −20° C. | sol'n | oil |
| S156 | GA | 2.2 | sol'n | sol'n | sol'n | sol'n | n/a | −20° C. | sol'n | oil |
| S157 | MA | 1.1 | ppt | turbid | gum | oil | n/a | maturation | oil | oil |
| S158 | MA | 2.2 | ppt | turbid | gum | oil | n/a | maturation | oil | oil |
| S159 | HPA | 1.1 | sol'n | sol'n | sol'n | oil | n/a | maturation | oil | oil |
| S160 | HPA | 2.2 | sol'n | sol'n | gum | sol'n | n/a | −20° C. | sol'n | oil |
| S161 | GLYA | 1.1 | sol'n | sol'n | oil | oil | n/a | maturation | oil | oil |
| S162 | GLYA | 2.2 | turbid | sol'n | oil | oil | n/a | maturation | oil | oil |
| S163 | LA | 1.1 | sol'n | sol'n | sol'n | oil | n/a | maturation | oil | oil |
| S164 | LA | 2.2 | sol'n | sol'n | sol'n | oil | n/a | maturation | oil | oil |
| S165 | ADA | 1.1 | sol'n | sol'n | sol'n | oil | n/a | maturation | oil | oil |
| S166 | NA | 1.1 | soln/acid | sol'n | sol'n | sol'n | n/a | −20° C. | sol'n | oil |
| S167 | PROA | 1.1 | sol'n | sol'n | sol'n | sol'n | n/a | −20° C. | sol'n | oil |
| S168 | CYA | 1.1 | sol'n | sol'n | sol'n | sol'n | n/a | −20° C. | sol'n | oil |
| S169 | ORA | 1.1 | soln/acid | turbid | turbid | turbid | n/a | maturation | turbid | oil | ppt = precipitate;
sol'n = solution;
−20° C. = placed in freezer;
acid = where acid was added as neat solid, acid particles were observed as opposed to precipitation of further solid;
= new crystalline or partially crystalline solids;
insuff. = insufficient material for analysis;
LC = low crystallinity;
*= crystalline or partially crystalline solids previously observed;
&= analyzed by XRPD although evidence of deliquescence was observed.

Results from salt experiments performed in isopropyl acetate are given below in Table 14c.

TABLE 14c

| Ex. | Counter-ion | Eq · s | Obs. on add'n | Obs after 1 h | Obs at 5° C. | TBME add'n | XRPD | Procedure | Obs. After Prev. Procedure | Maturation in Toluene |
|---|---|---|---|---|---|---|---|---|---|---|
| S170 | HCl | 1.1 | ppt | oil | oil | oil | maturation | oil | n/a | oil |
| S171 | HCl | 2.2 | ppt | oil | oil | turbid | maturation | turbid | n/a | oil |
| S172 | SUL$^a$ | 1.1 | ppt | ppt | ppt | n/a | n/a | n/a | SUL5# | n/a |
| S173 | SUL$^a$ | 2.2 | ppt | ppt | ppt | n/a | n/a | n/a | deliquesced* | n/a |
| S174 | SUL$^a$ | 0.6 | ppt | ppt | ppt | n/a | n/a | n/a | SUL5# | n/a |
| S175 | TCA | 1.1 | turbid | turbid | oil | turbid | maturation | oil | n/a | oil |
| S176 | TCA | 2.2 | turbid | turbid | ppt | n/a | n/a | n/a | deliquesced | n/a |
| S177 | BSA | 1 | ppt | ppt/gum | oil | turbid | maturation | oil | n/a | oil |
| S178 | BSA$^a$ | 2 | ppt | ppt/gum | ppt | n/a | n/a | n/a | amorphous | n/a |
| S179 | OXA$^a$ | 1.1 | ppt | ppt | ppt | n/a | n/a | n/a | OXA1 LC* | n/a |
| S180 | OXA | 2.2 | ppt | ppt | ppt | n/a | n/a | n/a | Amorphous* | n/a |
| S181 | OXA$^a$ | 0.6 | ppt | ppt | ppt | n/a | n/a | n/a | OXA1 LC* | n/a |
| S182 | ASP | 1.1 | soln/acid | turbid | ppt | n/a | n/a | n/a | mainly amorphous$ | n/a |
| S183 | ASP | 2.2 | soln/acid | turbid | ppt | n/a | n/a | n/a | deliquesced | n/a |
| S184 | ASP | 0.6 | soln/acid | turbid | oil | turbid | maturation | oil | n/a | oil |

TABLE 14c-continued

| Ex. | Counter-ion | Eq·s | Obs. on add'n | Obs after 1 h | Obs at 5° C. | TBME add'n | XRPD | Procedure | Obs. After Prev. Procedure | Maturation in Toluene |
|---|---|---|---|---|---|---|---|---|---|---|
| S185 | MEA | 1.1 | ppt | oil | oil | turbid | maturation | oil | n/a | oil |
| S186 | MEA | 2.2 | ppt | oil | oil | turbid | maturation | oil | n/a | oil |
| S187 | PHOA[a] | 1.1 | ppt | ppt | ppt | n/a | n/a | n/a | Amorphous | n/a |
| S188 | PHOA[a] | 2.2 | ppt | ppt | ppt | n/a | n/a | n/a | Amorphous | n/a |
| S189 | ESA | 1 | ppt | gum | oil | turbid | maturation | oil | n/a | oil |
| S190 | ESA[a] | 2 | ppt | gum | ppt | n/a | n/a | n/a | ESA1 LC[#] | n/a |
| S191 | GLU | 1.1 | soln/acid | turbid | turbid | turbid | maturation | oil | n/a | oil |
| S192 | GLU[a] | 2.2 | soln/acid | turbid | ppt | n/a | n/a | n/a | Glutamic acid | n/a |
| S193 | GLU | 0.6 | soln/acid | turbid | turbid | turbid | maturation | oil | n/a | oil |
| S194 | MLNA | 1.1 | ppt | gum | gum | turbid | maturation | oil | n/a | oil |
| S195 | MLNA | 2.2 | ppt | gum | gum | turbid | maturation | oil | n/a | oil |
| S196 | FUA[a] | 1.1 | ppt | gum | gum | turbid | maturation | ppt | FUA1 | n/a |
| S197 | FUA | 2.2 | sol'n | sol'n | sol'n | turbid | maturation | oil | n/a | amorphous solid |
| S198 | FUA[a] | 0.6 | ppt | ppt | ppt | n/a | n/a | n/a | FUA1 | n/a |
| S199 | CA | 1.1 | ppt | ppt | ppt | n/a | n/a | n/a | CA1 LC[@] | n/a |
| S200 | CA[a] | 2.2 | ppt | ppt | ppt | n/a | n/a | n/a | amorphous | n/a |
| S201 | GA | 1.1 | sol'n | sol'n | oil | turbid | maturation | oil | n/a | oil |
| S202 | GA | 2.2 | sol'n | turbid | oil | turbid | maturation | oil | n/a | oil |
| S203 | MA | 1.1 | ppt | ppt | ppt | n/a | n/a | n/a | deliquesced | n/a |
| S204 | MA[a] | 2.2 | ppt | ppt | gum | turbid | maturation | ppt | MA1 LC | n/a |
| S205 | HPA | 1.1 | turbid | turbid | sol'n | turbid | maturation | oil | n/a | oil |
| S206 | HPA | 2.2 | turbid | turbid | sol'n | turbid | maturation | oil | n/a | oil |
| S207 | GLYA | 1.1 | ppt | ppt | gum | turbid | maturation | oil | n/a | oil |
| S208 | GLYA | 2.2 | ppt | gum | gum | turbid | maturation | oil | n/a | oil |
| S209 | LA | 1.1 | sol'n | sol'n | sol'n | turbid | maturation | oil | n/a | oil |
| S210 | LA | 2.2 | sol'n | sol'n | sol'n | turbid | maturation | oil | n/a | oil |
| S211 | ADA | 1.1 | oil | oil | gum | turbid | maturation | sol'n | n/a | oil |
| S212 | NA | 1.1 | soln/acid | sol'n | sol'n | turbid | maturation | sol'n | n/a | oil |
| S213 | PROA | 1.1 | sol'n | sol'n | sol'n | sol'n | maturation | oil | n/a | oil |
| S214 | CYA | 1.1 | sol'n | sol'n | sol'n | sol'n | maturation | oil | n/a | Solid - impurity |
| S215 | ORA | 1.1 | soln/acid | ppt | ppt | n/a | n/a | n/a | Deliquesced[&,$] | n/a | ppt = precipitate;
sol'n = solution;
−20° C. = placed in freezer;
acid = where acid was added as neat solid, acid particles were observed as opposed to precipitation of further solid;
[#]= new crystalline or partially crystalline solids;
insuff. = insufficient material for analysis;
LC = low crystallinity;
[*]= crystalline or partially crystalline solids previously observed;
[&]= analyzed by XRPD although evidence of deliquescence was observed;
[$]= small peaks consistent with L-aspartic acid;
[a]= vacuum dried samples;
[@]= isolated by drying only (insufficient solid to filter).

The fumarate salt obtained after maturation from IPA/5% water (FUA2) was poorly crystalline. $^1$H NMR analysis was carried out suggesting that although salt formation had occurred (chemical shifts consistent with other salts), an excess of fumaric acid was present.

The poorly crystalline solid obtained from caprylic acid in IPAc was consistent with a crystalline impurity identified during the prior experiments. The $^1$H NMR spectrum is not consistent with the other salts formed throughout this project and suggests degradation (the integrals are different and there are a number of extra peaks not attributable to either the compound or caprylic acid).

Basic characterisation of the sulfate, benzenesulfonate, fumarate, ethanesulfonate, L-malate, and citrate salts was carried out where enough material was available. In the instances where insufficient material was available for characterisation, preparation was repeated on a slightly larger scale.

Characterization of Salts.

Crystalline or partially crystalline novel salts obtained throughout this study were characterized further.

Amorphous Example 1 was dissolved in 1-propanol or acetone (60 mg in 0.6 mL, 10 volumes) at 50° C. The selected acids (see table below for details) were added at 50° C. Precipitates were observed from both sulfate salt formation attempts at 50° C. Anti-solvent was added at 50° C. to the benzenesulfonate salt attempt, where precipitation was observed (TBME, 0.6 mL, 10 volumes). The temperature was maintained for 1 hour and a cooling ramp to 5° C. at 0.1° C./min was set up overnight. Solids were filtered, dried under vacuum overnight at ambient condition and analyzed by XRPD. Results are shown below in Table 15.

TABLE 15

| Acid | Eqs added | Solvent | Target Form | Form Obtained |
|---|---|---|---|---|
| Sulfuric | 1.1 | 1-propanol | SUL5 | SUL3 |
| Benzenesulfonic | 2.2 | 1-propanol/TBME | BSA1 | BSA1 |
| Sulfuric | 0.6 | acetone | SUL4 | SUL5 |

Crystalline or partially crystalline salts obtained throughout this study were 257haracterized further, e.g. for stoichiometry, solvent content, chemical purity by HPLC and stability at elevated temperature and humidity.

Sulfates.

SUL3 and SUL5 are both crystalline and confirmed by ion chromatography as mono salts. Both materials remained as solids after storage at 40° C./75% RH for four days, although changes were observed by XRPD (SUL3 showed changes whereas SUL5 became amorphous). Both materials displayed a weight loss (6.2% below 190° C. and 4.4% below 175° C. respectively) on heating in thermogravimetric experiments. SUL3 also contained roughly one mole equivalent of 1-propanol by $^1$H NMR indicating it may be a solvated form. HPLC analysis of this form showed a purity of 98.8%.

Benzenesulfonates.

BSA1 is partially crystalline and was confirmed as a bis-benzenesulfonate salt by $^1$H NMR. DSC showed a broad endotherm, consistent with a TG weight loss of 5.1% below 150° C., followed by a sharper endotherm with onset at 115.5° C. This material deliquesced upon storage at 40° C./75% RH overnight, and had a purity of 97.8%.

Fumarates.

FUA1 is poorly crystalline and was confirmed as a mono-fumarate salt by $^1$H NMR. A TG weight loss of 3.6% w/w was also observed below 150° C. DSC analysis of the sample was complex with multiple unresolved events. This material has a purity of 94.3% and deliquesced upon storage at 40° C./75% RH overnight.

The partially crystalline ESA1 is confirmed as a bis-ethanesulfonate salt. This material deliquesced upon storage at 40° C./75% RH overnight. A weight loss of 2.8% w/w was observed below 150° C.

The partially crystalline MA1 was also 257haracterized. The stoichiometry could not be accurately determined due to overlapping peaks in the $^1$H NMR spectrum. This material has a purity of 94.7% and deliquesced upon storage at 40° C./75% RH overnight. A TG weight loss of 7.4% w/w was observed below 150° C.

Finally, the partially crystalline CA1 was also characterized. The purity was the lowest of all isolated salts, with a value of 87.8%. The material also deliquesced upon storage at 40° C./75% RH overnight and the stoichiometry could not be accurately determined due to overlapping peaks in the $^1$H NMR spectrum. Results are shown below in Table 16.

TABLE 16

| Salt/ XRPD | Stoichiometry ($^1$HNMR or IC) | Storage 40° C./ 75% RH | TGA | DSC | Purity by HPLC | Solvent ($^1$HNMR) |
|---|---|---|---|---|---|---|
| SUL3 | Mono salt (0.9 equivalents) | Change observed after 4 days | 6.2% weight loss below 190° C. | Multiple overlapping events | 98.80% | 1 equivalent 1-ProH |
| SUL5* | Mono salt (0.9 equivalents) | Mainly amorphous solid after 4 days | 4.4% weight loss below 170° C. | Multiple overlapping events | Insufficient material | 0.1 equivalents acetone |
| BSA1 | Bis salt (1.8 equivalents) | Deliquesced overnight | 5.1% weight loss below 150° C. | Solvent loss broad endotherm (onset 34.8° C., ΔH = 25.8 J/g) followed by sharper endotherm (onset 115.5° C., ΔH = 17.0 J/g) | 97.80% | 0.6 equivalents 1-ProH |
| FUA1* | Mono salt (1.1 equivalents) | Deliquesced overnight | 3.6% weight loss below 150° C. | Multiple overlapping events | 94.30% | 0.1 equivalents IPAc |
| ESA1 | Bis salt (2.0 equivalents) | Deliquesced overnight | 2.8% weight loss below 150° C. | Multiple overlapping events | Insufficient material | No significant residual solvent |
| MA1 LC** | Unable to quantify, peak overlapping | Deliquesced overnight | 7.4% weight loss below 150° C. | Multiple overlapping events | 94.70% | 0.3 eqs IPAc, 1.5 eqs THF |
| CA1 | Unclear, peak overlapping | Deliquesced overnight | Insufficient material | Multiple overlapping events | 87.80% | 0.4 eqs IPAc |

LC = low crystallinity;
*Mono salts were obtained although hemi or bis salts were targeted;
**sample went amorphous at RT Preparation of Polymorphs of Salts of Example 1

A preliminary polymorphism assessment was carried out on the three most crystalline salt forms, the mono tartrate (TAR Form 1), mono oxalate (OXA Form 1), and bis tosylate (pTSA Form 2). Each salt was treated with the relevant solvent (10 vol, 30 mg in 300 μL) at 25° C. The samples were stirred for 10 minutes and then heated to 50°

C. for 1 hour. The resulting suspensions were matured for 24 hours and any resulting solutions were allowed to evaporate slowly. After maturation or evaporation, the solids were filtered and air-dried before analysis by XRPD. Any solids that showed a new XRPD pattern were characterized by $^1$H NMR, IC (if the counter-ion not seen in the NMR) and one weeks storage at 40° C. and 75% RH, if the amount of solid isolated was sufficient.

Tartrate.

Solvents used and results are shown below in Table 17.

TABLE 17

| Ex. | Solvent | Observations at 50° C. | Observations after treatment | XRPD |
|---|---|---|---|---|
| P1 | n-Heptane | suspension | suspension | no change in form |
| P2 | Isopropyl acetate | suspension | suspension | no change in form |
| P3 | MIBK | suspension | suspension | no change in form |
| P4 | Acetone | suspension | suspension | no change in form |
| P5 | 2-Methoxyethanol | gel | gel | TAR Form 3 |
| P6 | 1,4-Dioxane | suspension | suspension | no change in form |
| P7 | Dichloromethane | suspension | suspension | TAR Form 1 |
| P8 | Nitromethane | gum | gum | TAR Form 1 |
| P9 | THF:Water (95:5) | gel | suspension | TAR Form 3 |
| P10 | Acetone:Water (95:5) | gel | suspension | TAR Form 3 |

From the 10 solvents used in this small polymorphism assessment, five of the tartrate samples changed in form. Samples from DCM and nitromethane change to TAR Form 1, previously obtained in the initial salt experiment. A new pattern, TAR Form 3, was found from 2-methoxyethanol, THF:water and acetone:water.

Limited characterisation was performed on the samples. These studies indicated that the samples consistent with TAR Form 1 by XRPD converted to TAR Form 3 on storage. By high resolution XRPD it was noted that the sample from 2-methoxyethanol displayed some differences to the diffractograms from the other two TAR Form 3 samples. It should be noted that that samples which degraded on storage during the characterisation of scaled up tartrate salt (TAR Form 2) displayed peaks similar to TAR Form 3. Owing to material availability, it was not possible to assess the purity of the samples after the polymorphism assessment and storage conditions. Results are shown below in Table 18.

TABLE 18

| High Res XRPD | TAR Form 3 | TAR Form 1 | TAR Form 1 | TAR Form 3 | TAR Form 3 |
|---|---|---|---|---|---|
| $^1$H-NMR (DMSO-$d_6$) | Peak shifts to free base ~1 eq acid ~3 eq 2-methoxy-ethanol | Peak shifts to free base ~0.8 eq acid trace DCM | Peak shifts to free base ~0.8 eq acid trace nitromethane | Peak shifts to free base ~1 eq acid | Peak shifts to free base ~1 eq acid |
| Storage @ 40° C./75% RH | No change in form TAR Form 3 | Change in form TAR Form 3 | Change in form TAR Form 3 | No change in form TAR Form 3 | No change in form TAR Form 3 |

Tosylate.

Solvents used and results are shown below in Table 19.

TABLE 19

| Ex. | Solvent | Observations at 50° C. | Observations after treatment | XRPD |
|---|---|---|---|---|
| P11 | n-Heptane | suspension | suspension | no change in form |
| P12 | Isopropyl acetate | suspension | suspension | no change in form |
| P13 | MIBK | suspension | suspension | no change in form |
| P14 | Acetone | suspension | suspension | no change in form |
| P15 | 2-Methoxyethanol | suspension | suspension | no change in form |
| P16 | 1,4-Dioxane | suspension | suspension | no change in form |
| P17 | Dichloromethane | suspension | suspension | no change in form |
| P18 | Nitromethane | suspension | suspension | no change in form |
| P19 | THF:Water (95:5) | solution | gum | amorphous |
| P20 | Acetone:Water (95:5) | suspension | suspension | no change in form |

From the 10 solvents used, no change in crystalline form was noted in 9 of the tosylate samples. The amorphous trace from the THF:water sample is due to it becoming a gum after maturation. In this case, unlike the other solvents, the sample fully dissolved at 50° C. and a gum precipitated out on cooling. This finding indicates this would not be a good solvent system for obtaining the crystalline tosylate salt. Whilst none of the other samples changed form during this small polymorphism assessment, experiments showed that the tosylate salt had at least 2 forms.

Oxalate.

Solvents used and results are shown below in Table 20.

TABLE 20

| Ex. | Solvent | Observations at 50° C. | Observations after treatment | XRPD |
|---|---|---|---|---|
| P21 | n-Heptane | suspension | lumpy solid | no change in form |
| P22 | Isopropyl acetate | suspension | suspension | no change in form |
| P23 | MIBK | suspension | suspension | no change in form |
| P24 | Acetone | suspension | suspension | no change in form |
| P25 | 2-Methoxyethanol | gel | gel | no change in form |

TABLE 20-continued

| Ex. | Solvent | Observations at 50° C. | Observations after treatment | XRPD |
|---|---|---|---|---|
| P26 | 1,4-Dioxane | suspension | suspension | no change in form |
| P27 | Dichloromethane | suspension | suspension | no change in form |
| P28 | Nitromethane | gel | gel | no change in form |
| P29 | THF:Water (95:5) | gel | suspension | OXA Form 2 |
| P30 | Acetone:Water (95:5) | gel | gel | no change in form |

Out of the 10 solvents used in this small polymorphism assessment on the oxalate salt, only one change in form was observed. The sample from THF:water was found to be OXA Form 2, which was previously observed on exposure of OXA Form 1 and 3 to high humidity. It is believed that this form is another hydrated form of the oxalate.

Conclusion.

The tartrate was found to change under both temperature and humidity conditions with a drop in purity noted under the latter conditions. It also shows a propensity towards polymorphism with half of the samples in the polymorphism assessment changing form. The tartrate is also a highly hygroscopic material and displays complex thermal behaviour.

The oxalate changed form under humidity, but not temperature conditions. Only one of the samples from slurry experiments changed form. However, the material is hygroscopic and has undesirable thermal behaviour.

The tosylate salt, pTSA Form 2, did not change form under the majority of conditions tested, including the polymorphism assessment slurries. The exception to this was in THF:water where an amorphous solid was obtained. It is also the most crystalline salt identified during the course of the experiment and displays the best solid state properties.

Further Characterization of Tosylate Polymorphs.

First, the free base form of Example 1 was characterized in order to investigate its solid form and chemical properties. Consistent with pervious batches, the material was amorphous, with a purity of ca. 97.6%. The material is not stable at elevated storage conditions (deliquesced at 25° C./97% RH and 40° C./75% RH). The $^1$H-NMR is generally consistent with the structure and does not show any significant amounts of residual solvent aside from water. The amount of water was quantified by KF as 2.3%.

Preparation and Characterization of Amorphous Bis Tosylate Salt.

Initial conversion to the amorphous state increases the likelihood of identifying metastable forms in addition to the most thermodynamically stable one. For this reason the amorphous bis tosylate was used for this experiment. Amorphous Example 1 was dissolved in DCM (1 g in 10 mL) at ambient conditions. The resulting solution was treated with p-toluenesulfonic acid monohydrate (4044 µL, 1M in THF, 2.1 eq) at ambient. The solution was fast evaporated on the rotary evaporator and the recovered solid was analyzed by XRPD. The first such procedure yielded a semicrystalline pattern different from Form 2, which was re-dissolved in DCM (10 mL), fast-evaporated and re-analyzed by XRPD and confirmed to be Form 2. A second procedure described below yielded Form 2. Amorphous Example 1 bis tosylate prepared as above was briefly characterized in order to investigate its solid form and chemical properties. XRPD analysis confirmed the material to be amorphous; $^1$H-NMR was consistent with structure and indicated 2 equivalents of tosylate counterion; KF analysis indicated only 2.0% w/w water; and HPLC analysis indicated 97.6% purity, consistent with the starting material.

Preparation and Characterization of Form 2 Bis Tosylate Salt.

Example 1 was dissolved in ACN (2 g in 20 mL) at ambient conditions. The resulting solution was stirred at 50° C. and treated with p-toluenesulfonic acid monohydrate (8088 µL, 1M in THF, 2.1 eq). After stirring for 1h at 50° C., the clear solution was cooled to −4° C. (0.1° C./min) and then remained at −4° C. overnight. The recovered solid (Form 2 Batch 1) was filtered under vacuum and air dried for 2h and dried in the oven (RT, vacuum) overnight.

A second batch, described above (Form 2 Batch 2), was recovered after attempting to make amorphous bis tosylate. A semicrystalline trace was initially observed by XRPD and DCM (20 vol) was added to try to dissolve it again. However, a suspension was formed. After 2 hours stirring at 40° C., it was filtered, dried in the oven (RT/vacuum).

Both batches were consistent with Form 2 by XRPD. Thermal analyzes showed an event corresponding to the loss of the water, followed by the melt of the sample at ca. 170° C. Both batches were also stable at elevated conditions for 1 week. These results correlate with Form 2 obtained during previous experiments. During the PLM analysis of the two batches, different morphologies were observed. Instead of the agglomerated particles observed to date, in the sample obtained by slurrying in DCM, needles were present. Although these were too small to analyze by single crystal, this indicates there could be a possibility of growing suitable crystals. Results are shown below in Table 21.

TABLE 21

| Technique | Form 2 Batch 1 | Form 2 Batch 2 |
|---|---|---|
| XRPD | Form 2 | Form 2 |
| 1H-NMR (DMSO-d6) | Consistent with structure + ca. 0.02 eq of CAN | Consistent with structure No residual solvent |
| KF | 1.2% water | 2.3% water |
| HPLC (Purity %, AUC) | 99.2 | 98.7 |
| TGA | 1.7% of weight loss between RT and 125° C. Degradation from 280° C. | 3.7% of weight loss between RT and 85° C. Degradation from 250° C. |
| DSC | Endotherm at 33.3° C. (58.2 J/g); Endotherm at 171.7° C. (22.8 J/g) | Endotherm at 33.7° C. (77.9 J/g); Endotherm at 174.3° C. (52.2 J/g) |
| Storage for 7 days @ 40° C./75% RH | n/a | Unchanged - Form 2 |
| Storage for 7 days @ 25° C./97% RH | n/a | Unchanged - Form 2 |
| PLM | Irregular shape particles up to 100 µm | Needle shape particles up to 75 µm |

Slurry Experiments.

Amorphous bis tosylate was suspended in the solvent system below (30 mg in 150l) at ambient conditions. The suspensions were shaken in the maturation chamber between ambient and 50° C. for 19 h (8 h cycles), then allowed to stand at ambient conditions for 10 min. An aliquot of the solid was air dried and analyzed by XRPD and then placed for 1 week at 40° C./75% RH and re-analyzed. If solutions were recovered, the solvents were allowed to evaporate at ambient conditions and the residues were initially analyzed by XRPD. Results are shown below in Table 22.

TABLE 22

| Ex. | Solvent | Appearance after 19 h | XRPD | XRPD after 7 days @ 40 C. 75 RH |
|---|---|---|---|---|
| P31 | n-Heptane | Suspension | Amorphous | Form 2 |
| P32 | Diethyl Ether | Suspension | Amorphous | Form 2 |
| P33 | Ethyl Acetate | Suspension | Form 2 | Form 2 |
| P34 | Isopropyl Acetate | Suspension | Form 2 | Form 2 |
| P35 | Methylisobutyl Ketone | Suspension | Crystalline Form 3 | Form 2 |
| P36 | 2-Propanol | Suspension | Form 2 | Form 2 |
| P37 | Methylethyl Ketone | Suspension | Crystalline Form 5 | Form 2 |
| P38 | Acetone | Suspension | Form 2 | Form 2 |
| P39 | Dimethyl Sulfoxide | Solution | Oil | n/a |
| P40 | Water | Suspension | Form 2 | Form 2 |
| P41 | tert-Butylmethyl Ether | Suspension | Amorphous | Form 2 |
| P42 | Cyclohexane | Suspension | Amorphous | Form 2 |
| P43 | 1,4-Dioxane | Suspension | Crystalline Form 4 | Form 2 |
| P44 | Toluene | Suspension | Semi-crystalline Form 3 | Form 2 |
| P45 | Chloroform | Solution | Form 2 | Form 2 |
| P46 | 1,2-Dimethoxyethane | Suspension | Form 2 | Form 2 |
| P47 | Tetrahydrofuran | Suspension | Semi-crystalline Form 3 | Form 2 |
| P48 | N,N-Dimethylformamide | Solution | Oil | n/a |
| P49 | Acetonitrile | Suspension | Form 2 | Form 2 |
| P50 | Nitromethane | Suspension | Form 2 | Form 2 |
| P51 | N-Methylpyrrolidone | Solution | Oil | n/a |
| P52 | Tetrahydrofuran:water 95:5 | Suspension | Form 2 | Form 2 |
| P53 | 2-Propanol:water 95:5 | Suspension | Form 2 | Form 2 |
| P54 | Acetone:water 95:5 | Suspension | Form 2 | Form 2 |

Solubility.

Crystalline bis tosylate Form 2 (30 mg) was treated with increasing volumes of solvent (n-Heptane, diethyl ether, ethyl acetate, isopropyl acetate, methylisobutyl ketone, 2-propanol, methylethyl ketone, acetone, dimethyl sulfoxide, water, tert-butylmethyl ether, cyclohexane, 1,4-dioxane, toluene, chloroform, 1,2-dimethoxyethane, tetrahydrofuran, N,N-dimethylformamide, acetonitrile, nitromethane, N-methylpyrrolidone, tetrahydrofuran:water 95:5, 2-propanol:water 95:5, or acetone:water 95:5 at 5, 10, 20, 30, 50, 70, or 100 vol total) until the material fully dissolved or until a maximum of 100 vol had been added. After each addition of solvent, the system was shaken gently for 10 minutes at 50° C. and then allowed to stand at ambient conditions for 5 minutes before the addition of a new aliquot of solvent. After the assessment was completed, any suspensions obtained were matured and clear solutions were cooled to 4° C. and held isothermally. Example 1 bis tosylate Form 2 remained a suspension up to in all solvents up to 100 vol except for dimethylsulfoxide and N,N-dimethylformamide, where it was a solution at 5 vol, and tetrahydrofuran:water 95:5, where it was a solution at 10 vol.

Maturation.

Suspensions obtained after the solubility assessment were shaken in the maturation chamber between ambient and 50° C. (8h cycles). After 4 days the solids were filtered and air dried. Solids obtained were initially analyzed by XRPD. Maturation in n-heptane, diethyl ether, ethyl acetate, isopropyl acetate, methylisobutyl ketone, 2-propanol, methylethyl ketone, acetone, tert-butylmethyl ether, cyclohexane, 1,4-dioxane, toluene, chloroform, 1,2-dimethoxyethane, tetrahydrofuran, acetonitrile, nitromethane, and 2-propanol:water 95:5 yielded filtered solids of Form 2.

Slow Evaporation and Cooling.

Supernatants from the maturation experiments and solutions from cooling were allowed to slowly evaporate at ambient conditions. The residues were analyzed by XRPD. Slow evaporation from the following supernatants yielded: dimethyl sulfoxide, oil; water, oil; N,N-dimethylformamide, gum; N-methylpyrrolidone, oil; tetrahydrofuran:water 95:5, gum; and acetone:water 95:5 gum. Solutions obtained after the solubility assessment were placed in a fridge (4° C.) for 2 days and in a freezer (−20° C.) for another 2 days. No solids were recovered. Slow evaporation from two batches of n-heptane solution yielded a gum in from one batch and Form 2 from the other.

Slurring at 4° C. or 60° C.

Crystalline bis tosylate Form 2 (30 mg) was suspended in a solvent system (10 vol, 300 µl). Suspensions were stirred at 4° C. or 60° C. over the weekend. XRPD characterization of the 4° C. experiments yielded Form 2 from ethyl acetate, 2-propanol, methylethyl ketone, tert-butylmethyl ether, N,N-dimethylformamide, acetonitrile, ethanol, and nitromethane, a gum for tetrahydrofuran:water 95:5, and a solution for N-methylpyrrolidone. XRPD characterization of the 60° C. experiments yielded Form 2 from ethyl acetate, 2-propanol, methylethyl ketone, tert-butylmethyl ether, acetone, 1,4-dioxane, acetonitrile, ethanol, nitromethane, and N-methylpyrrolidone.

Results.

The majority of samples isolated in the bis-tosylate polymorph experiments were consistent with Form 2. However, three crystalline solids (Form 3 (P35 from methylisobutyl ketone), Form 5 (P37 from methylethyl ketone), and Form 4 (P43 from 1,4-dioxane)) displayed some differences. These were analyzed by high resolution X-ray powder diffraction (HR-XRPD). Results are shown in FIG. #. Some extra peaks were noticed in Form 3 and Form 4. It was decided to characterize these two new patterns further by HPLC, $^1$H-NMR and DSC. Form 5 by high resolution was consistent with Form 2 however, when the initial diffractogram (high throughput (HT) red trace) is compared with the new one (high resolution) a change can be seen. Based on these findings the material was concluded to be a metastable form, which rapidly transformed to a more stable one, Form 2, by the time it was isolated and analyzed by HR-XRPD.

Amorphous samples were matured for a further 7 days but no improvement in crystallinity was observed. The semicrystalline solids were also matured longer but did not show any improvement in crystallinity after further 6 days cycling. As these (semicrystalline Form 3 from tetrahydrofuran (P44) and semicrystalline Form 3 from toluene (P47)) displayed some differences to Form 2 by XRPD they were further investigated by DSC, HPLC and $^1$H-NMR. All solids obtained were also stored for 7 days at 40° C. and 75% RH and re-analyzed by XRPD. Form 2 was the only form observed after this time.

Form 3.

Thermal analysis of the solid from Form 3 (P35) showed an endothermic event at 37.6° C. indicating that Form 3 may be a hydrate. A broad endotherm was also observed at 145.8° C. Analysis by VT-XRPD showed a change to something similar to Form 2 at 135° C. This correlates with the diffractogram (data not shown) seen after 7 days at 40° C./75% RH indicating Form 3 is a metastable form, which readily converts to Form 2 with heat and/or humidity.

Form 4.

$^1$H-NMR of Form 4 revealed two equivalents of 1,4-dioxane. This result correlates with the endotherm at ca. 70.4° C. observed in the DSC. After the desolvation, an endotherm at 169.3° C. was seen. This melt is the same as Form 2, indicating Form 4 transforms to Form 2 once the solvent is released. Due to the amount of material obtained TGA and KF analysis could not be performed on the sample. Re-analysis by XRPD after 7 days at 40° C./75% RH confirmed Form 4 is metastable form, which converts to Form 2 with heat and/or humidity. The HPLC purity of this form was also lower than the others.

Analytical and Instrumental Methods

X-Ray Powder Diffraction (XRPD).

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gibel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analyzed and presented using Diffrac Plus EVA v15.0.0.0.

Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at 20° C./min and subsequently held isothermally for 1 minute before data collection was initiated.

High-Resolution XRPD.

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analyzed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: angular range: 2 to 42° 2θ; step size: 0.05° 2θ; collection time: 0.5 s/step.

Nuclear Magnetic Resonance (NMR).

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2012 or 2014.

Differential Scanning Calorimetry (DSC).

TA Instruments Q2000: DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 300° C. A purge of dry nitrogen at 50 mL/min was maintained over the sample. Modulated temperature DSC was carried out using an underlying heating rate of 2° C./min and temperature modulation parameters of ±0.318° C. (amplitude) every 60 seconds (period). The instrument control software was Advantage for Q Series v2.8.0.394 and Thermal Advantage v5.5.3 and the data were analyzed using Universal Analysis v4.5A.

TA Instruments Discovery DSC: DSC data were collected on a TA Instruments Discovery DSC equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 260° C.-300° C. A purge of dry nitrogen at 50 mL/min was maintained over the sample. The instrument control and data analysis software was TRIOS v3.2.0.3877.

Thermo-Gravimetric Analysis (TGA).

TGA data were collected on a TA Instruments Discovery TGA, equipped with a 25 position auto-sampler. The instrument was temperature calibrated using certified alumel and nickel. Typically 5-10 mg of each sample was loaded onto a pre-tared aluminium DSC pan and heated at 10° C./min from ambient temperature to 350° C. A nitrogen purge at 25 mL/min was maintained over the sample. The instrument control and data analysis software was TRIOS v3.2.0.3877.

Polarised Light Microscopy (PLM).

Samples were studied on a Leica LM/DM polarised light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a X false-color filter.

Chemical Purity Determination by HPLC.

Purity analysis was performed on an Agilent HP1100 series system equipped with a diode array detector and using ChemStation software vB.04.03 using one of the methods detailed below:

| Parameter | Value | | |
|---|---|---|---|
| Type of method | Reverse phase with gradient elution | | |
| Sample Preparation | 0.5 mg/mL in acetonitrile:water 1:1 | | |
| Column | Supelco Ascentis Express C18, 100 × 4.6 mm, 2.7 µm | | |
| Column Temperature (° C.) | 25 | | |
| Injection (µL) | 5 | | |
| Wavelength, Bandwidth (nm) | 255, 90 | | |
| Flow Rate (mL/min) | 2 | | |
| Phase A | 0.1% TFA in water | | |
| Phase B | 0.085% TFA in acetonitrile | | |
| | Time (min) | % Phase A | % Phase B |
| Timetable | 0 | 95 | 5 |
| | 6 | 5 | 95 |
| | 6.2 | 95 | 5 |
| | 8 | 95 | 5 |

| Parameter | Value |
| --- | --- |
| Type of method | Reverse phase with gradient elution |
| Column | Phenomenex Luna, C18 (2) 5 µm 50 × 4.6 mm |
| Column Temperature (° C.) | Ambient |
| Standard Injections (µL) | 5 |
| Wavelength, Bandwidth (nm) | 260, 90 |
| Flow Rate (ml/min) | 1 |
| Phase A | 0.1% TFA in water |
| Phase B | 0.085% TFA in acetonitrile |

| | Time (min) | % Phase A | % Phase B |
| --- | --- | --- | --- |
| Timetable | 0.0 | 95 | 5 |
| | 5.0 | 95 | 5 |
| | 12.0 | 75 | 25 |
| | 20.0 | 75 | 25 |
| | 30.0 | 40 | 60 |
| | 35.0 | 40 | 60 |
| | 40.0 | 5 | 95 |
| | 40.1 | 95 | 5 |
| | 45.1 | 95 | 5 |

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

Gravimetric Vapour Sorption (GVS).

Sorption isotherms were obtained using a SMS DVS Intrinsic moisture sorption analyzer, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 mL/min The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

| Parameter | Value |
| --- | --- |
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

Aqueous Solubility.

Aqueous solubility was determined by suspending sufficient compound in water to give a maximum final concentration of ≥10 mg/ml of the parent free-form of the compound. The suspension was equilibrated at 25° C. for 24 hours then the pH was measured. The suspension was then filtered through a glass fibre C filter. The filtrate was then diluted by an appropriate factor. Quantitation was by HPLC with reference to a standard solution of approximately 0.2 mg/ml in DMSO. Different volumes of the standard, diluted and undiluted sample solutions were injected. The solubility was calculated using the peak areas determined by integration of the peak found at the same retention time as the principal peak in the standard injection.

| Parameter | Value |
| --- | --- |
| Type of method | Reverse phase with gradient elution |
| Column | Phenomenex Luna, C18 (2) 5 µm 50 × 4.6 mm |
| Column Temperature (° C.) | 25 |
| Standard Injections (µL) | 1, 2, 3, 5, 7, 10 |
| Test Injections (µL) | 1, 2, 3, 10, 15, 20 |
| Detection: Wavelength, Bandwidth (nm) | 260, 90 |
| Flow Rate (ml/min) | 2 |
| Phase A | 0.1% TFA in water |
| Phase B | 0.085% TFA in acetonitrile |

| | Time (min) | % Phase A | % Phase B |
| --- | --- | --- | --- |
| Timetable | 0 | 95 | 5 |
| | 1 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.04.03.

Ion Chromatography (IC).

Data were collected on a Metrohm 930 Compact IC Flex with 858 Professional autosampler and 800 Dosimo dosage unit monitor, using IC MagicNet software v3.1. Accurately weighed samples were prepared as stock solutions in an appropriate dissolving solution and diluted appropriately prior to testing. Quantification was achieved by comparison with standard solutions of known concentration of the ion being analyzed.

| Type of method | Anion exchange | Cation exchange |
| --- | --- | --- |
| Column | Metrosep A Supp 5-150 (4.0 × 150 mm) | Metrosep C 4 - 250 (4.0 × 250 mm) |
| Column Temperature (° C.) | Ambient | Ambient |
| Injection (µL) | Various | Various |
| Detection | Conductivity detector | Conductivity detector |
| Flow Rate (ml/min) | 0.7 | 0.9 |
| Eluent | 3.2 mM sodium carbonate, 1.0 mM sodium hydrogen carbonate in a 5% acetone aqueous solution. | 1.7 mM Nitric Acid 0.7 mM Dipicolinic acid in a 5% acetone aqueous solution. |

Maturation/Slurry Ripening.

Suspensions for maturation are placed in a platform shaker incubator (Heidolph Titramax/Inkubator 1000) and subjected to a series of heat-cool cycles under shaking from ambient to 50° C. (8 hour cycles: heating to 50° C. for 4 hours and then the heating is switched off and the sample gradually cools to ambient conditions for a further 4 hours).

Water Determination by Karl Fischer Titration (KF).

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made. Data collection and analysis using Tiamo v2.2.

Biological Activity

The activity of the Examples above may be illustrated in the following assays. Compounds listed above, which may not yet have been made and/or tested, are predicted to have activity in these assays.

Assaying the inhibition of KDM1A can be determined in vitro, in cultured cells, and in animals. There are a variety of spectrophotometric methods to detect the results of demethylation of methylated lysines, viz., detecting the products of KDM1A demethylase oxidative activity on a peptide fragment of at least 18 amino acid representing the N-terminus of the histone H3 substrate that contains a monomethyl at the fourth lysine residue. Hydrogen peroxide, one product of the KDM1A demethylase reaction, reacts with horseradish peroxidase and dihydroxyphenoxazine (ADHP) to produce the fluorescent compound resorufin (excitation=530-560 nm:emission=590 nm). The KDM1A demethylase enzyme activity can obtained from mammalian cells or tissues expressing KDM1A from an endogenous or recombinant gene and purified or assayed from a whole cell extract. These methods can be used to determine the concentration of the disclosed compounds can inhibit fifty percent of the enzyme activity ($IC_{50}$). In one aspect, the disclosed compounds exhibit inhibition fifty percent of the KDM1A enzyme activity at a concentration of less than 500 nM, less than 100 nM, less than 50 nM or less than 10 nM.

The association of KDM1A with other proteins can be determined by a variety of both in vitro and in vivo methods known to one skilled in the art. For example, the disruption of KDM1A with associated proteins can be determined in an electromobility shift assay (EMSA). In various aspects, the disruption of the physical association of KDM1A with CoRest by the disclosed compounds can be observed using EMSA. In another example, the disruption of KDM1A with associated proteins can be determined by immunoprecipitation followed by separation of the co-precipitated proteins by mass spectroscopy or by get electrophoresis. In another example, the disruption of KDM1A association with CoRest can be determined by the ability of KDM1A to act on a nucleosomal substrate containing K4 or K9 methylated histone H3, a substrate that requires the presence of both KDM1A and CoRest. The disclosed compounds could be used to assay inhibition of CoRest association with KDM1A using nucleosomal substrate; such compounds may not inhibit KDM1A enzymatic activity as determined by the use of the histone H3 K4 methylated peptide substrate.

The inhibition of KDM1A can be determined in a cell-based assay. For example, KDM1A is an essential enzyme and prolonged inhibition of KDM1A will result in cell death, thus cell growth inhibition, arrest of cell growth or cell death can be assayed. In another aspect, genes induced by androgens and estrogens require KDM1A activity; inhibition by the disclosed compounds of KDM1A will abrogate the induction of gene expression in cells treated with androgens or estrogens. These effects can be measured, e.g., using quantitative PCR of mRNA to measure the magnitude of gene expression for androgen- and estrogen-dependent genes. KDM1A activity is required for the repression of transcription of specific genes. Inhibition of KDM1A by the disclosed compounds could de-repress the expression such genes in cell. These genes include Meis1, VEG-A, AIM1, HMOX1, VIM, SKAP1, BMP, EOMES, FOXA2, HNF4, SOX17, GH, PSA, pS2, GREB1, GR-1b, PRL, TSHB, SYN1, HBG, SCN1A, SCN2a, and SCN3A the expression of which can be assayed using quantitative PCR of mRNA before and at various time following the treatment of cells with the disclosed compounds. In another aspect, KDM1A is a regulator of leukemic stem cell potential and is required for oncogenic transformation of myeloid cells to acute myeloid leukemia (AML) by MLL-AF9. Inhibition of KDM1A in MLL-AF9-transformed cells grown in culture overcomes the arrest in differentiation to resulting in a more mature cell expressing the CD11b surface antigen, a monocytic cell antigen. Thus, inhibition of KDM1A can be assayed using an AML cell line such as THP-1 grown in culture quantifying the proportion of cells newly expressing the CD11b antigen using fluorescence activated cell sorting (FACS). A similar assay using FACS to count cells displaying the CD14 or CD86 can be also used, each of which are characteristic of more mature cells along the macrophage/monocytic lineage. Other cells lines derived from patients with acute myeloid leukemia such as MV4;11 or MOLM-13 cells can be used for this assay. Other markers of differentiation along the macrophage/monocyte lineage can be similarly assayed by FACS such as CD14 and CD86. Other AML cell lines such as MPLM-13 or MV4;11 can be assayed for the induction of either specific genes mentioned above or the differentiation markers as well as cell growth or apoptosis by Annexin V staining and FACS enumeration.

The selectivity of the disclosed compounds for KDM1A can be determined by assaying the $IC_{50}$ of the disclosed compounds for other FAD-dependent aminoxidases such as monoamine oxidase A (MAO-A), monoamine oxidase B (MAO-B), IL4I1, KDM1B, or SMOX. As such, a disclosed compound would inhibit KDM1A with an $IC_{50}$ that is 50-fold, or 100-fold or 250-fold or 500-fold less than for MAO-A or MAO-B.

Additional Demethylase Assays

The histone demethylase assay can be performed essentially as described in Shi, Y et al. Cell 199, 941-953 (2004). Briefly, bulk histones, histone peptides or nucleosomes are incubated with purified human recombinant KDM1A, in the histone demethylase activity (HDM) assay buffer 1 (50 mM Tris pH 8.5, 50 mM KCl, 5 mM MgCl, 0.5% BSA, and 5% glycerol) from 30 minutes to 4 hours at 37° C. A typical reaction is conducted in 100 microliters in which either 20 micrograms of purified bulk histones or 3 micrograms of modified histone peptides are used as substrates. Different amounts of KDM1A ranging from 1-20 micrograms are used in the reaction along with, as necessary, other co-factors such as FAD or CoREST, depending on the chosen substrate. The reaction mixture is analyzed by SDS-PAGE and Western blotting using histone methyl-specific antibodies or by formaldehyde formation assay to examine the removal and conversion of the methyl group to formaldehyde, or by mass spectrometry in the case of peptide substrates to identify the demethylated histone peptide.

Bulk histones (e.g., 4 mg) are incubated with the indicated amounts of recombinant proteins or complexes in histone demethylase (HDM) assay buffer A (50 mM Tris pH8.5, 50 mM KCl, 5 mM MgCl, 5% glycerol, 0.2 mM phenylmethylsulphonyl fluoride and 1 mM dithiothreitol) in a final volume of 10 ml for 12-16 h at 37 8 C. For nucleosomes (0.3 mg) or mononucleosome (0.3 mg), HDM buffer A containing 0.1% NP40 can be used. The reaction mixture can then be analyzed by SDS-PAGE followed by Western blotting. Antibodies against mono- or di-methyl K4 in histone H3 and acetyl-K9/K14 of histone H3 are used to detect the degree of methylation and acetylation, respectively. Western blots are then quantified by densitometry or by intensity of luminescence.

Alternatively, a standard flurogenic assay can be used in which the methylated histone substrate is tethered to the bottom of a 96 well plate (or to beads resting in the plate) using biotin conjugated to the histone methylated substrate and strepavidin (SA) on beads or SA attached to the plate to secure the biotinylated substrate. After incubation of the KDM1A enzyme in histone demethylase buffer A, the demethylated histone substrate can be detected using antibodies specific for demethylated H3K4 substrate conjugated to a fluor or some other agent that can be detected. A variation on that assay method would employ an antibody directed against the methylated version of the histone in which the amount of substrate is quantified before and after incubation with the enzyme. Yet another version of a similar assay would employ a fluorescence resonance energy transfer (FRET) system of detection in which the antibody recognizing the methylated version is conjugated or otherwise linked to an entity, e.g., a bead or a large carrier molecule on which a fluorophore (donor) is attached and the fluorophore (acceptor) is bound to an entity linked to the substrate.

Alternatively, the production of $H_2O_2$ during the KDM1A reaction can be detected fluometrically. In this system, the production of $H_2O_2$ is detected in the HDM assay buffer after exposure to substrate, co-factor and enzyme using ADHP (10-Acetyl-3, 7-dihydroxyphenoxazine) as a fluorogenic substrate for horse radish peroxidase (HRP). ADHP (also known as Amplex Red Reagent) is the most stable and sensitive fluorogenic substrate for HRP. The florescent product is resorufin. Sensitivity can be as low as $10^{-15}$ M of target protein. The signal is read using a fluorescence microplate reader at excitation and emission wavelengths of 530-560 nm and 590 nm, respectively.

Additionally, the KDM1A reaction can include other factors which may influence the activity of KDM1A. Such factors might include CoREST, NuRD complexes, DNMT1, HDAC1, HDAC2, and HDAC3, for example, as proteins known to associate with KDM1A or KDM1A-containing complexes. Interactions that influence any aspect of the KDM1A activity including specificity for template, substrate, $K_m$, $K_{cat}$, or sensitivity to FAD concentrations can be assayed. For example, an in vitro interaction assay between KDM1A and CoREST can be performed adding recombinant KDM1A (e.g., 10 mg) and CoREST (e.g., 5 mg) mixed and incubated for 1 h at 4-8° C., fractionated by Superdex 200 gel filtration column in a buffer containing 20 mM Tris-HCl pH 7.9, 500 mM KCl, 10% glycerol, 0.2 mM EDTA, 1 mM dithiothreitol, 0.1% Nonidet P40 and 0.2 mM phenylmethylsulphonyl fluoride, and then analyzed by silver staining.

For co-immunoprecipitation of mononucleosomes with KDM1A and CoREST, nucleosomes (1.5 mg) can be digested with micrococcal nuclease and incubated with recombinant KDM1A (e.g., 1 mg), CoREST (e.g., 500 ng) or both proteins in HDM buffer A containing 0.1% NP40 for 1 h at 4-8° C. Antibodies directed against KDM1A or CoREST attached to an affinity resin are added and after extensive washing with HDM buffer A containing 0.1% NP40, the bound proteins are eluted with a wash buffer. KDM1A activity can be assayed in the eluate or the concentration of KDM1A can be determined by quantitative Western blotting.

Compounds were tested in a 10-dose $IC_{50}$ mode fluorescence coupling enzyme assay with 3-fold serial dilution in duplicate starting at 100 µM. The production of FAD-dependent $H_2O_2$ as a result of demethylase activity of LSD1 on 10 µM histone H3(1-21)K4me2 peptide substrate was measured by coupling with HRP and Amplex Red to yield resorufin (fluorescence measured at Ex/Em=535/590 nm on EnVision, Perkin Elmer). Results are given below in Table 1.

TABLE 2

Biological Activity

| Example | KDM1A $IC_{50}$ |
|---|---|
| 1 | 28 |
| 2 | 13 |
| 3 | 37 |
| 4 | 12 |
| 5 | 5 |
| 6 | 22 |
| 7 | 5 |
| 8 | 5 |
| 9 | 6 |
| 10 | 34 |
| 11 | 129 |
| 12 | 17 |
| 13 | 6 |
| 14 | 27 |
| 15 | 50 |
| 16 | 98 |
| 17 | 13 |
| 18 | 10 |
| 19 | 3 |
| 20 | 5 |
| 21 | 45 |
| 22 | |
| 23 | 5 |
| 24 | 19 |
| 25 | 22 |
| 26 | 11 |
| 27 | 65 |
| 28 | 24 |
| 29 | 20 |
| 30 | 4 |
| 31 | 13 |
| 32 | 8 |
| 33 | 2 |
| 34 | ND |
| 35 | 3 |
| 36 | 9 |
| 37 | ND |
| 38 | 8 |
| 41 | 11 |
| 42 | 18 |
| 43 | 20 |
| 44 | 10 |
| 45 | 20 |
| 46 | 13 |
| 47 | 13 |
| 48 | 11 |
| 49 | 3 |
| 50 | 23 |
| 51 | 4 |
| 52 | 14 |
| 53 | 50 |
| 54 | 20 |
| 55 | 9 |
| 56 | 35 |
| 57 | 10 |
| 58 | 10 |
| 59 | 17 |
| 60 | ND |
| 61 | 7 |

TABLE 2-continued

Biological Activity

| Example | KDM1A IC$_{50}$ |
|---|---|
| 62 | 52 |
| 63 | 112 |
| 64 | 38 |
| 65 | 27 |
| 66 | 24 |
| 67 | 14 |
| 68 | 21 |
| 69 | 34 |
| 70 | 10 |
| 71 | ND |
| 72 | 19 |
| 73 | 11 |
| 74 | 226 |
| 75 | 4 |
| 76 | 20 |
| 77 | 10 |
| 78 | 22 |
| 79 | 18 |
| 80 | 56 |
| 81 | 50 |
| 82 | 17 |
| 83 | 28 |
| 84 | 15 |
| 85 | 8 |
| 86 | 7 |
| 89 | 5 |
| 90 | 6 |
| 91 | 210 |
| 92 | 4 |
| 93 | 19 |
| 94 | 12 |
| 95 | 18 |
| 96 | 8 |
| 97 | 5 |
| 98 | 20 |
| 99 | 12 |
| 100 | 13 |
| 101 | 19 |
| 102 | 170 |
| 103 | ND |
| 104 | 9 |
| 105 | 13 |
| 106 | 10 |
| 107 | 5 |
| 108 | 5 |
| 109 | >1000 |
| 110 | 45 |
| 111 | 16 |
| 112 | ND |
| 113 | 23 |
| 114 | ND |
| 115 | 7 |
| 116 | ND |
| 117 | 20 |
| 118 | 13 |
| 119 | 16 |
| 120 | 7 |
| 121 | 10 |
| 122 | 14 |
| 123 | 6 |
| 124 | 8 |
| 125 | 34 |
| 126 | 482 |
| 127 | ND |
| 128 | 2 |
| 129 | 51 |
| 130 | 11 |
| 131 | 40 |
| 132 | 173 |
| 133 | 47 |
| 134 | 14 |
| 135 | 10 |
| 136 | ND |
| 137 | ND |
| 138 | ND |
| 139 | ND |
| 140 | ND |
| 141 | 6 |
| 142 | 108 |
| 143 | 58 |
| 144 | 28 |
| 145 | 114 |
| 146 | 7 |
| 147 | 1 |
| 148 | 5 |
| 149 | 23 |
| 150 | 24 |
| 151 | 11 |
| 152 | 3 |
| 153 | 13 |
| 154 | ND |
| 155 | 127 |
| 156 | 14 |
| 157 | 10 |
| 158 | 10 |
| 159 | 3 |
| 160 | 4 |
| 161 | 46 |
| 162 | 6 |
| 163 | 35 |
| 164 | 10 |
| 165 | 157 |
| 166 | 14 |
| 167 | 11 |
| 168 | 11 |
| 169 | 64 |
| 170 | 65 |
| 171 | 4 |
| 172 | 5 |
| 173 | 5 |
| 174 | 3 |
| 175 | 10 |
| 176 | 3 |
| 177 | 2 |
| 178 | 0.8 |
| 179 | ND |
| 180 | 2 |
| 181 | 4 |
| 182 | 27 |
| 183 | 10 |
| 184 | 18 |
| 185 | >1000 |
| 186 | 9 |
| 187 | 4 |
| 188 | 42 |

Ex Vivo Differentiation of Purified Human CD34$^+$ Cells into the Erythroid Lineage Human CD34+ cells isolated from the venous blood of healthy donors after mobilization by granulocyte colony stimulating factor (G-CSF) are grown and differentiated ex vivo for a 14 day incubation using a two-phase culture method described in Cui, S., et al. Mol Cell Biol 31, 3298-3311 (2011). Cells are counted using a hemocytometer and viability determined by trypan blue exclusion. Test article (candidate compounds) dissolved in an appropriate solvent compatible with physiologic conditions is added daily to fresh culture medium beginning on Day 4 through Day 14 at a range of test concentrations. Cell morphology and stage of differentiation is determined by Wright-Giemsa staining.

Flow Cytometry to Determine Differentiation Surface Markers and HbF Content

Cultured erythroid cells are stained with phycoerythrin (PE)-Cy7-conjugated anti-CD34, PE-conjugated anti-CD71, and PECy5-conjugated anti-glycophorin A antibodies. To determine the concentration of cytoplasmic HbF, cells are fixed in 0.05% glutaraldehyde for 10 minutes, permeabilized with 0.1% Triton X-100 for 5 minutes and stained with allophycocyanin-conjugated anti-HbF antibody. Stained cells are sorted and counted using a FACS analyzer.

Western Blots to Determine Presence and Concentration of KDM1A and Histone H3 and H3 Modifications.

Cells are lysed in Laemmli sample buffer and subjected to SDS-PAGE. Proteins are transferred from the gel to nitrocellulose and probed with antibodies against KDM1A, and/or histone H3, mono-methyl (H3K4me1) and/or dimethyl histone H3K4 (H3K4me2) and then probed with fluorescence-conjugated secondary antibodies. Proteins concentrations are quantified with an imaging system.

Chromatin Immunoprecipitation (ChIP) Assays to Determine Protein Occupancy at Genome-Specific Sites.

ChIP assays are carried out in an immunoprecipitation (IP) buffer with or without SDS depending on the sensitivity of the KDM1A antibody to SDS. Briefly, typically 3×107 cells are used per KMD1A ChIP and 3×106 cells per H3K4me2 ChIP. After 10 minutes of 0.75% formaldehyde treatment, cells are harvested and sonicated in the ChIP lysis buffer (1% Triton X-100, 10 mM EDTA, 50 mM Tris-HCl and protease inhibitors) to produce soluble chromatin with average sizes between 300 and 1000 bp. The chromatin samples are then diluted 10-fold in the dilution buffer (5 mM EDTA, 25 mM Tris-HCl, 167 mM NaCl, and cocktails of protease inhibitors) and pre-cleaned for 1 hour using salmon sperm DNA/protein-A agarose beads. Ten micrograms of rabbit anti-KDM1A antibody, 3 microliters of anti-H3K4me2 or control antibodies are then added to each sample and incubated overnight at 4° C. To collect the immunocomplexes, 40 microliters of salmon sperm DNA/protein-A agarose beads are added to the samples for 1 hour at 4° C. The beads are washed three times in wash buffer (0.1% Triton X-100, 5 mM EDTA, 30 mM Tris-HCl, 150 mM NaCl and the washed once in wash buffer 2 (1% Triton X-100, 5 mM EDTA, 30 mM Tris-HCl, 150 mM NaCl). The bound protein-DNA complexes are eluted with 100 microliters of elution buffer (1% SDS, 0.1 M $NaHCO_3$, 250 mM NaCl, and 0.2 micrograms protease K) and de-cross-linked at 65° C. for 4 hr. The de-crosslinked chromatin DNA is further purified by QIAquick polymerase chain reaction (PCR) Purification Kit (Qiagen) and eluted in 100 microliters of TE buffer. Four microliters of eluted DNA sample is used for each PCR reaction. Thirty-six PCR cycles can be used for KDM1A ChIP and 32 PCR cycles for H3K4mme2 ChIP. Appropriate primers for loci of interest, e.g., the gamma globin gene, are used.

For globin-specific ChIP analysis, the assays are performed as described in Cui, S., et al. Mol Cell Biol 31, 3298-3311 (2011). For example, ethylene glycol bis(succinimidyl succinate) or formaldehyde can be used as a cross-linker. Antibodies against target proteins such as KDM1A and histone H3 with or without methyl modifications can be used for immunoprecipitation. DNA contained in the immunoprecipitate can be quantified by real-time quantitative PCR (RT-qPCR) assay using primer for human embryonic, gamma, and adult beta-globin promoter sequences; primers for intergenic regions between the embryonic and gammaG-globin genes can be used as a negative control.

Hemoglobin Analysis by HPLC

Cells are lysed and can be analyzed for hemoglobin composition using the Bio-Rad Variant II Hemoglobin Testing System equipped with an ion-exchange HPLC column (Hercules).

Mouse Models for Testing Induction of Gamma Globin Gene Expression

Test article can be dissolved in a physiologically compatible solvent for injection into normal mice or mice transgenic for the yeast artificial chromosome (YAC) containing the entirety of the human beta-globin locus as described in Tanabe, O., et al. EMBO J 26, 2295-2306 (2007) or portions of the human beta-globin locus. Test article can be administered daily intraperitoneally or subcutaneously or by gavage at appropriate test doses for up to 26 weeks. At intervals, peripheral whole blood and bone marrow cells are harvested to determine gene expression by RT-qPCR of the mouse embryonic beta-like globin genes or the beta-like globin composition of red cell lysates or in the case transgenic mice carrying human beta-like globin genes both the human and mouse fetal γ- and adult β-globin genes.

Testing for Induction of Human Gamma Globin Gene Expression or HbF.

Patients with hemoglobinopathies including sickle cell disease and beta-thalassemia might benefit from treatment with an inhibitor of KDM1A. After appropriate dosing, the measure of HbF can be determined as described above. Gamma globin gene expression can be assayed in bone marrow cells using qPCR. Further, the clinical benefit of an agent inducing HbF can be measured as an increase in total hemoglobin, a reduction in sickle cell crises, a decrease in transfusion dependence, a decrease in ineffective hematopoiesis, and decrease in inflammatory biomarkers such as plasma levels of GDF15, etc.

Pharmacokinetics

The pharmacokinetic properties of the Examples above, including absorption, distribution, metabolism, and excretion, may be illustrated in the following assays. Compounds listed above, which may not yet have been made and/or tested, are predicted to have activity in these assays.

Metabolic Stability in Human and Murine Liver Microsomes

The metabolic stability of compounds disclosed herein in pooled human liver microsomes (HLM) and pooled male mouse liver microsomes (MMLM) may be determined according to the following protocol, in which the concentrations of compounds in reaction systems were evaluated by LC/MS/MS for estimating the stability in liver microsomes.

Study Design

Pooled human liver microsomes (HMMCPL; PL050B) and pooled male mouse liver microsomes (MSMCPL; MS033) are purchased from CellzDirect (Invitrogen). Microsomes are stored at −80 C prior to use.

A master solution is prepared containing microsome (stock concentration 5 mg/mL, volume 50 μL, final concentration 0.5 mg/mL), $MgCl_2$ solution (stock concentration 50 mM, volume 50 μL, final concentration 5 mM), phosphate buffer (stock concentration 200 mM, volume 250 μL, final concentration 100 mM), and water (volume 95 μL. Five μL of 200 μM test compounds or control solution (control compound: verapamil) are then added. The final concentration of test compounds or verapamil in the reaction system is 2 μM. The mixture is pre-warmed at 37 C for 5 min.

The reaction is started with the addition of 50 μL of 10 mM NADPH solution at the final concentration of 1 mM and carried out at 37 C. 50 μL of ultra-pure $H_2O$ is used instead of NADPH solution in the negative control.

Aliquots of 50 μL are taken from the reaction solution at 0 and 30 min. The reaction is stopped by the addition of 3 volumes of cold methanol with IS (200 nM imipramine, 200 nM labetalol and 2 μM ketoprofen) at the designated time points. Samples are centrifuged at 16,000 g for 10 minutes to precipitate protein. Aliquot of 100 μL of the supernatant is diluted by 100 μL ultra-pure $H_2O$, and the mixture is used for LC/MS/MS analysis. All experiments may be performed in duplicate.

Bioanalytical Method

Samples are analyzed using liquid chromatography-mass spectrometry. An LC system may comprise, for example, a Shimadzu liquid chromatograph separation system equipped with degasser DGU-20A3, solvent delivery unit LC-20AD, system controller CBM-20A, column oven CTO-10ASVP and CTC Analytics HTC PAL System. Chromatographic conditions may include a Phenomenex column, 5.0 t C18 (2.0×50 mm); a mobile phase of 0.1% formic acid in acetonitrile and 0.1% formic acid in water; an elution rate of 500 μL/min; column temperature 25 C; injection volume 10 μL. Mass spectrometric analysis is performed using an API 4000 instrument from AB Inc. (Canada) with an ESI interface. Data acquisition and control system are created using, e.g., Analyst 1.5.1 software from ABI Inc. A turbo spray ion source and electrospray ionization are employed in a multiple reaction monitoring (MRM) scan. Additional parameters include: collision gas, 6 L/min; curtain gas, 30 L/min; nebulize gas, 50 L/min; auxiliary gas, 50 L/min; temperature, 500 C; ionspray voltage, +5500 v (positive MRM). Quadripoles Q1 and Q3 are set to 456.2 and 200.2, respectively; declustering potential (DP), entrance potential (EP), and collision cell entrance potential (CE) are set to 120, 10, and 55 v, respectively; collision cell exit potential (CXP) is 12 v.

Analysis

All calculations may be carried out using Microsoft Excel. Peak areas are determined from extracted ion chromatograms. The control compounds are included in the assay. Any value of the compounds that is not within the specified limits is rejected and the experiment is repeated. The reaction system without the cofactors is used to exclude any misleading factor that results from instability of chemical itself.

Results

In pharmaceutical and medicinal chemistry, it is often desirable to have potent compounds with properties lending suitability to drug development, such as solubility, stability, and reliability of synthesis. For example, compounds comprising a moiety —$(CH_2)_m$—Y—$(CH_2)_n$—Z— resulting in —$(CH_2)_3$—$NR^{4b}$— have shown to be amenable to synthesis with few undesired by products and/or relatively good stability. Additionally, as disclosed in the table above, compounds wherein $R^3$ is aryl substituted with heteroaryl, cyano, or —$S(O)_2N(CH_3)_2$ (called $R^6$ or $R^{6a}$) have in general demonstrated good potency.

Compositions

The following are examples of compositions which may be used to deliver compounds disclosed herein. These may be encapsulated or wet granulated using methods known in the art.

Composition Example 1

| Ingredients | Concentration (w/w %) |
|---|---|
| Compound of Formula I | 30% |
| Lactose | 68% |
| Magnesium Stearate | 2% |

Composition Example 2

| Ingredients | Concentration (w/w %) |
|---|---|
| Compound of Formula I | 50% |
| Lactose | 48% |
| Magnesium Stearate | 2% |

From the foregoing description, one skilled in the art can easily ascertain the essential characteristics of this invention, and without departing from the spirit and scope thereof, can make various changes and modifications of the invention to adapt it to various usages and conditions.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinence of the cited references.

What is claimed is:

1. A compound of Formula V:

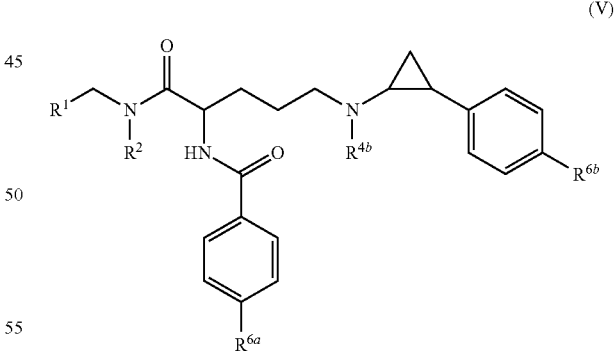

or a salt thereof, wherein:

$R^1$ and $R^2$ are each independently chosen from alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;

$R^{4b}$ is hydrogen;

$R^{6a}$ is chosen from heteroaryl, cyano, and $S(O)_2N(CH_3)_2$;

each $R^6$ and $R^{6b}$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^7$, $SO_2R^7$, $NHSO_2R^7$, $NHSO_2NHR^7$, $NHCOR^7$, $NHCONHR^7$, $CONHR^7$, and $CONR^7R^8$; and $R^7$ and $R^8$ are independently chosen from hydrogen, aryl, and lower alkyl; or $R^7$ and $R^8$ may be taken together to form a nitrogen-containing heterocycloalkyl or heteroaryl ring, which may be optionally substituted with lower alkyl.

2. The compound as recited in claim 1, wherein $R^{6a}$ is chosen from cyano,

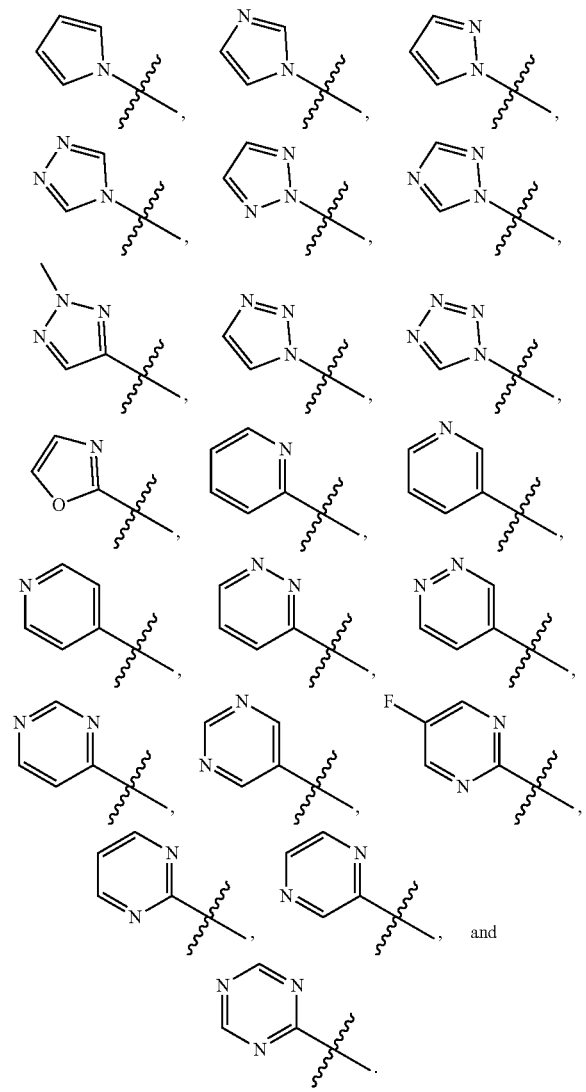

3. The compound as recited in claim 1, wherein $R^1$ and $R^2$ are each independently chosen from alkyl, aminoalkyl, alkylsulfonylalkyl, alkoxyalkyl, and heteroaryl, and $R^1$ and $R^2$, together with the nitrogen to which they attach, form a nitrogen-containing heterocycloalkyl or heteroaryl ring, which may be optionally substituted with between 0 and 3 $R^6$ groups.

4. The compound as recited in claim 2, wherein the nitrogen-containing heterocycloalkyl or heteroaryl ring formed by $R^1$ and $R^2$ together with the nitrogen to which they are attached contains 3 to eight atoms.

5. The compound as recited in claim 3, wherein $R^1$ and $R^2$ are taken together to form a nitrogen-containing heterocycloalkyl, which may be optionally substituted with between 0 and 3 $R^6$ groups.

6. The compound as recited in claim 4, wherein the nitrogen-containing heterocycloalkyl is chosen from:

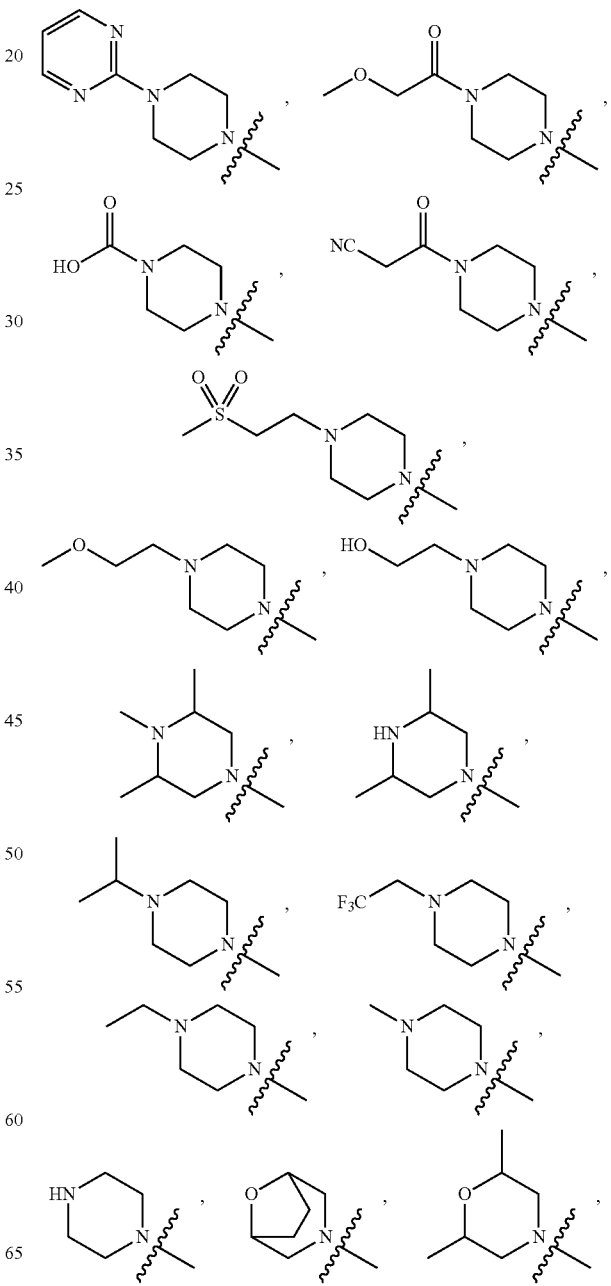

-continued
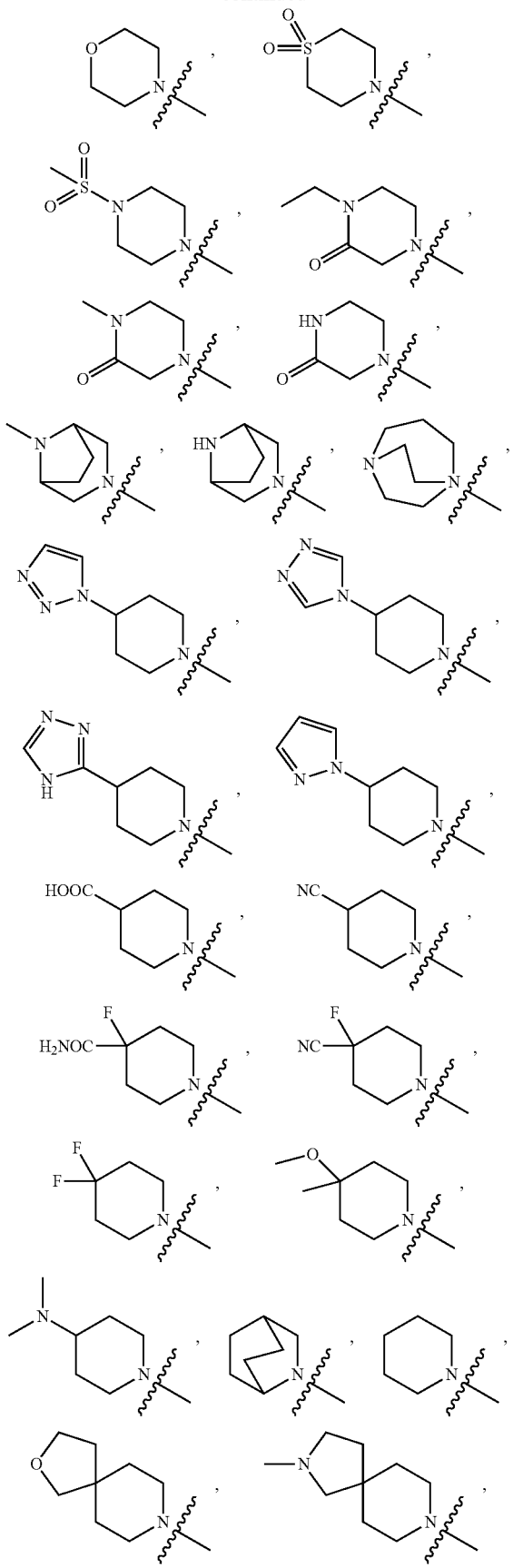
-continued
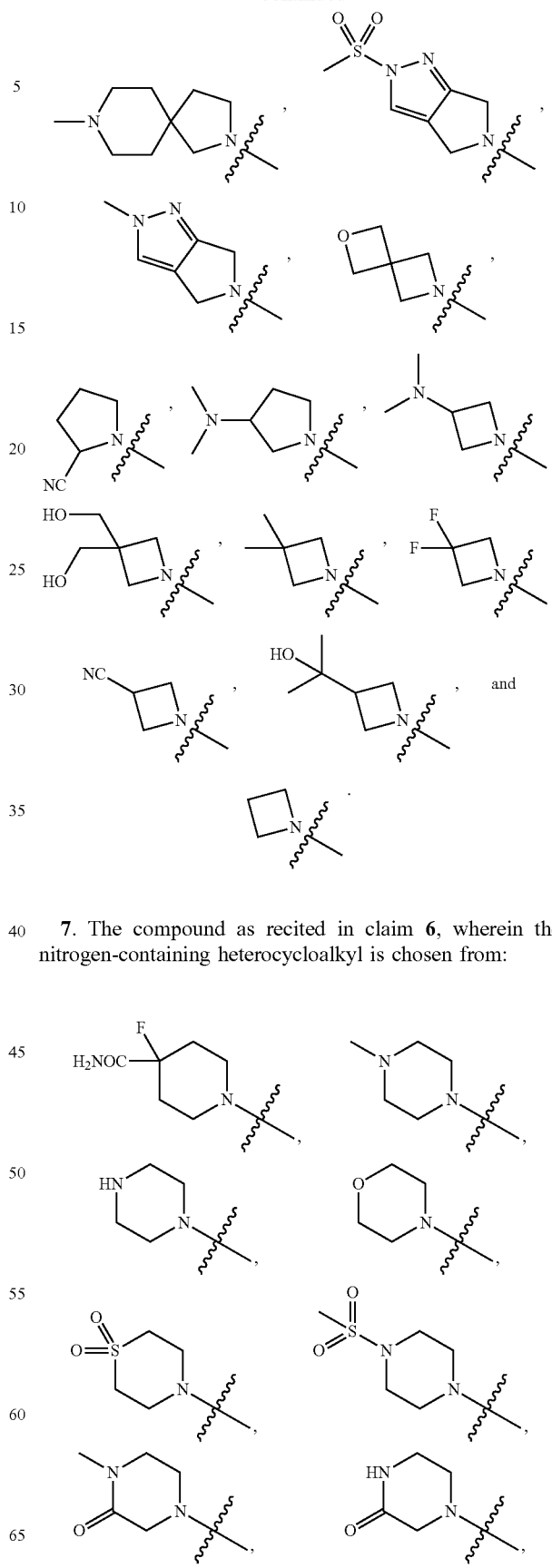
7. The compound as recited in claim 6, wherein the nitrogen-containing heterocycloalkyl is chosen from:

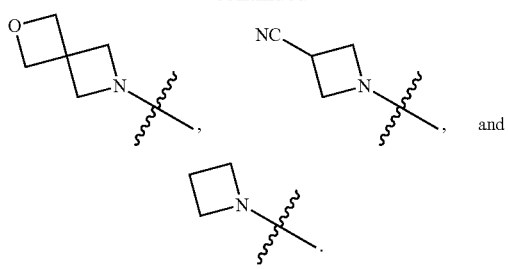
8. The compound as recited in claim 7, wherein the nitrogen-containing heterocycloalkyl is:
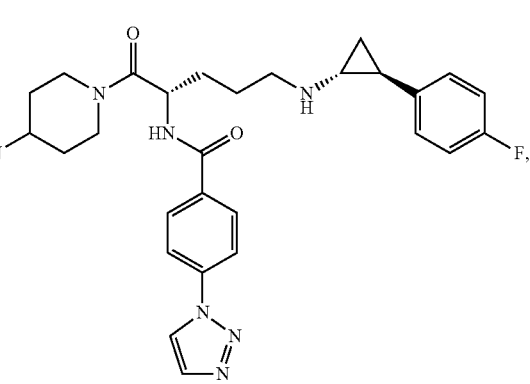
9. The compound as recited in claim 7, wherein $R^{6b}$ is chosen from fluoro and methoxy.
10. The compound as recited in claim 8, wherein $R^{6b}$ is fluoro.
11. The compound as recited in claim 1, chosen from:
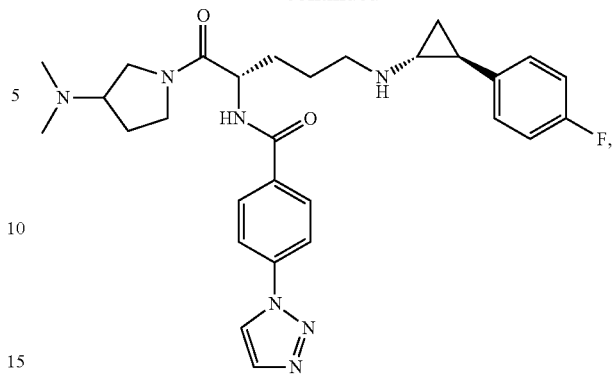

377
-continued
378
-continued
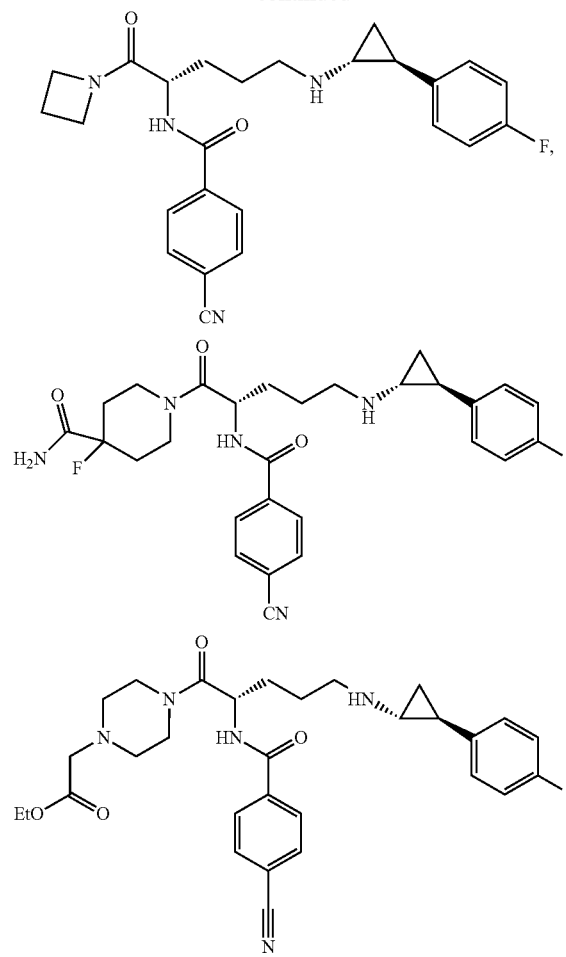
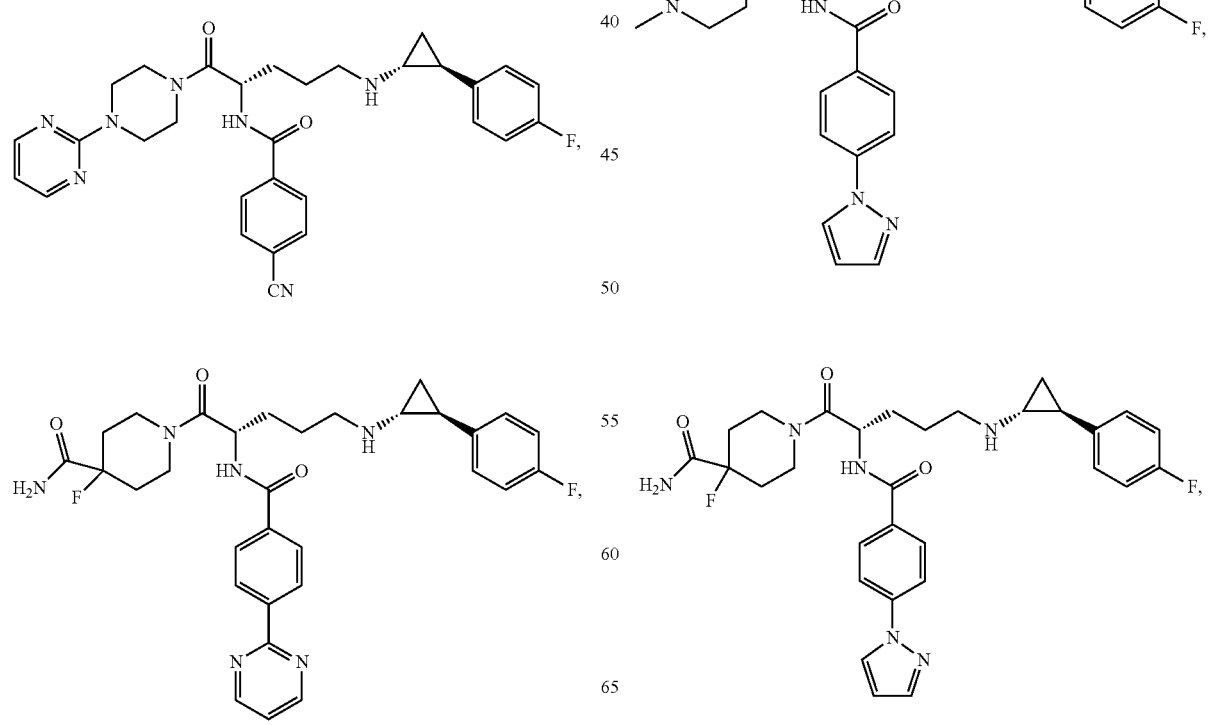

379
-continued
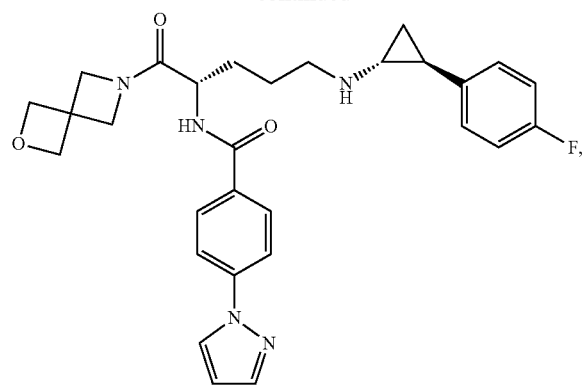
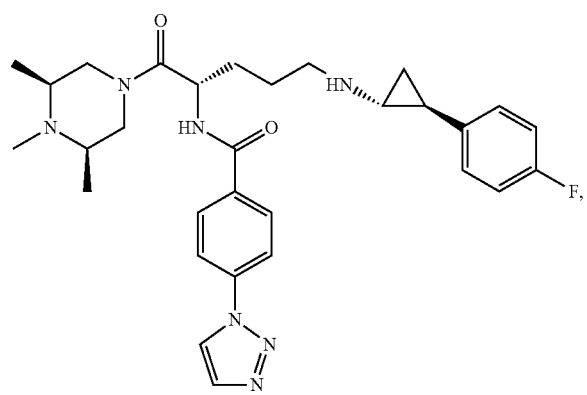
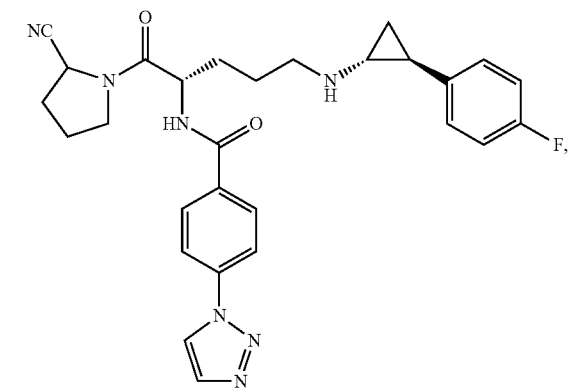
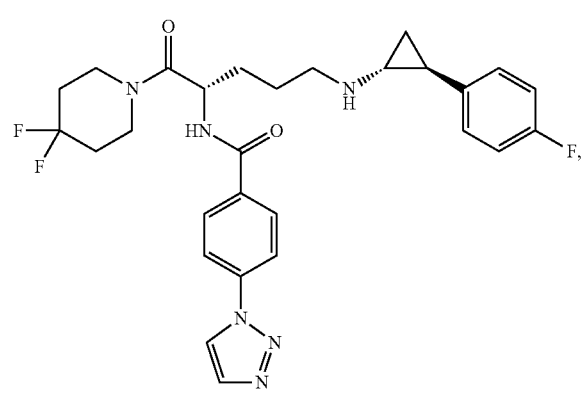
380
-continued
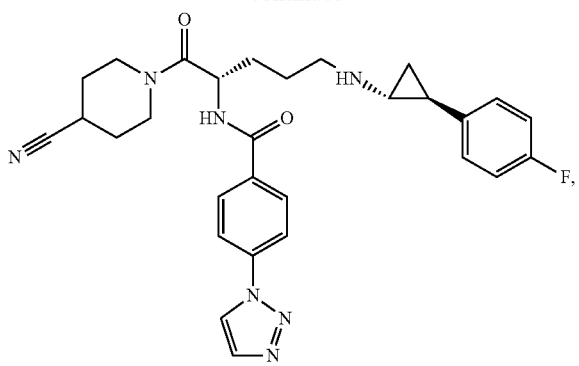
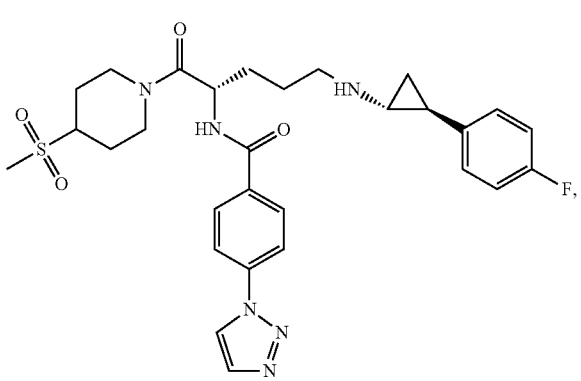
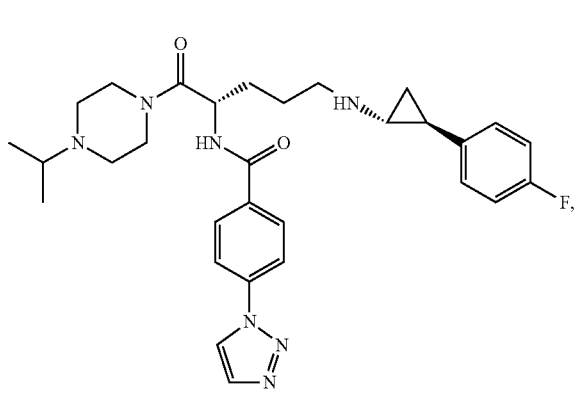

381
-continued
382
-continued
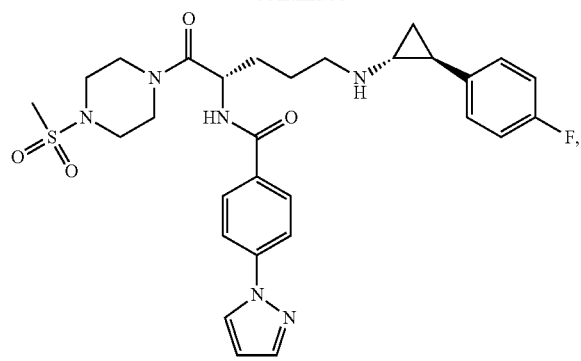
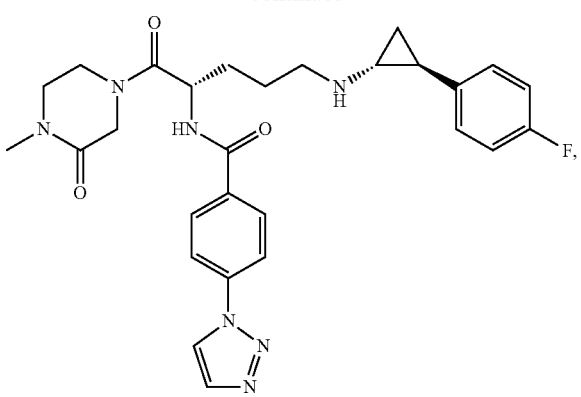
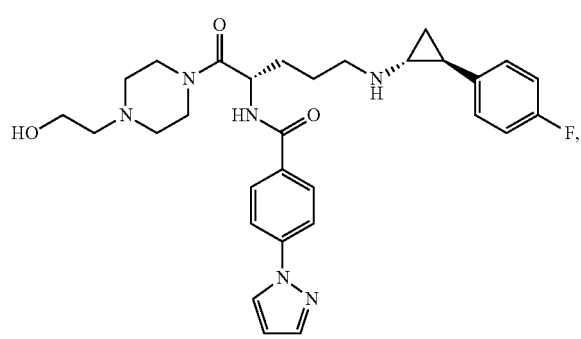
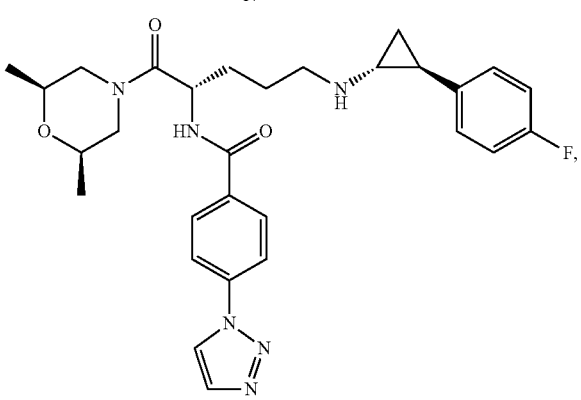
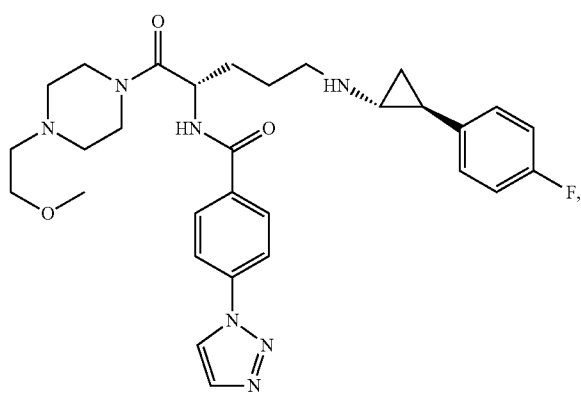
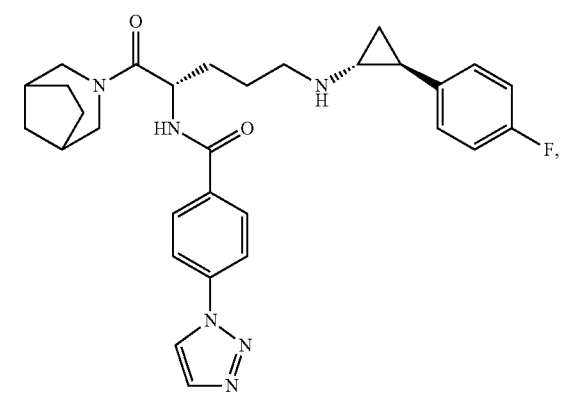
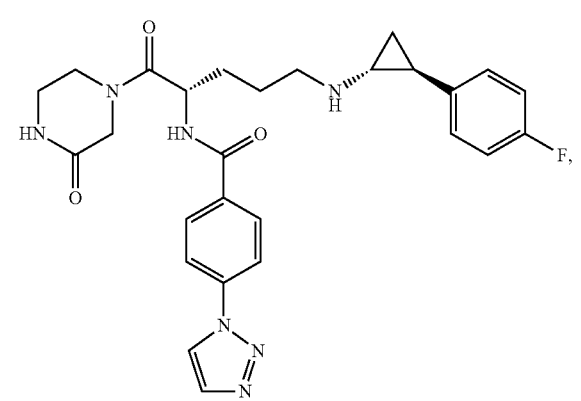
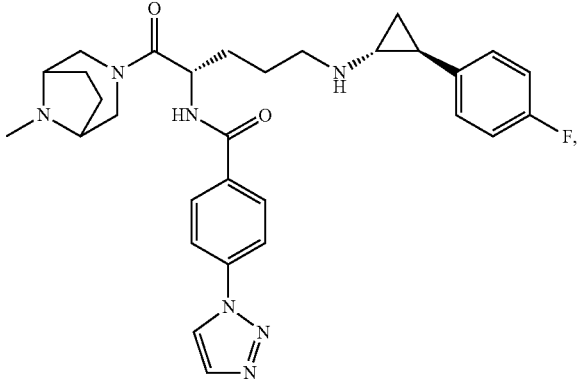

383
-continued
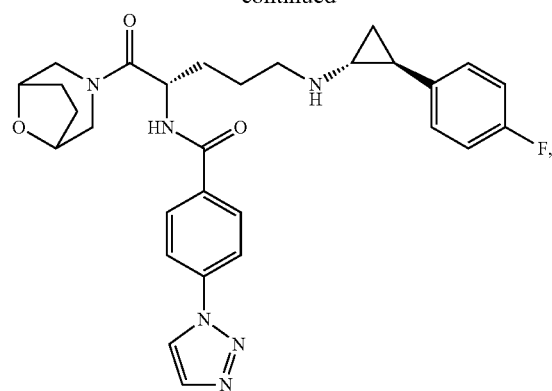
384
-continued
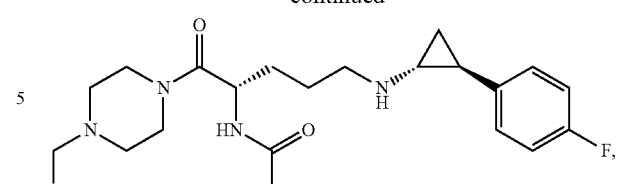
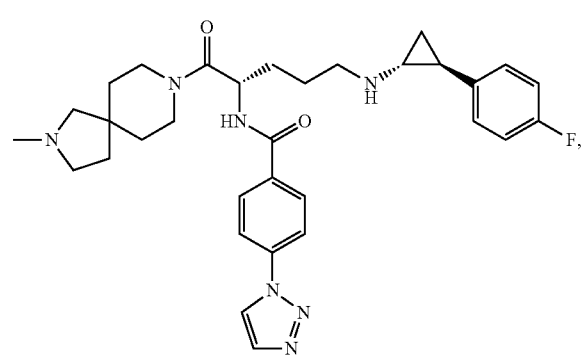
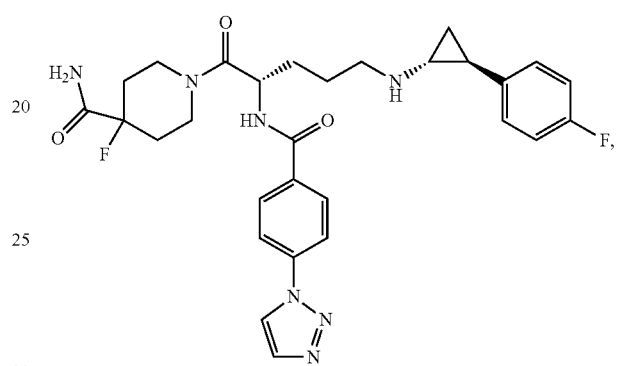
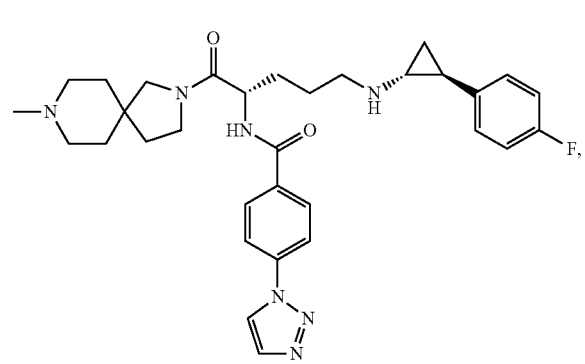
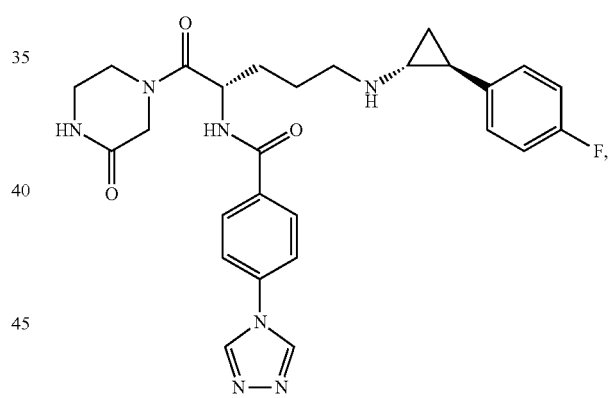
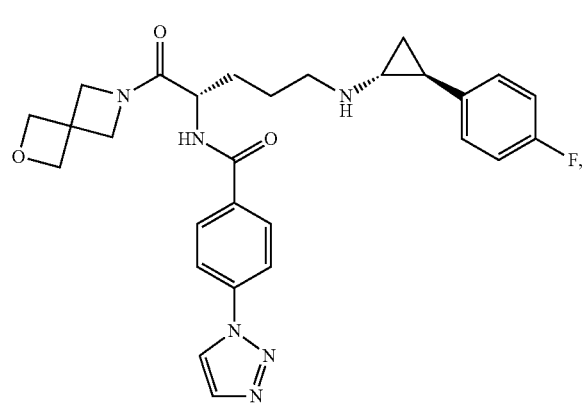
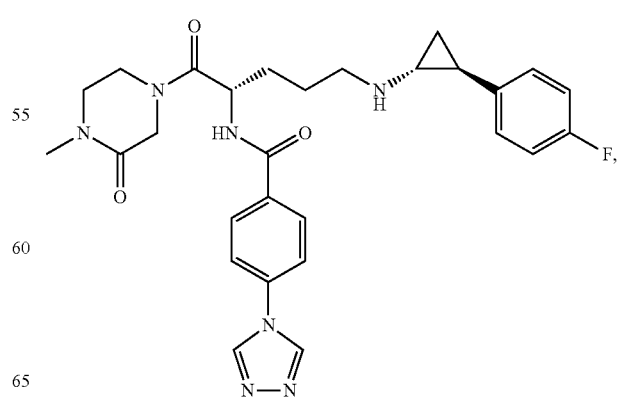

385
-continued
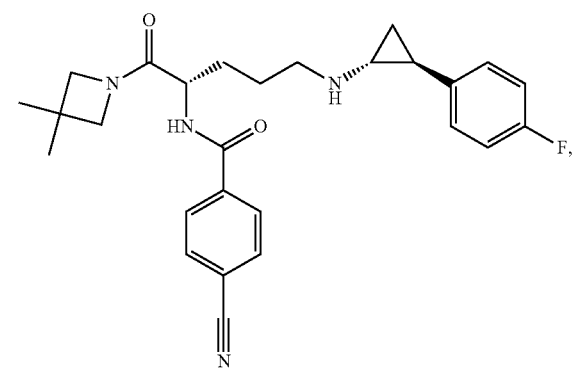
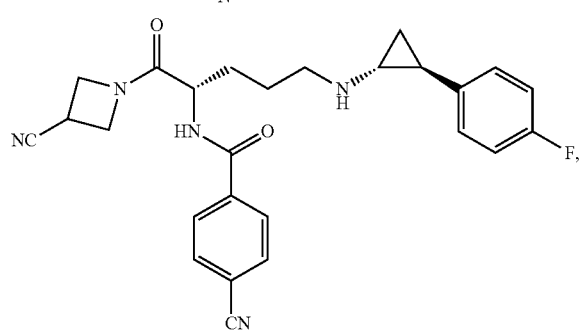
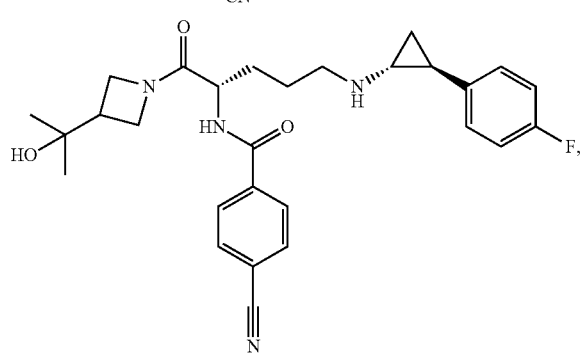
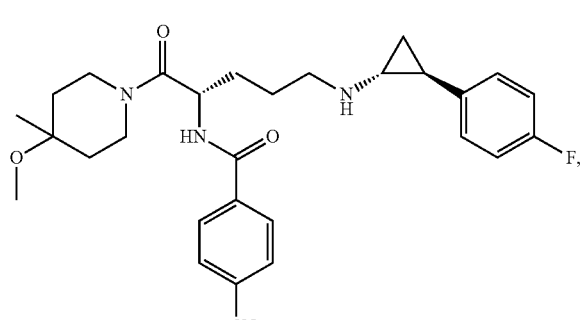
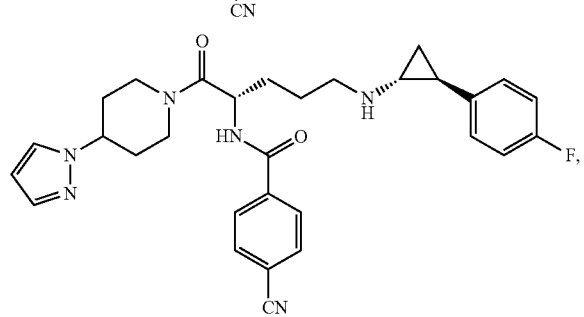
386
-continued
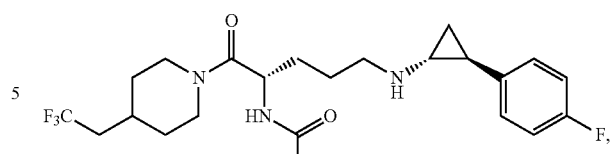
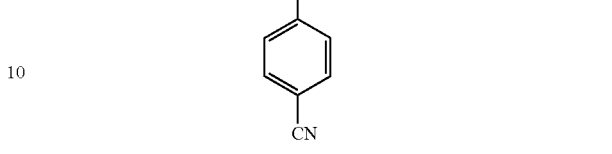
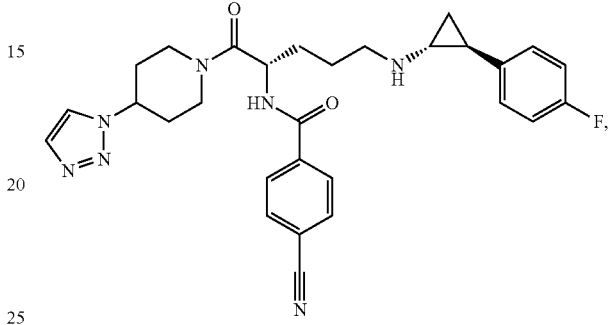
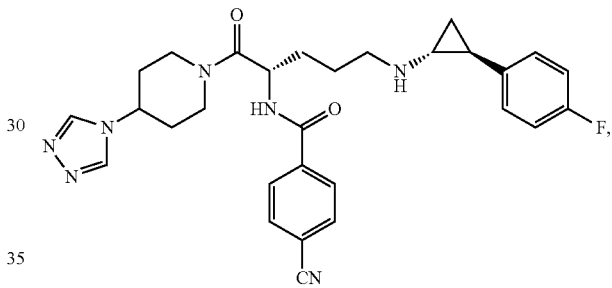
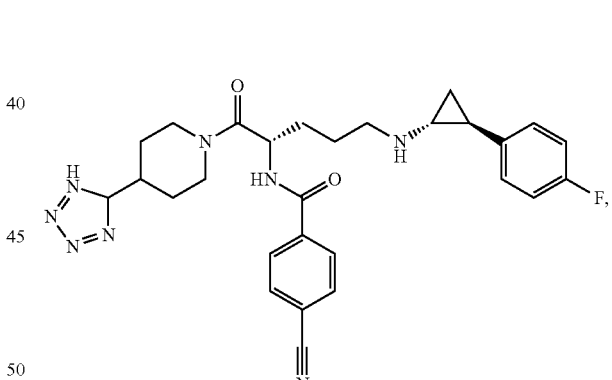
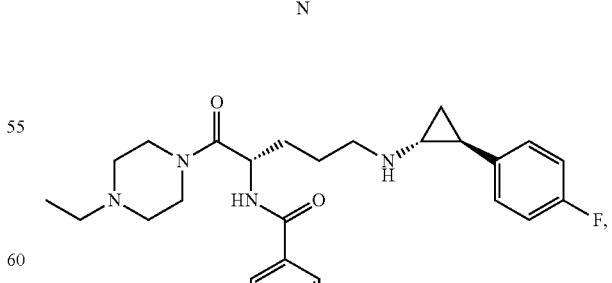
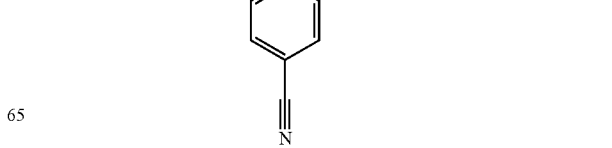

387
-continued
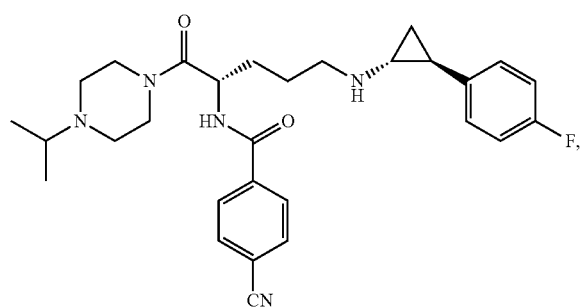
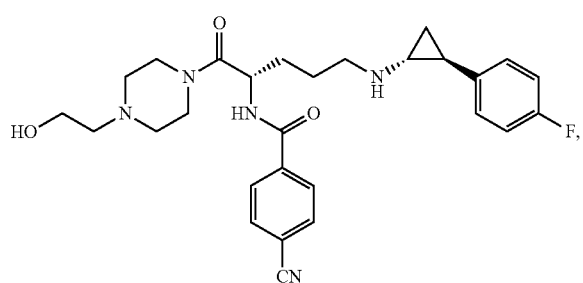
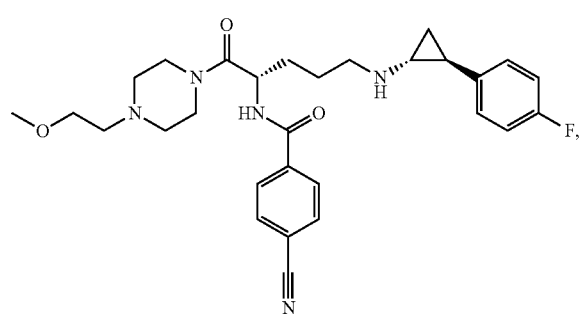
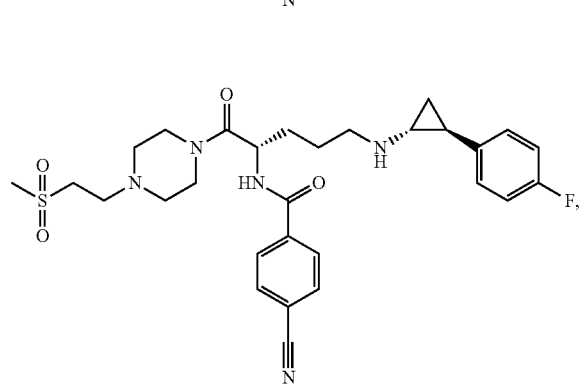
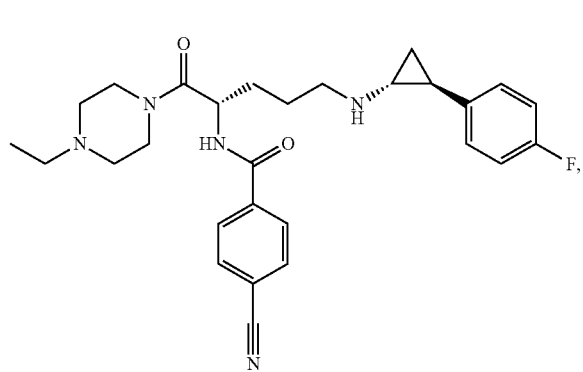
388
-continued
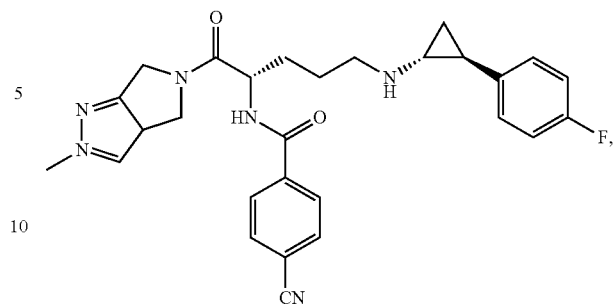
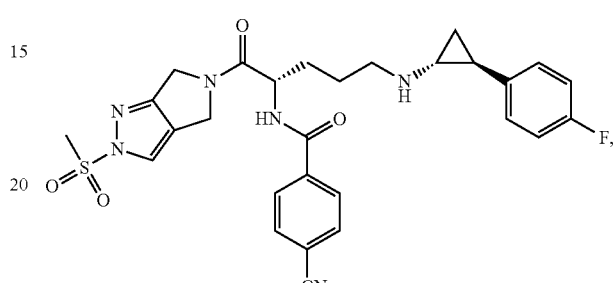
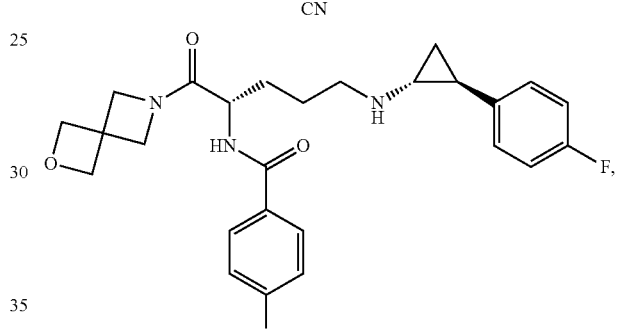
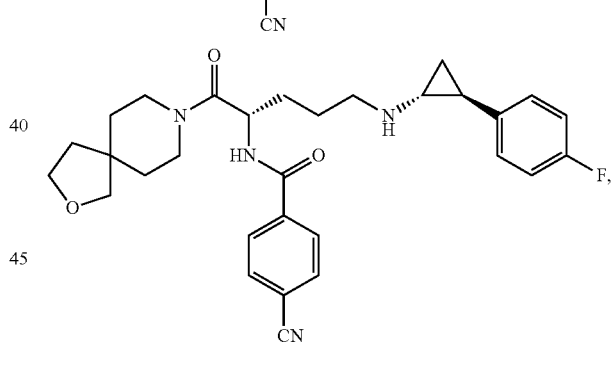
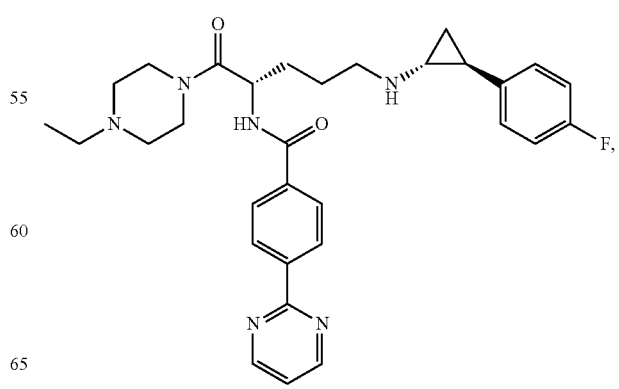

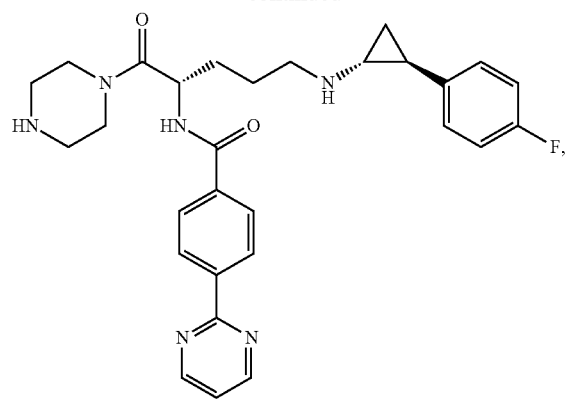
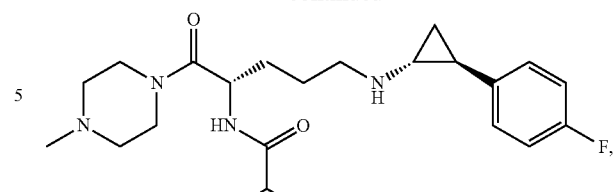
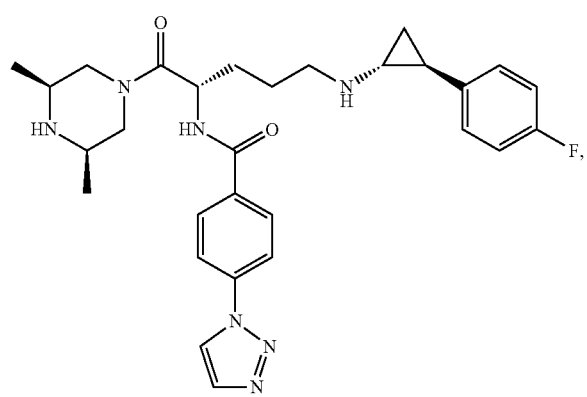
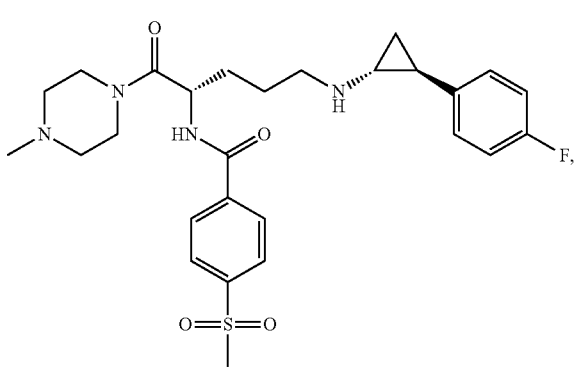
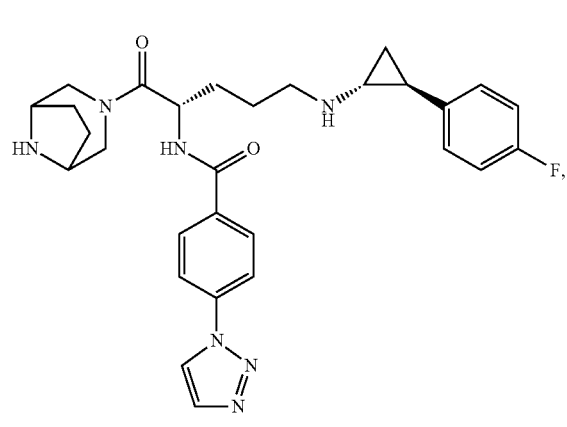
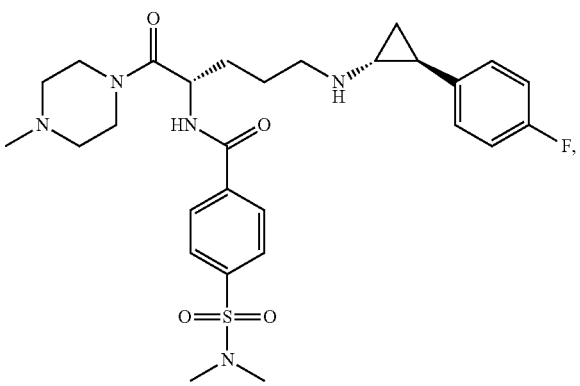
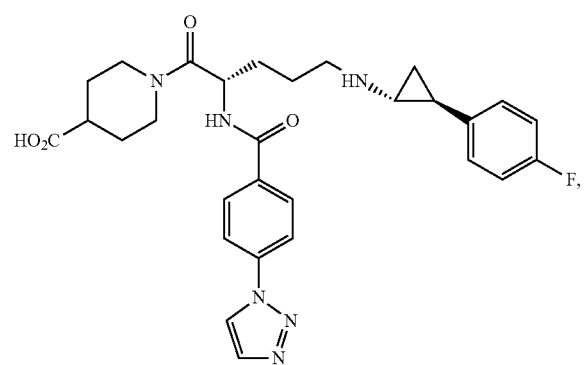
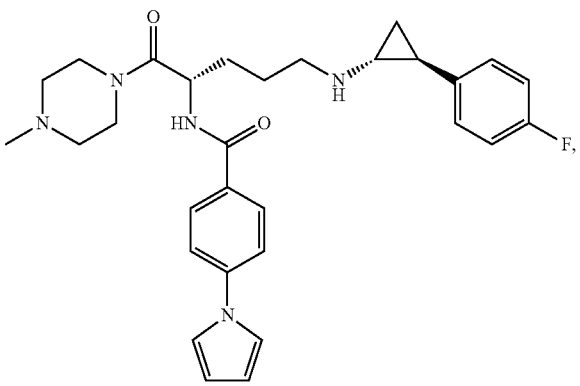

391
-continued
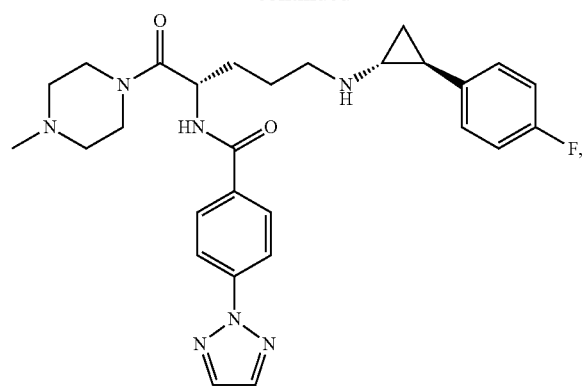
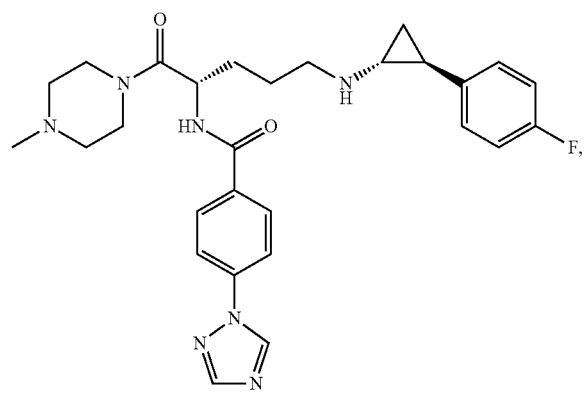
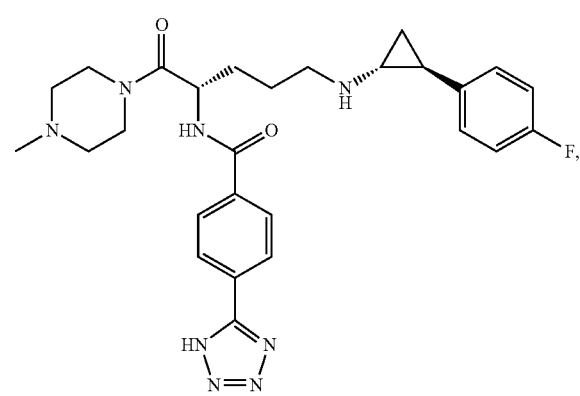
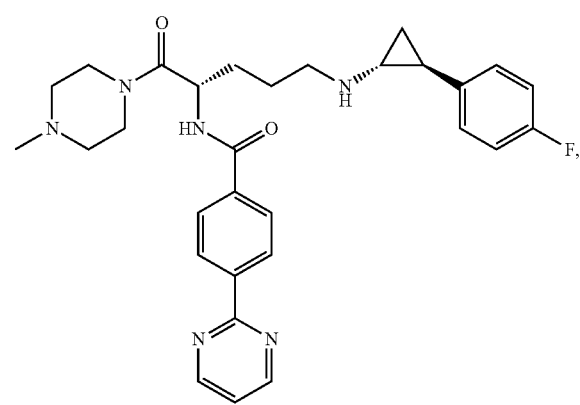
392
-continued
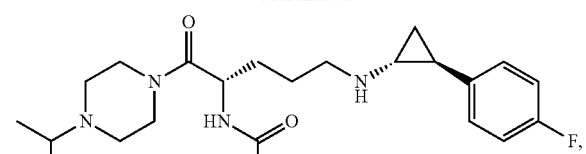
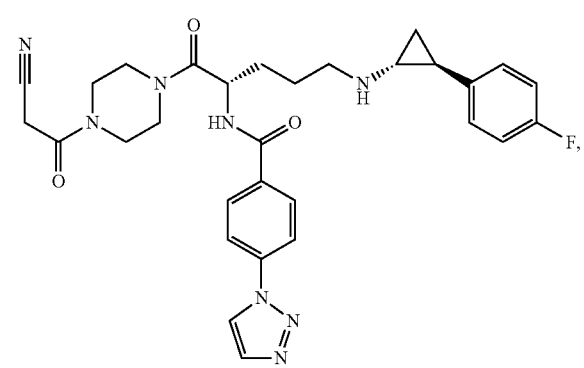
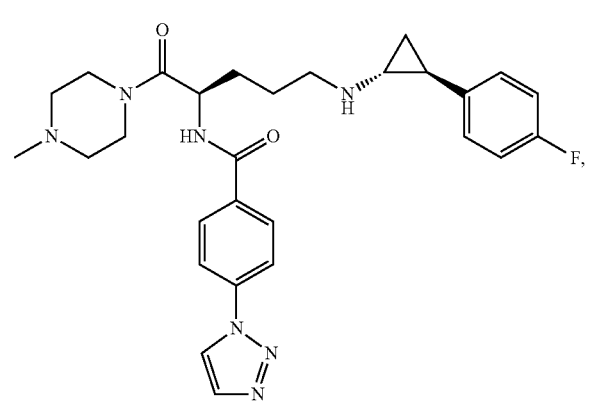

393
-continued
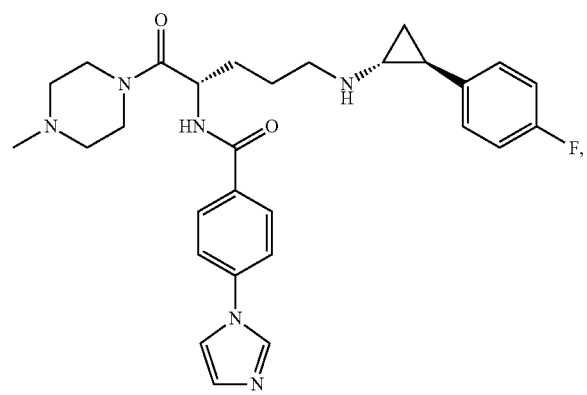
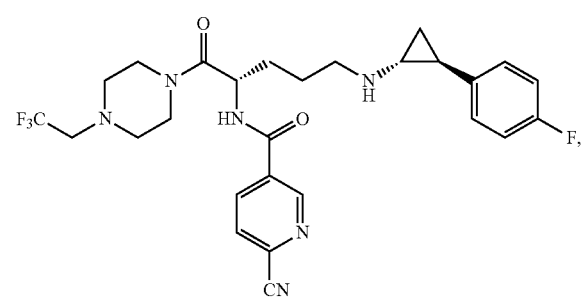
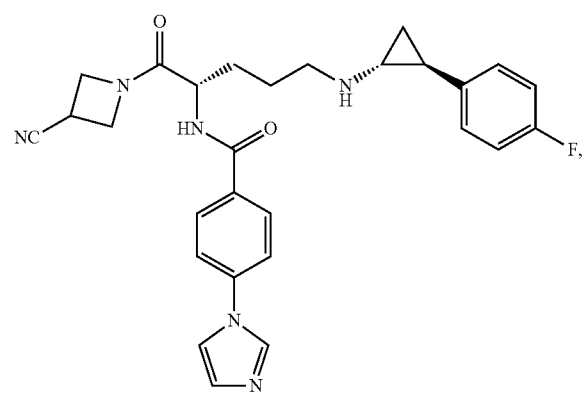
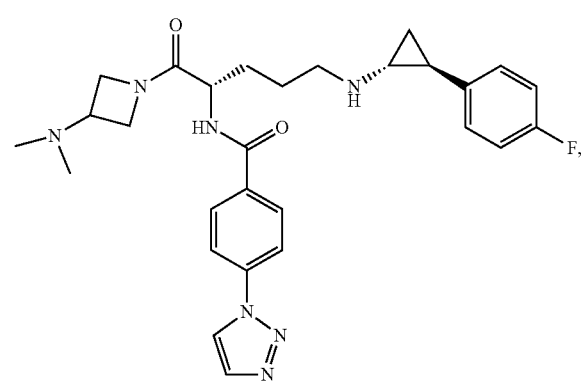
394
-continued
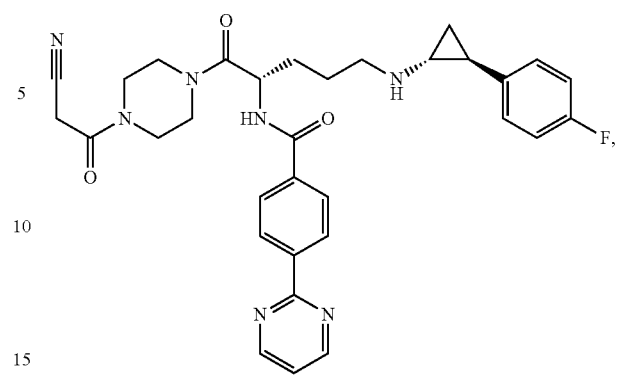
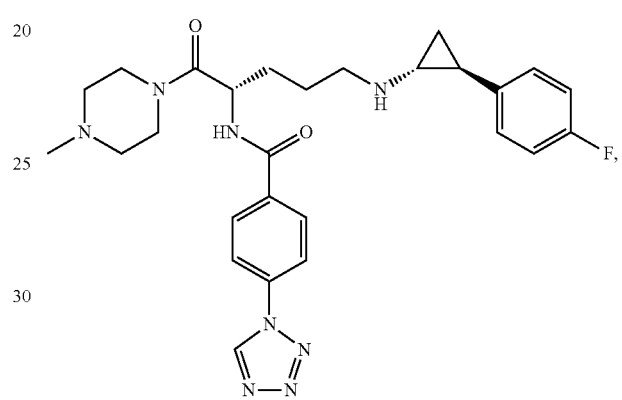
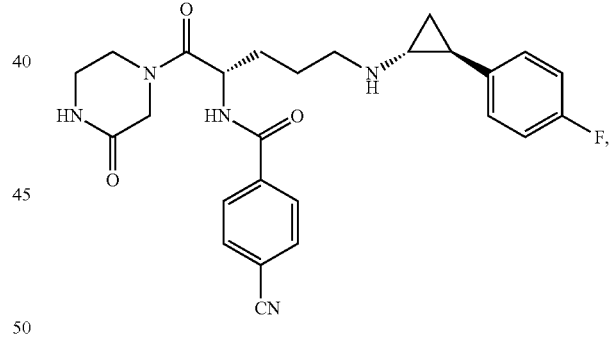
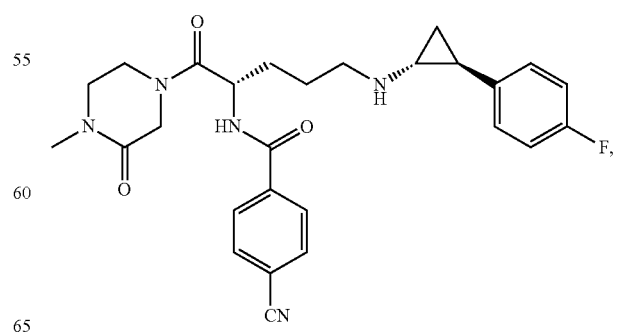

395
-continued
396
-continued
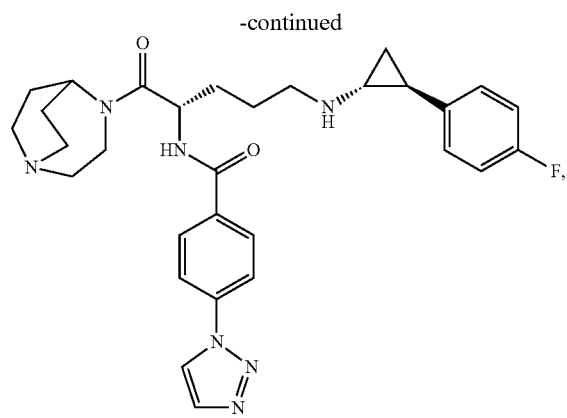
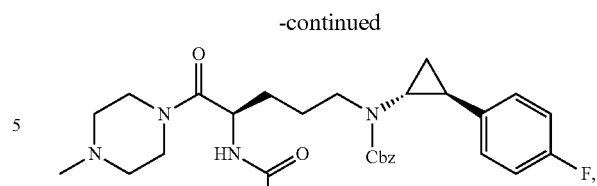
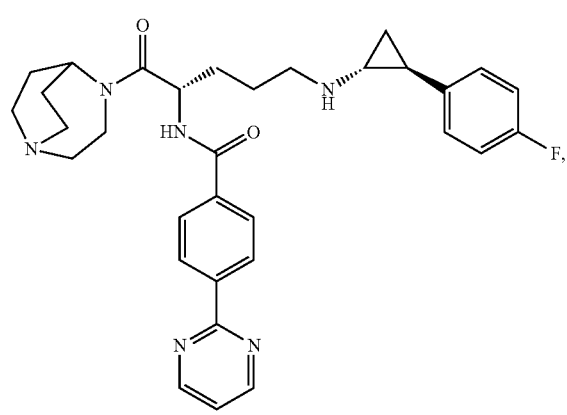
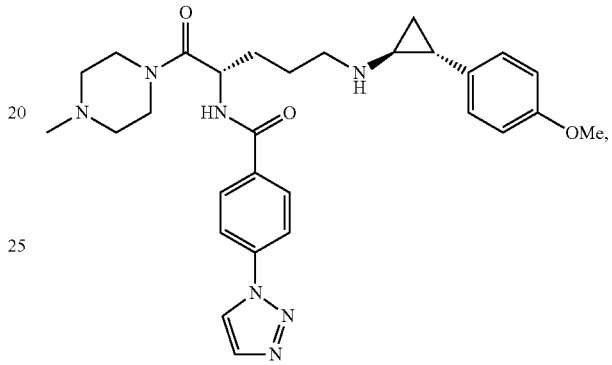
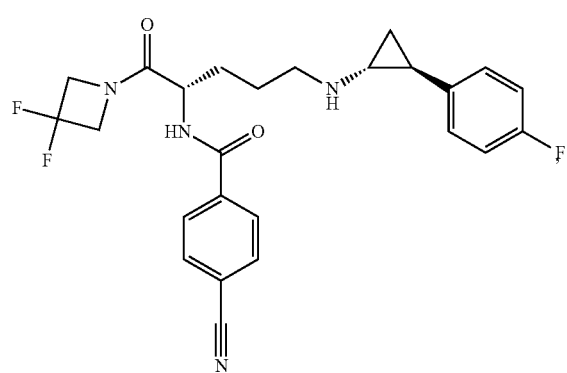
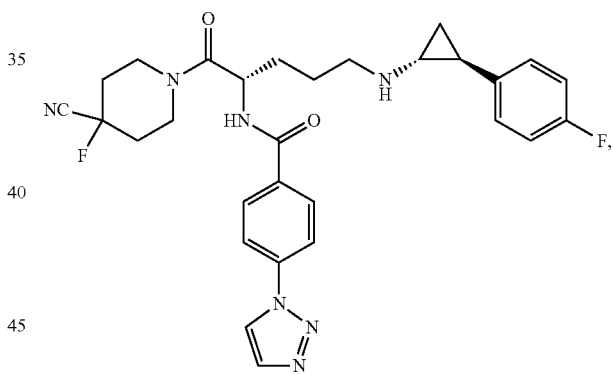
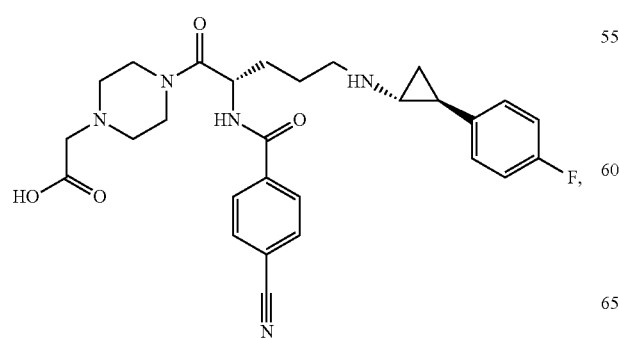
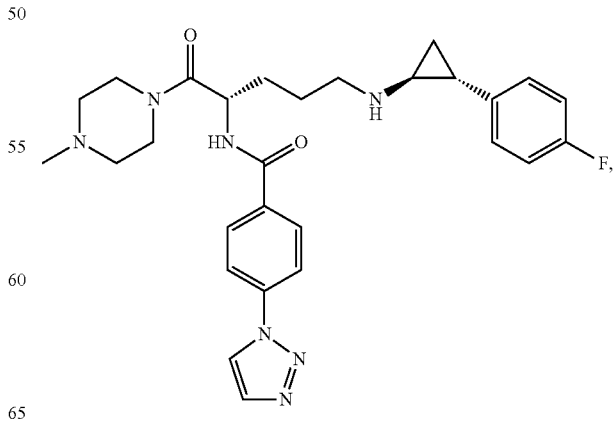

397
-continued
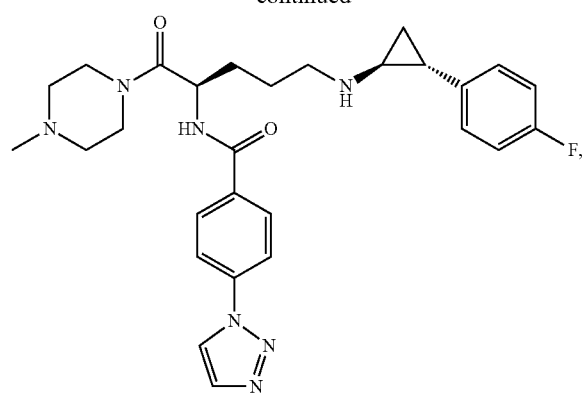
398
-continued
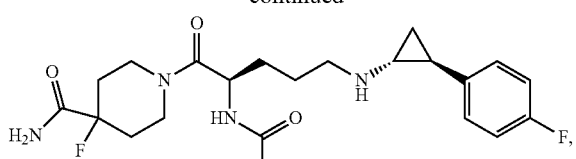
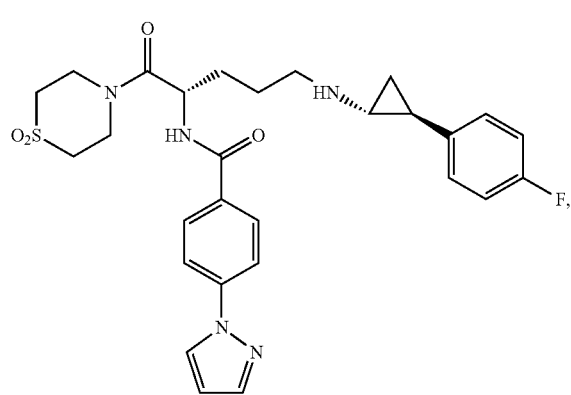
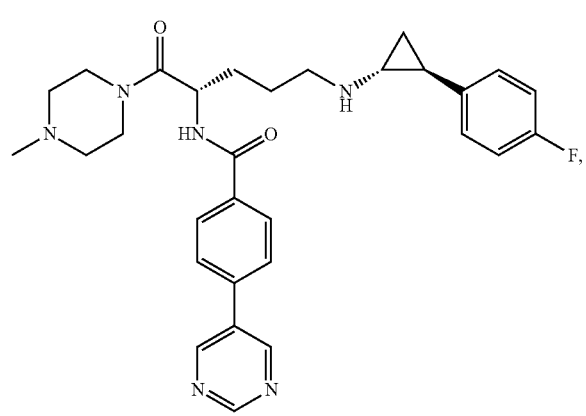
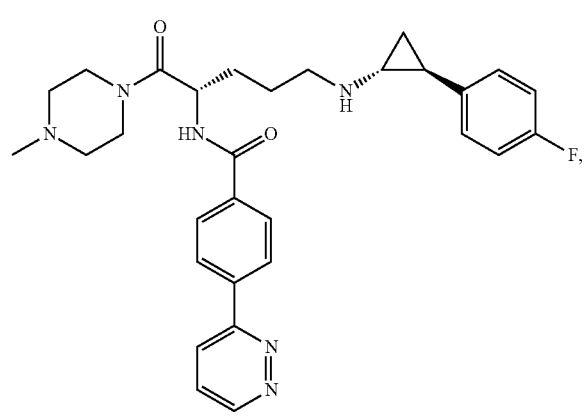

399
-continued
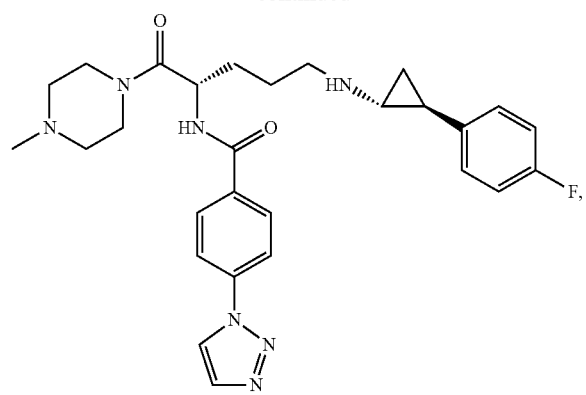
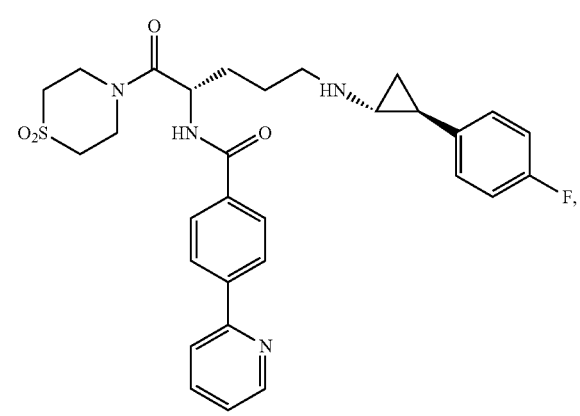
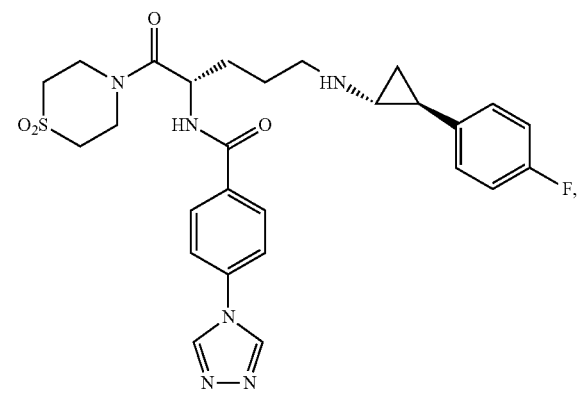
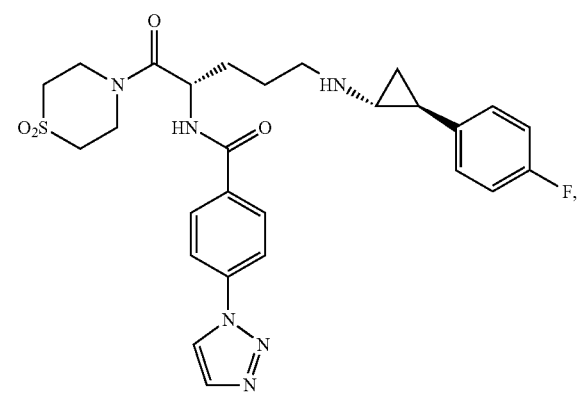
400
-continued
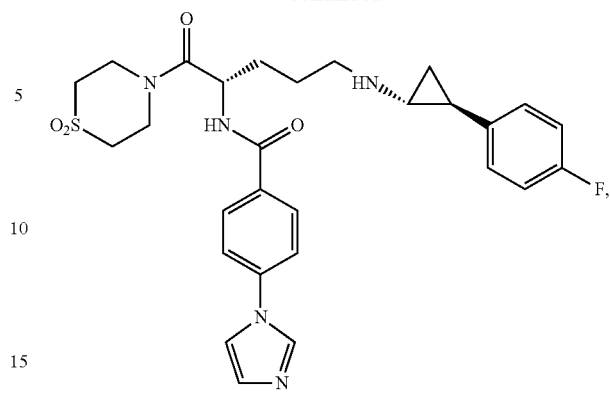
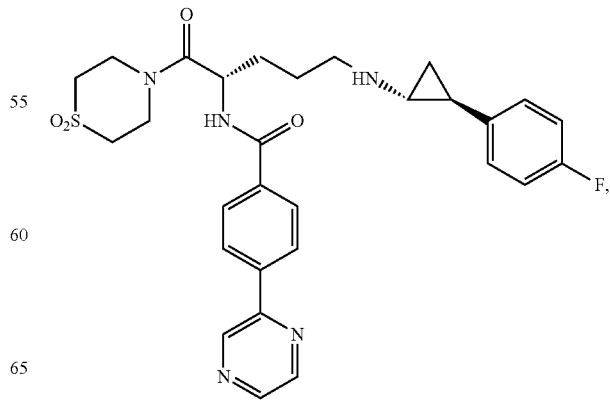

-continued

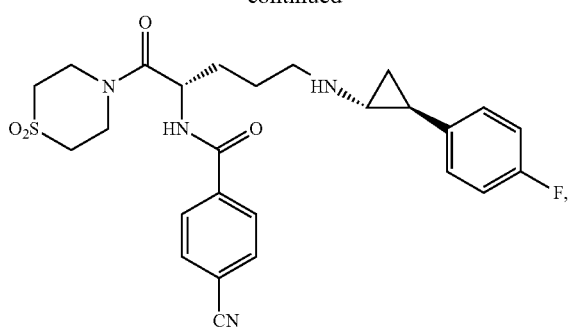

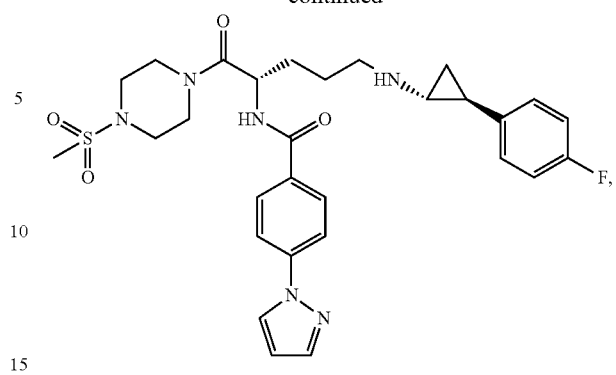

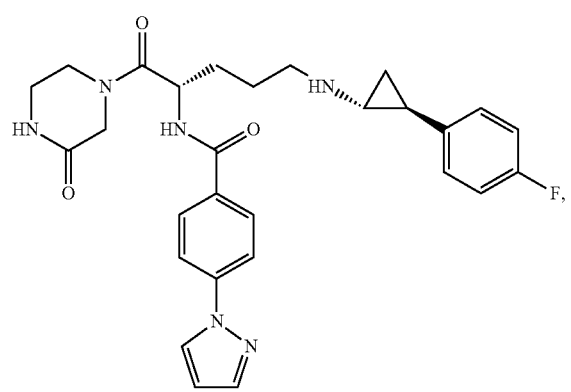

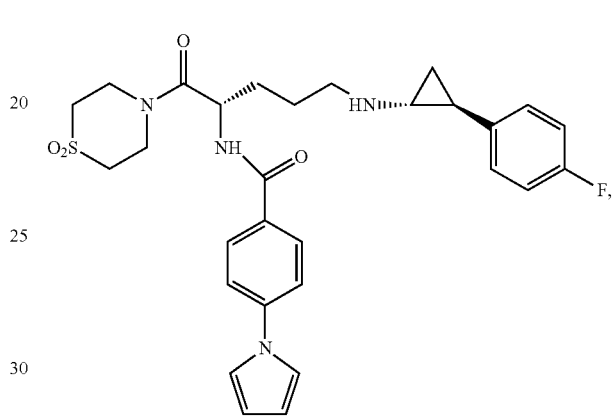

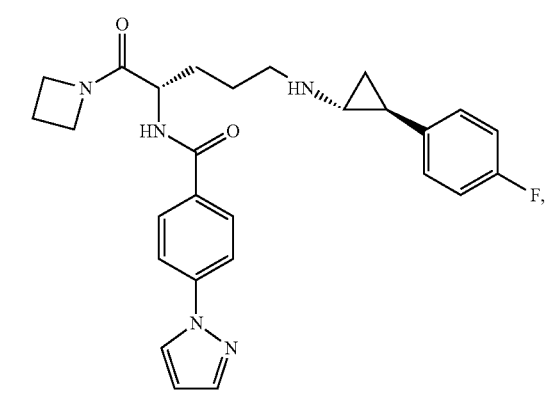

and

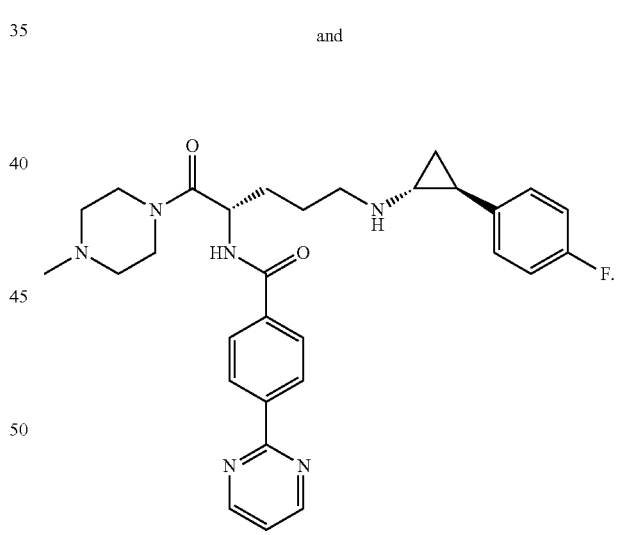

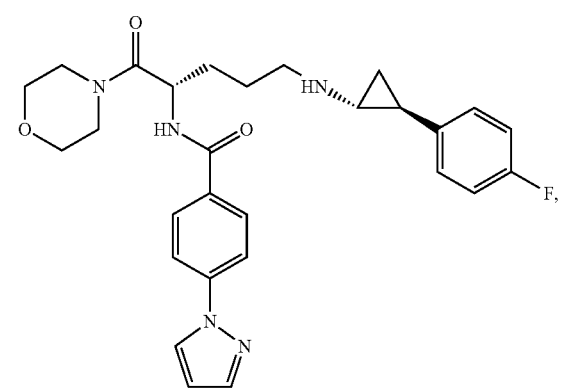

12. A tosylate salt of a compound as recited in claim 1.

13. A bis-tosylate salt of a compound as recited in claim 1.

14. A pharmaceutical composition comprising a compound as recited in claim 1, together with a pharmaceutically acceptable carrier.

15. The pharmaceutical composition as recited in claim 14, formulated for oral administration.

16. The pharmaceutical composition as recited in claim 15, additionally comprising another therapeutic agent.

17. A compound chosen from
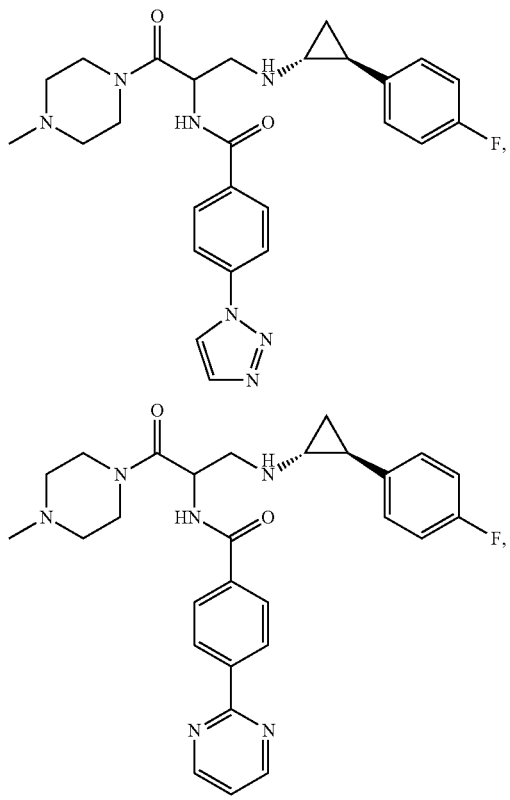
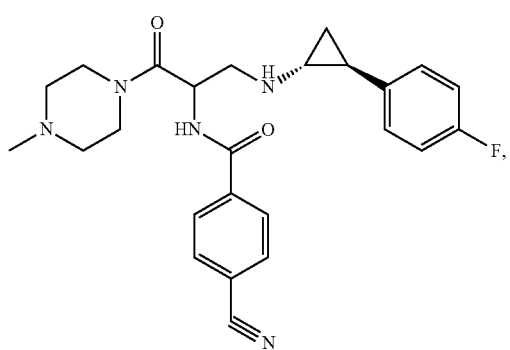
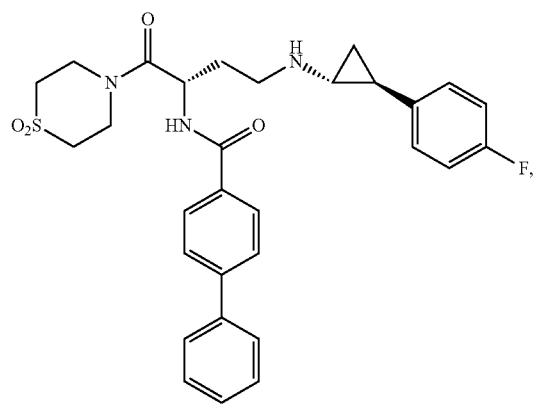
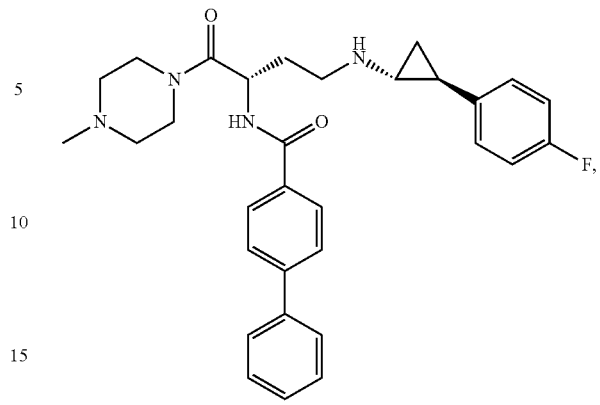
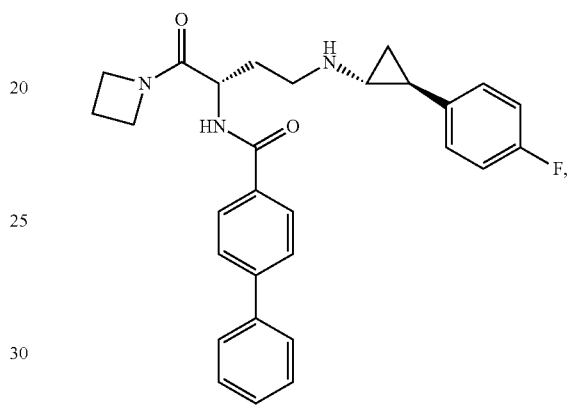
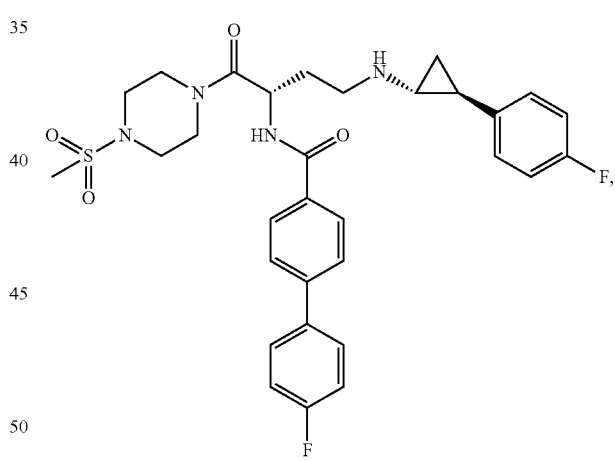
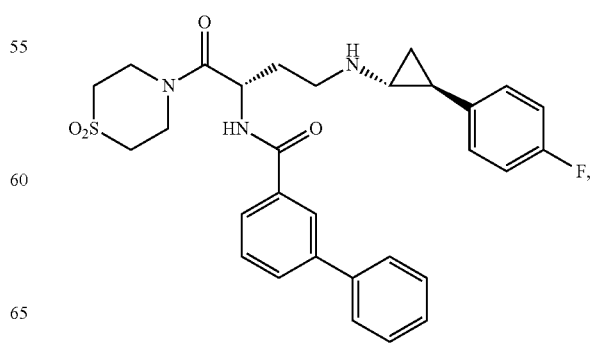

405
-continued
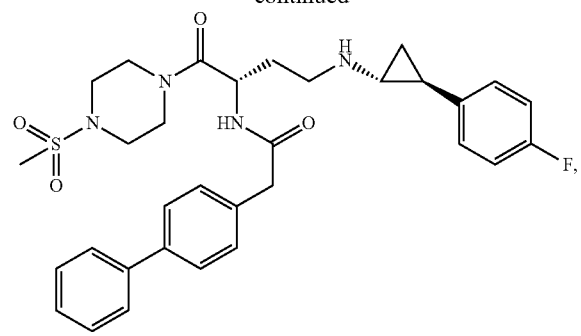
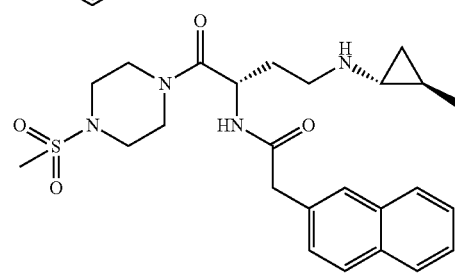
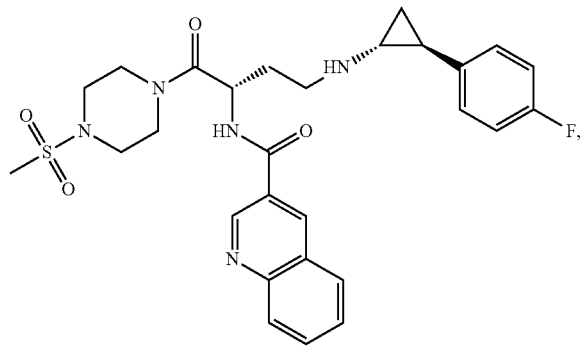
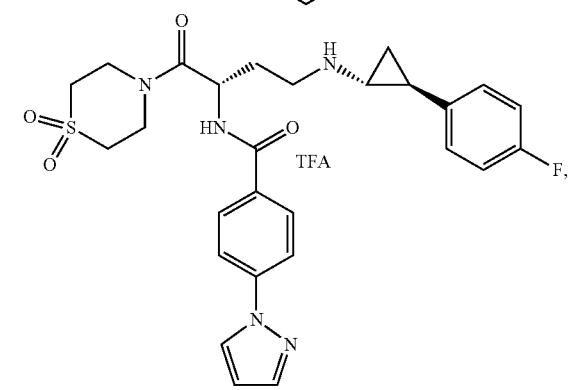
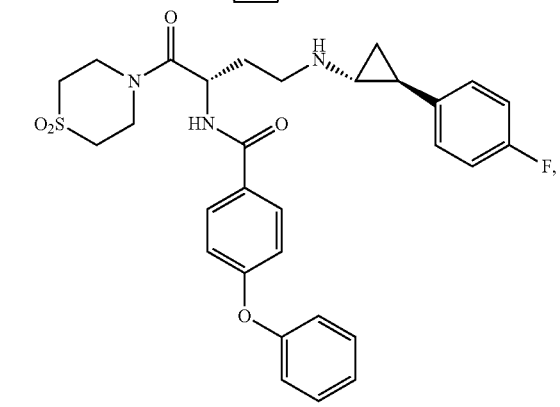
406
-continued
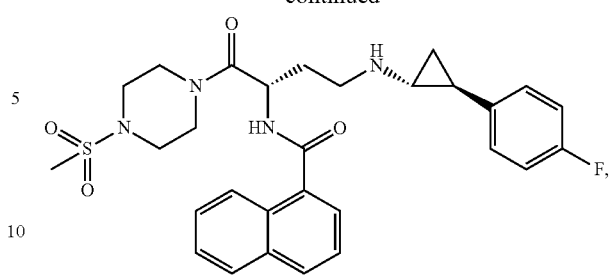
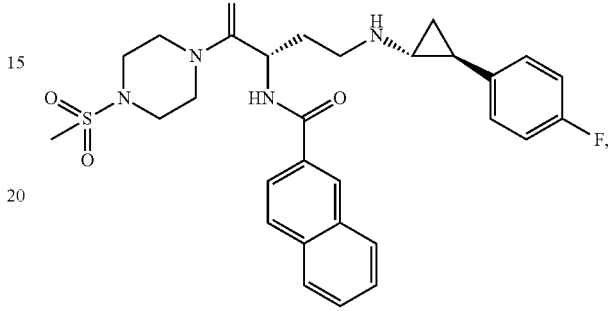
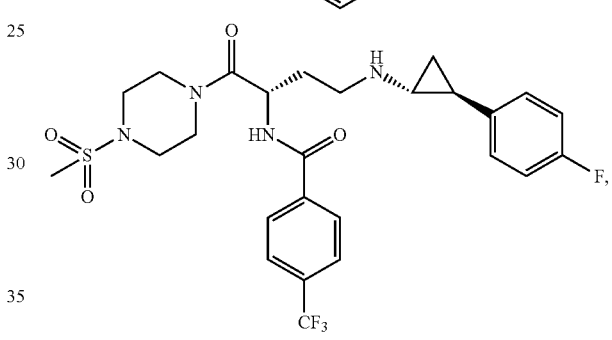
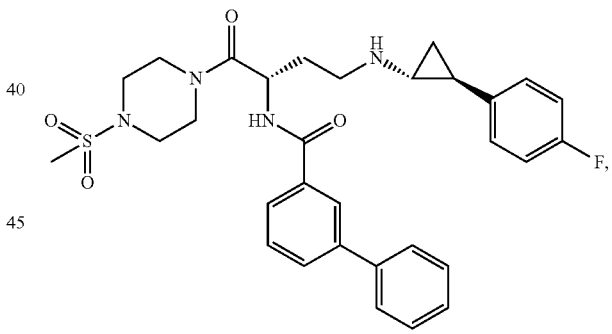
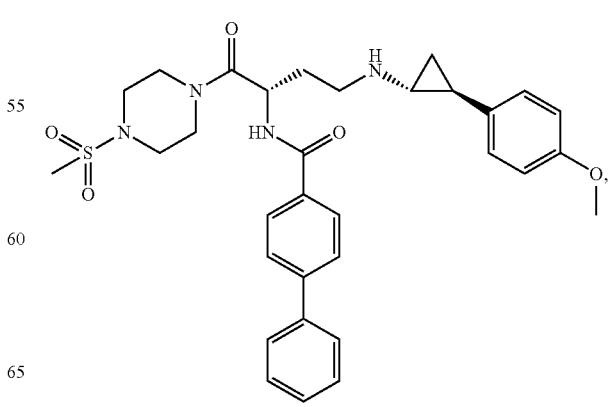

407
-continued
408
-continued
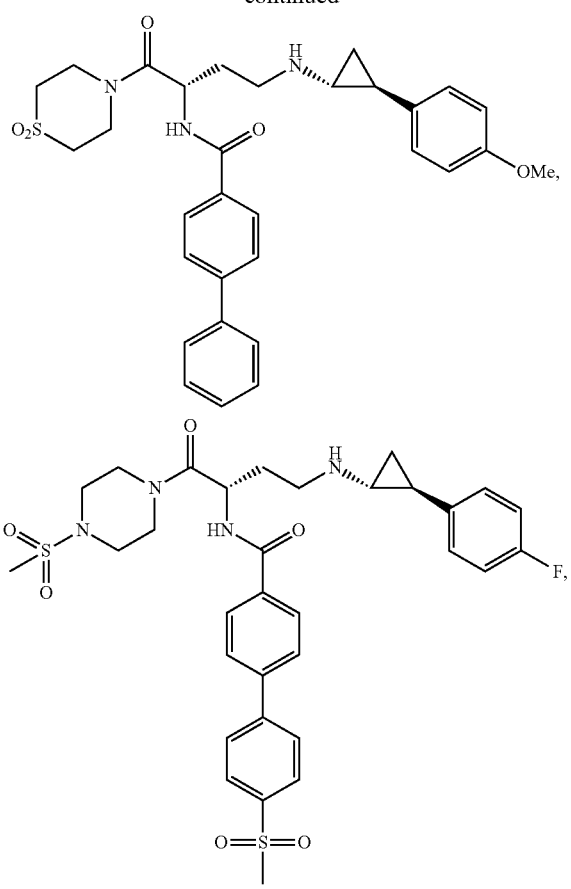
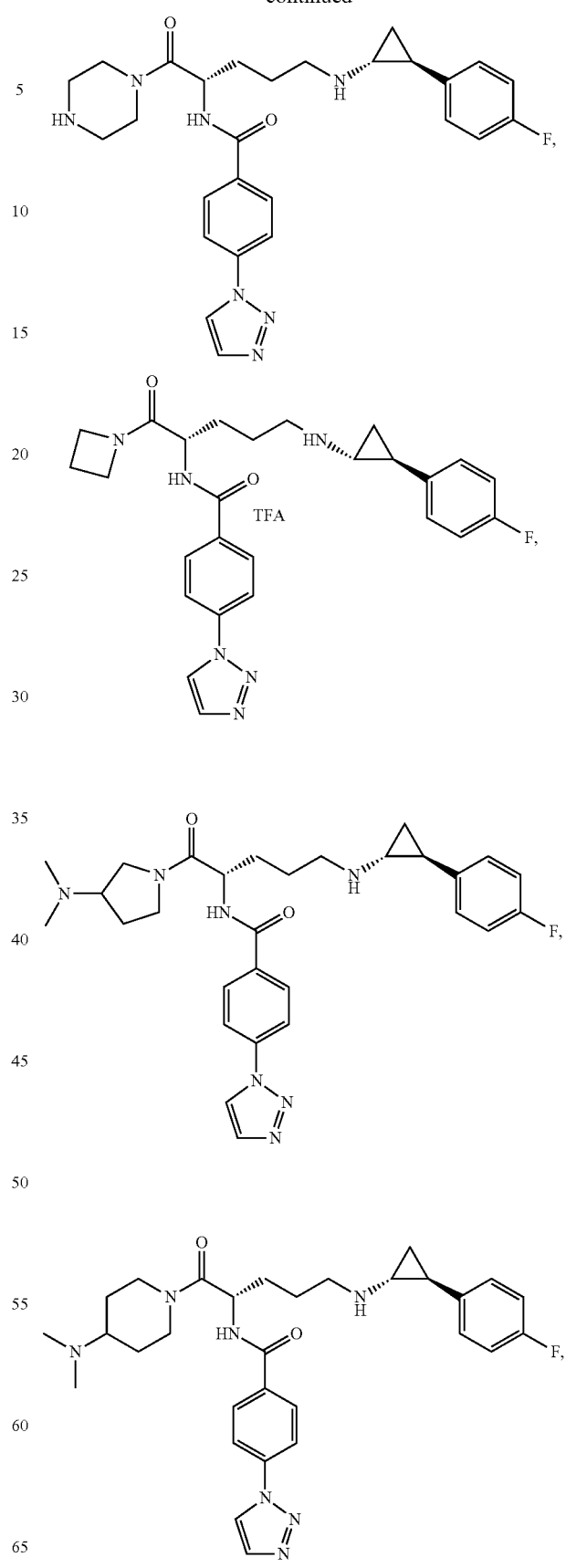

409
-continued
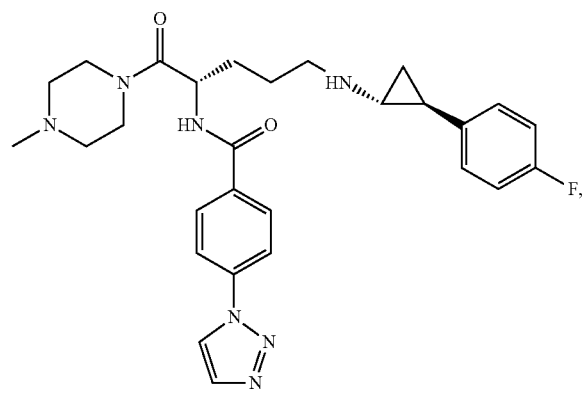
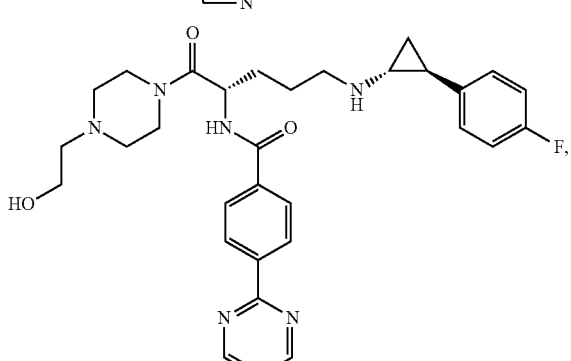
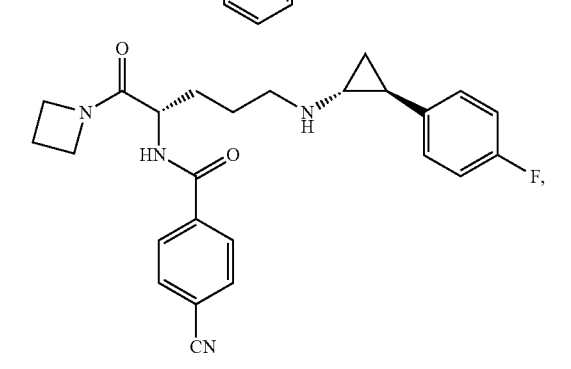
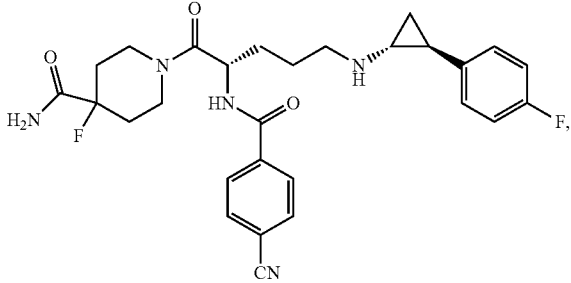
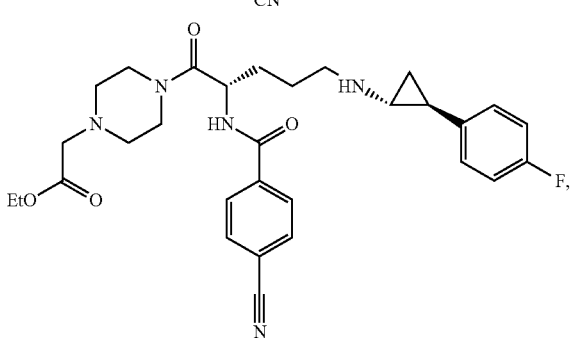
410
-continued
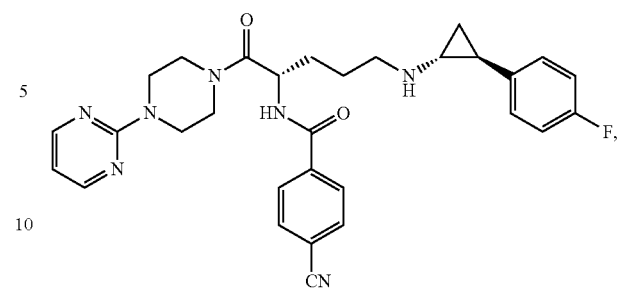
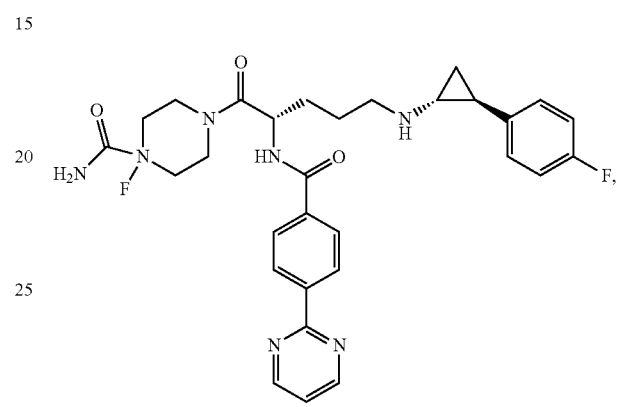
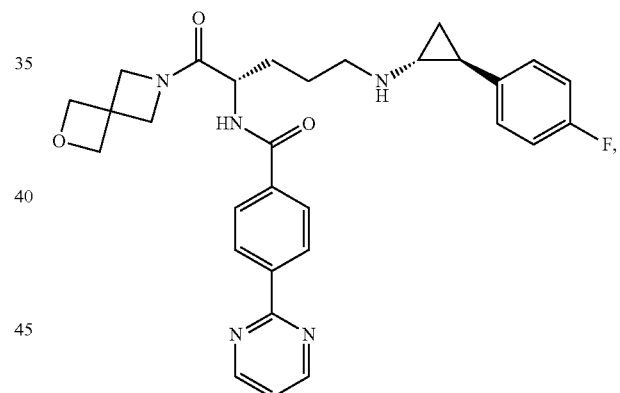
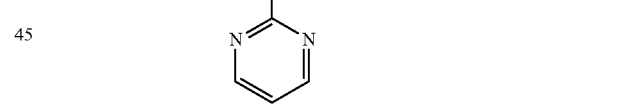
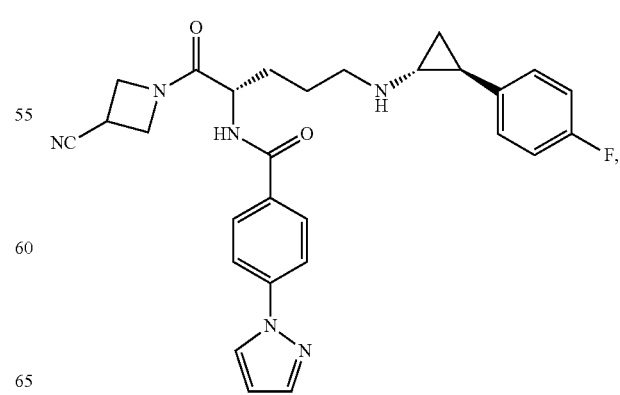

411
-continued
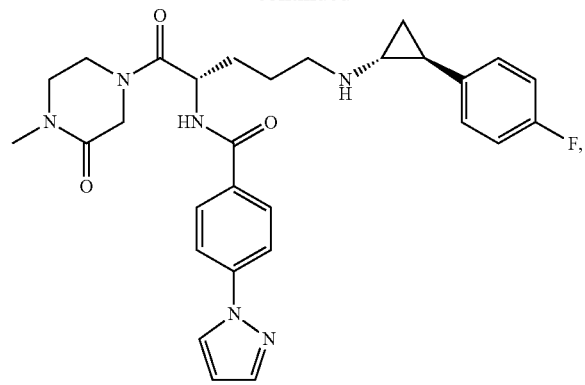
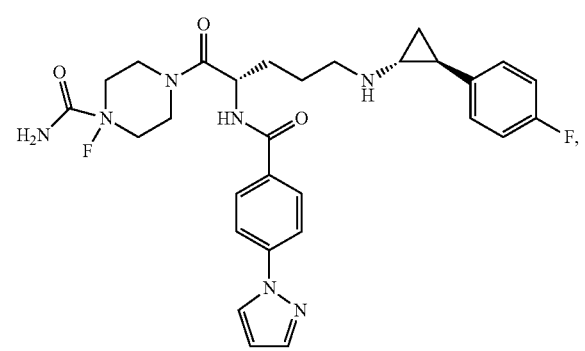
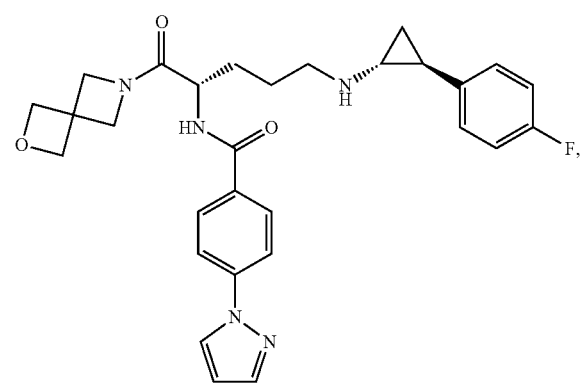
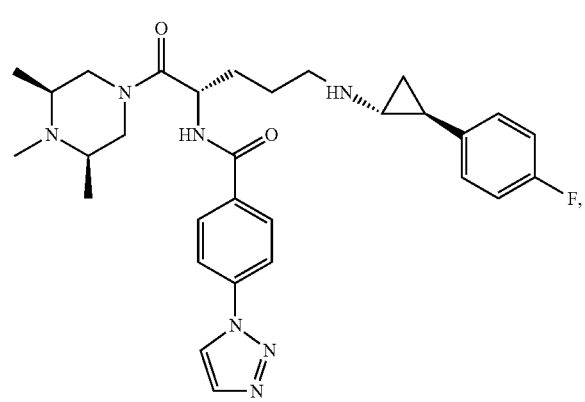
412
-continued
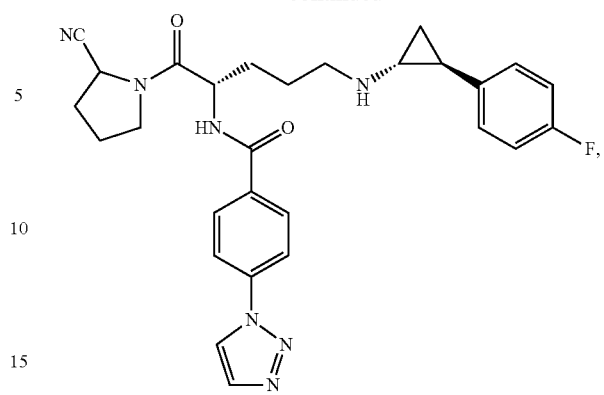
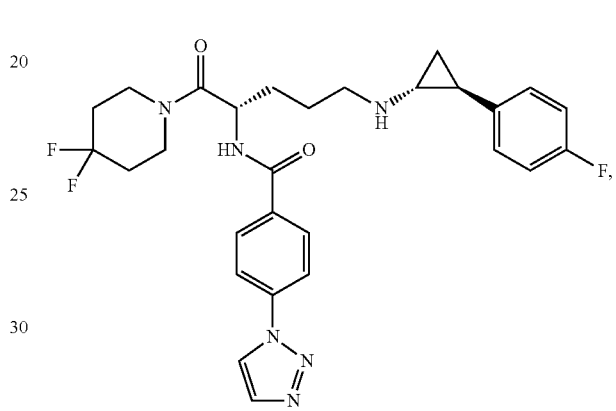
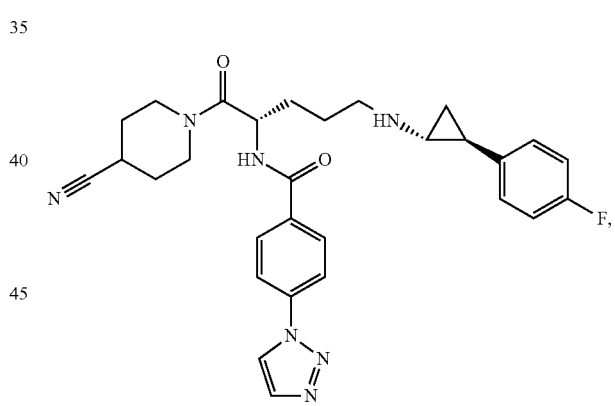
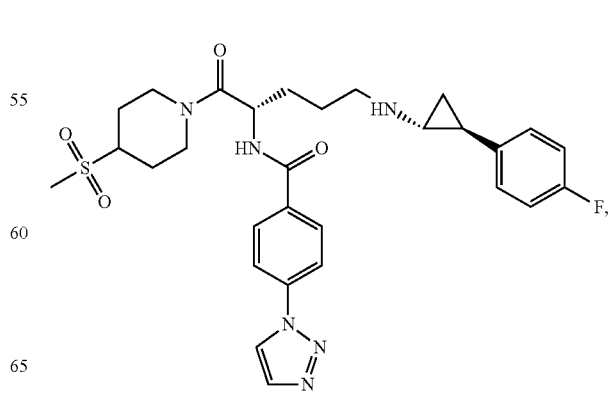

413
-continued
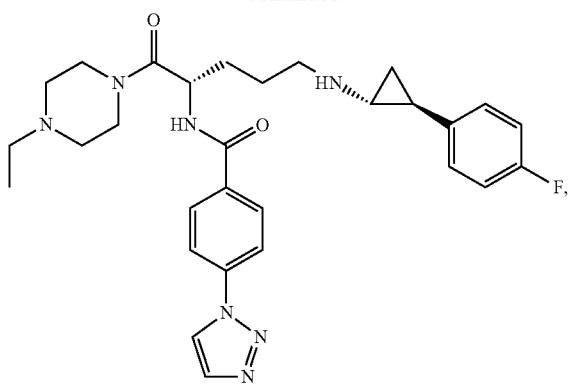
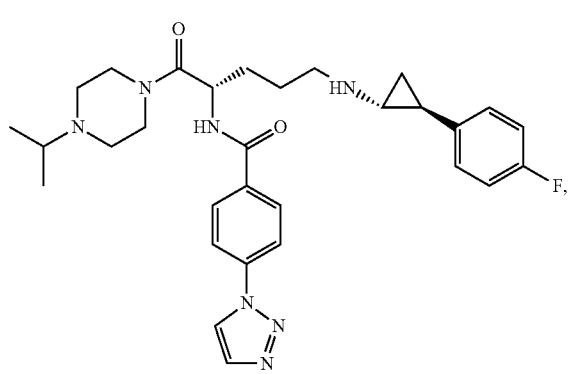
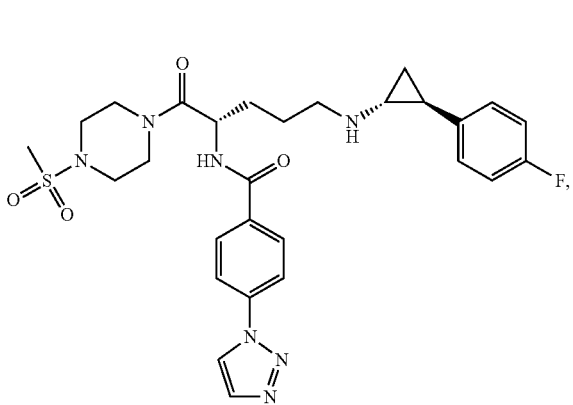
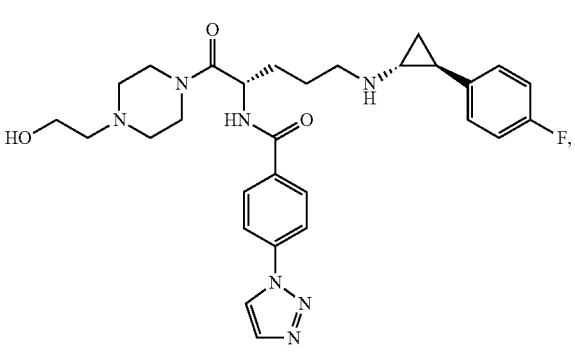
414
-continued
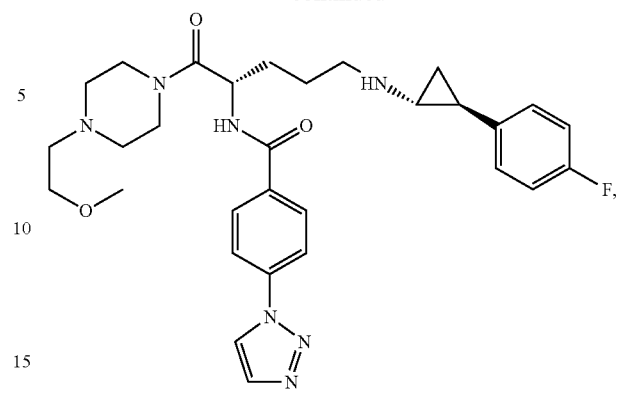
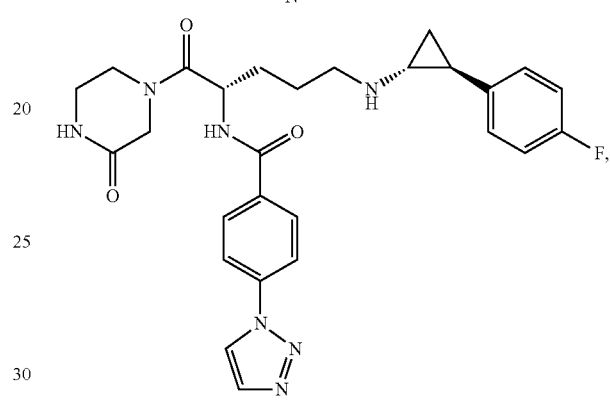
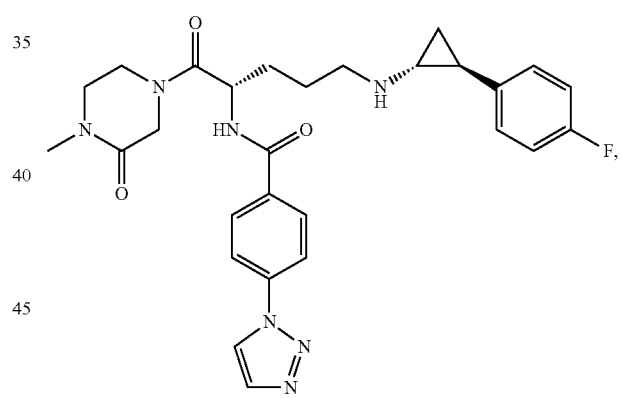
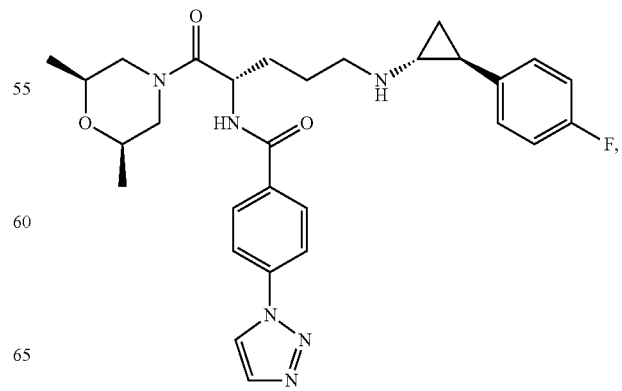

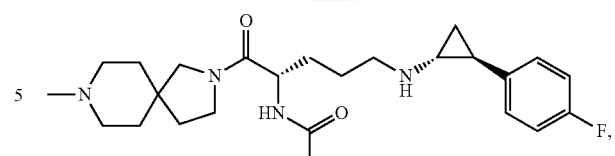
| 415 -continued | 416 -continued |
|---|---|
| 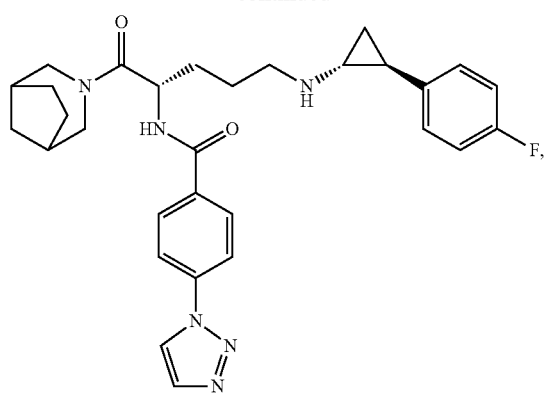 | 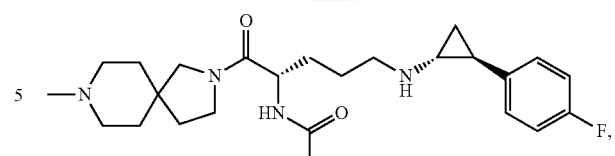 |
| 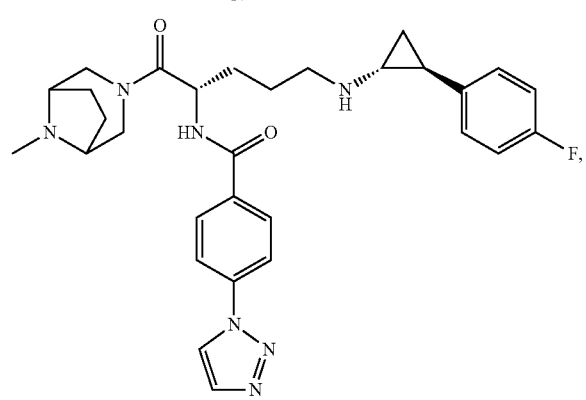 | 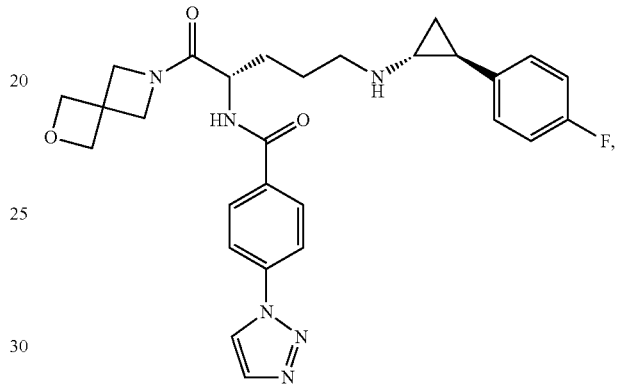 |
| 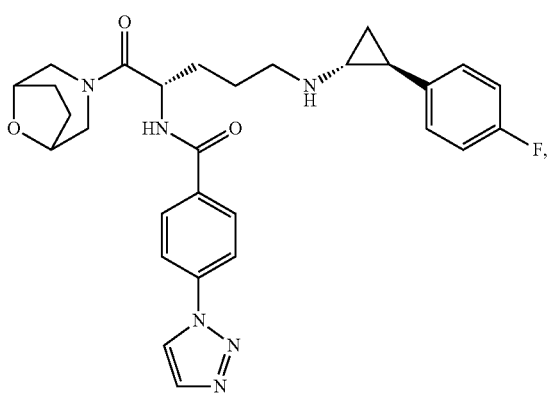 | 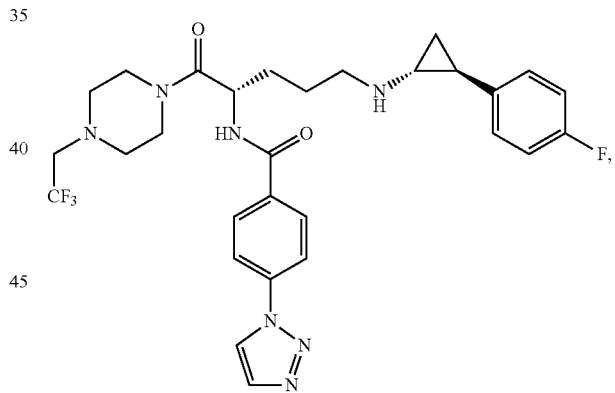 |
| 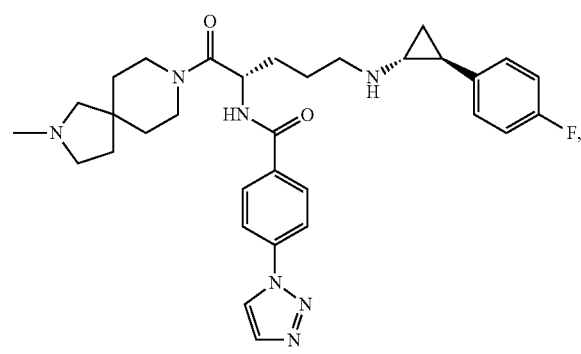 | 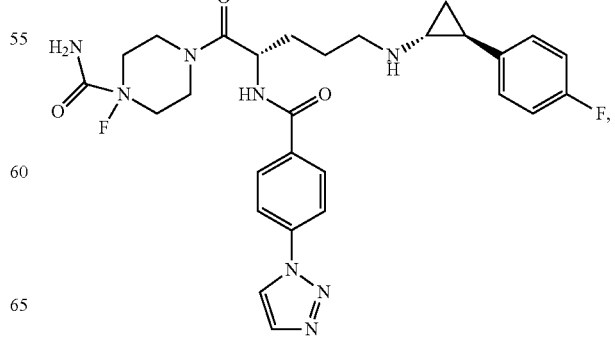 |

417
-continued
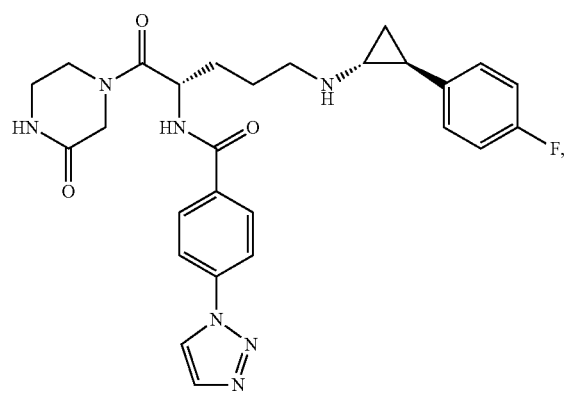
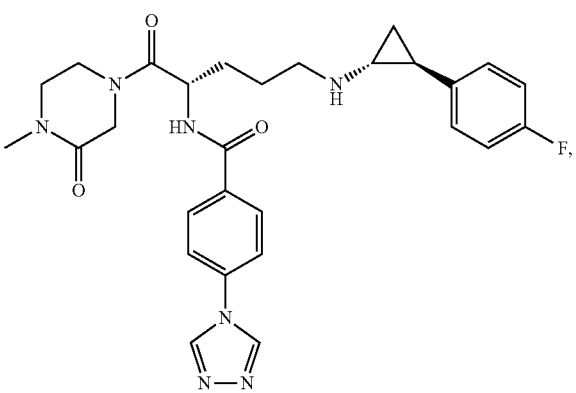
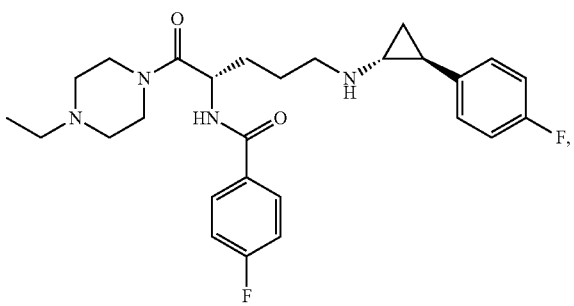
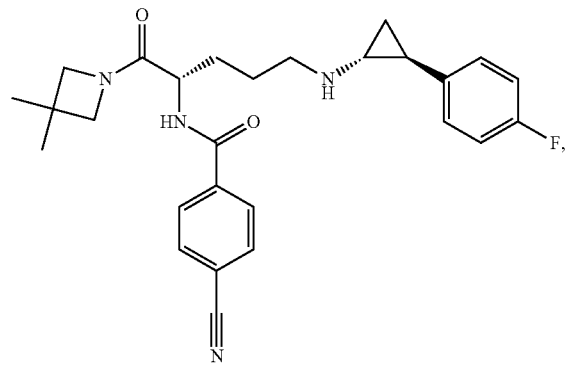
418
-continued
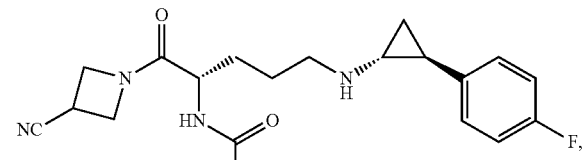
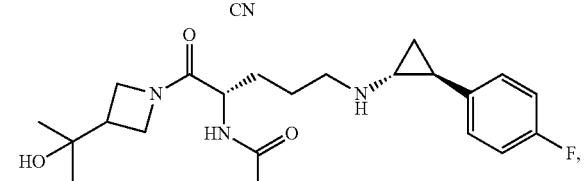
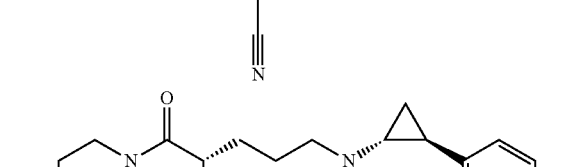
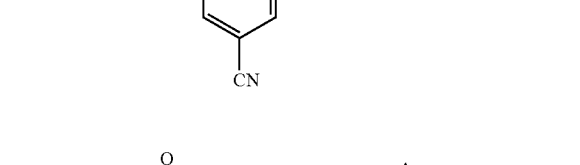
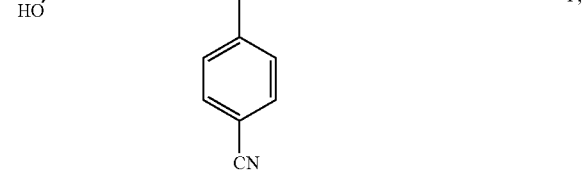
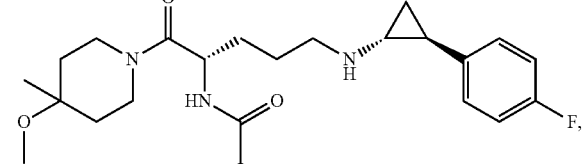

419
-continued
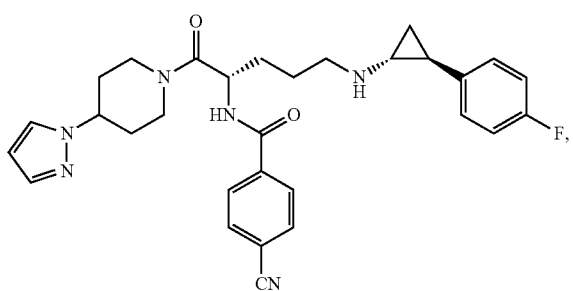
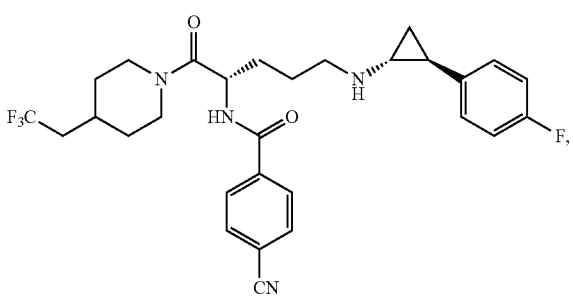
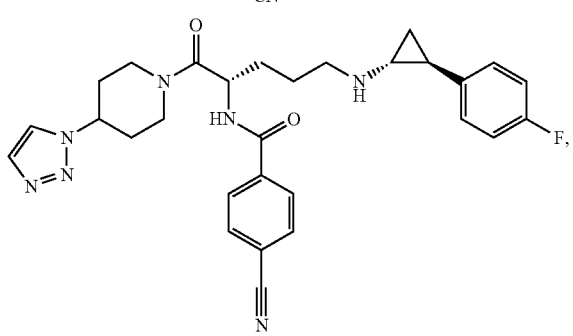
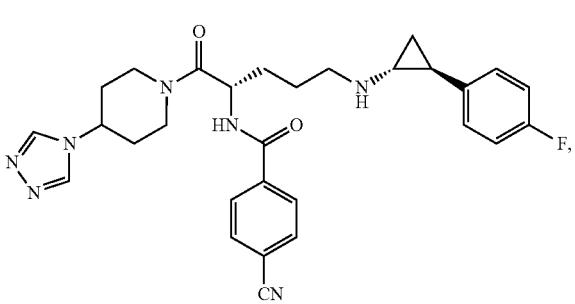
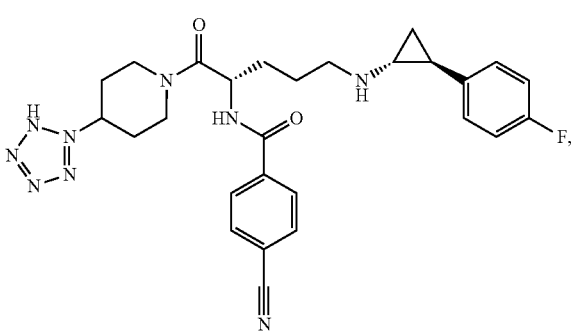
420
-continued
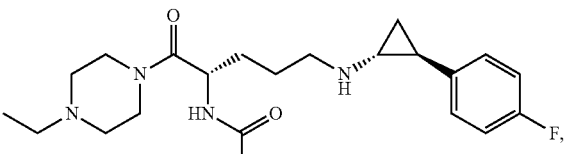
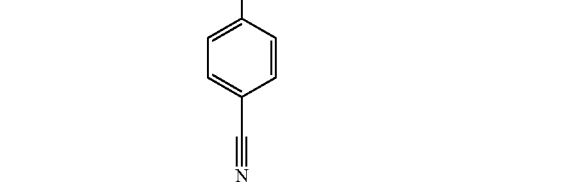
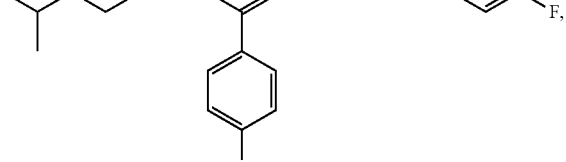
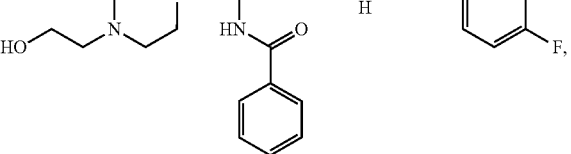
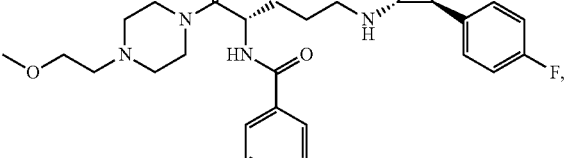
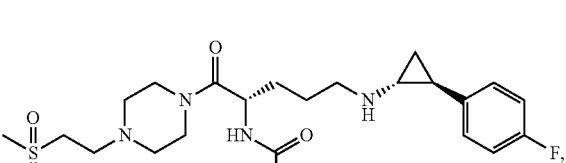

421
-continued
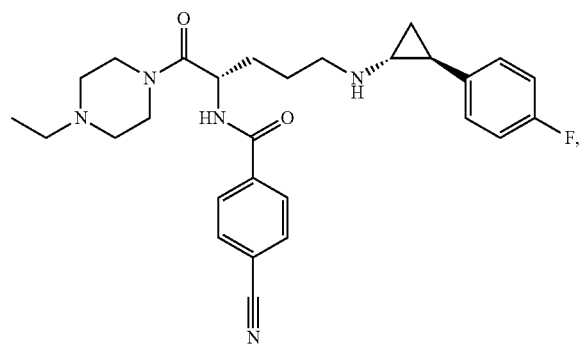
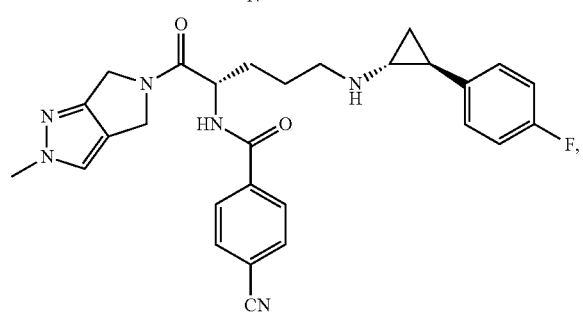
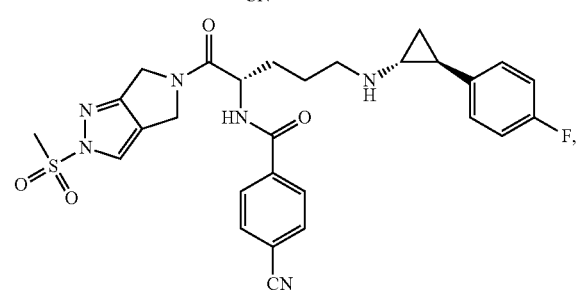
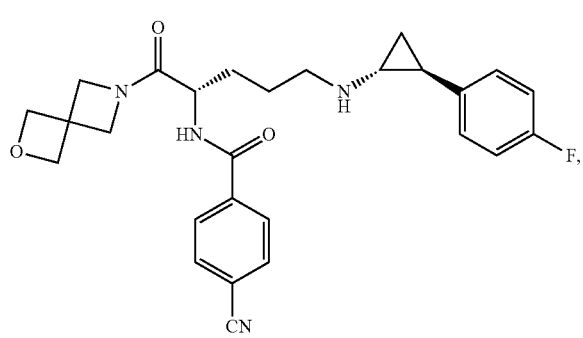
422
-continued
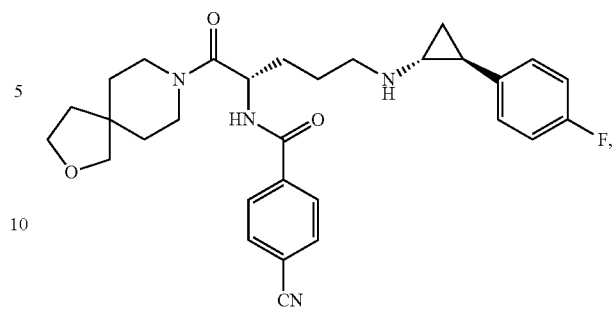
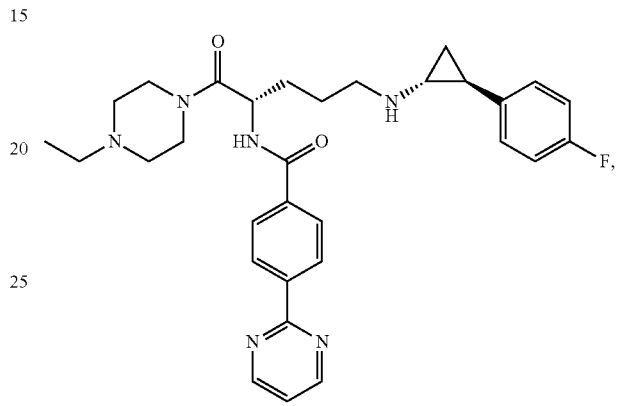
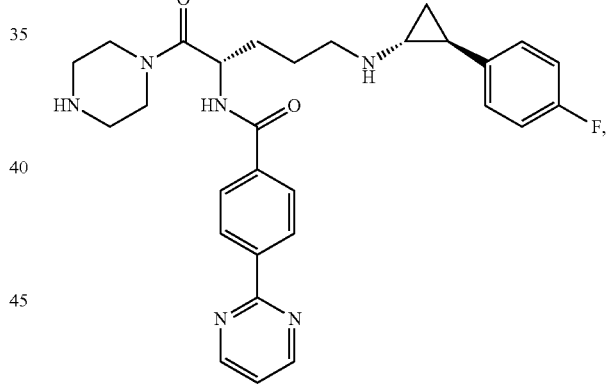
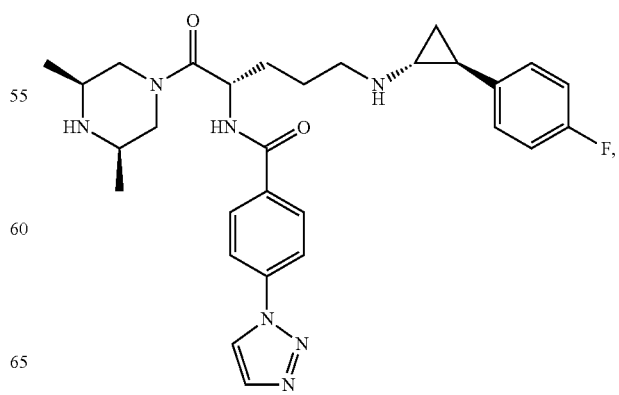

423
-continued
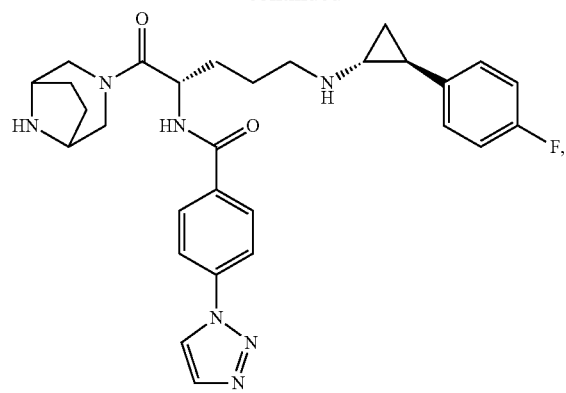
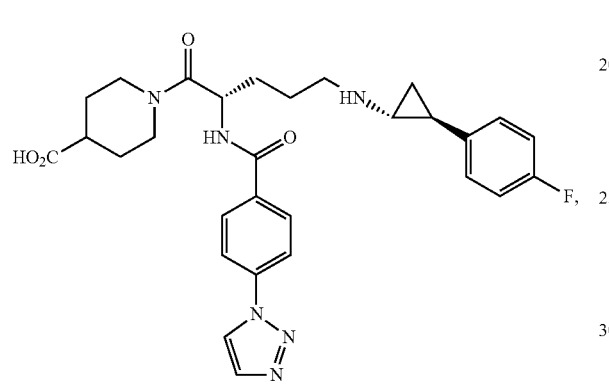
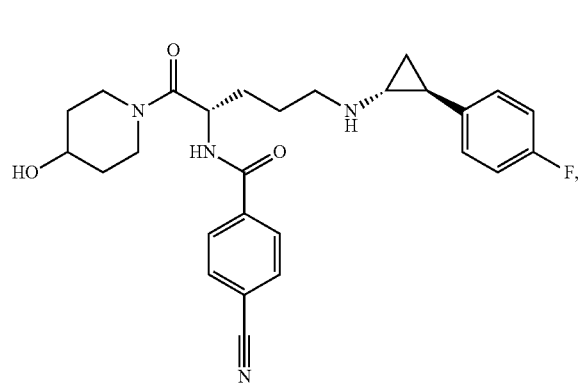
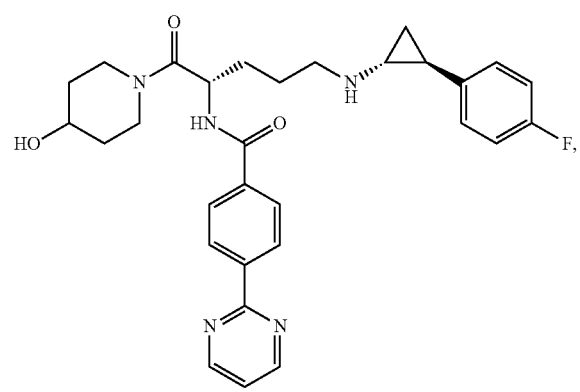
424
-continued
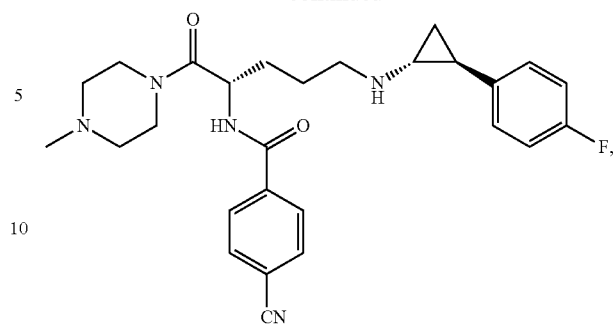
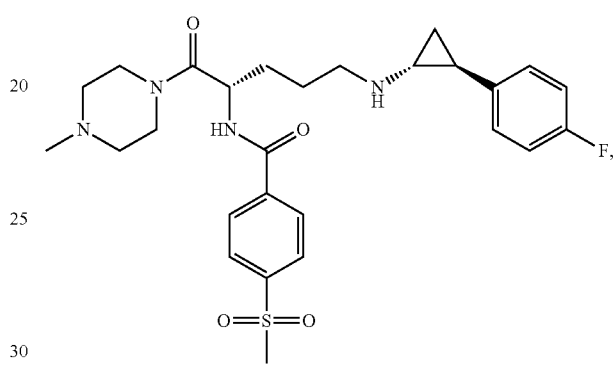
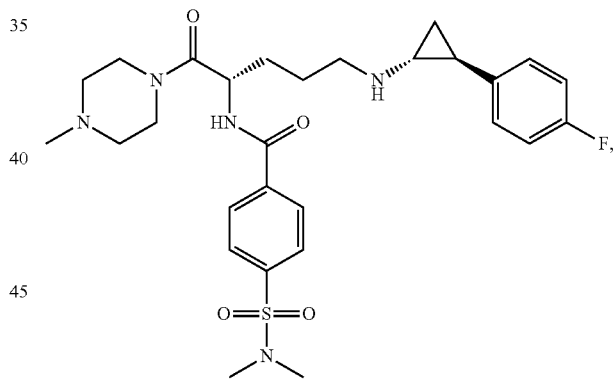
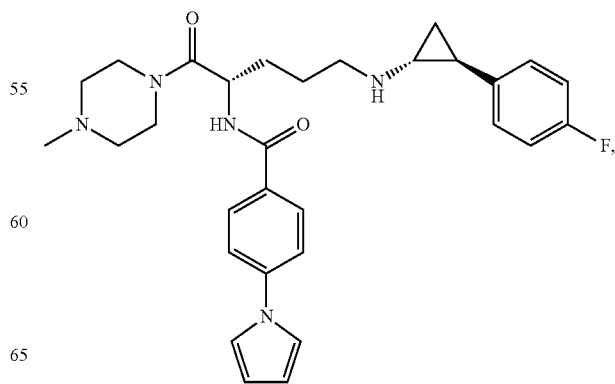

425
-continued
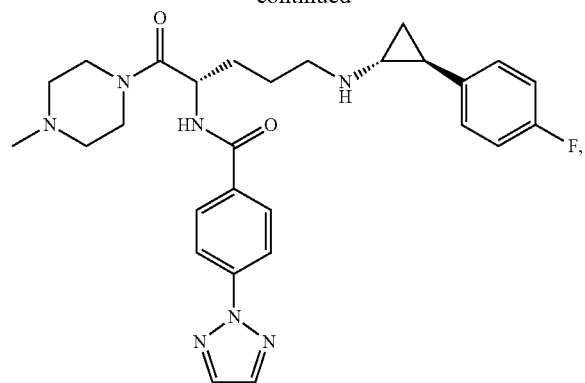
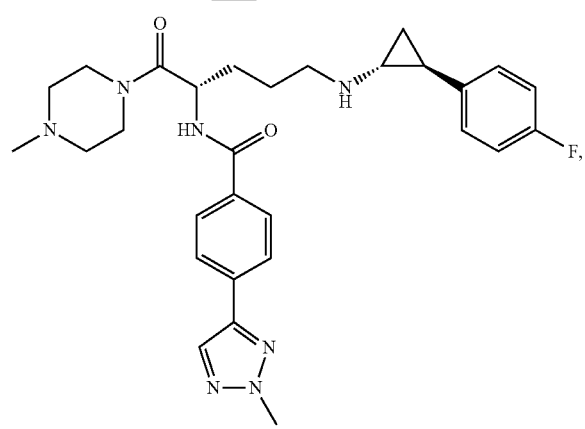
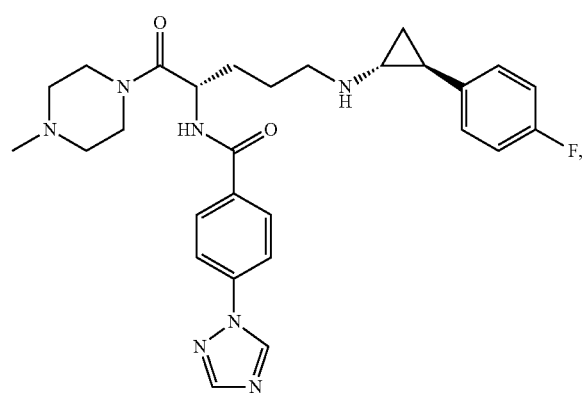
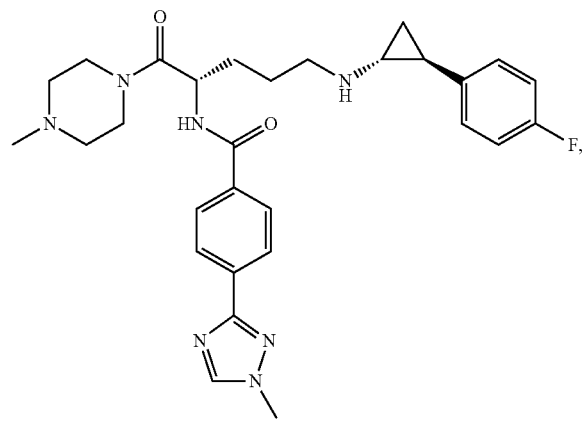
426
-continued
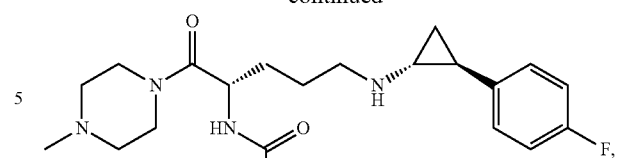
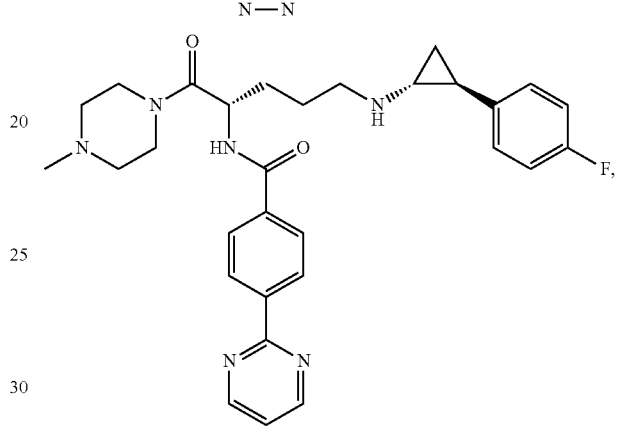
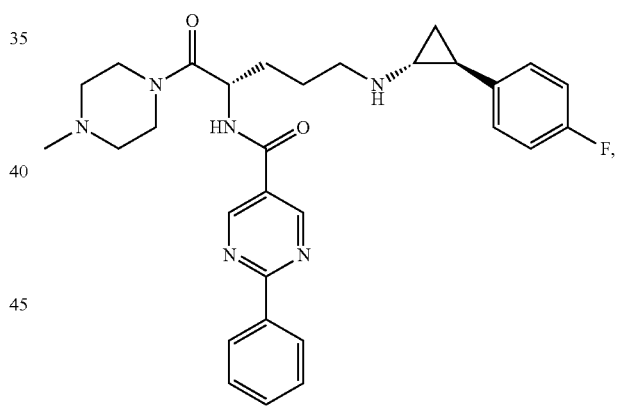
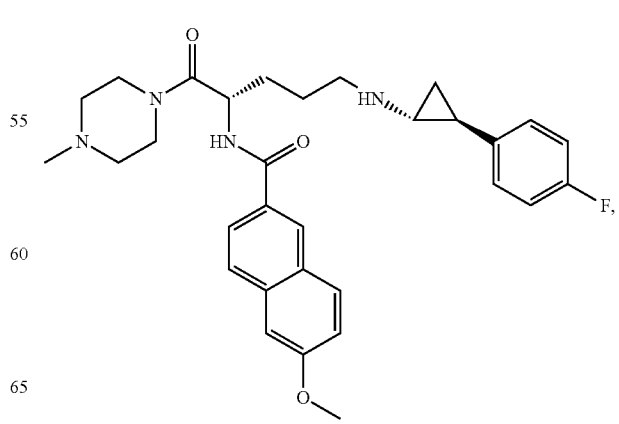

427
-continued
428
-continued
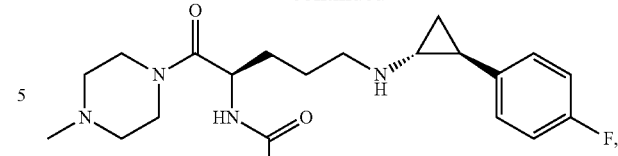
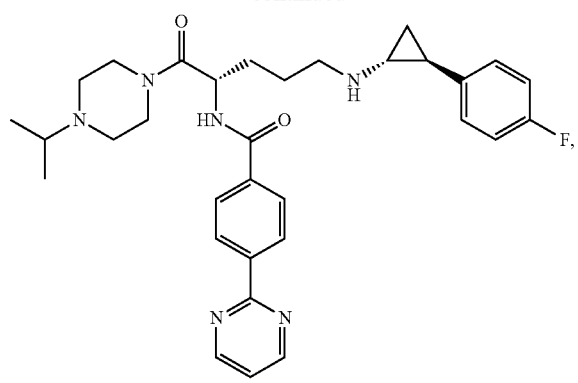
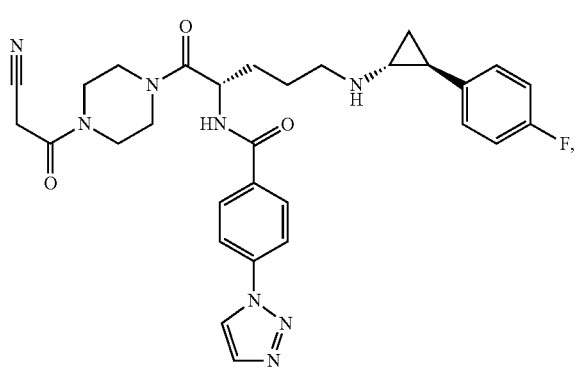
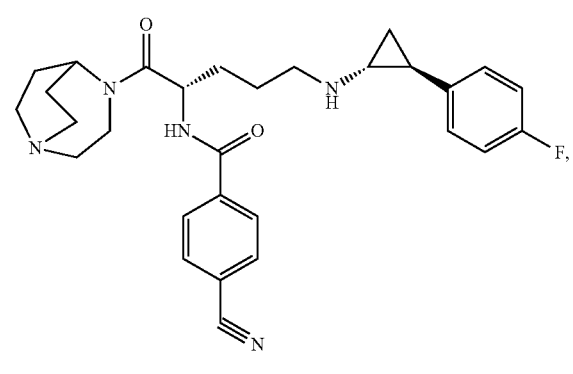
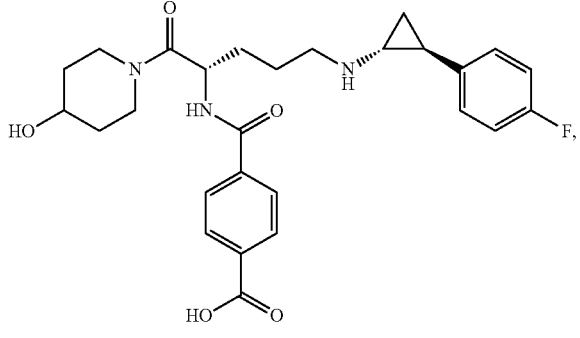
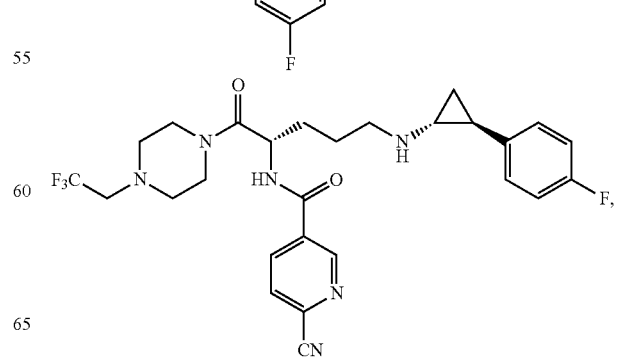

429
-continued
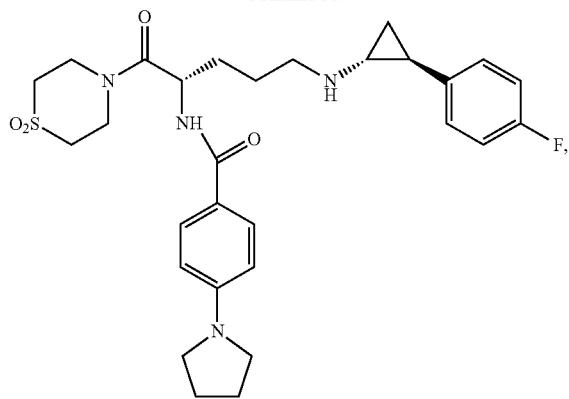
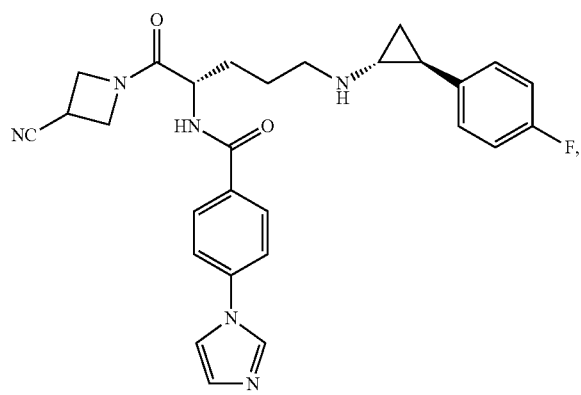
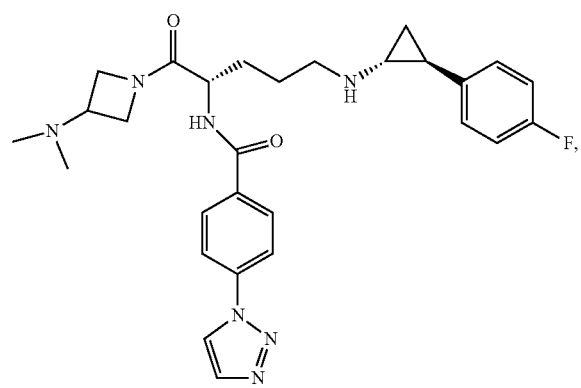
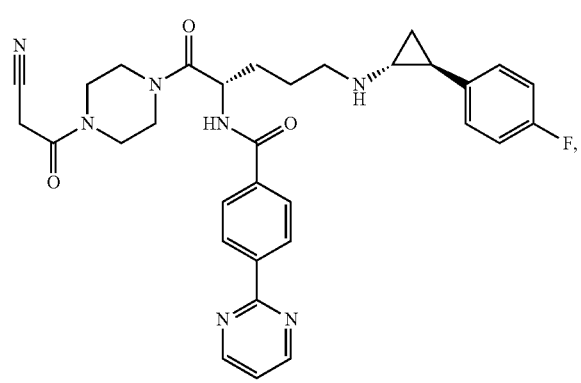
430
-continued
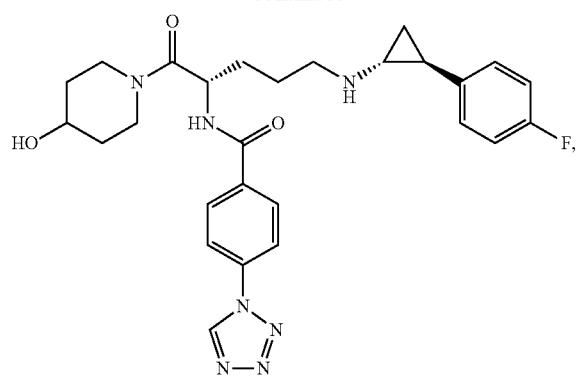
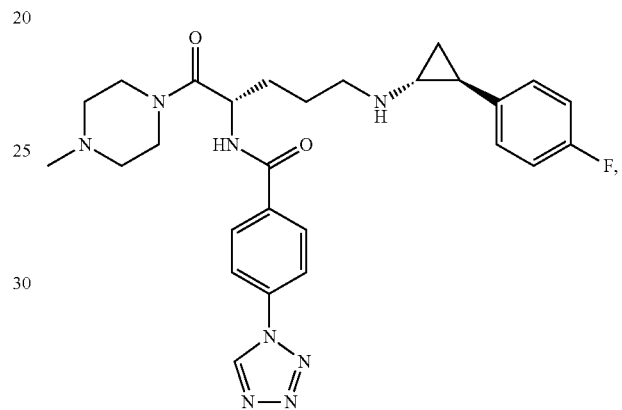
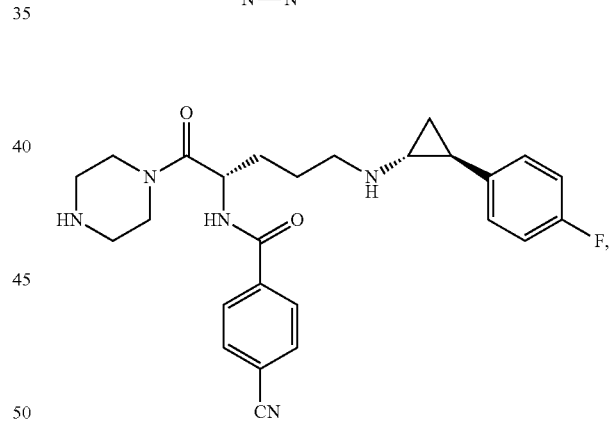
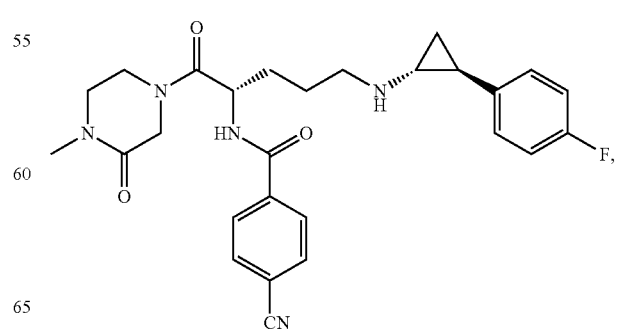

431
-continued
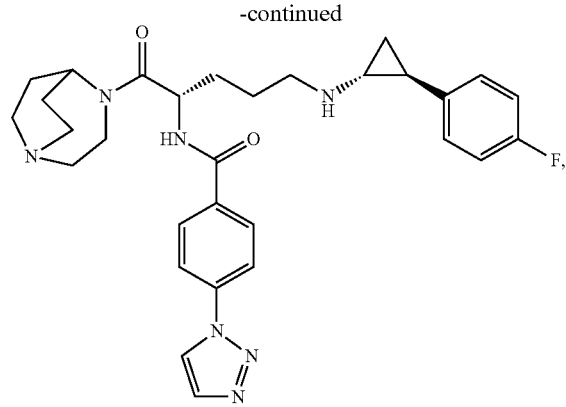
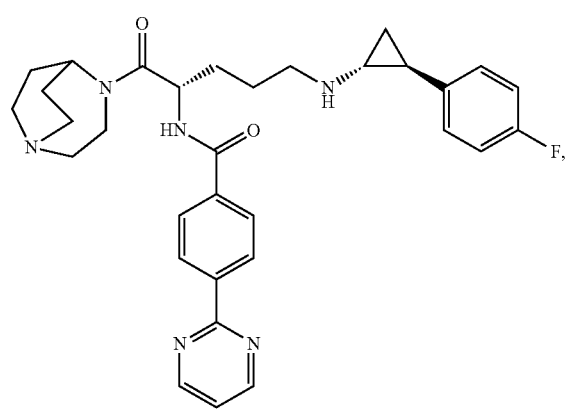
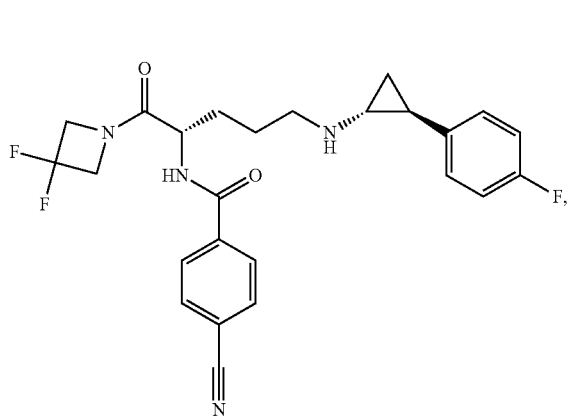
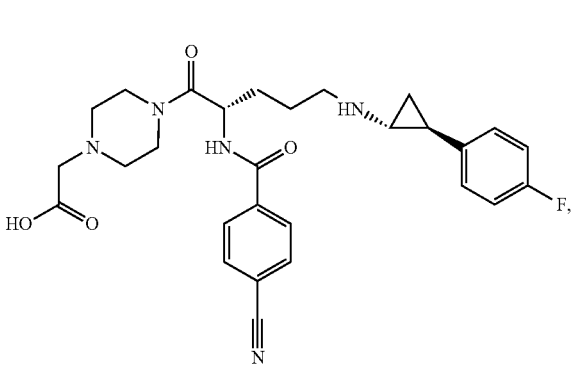
432
-continued
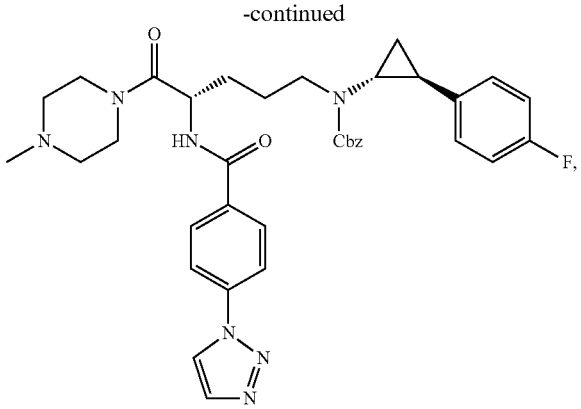
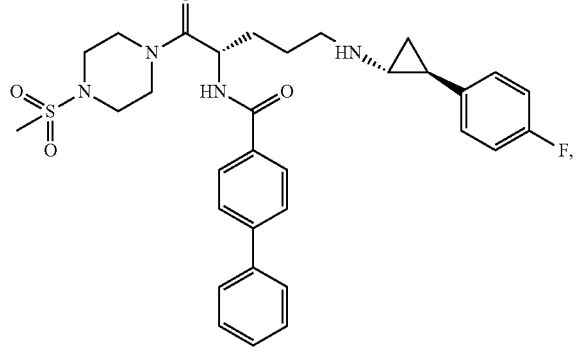
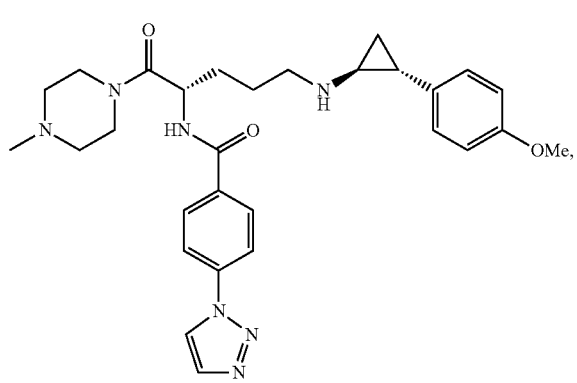
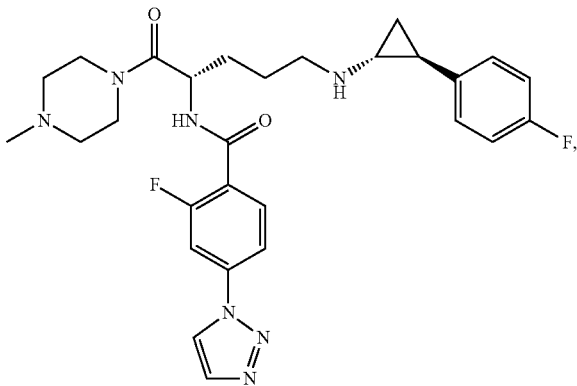

433
-continued
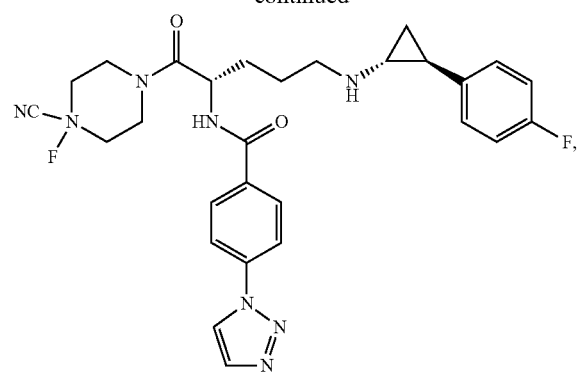
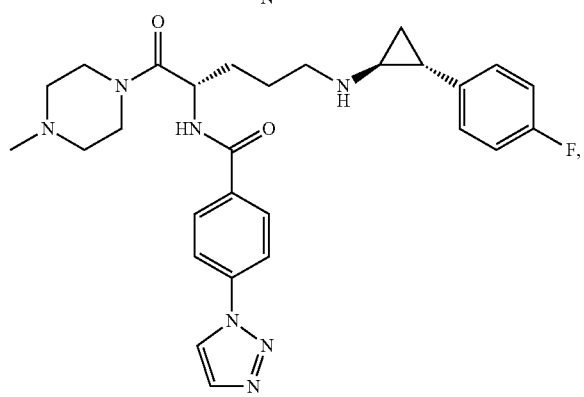
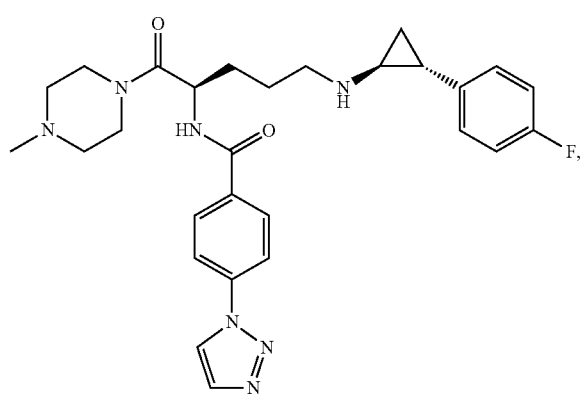
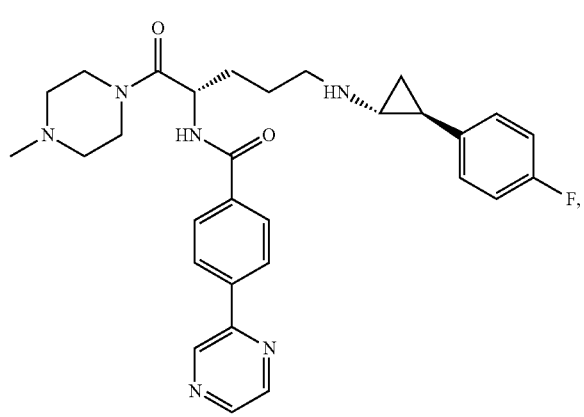
434
-continued
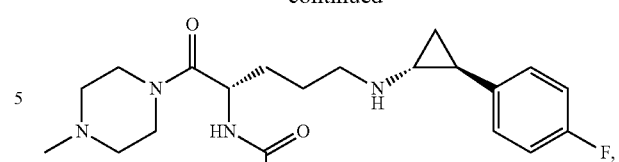
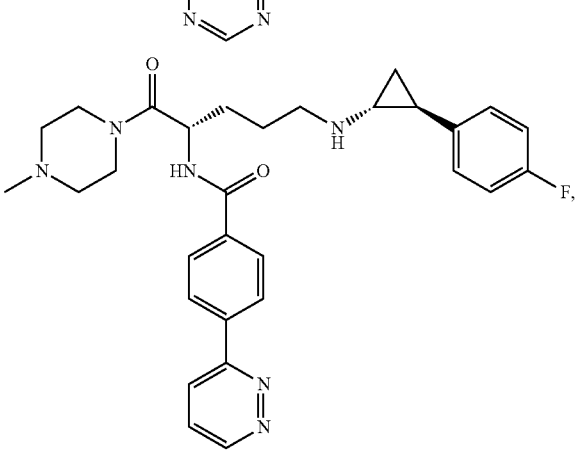
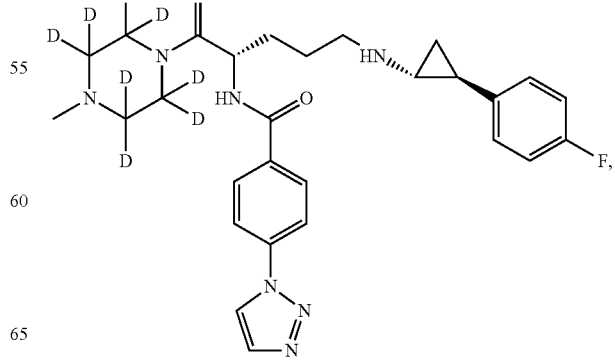

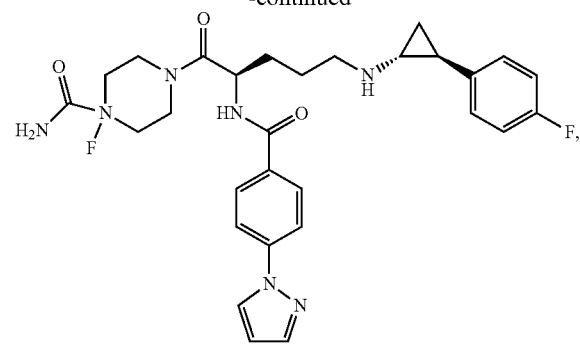
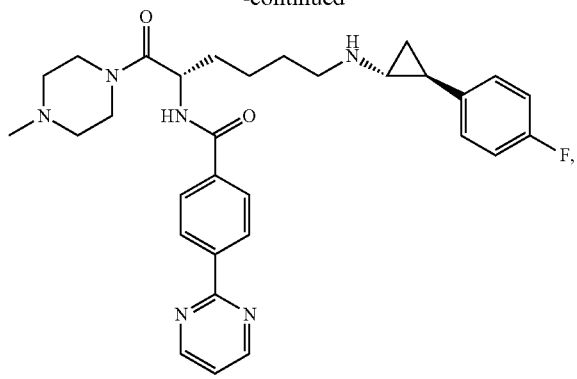
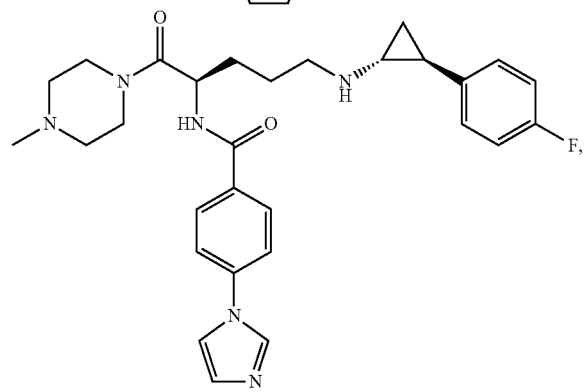
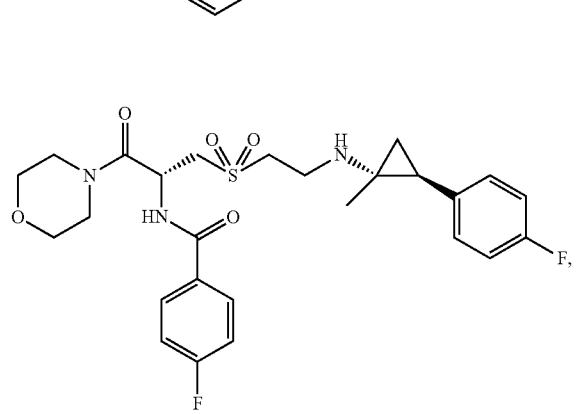
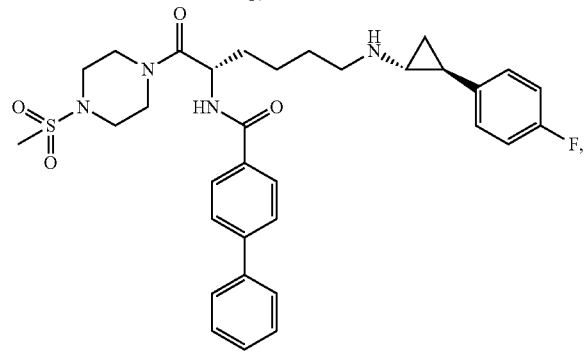
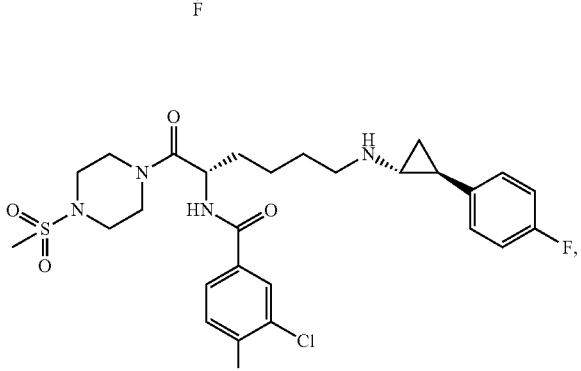
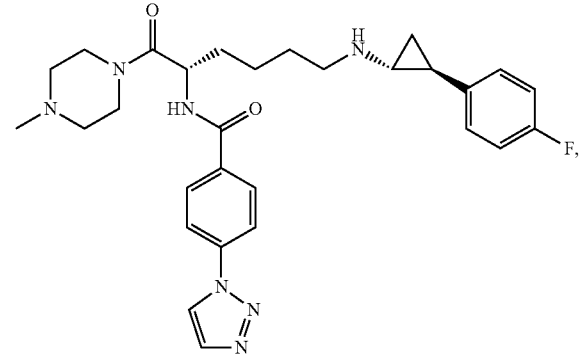
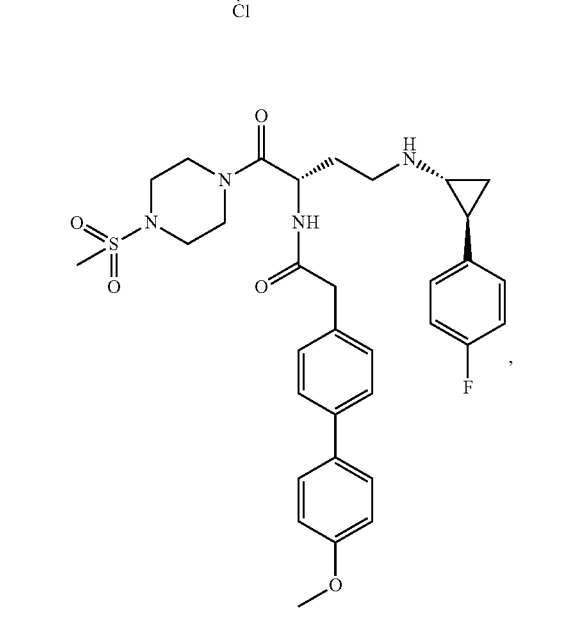
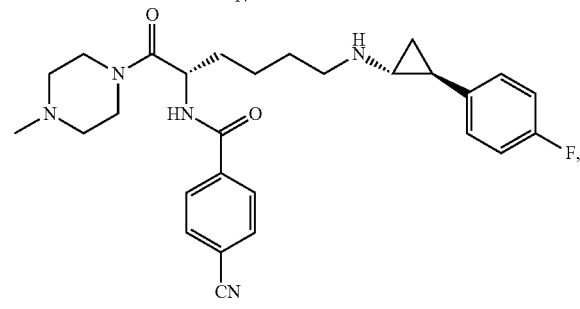

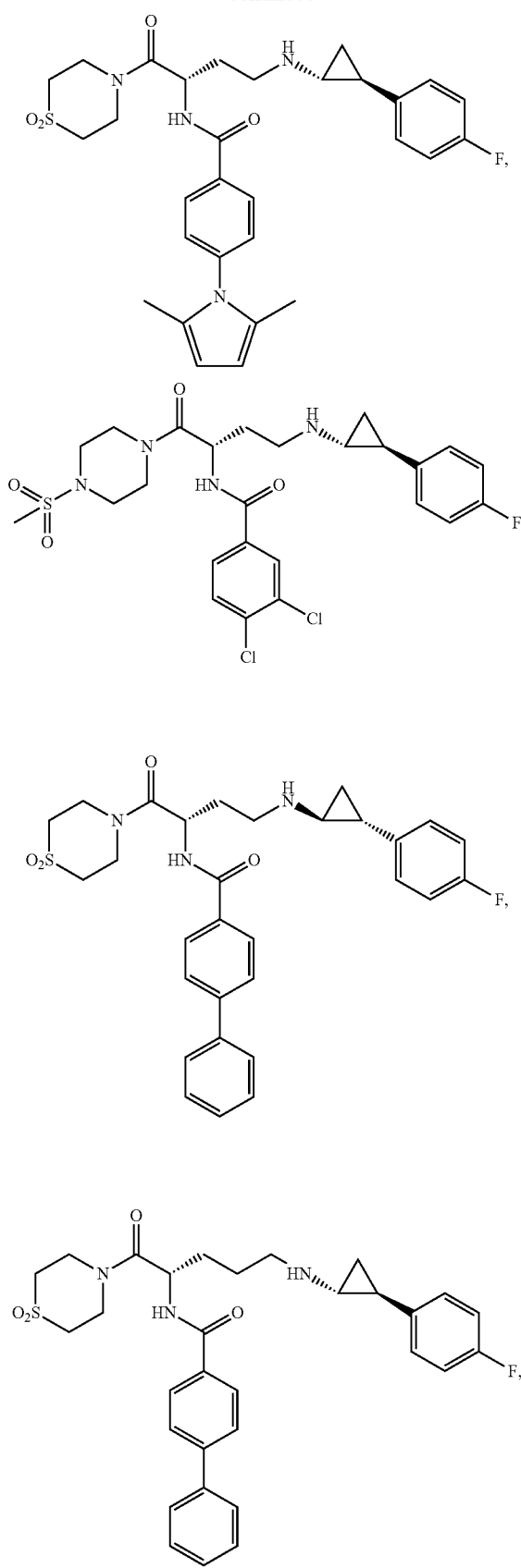
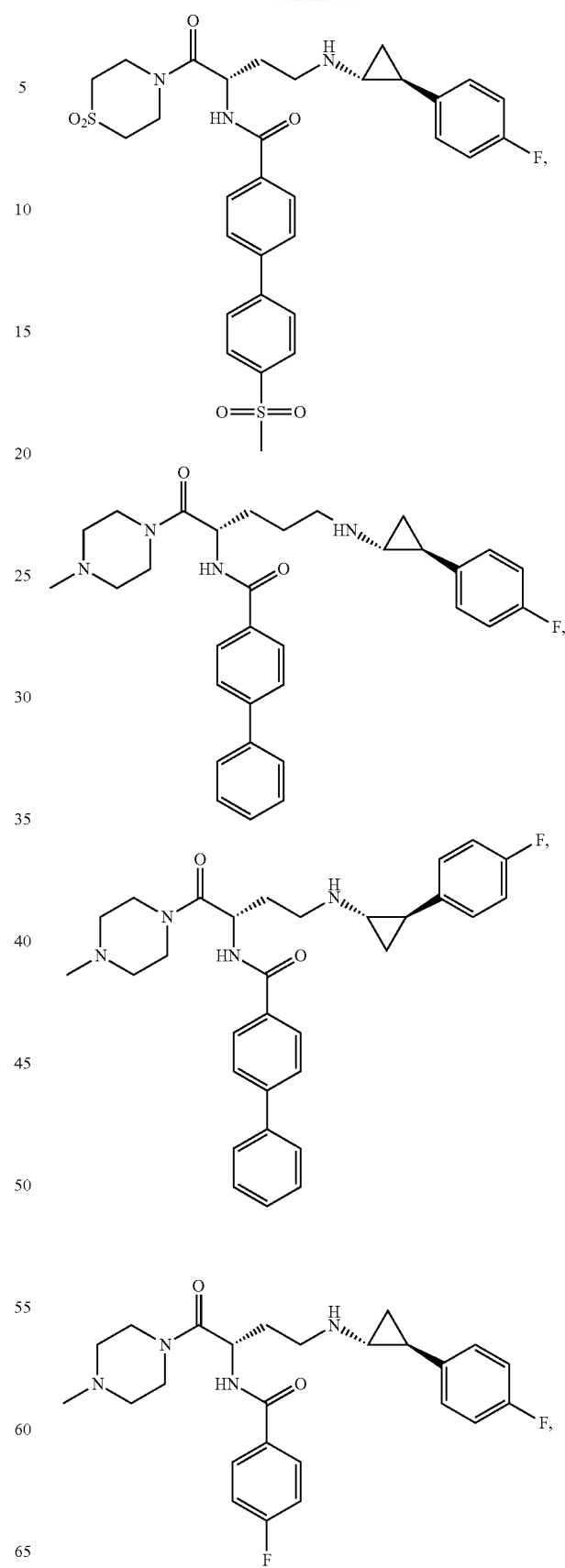

439
-continued
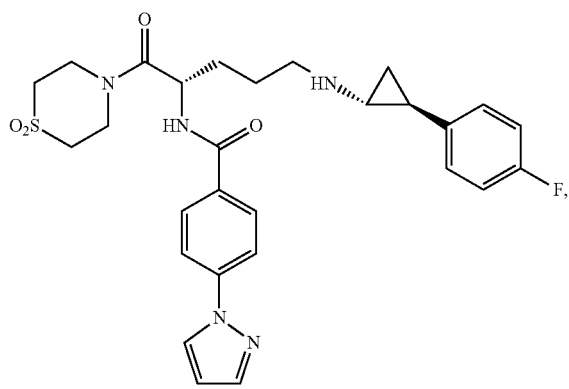
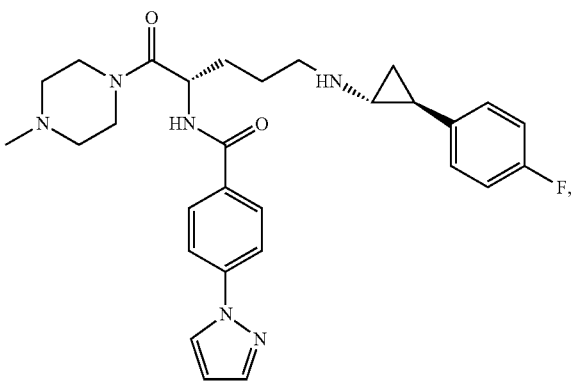
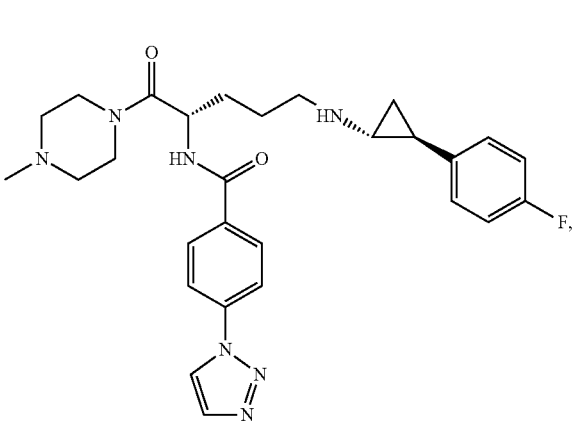
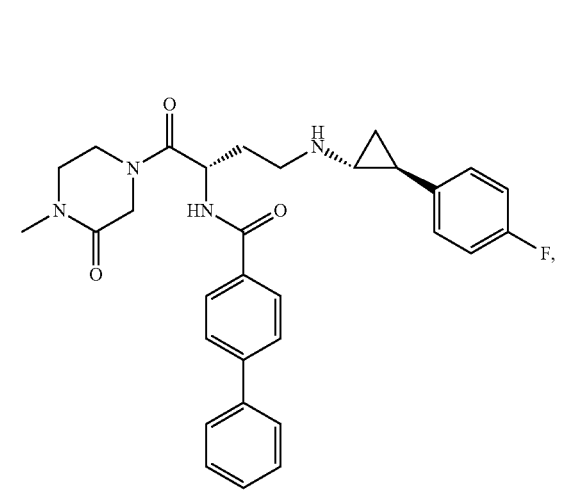
440
-continued
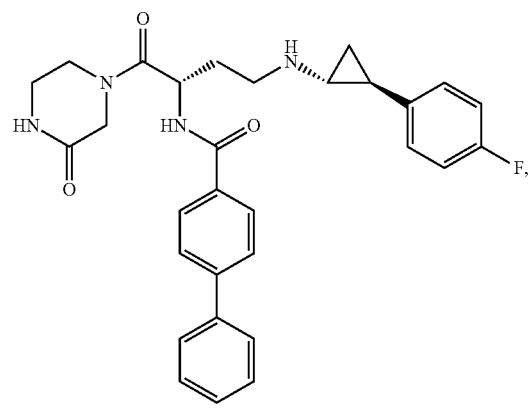
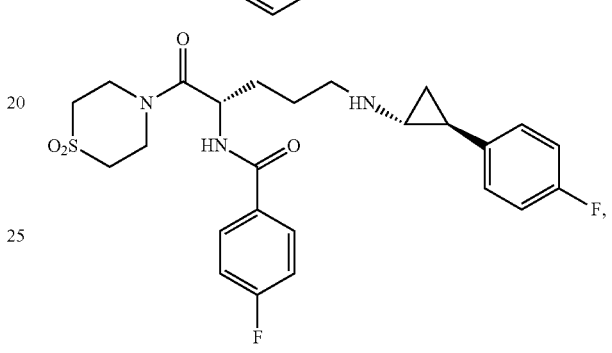
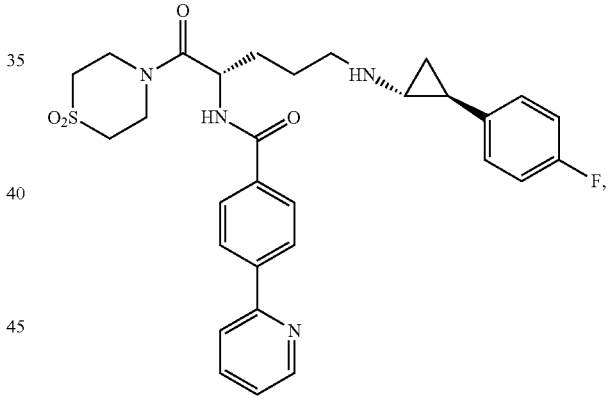
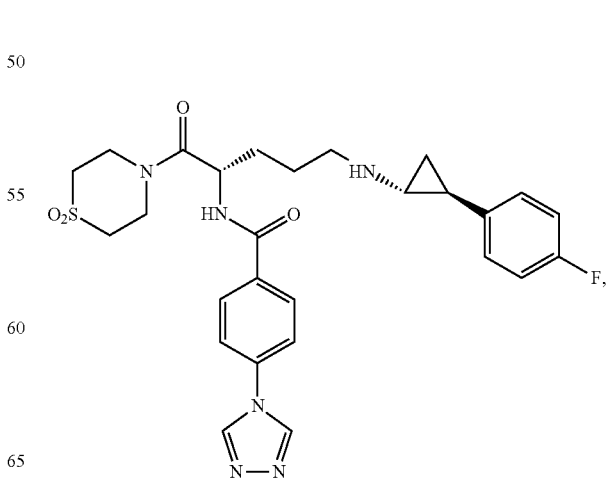

441
-continued
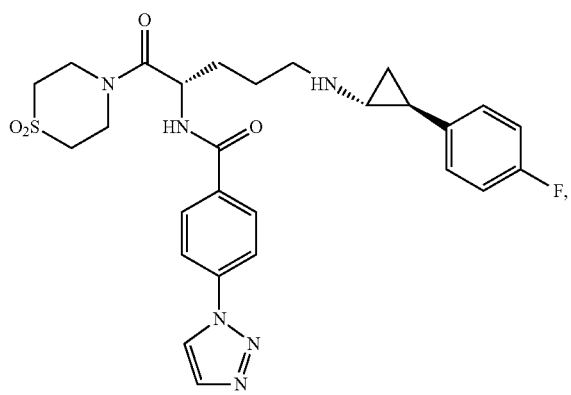
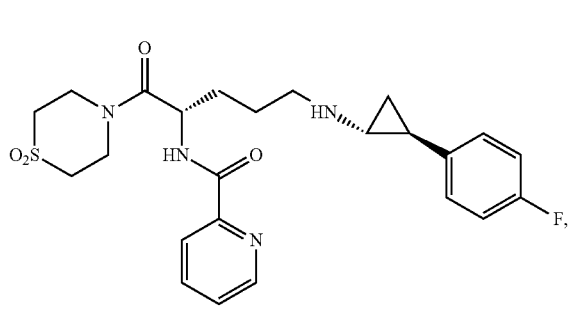
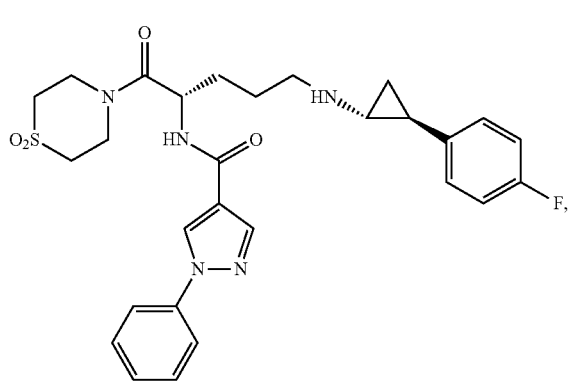
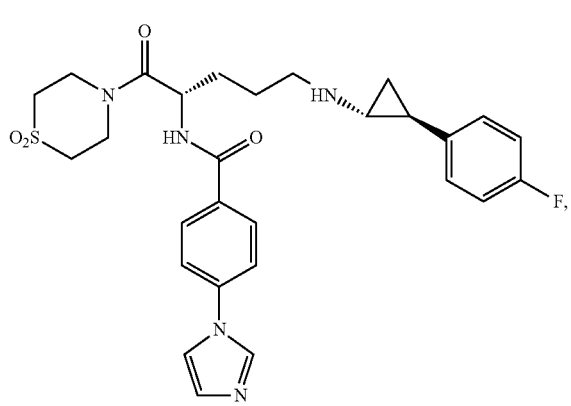
442
-continued
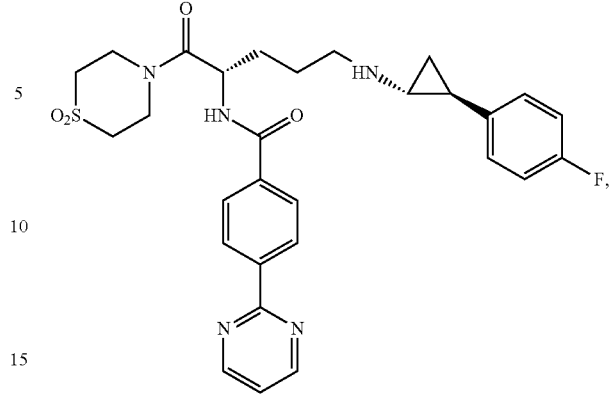
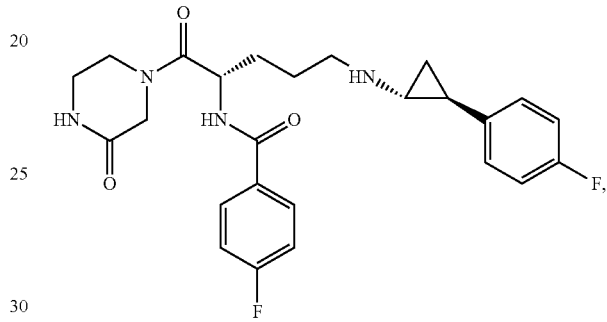
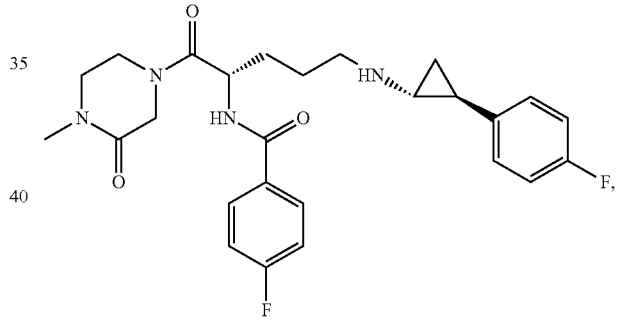
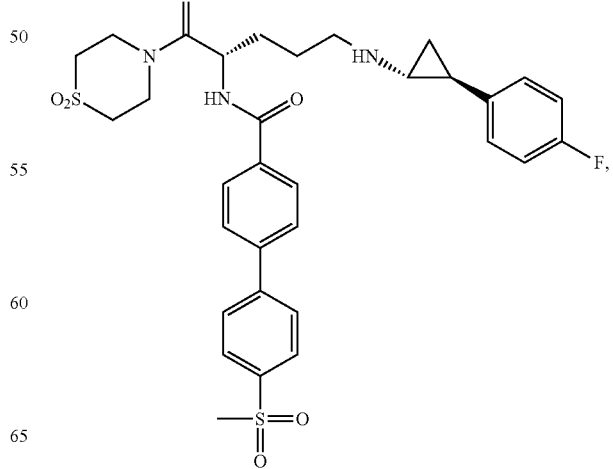

443
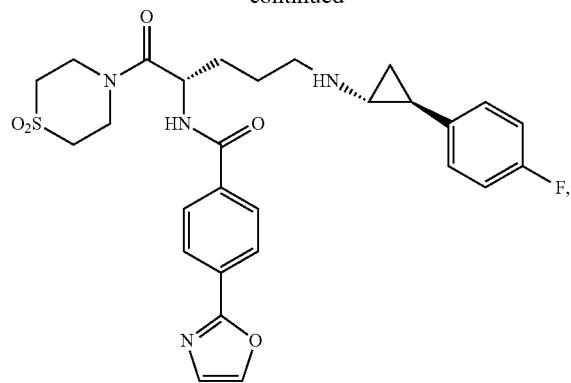
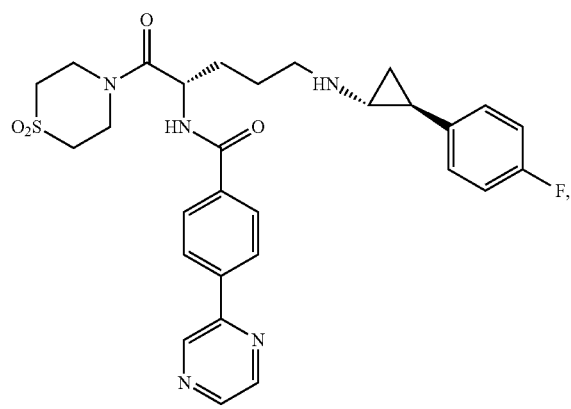
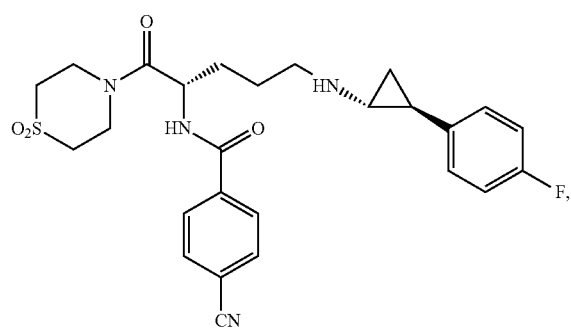
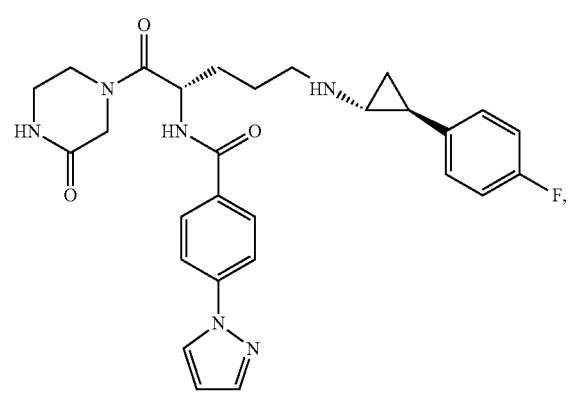
444
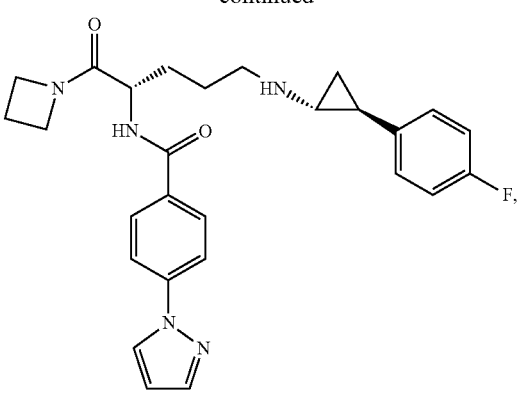
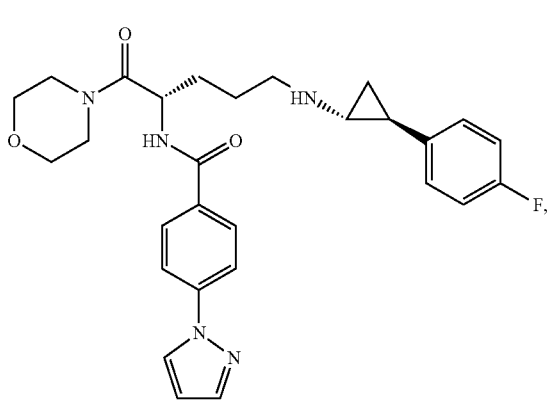
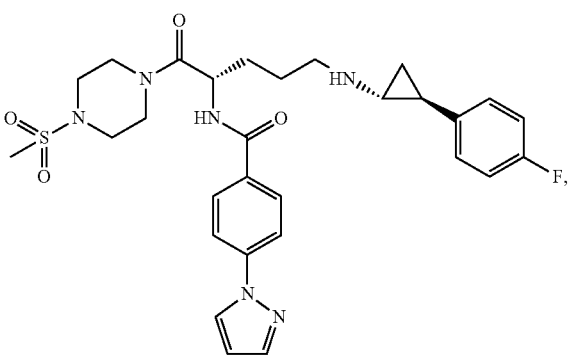
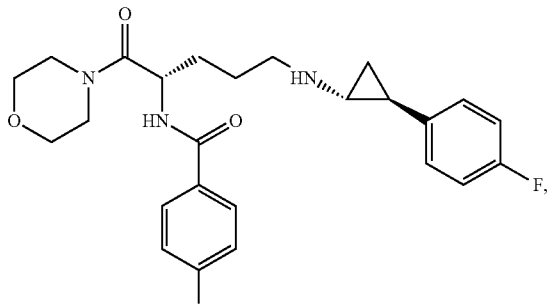

445
-continued
446
-continued
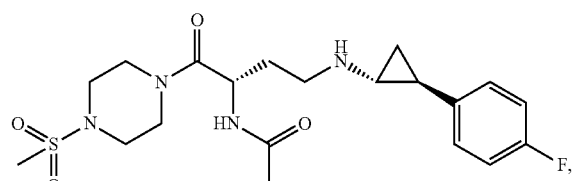
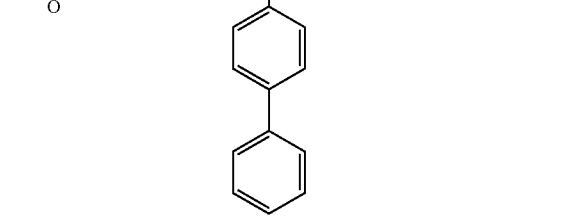
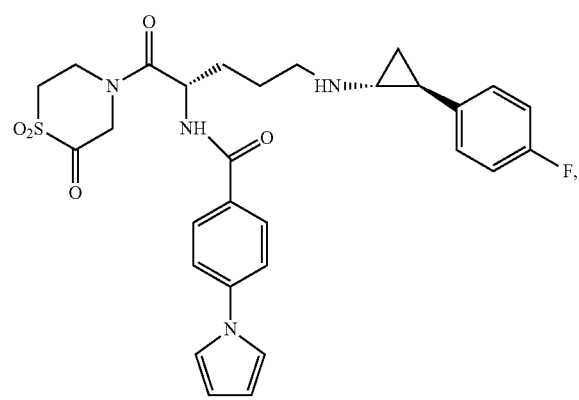
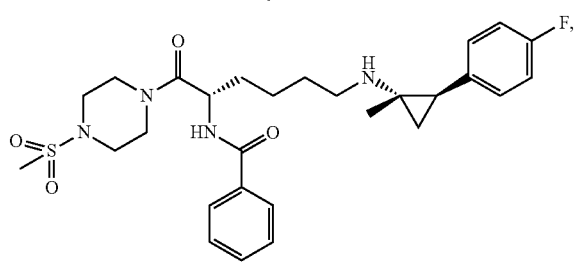
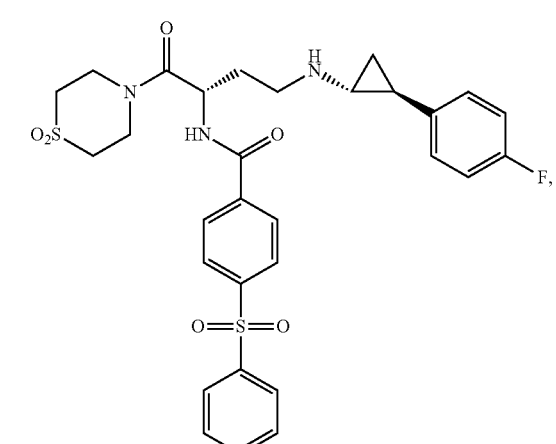
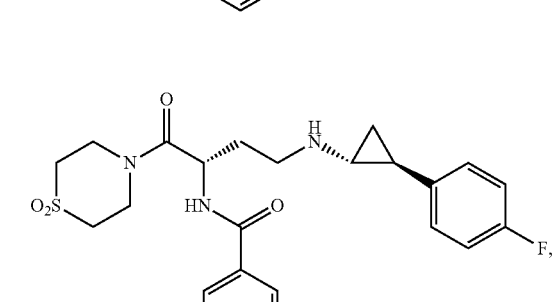
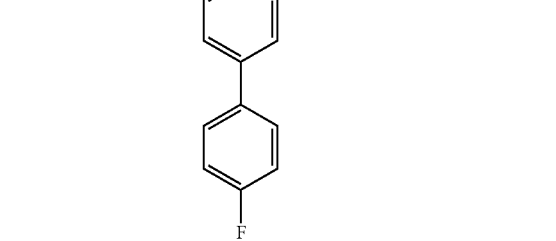

-continued and

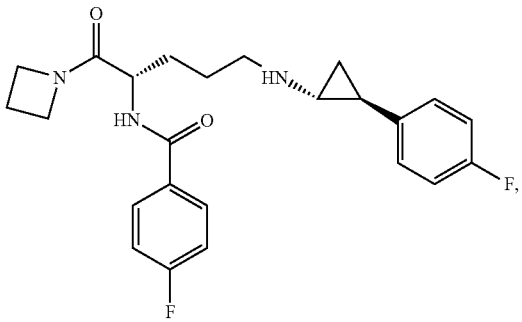 [SMILES: O=C(N[C@@H](CCCN[C@@H]1C[C@H]1c1ccc(F)cc1)C(=O)N1CCC1)c1ccc(F)cc1]

or a salt thereof.

18. A pharmaceutical composition comprising a compound as recited in claim 17, or a salt thereof, together with a pharmaceutically acceptable carrier.

19. The pharmaceutical composition as recited in claim 18, formulated for oral administration.

20. The pharmaceutical composition as recited in claim 19, additionally comprising another therapeutic agent.

21. A method of treatment of a KDM1A-mediated myeloid disease chosen from myelofibrosis, polycythemia vera, essential thrombocythemia, myelodysplastic syndrome (MDS), acute myelogenous leukemia (AML), and chronic myelogenous leukemia (CML), comprising the administration of a therapeutically effective amount of a compound as recited in claim 1, or a salt thereof, to a patient with said disease.

22. The method as recited in claim 21, wherein the disease is myelofibrosis.

* * * * *